US011117901B2

United States Patent
Badari et al.

(10) Patent No.: US 11,117,901 B2
(45) Date of Patent: Sep. 14, 2021

(54) SUBSTITUTED PYRAZOLO[4,3-H]QUINAZOLINES AS CHOLINE KINASE INHIBITORS

(71) Applicant: NERVIANO MEDICAL SCIENCES S.R.L., Nerviano (IT)

(72) Inventors: Alessandra Badari, Vedano al Lambro (IT); Elena Casale, Somma Lombardo (IT); Marcella Nesi, Saronno (IT); Francesca Quartieri, Arona (IT)

(73) Assignee: NERVIANO MEDICAL SCIENCES S.R.L., Nerviano (IT)

( * ) Notice: Subject to any disclaimer, the term of this patent is extended or adjusted under 35 U.S.C. 154(b) by 0 days.

(21) Appl. No.: 16/630,208

(22) PCT Filed: Jul. 3, 2018

(86) PCT No.: PCT/EP2018/067896
§ 371 (c)(1),
(2) Date: Jan. 10, 2020

(87) PCT Pub. No.: WO2019/011715
PCT Pub. Date: Jan. 17, 2019

(65) Prior Publication Data
US 2020/0131188 A1    Apr. 30, 2020

(30) Foreign Application Priority Data
Jul. 11, 2017    (EP) .................................... 17180772

(51) Int. Cl.
*A61K 31/519*    (2006.01)
*C07D 487/06*    (2006.01)
*C07D 487/04*    (2006.01)

(52) U.S. Cl.
CPC ................................ *C07D 487/04* (2013.01)

(58) Field of Classification Search
CPC ........................... A61K 31/519; C07D 487/06
USPC .......................................... 514/267; 544/251
See application file for complete search history.

(56) References Cited

U.S. PATENT DOCUMENTS

2011/0105542 A1    5/2011    Caldareli et al.
2011/0212994 A1    9/2011    Clem et al.

FOREIGN PATENT DOCUMENTS

| WO | WO 2004/104007 A1 | 12/2004 | |
|---|---|---|---|
| WO | 2005/068429 A1 | 7/2005 | |
| WO | 2007/077203 A2 | 7/2007 | |
| WO | 2008/011191 A1 | 1/2008 | |
| WO | 2013/043960 A1 | 3/2013 | |
| WO | 2013/043961 A1 | 3/2013 | |
| WO | 2014/151761 A1 | 9/2014 | |
| WO | 2015/185780 A1 | 12/2015 | |
| WO | WO-2019011715 A1 * | 1/2019 | ............. A61P 35/00 |

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: Wiley-VCH Verlag GmbH & Co. KGaA, 2005, Preface.*
Hackam, et al. JAMA, 296(14), 2006, 1731-1732.*
International Search Report dated Aug. 9, 2018 issued in PCT/EP2018/067896.
Arlauckas et al., "Choline kinase alpha—Putting the choK-hold on tumor metabolism", Progress in Lipid Research (Apr. 9, 2016), vol. 63, No. 9, pp. 28-40.
Zhang J-H et al., "A Simple Statistical Parameter for Use in Evaluation and Validation of High Throughput Screening Assays", *Journal of Biomolecular Screening* 4(2):67-73 (Nov. 2, 1999).
Aoyama C. et al., "Structure and Function of Choline Kinase Isoforms in Mammalian Cells", Progress in Lipid Research 43:266-281 (2004).
Asim M. et al., "Choline Kinase Alpha as an Androgen Receptor Chaperone and Prostate Cancer Therapeutic Target", JNCI J Natl. Cancer Inst 108(5):371-384 (2016).
Bagnoli M. et al., "Choline Metabolism Alteration: A Focus on Ovarian Cancer", Frontiers in Oncology 6(153):1-7 (Jun. 2016).
Banez-Coronel M. et al., "Choline Kinase Alpha Depletion Selectively Kills Tumoral Cells", Current Cancer Drug Targets 8(8):709-719 (2008).
Beloueche-Babari M. et al., "Acquired Resistance to EGFR Tyrosine Kinase Inhibitors Alters the Metabolism of Human Head and Neck Squamous Carcinoma Cells and Xenograft Tumours", British Journal of Cancer 112:1206-1214 (2015).

(Continued)

*Primary Examiner* — Douglas M Willis
(74) *Attorney, Agent, or Firm* — Scully, Scott, Murphy & Presser, P.C.

(57) ABSTRACT

The present invention relates to substituted pyrazolo-quinazoline derivatives which modulate the activity of Choline Kinase (ChoK). The compounds of this invention are therefore useful in treating diseases caused by an altered choline metabolism, such as cancer, cell proliferative disorders, infectious diseases of different origin, immune-related disorders and neurodegenerative disorders. The present invention also provides methods for preparing these compounds, pharmaceutical compositions comprising these compounds, and methods of treating diseases utilizing pharmaceutical compositions comprising these compounds. The compounds of this disclosure include those of formula (I):

23 Claims, No Drawings

(56) References Cited

OTHER PUBLICATIONS

Canese R. et al., "Characterisation of in Vivo Ovarian Cancer Models by Quantitative 1H Magnetic Resonance Spectroscopy and Diffusion-Weighted Imaging", NMR Biomed. 25:632-642 (2012).
Chen J-H et al., "Clinical Characteristics and Biomarkers of Breast Cancer Associated With Choline Concentration Measured by 1H MR Spectroscopy", NMR Biomed. 24(3):316-324 (Apr. 2011).
Chung T. et al., "ATP-Dependent Choline Phosphate-Induced Mitogenesis in Fibroblasts Involves Activation of pp70 S6 Kinase and Phosphatidylinositol 3'-Kinase Through an Extracellular Site", The Journal of Biological Chemistry 272(5):3064-3072 (Jan. 31, 1997).
Colombo M. et al., "A Fully Automated Method for Accurate Mass Determination Using High-Performance Liquid Chromatography With a Quadrupole/Orthogonal Acceleration Time-of-Flight Mass Spectrometer", Rapid Communications in Mass Spectrometry 18:511-517 (2004).
De La Cueva A. et al., "Combined 5-FU and ChoKα Inhibitors as a New Alternative Therapy of Colorectal Cancer: Evidence in Human Tumor-Derived Cell Lines and Mouse Xenografts", PLOS One 8(6):e64961-e67974 (Jun. 2013).
Gadiya M. et al., "Phospholipase D1 and Choline Kinase-α are Interactive Targets in Breast Cancer", Cancer Biology & Therapy 15(5):593-601 (May 2014).
Gallego-Ortega D. et al., "Involvement of Human Choline Kinase Alpha and Beta in Carcinogenesis" A Different Role in Lipid Metabolism and Biological Functions, Advances in Enzyme Regulations 51:183-194 (2011).
Gallego-Ortega D. et al., "Differential Role of Human Choline Kinase α and β Enzymes in Lipid Metabolism: Implications in Cancer Onset and Treatment", PLOS One 4(11):e7819 (Nov. 2009).
Gibellini F. et al., "The Kennedy Pathway—De Novo Synthesis of Phosphatidylethanolamine and Phosphatidylcholine", IUBMB Life 62(6):414-428 (Jun. 2010).
Glunde K. et al., "Choline Metabolism-Based Molecular Diagnosis of Cancer: An Update", Expert Rev Mol Diagn. 15(6):735-747 (Jun. 2015).
Glunde K. et al., "Choline Metabolism in Malignant Transformation", Nat Rev Cancer 11(12):835-848 (Feb. 23, 2015).
Glunde K. et al., "Metabolic Tumor Imaging Using Magnetic Resonance Spectroscopy", Semin Oncol. 38(1):26-41 (Feb. 2011).
Glunde K. et al., "RNA Interference-Mediated Choline Kinase Suppression in Breast Cancer Cells Induces Differentiation and Reduces Proliferation", Cancer Research 65(23):11034-11043 (Dec. 1, 2005).
Granata A. et al., "Global Metabolic Profile Indentifies Choline Kinase Alpha as a Key Regulator or Glutathione-Dependent Antioxidant Cell Defense in Ovarian Carcinoma", Oncotarget 6(13):11216-11230 (2015).
Granata A. et al., "Choline Kinase-Alpha by Regulating Cell Aggressiveness and Drug Sensitivity is a Potential Druggable Target for Ovarian Cancer", British Journal of Cancer 110:330-340 (2014).
Grinde M.T. et al., Interplay of Choline Metabolites and Genes in Patient-Derived Breast Cancer Xenografts, Breast Cancer Research 16:R5 (2014).
Gruber J. et al., "Balance of Human Choline Kinase Isoforms is Critical for Cell Cycle Regulation", FEBS Journal 279:1915-1928 (2012).
Guma M. et al., "Choline Kinase Inhibition in Rheumatoid Arthritis", Ann Rheum Dis 74:1399-1407 (2015).
Haukaas T.H. et al., "Metabolic Clusters of Breast Cancer in Relation to Gene- and Protein Expression Subtypes", Cancer & Metabolism 4(12):1-14 (2016).
Hernando E. et al., "A Critical Role for Choline Kinase Alpha in the Aggressiveness of Bladder Carcinomas", Oncogene 28(26):2425-2435 (Jul. 2009).

Jiménze B. et al., "Generation of Phosphorylcholine as an Essential Event in the Activation of Raf-1 and MAP-Kinases in Growth Factors-Induced Mitogenic Stimulation", Journal of Cellular Biochemistry 57:141-149 (1995).
Krisfinamachary B. et al., "Noninvasive Detection of Lentiviral-Mediated Choline Kinase Targeting in a Human Breast Cancer Xenograft", Cancer Research 69(8):3464-3471 (Apr. 15, 2009).
Kroemer G. et al., "Tumor Cell Metabolism: Cancer's Achilles' Heel", Cancer Cell 13:472-482 (Jun. 2008).
Kumar M. et al., "Magnetic Resonance Spectroscopy for Detection of Choline Kinase Inhibition in the Treatment of Brain Tumors", Molecular Cancer Therapeutics 14(4):899-908 (2015).
Li Q. et al., "Integrative Functional Genomics of Hepatitis C Virus Infection Identifies Host Dependencies in Complete Viral Replication Cycle", PLOS Pathogens 10(5):e1004163-e1004177 (May 2014).
Li H. et al., "The Metabolic Responses to Hepatitis B Virus Infection Shed New Light on Pathogenesis and Targets for Treatment", Scientific Reports 5:8421-8429 (2014).
Li Z. et al., "Phosphatidylcholine and Choline Homeostasis", Journal of Lipid Research 49:1187-1194 (2008).
Local J C, "Choline Kinase as a Precision Medicine Target for Therapy in Cancer, Autoimmune Diseases and Malaria", Precision Medicine 2:e980 (2015).
Malito E. et al., "Elucidation of Human Choline Kinase Crystal Structures in Complex With the Products ADP or Phosphocholine", J. Mol. Biol. 364:136-151 (2006).
Mazarico J.M. et al., "Choline Kinase Alpha (CHKα) as a Therapeutic Target in Pancreatic Ductal Adenocarcinoma: Expression, Predictive Value, and Sensitivity to Inhibitors", Molecular Cancer Therapeutics 15(2):1-11 (2016).
Mitsuhashi S. et al., "A Congenital Muscular Dystrophy With Mitochondrial Structural Abnormalities Caused by Defective De Novo Phosphatidylcholine Biosynthesis", The American Journal of Human Genetics 88:845-851 (Jun. 10, 2011).
Mitsuhashi S. et al., "Megaconial Congenital Muscular Dystrophy Due to Loss-of-Function Mutations in Choline Kinase β", Current Opinion Neurol 26(5):536-543 (Oct. 2013).
Peyrottes S. et al., "Choline Analogues in Malaria Chemotherapy", Current Pharmaceutical Design 18(24):3454-3466 (2012).
Priolo C. et al., "AKT1 and MYC Induce Distinctive Metabolic Fingerprints in Human Prostate Cancer", Cancer Research 74(24):7198-7204 (Dec. 15, 2014).
Ramírez De Molina A. et al., "Expression of Choline Kinase Alpha to Predict Outcome in Patients With Early-Stage Non-Small-Cell Lung Cancer: A Retrospective Study", The Lancet 8:889-897 (Oct. 2007).
Ramírez De Molina A. et al., "Overexpression of Choline Kinase is a Frequent Feature in Human Tumor-Derived Cell Lines and in Lung, Prostate, and Colorectal Human Cancers", Biochemical and Biophysical Research Communications 296:580-583 (2002).
Rocha C.M. et al., "NMR Metabolomics of Human Lung Tumours Reveals Distinct Metabolic Signatures for Adenocarcinoma and Squamous Cell Carcinoma", Carcinogenesis 36(1):68-75 (2015).
Shah T. et al., "Choline Kinase Overexpression Increases Invasiveness and Drug Resistance of Human Breast Cancer Cells", NMR in Biomedicine 23:633-642 (2010).
Sher R.B. et al., "A Rostrocaudal Muscular Dystrophy Caused by a Defect in Choline Kinase Beta, the First Enzyme in Phosphatidylcholine Biosynthesis", The Journal of Biological Chemistry 281(8):4938-4948 (Feb. 24, 2006).
Trousil S. et al., "Alterations of Choline Phospholipid Metabolism in Endometrial Cancer are Caused by Choline Kinase Alpha Overexpression and a Hyperactivated Deacylation Pathway", Cancer Research 74(23):6867-6877 (Dec. 1, 2014).
Ward P.S. et al., "Signaling in Control of Cell Growth and Metabolism", Cold Spring Harb Perspect Biol 4:a006783 (2012).
Wu G. et al., "Early Embryonic Lethality Caused by Disruption of the Gene for Choline Kinase α, the First Enzyme in Phosphatidylcholine Biosynthesis", The Journal of Biological Chemistry 283(3):1456-1462 (Jan. 18, 2008).
Xiong J. et al., "Dysregulated Choline Metabolism in T-Cell Lymphoma: Role of Choline Kinase-α and Therapeutic Targeting", Blood Cancer Journal 5:287-296 (Mar. 2015).

(56) References Cited

OTHER PUBLICATIONS

Yalcin A. et al., "Selective Inhibition of Choline Kinase Simultaneously Attenuates MAPK and PI3K/AKT Signaling", Oncogene 29:139-149 (2010).
Zadra G. et al., "The Fat Side of Prostate Cancer", Biochimica et Biophysics Acta 1831:1518-1532 (2013).

* cited by examiner

SUBSTITUTED PYRAZOLO[4,3-H]QUINAZOLINES AS CHOLINE KINASE INHIBITORS

The present invention relates to certain substituted pyrazolo-quinazoline derivatives as Choline Kinase inhibitors analogues, which modulate the activity of Choline Kinase (ChoK). The compounds of this invention are therefore useful in treating diseases caused by an altered choline metabolism. The present invention also provides methods for preparing these compounds, pharmaceutical compositions comprising these compounds, and methods of treating diseases utilizing pharmaceutical compositions comprising these compounds.

BACKGROUND OF THE INVENTION

Metabolic reprogramming in cancer cells has been recognized as one of the most significant hallmarks of cancer. Tumorigenesis is dependent on the reprogramming of cellular metabolism as both direct and indirect consequence of oncogenic mutations. The alterations in intracellular and extracellular metabolites, that can accompany cancer-associated metabolic reprogramming, have profound effects on gene expression, cellular differentiation and tumor microenvironment and support rapid growth, metastasis, drug resistance and survival (*Cancer Cell* 2008, 13, 472-482; *Cold Spring Harb Perspect Biol* 2012, 4, a006783). Among the several changes of tumor metabolic pathways, abnormal choline metabolism is emerging as one of the metabolic hallmarks associated with oncogenesis and tumour progression. Activated choline metabolism, which is characterized by an increase in total choline-containing compounds (tCho) and, in particular, in phosphocholine (PCho) level, has been identified in tumor cells both in in vitro and in vivo studies, and by magnetic resonance spectroscopy (MRS) in primary tumors samples (*Cancer & Metabolism* 2016, 4, 12-14; *Biochimica et Biophysica Acta* 2013, 1831, 1518-1532; *NMR Biomed.* 2012, 25, 632-642; *Semin. Oncol.* 2011, 38, 26-41; *Lancet Oncol.* 2007, 8, 889-97). Choline phospholipid metabolism consists of a complex network of biosynthetic and catabolic pathways controlled by several regulatory enzymes that may be potential targets for anticancer therapy (*Prog. Lipid Res.* 2016, 63, 28-40; *Nat. Rev. Cancer,* 2011, 11, 835-848). Among the enzymes involved, Choline Kinase (ChoK) is ubiquitously distributed in eukaryotes and catalyzes the first step of the Kennedy pathway for the de novo synthesis of phosphatidylcholine (PtdCho), which is the most abundant phospholipid in mammalian cellular membranes (*IUBMB Life* 2010, 62, 414-428; *J. Lipid Res.* 2008, 49, 1187-1194). In mammalian cells two separate genes encode for three isoforms: ChoKα1, ChoKα2 and ChoKβ. ChoKα1 and ChoKα2 are formed as the result of alternative splicing of the CHKA transcript. The enzyme is active as homo or hetero dimers (*Prog. Lipid Res.* 2004, 43, 266-281). In the first step of the Kennedy pathway, ChoK converts choline into phosphocholine (PCho), which then reacts with cytidine triphosphate (CTP) to form cytidine diphosphate-choline (CDP-choline). The PCho moiety is then transferred to diacylglycerol to produce PtdCho. Moreover PCho is considered a putative second messenger involved in proliferation and its level increase is correlated to activity of ChoKα in cells (J Cell. Bloch. 1995, 57, 141-149; *J. Biol. Chem.* 1997, 272, 3064-3072).

Different and not redundant roles for ChoKα and ChoKβ have been suggested. ChoKα knock-out mice result in embryonic lethality (*J. Biol. Chem.* 2008, 283, 1456-1462), while ChoKβ knock-out mice develop a rostrocaudal muscular dystrophy and bone deformity (*J. Biol. Chem.* 2006, 281, 4938-4948). In human, an inactivating mutation in CHKB gene has been identified in congenital muscular dystrophy (*Am. J. Hum. Genet.* 2011, 88, 845-851; *Curr. Opin. Neurol.* 2013, 26: 536-543). Moreover ChoKα, but not ChoKβ, has been associated with malignancy and its down modulation using specific siRNA is sufficient to affect PCho level, invasion and migration of cancer cells (*FEBS Journal* 2012, 279, 1915-1928; *Adv. Enzyme Regul.* 2011, 51, 183-194; *PLoS ONE* 2009, 4, e7819). According to these data, ChoKα inhibition could be sufficient to have an antitumor activity avoiding potential toxic effect linked to ChoKβ inhibition.

Several data reported in the literature support the role of ChoKα in tumors. Down modulation or overexpression of ChoKα induce a clear effect on PCho levels and, consequently, affect in vitro invasiveness, migration and growth in several cell lines (i.e. ovary, breast, prostate cancer cells) (*Mol. Cancer Ther.* 2016, 15, 1-11; *JNCI J. Natl. Cancer Inst.* 2016, 108, 371-384; *Oncogene* 2010, 29, 139-149; *Current Cancer Drug Targets* 2008, 8, 709-719; *Cancer Res.* 2005, 65, 11034-43). Depletion of ChoKα in cell lines stably transfected with ChoKα specific shRNA showed a reduced ability to grow in vivo (*Cancer Res.* 2009, 69, 3464-3471), as well as forced over-expression has been shown to cause an increased tumor formation and aggressiveness of the disease (*NMR Biomed* 2010, 23, 633-642; *Oncogene* 2009, 28, 2425-2435).

In tumor samples, high expression of ChoKα or high levels of choline metabolites are correlated to aggressiveness of tumors like ovary, breast, brain and lung (*Front. Oncol.* 2016, 6, 153; *Carcinogenesis* 2015, 36, 68-75; *Mol. Cancer Ther.* 2015, 14, 899-908; *BJC* 2015, 112, 1206-1214; *Cancer Biol. Ther.* 2014, 15, 593-601; *Cancer Res.* 2014, 74, 6867-77; *BCR* 2014, 16, R5; *NMR Biomed.* 2011, 24, 316-324; *BBRC* 2002, 296, 580-3). Metabolomic analysis of prostate samples in in vitro and in vivo models as well as in tumor samples revealed that AKT1 activation is associated with accumulation of aerobic glycolysis metabolites, whereas MYC overexpression is associated with a dysregulated lipid metabolism and induction of ChoKα (*Cancer Res.* 2014, 74, 7198-204). Recently it has been reported that also T-cell lymphoma is characterized by high levels of ChoKα and choline metabolites and that genetic ablation of ChoKα, using specific siRNA, induces inhibition of proliferation and apoptotis both in vitro and in vivo (*Blood Cancer J.* 2015, 5, 287-296). Choline metabolites (total choline, tCho) can be monitored in patients by Magnetic Resonance Spectroscopy (MRS) or by Positron Emission Tomography (PET) and it is under evaluation as potential biomarker in preclinical and clinical studies (*Expert Rev. Mol. Diagn.* 2015, 15, 735-747).

Choline metabolism is also involved in drug resistance. Over-expression of ChoKα increases invasiveness and drug resistance to 5-fluorouracil (5FU) in human breast cancer cells (*NMR Biomed.* 2010, 23, 633-642), as well as inhibition of ChoKα activity seems to be sinergistic with 5FU in colon cancer cell lines both in vitro and in vivo (*PloS ONE* 2013, 8, e64961-74).

ChoKα silencing in different epithelial ovarian cancer cells induces a reduction in the tumorigenic properties of these cells. This antitumor activity was correlated to a specific altered ROS homeostasis induced by a reduction in cysteine and glutathione (GSH) levels in ChoKα-depleted cells. This effect was observed in tumor cells, but not in non-tumorigenic cells, and it is mediated by a decrease of the trans-sulphuration pathway (*BJC* 2014, 110, 330-340). This outcome in ovarian cancer cells is also linked to increased drug sensitivity to cisplatin, doxorubicin and paclitaxel (*Oncotarget* 2015, 6, 11216-11230).

Choline Kinase has been identified as a potential target also in other diseases. In rheumatoid arthritis (RA) it has been demonstrated that inhibition of ChoKα suppresses cell migration and resistance to apoptosis of cultured fibroblast-like synoviocytes (FLS), involved in cartilage destruction in RA. Moreover inhibition of ChoKα abrogates joint inflammation and damage in either pretreatment or established disease protocols in K/BxN arthritis mouse model (*Ann. Rheum. Dis.* 2015, 74, 1399-1407).

ChoK is the first enzyme in the Kennedy pathway (CDP-choline pathway) for the biosynthesis of PtdCho also in malaria-causing *Plasmodium* parasites. Based on pharmacological and genetic data, the de novo biosynthesis of PtdCho appears to be essential for the intraerythrocytic growth and survival of the malaria parasite. This highlights the potential use of ChoK inhibitors, active on ChoK of *Plasmodium* parasites (e.g. *Plasmodium falciparum*), in the fight against malaria (*Curr. Pharm. Des.* 2012, 18, 3454-3466; Precision Medicine 2015; 2: e980-992).

Functional genomics studies identified ChoKα as a new target for Hepatitis C (HCV) or B (HBV), because it seems to be involved in entry as well as in replication of the virus inside the target cells (*Scientific Reports* 2015, 5, 8421-8429; *PLOS Pathogens* 2014, 10, e1004163-77).

ChoK inhibitors have already been reported in WO2014151761 (ARIAD PHARMACEUTICALS INC.), WO200568429 (Consejo Superior de Investigacions Cientificas, Universidad de Granada), WO200777203 (Consejo Superior de Investigacions Cientificas, Universidad de la Laguna), WO2015185780 (Universidad de Granada and University degli Studi di Padova), WO2013043961 and WO2013043960 (both by Vertex).

Pyrazolo-quinazoline derivatives have been reported in WO2004104007 in the name of Pharmacia Italia S.p.A. as kinase inhibitors.

SUMMARY OF THE INVENTION

Considering the above arguments, there is a strong need for the development of ChoK inhibitors for the treatment of cancer as well as RA and infectious disease, which has motivated efforts to identify agents targeting ChoK. Accordingly, it is an object of the present invention to provide such inhibitor compounds.

DETAILED DESCRIPTION OF THE INVENTION

The present inventors have discovered that compounds of general formula (I), as defined below, are kinase inhibitors and in particular are inhibitors of Choline Kinase. Such compounds are thus useful to treat diseases caused by altered choline metabolism.

Accordingly, a first object of the present invention is to provide a substituted pyrazolo-quinazoline derivative of general formula (I):

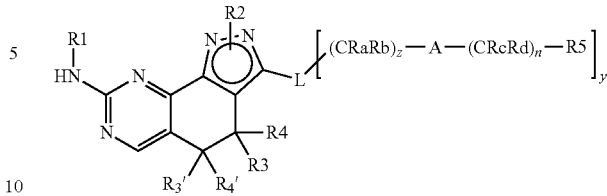

(I)

wherein

R1 is hydrogen or an optionally substituted group selected from straight or branched $(C_1-C_6)$alkyl and $(C_3-C_7)$cycloalkyl;

R2 is hydrogen or an optionally substituted group selected from straight or branched $(C_1-C_6)$alkyl, $(C_2-C_6)$alkenyl, $(C_2-C_6)$alkynyl, $(C_3-C_7)$cycloalkyl and heterocyclyl;

R3, R4, R3' and R4' are independently hydrogen, straight or branched $(C_1-C_6)$alkyl or, taken together with the carbon atom to which they are bonded, R3 and R4 or R3' and R4' form an optionally substituted 3-, 4-, 5- or 6-membered cycloalkyl;

y is independently 0 or 1;

z and n are independently 0, 1 or 2;

L is —CONR6aR7a or —NR8COR6a, when y is 0, or

L is —CONR8— or —NR8CO—, when y is 1;

wherein

R6a and R7a are independently hydrogen or an optionally substituted group selected from straight or branched $(C_1-C_6)$alkyl, $(C_3-C_7)$cycloalkyl, heterocyclyl, aryl, aryl$(C_1-C_6)$alkyl, heteroaryl and heteroaryl$(C_1-C_6)$alkyl or, taken together with the nitrogen atom to which they are bonded, R6a and R7a form an optionally substituted 5- or 6-membered heterocyclyl group optionally containing one additional heteroatom selected from N, O and S; and R8 is hydrogen or an optionally substituted straight or branched $(C_1-C_6)$alkyl;

Ra, Rb, Rc and Rd are independently hydrogen, an optionally substituted straight or branched $(C_1-C_6)$alkyl, fluoro or, taken together with the carbon atom to which they are bonded, Ra and Rb, and/or Rc and Rd, form a 3-membered cycloalkyl;

A is an optionally substituted ring selected from aryl, heteroaryl, $(C_3-C_7)$cycloalkyl and heterocyclyl;

R5 is an optionally substituted group selected from —COOR6, —COR6, —CONR6R7, —NR7COOR9, —NR7COR6, —NR7CONR6R7, —OR6 and —NR6R7;

wherein

R6 and R7 are independently hydrogen or an optionally substituted group selected from straight or branched $(C_1-C_6)$alkyl, $(C_3-C_7)$cycloalkyl, heterocyclyl, aryl, aryl$(C_1-C_6)$alkyl, heteroaryl and heteroaryl$(C_1-C_6)$alkyl or, taken together with the nitrogen atom to which they are bonded, R6 and R7 form an optionally substituted 5- or 6-membered heterocyclyl group optionally containing one additional heteroatom selected from N, O and S; and R9 is an optionally substituted group selected from $(C_1-C_6)$alkyl, $(C_3-C_7)$cycloalkyl, heterocyclyl, aryl, aryl$(C_1-C_6)$alkyl, heteroaryl and heteroaryl$(C_1-C_6)$alkyl;

provided that
R3, R4, R3' and R4' are not simultaneously hydrogen and
8-amino-1,4,4-trimethyl-4,5-dihydro-1H-pyrazolo[4,3-h]
quinazoline-3-carboxamide,
8-amino-N,1,4,4-tetramethyl-4,5-dihydro-1H-pyrazolo[4,3-h]quinazoline-3-carboxamide,
8-(cyclopentylamino)-1,4,4-trimethyl-4,5-dihydro-1H-pyrazolo[4,3-h]quinazoline-3-carboxamide hydrochloride and
8-(cyclopentylamino)-N,1,4,4-tetramethyl-4,5-dihydro-1H-pyrazolo[4,3-h]quinazoline-3-carboxamide hydrochloride
are excluded;
or a pharmaceutically acceptable salt thereof.

The present invention also provides methods of preparing pyrazolo-quinazoline compounds, represented by general formula (I), prepared through processes consisting of standard synthetic transformations.

The present invention also provides a method for treating diseases caused by and/or associated with altered choline metabolism, which comprises administering to a mammal in need thereof, more particularly a human, an effective amount of a compound of general formula (I) as defined above.

A preferred method of the present invention is to treat a disease caused by and/or associated with altered choline metabolism selected from the group consisting of cancer, cell proliferative disorders, infectious diseases of different origin (i.e. viral, parasites), immune-related disorders and neurodegenerative disorders.

The present invention also provides a compound of formula (I), or a pharmaceutically acceptable salt thereof, as defined above, for use in a method for treating diseases caused by and/or associated with altered choline metabolism, which comprises administering to a mammal in need thereof, more particularly a human, an effective amount of a compound of formula (I) as defined above.

A preferred embodiment of the present invention is to provide a compound of formula (I), or a pharmaceutically acceptable salt thereof, as defined above, for use in a method for treating a disease caused by and/or associated with altered choline metabolism, wherein the disease is selected from the group consisting of cancer, cell proliferative disorders, infectious diseases of different origin (i.e. viral, parasites), immune-related disorders and neurodegenerative disorders.

Another preferred embodiment of the present invention is to provide a compound of formula (I), or a pharmaceutically acceptable salt thereof, as defined above, for use in a method for treating a disease caused by and/or associated with altered choline metabolism, wherein the disease is cancer.

Another preferred embodiment of the present invention is to provide a compound of formula (I), or a pharmaceutically acceptable salt thereof, as defined above, for use in a method for treating specific types of cancer including but not limited to: carcinomas, such as bladder, breast, colon, kidney, liver, lung, including small cell lung cancer, esophagus, gallbladder, ovary, pancreas, stomach, cervix, thyroid, prostate, and skin, including squamous cell carcinoma; hematopoietic tumors of lymphoid lineage including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkitt's lymphoma; hematopoietic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including astrocytoma neuroblastoma, glioma and schwannomas; and other tumors, including melanoma, seminoma, teratocarcinoma, osteosarcoma, xeroderma pigmentosum, keratoxanthoma, thyroid cancers, such as papillary thyroid carcinoma and medullary thyroid carcinoma, and Kaposi's sarcoma.

Another preferred embodiment of the present invention is to provide a compound of formula (I), or a pharmaceutically acceptable salt thereof, as defined above, for use in a method for treating specific cellular proliferation disorders such as, for example, benign prostate hyperplasia, familial adenomatosis, polyposis, neurofibromatosis, psoriasis, vascular smooth cell proliferation associated with atherosclerosis, pulmonary fibrosis, arthritis, glomerulonephritis and post-surgical stenosis and restenosis.

Another preferred embodiment of the present invention is to provide a compound of formula (I), or a pharmaceutically acceptable salt thereof, as defined above, for use in a method for treating viral infections like HCV or HBV, comprising the prevention of AIDS development in HIV-infected individuals.

Another preferred embodiment of the present invention is to provide a compound of formula (I), or a pharmaceutically acceptable salt thereof, as defined above, for use in a method for treating parasites infections, like *Plasmodium*-caused malaria.

Another preferred embodiment of the present invention is to provide a compound of formula (I), or a pharmaceutically acceptable salt thereof, as defined above, for use in a method for treating immune-related disorders including but not limited to: transplant rejection, skin disorders like psoriasis, allergies, asthma and autoimmune-mediated diseases such as rheumatoid arthritis (RA), systemic lupus erythematosus (SLE), Crohn's disease and amyotrophic lateral sclerosis.

Another preferred embodiment of the present invention is to provide a compound of formula (I), or a pharmaceutically acceptable salt thereof, as defined above, for use in a method for treating neurodegenerative disorders including but not limited to: Alzheimer's disease, degenerative nerve diseases, encephalitis, Stroke, Parkinson's Disease, Multiple Sclerosis, Amyotrophic Lateral Sclerosis (ALS or Lou Gehrig's Disease), Huntington's Disease and Pick's Disease.

In addition, the preferred embodiment of the present invention also provides a compound of formula (I), or a pharmaceutically acceptable salt thereof, as defined above, for use in a method for treating tumor angiogenesis and metastasis inhibition as well as in the treatment of organ transplant rejection and host versus graft disease.

Moreover, the embodiment of the present invention also provides a compound of formula (I), or a pharmaceutically acceptable salt thereof, as defined above, for use in a method of subjecting the mammal in need thereof to a radiation therapy or chemotherapy regimen in combination with at least one cytostatic or cytotoxic agent.

The present invention also provides a pharmaceutical composition comprising a therapeutically effective amount of a compound of formula (I) or a pharmaceutically acceptable salt thereof, as defined above, and at least one pharmaceutically acceptable excipient, carrier or diluent.

The present invention further provides a pharmaceutical composition of a compound of formula (I) further comprising one or more chemotherapeutic—e.g. cytostatic or cytotoxic—agents, antibiotic-type agents, alkylating agents, antimetabolite agents, hormonal agents, immunological agents, interferon-type agents, cyclooxygenase inhibitors (e.g. COX-2 inhibitors), matrixmetalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

Moreover the invention provides an in vitro method for inhibiting ChoK protein activity which comprises contacting the said protein with an effective amount of a compound of formula (I) as defined above.

Additionally, the invention provides a product comprising a compound of formula (I) or a pharmaceutically acceptable salt thereof, as defined above, and one or more chemotherapeutic agents, as a combined preparation for simultaneous, separate or sequential use in anticancer therapy.

In yet another aspect the invention provides a compound of formula (I) or a pharmaceutically acceptable salt thereof, as defined above, for use as a medicament.

Moreover the invention provides a compound of formula (I) or a pharmaceutically acceptable salt thereof, as defined above, for use in a method of treating cancer.

Finally, the invention provides the use of a compound of formula (I) or a pharmaceutically acceptable salt thereof, as defined above, in the manufacture of a medicament with anticancer activity.

If a stereogenic center or another form of an asymmetric center is present in a compound of the present invention, all forms of such optical isomer or isomers, including enantiomers and diastereomers, are intended to be covered herein. Compounds containing a stereogenic center may be used as a racemic mixture, an enantiomerically enriched mixture, or the racemic mixture may be separated using well-known techniques and an individual enantiomer may be used alone. In cases in which compounds have unsaturated carbon-carbon double bonds, both the cis (Z) and trans (E) isomers are within the scope of this invention.

In cases wherein compounds may exist in tautomeric forms, such as keto-enol tautomers, each tautomeric form is contemplated as being included within this invention whether existing in equilibrium or predominantly in one form.

Pharmaceutically acceptable salts of the compounds of formula (I) include the salts with inorganic or organic acids. Pharmaceutically acceptable salts of the compounds of formula (I) also include the salts with inorganic or organic bases.

With the term "$(C_1-C_6)$alkyl", we intend an aliphatic $(C_1-C_6)$ hydrocarbon chain, containing carbon-carbon single bonds only, which can be straight or branched. Representative examples include, but are not limited to, methyl, ethyl, n-propyl, isopropyl, n-butyl, isobutyl, tert-butyl, sec-butyl, n-pentyl, n-hexyl, and the like.

With the term "$(C_3-C_7)$cycloalkyl", we intend, unless otherwise provided, a 3- to 7-membered all-carbon monocyclic ring, which may contain one or more double bonds, but does not have a completely conjugated 7-electron system. Examples of $(C_3-C_7)$cycloalkyl groups, without limitation, are cyclopropyl, cyclobutyl, cyclopentyl, cyclopentenyl, cyclohexanyl, cyclohexenyl and cyclohexadienyl. The $(C_3-C_7)$cycloalkyl ring can be optionally further fused or linked to aromatic and non-aromatic carbocyclic and heterocyclic rings.

With the term "heterocyclyl", we intend a 3- to 7-membered, saturated or partially unsaturated carbocyclic ring where one or more carbon atoms are replaced by heteroatoms such as nitrogen, oxygen and sulfur. Non limiting examples of heterocyclyl groups are, for instance, pyranyl, tetrahydropyranyl, pyrrolidinyl, pyrrolinyl, imidazolinyl, imidazolidinyl, pyrazolidinyl, pyrazolinyl, thiazolinyl, thiazolidinyl, dihydrofuranyl, tetrahydrofuranyl, tetrahydropyridinyl, 1,3-dioxolanyl, piperidinyl, piperazinyl, morpholinyl and the like. The heterocyclyl ring can be optionally further fused or linked to aromatic and non-aromatic carbocyclic and heterocyclic rings.

With the term "$(C_2-C_6)$alkenyl", we intend an aliphatic $(C_2-C_6)$ hydrocarbon chain containing at least one carbon-carbon double bond and which can be straight or branched. Representative examples include, but are not limited to, ethenyl, 1-propenyl, 2-propenyl, 1- or 2-butenyl, and the like.

With the term "$(C_2-C_6)$alkynyl", we intend an aliphatic $(C_2-C_6)$ hydrocarbon chain containing at least one carbon-carbon triple bond and which can be straight or branched. Representative examples include, but are not limited to, ethynyl, 1-propynyl, 2-propynyl, 1- or 2-butynyl, and the like.

With the term "$(C_1-C_6)$alkoxy", we intend any of the above defined $(C_1-C_6)$alkyl linked to the rest of the molecule through an oxygen atom (—O—).

The term "aryl" refers to a mono-, bi- or poly-carbocyclic hydrocarbon with from 1 to 4 ring systems, optionally further fused or linked to each other by single bonds, wherein at least one of the carbocyclic rings is "aromatic", wherein the term "aromatic" refers to completely conjugated 7-electron bond system. Non limiting examples of such aryl groups are phenyl, α- or β-naphthyl, α- or β-tetrahydronaphthalenyl, biphenyl, and indanyl groups.

The term "heteroaryl" refers to aromatic heterocyclic rings, typically 5- to 7-membered heterocycles with from 1 to 3 heteroatoms selected among N, O or S; the heteroaryl ring can be optionally further fused or linked to aromatic and non-aromatic carbocyclic and heterocyclic rings. Not limiting examples of such heteroaryl groups are, for instance, pyridyl, pyrazinyl, pyrimidinyl, pyridazinyl, indolyl, imidazolyl, thiazolyl, isothiazolyl, pyrrolyl, furanyl, oxazolyl, isoxazolyl, pyrazolyl, thiophenyl, thiadiazolyl, isoxazolyl, isothiazolyl, oxadiazolyl, indazolyl, cinnolinyl, benzo[1,3]dioxolyl, benzo[1,4]dioxinyl, benzothiazolyl, benzothiophenyl, benzofuranyl, isoindolinyl, benzoimidazolyl, benzoxazolyl, quinolinyl, isoquinolinyl, 1,2,3-triazolyl, 1-phenyl-1,2,3-triazolyl, 2,3-dihydroindolyl, 2,3-dihydrobenzofuranyl, 2,3-dihydrobenzothiophenyl, benzopyranyl, 2,3-dihydrobenzoxazinyl, 2,3-dihydroquinoxalinyl, 4,5,6,7-tetrahydropyrido-[1,3]thiazolyl and the like.

With the term "halogen", we intend fluoro, chloro, bromo or iodo atom.

With the term "polyfluorinated $(C_1-C_6)$alkyl" or "polyfluorinated $(C_1-C_6)$alkoxy", we intend any of the above defined $(C_1-C_6)$alkyl or $(C_1-C_6)$alkoxy groups which are substituted by more than one fluoro atom such as, for instance, trifluoromethyl, trifluoroethyl, 1,1,1,3,3,3-hexafluoropropyl, trifluoromethoxy and the like.

With the term "hydroxy$(C_1-C_6)$alkyl" we intend any of the above defined $(C_1-C_6)$alkyl groups, bearing a hydroxyl group such as, for instance, hydroxymethyl, 2-hydroxyethyl, 3-hydroxypropyl and the like.

According to the present invention and unless otherwise provided, R1, R2, R3, R4, R3', R4', R6, R7, R6a, R7a, R8, R9 and A may be optionally substituted, in any of their free positions, by one or more groups, for instance 1 to 6 groups, independently selected from: halogen, nitro, oxo group (=O), cyano, $(C_1-C_6)$alkyl, polyfluorinated $(C_1-C_6)$alkyl, polyfluorinated $(C_1-C_6)$alkoxy, $(C_2-C_6)$alkenyl, $(C_2-C_6)$alkynyl, aryl, aryl$(C_1-C_6)$alkyl, $(C_1-C_6)$alkylaryl, aryl$(C_1-$ $C_6$)alkoxy, heteroaryl, heteroaryl($C_1$-$C_6$)alkyl, ($C_1$-$C_6$)alkylheteroaryl, heterocyclyl, heterocyclyl($C_1$-$C_6$)alkyl, ($C_1$-$C_6$)alkylheterocyclyl, polyfluorinatedheterocyclyl, ($C_1$-$C_6$) alkylheterocyclyl($C_1$-$C_6$)alkyl, tri($C_1$-$C_6$)alkylsilyl, ($C_3$-$C_7$) cycloalkyl, ($C_3$-$C_7$)cycloalkyl($C_1$-$C_6$)alkyl, ($C_1$-$C_6$)alkoxy, aryloxy, heterocyclyloxy, methylenedioxy, ($C_1$-$C_6$)alkylcarbonyloxy, arylcarbonyloxy, di($C_1$-$C_6$)alkylaminoheterocyclyl($C_1$-$C_6$)alkyl, ($C_3$-$C_7$)cycloalkenyloxy, heterocyclylcarbonyloxy, ($C_1$-$C_6$)alkylideneaminooxy, carboxy, ($C_1$-$C_6$) alkoxycarbonyl, aryloxycarbonyl, ($C_3$-$C_7$)cycloalkyloxycarbonyl, amino, heterocyclyl($C_1$-$C_6$)alkoxycarbonylamino, ureido, ($C_1$-$C_6$)alkylamino, amino($C_1$-$C_6$)alkyl, di($C_1$-$C_6$)alkylamino, arylamino, diarylamino, heterocyclylamino, hydroxyl, hydroxy($C_1$-$C_6$)alkyl, formylamino, ($C_1$-$C_6$)alkylcarbonylamino, arylcarbonylamino, heterocyclylcarbonylamino, aminocarbonyl, ($C_1$-$C_6$)alkylaminocarbonyl, ($C_1$-$C_6$)alkylaminocarbonylamino, di($C_1$-$C_6$)alkyl aminocarbonyl, arylaminocarbonyl, heteroarylaminocarbonyl, arylaminocarbonyl($C_1$-$C_6$)alkyl, ($C_3$-$C_7$)cycloalkylaminocarbonyl, heterocyclyl aminocarbonyl, ($C_1$-$C_6$)alkoxycarbonyl amino, hydroxyaminocarbonyl, ($C_1$-$C_6$)alkoxyimino, ($C_1$-$C_6$)alkylsulfonylamino, arylsulfonylamino, heterocyclylsulfonylamino, formyl, ($C_1$-$C_6$)alkylcarbonyl, arylcarbonyl, ($C_3$-$C_7$)cycloalkylcarbonyl, heterocyclylcarbonyl, heterocyclylcarbonyl($C_1$-$C_6$)alkyl, ($C_1$-$C_6$)alkylsulfonyl, polyfluorinated ($C_1$-$C_6$)alkylsulfonyl, arylsulfonyl, aminosulfonyl, ($C_1$-$C_6$)alkylaminosulfonyl, di($C_1$-$C_6$)alkyl aminosulfonyl, arylaminosulfonyl, heterocyclylaminosulfonyl, arylthio, ($C_1$-$C_6$)alkylthio; in their turn, whenever appropriate, each of the above substituents may be further substituted by one or more of the aforementioned groups.

From all of the above, it is clear to the skilled person that any group which name is a composite name such as, for instance, "arylamino" has to be intended as conventionally construed by the parts from which it derives, e.g. by an amino group which is substituted by aryl, wherein aryl is as above defined.

Likewise, any of the terms such as, for instance, ($C_1$-$C_6$) alkylthio, ($C_1$-$C_6$)alkylamino, di($C_1$-$C_6$)alkylamino, ($C_1$-$C_6$)alkoxycarbonyl, ($C_1$-$C_6$)alkoxycarbonylamino, heterocyclylcarbonyl, heterocyclylcarbonylamino, ($C_3$-$C_7$) cycloalkyloxycarbonyl and the like, include groups wherein the ($C_1$-$C_6$)alkyl, ($C_1$-$C_6$)alkoxy, ($C_3$-$C_7$)cycloalkyl and heterocyclyl moieties are as above defined.

Preferred compounds of formula (I) are the compounds wherein:
R2 is hydrogen or an optionally substituted group selected from straight or branched ($C_1$-$C_6$)alkyl, ($C_3$-$C_7$)cycloalkyl and heterocyclyl;
R3, R4, R3' and R4' are independently hydrogen, straight or branched ($C_1$-$C_6$)alkyl or, taken together with the carbon atom to which they are bonded, R3 and R4 or R3' and R4' form an optionally substituted 3-, 4- or 5-membered cycloalkyl;
z and n are independently 0 or 1;
A is an optionally substituted ring selected from aryl or heteroaryl;
R5 is an optionally substituted group selected from —CONR6R7, —NR7COR6, —NR7CONR6R7, —OR6 and NR6R7;
wherein R6 and R7 are as defined above;
provided that
R3, R4, R3' and R4' are not simultaneously hydrogen and 8-amino-1,4,4-trimethyl-4,5-dihydro-1H-pyrazolo[4,3-h]quinazoline-3-carboxamide, 8-amino-N,1,4,4-tetramethyl-4,5-dihydro-1H-pyrazolo[4,3-h]quinazoline-3-carboxamide, 8-(cyclopentylamino)-1,4,4-trimethyl-4,5-dihydro-1H-pyrazolo[4,3-h]quinazoline-3-carboxamide hydrochloride and 8-(cyclopentylamino)-N,1,4,4-tetramethyl-4,5-dihydro-1H-pyrazolo[4,3-h] quinazoline-3-carboxamide hydrochloride are excluded;
or a pharmaceutically acceptable salt thereof.

More preferred compounds of formula (I) are the compounds wherein:
R2 is hydrogen or an optionally substituted group selected from straight or branched ($C_1$-$C_6$)alkyl;
R3, R4, R3' and R4' are independently hydrogen, straight or branched ($C_1$-$C_6$)alkyl or, taken together with the carbon atom to which they are bonded, R3 and R4 or R3' and R4' form an optionally substituted 4- or 5-membered cycloalkyl;
z is 0 and n is 1;
L is —CONR6aR7a or —NR8COR6a, when y is 0, or
L is —CONR8- or —NR8CO—, when y is 1;
wherein
R6a and R7a are independently hydrogen or an optionally substituted group selected from ($C_3$-$C_7$)cycloalkyl, heterocyclyl, aryl and heteroaryl or, taken together with the nitrogen atom to which they are bonded, R6a and R7a form an optionally substituted 5- or 6-membered heterocyclyl group optionally containing one additional heteroatom selected from N, O and S; and
R8 is hydrogen;
Rc and Rd are independently hydrogen, an optionally substituted straight or branched ($C_1$-$C_3$)alkyl or fluoro;
R5 is an optionally substituted group selected from —CONR6R7, —NR7COR6, —OR6;
wherein R6 and R7 are independently hydrogen or an optionally substituted group selected from straight or branched ($C_1$-$C_6$)alkyl, ($C_3$-$C_7$)cycloalkyl, heterocyclyl, aryl and heteroaryl or, taken together with the nitrogen atom to which they are bonded, R6 and R7 form an optionally substituted 5- or 6-membered heterocyclyl group optionally containing one additional heteroatom selected from N, O and S; provided that
R3, R4, R3' and R4' are not simultaneously hydrogen and 8-amino-1,4,4-trimethyl-4,5-dihydro-1H-pyrazolo[4,3-h]quinazoline-3-carboxamide and 8-(cyclopentylamino)-1,4,4-trimethyl-4,5-dihydro-1H-pyrazolo[4,3-h]quinazoline-3-carboxamide hydrochloride are excluded;
or a pharmaceutically acceptable salt thereof.

Even more preferred are compounds wherein:
R1 is hydrogen or an optionally substituted straight or branched ($C_1$-$C_3$)alkyl;
L is —CONR6aR7a, when y is 0, or
L is —CONR8, when y is 1;
wherein
R6a and R7a are independently hydrogen or an optionally substituted group selected from heterocyclyl, aryl and heteroaryl or, taken together with the nitrogen atom to which they are bonded, R6a and R7a form an optionally substituted 5- or 6-membered heterocyclyl group optionally containing one additional heteroatom selected from N, O and S; and
R8 is hydrogen;
Rc and Rd are hydrogen;
R5 is an optionally substituted group selected from —CONR6R7, —OR6;

wherein
R6 and R7 are independently hydrogen or an optionally substituted group selected from straight or branched ($C_1$-$C_6$)alkyl, ($C_3$-$C_7$)cycloalkyl, heterocyclyl or, taken together with the nitrogen atom to which they are bonded, R6 and R7 form an optionally substituted 5- or 6-membered heterocyclyl group optionally containing one additional heteroatom selected from N, O and S;
provided that
R3, R4, R3' and R4' are not simultaneously hydrogen and 8-amino-1,4,4-trimethyl-4,5-dihydro-1H-pyrazolo[4,3-h]quinazoline-3-carboxamide and 8-(cyclopentylamino)-1,4,4-trimethyl-4,5-dihydro-1H-pyrazolo[4,3-h]quinazoline-3-carboxamide hydrochloride are excluded;
or a pharmaceutically acceptable salt thereof.

Preferred specific compounds (cpd) of formula (I), or a pharmaceutically acceptable salt thereof, are the compounds listed below:
8-amino-N-(3-methoxyphenyl)-4,4-dimethyl-4,5-dihydro-1H-pyrazolo[4,3-h]quinazoline-3-carboxamide (cpd 1);
8-amino-N-(4-methoxyphenyl)-4,4-dimethyl-4,5-dihydro-1H-pyrazolo[4,3-h]quinazoline-3-carboxamide (cpd 2);
8-amino-4,4-dimethyl-N-[4-(trifluoromethoxy)phenyl]-4,5-dihydro-1H-pyrazolo[4,3-h]quinazoline-3-carboxamide (cpd 3);
8-amino-N-(1,3-benzodioxol-5-yl)-4,4-dimethyl-4,5-dihydro-1H-pyrazolo[4,3-h]quinazoline-3-carboxamide (cpd 4);
ethyl 4-{[(8-amino-4,4-dimethyl-4,5-dihydro-1H-pyrazolo[4,3-h]quinazolin-3-yl)carbonyl]amino}benzoate (cpd 5);
8-amino-4,4-dimethyl-N-[4-(4-methylpiperazin-1-yl)phenyl]-4,5-dihydro-1H-pyrazolo[4,3-h]quinazoline-3-carboxamide (cpd 6);
8-amino-4,4-dimethyl-N-{4-[(1-methylpiperidin-4-yl)carbamoyl]phenyl}-4,5-dihydro-1H-pyrazolo[4,3-h]quinazoline-3-carboxamide (cpd 8);
8-amino-1-(3-hydroxypropyl)-4,4-dimethyl-N-{4-[(1-methylpiperidin-4-yl)carbamoyl]phenyl}-4,5-dihydro-1H-pyrazolo[4,3-h]quinazoline-3-carboxamide (cpd 9);
8-amino-4,4-dimethyl-N-{3-[(1-methylpiperidin-4-yl)carbamoyl]phenyl}-4,5-dihydro-1H-pyrazolo[4,3-h]quinazoline-3-carboxamide (cpd 10);
8-amino-4,4-dimethyl-N-[4-(tetrahydro-2H-pyran-4-ylcarbamoyl)phenyl]-4,5-dihydro-1H-pyrazolo[4,3-h]quinazoline-3-carboxamide (cpd 11);
8-amino-4,4-dimethyl-N-(4-{[4-(pyrrolidin-1-yl)piperidin-1-yl]carbonyl}phenyl)-4,5-dihydro-1H-pyrazolo[4,3-h]quinazoline-3-carboxamide (cpd 13);
8-amino-N-(4-{[4-(dimethylamino)piperidin-1-yl]carbonyl}phenyl)-4,4-dimethyl-4,5-dihydro-1H-pyrazolo[4,3-h]quinazoline-3-carboxamide (cpd 14);
8-amino-N-[4-(cyclohexylcarbamoyl)phenyl]-4,4-dimethyl-4,5-dihydro-1H-pyrazolo[4,3-h]quinazoline-3-carboxamide (cpd 16);
ethyl 3-{[(8-amino-4,4-dimethyl-4,5-dihydro-1H-pyrazolo[4,3-h]quinazolin-3-yl)carbonyl]amino}benzoate (cpd 17);
3-{[(8-amino-4,4-dimethyl-4,5-dihydro-1H-pyrazolo[4,3-h]quinazolin-3-yl)carbonyl]amino}benzoic acid (cpd 18);
8-amino-N-[4-(1,4'-bipiperidin-1-ylcarbonyl)phenyl]-4,4-dimethyl-4,5-dihydro-1H-pyrazolo[4,3-h]quinazoline-3-carboxamide (cpd 20);
8-amino-N-[3-(cyclohexylcarbamoyl)phenyl]-4,4-dimethyl-4,5-dihydro-1H-pyrazolo[4,3-h]quinazoline-3-carboxamide (cpd 25);
8-amino-4,4-dimethyl-N-(3-{[4-(pyrrolidin-1-yl)piperidin-1-yl]carbonyl}phenyl)-4,5-dihydro-1H-pyrazolo[4,3-h]quinazoline-3-carboxamide (cpd 26);
8-amino-4,4-dimethyl-N-[4-(methylcarbamoyl)phenyl]-4,5-dihydro-1H-pyrazolo[4,3-h]quinazoline-3-carboxamide (cpd 27);
8-amino-N-{4-[(trans-4-hydroxycyclohexyl)carbamoyl]phenyl}-4,4-dimethyl-4,5-dihydro-1H-pyrazolo[4,3-h]quinazoline-3-carboxamide (cpd 28);
8-amino-N-[4-(cyclopentylcarbamoyl)phenyl]-4,4-dimethyl-4,5-dihydro-1H-pyrazolo[4,3-h]quinazoline-3-carboxamide (cpd 29);
8-amino-N-[4-(cyclobutylcarbamoyl)phenyl]-4,4-dimethyl-4,5-dihydro-1H-pyrazolo[4,3-h]quinazoline-3-carboxamide (cpd 30);
8-amino-N-[4-(cyclopropylcarbamoyl)phenyl]-4,4-dimethyl-4,5-dihydro-1H-pyrazolo[4,3-h]quinazoline-3-carboxamide (cpd 31);
8-amino-4,4-dimethyl-N-(4-methyl-1,3-thiazol-2-yl)-4,5-dihydro-1H-pyrazolo[4,3-h]quinazoline-3-carboxamide (cpd 32);
ethyl (2-{[(8-amino-4,4-dimethyl-4,5-dihydro-1H-pyrazolo[4,3-h]quinazolin-3-yl)carbonyl]amino}-1,3-thiazol-4-yl)acetate (cpd 33);
8-amino-N-cyclohexyl-4,4-dimethyl-4,5-dihydro-1H-pyrazolo[4,3-h]quinazoline-3-carboxamide (cpd 34);
8-amino-N-{4-[2-(cyclohexylamino)-2-oxoethyl]-1,3-thiazol-2-yl}-4,4-dimethyl-4,5-dihydro-1H-pyrazolo[4,3-h]quinazoline-3-carboxamide (cpd 35);
(8-amino-4,4-dimethyl-4,5-dihydro-1H-pyrazolo[4,3-h]quinazolin-3-yl)[4-(pyrrolidin-1-yl)piperidin-1-yl]methanone (cpd 36);
8-amino-4,4-dimethyl-N-(4-{2-oxo-2-[4-(pyrrolidin-1-yl)piperidin-1-yl]ethyl}-1,3-thiazol-2-yl)-4,5-dihydro-1H-pyrazolo[4,3-h]quinazoline-3-carboxamide (cpd 37);
(8-amino-4,4-dimethyl-4,5-dihydro-1H-pyrazolo[4,3-h]quinazolin-3-yl)(1,4'-bipiperidin-1-yl)methanone (cpd 38);
8-amino-N-{4-[2-(1,4'-bipiperidin-1'-yl)-2-oxoethyl]-1,3-thiazol-2-yl}-4,4-dimethyl-4,5-dihydro-1H-pyrazolo[4,3-h]quinazoline-3-carboxamide (cpd 39);
8-amino-4,4-dimethyl-N-(4-{[4-(4-methylpiperazin-1-yl)piperidin-1-yl]carbonyl}phenyl)-4,5-dihydro-1H-pyrazolo[4,3-h]quinazoline-3-carboxamide (cpd 41);
(2-{[(8-amino-4,4-dimethyl-4,5-dihydro-1H-pyrazolo[4,3-h]quinazolin-3-yl)carbonyl]amino}-1,3-thiazol-4-yl)acetic acid (cpd 42);
tert-butyl {1-[(2-{[(8-amino-4,4-dimethyl-4,5-dihydro-1H-pyrazolo[4,3-h]quinazolin-3-yl)carbonyl]amino}-1,3-thiazol-4-yl)acetyl]piperidin-4-yl}carbamate (cpd 43);
8-amino-N-{4-[2-(4-aminopiperidin-1-yl)-2-oxoethyl]-1,3-thiazol-2-yl}-4,4-dimethyl-4,5-dihydro-1H-pyrazolo[4,3-h]quinazoline-3-carboxamide (cpd 44);
8-amino-4,4-dimethyl-N-{4-[2-oxo-2-(4-oxopiperidin-1-yl)ethyl]-1,3-thiazol-2-yl}-4,5-dihydro-1H-pyrazolo[4,3-h]quinazoline-3-carboxamide (cpd 45);
tert-butyl [1-(4-{[(8-amino-4,4-dimethyl-4,5-dihydro-1H-pyrazolo[4,3-h]quinazolin-3-yl)carbonyl]amino}benzoyl)piperidin-4-yl]carbamate (cpd 46);
8-amino-N-(4-{2-[4-(azepan-1-yl)piperidin-1-yl]-2-oxoethyl}-1,3-thiazol-2-yl)-4,4-dimethyl-4,5-dihydro-1H-pyrazolo[4,3-h]quinazoline-3-carboxamide (cpd 47);
8-amino-N-{4-[(4-aminopiperidin-1-yl)carbonyl]phenyl}-4,4-dimethyl-4,5-dihydro-1H-pyrazolo[4,3-h]quinazoline-3-carboxamide (cpd 49);
8-amino-4,4-dimethyl-N-(4-{[4-(morpholin-4-yl)piperidin-1-yl]carbonyl}phenyl)-4,5-dihydro-1H-pyrazolo[4,3-h]quinazoline-3-carboxamide (cpd 50);

8-amino-N-{4-[(4,4-difluoro-1,4'-bipiperidin-1'-yl)carbonyl]phenyl}-4,4-dimethyl-4,5-dihydro-1H-pyrazolo[4,3-h]quinazoline-3-carboxamide (cpd 51);

8-amino-4,4-dimethyl-N-{4-[(4-methyl-1,4'-bipiperidin-1'-yl)carbonyl]phenyl}-4,5-dihydro-1H-pyrazolo[4,3-h]quinazoline-3-carboxamide (cpd 52);

8-amino-N-[4-({4-[(4-hydroxybutanoyl)amino]piperidin-1-yl}carbonyl)phenyl]-4,4-dimethyl-4,5-dihydro-1H-pyrazolo[4,3-h]quinazoline-3-carboxamide (cpd 53);

8-amino-4,4-dimethyl-N-(4-{[4-(2-oxo-1,3-oxazolidin-3-yl)piperidin-1-yl]carbonyl}phenyl)-4,5-dihydro-1H-pyrazolo[4,3-h]quinazoline-3-carboxamide (cpd 56);

8-amino-4,4-dimethyl-N-{4-[2-(4-methyl-1,4'-bipiperidin-1'-yl)-2-oxoethyl]-1,3-thiazol-2-yl}-4,5-dihydro-1H-pyrazolo[4,3-h]quinazoline-3-carboxamide (cpd 58);

8-amino-4,4-dimethyl-N-(4-{[4-(piperidin-1-ylmethyl)phenyl]carbamoyl}phenyl)-4,5-dihydro-1H-pyrazolo[4,3-h]quinazoline-3-carboxamide (cpd 59);

8-amino-4,4-dimethyl-N-(1,3-thiazol-2-yl)-4,5-dihydro-1H-pyrazolo[4,3-h]quinazoline-3-carboxamide (cpd 61);

8-amino-N-(1,3-benzothiazol-2-yl)-4,4-dimethyl-4,5-dihydro-1H-pyrazolo[4,3-h]quinazoline-3-carboxamide (cpd 62);

8-amino-N-(6-methoxy-1,3-benzothiazol-2-yl)-4,4-dimethyl-4,5-dihydro-1H-pyrazolo[4,3-h]quinazoline-3-carboxamide (cpd 63);

8-amino-N-(6-chloro-1,3-benzothiazol-2-yl)-4,4-dimethyl-4,5-dihydro-1H-pyrazolo[4,3-h]quinazoline-3-carboxamide (cpd 64);

8-amino-4,4-dimethyl-N-(5-methyl-1,3-thiazol-2-yl)-4,5-dihydro-1H-pyrazolo[4,3-h]quinazoline-3-carboxamide (cpd 65);

8-amino-N-(5-chloro-1,3-thiazol-2-yl)-4,4-dimethyl-4,5-dihydro-1H-pyrazolo[4,3-h]quinazoline-3-carboxamide (cpd 66);

2-{[(8-amino-4,4-dimethyl-4,5-dihydro-1H-pyrazolo[4,3-h]quinazolin-3-yl)carbonyl]amino}-1,3-thiazole-4-carboxylic acid (cpd 67);

8-amino-N-[4-(cyclohexylcarbamoyl)-1,3-thiazol-2-yl]-4,4-dimethyl-4,5-dihydro-1H-pyrazolo[4,3-h]quinazoline-3-carboxamide (cpd 68);

8-amino-4,4-dimethyl-N-{4-[(1-methylpiperidin-4-yl)carbamoyl]-1,3-thiazol-2-yl}-4,5-dihydro-1H-pyrazolo[4,3-h]quinazoline-3-carboxamide (cpd 69);

8-amino-N-[4-(1,4'-bipiperidin-1-ylcarbonyl)-1,3-thiazol-2-yl]-4,4-dimethyl-4,5-dihydro-1H-pyrazolo[4,3-h]quinazoline-3-carboxamide (cpd 70);

8-amino-N-[4-(2-{4-[(tert-butylcarbamoyl)amino]piperidin-1-yl}-2-oxoethyl)-1,3-thiazol-2-yl]-4,4-dimethyl-4,5-dihydro- 1H-pyrazolo[4,3-h]quinazoline-3-carboxamide (cpd 71);

(2-{[(8-amino-4,4-dimethyl-4,5-dihydro-1H-pyrazolo[4,3-h]quinazolin-3-yl)carbonyl]amino}-1,3-thiazol-5-yl)acetic acid (cpd 72);

8-amino-N-{5-[2-(cyclohexylamino)-2-oxoethyl]-1,3-thiazol-2-yl}-4,4-dimethyl-4,5-dihydro-1H-pyrazolo[4,3-h]quinazoline-3-carboxamide (cpd 73);

8-amino-4,4-dimethyl-N-(5-{2-[(1-methylpiperidin-4-yl)amino]-2-oxoethyl}-1,3-thiazol-2-yl)-4,5-dihydro-1H-pyrazolo[4,3-h]quinazoline-3-carboxamide (cpd 74);

8-amino-N-{5-[2-(1,4'-bipiperidin-1'-yl)-2-oxoethyl]-1,3-thiazol-2-yl}-4,4-dimethyl-4,5-dihydro-1H-pyrazolo[4,3-h]quinazoline-3-carboxamide (cpd 75);

8-amino-N-[5-(cyclohexylcarbamoyl)-4-methyl-1,3-thiazol-2-yl]-4,4-dimethyl-4,5-dihydro-1H-pyrazolo[4,3-h]quinazoline-3-carboxamide (cpd 77); 8-amino-N-[5-(1,4'-bipiperidin-1-ylcarbonyl)-4-methyl-1,3-thiazol-2-yl]-4,4-dimethyl-4,5-dihydro-1H-pyrazolo[4,3-h]quinazoline-3-carboxamide (cpd 78);

8-amino-4,4-dimethyl-N-{4-methyl-5-[(1-methyl piperidin-4-yl)carbamoyl]-1,3-thiazol-2-yl}-4,5-dihydro-1H-pyrazolo[4,3-h]quinazoline-3-carboxamide (cpd 79);

8-amino-1,4,4-trimethyl-N-{4-[2-(4-methyl-1,4'-bipiperidin-1'-yl)-2-oxoethyl]-1,3-thiazol-2-yl}-4,5-dihydro-1H-pyrazolo[4,3-h]quinazoline-3-carboxamide (cpd 80);

ethyl 2-{[(8-amino-4,4-dimethyl-4,5-dihydro-1H-pyrazolo[4,3-h]quinazolin-3-yl)carbonyl]amino}-1,3-thiazole-5-carboxylate (cpd 81);

2-{[(8-amino-4,4-dimethyl-4,5-dihydro-1H-pyrazolo[4,3-h]quinazolin-3-yl)carbonyl]amino}-1,3-thiazole-5-carboxylic acid (cpd 82);

8-amino-N-[5-(1,4'-bipiperidin-1-ylcarbonyl)-1,3-thiazol-2-yl]-4,4-dimethyl-4,5-dihydro-1H-pyrazolo[4,3-h]quinazoline-3-carboxamide (cpd 84);

1,4,4-trimethyl-8-(methylamino)-N-{4-[2-(4-methyl-1,4'-bipiperidin-1'-yl)-2-oxoethyl]-1,3-thiazol-2-yl}-4,5-dihydro-1H-pyrazolo[4,3-h]quinazoline-3-carboxamide (cpd 85);

8-amino-4,4-dimethyl-N-(4-{2-[(1-methylpiperidin-4-yl)amino]-2-oxoethyl}-1,3-thiazol-2-yl)-4,5-dihydro-1H-pyrazolo[4,3-h]quinazoline-3-carboxamide (cpd 86);

8-amino-N-(4-{2-[(3R)-3-hydroxypyrrolidin-1-yl]-2-oxoethyl}-1,3-thiazol-2-yl)-4,4-dimethyl-4,5-dihydro-1H-pyrazolo[4,3-h]quinazoline-3-carboxamide (cpd 87);

8-amino-N-(4-{2-[(3S)-3-hydroxypyrrolidin-1-yl]-2-oxoethyl}-1,3-thiazol-2-yl)-4,4-dimethyl-4,5-dihydro-1H-pyrazolo[4,3-h]quinazoline-3-carboxamide (cpd 88);

8-amino-N-(4-{2-[4-(dimethylamino)piperidin-1-yl]-2-oxoethyl}-1,3-thiazol-2-yl)-4,4-dimethyl-4,5-dihydro-1H-pyrazolo[4,3-h]quinazoline-3-carboxamide (cpd 89);

8-amino-N-{4-[2-(4-carbamoylpiperidin-1-yl)-2-oxoethyl]-1,3-thiazol-2-yl}-4,4-dimethyl-4,5-dihydro-1H-pyrazolo[4,3-h]quinazoline-3-carboxamide (cpd 90);

8-amino-N-(4-{2-[4-(hydroxymethyl)piperidin-1-yl]-2-oxoethyl}-1,3-thiazol-2-yl)-4,4-dimethyl-4,5-dihydro-1H- pyrazolo[4,3-h]quinazoline-3-carboxamide (cpd 91);

8-amino-N-{4-[2-(4-hydroxypiperidin-1-yl)-2-oxoethyl]-1,3-thiazol-2-yl}-4,4-dimethyl-4,5-dihydro-1H-pyrazolo[4,3-h]quinazoline-3-carboxamide (cpd 92);

8-amino-N-(4-{2-[(3S)-3-(dimethylamino)pyrrolidin-1-yl]-2-oxoethyl}-1,3-thiazol-2-yl)-4,4-dimethyl-4,5-dihydro-1H-pyrazolo[4,3-h]quinazoline-3-carboxamide (cpd 93);

8-amino-N-[4-(2-amino-2-oxoethyl)-1,3-thiazol-2-yl]-4,4-dimethyl-4,5-dihydro-1H-pyrazolo[4,3-h]quinazoline-3-carboxamide (cpd 94);

8-amino-N-[4-(2-{[3-(dimethylamino)propyl]amino}-2-oxoethyl)-1,3-thiazol-2-yl]-4,4-dimethyl-4,5-dihydro-1H-pyrazolo[4,3-h]quinazoline-3-carboxamide (cpd 95);

ethyl (4-{[(8-amino-4,4-dimethyl-4,5-dihydro-1H-pyrazolo[4,3-h]quinazolin-3-yl)carbonyl]amino}phenyl)acetate (cpd 96);

8-amino-N-{4-[2-(1,4'-bipiperidin-1'-yl)-2-oxoethyl]phenyl}-4,4-dimethyl-4,5-dihydro-1H-pyrazolo[4,3-h]quinazoline-3-carboxamide (cpd 98);

8-amino-N-(4-hydroxyphenyl)-4,4-dimethyl-4,5-dihydro-1H-pyrazolo[4,3-h]quinazoline-3-carboxamide (cpd 105);

8-amino-N-[3-(1,3-dioxan-2-yl)phenyl]-4,4-dimethyl-4,5-dihydro-1H-pyrazolo[4,3-h]quinazoline-3-carboxamide (cpd 106);

8-amino-N-(3-formylphenyl)-4,4-dimethyl-4,5-dihydro-1H-pyrazolo[4,3-h]quinazoline-3-carboxamide (cpd 107);

8-amino-N-{4-[2-(1,4'-bipiperidin-1'-yl)-2-oxoethyl]-1,3-thiazol-2-yl}-1,4,4-trimethyl-4,5-dihydro-1H- pyrazolo[4,3-h]quinazoline-3-carboxamide (cpd 108);

8-amino-N-[3-(1,4'-bipiperidin-1'-ylmethyl)phenyl]-1,4,4-trimethyl-4,5-dihydro-1H-pyrazolo[4,3-h]quinazoline-3-carboxamide (cpd 109);

8-amino-N-[3-(1,4'-bipiperidin-1-ylmethyl)phenyl]-4,4-dimethyl-4,5-dihydro-1H-pyrazolo[4,3-h]quinazoline-3-carboxamide (cpd 110);

8-amino-1,4,4-trimethyl-N-{3-[(4-methyl-1,4'-bipiperidin-1'-yl)methyl]phenyl}-4,5-dihydro-1H-pyrazolo[4,3-h]quinazoline-3-carboxamide (cpd 111);

8-amino-4,4-dimethyl-N-{3-[(4-methyl-1,4'-bipiperidin-1'-yl)methyl]phenyl}-4,5-dihydro-1H-pyrazolo[4,3-h]quinazoline- 3-carboxamide (cpd 112);

tert-butyl [1-(3-{[(8-amino-4,4-dimethyl-4,5-dihydro-1H-pyrazolo[4,3-h]quinazolin-3-yl)carbonyl]amino}benzyl)piperidin-4-yl]carbamate (cpd 114);

8-amino-N-(4-{2-[(3R)-3-(dimethylamino)pyrrolidin-1-yl]-2-oxoethyl}-1,3-thiazol-2-yl)-4,4-dimethyl-4,5-dihydro-1H-pyrazolo[4,3-h]quinazoline-3-carboxamide (cpd 116);

8-amino-N-(4-{[4-(dimethylamino)piperidin-1-yl]methyl}phenyl)-1,4,4-trimethyl-4,5-dihydro-1H-pyrazolo[4,3-h]quinazoline-3-carboxamide (cpd 117);

8-amino-N-(4-{[4-(dimethylamino)piperidin-1-yl]methyl}phenyl)-4,4-dimethyl-4,5-dihydro-1H-pyrazolo[4,3-h]quinazoline-3-carboxamide (cpd 118);

8-amino-4,4-dimethyl-N-(4-{2-[4-(methylamino)piperidin-1-yl]-2-oxoethyl}-1,3-thiazol-2-yl)-4,5-dihydro-1H-pyrazolo[4,3-h]quinazoline-3-carboxamide (cpd 119);

8-amino-N-{3-[2-(1,4'-bipiperidin-1'-yl)-2-oxoethyl]phenyl}-4,4-dimethyl-4,5-dihydro-1H-pyrazolo[4,3-h]quinazoline-3-carboxamide (cpd 120);

N-{4-[2-(1,4'-bipiperidin-1-yl)-2-oxoethyl]-1,3-thiazol-2-yl}-4,4-dimethyl-8-(methylamino)-4,5-dihydro-1H-pyrazolo[4,3-h]quinazoline-3-carboxamide (cpd 121);

4,4-dimethyl-8-(methylamino)-N-{4-[2-(4-methyl-1,4'-bipiperidin-1'-yl)-2-oxoethyl]-1,3-thiazol-2-yl}-4,5-dihydro-1H-pyrazolo[4,3-h]quinazoline-3-carboxamide (cpd 122);

8-amino-N,4,4-trimethyl-N-{4-[2-(4-methyl-1,4'-bipiperidin-1'-yl)-2-oxoethyl]-1,3-thiazol-2-yl}-4,5-dihydro-1H-pyrazolo[4,3-h]quinazoline-3-carboxamide (cpd 123);

8-amino-N-{4-[2-(1,4'-bipiperidin-1'-yl)-2-oxoethyl]-1,3-thiazol-2-yl}-N, 1,4,4-tetramethyl-4,5-dihydro-1H- pyrazolo[4,3-h]quinazoline-3-carboxamide (cpd 124);

8-amino-N-[4-(1,4'-bipiperidin-1-ylmethyl)phenyl]-4,4-dimethyl-4,5-dihydro-1H-pyrazolo[4,3-h]quinazoline-3-carboxamide bistrifluoroacetate (cpd 125);

8-amino-N-[4-({[4-(1,4'-bipiperidin-1'-ylmethyl)phenyl]amino}methyl)phenyl]-4,4-dimethyl-4,5-dihydro-1H-pyrazolo[4,3-h]quinazoline-3-carboxamide bistrifluoroacetate (cpd 126);

methyl 1-(2-{[(8-amino-4,4-dimethyl-4,5-dihydro-1H-pyrazolo[4,3-h]quinazolin-3-yl)carbonyl]amino}-1,3-thiazol-4-yl)cyclopropanecarboxylate (cpd 127);

8-amino-N-[4-(1,4'-bipiperidin-1-ylmethyl)phenyl]-1,4,4-trimethyl-4,5-dihydro-1H-pyrazolo[4,3-h]quinazoline-3-carboxamide (cpd 128);

1-(2-{[(8-amino-4,4-dimethyl-4,5-dihydro-1H-pyrazolo[4,3-h]quinazolin-3-yl)carbonyl]amino}-1,3-thiazol-4-yl)cyclopropanecarboxylic acid (cpd 129);

8-amino-N-[4-(1-{[(3R)-3-(dimethylamino)pyrrolidin-1-yl]carbonyl}cyclopropyl)-1,3-thiazol-2-yl]-4,4-dimethyl-4,5-dihydro-1H-pyrazolo[4,3-h]quinazoline-3-carboxamide (cpd 130);

8-amino-N-{4-[1-(1,4'-bipiperidin-1'-ylcarbonyl)cyclopropyl]-1,3-thiazol-2-yl}-4,4-dimethyl-4,5-dihydro-1H-pyrazolo[4,3-h]quinazoline-3-carboxamide (cpd 131);

tert-butyl [1-(4-{[(8-amino-4,4-dimethyl-4,5-dihydro-1H-pyrazolo[4,3-h]quinazolin-3-yl)carbonyl]amino}benzyl)piperidin-4-yl]carbamate (cpd 133);

(3-{[(8-amino-4,4-dimethyl-4,5-dihydro-1H-pyrazolo[4,3-h]quinazolin-3-yl)carbonyl]amino}phenyl)acetic acid (139);

8-amino-N-[4-(1,4'-bipiperidin-1-ylmethyl)-1,3-thiazol-2-yl]-1,4,4-trimethyl-4,5-dihydro-1H-pyrazolo[4,3-h]quinazoline-3-carboxamide (cpd 141);

8-amino-N-(3-{2-[(3R)-3-(dimethylamino)pyrrolidin-1-yl]-2-oxoethyl}phenyl)-4,4-dimethyl-4,5-dihydro-1H-pyrazolo[4,3-h]quinazoline-3-carboxamide (cpd 142);

8-amino-N-[4-(1,4'-bipiperidin-1-ylmethyl)-1,3-thiazol-2-yl]-4,4-dimethyl-4,5-dihydro-1H-pyrazolo[4,3-h]quinazoline-3-carboxamide (cpd 143);

8-amino-N-(1H-imidazol-2-yl)-4,4-dimethyl-4,5-dihydro-1H-pyrazolo[4,3-h]quinazoline-3-carboxamide (cpd 144);

8-amino-N-(4-{2-[(1-cyclohexylpiperidin-4-yl)amino]-2-oxoethyl}-1,3-thiazol-2-yl)-4,4-dimethyl-4,5-dihydro-1H- pyrazolo[4,3-h]quinazoline-3-carboxamide (cpd 145);

8-amino-N-(3-{2-[4-(dimethylamino)piperidin-1-yl]-2-oxoethyl}phenyl)-4,4-dimethyl-4,5-dihydro-1H-pyrazolo[4,3-h]quinazoline-3-carboxamide (cpd 146);

8-amino-N-(4-{[(3R)-3-(dimethylamino)pyrrolidin-1-yl]methyl}-1,3-thiazol-2-yl)-1,4,4-trimethyl-4,5-dihydro-1H-pyrazolo[4,3-h]quinazoline-3-carboxamide (cpd 147);

8-amino-N-(4-{[(3R)-3-(dimethylamino)pyrrolidin-1-yl]methyl}-1,3-thiazol-2-yl)-4,4-dimethyl-4,5-dihydro-1H-pyrazolo[4,3-h]quinazoline-3-carboxamide dihydrochloride (cpd 148);

8-amino-N-{3-[2-(4-aminopiperidin-1-yl)-2-oxoethyl]phenyl}-4,4-dimethyl-4,5-dihydro-1H-pyrazolo[4,3-h]quinazoline-3-carboxamide hydrochloride (cpd 149);

8-amino-N-{4-[2-(4-cyclohexylpiperazin-1-yl)-2-oxoethyl]-1,3-thiazol-2-yl}-4,4-dimethyl-4,5-dihydro-1H-pyrazolo[4,3-h]quinazoline-3-carboxamide (cpd 150);

8-amino-4,4-dimethyl-N-(5-methyl-4,5,6,7-tetrahydro[1,3]thiazolo[5,4-c]pyridin-2-yl)-4,5-dihydro-1H-pyrazolo[4,3-h]quinazoline-3-carboxamide dihydrochloride (cpd 151);

8-amino-N-{4-[(4-aminopiperidin-1-yl)methyl]-1,3-thiazol-2-yl}-4,4-dimethyl-4,5-dihydro-1H-pyrazolo[4,3-h]quinazoline-3-carboxamide dihydrochloride (cpd 152);

8-amino-1,4,4-trimethyl-N-(4-{2-[4-(1-oxidopiperidin-1-yl)piperidin-1-yl]-2-oxoethyl}-1,3-thiazol-2-yl)-4,5-dihydro-1H-pyrazolo[4,3-h]quinazoline-3-carboxamide (153);

8-amino-N-(4-{2-[(3R)-3-(dimethylnitroryl)pyrrolidin-1-yl]-2-oxoethyl}-1,3-thiazol-2-yl)-4,4-dimethyl-4,5-dihydro-1H-pyrazolo[4,3-h]quinazoline-3-carboxamide (cpd 154);

8-amino-1,4,4-trimethyl-N-(4-methyl-1,3-thiazol-2-yl)-4,5-dihydro-1H-pyrazolo[4,3-h]quinazoline-3-carboxamide (cpd 155);

8-amino-N-(4-{[(1-cyclohexylpiperidin-4-yl)amino]methyl}-1,3-thiazol-2-yl)-4,4-dimethyl-4,5-dihydro-1H-pyrazolo[4,3-h]quinazoline-3-carboxamide dihydrochloride (cpd 156);

8-amino-N-(4-{[(1-cyclohexylpiperidin-4-yl)oxy]methyl}-1,3-thiazol-2-yl)-4,4-dimethyl-4,5-dihydro-1H-pyrazolo[4,3-h]quinazoline-3-carboxamide (cpd 157);

8-amino-4,4-dimethyl-N-{4-[2-oxo-2-(4-phenylpiperazin-1-yl)ethyl]-1,3-thiazol-2-yl}-4,5-dihydro-1H-pyrazolo[4,3-h]quinazoline-3-carboxamide (cpd 160);

(8-amino-4,4-dimethyl-4,5-dihydro-1H-pyrazolo[4,3-h]quinazolin-3-yl)(4-phenylpiperazin-1-yl)methanone (cpd 161);

8-amino-N-[4-(1,4'-bipiperidin-1-ylcarbonyl)benzyl]-4,4-dimethyl-4,5-dihydro-1H-pyrazolo[4,3-h]quinazoline-3-carboxamide (cpd 165):

8-amino-4,4-dimethyl-N-{4-[(1-methylpiperidin-4-yl)carbamoyl]benzyl}-4,5-dihydro-1H-pyrazolo[4,3-h]quinazoline-3-carboxamide (cpd 166);

8-amino-4,4-dimethyl-N-[4-({[trans-4-(4-methylpiperidin-1-yl)cyclohexyl]oxy}methyl)-1,3-thiazol-2-yl]-4,5-dihydro-1H- pyrazolo[4,3-h]quinazoline-3-carboxamide (cpd 170);

8-amino-1-(2-hydroxyethyl)-4,4-dimethyl-N-(4-methyl-1,3-thiazol-2-yl)-4,5-dihydro-1H-pyrazolo[4,3-h]quinazoline-3-carboxamide (cpd 182);

8-amino-N-{4-[2-(1,4'-bipiperidin-1'-yl)-1,1-difluoro-2-oxoethyl]-1,3-thiazol-2-yl}-4,4-dimethyl-4,5-dihydro-1H-pyrazolo[4,3-h]quinazoline-3-carboxamide (cpd 183);

8-amino-N-[4-({[1-(4,4-difluorocyclohexyl)piperidin-4-yl]oxy}methyl)-1,3-thiazol-2-yl]-4,4-dimethyl-4,5-dihydro-1H- pyrazolo[4,3-h]quinazoline-3-carboxamide (cpd 189);

8-amino-N-[4-({[1-(4,4-dimethylcyclohexyl)piperidin-4-yl]oxy}methyl)-1,3-thiazol-2-yl]-4,4-dimethyl-4,5-dihydro-1H- pyrazolo[4,3-h]quinazoline-3-carboxamide (cpd 190);

8-amino-N-{4-[1,1-difluoro-2-(4-methyl-1,4'-bipiperidin-1-yl)-2-oxoethyl]-1,3-thiazol-2-yl}-4,4-dimethyl-4,5-dihydro-1H-pyrazolo[4,3-h]quinazoline-3-carboxamide (cpd 191);

8-amino-N-(4-{[(1-cycloheptylpiperidin-4-yl)oxy]methyl}-1,3-thiazol-2-yl)-4,4-dimethyl-4,5-dihydro-1H-pyrazolo[4,3-h]quinazoline-3-carboxamide (cpd 209);

8-amino-2,4,4-trimethyl-N-{4-[2-(4-methyl-1,4'-bipiperidin-1'-yl)-2-oxoethyl]-1,3-thiazol-2-yl}-4,5-dihydro-2H-pyrazolo[4,3-h]quinazoline-3-carboxamide (cpd 211);

8-amino-N-[4-({[1-(cyclohexylmethyl)piperidin-4-yl]oxy}methyl)-1,3-thiazol-2-yl]-4,4-dimethyl-4,5-dihydro-1H-pyrazolo[4,3-h]quinazoline-3-carboxamide (cpd 212);

8-amino-N-(4-{[(1-benzylpiperidin-4-yl)oxy]methyl}-1,3-thiazol-2-yl)-4,4-dimethyl-4,5-dihydro-1H-pyrazolo[4,3-h]quinazoline-3-carboxamide (cpd 213);

8-amino-N-(4-{[(1-cycloheptylpiperidin-4-yl)oxy]methyl}-1,3-thiazol-2-yl)-1,4,4-trimethyl-4,5-dihydro-1H-pyrazolo[4,3-h]quinazoline-3-carboxamide (cpd 217);

8-amino-N-{4-[2-(4,4-dimethyl-1,4'-bipiperidin-1'-yl)-2-oxoethyl]-1,3-thiazol-2-yl}-4,4-dimethyl-4,5-dihydro-1H-pyrazolo[4,3-h]quinazoline-3-carboxamide hydrochloride (cpd 218);

8-amino-N-{4-[2-(3,3-dimethyl-1,4'-bipiperidin-1'-yl)-2-oxoethyl]-1,3-thiazol-2-yl}-4,4-dimethyl-4,5-dihydro-1H-pyrazolo[4,3-h]quinazoline-3-carboxamide (cpd 219);

8-amino-N-(4-{2-[(2,6-dimethyl-4-oxohept-5-en-2-yl)amino]-2-oxoethyl}-1,3-thiazol-2-yl)-4,4-dimethyl-4,5-dihydro-1H-pyrazolo[4,3-h]quinazoline-3-carboxamide (cpd 220);

8-amino-N-[4-({[1-(4,4-dimethylcyclohexyl)piperidin-4-yl]oxy}methyl)-1,3-thiazol-2-yl]-4,4-dimethyl-4,5-dihydro-1H- pyrazolo[4,3-h]quinazoline-3-carboxamide trihydrochloride (cpd 221);

8-amino-N-{4-[2-(3,3-difluoro-1,4'-bipiperidin-1-yl)-2-oxoethyl]-1,3-thiazol-2-yl}-4,4-dimethyl-4,5-dihydro-1H-pyrazolo[4,3-h]quinazoline-3-carboxamide (cpd 222);

8-amino-N-(4-{[(1-cycloheptylpiperidin-4-yl)oxy]methyl}-1,3-thiazol-2-yl)-4,4-dimethyl-4,5-dihydro-1H-pyrazolo[4,3-h]quinazoline-3-carboxamide trihydrochloride (cpd 223);

8-amino-4,4-dimethyl-N-{4-[2-(3-methyl-1,4'-bipiperidin-1-yl)-2-oxoethyl]-1,3-thiazol-2-yl}-4,5-dihydro-1H-pyrazolo[4,3-h]quinazoline-3-carboxamide (cpd 224);

8-amino-1,5,5-trimethyl-N-{4-[2-(4-methyl-1,4'-bipiperidin-1'-yl)-2-oxoethyl]-1,3-thiazol-2-yl}-4,5-dihydro-1H-pyrazolo[4,3-h]quinazoline-3-carboxamide (cpd 225);

8-amino-N-(4-{[(1-cycloheptyl-4-methylpiperidin-4-yl)oxy]methyl}-1,3-thiazol-2-yl)-4,4-dimethyl-4,5-dihydro-1H-pyrazolo[4,3-h]quinazoline-3-carboxamide (cpd 226);

8-amino-N-{4-[2-(4,4'-dimethyl-1,4'-bipiperidin-1'-yl)-2-oxoethyl]-1,3-thiazol-2-yl}-4,4-dimethyl-4,5-dihydro-1H-pyrazolo[4,3-h]quinazoline-3-carboxamide (cpd 227);

8-amino-4,4-dimethyl-N-{6-[(4-methyl-1,4'-bipiperidin-1'-yl)carbonyl]-1,3-benzothiazol-2-yl}-4,5-dihydro-1H-pyrazolo[4,3-h]quinazoline-3-carboxamide (cpd 228);

8-amino-N-{4-[2-(4,4-difluoro-1,4'-bipiperidin-1'-yl)-2-oxoethyl]-1,3-thiazol-2-yl}-4,4-dimethyl-4,5-dihydro-1H-pyrazolo[4,3-h]quinazoline-3-carboxamide (cpd 229);

8-amino-4,4-dimethyl-N-[4-({[1-(spiro[2.5]oct-6-yl)piperidin-4-yl]oxy}methyl)-1,3-thiazol-2-yl]-4,5-dihydro-1H-pyrazolo[4,3-h]quinazoline-3-carboxamide (cpd 230);

8-amino-5,5-dimethyl-N-{4-[2-(4-methyl-1,4'-bipiperidin-1-yl)-2-oxoethyl]-1,3-thiazol-2-yl}-4,5-dihydro-1H-pyrazolo[4,3-h]quinazoline-3-carboxamide (cpd 231); and 8-amino-N-(4-{[(1-cycloheptylpiperidin-4-yl)oxy]methyl}-1,3-thiazol-2-yl)-5,5-dimethyl-4,5-dihydro-1H-pyrazolo[4,3-h]quinazoline-3-carboxamide trihydrochloride (cpd 232).

The present invention also provides processes for the preparation of the compound of general formula (I) as defined above, by using the reaction routes and synthetic schemes described below, employing the techniques available in the art and starting materials readily available. The preparation of certain embodiments of the present invention is described in the examples that follow, but those of ordinary skill in the art will recognize that the preparations described may be readily adapted to prepare other embodiments of the present invention. For example, the synthesis of non-exemplified compounds according to the invention may be performed by apparent modifications to those skilled in the art, for instance by appropriately protecting interfering groups, by suitably replacing reagents with others known in the art, or by making routine modifications of reaction conditions. Alternatively, other reactions referred to herein or known in the art will be recognized as having adaptability for preparing other compounds of the invention. The compounds of this invention can be prepared from readily available starting materials using the following general methods and procedures. Unless otherwise indicated, the starting materials are known compounds or may be prepared from known compounds according to well known procedures. It will be appreciated that, where typical or preferred process conditions (i.e., reaction temperatures, times, mole ratios of reactants, solvents, pressures) are described, different process conditions can also be used unless otherwise stated. Optimum reaction conditions may vary with the particular reactants or solvent used, but such conditions can be determined by one skilled in the art by routine optimization procedures. Additionally, as it will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, several protecting groups are described in T. Greene and P. G. M. Wuts, Protecting Groups in Organic Synthesis, Second Edition, Wiley, New York, 1991, and references cited therein.

The compounds of general formula (I), as defined above, can be prepared according to the general synthetic processes described in Scheme 1 [when y=1, compounds (Ia) and (Ib)] and Scheme 2 [when y=0, compounds (Ic) and (Id)], starting in both cases from intermediate compounds of formula (III) or (V):

Scheme 1 (y=1)

R1 is hydrogen or an optionally substituted group selected from straight or branched ($C_1$-$C_6$)alkyl and ($C_3$-$C_7$)cycloalkyl; R2 is hydrogen or an optionally substituted group selected from straight or branched ($C_1$-$C_6$)alkyl, ($C_2$-$C_6$)alkenyl, ($C_2$-$C_6$)alkynyl, ($C_3$-$C_7$)cycloalkyl and heterocyclyl; R3, R4, R3' and R4' are independently hydrogen, straight or branched ($C_1$-$C_6$)alkyl or, taken together with the carbon atom to which they are bonded, R3 and R4 or R3' and R4' form an optionally substituted 3-, 4-, 5- or 6-membered cycloalkyl; z and n are independently 0, 1 or 2; L is CONR8- or —NR8CO—; R8 is hydrogen or an optionally substituted straight or branched ($C_1$-$C_6$)alkyl; Ra, Rb, Rc and Rd are independently hydrogen, an optionally substituted straight or branched ($C_1$-$C_6$)alkyl, fluoro or, taken together with the carbon atom to which they are bonded, Ra and Rb, and/or Rc and Rd, form a 3-membered cycloalkyl; A is an optionally substituted ring selected from aryl, heteroaryl, ($C_3$-$C_7$)cycloalkyl and heterocyclyl; R5 is an optionally substituted group selected from —COOR6, —COR6, —CONR6R7, —NR7COOR9, —NR7COR6, —NR7CONR6R7, —OR6 and —NR6R7; R6 and R7 are independently hydrogen or an optionally substituted group selected from straight or branched ($C_1$-$C_6$)alkyl, ($C_3$-$C_7$)cycloalkyl, heterocyclyl, aryl, aryl($C_1$-$C_6$)alkyl, heteroaryl and heteroaryl($C_1$-$C_6$)alkyl or, taken together with the nitrogen atom to which they are bonded, R6 and R7 form an optionally substituted 5- or 6-membered heterocyclyl group optionally containing one additional heteroatom selected from N, O and S; and R9 is an optionally substituted group selected from ($C_1$-$C_6$)alkyl, ($C_3$-$C_7$)cycloalkyl, heterocyclyl, aryl, aryl($C_1$-$C_6$)alkyl, heteroaryl and heteroaryl($C_1$-$C_6$)alkyl.

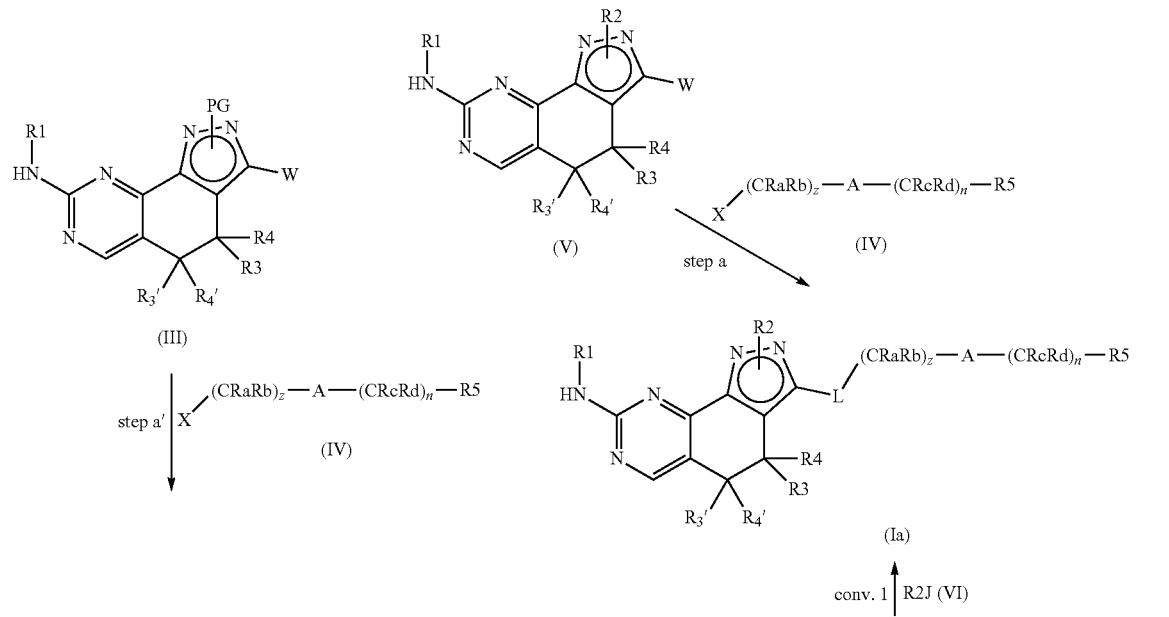

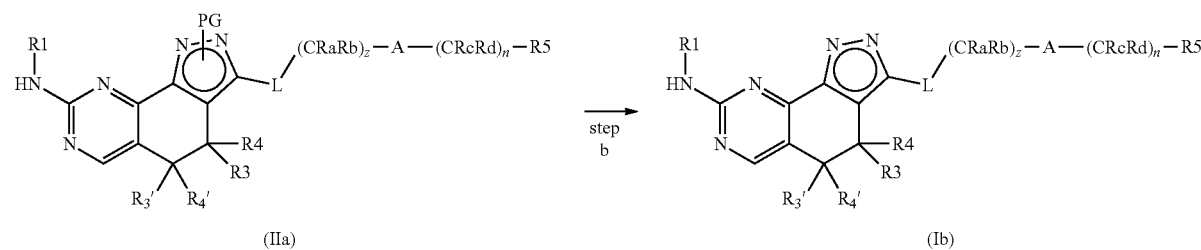

According to Scheme 1, a process of the present invention comprises one of the following sequences of steps: either
Sequence a:
Step a) Reacting an Intermediate Compound of Formula (V):

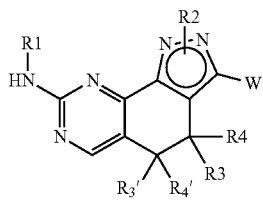

wherein R1, R2, R3, R4, R3' and R4' are as defined above and W is —COOH or —NHR8, wherein R8 is as defined above, with an intermediate compound of formula (IV):

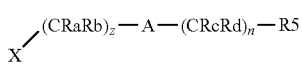

wherein A, R5, Ra, Rb, Rc, Rd, z and n are as defined above and X is —NHR8, when W is —COOH, or —COOH, when W is —NHR8;
to yield a compound of formula (Ia), which is a compound of formula (I) as defined above wherein R2 is different from hydrogen and y is 1;
or
Sequence B
Step a') Reacting an Intermediate Compound of Formula (III):

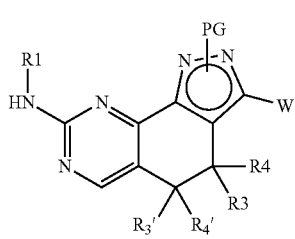

wherein R1, R3, R4, R3', R4' and W are as defined above and PG is a suitable pyrazole nitrogen protecting group, such as for instance trityl, tetrahydropyranyl, 2-(trimethylsilyl)ethoxymethyl (SEM) or —COOR10, wherein R10 is straight or branched $(C_1-C_6)$alkyl, such as for instance methyl, ethyl or tert-butyl, or aryl$(C_1-C_6)$alkyl, such as for instance benzyl, with an intermediate compound of formula (IV), as defined in step a and in the conditions described therein;
Step b) Removing the Protecting Group PG of the Resultant Intermediate Compound of Formula (IIa)

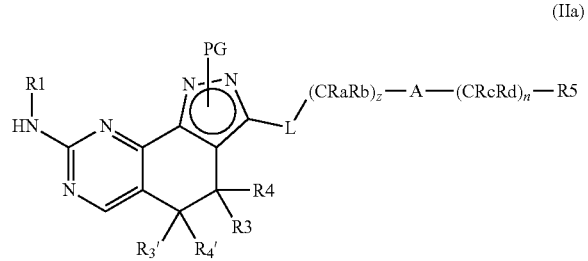

wherein PG, R1, R3, R4, R3', R4', L, A, R5, Ra, Rb, Rc, Rd, z and n are as defined above, to yield a compound of formula (Ib);

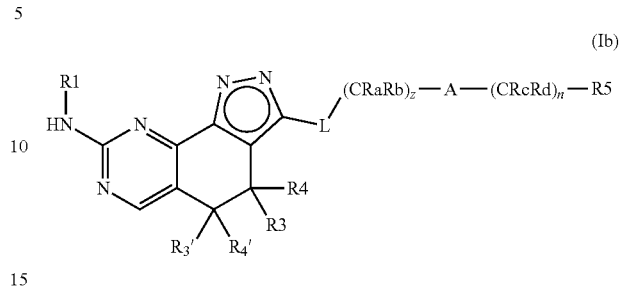

which is a compound of formula (I) as defined above wherein R2 is hydrogen and y is 1;
and if desired
Conv. 1) alkylating the intermediate compound of formula (Ib), resulting from step b, with an intermediate compound of formula R2J (VI), wherein J is selected from the group consisting of bromo, iodo, hydroxy, methansulfonyl (-OMs) and p-toluensulfonyl (-OTs) and R2 is as defined above except from hydrogen, to yield a compound of formula (Ia), as defined above;
or
optionally converting a first compound of formula (I) into a second compound of formula (I), and, if desired, converting a compound of formula (I) into a pharmaceutically acceptable salt thereof or converting a salt into the free compound (I).

According to step a, the amidation of a compound of formula (V), as defined above, with an intermediate of formula (IV) is carried out under basic conditions, preferably with DIPEA or TEA, in a suitable solvent such as DCM, DMF, THF, 1,4-dioxane or DMA, in the presence of a suitable condensing agent, for instance dicyclohexylcarbodiimide (DCC), 1-ethyl-3-(3'-dimethylaminopropyl)carbodiimide (EDC), 3,4-dihydro-3-hydroxy-4-oxo-1,2,3-benzotriazine (DHBT), O-benzotriazolyltetramethylisouronium tetrafluoroborate (TBTU), benzotriazol-1-yloxytripyrrolidinophosphonium hexafluorophosphate (PyBOP), or 2-(1H-benzotriazole-1-yl)-1,1,3,3-tetramethyluronium hexafluorophosphate (HBTU) at a temperature ranging from about −10° C. to reflux and for a suitable time, for instance from about 30 minutes to about 96 h. Said reaction is optionally carried out in the presence of a suitable catalyst such as DMAP, or in the presence of a further coupling reagent such as N-hydroxybenzotriazole (HOBT). Alternatively, this same reaction is also carried out, for example through a mixed anhydride method, by using an alkyl chloroformate such as ethyl, isopropyl, benzyl chloroformate, in the presence of a tertiary amine, such as TEA, DIPEA or pyridine, in a suitable solvent, such as, for instance toluene, DCM, THF, DMF and the like, at room temperature.

Alternatively the carboxylic acid (when W or X are —COOH) is converted into the corresponding acyl chloride in the presence of an activating agent such as thionyl chloride, oxalyl chloride, cyanuric chloride or 1-chloro-N,N,2-trimethylpropenylamine (Ghosez's reagent) neat or in a suitable solvent, such as toluene or DCM, optionally in the presence of a catalytic amount of DMF, at a temperature ranging from about −10° C. to reflux and for a suitable time, for instance from about 30 minutes to about 4 h. Said acyl chloride is then reacted with an intermediate amine (when X or W are —NHR8), in a suitable solvent such as DCM, chloroform, THF, diethyl ether, 1,4-dioxane, ACN, toluene, or DMF and the like at a temperature ranging from about −10° C. to reflux and for a suitable time, for instance from about 30 minutes to about 96 h. The reaction is carried out in the presence of a suitable base such as TEA, DIPEA or pyridine.

According to step a', the amidation of an intermediate compound of formula (III) can be carried out with an intermediate of formula (IV) as described for step a.

According to step b, the deprotection of an intermediate of formula (IIa) as defined above, can be carried out under acidic conditions, such as for instance TFA, HCl and the like, or with a catalytic amount of CuCl, or in basic conditions, for instance with NaOH, LiOH, KOH or TEA, in a suitable solvent such as DCM, 1,4-dioxane, MeOH, EtOH or a mixture EtOH/water, at a temperature ranging from room temperature to reflux and for a time ranging from 1 to about 12 h. Alternatively when PG is —COOR10 and R10 is aryl($C_1$-$C_6$)alkyl, such as for instance benzyl, the reaction can be carried out in the presence of gaseous hydrogen or a hydrogen source, such as, for instance, formic acid, ammonium formate, cyclohexene and 1,4-cyclohexadiene, and a hydrogenation catalyst, such as palladium on carbon, in a suitable solvent, such as EtOH, MeOH, AcOEt or a mixture thereof, at temperatures ranging from room temperature to reflux for a time varying from 30 minutes to 24 h.

According to conv. 1, the alkylation of an intermediate of formula (Ib) with an intermediate of formula R2J (VI), wherein J is bromo, iodo, -OMs or -OTs, can be carried out in the presence of a suitable base, such as $Na_2CO_3$, $K_2CO_3$, $Cs_2CO_3$, NaH, KH, tBuOLi and the like, in a suitable solvent, such as DMF, DMA, ACN, acetone, THF and the like, at a temperature ranging from 0° C. to reflux to give a compound of formula (Ia), as defined above. When an intermediate of formula R2J (VI), wherein J is hydroxy, is used, the reaction is preferentially carried out under Mitsunobu alkylation conditions in the presence of a suitable reagent such as, for instance, diethylazodicarboxylate (DEAD), diisopropylazodicarboxylate (DIAD), ditertbutylazodicarboxylate (DBAD), 1,1'-(azodicarbonyl)dipiperidine (ADDP), and a phosphine reagent such as, for instance, trimethylphosphine, tritertbutylphosphine, triphenylphosphine and the like, in a suitable solvent, such as THF, DMF, DCM, toluene, benzene and the like, at a temperature ranging from 0° C. to 65° C.

Scheme 2 (y=0)

R1 is hydrogen or an optionally substituted group selected from straight or branched ($C_1$-$C_6$)alkyl and ($C_3$-$C_7$)cycloalkyl; R2 is hydrogen or an optionally substituted group selected from straight or branched ($C_1$-$C_6$)alkyl, ($C_2$-$C_6$)alkenyl, ($C_2$-$C_6$)alkynyl, ($C_3$-$C_7$)cycloalkyl and heterocyclyl; R3, R4, R3' and R4' are independently hydrogen, straight or branched ($C_1$-$C_6$)alkyl or, taken together with the carbon atom to which they are bonded, R3 and R4 or R3' and R4' form an optionally substituted 3-, 4-, 5- or 6-membered cycloalkyl; L is —CONR6aR7a or —NR8COR6a; R6a and R7a are independently hydrogen or an optionally substituted group selected from straight or branched ($C_1$-$C_6$)alkyl, ($C_3$-$C_7$)cycloalkyl, heterocyclyl, aryl, aryl($C_1$-$C_6$)alkyl, heteroaryl and heteroaryl($C_1$-$C_6$)alkyl or, taken together with the nitrogen atom to which they are bonded, R6a and R7a form an optionally substituted 5- or 6-membered heterocyclyl group optionally containing one additional heteroatom selected from N, O and S; and R8 is hydrogen or an optionally substituted straight or branched ($C_1$-$C_6$)alkyl.

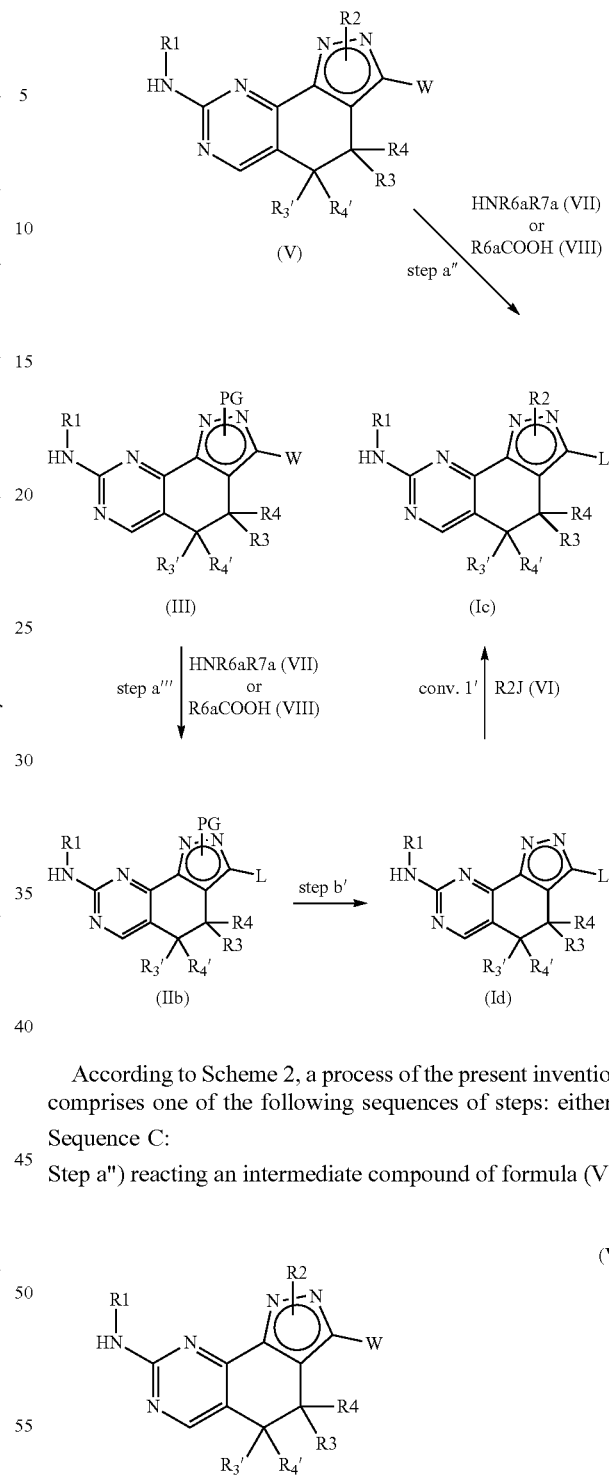

According to Scheme 2, a process of the present invention comprises one of the following sequences of steps: either Sequence C:

Step a″) reacting an intermediate compound of formula (V):

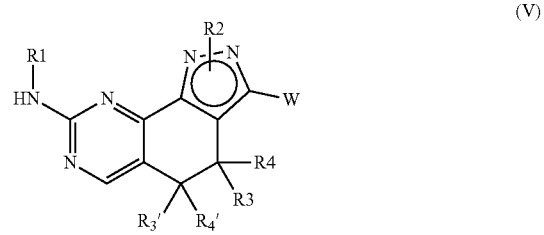

wherein R1, R2, R3, R4, R3' and R4' are as defined above, and W is —COOH or —NHR8, wherein R8 is as defined above, with an intermediate compound of formula HNR6aR7a (VII), wherein R6a and R7a are as defined above, when W is —COOH, or with an intermediate compound of formula R6aCOOH (VIII), when W is —NHR8, wherein R8 is as defined above, to yield a compound of formula (Ic), wherein L is —CONR6aR7a or —NR8COOR6a and R1, R2, R3, R4, R3', R4', R6a, R7a and R8 are as defined above;
or
Sequence D
Step a''') Reacting an Intermediate Compound of Formula (III):

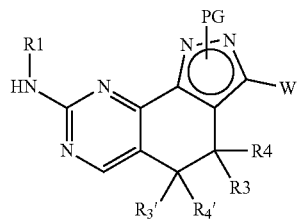

(V)

wherein R1, R3, R4, R3', R4' and W are as defined in step a'' and PG is a suitable pyrazole nitrogen protecting group, such as for instance trityl, tetrahydropyranyl, 2-(trimethyl-silyl)ethoxymethyl (SEM) or —COOR10, wherein R10 is $(C_1-C_6)$alkyl, such as for instance methyl, ethyl or tert-butyl, or aryl$(C_1-C_6)$alkyl, such as for instance benzyl, with an intermediate compound of formula HNR6aR7a (VII), when W is —COOH, or R6aCOOH (VIII), when W is —NHR8, wherein R6a, R7a and R8 are as defined in step a'';
Step b') Removing the Protecting Group PG of the Resultant Intermediate Compound of Formula (IIb)

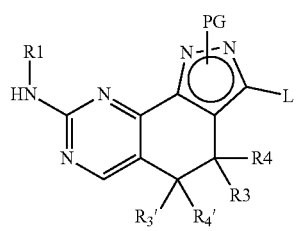

(IIb)

wherein R1, R3, R4, R3', R4', PG and L are as defined above, to yield a compound of formula (Id);

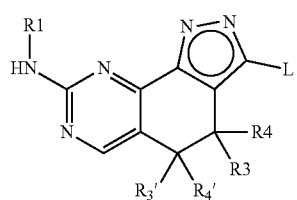

(Id)

which is a compound of formula (I) as defined above wherein R2 is hydrogen and y is O;
and if desired
Conv. 1') alkylating the intermediate compound of formula (Id), resulting from step b', with an intermediate compound of formula R2J (VI), as defined for conv. 1 in Scheme 1, to yield a compound of general formula (Ic), which is a compound of formula (I) as defined above wherein R2 is different from hydrogen and y is 0;
or
optionally converting a first compound of formula (I) into a second compound of formula (I), and, if desired, converting a compound of formula (I) into a pharmaceutically acceptable salt thereof or converting a salt into the free compound (I).

According to step a'', the amidation of an intermediate compound of formula (V), as defined above, with an intermediate of formula HNR6aR7a (VII) or R6aCOOH (VIII) is carried out as described for step a.

According to step a''', the amidation of an intermediate compound of formula (III), as defined above, with an intermediate of formula HNR6aR7a (VII) or R6aCOOH (VIII) can be carried out as described for step a'.

According to step b', the deprotection of an intermediate of formula (IIb) as defined above, can be carried out as described for step b.

According to conv. 1', the alkylation of an intermediate of formula (Id) with an intermediate of formula R2J (VI), can be carried out as described for conv. 1 in Scheme 1.

Moreover, further references are reported in WO2004104007 (pag. 115, pag. 157 and pag. 179 for step a'' and step a'''; pag. 149 for step b'; pag. 72 and 73 for conv. 1).

A first compound of general formula (I) can be conveniently converted into a second compound of general formula (I) by operating according to well-known synthetic conditions.

A first compound of general formula (I), wherein R5 is —COOR6, namely a compound of formula (Ie), can be conveniently converted into a second compound of formula (I), wherein R5 has the meanings of —COOH, —CONR6R7 or —COR6 and R6 and R7 are as defined in Scheme 1, namely a compound of formula (If), (Ig) or (Ih), by operating according to well-known synthetic conditions, as shown in Scheme 3:

Scheme 3

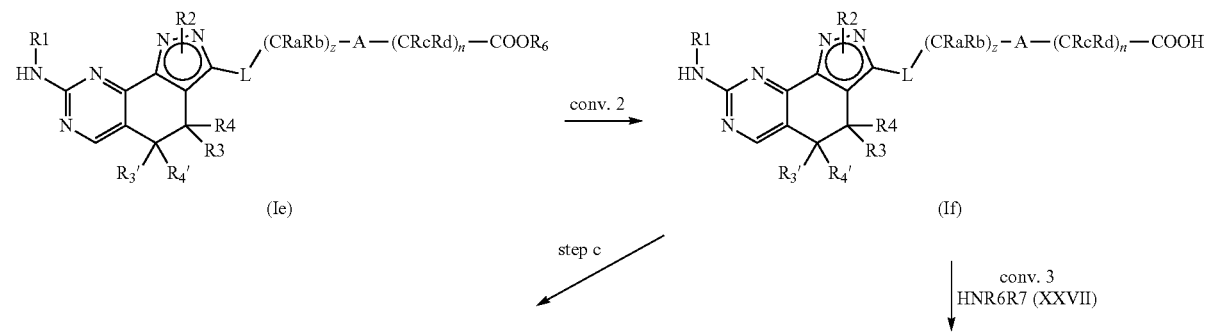

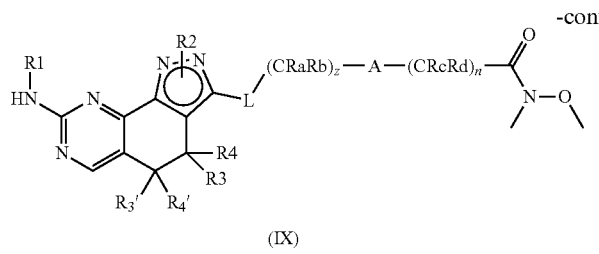

(IX)

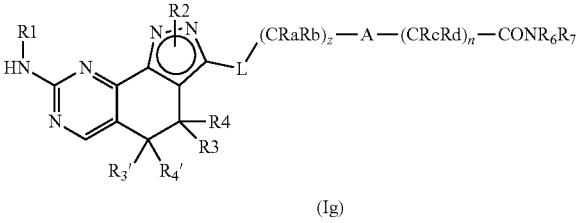

(Ig)

R6Z (X) | step d

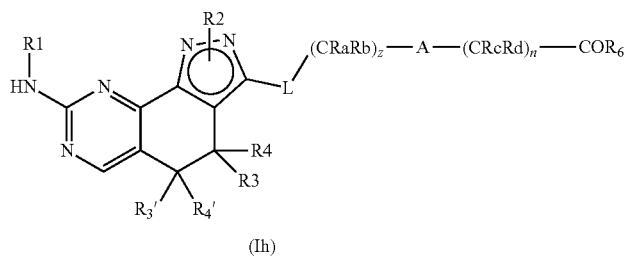

(Ih)

According to Scheme 3, a process of the present invention comprises:

conv. 2) converting a compound of formula (Ie), wherein R1, R2, R3, R4, R3', R4', L, A, Ra, Rb, Rc, Rd, z and n are as defined above, and R6 is a straight or branched ($C_1$-$C_6$) alkyl or aryl($C_1$-$C_6$)alkyl, to yield a compound of general formula (If), wherein R1, R2, R3, R4, R3', R4', L, A, Ra, Rb, Rc, Rd, z and n are as defined above, under acidic or basic conditions;

conv. 3) converting a compound of formula (If), as defined in conv. 2, into a compound of formula (Ig), wherein R1, R2, R3, R4, R3', R4', R6, R7, L, A, Ra, Rb, Rc, Rd, z and n are as defined above;

step c) reacting a compound of formula (If), as defined in conv. 2, with NHMeOMe hydrochloride and in the presence of a suitable condensing agent, to obtain an intermediate Weinreb amide of formula (IX), wherein R1, R2, R3, R4, R3', R4', L, A, Ra, Rb, Rc, Rd, z and n are as defined above;

step d) reacting an intermediate Weinreb amide of formula (IX), as defined in step c, with a reagent of formula R6-Z (X), wherein R6 is as defined for a compound of general formula (I) and is different from hydrogen, and Z is Li or MgBr, to obtain a compound of formula (Ih), wherein R1, R2, R3, R4, R3', R4', L, A, Ra, Rb, Rc, Rd, z and n are as defined above and R6 is as defined for a compound of general formula (I) and is different from hydrogen.

According to conv. 2, a compound of general formula (Ie), as defined above, is converted into a compound of formula (If), as defined above, through basic or acidic hydrolysis conditions, widely known in the art. The reaction is carried out with aqueous alkaline solutions, such as aqueous LiOH, NaOH or KOH, or in acidic conditions, for instance with AcOH, TFA or HCl, in the presence of a suitable solvent, such as a lower alcohol, THF, DMF, DCM or 1,4-dioxane or mixtures thereof, at a temperature ranging from room temperature to about 80° C. for a time ranging from about 1 to about 12 h.

Alternatively, when R6 is aryl($C_1$-$C_6$)alkyl, such as for instance benzyl, the reaction can be carried out in the presence of gaseous hydrogen or a hydrogen source, such as, for instance, formic acid, ammonium formate, cyclohexene and 1,4-cyclohexadiene, and a hydrogenation catalyst, such as palladium on carbon, in a suitable solvent, such as EtOH, MeOH, AcOEt or a mixture thereof, at temperatures ranging from room temperature to reflux for a time varying from 30 minutes to 24 h.

According to conv. 3, the amidation of a compound of formula (If), as defined above, is carried out in the presence of a suitable primary or secondary amine of formula HNR6R7 (XXVII), under basic conditions, preferably with DIPEA or TEA, in a suitable solvent such as DCM, DMF, THF, 1,4-dioxane or DMA, in the presence of a suitable condensing agent, for instance dicyclohexylcarbodiimide (DCC), 1-ethyl-3-(3'-dimethylaminopropyl)carbodiimide (EDC), 3,4-dihydro-3-hydroxy-4-oxo-1,2,3-benzotriazine (DHBT), O-benzotriazolyltetramethylisouronium tetrafluoroborate (TBTU), benzotriazol-1-yloxytripyrrolidinophosphonium hexafluorophosphate (PyBOP), or 2-(1H-benzotriazole-1-yl)-1,1,3,3-tetramethyluronium hexafluorophosphate (HBTU) at a temperature ranging from about −10°

C. to reflux and for a suitable time, for instance from about 30 minutes to about 96 h. Said reaction is optionally carried out in the presence of a suitable catalyst such as DMAP, or in the presence of a further coupling reagent such as N-hydroxybenzotriazole (HOBT). Alternatively, this same reaction is also carried out, for example through a mixed anhydride method, by using an alkyl chloroformate such as ethyl, isopropyl, benzyl chloroformate, in the presence of a tertiary amine, such as TEA, DIPEA or pyridine, in a suitable solvent, such as, for instance toluene, DCM, THF, DMF and the like, at room temperature.

Alternatively the carboxylic acid is converted into the corresponding acyl chloride in the presence of an activating agent such as thionyl chloride, oxalyl chloride, cyanuric chloride or 1-chloro-N,N,2-trimethylpropenylamine (Ghosez's reagent) neat or in a suitable solvent, such as toluene or DCM, optionally in the presence of a catalytic amount of DMF, at a temperature ranging from about −10° C. to reflux and for a suitable time, for instance from about 30 minutes to about 4 h. Said acyl chloride is then reacted with a suitable primary or secondary amine of formula HNR6R7 (XXVII), in a suitable solvent such as DCM, chloroform, THF, diethyl ether, 1,4-dioxane, ACN, toluene, or DMF and the like at a temperature ranging from about −10° C. to reflux and for a suitable time, for instance from about 30 minutes to about 96 h. The reaction is carried out in the presence of a suitable base such as TEA, DIPEA or pyridine. According to step c, a compound of formula (If), as defined above, is reacted with NHMeOMe hydrochloride under the same reaction conditions described for conv. 3.

According to step d, an intermediate Weinreb amide of formula (IX), wherein R1, R2, R3, R4, R3', R4', L, A, Ra, Rb, Rc, Rd, z and n are as defined above, is reacted with a compound of formula R6-Z (X), wherein R6 is as described for a compound of general formula (I) and is different from hydrogen, and Z is Li or MgBr, in an ether solvent such as THF, diethylether, 1,4-dioxane and the like, at a temperature ranging from 78° C. to room temperature for a suitable time, for instance from 30 minutes to 24 h.

Moreover, a first compound of general formula (Ii) can be conveniently converted into a second compound of formula (Im)' by operating according to other well-known synthetic conditions, said conversion comprising:

conv. 4) reacting a compound of formula (Ii), wherein R1, R2, R3, R4, R3', R4', L, A, Ra, Rb, Rc, Rd and z are as defined above, and n is 0 or 1, with a reagent of general formula HNR6R7 (XXVII), to yield a compound of general formula (Im)', wherein R1, R2, R3, R4, R3', R4', L, A, Ra, Rb, Rc, Rd and z are as defined above, n is 1 or 2 and R6 and R7 are as defined for a compound of general formula (I), under reductive amination conditions.

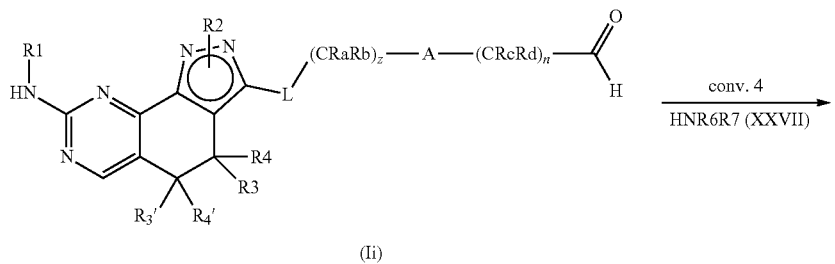

(Ii)

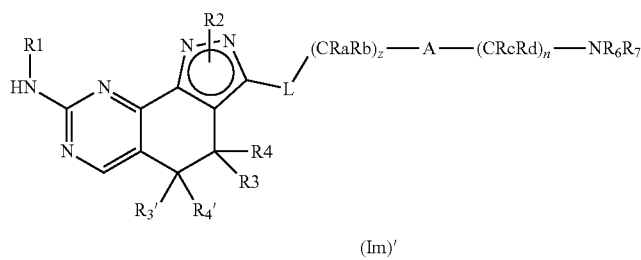

(Im)'

According to conv. 4, a compound of formula (Ii), as defined above, is reacted with an amine of formula HNR6R7 (XXVII), as defined above, in the presence of a reductive agent such as $NaBH_4$, $NaCNBH_3$, $NaBH(OAc)_3$ and the like, in a solvent such as MeOH, EtOH, 2,2,2-trifluoroethanol, DMF and the like, at a temperature ranging from room temperature to 40° C. and for a time ranging from 1 h to about 12 h. Said reaction is optionally carried out in the presence of a suitable catalyst such as AcOH, TFA and the like.

Moreover, a compound of general formula (I), wherein R5 is —NR6R7 or —OR6, namely a compound of formula (Im), can be prepared according to other well-known synthetic conditions as shown in Scheme 4:

According to step e, the reaction is carried out as described for step a.

According to step f, the reaction can be carried out in a suitable solvent such as DMF, DMA, n-butanol, NMP and THF, at a temperature ranging from room temperature to 150° C. and for a time ranging from 1 h to about 48 h in classical thermal conditions or in a microwave apparatus. In addition, when using R6OH (XIII), the reaction can be carried out in the presence of a base, such as NaH, and a crown ether, like for instance 15-crown-5 (ref. WO2008011191).

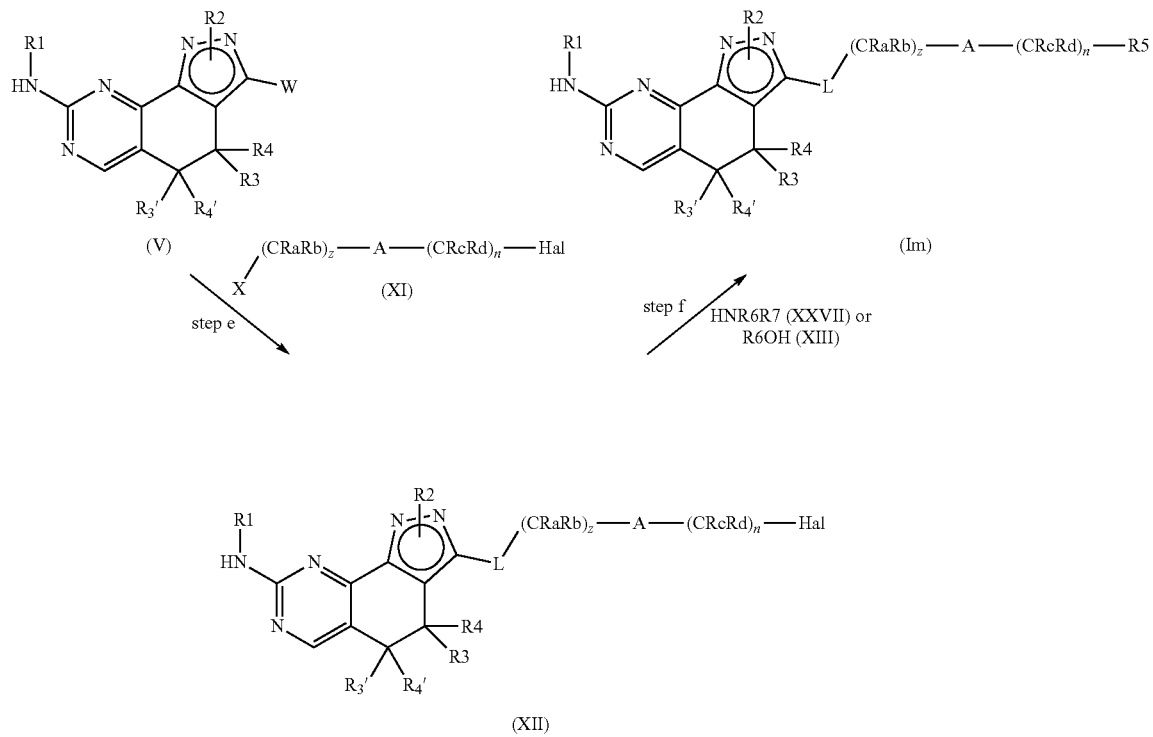

Scheme 4

According to Scheme 4, a process of the present invention comprises:
step e) reacting an intermediate compound of formula (V), as defined above, with an intermediate compound of formula (XI), wherein A, Ra, Rb, Rc, Rd, z and n are as defined above, Hal is a halogen atom selected from chloro, bromo or iodo and X is —NHR8, when W is —COOH, or —COOH, when W is —NHR8, to yield an intermediate compound of formula (XII);
step f) reacting the resulting intermediate of formula (XII), wherein R1, R2, R3, R4, R3', R4', L, A, Ra, Rb, Rc, Rd, Hal, z and n are as defined above, with HNR6R7 (XXVII) or R6OH (XIII), as defined above, to obtain a compound of formula (Im), wherein R1, R2, R3, R4, R3', R4', L, A, Ra, Rb, Rc, Rd, z and n are as defined above, R5 is —NR6R7 or —OR6 and R6 and R7 are as defined above, under nucleophilic substitution conditions or under palladium-catalyzed reaction conditions.

Alternatively, the reaction is carried out in a suitable solvent such as THF, dioxane, toluene, DMF or ACN, in the presence of a Pd-based catalyst such as $Pd(OAc)_2$ or $Pd_2(dba)_3$, a phosphine ligand like 2-dicyclohexylphosphino-2'-(N, N-dimethylamino)-biphenyl, BINAP or 2-(dicyclohexylphosphino)-2',4',6'-triisopropyl-1,1'-biphenyl (XPhos) and a base such as LiHTMS, $Cs_2CO_3$, $K_2CO_3$ or KOtBu at a temperature ranging from room temperature to reflux and for a time ranging from 1 h to about 48 h.

Moreover, a compound of general formula (I), wherein R5 is —NR7COOR9, namely a compound of formula (In), can be conveniently converted into a compound of formula (I), wherein R5 is —NHR7, —NR7COR6 or —NR7CONR6R7, i.e. respectively a compound of formula (Io), (Ip) or (Iq), by operating according to well-known synthetic conditions, as shown in Scheme 5:

Scheme 5

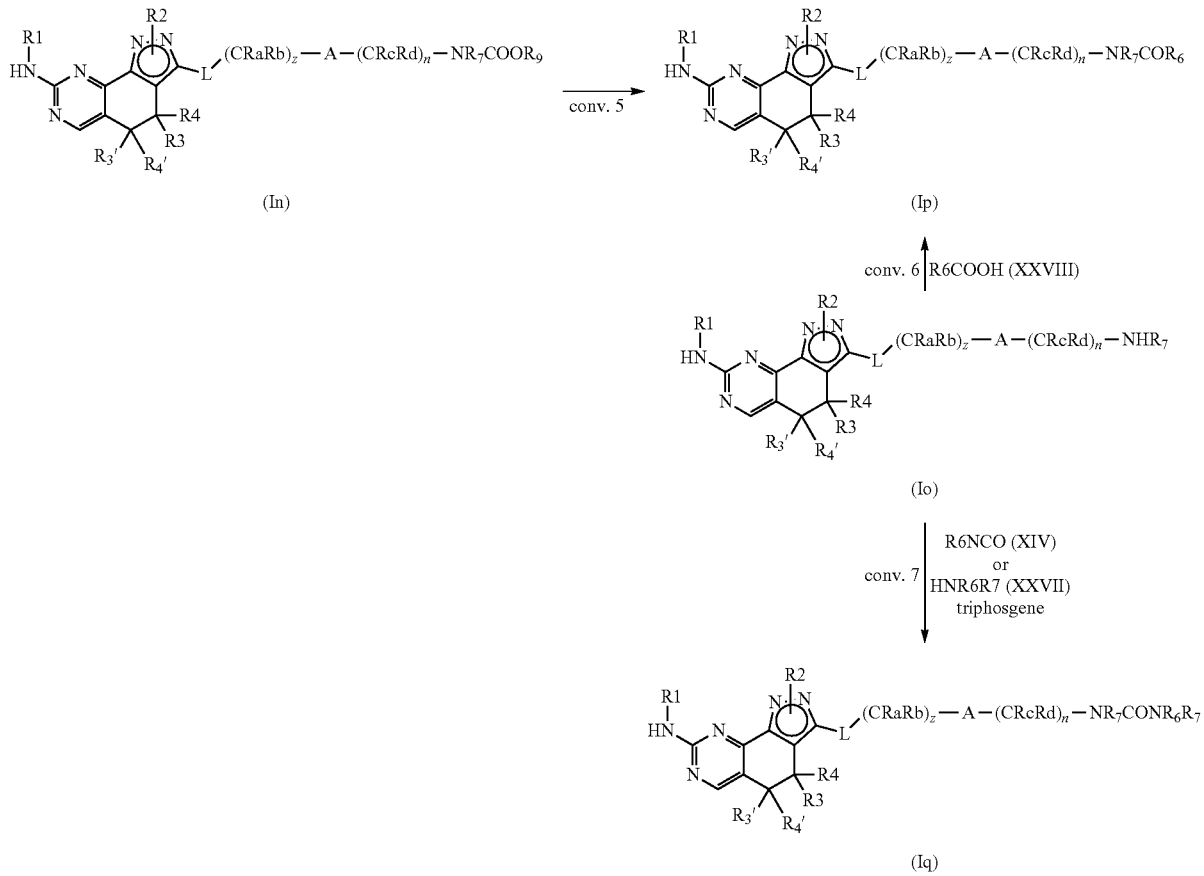

According to Scheme 5, a process of the present invention comprises:

conv. 5) converting a compound of formula (In), wherein R1, R2, R3, R4, R3', R4', L, R7, A, Ra, Rb, Rc, Rd, z and n are as defined above, and R9 is a straight or branched $(C_1$-$C_6)$alkyl or aryl$(C_1$-$C_6)$alkyl, such as for instance benzyl, into a compound of formula (Io), wherein R1, R2, R3, R4, R3', R4', L, R7, A, Ra, Rb, Rc, Rd, z and n are as defined above:

conv. 6) converting the resulting compound of formula (Io), as defined in conv. 5, into a compound of formula (Ip), wherein R1, R2, R3, R4, R3', R4', L, R6, R7, A, Ra, Rb, Rc, Rd, z and n are as defined above, by reaction with a reagent of formula R6COOH (XXVIII), as defined in step a";

conv. 7) converting a first compound of formula (Io), as defined in conv. 5, into a second compound of formula (Iq), wherein R1, R2, R3, R4, R3', R4', L, R6, R7, A, Ra, Rb, Rc, Rd, z and n are as defined above, by reaction with an isocyanate of formula R6NCO (XIV), wherein R6 is as defined above, or with an amine of general formula HNR6R7 (XXVII), as defined in step a", and triphosgene.

According to conv. 5, the reaction can be carried out as described for conv. 2.

According to conv. 6, a compound of formula (Io), as defined above, is converted into a compound of formula (Ip) as described for step a".

According to conv. 7, a compound of formula (Io), as defined above, is reacted with an isocyanate of formula R6NCO (XIV), as defined above, in a suitable solvent such as DCM or THF, normally at a temperature ranging from about −10° C. to reflux and for a time varying from about 30 minutes to about 96 h. Alternatively an amine of general formula HNR6R7 (XXVII), as defined above, can be reacted with triphosgene (bis(trichloromethyl) carbonate, O=C(OCCl$_3$)$_2$) followed by the addition of the compound of formula (Io), as defined above. This reaction can be carried out in the presence of a base such as DIPEA, TEA and Na$_2$CO$_3$, in a solvent such as DCM, chloroform, at a temperature ranging from about −10° C. to reflux and for a time varying from about 30 minutes to about 96 h.

Conversions from 2 to 7 and steps from c to f described above can also be carried out on intermediates of formula (IIa),

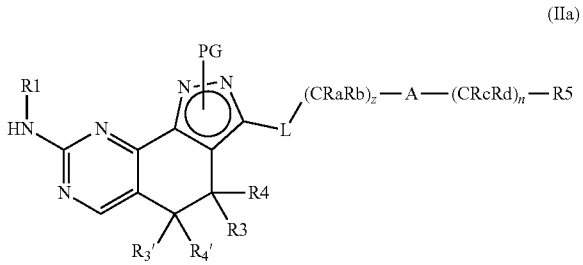

wherein PG is a suitable protecting group that is not removed during R5 manipulation. For example when R5 is —NR7COOR9 and PG is —COOR10, then R9 is a straight (C$_1$-C$_6$)alkyl, such as for instance methyl or ethyl, and R10 is a branched (C$_1$-C$_6$)alkyl, such as tert-butyl, or an aryl(C$_1$-C$_6$)alkyl, such as for instance benzyl.

Intermediate compounds of formula (IIIa) and (Va) can be prepared according to the synthetic procedures reported in WO2004/104007 (Example 14, pag. 86; example 16, pag. 91; example 49, pag. 145).

Intermediate compounds of formula (IIIb) can be prepared according to the general synthetic processes described in Scheme 6.

an intermediate of formula (IIIb)', as defined in step h, into an intermediate of formula (IIIb), wherein R1, R3, R4, R3', R4' and PG are as defined above and R8 is an optionally substituted a straight or branched (C$_1$-C$_6$)alkyl, by reaction with a reagent of formula R11R12CO (XVII), wherein R11 and R12 are independently hydrogen or an optionally substituted straight or branched (C$_1$-C$_6$)alkyl, under reductive amination conditions;
or
step i) alkylating an intermediate of formula (XVI), as described in step g, to yield an intermediate of general

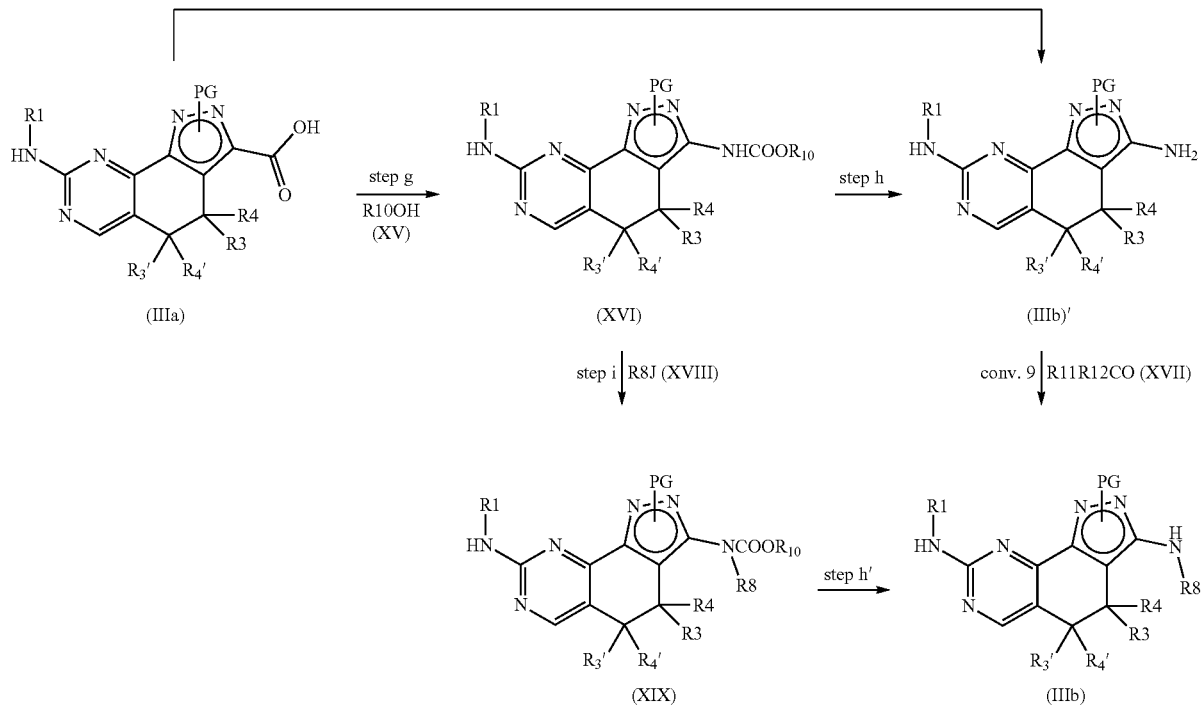

According to Scheme 6, a process of the present invention comprises:
conv. 8) converting an intermediate compound of general formula (IIIa), wherein R1, R3, R4, R3' and R4' are as defined above and PG is a suitable pyrazole nitrogen protecting group, such as for instance trityl, tetrahydropyranyl, 2-(trimethylsilyl)ethoxymethyl (SEM) or —COOR10, wherein R10 is a straight or branched (C$_1$-C$_6$)alkyl or aryl(C$_1$-C$_6$)alkyl, into an intermediate of general formula (IIIb)', wherein R1, R3, R4, R3', R4' and PG are as defined above, under Curtius rearrangement conditions;
alternatively:
step g) reaction of an intermediate compound of general formula (IIIa), as defined in conv. 8, with an alcohol of general formula R10OH (XV), wherein R10 is a straight or branched (C$_1$-C$_6$)alkyl or aryl(C$_1$-C$_6$)alkyl, to yield an intermediate compound of formula (XVI), wherein R1, R3, R4, R3', R4', PG and R10 as defined as above, under Curtius rearrangement conditions; and
step h) deprotecting an intermediate of formula (XVI), as defined in step g, to yield an intermediate of general formula (IIIb)', wherein R1, R3, R4, R3', R4' and PG are as defined above and, as described in conv. 5; then conv. 9) converting formula (XIX), wherein R1, R3, R4, R3', R4', R8, R10 and PG are as defined above, with a reagent of formula R8J (XVIII), wherein R8 is as defined above and J is selected from the group consisting of bromo, iodo, hydroxy, methansulfonyl (-OMs) and p-toluensulfonyl (-OTs); and step h') deprotecting an intermediate of formula (XIX), as defined in step i, as described in conv. 5.

According to conv. 8, an intermediate of formula (IIIa), as defined above, is reacted with diphenylphosphoryl azide (DPPA) in the presence of a base such as TEA, DIPEA, in a solvent like 1,4-dioxane, benzene, toluene and with the addition of an inorganic acid such as hydrochloric acid, at a temperature ranging from room temperature to reflux and for a suitable time, for instance from about 30 minutes to about 24 h. Alternatively, the carboxylic acid is converted into the corresponding acyl chloride in the presence of an activating agent such as thionyl chloride, oxalyl chloride, cyanuric chloride or 1-chloro-N,N,2-trimethylpropenylamine (Ghosez's reagent) neat or in a suitable solvent, such as toluene or DCM, optionally in the presence of a catalytic amount of DMF, at a temperature ranging from about −10° C. to reflux and for a suitable time, for instance from about 30 minutes to about 4 h. Said acyl chloride is then treated with sodium azide (NaN$_3$) or trimethylsylylazide (TMSN$_3$), with the addition of an inorganic acid such as hydrochloric acid, at a temperature ranging from room temperature to reflux and for a suitable time, for instance from about 30 minutes to about 24 h.

According to step g, an intermediate of general formula (IIIa), as defined above, is reacted with diphenylphosphoryl azide (DPPA) in the presence of a base such as TEA, DIPEA, in a solvent like 1,4-dioxane, benzene, toluene and with the addition of R10OH (XV), wherein R10 is as defined above, at a temperature ranging from room temperature to reflux and for a suitable time, for instance from about 30 minutes to about 24 h. Alternatively, the carboxylic acid is converted into the corresponding acyl chloride in the presence of an activating agent such as thionyl chloride, oxalyl chloride, cyanuric chloride or 1-chloro-N,N,2-trimethylpropenylamine (Ghosez's reagent) neat or in a suitable solvent, such as toluene or DCM, optionally in the presence of a catalytic amount of DMF, at a temperature ranging from about −10° C. to reflux and for a suitable time, for instance from about 30 minutes to about 4 h. Said acyl chloride is then treated with sodium azide (NaN$_3$) or trimethylsylylazide (TMSN$_3$) with the addition of R10OH (XV), at a temperature ranging from room temperature to reflux and for a suitable time, for instance from about 30 minutes to about 24 h.

According to step h, the deprotection of intermediate (XVI) can be carried out as described for conv. 5.

According to conv. 9, the reaction can be carried out as described for conv. 4.

According to step i, the reaction can be carried out as described for conv. 1.

According to step h', the reaction can be carried out as described for step h.

Intermediate compounds of formula (Vb) can be prepared according to the general synthetic processes described in Scheme 7.

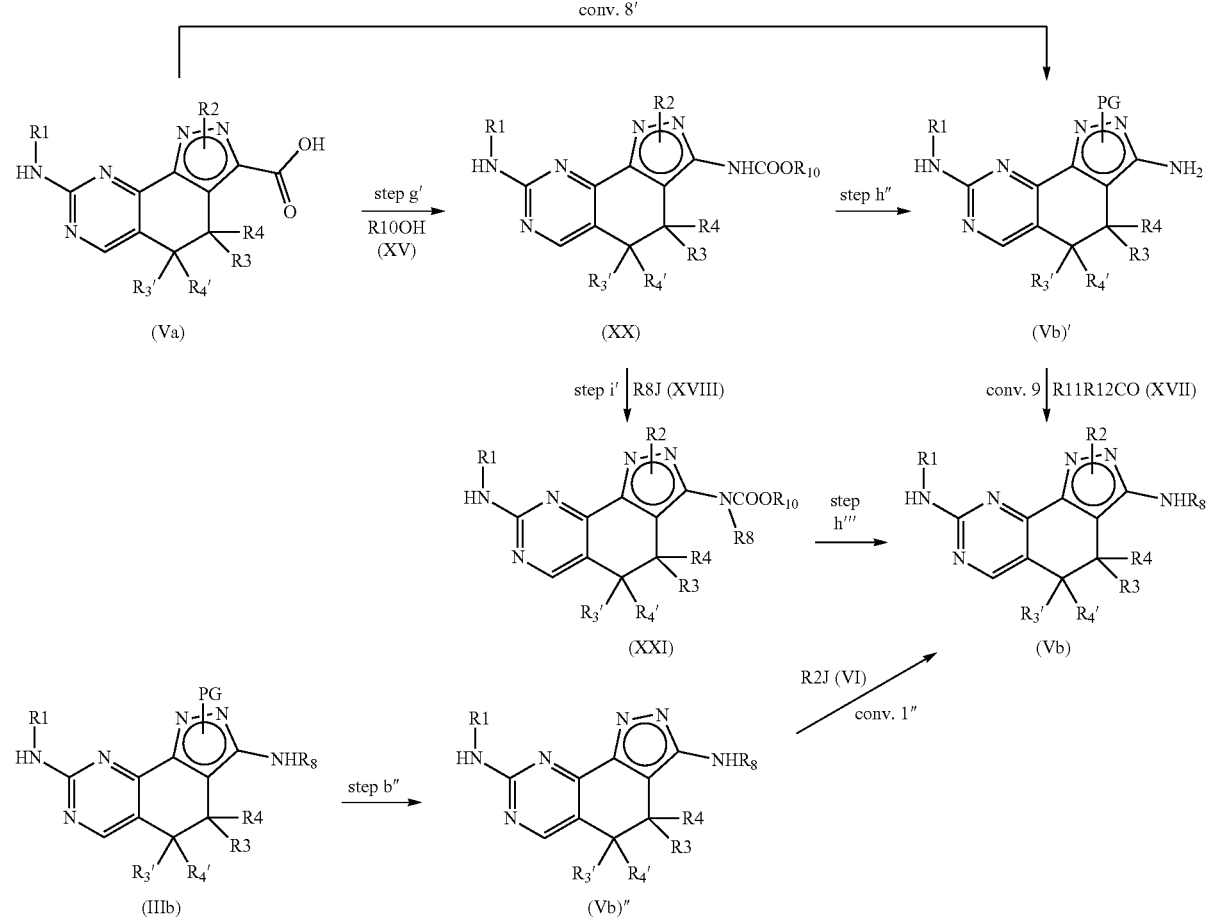

Scheme 7

According to Scheme 7, a process of the present invention comprises:

conv. 8') converting an intermediate compound of general formula (Va), wherein R1, R2, R3, R4, R3' and R4' are as defined above, into an intermediate of formula (Vb)', wherein R1, R2, R3, R4, R3' and R4' are as defined above, as described in conv. 8;

step g') reaction of an intermediate compound of formula (Va), as defined in conv. 8', with an alcohol of formula R10OH (XV), wherein R10 is a straight or branched (C$_1$-C$_6$)alkyl, to yield an intermediate compound of formula (XX), wherein R1, R2, R3, R4, R3', R4' and R10 as defined above, as described in step g;

step h") deprotecting an intermediate of formula (XX), as defined in step g', to yield an intermediate of formula (Vb)', wherein R1, R2, R3, R4, R3' and R4' are as defined above, as described in conv. 5;

conv. 9') converting an intermediate of formula (Vb)', as defined in step h", into an intermediate of formula (Vb), wherein R1, R2, R3R4, R3' and R4' are as defined above and R8 is an optionally substituted straight or branched ($C_1$-$C_6$) alkyl, by reaction with a reagent of formula R11R12CO (XVII), wherein R11 and R12 are independently hydrogen or an optionally substituted straight or branched ($C_1$-$C_6$) alkyl, as described in conv. 9;

step i') alkylating an intermediate of formula (XX), as described in step g', to yield an intermediate of formula (XXI), wherein R1, R2, R3, R4, R3' and R4' are as defined above and R8 is as defined above except hydrogen, with a reagent of formula R8J (XVIII), wherein R8 is as defined above except hydrogen and J is selected from the group consisting of bromo, iodo, hydroxy, methansulfonyl (-OMs) and p-toluensulfonyl (-OTs);

step h''') deprotecting an intermediate of formula (XXI), as defined in step i', as described in conv. 5;

alternatively:

step b") deprotecting an intermediate of formula (IIIb), as defined in conv. 9, to yield an intermediate of general formula (Vb)", wherein R1, R3, R4, R3', R4' and R8 are as defined above, as described in step b; conv. 1") converting an intermediate of general formula (Vb)", wherein R1, R3, R4, R3', R4' and R8 are as defined above and R2 is hydrogen, as defined in step b", into an intermediate of general formula (Vb), wherein R1, R2, R3, R4, R3', R4' and R8 are as defined above, as described for conv. 1.

According to conv. 8', the reaction can be carried out as described for conv. 8.

According to step g', the reaction can be carried out as described for step g.

According to step h", the reaction can be carried out as described for step h.

According to conv. 9', the reaction can be carried out as described for conv. 9.

According to step i', the reaction can be carried out as described for step i.

According to step h''', the reaction can be carried out as described for step h.

According to step b", the reaction can be carried out as described for step b.

According to conv. 1", the reaction can be carried out as described for conv. 1.

Conversions from 2 to 7 and steps from c to f described above can also be carried out on intermediates of formula (XXII),

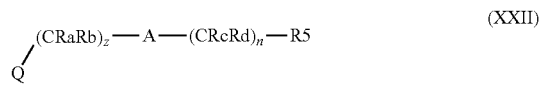

(XXII)

wherein Q is —NR8COOR10 or —COOR10 and R8 and R10 are as defined above. Moreover, —COOR10 is a suitable group that is not removed during R5 manipulation. For example, when R5 is —COOR6 or —NR7COOR9, then R6 or R9 are a straight ($C_1$-$C_6$)alkyl, such as for instance methyl or ethyl, and R10 is a branched ($C_1$-$C_6$)alkyl, such as tert-butyl, or an aryl($C_1$-$C_6$)alkyl, such as for instance benzyl.

Intermediate compounds of general formula (IV), as defined above, can be obtained by deprotection of intermediates of formula (XXII) according to well-known synthetic conditions:

step l) deprotecting intermediate compounds of formula (XXII), wherein A, R5, Ra, Rb, Rc, Rd, z and n are as defined above and Q is —NR8COOR10 or —COOR10, wherein R8 and R10 are as defined above, to yield intermediate compounds of formula (IV), wherein A, R5, Ra, Rb, Rc, Rd, z and n are as defined above and X is NHR8 or —COOH.

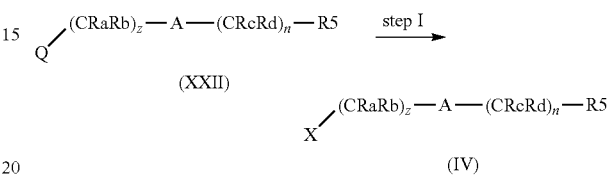

According to step l, the deprotection of an intermediate compound of general formula (XXII) can be carried out as described for conv. 2 or conv. 5.

When preparing the compounds of general formula (I) according to any of the above variants of the process, optional functional groups within the starting materials, the reagents or the intermediates thereof, and which could give rise to unwanted side reactions, need to be properly protected according to conventional techniques. Likewise, the conversion of these latter into the free deprotected compounds may be carried out according to known procedures.

The compounds of every general formula can be further transformed in other compounds of the same general formula according to methods well known in the literature, as reported in the experimental section.

The final compounds may be isolated and purified using conventional procedures, for example chromatography and/or crystallization and salt formation.

The compounds of general formula (I) as defined above can be converted into pharmaceutically acceptable salts.

The compounds of general formula (I) as defined above, or the pharmaceutically acceptable salts thereof, can be subsequently formulated with a pharmaceutically acceptable carrier or diluent to provide a pharmaceutical composition.

The synthesis of a compound of general formula (I), according to the synthetic processes described above, can be conducted in a stepwise manner, whereby each intermediate is isolated and purified if needed by standard purification techniques, like, for example, column chromatography, before carrying out the subsequent reaction. Alternatively, two or more steps of the synthetic sequence can be carried out in a so-called "one-pot" procedure, as known in the art, whereby only the compound resultant from the two or more steps is isolated and purified.

In cases where a compound of general formula (I) contains one or more asymmetric centers, said compound can be separated into the single stereoisomers by procedures known to those skilled in the art. Such procedures comprise standard chromatographic techniques, including chromatography using a chiral stationary phase, or crystallization. General methods for separation of compounds containing one or more asymmetric centers are reported, for instance, in Jacques, Jean; Collet, André; Wilen, Samuel H., Enantiomers, Racemates, and Resolutions, John Wiley & Sons Inc., New York (N.Y.), 1981.

From all of the above, the novel compounds of formula (I) of present invention appear to be particularly advantageous in the therapy of diseases caused by altered choline metabolism, in particular cancer.

The compounds of the present invention can be administered either as single agents or, alternatively, in combination with known anticancer treatments such as radiation therapy or chemotherapy regimen in combination with, for example, antihormonal agents such as antiestrogens, antiandrogens and aromatase inhibitors, topoisomerase I inhibitors, topoisomerase II inhibitors, agents that target microtubules, platin-based agents, alkylating agents, DNA damaging or intercalating agents, antineoplastic antimetabolites, other kinase inhibitors, other anti-angiogenic agents, inhibitors of kinesins, therapeutic monoclonal antibodies, inhibitors of mTOR, histone deacetylase inhibitors, farnesyl transferase inhibitors, and inhibitors of hypoxic response.

If formulated as a fixed dose, such combination products employ the compounds of this invention within the dosage range described below and the other pharmaceutically active agent within the approved dosage range.

Compounds of formula (I) may be used sequentially with known anticancer agents when a combination formulation is inappropriate.

The compounds of formula (I) of the present invention, suitable for administration to a mammal, e.g. to humans, can be administered by the usual routes and the dosage level depends upon the age, weight, and conditions of the patient and administration route.

For example, a suitable dosage adopted for oral administration of a compound of formula (I) may range from about 1 to about 1000 mg per dose, from 1 to 5 times daily. The compounds of the invention can be administered in a variety of dosage forms, e.g. orally, in the form of tablets, capsules, sugar or film coated tablets, liquid solutions or suspensions; rectally in the form of suppositories; parenterally, e.g. intramuscularly, or through intravenous and/or intrathecal and/or intraspinal injection or infusion.

The present invention also includes pharmaceutical compositions comprising a compound of formula (I) or a pharmaceutically acceptable salt thereof in association with a pharmaceutically acceptable excipient, which may be a carrier or a diluent.

The pharmaceutical compositions containing the compounds of the invention are usually prepared following conventional methods and are administered in a suitable pharmaceutical form.

For example, the solid oral forms may contain, together with the active compound, diluents, e.g. lactose, dextrose, saccharose, sucrose, cellulose, corn starch or potato starch; lubricants, e.g. silica, talc, stearic acid, magnesium or calcium stearate, and/or polyethylene glycols; binding agents, e.g. starches, arabic gum, gelatine methylcellulose, carboxymethylcellulose or polyvinyl pyrrolidone; disintegrating agents, e.g. starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. These pharmaceutical preparations may be manufactured in known manner, for example, by means of mixing, granulating, tabletting, sugar-coating, or film-coating processes.

The liquid dispersions for oral administration may be, e.g. syrups, emulsions and suspensions.

As an example the syrups may contain, as a carrier, saccharose or saccharose with glycerine and/or mannitol and sorbitol.

The suspensions and the emulsions may contain, as examples of carriers, natural gum, agar, sodium alginate, pectin, methylcellulose, carboxymethylcellulose or polyvinyl alcohol.

The suspension or solutions for intramuscular injections may contain, together with the active compound, a pharmaceutically acceptable carrier, e.g. sterile water, olive oil, ethyl oleate, glycols, e.g. propylene glycol and, if desired, a suitable amount of lidocaine hydrochloride.

The solutions for intravenous injections or infusions may contain, as a carrier, sterile water or preferably they may be in the form of sterile, aqueous, isotonic, saline solutions or they may contain propylene glycol as a carrier.

The suppositories may contain, together with the active compound, a pharmaceutically acceptable carrier, e.g. cocoa butter, polyethylene glycol, a polyoxyethylene sorbitan fatty acid ester surfactant or lecithin.

EXPERIMENTAL PART

Biology
Protein Production

HumanΔ49ChoKα (□□Δ49N-hChoKα) cDNA fragment 362-1534, corresponding to aminoacids 50 457 (*J. Mol. Biol.* 2006, 364, 136-151), and hChoKβ full length (FL), corresponding to aminoacids 2-395 ((*PLoS ONE* 2009, 4, e7819), were amplified by PCR from human library and cloned, inserting upstream a Prescission Protease recognition site, in pDonor 221 vector, using the Gateway Technology® (Invitrogen). After sequence control, LR reaction was performed in the final expression pGEX 2Tg vector. Both the proteins were expressed in *Escherichia coli* BL21pLysS (DE3) strain in auto-induction (Kessler) medium in the presence of 50 mg/mL carbenicillin at 25° C. for 16 h. Cells were harvested by centrifugation, the pellet was re-suspended in Lysis buffer (50 mM Tris-HCl pH 7.8, 150 mM NaCl, 10% glycerol, 0.2% CHAPS, 20 mM DTT, Protease Inhibitor Cocktail Tablets from Roche Biochemicals) and lysed by Gaulin homogenizer (Niro Soavi). The lysate was cleared by centrifugation. The supernatant was added to GSH resin and let flow by gravity. The GSH resin was washed with 5 column volume (CV) of cold wash buffer (50 mM Tris-HCl pH 7.8, 150 mM NaCl, 10% glycerol), then with 10 CV of the same buffer containing 2 mM of DTT. Both GST-Δ49N-hChoKα and hChoKβ were subjected to on-column cleavage of the GST tag with Prescission Protease overnight. The eluted cleaved proteins were further purified by ion exchange (ResQ 6 mL chromatography column from GE healthcare) with a gradient from 50 to 500 mM NaCl in 30 CV. The fractions containing □□Δ49N-hChoKα or hChoKβ were pooled, concentrated and gel filtered on a Superdex200 16/60 (GE Healthcare). The final protein concentration was estimated using the Bradford assay. All the samples purified were resolved by SDS-PAGE.
Biochemical Kinase inhibition Assay on Δ49N-hChoKα and hChoKβFL The biochemical activity of compounds against Δ49N-ChoKα and ChoK3 FL were determined using the Kinase-Glo™ Luminescent Kinase Assay (Promega cat. V6711). The assay is based on incubation of the recombinant Δ49N-hChoKα and hChoKβ FL produced in house, 2.2 nM and 30 nM, respectively, with the specific substrates, choline (Sigma-Aldrich-C7017) and ATP, followed by quantification, at the end of reaction time, of the residual not reacted ATP.

Compounds were 3-fold serially diluted from 10 to 0.0005 μM, then incubated for 60 minutes at room temperature in the presence of ATP 5 µM, choline (5 µM for ChoKα and 20 µM for ChoKβ) and enzyme in a final volume of 19 µL of kinase buffer (50 mM Hepes pH 7.5, 10 mM MgCl₂, 1 mM DTT, 3 µM Na₃VO₄ and 0.2 mg/mL BSA). The final concentration of DMSO was 1%. The assay was run in a robotized format on 384-well plates (Perkin Elmer cat. #6005301).

At the end of the incubation, an amount of 19 µL of KinaseGlo Reagent was added to each well to stop the reaction and after 30 minutes the luminescence signal was measured using ViewLux reader (Perkin Elmer).

Each 384-well plate contained at least one curve of a standard cpd, and reference wells (total enzyme activity vs enzyme completely inhibited) for the Z' and signal to background evaluation (J. Biomol. Screening, 1999, 4, 67-73).

All information about plate dilution, distribution and raw data of inhibition are tracked via barcode reading and stored in an Oracle DB. The data per each molecule are analyzed by an internally customized version of the SW package "Assay Explorer" which provides sigmoidal fittings of the ten-dilution curves for IC$_{50}$ determination using a 4 parameter logistic equation:

$$y = \text{bottom} + (\text{top} - \text{bottom})/(1 + 10^{((\log IC_{50} - x) * \text{slope})})$$

where x is the logarithm of the inhibitor concentration, y is the response;

y starts at bottom and goes to top with a sigmoid shape.

The Kinase-Glo™ assay is more suitable than the NADH coupled assay reported in the literature for the screening of a library of compounds in terms of cost, automation procedure and sensitivity in the assay conditions described above.

Biochemical Activity

Biochemical potencies both on ChoKα and ChoKβ of representative compounds, which were determined according to the above described assays, are reported in Table 1 as IC$_{50}$ values (µM, NT=Not Tested), in comparison with the closest compounds of the prior art (Ref. compounds 1, 2, 3 and 4), described in WO2004/104007 (page 119, Table XI, compounds B73-X00-M03(C01)-D03 and B73-X00-M03 (C01)-D04; page 185, Example 61, compounds B00-X00-M03(C01)-D03 and B00-X00-M03(C01)-D04), having the following structures:

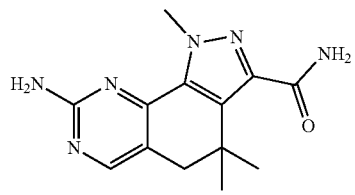

Ref. cpd 1

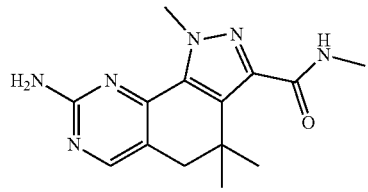

Ref. cpd 2

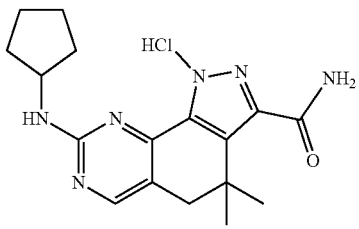

Ref. cpd 3

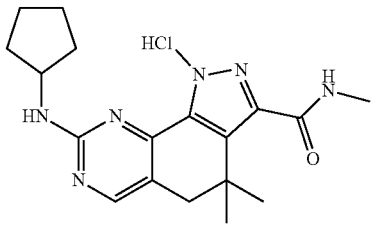

Ref. cpd 4

TABLE 1

| cpd | ChoKα IC$_{50}$ (µM) | ChoKβ IC$_{50}$ (µM) |
|---|---|---|
| 1 | 0.257 | 1.584 |
| 2 | 0.247 | 0.974 |
| 3 | 0.992 | >10 |
| 4 | 0.244 | 1.120 |
| 5 | 0.481 | 2.590 |
| 6 | 0.735 | 0.317 |
| 8 | 0.087 | 0.565 |
| 9 | 0.693 | 5.392 |
| 10 | 0.173 | 0.817 |
| 11 | 0.195 | 0.395 |
| 13 | 0.042 | 0.122 |
| 14 | 0.198 | 0.037 |
| 16 | 0.075 | 0.063 |
| 17 | 0.795 | 2.285 |
| 18 | 0.641 | 6.350 |
| 20 | 0.024 | 0.076 |
| 25 | 0.253 | 0.625 |
| 26 | 0.266 | 0.435 |
| 27 | 0.267 | 0.444 |
| 28 | 0.511 | 3.106 |
| 29 | 0.132 | 0.071 |
| 30 | 0.110 | 0.136 |
| 31 | 0.257 | 0.431 |
| 32 | 0.066 | 1.092 |
| 33 | 0.430 | >10 |
| 34 | 0.748 | >10 |
| 35 | 0.047 | 0.439 |
| 36 | 0.480 | >10 |
| 37 | 0.003 | 0.069 |
| 38 | 0.682 | >10 |
| 39 | 0.002 | 0.084 |
| 41 | 0.070 | 0.471 |
| 42 | 0.054 | >10 |
| 43 | 0.007 | 1.033 |
| 44 | 0.025 | 0.256 |
| 45 | 0.121 | >10 |
| 46 | 0.110 | 1.623 |
| 47 | 0.002 | 0.086 |
| 49 | 0.623 | 0.765 |
| 50 | 0.215 | 0.716 |
| 51 | 0.151 | 0.273 |
| 52 | 0.003 | 0.070 |
| 53 | 0.715 | 3.513 |
| 56 | 0.210 | 0.810 |
| 58 | 0.002 | 0.081 |
| 59 | 0.032 | 0.734 |
| 61 | 0.241 | 2.630 |
| 62 | 0.085 | 0.465 |
| 63 | 0.026 | 0.447 |

TABLE 1-continued

| cpd | ChoKα IC$_{50}$ (μM) | ChoKβ IC$_{50}$ (μM) |
|---|---|---|
| 64 | 0.306 | 4.918 |
| 65 | 0.139 | 1.610 |
| 66 | 0.710 | 5.811 |
| 67 | 0.081 | 0.703 |
| 68 | 0.161 | >10 |
| 69 | 0.036 | 0.088 |
| 70 | 0.035 | 1.078 |
| 71 | 0.009 | 1.951 |
| 72 | 0.268 | 2.513 |
| 73 | 0.138 | 0.604 |
| 74 | 0.079 | 1.351 |
| 75 | 0.047 | 1.749 |
| 77 | 0.200 | 1.155 |
| 78 | 0.218 | 2.586 |
| 79 | 0.069 | 2.377 |
| 80 | 0.005 | 3.156 |
| 81 | 0.428 | 5.340 |
| 82 | 0.300 | 1.725 |
| 84 | 0.111 | 1.327 |
| 85 | 0.052 | >10 |
| 86 | 0.057 | 1.387 |
| 87 | 0.149 | >10 |
| 88 | 0.141 | >10 |
| 89 | 0.010 | 0.400 |
| 90 | 0.161 | >10 |
| 91 | 0.098 | >10 |
| 92 | 0.228 | >10 |
| 93 | 0.012 | 0.761 |
| 94 | 0.073 | 1.417 |
| 95 | 0.015 | 0.126 |
| 96 | 0.198 | 0.934 |
| 98 | 0.057 | 1.294 |
| 105 | 0.229 | 0.398 |
| 106 | 0.343 | 5.196 |
| 107 | 0.737 | 2.685 |
| 108 | 0.005 | 3.967 |
| 109 | 0.431 | >10 |
| 110 | 0.135 | 2.851 |
| 111 | 0.640 | >10 |
| 112 | 0.187 | 2.126 |
| 114 | 0.562 | 2.394 |
| 116 | 0.004 | 0.077 |
| 117 | 0.016 | >10 |
| 118 | 0.033 | 0.072 |
| 119 | 0.053 | 0.066 |
| 120 | 0.019 | 0.913 |
| 121 | 0.018 | >10 |
| 122 | 0.011 | >10 |
| 123 | 0.053 | >10 |
| 124 | 0.187 | >10 |
| 125 | 0.096 | 0.480 |
| 126 | 0.003 | 0.592 |
| 127 | 0.617 | >10 |
| 128 | 0.126 | >10 |
| 129 | 0.220 | >10 |
| 130 | 0.534 | >10 |
| 131 | 0.233 | 3.935 |
| 133 | 0.536 | 1.435 |
| 139 | 0.814 | >10 |
| 141 | 0.622 | >10 |
| 142 | 0.110 | 0.671 |
| 143 | 0.142 | 2.159 |
| 144 | 0.546 | 0.688 |
| 145 | 0.011 | 0.928 |
| 146 | 0.065 | 0.551 |
| 147 | 0.594 | >10 |
| 148 | 0.357 | 1.103 |
| 149 | 0.164 | 3.209 |
| 150 | 0.006 | 0.352 |
| 151 | 0.174 | 5.341 |
| 152 | 0.534 | >10 |
| 153 | 0.018 | >10 |
| 154 | 0.014 | 0.564 |
| 155 | 0.629 | >10 |
| 156 | 0.003 | 0.249 |
| 157 | 0.006 | 0.292 |
| 160 | 0.025 | 2.214 |
| 161 | 0.507 | >10 |
| 165 | 0.180 | 0.069 |
| 166 | 0.136 | 0.134 |
| 170 | 0.017 | 0.887 |
| 182 | 0.458 | >10 |
| 183 | 0.013 | 0.654 |
| 189 | 0.031 | 1.560 |
| 190 | 0.008 | 0.546 |
| 191 | 0.007 | 0.303 |
| 209 | 0.005 | 0.230 |
| 211 | 0.108 | >10 |
| 212 | 0.008 | 0.457 |
| 213 | 0.016 | 0.450 |
| 217 | 0.018 | 3.554 |
| 218 | 0.002 | 0.254 |
| 219 | 0.002 | 0.296 |
| 220 | 0.030 | 1.380 |
| 221 | 0.010 | 0.782 |
| 222 | 0.010 | 1.648 |
| 223 | 0.004 | 0.184 |
| 224 | 0.005 | 0.213 |
| 225 | 0.009 | 2.259 |
| 226 | 0.020 | 0.376 |
| 227 | 0.002 | 0.026 |
| 228 | 0.009 | 0.963 |
| 229 | 0.018 | 0.840 |
| 230 | 0.024 | 0.594 |
| 231 | 0.003 | 0.104 |
| 232 | 0.008 | 0.146 |
| Ref. cpd 1 | >10 | NT |
| Ref. cpd 2 | >10 | NT |
| Ref. cpd 3 | >10 | NT |
| Ref. cpd 4 | >10 | NT |

From the above data, it is clear to the person skilled in the art that compounds of formula (I) of the present invention are highly potent as ChoK inhibitors.

Phosphocholine Determination Assay (Demonstration of Target Inhibition in Cells)

For the determination of phosphocholine in cells, extracts were prepared according to ref. Cancer Res., 2005, 65, 9369-9376 with some modifications. MDA-MB-468 breast cancer cell line was plated at 1×10$^6$ cells in 10 cm petri dish culture in RPMI, 10% FCS culture medium. After 24 h, fresh medium and a compound of general formula (I) were added for further 24 h. At the end of the treatment, the cells were trypsinised, counted and the diameter was determined using a Coulter Counter (Multisizer 3, Beckman). Cells were washed twice with ice-cold physiologic saline solution and 2×10$^6$ cells resuspended in 0.3 mL ice-cold twice-distilled water. Then, 0.7 mL ice-cold absolut EtOH were added (final ratio EtOH/H$_2$O 70:30, v/v). After 24 h at −20° C. the samples were sonicated and centrifuged at 14,000×g for 30 minutes.

Phosphocholine concentration levels were assessed in the supernatants using an Ultra High Pressure Liquid Chromatography system (UPLC®, Waters) coupled with a triple quadrupoles mass spectrometer (TQD, Waters) operating in single reaction monitoring mode (SRM). Analyses were performed using Acquity HSS T3 column 2.1×50 mm column, 1.8 μm particle size. Mobile phase A was H$_2$O, modified with 0.15% formic acid, and mobile phase B was MeOH (100% A→97% A over 1 min, flow rate 0.5 mL/min). Waters TQD triple quad mass spectrometer was equipped with an electrospray ion source operating in the positive mode. Source parameters were set as follows: desolvation gas flow 1000 L/h, cone gas flow 50 L/h; collision gas flow 0.2 mL/min; source temperature 130° C.; desolvation temperature 450° C. Dimethyl glicine (DMG) was added to samples as internal standard at 100 μM final concentration. The monitored transitions were m/z 184.00 to 85.7 (collision energy 24 eV) for phosphocholine and m/z 103.0 to 57.5 (collision energy 13 eV) for DMG. The concentration of PCho in the sample was normalized to the total volume of cells (number cells×volume of single cell considered like a sphere).

As an example, the mechanism of action of cpd 39 is reported in Table 2 (Control refers to untreated cells).

TABLE 2

| Cpd 39 | [Phosphocholine] in MDA-MB-468 cell extracts | |
| --- | --- | --- |
| Concentration | mM | Inhibition |
| 0 μM (Control) | 6.34 | — |
| 0.08 μM | 4.12 | 35% |
| 0.4 μM | 0.82 | 87% |
| 2 μM | 0.10 | 98% |

For the determination of phosphocholine in cell culture medium, cell culture supernatants (500 μL) were denatured by adding 100 μL of trichloroacetic acid (TCA) 1M containing dimethyl glicine (DMG) (100 μM), used as internal standard. Samples were mildly vortexed for 10 minutes and centrifuged at 14,000×g for 3 min. The supernatants were subsequently analyzed for phosphocholine determination.

As an example, the mechanism of action of cpd 39 is reported in Table 3 (Control refers to untreated cells).

TABLE 3

| Cpd 39 | [Phosphocholine] in MDA-MB-468 cell supernatants | |
| --- | --- | --- |
| Concentration | μM | Inhibition |
| 0 μM (Control) | 10.0 | — |
| 0.08 μM | 5.8 | 42% |
| 0.4 μM | 1.5 | 85% |
| 2 μM | 1.2 | 88% |

Preparation of Compounds of Formula (I)

For a reference to any specific compound of formula (I) of the invention, optionally in the form of a pharmaceutically acceptable salt, see the experimental section and claims. Referring to the examples that follow, compounds of the present invention were synthesized using the methods described herein, or other methods, which are well known in the art.

The short forms and abbreviations used herein have the following meaning:

| | |
| --- | --- |
| g (grams) | mg (milligrams) |
| mL (milliliters) | μL (microliters) |
| mM (millimolar) | mmol (millimoles) |
| μM (micromolar) | MHz (Mega-Hertz) |
| h (hours) | Hz (Hertz) |
| mm (millimeters) | min (minutes) |
| μm (micron) | h (hour/s) |
| M (molar) | KOtBu (potassium tert-butoxide) |
| rt (room temperature) | TEA (triethylamine) |
| DMAP (4-dimethylaminopyridine) | DME (1,2-dimethoxyethane) |
| TFA (trifluoroacetic acid) | Na$_2$SO$_4$ (sodium sulphate) |
| AcOH (acetic acid) | ESI (electrospray ionization) |
| Na$_2$CO$_3$ (sodium carbonate) | K$_2$CO$_3$ (potassium carbonate) |
| Cs$_2$CO$_3$ (caesium carbonate) | K$_3$PO$_4$ (potassium phosphate) |
| LiOH (lithium hydroxide) | NaOH (sodium hydroxide) |

-continued

| | |
| --- | --- |
| KOH (potassium hydroxide) | p-TsOH (p-toluensulfonic acid) |
| EtOAc (ethyl acetate) | LiHDMS (lithium bis(trimethylsilyl)amide) |
| NMP (N-methyl-2-pyrrolidone) | NaH (sodium hydride) |
| DMA (N,N-dimethylacetamide) | KH (potassium hydride) |
| DMF (N,N-dimethylformamide) | DCM (dichloromethane) |
| DIPEA (N,N-diisopropyl-N-ethylamine) | hex (hexane) |
| THF (tetrahydrofuran) | DMSO (dimethylsulfoxide) |
| MeOH (methanol) | ACN (acetonitrile) |
| EtOH (ethanol) | Bn (benzyl) |
| -Ms (mesylate) | -OTs (tosylate) |
| HOBT (N-hydroxy-benzotriazole) | DCC (1,3-dicyclohexylcarbodiimide) |
| EDCI (1-ethyl-3-(3-dimethylaminopropyl)carbodiimide hydrochloride) | |
| TBTU (N,N,N',N'-tetramethyl-O-(benzotriazol-1-yl)uronium-tetrafluoroborate) | |
| RP-HPLC (reverse phase high performance liquid chromatography) | |
| PL-HCO$_3$ (Polymer linked carbonate resin) | |

With the aim at better illustrating the present invention, without posing any limitation to it, the following examples are given.

As used herein the symbols and conventions used in the processes, schemes and examples are consistent with those used in the contemporary scientific literature, for example, the *Journal of the American Chemical Society* or the *Journal of Biological Chemistry*.

Compound names are IUPAC names, generated by using ACD Name (by Advanced Chemistry Development, Inc.).

Unless otherwise noted, all materials, including anhydrous solvent such as DMF, THF, DCM, were obtained from commercial suppliers, of the best grade and used without further purification. All reactions involving air- or moisture-sensitive compounds were performed under nitrogen or argon atmosphere.

General Purification and Analytical Methods

Flash Chromatography was performed on silica gel (Merck grade 9395, 60A).

The HPLC equipment consisted of a Waters Alliance™ HT 2795 system equipped with a Waters 996 PDA detector and Waters mod. ZQ 2000 single quadrupole mass spectrometer, equipped with an electrospray (ESI) ion source.

Instrument control, data acquisition and data processing were provided by Empower 2 and MassLynx 4.1 softwares. HPLC was carried out at 25° C. at a flow rate of 1.2 mL/min using a YMC-Triart C18 (4.6×50 mm, 3 μm) column. Mobile phase B was ammonium acetate 5 mM pH=5.2 buffer with acetonitrile (95:5), and mobile phase C was H$_2$O/acetonitrile (5:95); the gradient was from 10 to 90% C in 5 minutes then ramp to 100% C in 0.1 minutes. The injection volume was 10 μL. The mass spectrometer operated in positive and in negative ion mode, the capillary voltage was set up at 3.5 kV (ES$^+$) and 2.8 kV (ES$^-$); cone voltage was 14 V (ES$^+$) and 28 V (ES$^-$); the source temperature was 120° C.; full scan, mass range from 100 to 800 amu was set up.

The preparative HPLC equipment consisted of a Shimadzu HPLC system equipped with SCL-8A System Controller, two LC-8A Pumps, SPD-6A UV Spectrophotometric Detector and manual Rheodyne injection system. Data acquisition (analogic signal) and data processing were provided by Empower 2 software. Purification was carried out at 25° C. at a flow rate of 15 mL/min using a Waters X-Terra MS RP18 (150×30 mm, 10 μm) column. Mobile phase A was 0.1% TFA in water/acetonitrile (95:5) or, alternatively, Mobile phase A was 0.05% NH$_3$ in water/acetonitrile (95:5) and mobile phase B was H$_2$O/acetonitrile (5:95); the gradient was from 10 to 90% B in 15 minutes then ramp to 100% B in 0.1 minutes. Injection volume max 500 µL.

$^1$H-NMR spectra were recorded at a constant temperature of 28° C. on a Varian INOVA 400 spectrometer operating at 400.5 MHz and equipped with a 5 mm $^1$H{$^{15}$N-$^{31}$P} z-axis PFG Indirect Detection probe and on a Varian INOVA 500 spectrometer operating at 499.7 MHz and equipped with a 5 mm $^1$H{$^{13}$C-$^{15}$N} triple resonance Indirect Detection probe. Chemical shifts were referenced with respect to the residual solvent signals (DMSO-d$_6$: 2.50 ppm for $^1$H). Data are reported as follows: chemical shift (δ), multiplicity (s=singlet, d=doublet, t=triplet, q=quartet, br. s=broad singlet, dd=doublet of doublets, ddd=doublet of doublets of doublets, m=multiplet), coupling constants (J, Hz) and number of protons.

As formerly reported (M. Colombo, F. R. Sirtori, V. Rizzo, Rapid Commun Mass Spectrom 2004, 18(4), 511-517), ESI(+) high-resolution mass spectra (HRMS) were obtained on a Q-Tof Ultima (Waters, Manchester, UK) mass spectrometer directly connected with an Agilent 1100 micro-HPLC system (Palo Alto, US).

Example 1

Sequence A or C 8-amino-N-(3-methoxyphenyl)-4,4-dimethyl-4,5-dihydro-1H-pyrazolo[4,3-h]quinazoline-3-carboxamide (I), Cpd 1

[R1=R2=R3'=R4'=H, R3=R4=(C$_1$-C$_6$)alkyl, y=0, L=CONR6aR7a, R6a=substituted aryl, R7a=H]

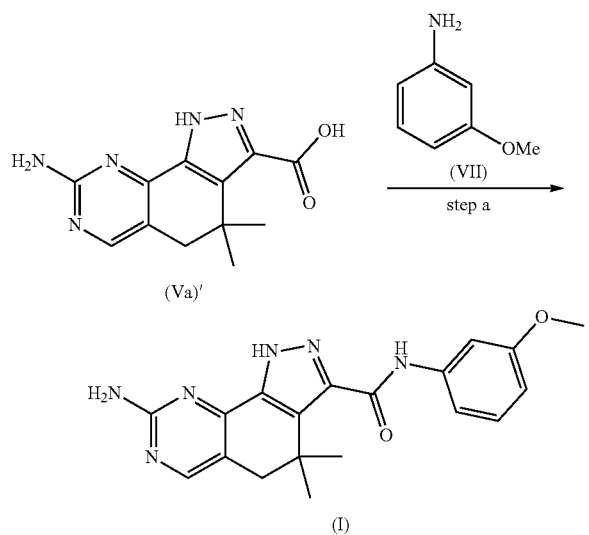

Step a

8-Amino-4,4-dimethyl-4,5-dihydro-1H-pyrazolo[4,3-h]quinazoline-3-carboxylic acid (Va)' (100 mg, 0.386 mmol) in dry DMF (1.5 mL) was treated with 3-methoxyaniline (VII) (0.065 mL, 0.579 mmol), DIPEA (0.099 mL, 0.579 mmol) and finally TBTU (186 mg, 0.579 mmol) and stirred overnight at rt. The reaction mixture was poured into saturated aqueous NaHCO$_3$ (20 mL) and the solid thus obtained filtered under suction, washed thoroughly with water and dried at 50° C., under vacuum. The crude was purified by column chromatography over silica gel (DCM: 7 N NH$_3$ in MeOH=9:1) to give the title compound as whitish solid (57 mg, 40%).

$^1$H NMR (499.7 MHz, DMSO-d$_6$) δ ppm 1.34 (s, 6H), 2.65 (s, 2H), 3.74 (s, 3H), 6.37 (br. s., 2H), 6.66 (dd, J=8.2, 2.0 Hz, 1H), 7.22 (dd, J=8.2, 8.1 Hz, 1H), 7.39 (d, J=8.1 Hz, 1H), 7.49 (s, 1H), 8.19 (s, 1H), 10.20 (s, 1H), 14.06 (s, 1H).

HRMS (ESI+): calcd. for C$_{19}$H$_{21}$N$_6$O$_2$ [M+H]$^+$ 365.1721; found 365.1721.

Alternatively:

after treatment with saturated aqueous NaHCO$_3$, the aqueous layer was extracted with EtOAc (×3) and the organic layer was dried over Na$_2$SO$_4$, filtered and evaporated under vacuum. The product was purified by column chromatography over silica gel.

Operating in an analogous way, but employing suitably substituted reagents (VII) or (IV), the following compounds were obtained:

8-amino-4,4-dimethyl-4,5-dihydro-1H-pyrazolo[4,3-h]quinazoline-3-carboxamide (I), Cpd 173

[R1=R2=R3'=R4'=H, R3=R4=(C$_1$-C$_6$)alkyl, y=0, L=CONR6aR7a, R6a=R7a=H]

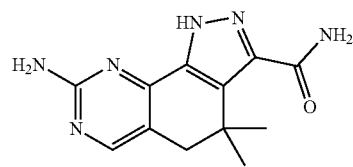 [SMILES: CC1(C)Cc2cnc(N)nc2-c2[nH]nc(C(N)=O)c21]

$^1$H NMR (499.7 MHz, DMSO-d$_6$) δ ppm 1.32 (s, 6H), 2.62 (s, 2H), 6.34 (br. s., 2H), 7.23 (br. s., 1H) 7.55 (br. s., 1H), 8.15 (s, 1H), 13.83 (s, 1H).

HRMS (ESI+): calcd. for C$_{12}$H$_{15}$N$_6$O [M+H]$^+$ 259.1302; found 259.1307.

8-amino-N-(4-methoxyphenyl)-4,4-dimethyl-4,5-dihydro-1H-pyrazolo[4,3-h]quinazoline-3-carboxamide (I), Cpd 2

[R1=R2=R3'=R4'=H, R3=R4=(C$_1$-C$_6$)alkyl, y=0, L=CONR6aR7a, R6a=substituted aryl, R7a=H]

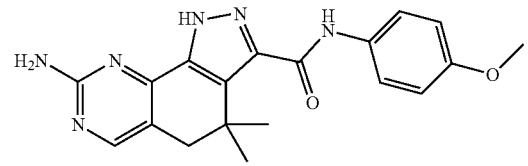 [SMILES: COc1ccc(NC(=O)c2n[nH]c3c2C(C)(C)Cc2cnc(N)nc2-3)cc1]

$^1$H NMR (499.7 MHz, DMSO-d$_6$) δ ppm 1.33 (s, 6H), 2.65 (s, 2H), 3.74 (s, 3H), 6.37 (br. s., 2H), 6.90 (d, J=9.0 Hz, 2H), 7.70 (d, J=9.0 Hz, 2H), 8.18 (s, 1H), 10.11 (s, 1H), 14.01 (s, 1H).

HRMS (ESI+): calcd. for C$_{19}$H$_{21}$N$_6$O$_2$[M+H]$^+$ 365.1721; found 365.1734.

8-amino-4,4-dimethyl-N-[4-(trifluoromethoxy)phe-
nyl]-4,5-dihydro-1H-pyrazolo[4,3-h]quinazoline-3-
carboxamide (I), Cpd 3

[R1=R2=R3'=R4'=H, R3=R4=(C$_1$-C$_6$)alkyl, y=0, L=CONR6aR7a, R6a=substituted aryl, R7a=H]

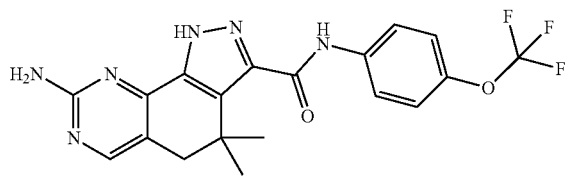 [SMILES: CC1(C)Cc2cnc(N)nc2-c2[nH]nc(C(=O)Nc3ccc(OC(F)(F)F)cc3)c21]

$^1$H NMR (499.7 MHz, DMSO-d$_6$) δ ppm 1.34 (s, 6H), 2.66 (s, 2H), 6.38 (br. s., 2H), 7.34 (d, J=8.8 Hz, 2H), 7.92 (d, J=8.8 Hz, 2H), 8.19 (s, 1H), 10.49 (s, 1H), 14.12 (s, 1H).
HRMS (ESI+): calcd. for C$_{19}$H$_{18}$N$_6$O$_2$F$_3$[M+H]$^+$ 419.1438; found 419.1443.

8-amino-N-(1,3-benzodioxol-5-yl)-4,4-dimethyl-4,5-
dihydro-1H-pyrazolo[4,3-h]quinazoline-3-carbox-
amide (I), Cpd 4

[R1=R2=R3'=R4'=H, R3=R4=(C$_1$-C$_6$)alkyl, y=0, L=CONR6aR7a, R6a=substituted aryl, R7a=H]

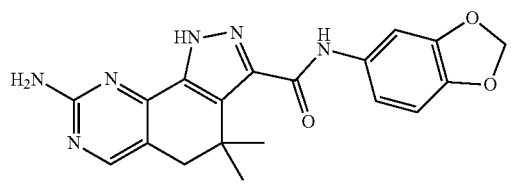 [SMILES: CC1(C)Cc2cnc(N)nc2-c2[nH]nc(C(=O)Nc3ccc4c(c3)OCO4)c21]

$^1$H NMR (499.7 MHz, DMSO-d$_6$) δ ppm 1.33 (s, 6H), 2.64 (s, 2H), 5.99 (s, 2H), 6.37 (br. s., 2H), 6.87 (d, J=8.4 Hz, 1H), 7.26 (dd, J=8.4, 1.7 Hz, 1H), 7.46 (d, J=1.7 Hz, 1H), 8.18 (s, 1H), 10.16 (s, 1H), 14.03 (s, 1H).
HRMS (ESI+): calcd. for C$_{19}$H$_{19}$N$_6$O$_3$ [M+H]$^+$ 379.1513; found 379.1525.

ethyl 4-{[(8-amino-4,4-dimethyl-4,5-dihydro-1H-
pyrazolo[4,3-h]quinazolin-3-yl)carbonyl]
amino}benzoate (I), Cpd 5

[R1=R2=R3'=R4'=H, R3=R4=(C$_1$-C$_6$)alkyl, y=1, L=CONR8, z=n=0, A=aryl, R5=COOR6, R6=(C$_1$-C$_6$)alkyl, R8=H]

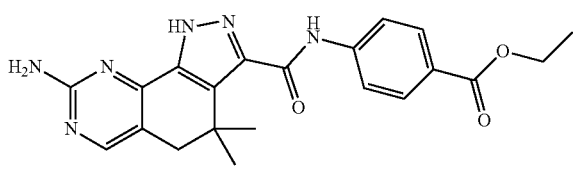 [SMILES: CCOC(=O)c1ccc(NC(=O)c2n[nH]c3c2C(C)(C)Cc2cnc(N)nc2-3)cc1]

$^1$H NMR (499.7 MHz, DMSO-d$_6$) δ ppm 1.32 (t, J=7.2 Hz, 3H), 1.35 (s, 6H), 2.66 (s, 2H), 4.30 (q, J=7.2 Hz, 2H), 6.38 (br. s., 2H), 7.90-7.99 (m, 4H), 8.20 (s, 1H), 10.62 (s, 1H), 14.16 (s, 1H).
HRMS (ESI+): calcd. for C$_{21}$H$_{23}$N$_6$O$_3$ [M+H]$^+$ 407.1826; found 407.1827.

8-amino-4,4-dimethyl-N-[4-(4-methylpiperazin-1-yl)
phenyl]-4,5-dihydro-1H-pyrazolo[4,3-h]quinazoline-
3-carboxamide (I), Cpd 6

[R1=R2=R3'=R4'=H, R3=R4=(C$_1$-C$_6$)alkyl, y=1, L=CONR8, z=n=0, A=aryl, R5=NR6R7, R6 and R7=taken together form an optionally substituted heterocyclyl group, R8=H]

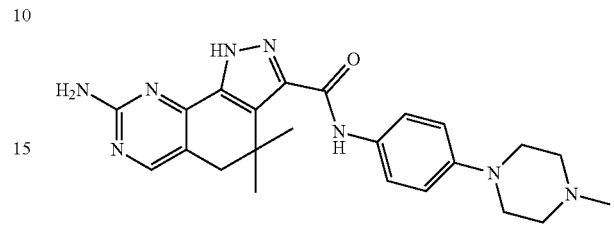

$^1$H NMR (400.4 MHz, DMSO-d$_6$) δ ppm 1.33 (s, 6H), 2.23 (s, 3H), 2.43-2.49 (m, 4H), 2.64 (s, 2H), 3.05-3.13 (m, 4H), 6.33 (br. s., 2H), 6.90 (d, J=9.1 Hz, 2H), 7.62 (d, J=9.1 Hz, 2H), 8.17 (s, 1H), 9.97 (br. s., 1H), 13.96 (br. s., 1H).
HRMS (ESI+): calcd. for C$_{23}$H$_{29}$N$_8$O [M+H]$^+$ 433.2459; found 433.2459.

8-amino-4,4-dimethyl-N-(4-methyl-1,3-thiazol-2-
yl)-4,5-dihydro-1H-pyrazolo[4,3-h]quinazoline-3-
carboxamide (I), Cpd 32

[R1=R2=R3'=R4'=H, R3=R4=(C$_1$-C$_6$)alkyl, y=0, L=CONR6aR7a, R6a=substituted heteroaryl, R7a=H]

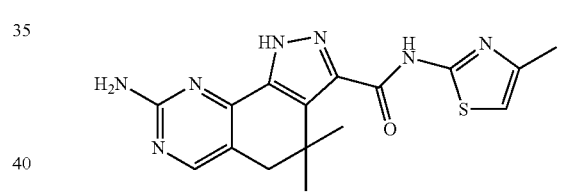

$^1$H NMR (499.7 MHz, DMSO-d$_6$) δ ppm 1.33 (s, 6H), 2.29 (s, 3H), 2.66 (m, 2H), 6.40 (br. s., 2H), 6.82 (s, 1H), 8.19 (s, 1H), 11.96 (br. s., 1H), 14.21 (br. s., 1H).
HRMS (ESI+): calcd. for C$_{16}$H$_{18}$N$_7$OS [M+H]$^+$ 356.1288; found 356.1288.

8-amino-N-ethyl-4,4-dimethyl-N-(propan-2-yl)-4,5-
dihydro-1H-pyrazolo[4,3-h]quinazoline-3-carbox-
amide trifluoroacetate (I), Cpd 158

[R1=R2=R3'=R4'=H, R3=R4=(C$_1$-C$_6$)alkyl, y=0, L=CONR6aR7a, R6a=R7a=(C$_1$-C$_6$)alkyl]

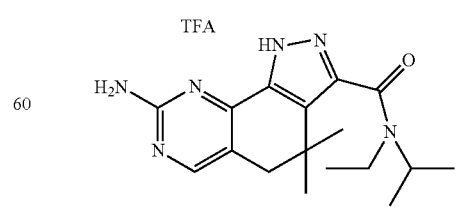

$^1$H NMR (499.7 MHz, DMSO-d$_6$, mixture of conformers) δ ppm 1.04-1.27 (m, 15H), 2.64 (s, 2H), 3.21-3.27 (m partially overlapped by water signal, 2H), 3.91 and 4.45 (2×br. s., 1H), 6.94 (br. s., 2H), 8.19 (s, 1H), 13.75 (br. s., 1H).

HRMS (ESI+): calcd. for $C_{17}H_{25}N_6O$ [M+H]$^+$ 329.2085; found 329.2082.

8-amino-N-cyclohexyl-4,4-dimethyl-4,5-dihydro-1H-pyrazolo[4,3-h]quinazoline-3-carboxamide (I), Cpd 34

[R1=R2=R3'=R4'=H, R3=R4=($C_1$-$C_6$)alkyl, y=0, L=CONR6aR7a, R6a=unsubstituted cycloalkyl, R7a=H]

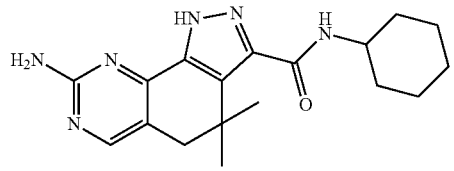 [SMILES: CC1(C)Cc2cnc(N)nc2-c2[nH]nc(C(=O)NC3CCCCC3)c21]

$^1$H NMR (499.7 MHz, DMSO-$d_6$) δ ppm 1.06-1.18 (m, 1H), 1.20-1.40 (m, 2H), 1.29 (s, 6H), 1.55-1.62 (m, 1H), 1.65-1.85 (m, 4H), 2.60 (s, 2H), 3.67-3.75 (m, 1H), 6.34 (br. s., 2H), 7.92 (d, J=7.6 Hz, 1H), 8.15 (s, 1H), 13.80 (br. s., 1H).

HRMS (ESI+): calcd. for $C_{18}H_{25}N_6O$ [M+H]$^+$ 341.2085; found 341.2075.

(8-amino-4,4-dimethyl-4,5-dihydro-1H-pyrazolo[4,3-h]quinazolin-3-yl)[4-(pyrrolidin-1-yl)piperidin-1-yl]methanone (I), Cpd 36

[R1=R2=R3'=R4'=H, R3=R4=($C_1$-$C_6$)alkyl, y=0, L=CONR6aR7a, R6a and R7a=taken together form an optionally substituted heterocyclyl group]

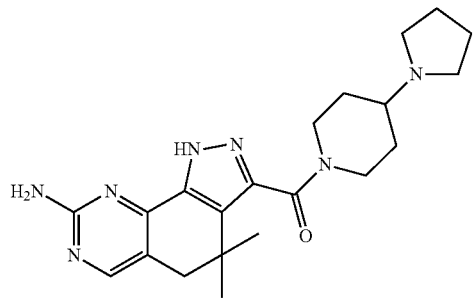 [SMILES: CC1(C)Cc2cnc(N)nc2-c2[nH]nc(C(=O)N3CCC(N4CCCC4)CC3)c21]

$^1$H NMR (499.7 MHz, DMSO-$d_6$) δ ppm 1.17 (s, 3H), 1.20 (s, 3H), 1.26-1.40 (m, 2H), 1.62-1.75 (m, 4H), 1.78-1.85 (m, 1H), 1.87-1.97 (m, 1H), 2.17-2.34 (m, 1H), 2.42-2.65 (m, 4H), 2.59 (s, 2H), 2.91-3.01 (m, 1H), 3.05-3.13 (m, 1H), 3.67-3.77 (m, 1H), 4.29-4.39 (m, 1H), 6.36 (br. s., 2H), 8.15 (s, 1H), 13.71 (br. s., 1H).

HRMS (ESI+): calcd. for $C_{21}H_{30}N_7O$ [M+H]$^+$ 396.2507; found 396.2495.

(8-amino-4,4-dimethyl-4,5-dihydro-1H-pyrazolo[4,3-h]quinazolin-3-yl)(1,4'-bipiperidin-1'-yl)methanone (I), Cpd 38

[R1=R2=R3'=R4'=H, R3=R4=($C_1$-$C_6$)alkyl, y=0, L=CONR6aR7a, R6a and R7a=taken together form an optionally substituted heterocyclyl group]

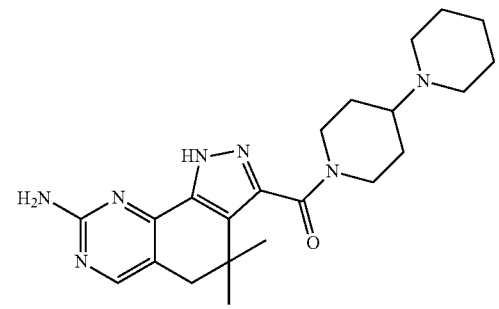 [SMILES: CC1(C)Cc2cnc(N)nc2-c2[nH]nc(C(=O)N3CCC(N4CCCCC4)CC3)c21]

$^1$H NMR (499.7 MHz, DMSO-$d_6$) δ ppm 1.16 (s, 3H), 1.20 (s, 3H), 1.28-1.40 (m, 4H), 1.43-1.51 (m, 4H), 1.65-1.71 (m, 1H), 1.78-1.85 (m, 1H), 2.44-2.47 (m, 4H), 2.60 (s, 2H), 2.70-2.79 (m, 1H), 2.96-3.06 (m, 1H), 3.74-3.81 (m, 1H), 4.50-4.57 (m, 1H), 6.35 (br. s., 2H), 8.15 (s, 1H), 13.70 (br. s., 1H).

HRMS (ESI+): calcd. for $C_{22}H_{32}N_7O$ [M+H]$^+$ 410.2663; found 410.2653.

(8-amino-4,4-dimethyl-4,5-dihydro-1H-pyrazolo[4,3-h]quinazolin-3-yl)(4-phenylpiperazin-1-yl)methanone (I), Cpd 161

[R1=R2=R3'=R4'=H, R3=R4=($C_1$-$C_6$)alkyl, y=0, L=CONR6aR7a, R6a and R7a=taken together form an optionally substituted heterocyclyl group]

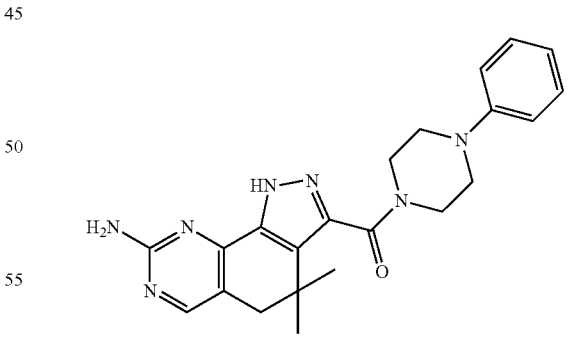

$^1$H NMR (499.7 MHz, DMSO-$d_6$) δ ppm 1.21 (s, 6H), 2.61 (s, 2H), 3.07-3.14 (m, 2H), 3.18-3.23 (m, 2H), 3.53-3.61 (br. s., 2H), 3.78-3.84 (m, 2H), 6.37 (br. s., 2H), 6.80-6.84 (m, 1H), 6.94-7.00 (m, 2H), 7.20-7.26 (m, 2H), 8.16 (s, 1H), 13.80 (br. s., 1H).

HRMS (ESI+): calcd. for $C_{22}H_{26}N_7O$ [M+H]$^+$ 404.2194; found 404.2188.

ethyl 3-{[(8-amino-4,4-dimethyl-4,5-dihydro-1H-pyrazolo[4,3-h]quinazolin-3-yl)carbonyl]amino}benzoate (I), Cpd 17

[R1=R2=R3'=R4'=H, R3=R4=(C$_1$-C$_6$)alkyl, y=1, L=CONR8, z=n=0, A=aryl, R5=COOR6, R6=(C$_1$-C$_6$)alkyl, R8=H]

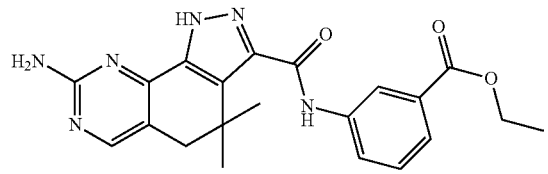 [SMILES: CCOC(=O)c1cccc(NC(=O)c2n[nH]c3c2C(C)(C)Cc2cnc(N)nc2-3)c1]

$^1$H NMR (400.4 MHz, DMSO-d$_6$) δ ppm 1.33 (t, J=7.1 Hz, 3H), 1.35 (s, 6H), 2.66 (s, 2H), 4.33 (q, J=7.1 Hz, 2H), 6.34 (br. s., 2H), 7.48 (t, J=8.0 Hz, 1H) 7.68 (dt, J=8.0, 1.2 Hz, 1H), 8.02 (ddd, J=8.0, 2.2, 1.0 Hz, 1H), 8.19 (s, 1H), 8.51 (dd, J=2.2, 1.2 Hz, 1H), 10.49 (s, 1H), 14.09 (br. s., 1H).

HRMS (ESI+): calcd. for C$_{21}$H$_{23}$N$_6$O$_3$ [M+H]$^+$ 407.1826; found 407.1828.

ethyl 6-{[(8-amino-4,4-dimethyl-4,5-dihydro-1H-pyrazolo[4,3-h]quinazolin-3-yl)carbonyl]amino}pyridine-3-carboxylate (I), Cpd 40

[R1=R2=R3'=R4'=H, R3=R4=(C$_1$-C$_6$)alkyl, y=1, L=CONR8, z=n=0, A=heteroaryl, R5=COOR6, R6=(C$_1$-C$_6$)alkyl, R8=H]

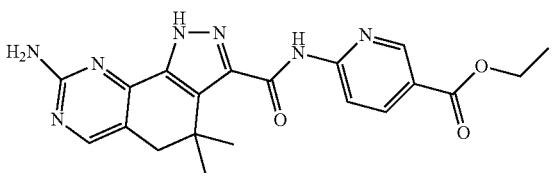 [SMILES: CCOC(=O)c1ccc(NC(=O)c2n[nH]c3c2C(C)(C)Cc2cnc(N)nc2-3)nc1]

$^1$H NMR (400.4 MHz, DMSO-d$_6$) δ ppm 1.34 (t, J=7.1 Hz, 3H), 1.38 (s, 6H), 2.69 (s, 2H), 4.34 (q, J=7.1 Hz, 2H), 6.38 (br. s., 2H), 8.20 (s, 1H), 8.30-8.40 (m, 2H), 8.87-8.89 (m, 1H), 10.23 (s, 1H), 14.30 (br. s., 1H).

HRMS (ESI+): calcd. for C$_{20}$H$_{22}$N$_7$O$_3$ [M+H]$^+$ 408.1779; found 408.1777.

ethyl (4-{[(8-amino-4,4-dimethyl-4,5-dihydro-1H-pyrazolo[4,3-h]quinazolin-3-yl)carbonyl]amino}phenyl)acetate (I), Cpd 96

[R1=R2=R3'=R4'=H, R3=R4=(C$_1$-C$_6$)alkyl, y=1, L=CONR8, z=0, A=aryl, n=1, Rc=Rd=H, R5=COOR6, R6=(C$_1$-C$_6$)alkyl, R8=H]

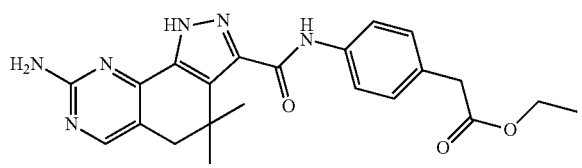 [SMILES: CCOC(=O)Cc1ccc(NC(=O)c2n[nH]c3c2C(C)(C)Cc2cnc(N)nc2-3)cc1]

$^1$H NMR (499.7 MHz, DMSO-d$_6$) δ ppm 1.18 (t, J=5.4 Hz, 3H), 1.34 (s, 6H), 2.65 (s, 2H), 3.61 (s, 2H), 4.07 (q, J=5.4 Hz, 2H), 6.36 (br. s., 2H), 7.21 (d, J=8.4 Hz, 2H), 7.73 (d, J=8.4 Hz, 2H), 8.19 (s, 1H), 10.22 (s, 1H), 14.05 (s, 1H).

HRMS (ESI+): calcd. for C$_{22}$H$_{25}$N$_6$O$_3$ [M+H]$^+$ 421.1983; found 421.1969.

ethyl (3-{[(8-amino-4,4-dimethyl-4,5-dihydro-1H-pyrazolo[4,3-h]quinazolin-3-yl)carbonyl]amino}phenyl)acetate (I), Cpd 137

[R1=R2=R3'=R4'=H, R3=R4=(C$_1$-C$_6$)alkyl, y=1, L=CONR8, z=0, A=aryl, n=1, Rc=Rd=H, R5=COOR6, R6=(C$_1$-C$_6$)alkyl, R8=H]

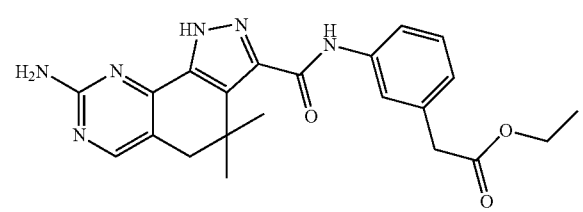 [SMILES: CCOC(=O)Cc1cccc(NC(=O)c2n[nH]c3c2C(C)(C)Cc2cnc(N)nc2-3)c1]

$^1$H NMR (499.7 MHz, DMSO-d$_6$) δ ppm 1.19 (t, J=7.1 Hz, 3H), 1.34 (s, 6H), 2.65 (s, 2H), 3.64 (s, 2H), 4.09 (q, J=7.1 Hz, 2H), 6.37 (br. s., 2H), 6.98 (d, J=7.5 Hz, 1H), 7.27 (dd, J=8.2, 7.5 Hz, 1H), 7.63 (d, J=8.2 Hz, 1H), 7.79 (s, 1H), 8.19 (s, 1H), 10.23 (s, 1H), 14.05 (s, 1H).

HRMS (ESI+): calcd. for C$_{22}$H$_{25}$N$_6$O$_3$ [M+H]$^+$ 421.1983; found 421.1984.

ethyl (2-{[(8-amino-4,4-dimethyl-4,5-dihydro-1H-pyrazolo[4,3-h]quinazolin-3-yl)carbonyl]amino}-1,3-thiazol-4-yl)acetate (I), Cpd 33

[R1=R2=R3'=R4'=H, R3=R4=(C$_1$-C$_6$)alkyl, y=1, L=CONR8, z=0, A=heteroaryl, n=1, Rc=Rd=H, R5=COOR6, R6=(C$_1$-C$_6$)alkyl, R8=H]

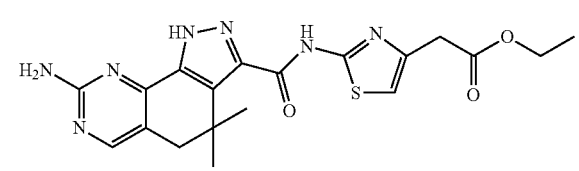 [SMILES: CCOC(=O)Cc1csc(NC(=O)c2n[nH]c3c2C(C)(C)Cc2cnc(N)nc2-3)n1]

$^1$H NMR (499.7 MHz, DMSO-d$_6$) δ ppm 1.19 (d, J=7.2 Hz, 3H), 1.33 (s, 6H), 2.66 (s, 2H), 3.72 (s, 2H), 4.10 (d, J=7.2 Hz, 2H), 6.39 (br. s., 2H), 7.05 (s, 1H), 8.19 (s, 1H), 12.14 (br. s., 1H), 14.22 (br. s., 1H).

HRMS (ESI+): calcd. for C$_{19}$H$_{22}$N$_7$O$_3$S [M+H]$^+$ 428.15; found 428.1489.

ethyl (2-{[(8-amino-4,4-dimethyl-4,5-dihydro-1H-pyrazolo[4,3-h]quinazolin-3-yl)carbonyl]amino}-1,3-thiazol-5-yl)acetate (I), Cpd 174

[R1=R2=R3'=R4'=H, R3=R4=(C$_1$-C$_6$)alkyl, y=1, L=CONR8, z=0, A=heteroaryl, n=1, Rc=Rd=H, R5=COOR6, R6=(C$_1$-C$_6$)alkyl, R8=H]

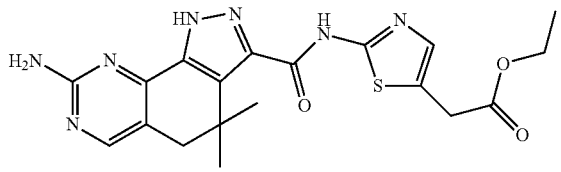 [SMILES: CCOC(=O)Cc1cnc(NC(=O)c2n[nH]c3c2C(C)(C)Cc2cnc(N)nc2-3)s1]

HRMS (ESI+): calcd. for C$_{19}$H$_{22}$N$_7$O$_3$S [M+H]$^+$ 428.1499; found 428.1498.

ethyl 2-{[(8-amino-4,4-dimethyl-4,5-dihydro-1H-pyrazolo[4,3-h]quinazolin-3-yl)carbonyl]amino}-1,3-thiazole-4-carboxylate (I), Cpd 57

[R1=R2=R3'=R4'=H, R3=R4=(C$_1$-C$_6$)alkyl, y=1, L=CONR8, z=n=0, A=heteroaryl, R5=COOR6, R6=(C$_1$-C$_6$)alkyl, R8=H]

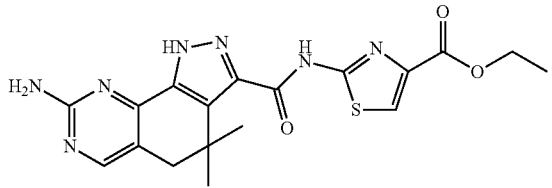 [SMILES: CCOC(=O)c1csc(NC(=O)c2n[nH]c3c2C(C)(C)Cc2cnc(N)nc2-3)n1]

$^1$H NMR (499.7 MHz, DMSO-d$_6$) δ ppm 1.31 (t, J=7.1 Hz, 3H), 1.33 (s, 6H), 2.67 (s, 2H), 4.29 (q, J=7.1 Hz, 2H), 6.40 (br. s., 2H), 8.11 (s, 1H), 8.19 (s, 1H), 12.57 (s, 1H) 14.27 (s, 1H).

HRMS (ESI+): calcd. for C$_{18}$H$_{20}$N$_7$O$_3$S [M+H]$^+$ 414.1343; found 414.1341.

8-amino-1,4,4-trimethyl-N-{4-[2-(4-methyl-1,4'-bipiperidin-1'-yl)-2-oxoethyl]-1,3-thiazol-2-yl}-4,5-dihydro-1H-pyrazolo[4,3-h]quinazoline-3-carboxamide (I), Cpd 80

[R1=R3'=R4'=H, R2=R3=R4=(C$_1$-C$_6$)alkyl, y=1, L=CONR8, z=0, A=heteroaryl, n=1, Rc=Rd=H, R5=CONR6R7, R6 and R7=taken together form an optionally substituted heterocyclyl group, R8=H]

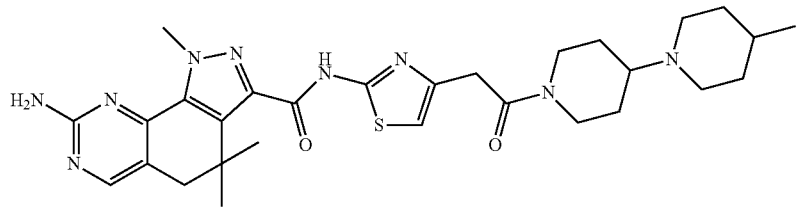 [SMILES: CC1CCN(C2CCN(C(=O)Cc3csc(NC(=O)c4nn(C)c5c4C(C)(C)Cc4cnc(N)nc4-5)n3)CC2)CC1]

$^1$H NMR (499.7 MHz, DMSO-d$_6$) δ ppm 0.84 (d, J=6.5 Hz, 3H), 1.00-1.10 (m, 2H), 1.16-1.28 (m, 3H), 1.30 (s, 6H), 1.50-1.57 (m, 2H), 1.62-1.72 (m, 2H), 2.03-2.13 (m, 2H), 2.39-2.47 (m, 1H), 2.63 (s, 2H), 2.72-2.78 (m, 2H), 2.93-3.03 (m, 1H), 3.69-3.76 (m, 2H), 3.95-4.01 (m, 1H), 4.34 (s, 3H), 4.36-4.42 (m, 1H), 6.61 (br. s., 2H), 6.94 (s, 1H), 8.19 (s, 1H), 12.07 (br. s., 1H).

HRMS (ESI+): calcd. for C$_{29}$H$_{40}$N$_9$O$_2$S [M+H]$^+$ 578.3020; found 578.3020.

1,4,4-trimethyl-8-(methylamino)-N-{4-[2-(4-methyl-1,4'-bipiperidin-1'-yl)-2-oxoethyl]-1,3-thiazol-2-yl}-4,5-dihydro-1H-pyrazolo[4,3-h]quinazoline-3-carboxamide (I), Cpd 85

[R1=R2=R3=R4=(C$_1$-C$_6$)alkyl, R3'=R4'=H, y=1, L=CONR8, z=0, A=heteroaryl, n=1, Rc=Rd=H, R5=CONR6N7, R6 and R7=taken together form an optionally substituted heterocyclyl group, R8=H]

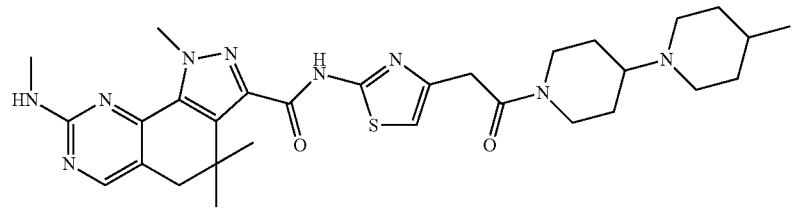 [SMILES: CNc1ncc2c(n1)-c1c(c(C(=O)Nc3nc(CC(=O)N4CCC(N5CCC(C)CC5)CC4)cs3)nn1C)C(C)(C)C2]

¹H NMR (499.7 MHz, DMSO-d$_6$) δ ppm 0.85 (d, J=6.4 Hz, 3H), 1.00-1.11 (m, 2H), 1.16-1.29 (m, 3H), 1.31 (s, 6H), 1.50-1.58 (m, 2H), 1.60-1.72 (m, 2H), 2.08 (br. s., 2H), 2.44 (br. s., 2H), 2.65 (s, 2H), 2.76 (br. s., 2H), 2.85 (d, J=4.8 Hz, 3H), 2.93-3.00 (m, 1H), 3.73 (s, 2H), 3.95-4.05 (m, 1H), 4.36 (s, 3H), 4.36-4.42 (m, 1H), 6.94 (s, 1H), 7.10 (q, J=4.8 Hz, 1H), 8.23 (s, 1H), 12.07 (br. s., 1H).

HRMS (ESI+): calcd. for $C_{30}H_{42}N_9O_2S$ [M+H]$^+$ 592.3177; found 592.3195.

8-amino-N-{4-[2-(1,4'-bipiperidin-1'-yl)-2-oxo-ethyl]-1,3-thiazol-2-yl}-N,1,4,4-tetramethyl-4,5-dihydro-1H- pyrazolo[4,3-h]quinazoline-3-carbox-amide (I), Cpd 124

[R1=R3'=R4'=H, R2=R3=R4=(C$_1$-C$_6$)alkyl, y=1, L=CONR8, z=0, A=heteroaryl, n=1, Rc=Rd=H, R5=CONR6N7, R6 and R7=taken together form an optionally substituted heterocyclyl group, R8=(C$_1$-C$_6$)alkyl]

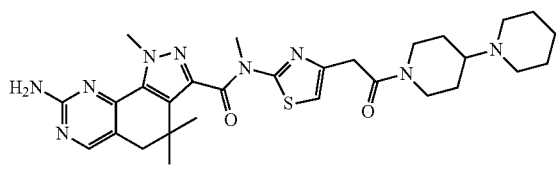

¹H NMR (499.7 MHz, DMSO-d$_6$) δ ppm 1.18 (s, 6H), 1.20-1.29 (m, 2H), 1.32-1.38 (m, 2H), 1.41-1.51 (m, 4H), 1.62-1.74 (m, 2H), 2.32-2.45 (m, 5H), 2.63 (s, 2H), 2.95-3.03 (m, 1H), 3.34 (m overlapped by water signal, 1H), 3.61 (s, 3H), 3.71-3.87 (m, 2H), 3.99-4.08 (m, 1H), 4.33 (s, 3H), 4.36-4.45 (m, 1H), 6.63 (br. s., 2H), 7.07 (s, 1H), 8.19 (s, 1H).

HRMS (ESI+): calcd. for $C_{29}H_{40}N_9O_2S$ [M+H]$^+$ 578.3020; found 578.3008.

8-amino-N-[4-(2-{4-[(tert-butylcarbamoyl)amino]piperidin-1-yl}-2-oxoethyl)-1,3-thiazol-2-yl]-4,4-dimethyl-4,5-dihydro-1H-pyrazolo[4,3-h]quinazo-line-3-carboxamide (I), Cpd 71

[R1=R2=R3'=R4'=H, R3=R4=(C$_1$-C$_6$)alkyl, y=1, L=CONR8, z=0, A=heteroaryl, n=1, Rc=Rd=H, R5=CONR6N7, R6 and R7=taken together form an optionally substituted heterocyclyl group, R8=H]

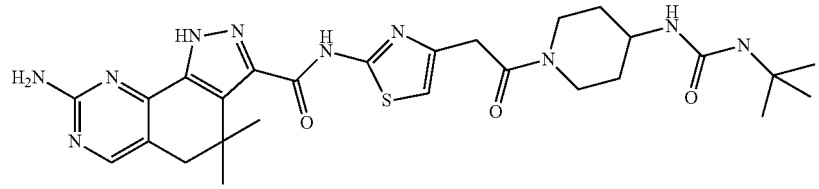 [SMILES: CC(C)(C)NC(=O)NC1CCN(C(=O)Cc2csc(NC(=O)c3n[nH]c4c3C(C)(C)Cc3cnc(N)nc3-4)n2)CC1]

¹H NMR (499.7 MHz, DMSO-d$_6$) δ ppm 1.00-1.14 (m, 2H), 1.20 (s, 9H), 1.33 (s, 6H), 1.70-1.76 (m, 2H), 2.66 (s, 2H), 2.77-2.84 (m, 1H), 3.10-3.19 (m, 1H), 3.50-3.60 (m, 1H), 3.74 (s, 2H, 3.82-3.89 (m, 1H), 4.08-4.14 (m, 1H), 5.51 (s, 1H), 5.66 (d, J=7.5 Hz, 1H), 6.39 (br. s., 2H), 6.94 (s, 1H), 8.19 (s, 1H), 12.07 (br. s., 1H), 14.23 (br. s., 1H).

HRMS (ESI+): calcd. for $C_{27}H_{37}N_{10}O_3S$ [M+H]$^+$ 581.2766; found 581.2769.

ethyl 2-{[(8-amino-4,4-dimethyl-4,5-dihydro-1H-pyrazolo[4,3-h]quinazolin-3-yl)carbonyl]amino}-1,3-thiazole-5-carboxylate (I), Cpd 81

[R1=R2=R3'=R4'=H, R3=R4=(C$_1$-C$_6$)alkyl, y=1, L=CONR8, z=n=0, A=heteroaryl, R5=COOR6, R6=(C$_1$-C$_6$)alkyl, R8=H]

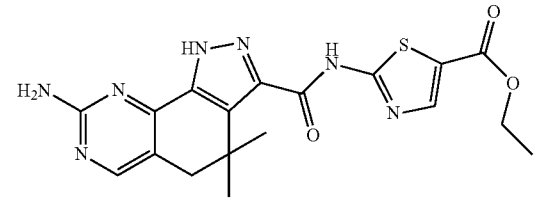 [SMILES: CCOC(=O)c1cnc(NC(=O)c2n[nH]c3c2C(C)(C)Cc2cnc(N)nc2-3)s1]

¹H NMR (499.7 MHz, DMSO-d$_6$) δ ppm 1.31 (t, J=7.1 Hz, 3H), 1.34 (s, 6H), 2.68 (s, 2H), 4.29 (q, J=7.1 Hz, 2H), 6.41 (br. s., 2H), 8.20 (s, 1H), 12.76 (br. s., 1H), 14.38 (br. s., 1H).

HRMS (ESI+): calcd. for $C_{18}H_{20}N_7O_3S$ [M+H]$^+$ 414.1343; found 414.1334.

ethyl 2-{[(8-amino-4,4-dimethyl-4,5-dihydro-1H-pyrazolo[4,3-h]quinazolin-3-yl)carbonyl]amino}-4-methyl-1,3-thiazole-5-carboxylate (I), Cpd 175

[R1=R2=R3'=R4'=H, R3=R4=(C$_1$-C$_6$)alkyl, y=1, L=CONR8, z=n=0, A=heteroaryl R5=COOR6, R6=(C$_1$-C$_6$)alkyl, R8=H]

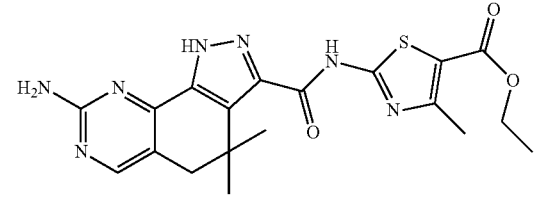 [SMILES: CCOC(=O)c1sc(NC(=O)c2n[nH]c3c2C(C)(C)Cc2cnc(N)nc2-3)nc1C]

HRMS (ESI+): calcd. for $C_{19}H_{21}N_7O_3S$ [M+H]$^+$ 428.1499; found 429.1497.

methyl 1-(2-{[(8-amino-4,4-dimethyl-4,5-dihydro-1H-pyrazolo[4,3-h]quinazolin-3-yl)carbonyl]amino}-1,3-thiazol-4-yl)cyclopropanecarboxylate (I), Cpd 127

[R1=R2=R3'=R4'=H, R3=R4=(C$_1$-C$_6$)alkyl, y=1, L=CONR8, z=0, A=heteroaryl, n=1, Rc and Rd=taken together form a 3-membered cycloalkyl, R5=COOR6, R6=(C$_1$-C$_6$)alkyl, R8=H]

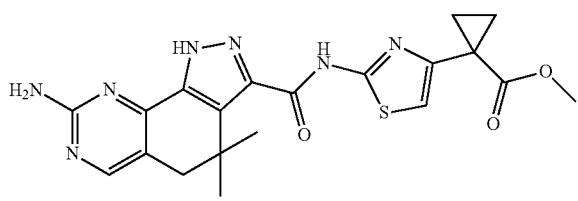 [SMILES: COC(=O)C1(c2csc(NC(=O)c3n[nH]c4c3C(C)(C)Cc3cnc(N)nc3-4)n2)CC1]

¹H NMR (499.7 MHz, DMSO-d₆) δ ppm 1.33 (s, 6H), 1.34-1.38 (m, 2H), 1.49-1.51 (m, 2H), 2.66 (s, 2H), 3.61 (s, 3H), 6.39 (br. s., 2H), 7.20 (s, 1H), 8.19 (s, 1H), 12.10 (s, 1H), 14.22 (s, 1H).

HRMS (ESI+): calcd. for $C_{20}H_{22}N_7O_3S$ [M+H]⁺ 440.15; found 440.1489.

8-amino-N-(3-methoxybenzyl)-4,4-dimethyl-4,5-dihydro-1H-pyrazolo[4,3-h]quinazoline-3-carboxamide (I), cpd 162

[R1=R2=R3'=R4'=H, R3=R4=($C_1$-$C_6$)alkyl, y=0, L=CONR6aR7a, R6a=substituted aryl($C_1$-$C_6$)alkyl, R7a=H]

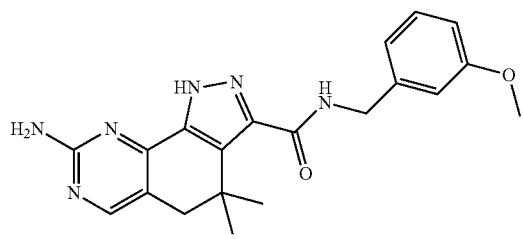 [SMILES: COc1cccc(CNC(=O)c2n[nH]c3c2C(C)(C)Cc2cnc(N)nc2-3)c1]

¹H NMR (499.7 MHz, DMSO-d₆) δ ppm 1.31 (s, 6H), 2.62 (s, 2H), 3.73 (s, 3H), 4.40 (d, J=6.2 Hz, 2H), 6.34 (br. s., 2H), 6.80 (dd, J=8.9, 2.3 Hz, 1H), 6.87-6.91 (m, 2H), 7.20-7.27 (m, 1H), 8.16 (s, 1H), 8.75 (t, J=6.2 Hz, 1H), 13.89 (br. s., 1H).

HRMS (ESI+): calcd. for $C_{20}H_{23}N_6O_2$ [M+H]⁺ 379.1877; found 379.1879.

methyl 4-({[(8-amino-4,4-dimethyl-4,5-dihydro-1H-pyrazolo[4,3-h]quinazolin-3-yl)carbonyl]amino}methyl) benzoate (I), Cpd 163

[R1=R2=R3'=R4'=H, R3=R4=($C_1$-$C_6$)alkyl, y=1, L=CONR8, z=1, Ra=Rb=H, A=aryl, n=0, R5=COOR6, R6=($C_1$-$C_6$)alkyl, R8=H]

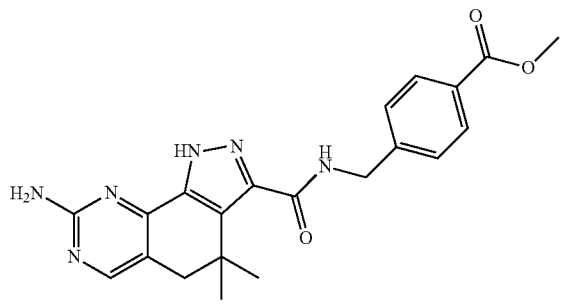 [SMILES: COC(=O)c1ccc(CNC(=O)c2n[nH]c3c2C(C)(C)Cc2cnc(N)nc2-3)cc1]

¹H NMR (499.7 MHz, DMSO-d₆) δ ppm 1.30 (s, 6H), 2.62 (s, 2H), 3.84 (s, 3H), 4.50 (d, J=6.2 Hz, 2H), 6.35 (br. s., 2H), 7.45 (d, J=8.4 Hz, 2H), 7.92 (d, J=8.4 Hz, 2H), 8.16 (s, 1H), 8.90 (t, J=6.2 Hz, 1H), 13.93 (s, 1H).

HRMS (ESI+): calcd. for $C_{21}H_{23}N_6O_3$ [M+H]⁺ 407.1826; found 407.1826.

8-amino-4,4-dimethyl-N-[4-(4-phenoxyphenyl)-1,3-thiazol-2-yl]-4,5-dihydro-1H-pyrazolo[4,3-h]quinazoline-3-carboxamide (I), Cpd 76

[R1=R2=R3'=R4'=H, R3=R4=($C_1$-$C_6$)alkyl, y=0, L=CONR6aR7a, R6a=substituted heteroaryl, R7a=H]

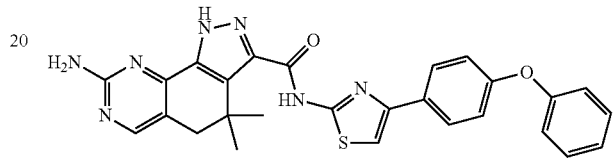

HRMS (ESI+): calcd. for $C_{27}H_{24}N_7O_2S$ [M+H]⁺ 510.1707; found 510.1699.

8-amino-1,4,4-trimethyl-N-(4-methyl-1,3-thiazol-2-yl)-4,5-dihydro-1H-pyrazolo[4,3-h]quinazoline-3-carboxamide (I), Cpd 155

[R1=R3'=R4'=H, R2=R3=R4=($C_1$-$C_6$)alkyl, y=0, L=CONR6aR7a, R6a=substituted heteroaryl, R7a=H]

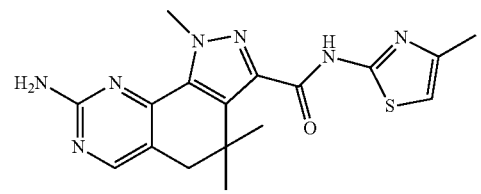 [SMILES: Cc1csc(NC(=O)c2nn(C)c3c2C(C)(C)Cc2cnc(N)nc2-3)n1]

¹H NMR (499.7 MHz, DMSO-d₆) δ ppm 1.34 (s, 6H), 2.32 (d, J=0.9 Hz, 3H), 2.67 (s, 2H), 4.38 (s, 3H), 6.65 (s, 2H), 6.85 (d, J=0.9 Hz, 1H), 8.22 (s, 1H), 12.02 (s, 1H).

HRMS (ESI+): calcd. for $C_{17}H_{20}N_7OS$ [M+H]⁺ 370.1445; found 370.1443.

8-amino-N,4,4-trimethyl-N-{4-[2-(4-methyl-1,4'-bipiperidin-1'-yl)-2-oxoethyl]-1,3-thiazol-2-yl}-4,5-dihydro-1H-pyrazolo[4,3-h]quinazoline-3-carboxamide (I), Cpd 123

[R1=R2=R3'=R4'=H, R3=R4=($C_1$-$C_6$)alkyl, y=1, L=CONR8, z=0, A=heteroaryl, n=1, Rc=Rd=H, R5=CONR6N7, R6 and R7=taken together form an optionally substituted heterocyclyl group, R8=($C_1$-$C_6$)alkyl]

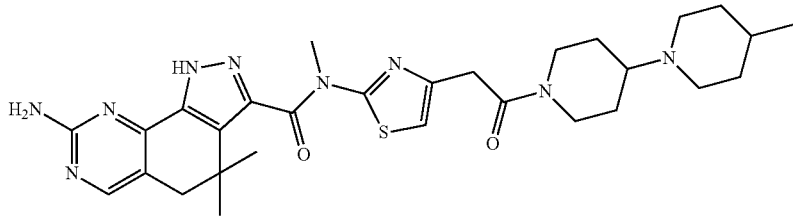 [SMILES: CC1CCN(C2CCN(C(=O)Cc3csc(N(C)C(=O)c4n[nH]c5c4C(C)(C)Cc4cnc(N)nc4-5)n3)CC2)CC1]

¹H NMR (400.4 MHz, DMSO-d₆) δ ppm 0.86 (d, J=6.5 Hz, 3H), 0.99-1.11 (m, 2H), 1.20 (s, 6H), 1.18-1.32 (m, 3H), 1.50-1.59 (m, 2H), 1.64-1.74 (m, 2H), 2.00-2.12 (m, 2H), 2.38-2.50 (m, 1H), 2.64 (s, 2H), 2.71-2.79 (m, 2H), 2.96-3.05 (m, 1H), 3.20-3.28 (m, 1H), 3.62 (s, 3H), 3.69-3.84 (m, 2H), 4.00-4.09 (m, 1H), 4.37-4.46 (m, 1H), 6.37 (br. s., 2H), 7.05 (s, 1H), 8.18 (s, 1H), 13.94 (br. s., 1H).

HRMS (ESI+): calcd. for $C_{28}H_{40}N_9O_2S$ [M+H]⁺ 578.3020; found 578.3022.

8-amino-N-{4-[2-(1,4'-bipiperidin-1'-yl)-2-oxo-ethyl]-1,3-thiazol-2-yl}-1,4,4-trimethyl-4,5-dihydro-1H- pyrazolo[4,3-h]quinazoline-3-carboxamide (I), Cpd 108

[R1=R3'=R4'=H, R2=R3=R4=(C₁-C₆)alkyl, y=1, L=CONR8, z=0, A=heteroaryl, n=1, Rc=Rd=H, R5=CONR6N7, R6 and R7=taken together form an optionally substituted heterocyclyl group, R8=H]

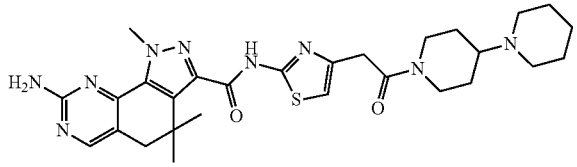 [SMILES: Cn1nc(C(=O)Nc2nc(CC(=O)N3CCC(N4CCCCC4)CC3)cs2)c2c1-c1nc(N)ncc1CC2(C)C]

¹H NMR (499.7 MHz, DMSO-d₆) δ ppm 1.15-1.28 (m, 2H), 1.30 (s, 6H), 1.30-1.38 (m, 2H), 1.41-1.51 (m, 4H), 1.62-1.72 (m, 2H), 2.37-2.47 (br. s., 4H), 2.62 (br. s., 1H), 2.63 (s, 2H), 2.93-3.01 (m, 1H), 3.34 (m overlapped by water signal, 1H), 3.73 (s, 2H), 3.96-4.04 (m, 1H), 4.34 (s, 3H), 4.37-4.44 (m, 1H), 6.62 (br. s., 2H), 6.94 (s, 1H), 8.19 (s, 1H), 12.07 (br. s., 1H).

HRMS (ESI+): calcd. for $C_{28}H_{39}N_9O_2S$ [M+H]⁺ 564.2864; found 564.2868.

8-amino-N-{3-[2-(1,4'-bipiperidin-1'-yl)-2-oxoethyl]phenyl}-4,4-dimethyl-4,5-dihydro-1H-pyrazolo[4,3-h]quinazoline-3-carboxamide (I), Cpd 120

[R1=R2=R3'=R4'=H, R3=R4=(C₁-C₆)alkyl, y=1, L=CONR8, z=0, A=aryl, n=1, Rc=Rd=H, R5=CONR6N7, R6 and R7=taken together form an optionally substituted heterocyclyl group, R8=H]

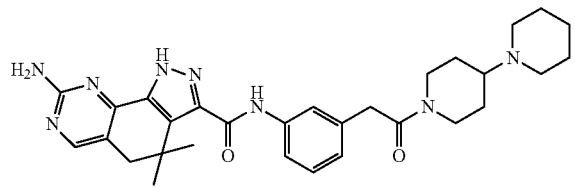 [SMILES: CC1(C)Cc2cnc(N)nc2-c2[nH]nc(C(=O)Nc3cccc(CC(=O)N4CCC(N5CCCCC5)CC4)c3)c21]

¹H NMR (499.7 MHz, DMSO-d₆) δ ppm 1.07-1.30 (m, 2H), 1.33 (s, 6H), 1.37-1.47 (m, 6H), 1.55-1.71 (m, 2H), 2.30-2.44 (m, 5H), 2.64 (s, 2H), 2.89-2.98 (m, 1H), 3.34 (m overlapped by water signal, 1H), 3.63-3.76 (m, 2H), 3.89-3.96 (m, 1H), 4.38-4.49 (m, 1H), 6.37 (br. s., 2H), 6.93 (d, J=7.5 Hz, 1H), 7.26 (dd, J=7.5, 8.4 Hz, 1H), 7.58 (d, J=8.4 Hz, 1H), 7.76 (s, 1H), 8.18 (s, 1H), 10.22 (br. s., 1H), 14.03 (br. s., 1H).

HRMS (ESI+): calcd. for $C_{30}H_{39}N_8O_2$ [M+H]⁺ 543.3191; found 543.3191.

N-{4-[2-(1,4'-bipiperidin-1'-yl)-2-oxoethyl]-1,3-thiazol-2-yl}-4,4-dimethyl-8-(methylamino)-4,5-dihydro-1H- pyrazolo[4,3-h]quinazoline-3-carboxamide (I), Cpd 121

[R2=R3'=R4'=H, R1=R3=R4=(C₁-C₆)alkyl, y=1, L=CONR8, z=0, A=heteroaryl, n=1, Rc=Rd=H, R5=CONR6N7, R6 and R7=taken together form an optionally substituted heterocyclyl group, R8=H]

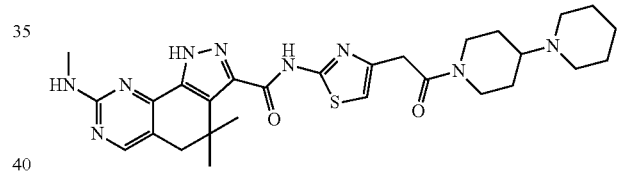

¹H NMR (499.7 MHz, DMSO-d₆) δ ppm 1.33 (s, 6H), 1-18-1.92 (m, 10H), 2.66 (s, 2H), 2.50-2.85 (br. s., 5H), 2.87 (d, J=4.4 Hz, 3H), 2.96-3.04 (m, 2H), 3.34 (m overlapped by water signal, 1H), 3.76 (s, 2H), 4.02-4.10 (m, 1H), 4.43-4.50 (m, 1H), 6.83 (br. s., 2H), 6.96 (s, 1H), 8.21 (s, 1H), 12.08 (br. s., 1H), 14.19 (br. s., 1H).

HRMS (ESI+): calcd. for $C_{28}H_{38}N_9O_2S$ [M+H]⁺ 564.2864; found 564.2856.

8-amino-N-[3-(1,3-dioxan-2-yl)phenyl]-1,4,4-trimethyl-4,5-dihydro-1H-pyrazolo[4,3-h]quinazoline-3-carboxamide (I), Cpd 99

[R1=R3'=R4'=H, R2=R3=R4=(C₁-C₆)alkyl, y=0, L=CONR6aR7a, R6a=substituted aryl, R7a=H]

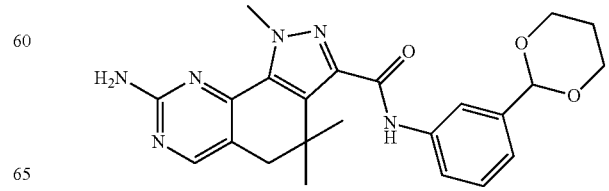

¹H NMR (499.7 MHz, DMSO-d₆) δ ppm 1.32 (s, 6H), 1.42-1.49 (m, 1H), 1.92-2.06 (m, 1H), 2.62 (s, 2H), 3.89-4.00 (m, 2H), 4.13-4.19 (m, 2H), 4.35 (s, 3H), 5.50 (s, 1H), 6.60 (br. s., 2H), 7.11 (d, J=7.6 Hz, 1H), 7.30 (dd, J=7.6, 7.5 Hz, 1H), 7.64 (d, J=7.5 Hz, 1H), 7.99 (s, 1H), 8.18 (s, 1H), 10.30 (br. s., 1H).

HRMS (ESI+): calcd. for $C_{23}H_{27}N_6O_3$ [M+H]⁺ 435.2139; found 435.2126.

8-amino-N-(4-hydroxyphenyl)-4,4-dimethyl-4,5-dihydro-1H-pyrazolo[4,3-h]quinazoline-3-carboxamide (I), cpd 105

[R1=R2=R3'=R4'=H, R3=R4=(C₁-C₆)alkyl, y=0, L=CONR6aR7a, R6a=substituted aryl, R7a=H]

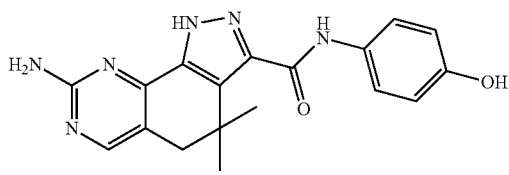 [SMILES: CC1(C)Cc2cnc(N)nc2-c2[nH]nc(C(=O)Nc3ccc(O)cc3)c21]

¹H NMR (499.7 MHz, DMSO-d₆) δ ppm 1.33 (s, 6H), 2.64 (s, 2H), 6.36 (br. s., 2H), 6.71 (d, J=8.8 Hz, 2H), 7.55 (d, J=8.8 Hz, 2H), 8.18 (s, 1H), 9.21 (s, 1H), 9.97 (s, 1H), 13.97 (s, 1H).

HRMS (ESI+): calcd. for $C_{18}H_{19}N_6O_2$[M+H]⁺ 351.1564; found 351.1561.

8-amino-N-[3-(1,3-dioxan-2-yl)phenyl]-4,4-dimethyl-4,5-dihydro-1H-pyrazolo[4,3-h]quinazoline-3-carboxamide (I), Cpd 106

[R1=R2=R3'=R4'=H, R3=R4=(C₁-C₆)alkyl, y=0, L=CONR6aR7a, R6a=substituted aryl, R7a=H]

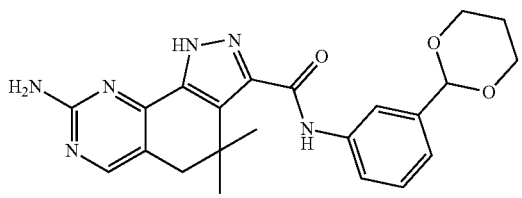 [SMILES: CC1(C)Cc2cnc(N)nc2-c2[nH]nc(C(=O)Nc3cccc(C4OCCCO4)c3)c21]

¹H NMR (499.7 MHz, DMSO-d₆) δ ppm 1.34 (s, 6H), 1.42-1.48 (m, 1H), 1.92-2.06 (m, 1H), 2.65 (s, 2H), 3.92-3.99 (m, 2H), 4.12-4.18 (m, 2H), 5.50 (s, 1H), 6.37 (br. s., 2H), 7.11 (d, J=7.8 Hz, 1H), 7.30 (dd, J=8.7, 7.8 Hz, 1H), 7.64 (d, J=8.7 Hz, 1H), 8.01 (m, 1H), 8.19 (s, 1H), 10.27 (s, 1H) 14.05 (s, 1H).

HRMS (ESI+): calcd. for $C_{22}H_{25}N_6O_3$ [M+H]⁺ 421.1983; found 421.1981.

8-amino-N-[4-(1,4'-bipiperidin-1'-ylmethyl)phenyl]-1,4,4-trimethyl-4,5-dihydro-1H-pyrazolo[4,3-h]quinazoline-3-carboxamide (I), Cpd 128

[R1=R3'=R4'=H, R2=R3=R4=(C₁-C₆)alkyl, y=1, L=CONR8, z=0, A=aryl, n=1, Rc=Rd=H, R5=NR6N7, R6 and R7=taken together form an optionally substituted heterocyclyl group, R8=H]

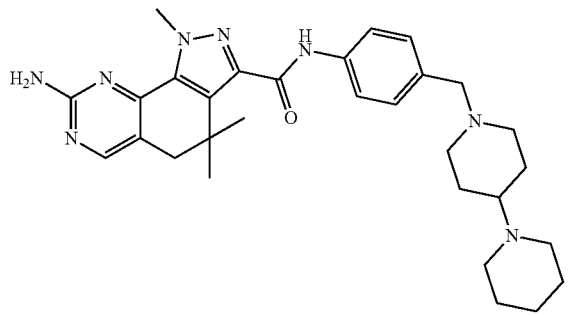 [SMILES: Cn1nc(C(=O)Nc2ccc(CN3CCC(N4CCCCC4)CC3)cc2)c2c1-c1nc(N)ncc1CC2(C)C]

¹H NMR (499.7 MHz, DMSO-d₆) δ ppm 1.31 (s, 6H), 1.33-1.50 (m, 6H), 1.61-1.68 (m, 2H), 1.83-1.90 (m, 2H), 2.10-2.22 (m, 1H), 2.38-2.46 (br. s., 4H), 2.62 (s, 2H), 2.80-2.86 (m, 2H), 3.38 (s, 2H), 4.35 (s, 3H), 6.60 (br. s., 2H), 7.22 (d, J=8.5 Hz, 2H), 7.71 (d, J=8.5 Hz, 2H), 8.18 (s, 1H), 10.24 (s, 1H).

HRMS (ESI+): calcd. for $C_{30}H_{41}N_8O$ [M+H]⁺ 529.3398; found 529.3409.

8-amino-N-[4-(1,4'-bipiperidin-1'-ylmethyl)phenyl]-4,4-dimethyl-4,5-dihydro-1H-pyrazolo[4,3-h]quinazoline-3-carboxamide trifluoroacetate (1:2) (I), Cpd 125

[R1=R2=R3'=R4'=H, R3=R4=(C₁-C₆)alkyl, y=1, L=CONR8, z=0, A=aryl, n=1, Rc=Rd=H, R5=NR6N7, R6 and R7=taken together form an optionally substituted heterocyclyl group, R8=H]

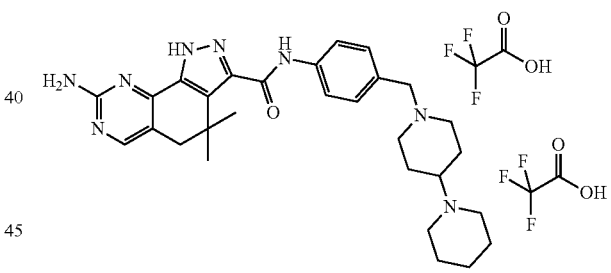

¹H NMR (499.7 MHz, DMSO-d₆) δ ppm 1.34 (s, 6H), 1.36-1.47 (m, 1H), 1.60-1.72 (m, 3H), 1.81-1.92 (m, 4H), 2.18-2.30 (m, 2H), 2.68 (s, 2H), 2.89-3.01 (m, 4H), 3.45 (m overlapped by water signal, 5H), 4.27 (br. s., 2H), 6.83 (br. s., 1H), 7.46 (d, J=8.5 Hz, 2H), 7.91 (d, J=8.5 Hz, 2H), 8.23 (s, 1H), 9.44 (br. s., 1H), 9.76 (br. s., 1H), 10.51 (br. s., 1H), 14.24 (br. s., 1H).

HRMS (ESI+): calcd. for $C_{29}H_{39}N_8O$ [M+H]⁺ 515.3242; found 515.3245.

8-amino-N-[4-({[4-(1,4'-bipiperidin-1'-ylmethyl)phenyl]amino}methyl)phenyl]-4,4-dimethyl-4,5-dihydro-1H-pyrazolo[4,3-h]quinazoline-3-carboxamide trifluoroacetate (1:2) (I), Cpd 126

[R1=R2=R3'=R4'=H, R3=R4=(C₁-C₆)alkyl, y=1, L=CONR8, z=0, A=aryl, n=1, Rc=Rd=H, R5=NR6N7, R6=substituted aryl, R7=R8=H]

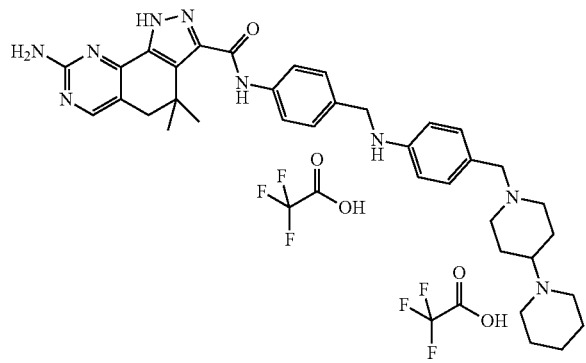

$^1$H NMR (499.7 MHz, DMSO-d$_6$) δ ppm 1.37 (s, 6H), 1.39-1.50 (m, 1H), 1.61-1.76 (m, 3H), 1.82-1.92 (m, 4H), 2.19-2.28 (m, 2H), 2.71 (s, 2H), 2.85-2.99 (m, 4H), 3.81-3.50 (m partially overlapped by water signal, 5H), 4.13 (br. s., 2H), 4.29 (s, 2H), 6.66 (d, J=8.5 Hz, 2H), 6.94 (br. s., 2H), 7.18 (d, J=8.5 Hz, 2H), 7.35 (d, J=8.5 Hz, 2H), 7.76 (d, J=8.5 Hz, 2H), 8.25 (s, 1H), 9.50 (br. s., 2H), 10.31 (br. s., 1H), 14.17 (br. s., 1H).

HRMS (ESI+): calcd. for C$_{36}$H$_{46}$N$_9$O [M+H]$^+$ 620.3820; found 620.3826.

8-amino-N-(4-{[4-(dimethylamino)piperidin-1-yl]methyl}phenyl)-1,4,4-trimethyl-4,5-dihydro-1H-pyrazolo[4,3-h]quinazoline-3-carboxamide (I), Cpd 117

[R1=R3'=R4'=H, R2=R3=R4=(C$_1$-C$_6$)alkyl, y=1, L=CONR8, z=0, A=aryl, n=1, Rc=Rd=H, R5=NR6N7, R6 and R7=taken together form an optionally substituted heterocyclyl group, R8=H]

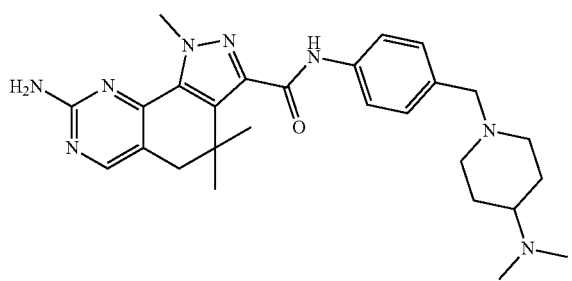 [SMILES: CN(C)C1CCN(Cc2ccc(NC(=O)c3nn(C)c4c3C(C)(C)Cc3cnc(N)nc3-4)cc2)CC1]

$^1$H NMR (499.7 MHz, DMSO-d$_6$) δ ppm 1.31 (s, 6H), 1.32-1.42 (m, 2H), 1.67-1.73 (m, 2H), 1.86-1.93 (m, 2H), 2.01-2.11 (m, 1H), 2.17 (s, 6H), 2.62 (s, 2H), 2.79-2.84 (m, 2H), 3.39 (s, 2H), 4.35 (s, 3H), 6.60 (br. s., 2H), 7.22 (d, J=8.4 Hz, 2H), 7.70 (d, J=8.4 Hz, 2H), 8.18 (s, 1H), 10.25 (br. s., 1H).

HRMS (ESI+): calcd. for C$_{27}$H$_{37}$N$_8$O [M+H]$^+$ 489.3085; found 489.3091.

8-amino-N-(4-{[4-(dimethylamino)piperidin-1-yl]methyl}phenyl)-4,4-dimethyl-4,5-dihydro-1H-pyrazolo[4,3-h]quinazoline-3-carboxamide (I), Cpd 118

[R1=R2=R3'=R4'=H, R3=R4=(C$_1$-C$_6$)alkyl, y=1, L=CONR8, z=0, A=aryl, n=1, Rc=Rd=H, R5=NR6N7, R6 and R7=taken together form an optionally substituted heterocyclyl group, R8=H]

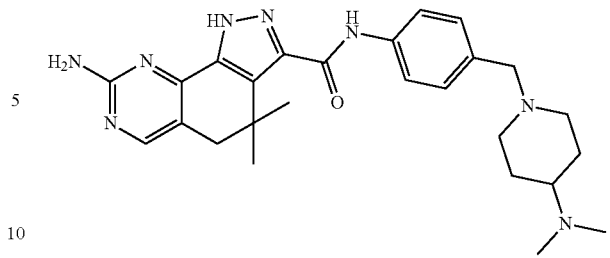

$^1$H NMR (499.7 MHz, DMSO-d$_6$) δ ppm 1.33 (s, 6H), 1.33-1.45 (m, 2H), 1.70-1.75 (m, 2H), 1.86-1.95 (m, 2H), 2.15-2.30 (br. s., 7H), 2.65 (s, 2H), 2.79-2.87 (m, 2H), 3.40 (s, 2H), 6.37 (br. s., 2H), 7.23 (d, J=8.5 Hz, 2H), 7.72 (d, J=8.5 Hz, 2H), 8.18 (s, 1H), 10.24 (br. s., 1H), 14.02 (br. s., 1H).

HRMS (ESI+): calcd. for C$_{26}$H$_{35}$N$_8$O [M+H]$^+$ 475.2929; found 475.2919.

tert-butyl [1-(4-{[(8-amino-1,4,4-trimethyl-4,5-dihydro-1H-pyrazolo[4,3-h]quinazolin-3-yl)carbonyl]amino}benzyl)piperidin-4-yl]carbamate (I), Cpd 132

[R1=R3'=R4'=H, R2=R3=R4=(C$_1$-C$_6$)alkyl, y=1, L=CONR8, z=0, A=aryl, n=1, Rc=Rd=H, R5=NR6N7, R6 and R7=taken together form an optionally substituted heterocyclyl group, R8=H]

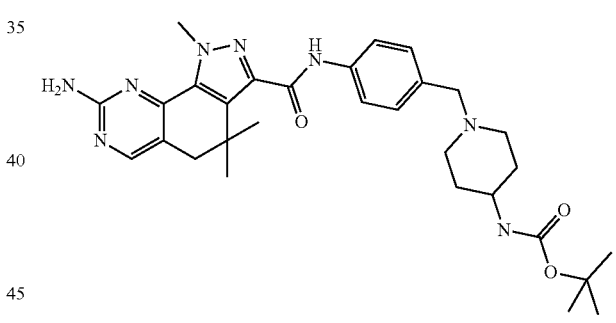

$^1$H NMR (499.7 MHz, DMSO-d$_6$) δ ppm 1.31 (s, 6H), 1.37 (s, 9H), 1.39-1.46 (m, 2H), 2.05-2.18 (br. s., 2H), 2.62 (m, 2H), 2.78-2.87 (m, 2H), 3.30 (s overlapped by water signal, 2H), 3.53 (br. s., 1H), 4.35 (s, 3H), 6.60 (s, 2H), 6.82 (d, J=7.5 Hz, 1H), 7.26 (d, J=8.4 Hz, 2H), 7.74 (d, J=8.4 Hz, 2H), 8.18 (s, 1H), 10.29 (s, 1H).

HRMS (ESI+): calcd. for C$_{30}$H$_{41}$N$_8$O$_3$ [M+H]$^+$ 561.3296; found 561.3287.

tert-butyl [1-(4-{[(8-amino-4,4-dimethyl-4,5-dihydro-1H-pyrazolo[4,3-h]quinazolin-3-yl)carbonyl]amino}benzyl)piperidin-4-yl]carbamate (I), Cpd 133

[R1=R2=R3'=R4'=H, R3=R4=(C$_1$-C$_6$)alkyl, y=1, L=CONR8, z=0, A=aryl, n=1, Rc=Rd=H, R5=NR6N7, R6 and R7=taken together form an optionally substituted heterocyclyl group, R8=H]

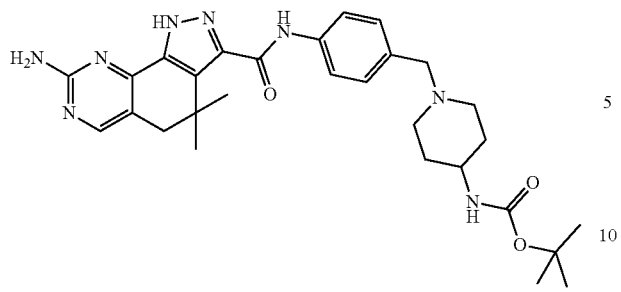

¹H NMR (499.7 MHz, DMSO-d₆) δ ppm 1.29-1.42 (m, 2H), 1.34 (s, 6H), 1.37 (s, 9H), 1.62-1.71 (m, 2H), 1.87-1.97 (m, 2H), 2.66 (m, 2H), 2.70-2.78 (m, 2H), 3.16-3.25 (m, 1H), 3.38 (s, 2H), 6.38 (br. s., 2H), 6.77 (d, J=8.2 Hz, 1H), 7.22 (d, J=8.2 Hz, 2H), 7.73 (d, J=8.2 Hz, 2H), 8.19 (s, 1H), 10.22 (br. s., 1H), 14.04 (br. s., 1H).

HRMS (ESI+): calcd. for $C_{29}H_{39}N_8O_3$ [M+H]⁺ 547.3140; found 547.3140.

8-amino-N-(4-{[4-(dimethylamino)piperidin-1-yl]methyl}-1,3-thiazol-2-yl)-1,4,4-trimethyl-4,5-dihydro-1H-pyrazolo[4,3-h]quinazoline-3-carboxamide (I), Cpd 136

[R1=R3'=R4'=H, R2=R3=R4=(C₁-C₆)alkyl, y=1, L=CONR8, z=0, A=heteroaryl, n=1, Rc=Rd=H, R5=NR6N7, R6 and R7=taken together form an optionally substituted heterocyclyl group, R8=H]

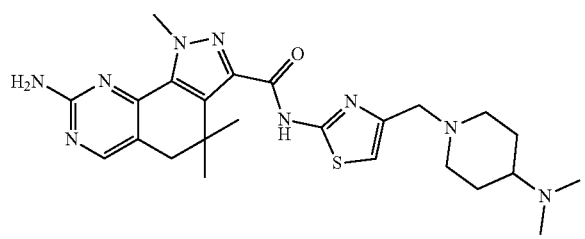 [SMILES: CN(C)C1CCN(Cc2csc(NC(=O)c3nn(C)c4c3C(C)(C)Cc3cnc(N)nc3-4)n2)CC1]

¹H NMR (499.7 MHz, DMSO-d₆) δ ppm 1.31 (s, 6H), 1.32-1.42 (m, 2H), 1.67-1.73 (m, 2H), 1.93-2.00 (m, 2H), 2.00-2.07 (m, 1H), 2.15 (s, 6H), 2.64 (s, 2H), 2.84-2.91 (m, 2H), 3.46 (s, 2H), 4.34 (s, 3H), 6.62 (s, 2H), 6.99 (s, 1H), 8.19 (s, 1H), 12.07 (br. s., 1H).

HRMS (ESI+): calcd. for $C_{24}H_{34}N_9OS$ [M+H]⁺ 496.2602; found 496.2589.

8-amino-N-(4-{[4-(dimethylamino)piperidin-1-yl]methyl}-1,3-thiazol-2-yl)-4,4-dimethyl-4,5-dihydro-1H-pyrazolo[4,3-h]quinazoline-3-carboxamide (I), Cpd 138

[R1=R2=R3'=R4'=H, R3=R4=(C₁-C₆)alkyl, y=1, L=CONR8, z=0, A=heteroaryl, n=1, Rc=Rd=H, R5=NR6N7, R6 and R7=taken together form an optionally substituted heterocyclyl group, R8=H]

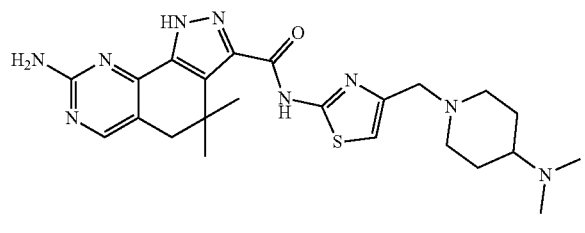 [SMILES: CN(C)C1CCN(Cc2csc(NC(=O)c3n[nH]c4c3C(C)(C)Cc3cnc(N)nc3-4)n2)CC1]

¹H NMR (499.7 MHz, DMSO-d₆) δ ppm 1.33 (s, 6H), 1.35-1.42 (m, 2H), 1.67-1.77 (m, 2H), 1.93-2.01 (m, 2H), 2.16-2.26 (m, 7H), 2.66 (s, 2H), 2.86-2.94 (m, 2H), 3.51 (s, 2H), 6.39 (br. s., 2H), 6.99 (s, 1H), 8.19 (s, 1H), 12.07 (br. s., 1H), 14.20 (br. s., 1H).

HRMS (ESI+): calcd. for $C_{23}H_{32}N_9OS$ [M+H]⁺ 482.2445; found 482.2449.

8-amino-N-(4-{[(3R)-3-(dimethylamino)pyrrolidin-1-yl]methyl}-1,3-thiazol-2-yl)-1,4,4-trimethyl-4,5-dihydro-1H-pyrazolo[4,3-h]quinazoline-3-carboxamide (I), Cpd 147

[R1=R3'=R4'=H, R2=R3=R4=(C₁-C₆)alkyl, y=1, L=CONR8, z=0, A=heteroaryl, n=1, Rc=Rd=H, R5=NR6N7, R6 and R7=taken together form an optionally substituted heterocyclyl group, R8=H]

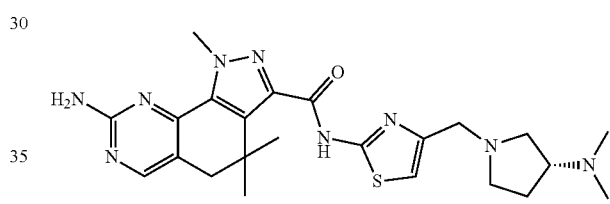

¹H NMR (499.7 MHz, DMSO-d₆) δ ppm 1.31 (s, 6H), 1.63-1.73 (m, 1H), 1.85-1.96 (m, 1H), 2.24 (br. s., 6H), 2.43-2.66 (m, 3H), 2.64 (s, 2H), 2.73-2.79 (m, 1H), 2.84-3.01 (m, 1H), 3.56-3.66 (m, 2H), 4.35 (s, 3H), 6.62 (s, 2H), 7.01 (s, 1H), 8.19 (s, 1H), 12.06 (br. s., 1H).

HRMS (ESI+): calcd. for $C_{23}H_{32}N_9OS$ [M+H]⁺ 482.2445; found 482.2452.

8-amino-N-(4-{[(3R)-3-(dimethylamino)pyrrolidin-1-yl]methyl}-1,3-thiazol-2-yl)-4,4-dimethyl-4,5-dihydro-1H-pyrazolo[4,3-h]quinazoline-3-carboxamide dihydrochloride (I), Cpd 148

[R1=R2=R3'=R4'=H, R3=R4=(C₁-C₆)alkyl, y=1, L=CONR8, z=0, A=heteroaryl, n=1, Rc=Rd=H, R5=NR6N7, R6 and R7=taken together form an optionally substituted heterocyclyl group, R8=H]

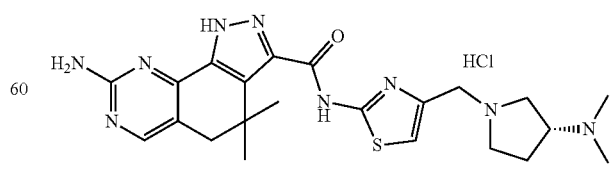

¹H NMR (499.7 MHz, DMSO-d₆) δ ppm 1.33 (s, 6H), 1.88-2.02 (m, 1H), 2.06-2.20 (m, 1H), 2.67 (s, 2H), 2.72 (br.

s., 6H), 2.60-3.00 (br. s., 5H), 3.74 (br. s., 2H), 6.41 (br. s., 2H), 7.10 (br. s., 1H), 8.20 (s, 1H), 12.06 (br. s., 1H), 14.27 (br. s., 1H).

HRMS (ESI+): calcd. for $C_{22}H_{30}N_9OS$ [M+H]$^+$ 468.2289; found 468.23.

8-amino-N-[4-(1,4'-bipiperidin-1'-ylmethyl)-1,3-thiazol-2-yl]-1,4,4-trimethyl-4,5-dihydro-1H-pyrazolo[4,3-h]quinazoline-3-carboxamide (I), Cpd 141

[R1=R3'=R4'=H, R2=R3=R4=$(C_1-C_6)$alkyl, y=1, L=CONR8, z=0, A=heteroaryl, n=1, Rc=Rd=H, R5=NR6N7, R6 and R7=taken together form an optionally substituted heterocyclyl group, R8=H]

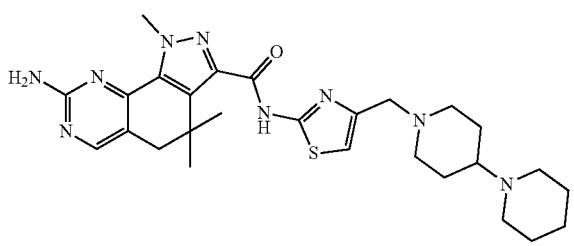 [SMILES: Cn1nc(C(=O)Nc2nc(CN3CCC(N4CCCCC4)CC3)cs2)c2c1-c1nc(N)ncc1CC2(C)C]

$^1$H NMR (499.7 MHz, DMSO-d$_6$) δ ppm 1.31 (s, 6H), 1.35-1.53 (m, 7H), 1.62-1.68 (m, 2H), 1.90-1.98 (m, 2H), 2.10-2.17 (m, 1H), 2.39-2.45 (m, 4H), 2.63 (s, 2H), 2.86-2.92 (m, 2H), 3.45 (s, 2H), 4.34 (s, 3H), 6.61 (br. s., 2H), 6.97 (br. s., 1H), 8.19 (s, 1H), 12.03 (br. s., 1H).

HRMS (ESI+): calcd. for $C_{27}H_{38}N_9OS$ [M+H]$^+$ 536.2915; found 536.2926.

8-amino-N-[4-(1,4'-bipiperidin-1'-ylmethyl)-1,3-thiazol-2-yl]-4,4-dimethyl-4,5-dihydro-1H-pyrazolo[4,3-h]quinazoline-3-carboxamide (I), Cpd 143

[R1=R2=R3'=R4'=H, R3=R4=$(C_1-C_6)$alkyl, y=1, L=CONR8, z=0, A=heteroaryl, n=1, Rc=Rd=H, R5=NR6N7, R6 and R7=taken together form an optionally substituted heterocyclyl group, R8=H]

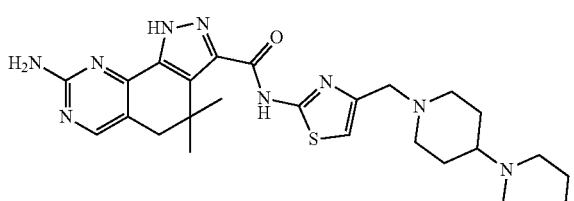

$^1$H NMR (499.7 MHz, DMSO-d$_6$) δ ppm 1.30-1.50 (m, 8H), 1.33 (s, 6H), 1.63-1.70 (m, 2H), 1.90-2.00 (m, 2H), 3.46 (s, 2H), 6.39 (br. s., 2H), 6.98 (s, 1H), 8.19 (s, 1H), 12.09 (br. s., 1H), 14.18 (br. s., 1H).

HRMS (ESI+): calcd. for $C_{26}H_{36}N_9OS$ [M+H]$^+$ 522.2758; found 522.2768.

8-amino-N,N,4,4-tetramethyl-4,5-dihydro-1H-pyrazolo[4,3-h]quinazoline-3-carboxamide (I), Cpd 184

[R1=R2=R3'=R4'=H, R3=R4=$(C_1-C_6)$alkyl, y=0, L=CONR6aR7a, R6a=R7a=$(C_1-C_6)$alkyl]

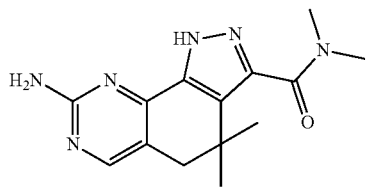 [SMILES: CN(C)C(=O)c1n[nH]c2c1C(C)(C)Cc1cnc(N)nc1-2]

$^1$H NMR (500 MHz, DMSO-d$_6$; mixture of rotamers) δ ppm 1.17 (s, 6H) 2.60 (s, 2H) 3.00 (s, 6H) 6.36 (br. s., 2H) 8.16 (s, 1H) 13.71 (br. s., 1H).

HRMS (ESI+): calcd. for $C_{14}H_{19}N_6O$ [M+H]$^+$ 287.1615; found 287.1617.

8-amino-2,4,4-trimethyl-N-(4-methyl-1,3-thiazol-2-yl)-4,5-dihydro-2H-pyrazolo[4,3-h]quinazoline-3-carboxamide (I), Cpd 195

[R1=R3'=R4'=H, R2=R3=R4=$(C_1-C_6)$alkyl, y=0, L=CONR6aR7a, R6a=substituted heteroaryl, R7a=H]

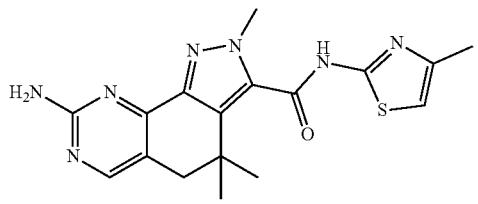 [SMILES: Cc1csc(NC(=O)c2c3c(nn2C)-c2nc(N)ncc2CC3(C)C)n1]

$^1$H NMR (499.7 MHz, DMSO-d$_6$) δ ppm 1.19 (s, 6H), 2.30 (s, 3H), 2.58 (s, 2H), 3.88 (s, 3H) 6.49 (br. s., 2H), 6.91 (br. s., 1H), 8.12 (s, 1H), 12.87 (br. s., 1H).

HRMS (ESI+): calcd. for $C_{17}H_{20}N_7OS$ [M+H]$^+$ 370.1445; found 370.1450.

8-amino-2,4,4-trimethyl-N-{4-[2-(4-methyl-1,4'-bipiperidin-1'-yl)-2-oxoethyl]-1,3-thiazol-2-yl}-4,5-dihydro-2H-pyrazolo[4,3-h]quinazoline-3-carboxamide (I), Cpd 211

[R1=R3'=R4'=H, R2=R3=R4=$(C_1-C_6)$alkyl, y=1, L=CONR8, z=0, A=heteroaryl, n=1, Rc=Rd=H, R5=CONR6N7, R6 and R7=taken together form an optionally substituted heterocyclyl group, R8=H]

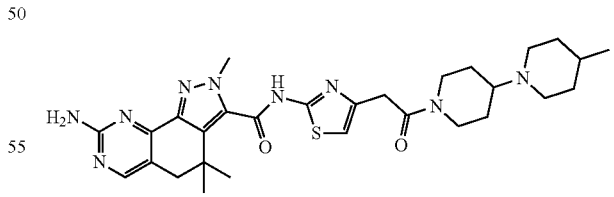

$^1$H NMR (499.7 DMSO-d$_6$) δ ppm 0.86 (d, J=6.5 Hz, 3H), 1.00-1.12 (m, 2H), 1.19 (s, 6H), 1.15-1.33 (m, 3H), 1.53-1.59 (m, 2H), 1.65-1.74 (m, 2H), 2.05-2.16 (m, 2H), 2.41-2.53 (m, 1H), 2.58 (s, 2H), 2.73-2.80 (m, 2H), 2.94-3.02 (m, 1H), 3.35 (m overlapped by water signal, 1H), 3.69-3.81 (m, 2H), 3.88 (s, 3H), 3.98-4.05 (m, 1H), 4.36-4.42 (m, 1H) 6.48 (br. s., 2H), 7.01 (br. s., 1H), 8.12 (s, 1H).

HRMS (ESI+): calcd. for $C_{29}H_{40}N_9O_2S$ [M+H]$^+$ 578.3020; found 578.3010.

8-amino-N-(3-methoxyphenyl)-1,4,4-trimethyl-4,5-dihydro-1H-pyrazolo[4,3-h]quinazoline-3-carboxamide (I), Cpd 215

[R1=R3'=R4'=H, R2=R3=R4=(C$_1$-C$_6$)alkyl, y=0, L=CONR6aR7a, R6a=substituted aryl, R7a=H]

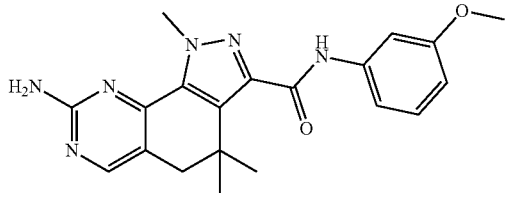 [SMILES: COc1cccc(NC(=O)c2nn(C)c3c2C(C)(C)Cc2cnc(N)nc2-3)c1]

$^1$H NMR (499.7 MHz, DMSO-d$_6$) δ ppm 1.31 (s, 6H), 2.62 (s, 2H), 3.74 (s, 3H), 4.35 (s, 3H), 6.60 (s, 2H), 6.67 (dd, J=8.2, 2.1 Hz, 1H), 7.23 (dd, J=8.2, 8.0 Hz, 1H), 7.36 (d, J=8.0 Hz, 1H), 7.47 (t, J=2.1 Hz, 1H), 8.18 (s, 1H), 10.24 (s, 1H).

HRMS (ESI+): calcd. for C$_{20}$H$_{23}$N$_6$O$_2$ [M+H]$^+$ 379.1877; found 379.1878.

8-amino-4,4-dimethyl-N-(4-methyl-1,3-thiazol-2-yl)-2-[2-(tetrahydro-2H-pyran-2-yloxy)ethyl]-4,5-dihydro-2H-pyrazolo[4,3-h]quinazoline-3-carboxamide (I), Cpd 216

[R1=R3'=R4'=H, R2=R3=R4=(C$_1$-C$_6$)alkyl, y=0, L=CONR6aR7a, R6a=substituted heteroaryl, R7a=H]

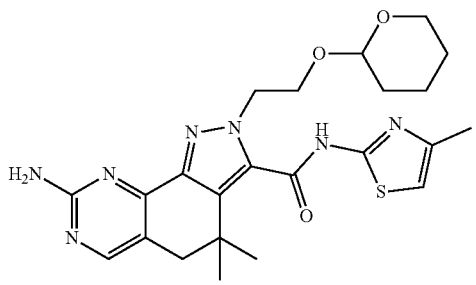 [SMILES: Cc1csc(NC(=O)c2c3c(nn2CCOC2CCCCO2)-c2nc(N)ncc2CC3(C)C)n1]

$^1$H NMR (499.7 MHz, DMSO-d$_6$) δ ppm 1.19 (s, 3H), 1.21 (s, 3H), 1.17-1.66 (m, 6H), 2.29 (s, 2H), 2.58 (s, 2H), 3.20-3.28 (m, 1H), 3.34-3.40 (m, 1H), 3.66-3.71 (m, 1H), 3.35-3.92 (m, 1H), 4.33-4.43 (m, 2H), 4.43- 4.45 (m, 1H), 6.52 (br. s., 2H), 6.89 (br. s., 1H), 8.12 (s, 1H), 12.75 (br. s., 1H).

HRMS (ESI+): calcd. for C$_{23}$H$_{30}$N$_7$O$_3$S [M+H]$^+$ 484.2126; found 484.2123.

8-amino-N-(4-{[(1-cycloheptylpiperidin-4-yl)oxy]methyl}-1,3-thiazol-2-yl)-1,4,4-trimethyl-4,5-dihydro-1H-pyrazolo[4,3-h]quinazoline-3-carboxamide (I), Cpd 217

[R1=R3'=R4'=H, R2=R3=R4=(C$_1$-C$_6$)alkyl, y=1, L=CONR8, z=0, A=heteroaryl, n=1, Rc=Rd=H, R5=OR6, R6=substituted heterocyclyl, R8=H]

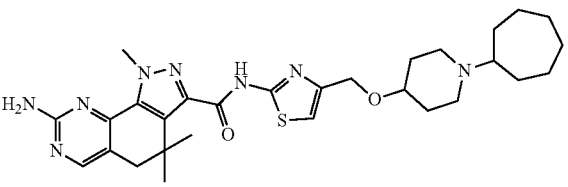 [SMILES: Cn1nc(C(=O)Nc2nc(COC3CCN(C4CCCCCC4)CC3)cs2)c2c1-c1nc(N)ncc1CC2(C)C]

$^1$H NMR (499.7 MHz, DMSO-d$_6$) δ ppm 1.31 (s, 6H), 1.27-1.52 (m, 10H), 1.56-1.64 (m, 2H), 1.65-1.73 (m, 2H), 1.82-1.89 (m 2H), 2.17-2.25 (m, 2H), 2.44-2.50 (m, 1H), 2.64/s, 2H), 2.63-2.70 (m, 2H), 3.33-3.38 (m, 1H), 4.34 (s, 3H), 4.46 (s, 2H), 0.62 (s, 2H), 7.08 (s, 1H), 8.19 (s, 1H), 12.13 (br. s., 1H).

HRMS (ESI+): calcd. for C$_{29}$H$_{41}$N$_8$O$_2$S [M+H]$^+$ 565.3068; found 565.3094.

8-amino-1,5,5-trimethyl-N-{4-[2-(4-methyl-1,4'-bipiperidin-1'-yl)-2-oxoethyl]-1,3-thiazol-2-yl}-4,5-dihydro-1H-pyrazolo[4,3-h]quinazoline-3-carboxamide (I), Cpd 225

[R1=R3=R4=H, R2=R3'=R4'=(C$_1$-C$_6$)alkyl, y=1, L=CONR8, z=0, A=heteroaryl, n=1, Rc=Rd=H, R5=CONR6N7, R6 and R7=taken together form an optionally substituted heterocyclyl group, R8=H]

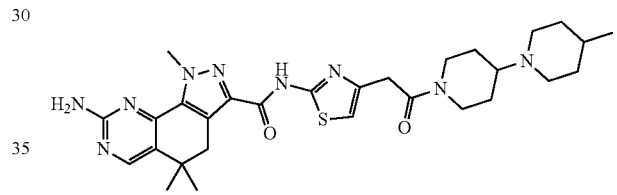

$^1$H NMR (499.7 MHz, DMSO-d$_6$) δ ppm 0.84 (d, J=6.6 Hz, 3H), 1.00-1.09 (m, 2H), 1.18-1.30 (m, 9H), 1.50-1.57 (m, 2H), 1.64-1.72 (m, 2H), 2.03-2.12 (m, 2H), 2.38-2.44 (m, 1H), 2.70-2.78 (m, 2H), 2.93 (s, 2H), 2.94-3.01 (m, 1H), 3.33 (m overlapped by water signal, 1H), 3.73 (s, 2H), 3.96-4.03 (m, 1H), 4.37 (s, 3H), 4.37-4.43 (m, 1H), 6.64 (br.s., 2H), 6.93 (s, 1H), 8.29 (s, 1H), 11.66 (br.s., 1H).

HRMS (ESI+): calcd. for C$_{29}$H$_{40}$N$_9$O$_2$S [M+H]$^+$ 578.3020; found 578.3018.

Alternatively:

8-amino-4,4-dimethyl-N-(5-methyl-1,3-thiazol-2-yl)-4,5-dihydro-1H-pyrazolo[4,3-h]quinazoline-3-carboxamide (I), Cpd 65

[R1=R2=R3'=R4'=H, R3=R4=(C$_1$-C$_6$)alkyl, y=0, L=CONR6aR7a, R6a=substituted heteroaryl, R7a=H]

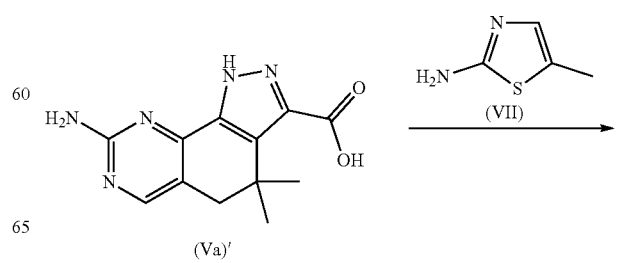

-continued

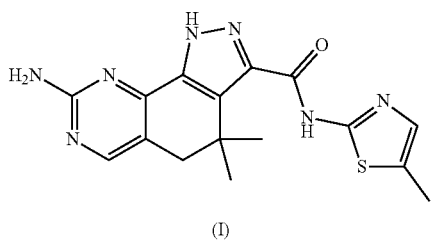

(I)

A suspension of 8-amino-4,4-dimethyl-4,5-dihydro-1H-pyrazolo[4,3-h]quinazoline-3-carboxylic acid (Va)' (30 mg, 0.115 mmol), TBTU (55.7 mg, 0.173 mmol), 5-methyl-1,3-thiazol-2-amine (VII) (20 mg, 0.173 mmol) and DIPEA (0.029 mL, 0.173 mmol) in dry DMF (0.460 mL) was stirred at rt for 72 hours. After dilution with water (2 mL), the resulting solid was filtered, washed with water (×3) and with diethyl ether (×3). The solid was taken with NaOH (2M)/EtOH (0.9 M) and the reaction mixture was stirred at reflux for 2 minutes. The solution was extracted with EtOAc (×3), the organic phase was dried over $Na_2SO_4$, filtered and evaporated in vacuum affording the title compound without any further purification (12 mg, 29%).

$^1$H NMR (499.7 MHz, DMSO-$d_6$) δ ppm 1.32 (s, 6H), 2.37 (s, 3H), 2.65 (s, 2H), 6.39 (br. s., 2H), 7.18 (s, 1H), 8.18 (s, 1H), 11.86 (br. s., 1H), 14.19 (br. s., 1H).

HRMS (ESI+): calcd. for $C_{16}H_{18}N_7OS$ [M+H]$^+$ 356.1288; found 356.1282.

Operating in an analogous way, but employing suitably substituted reagents (VII), the following compounds were obtained:

8-amino-N-(1H-imidazol-2-yl)-4,4-dimethyl-4,5-dihydro-1H-pyrazolo[4,3-h]quinazoline-3-carboxamide (I), Cpd 144

[R1=R2=R3'=R4'=H, R3=R4=($C_1$-$C_6$)alkyl, y=0, L=CONR6aR7a, R6a=unsubstituted heteroaryl, R7a=H]

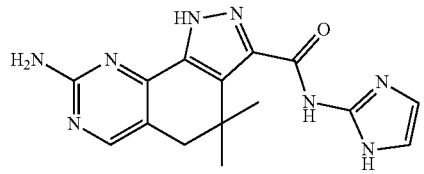 [SMILES: CC1(C)Cc2cnc(N)nc2-c2[nH]nc(C(=O)Nc3ncc[nH]3)c21]

$^1$H NMR (499.7 MHz, DMSO-$d_6$) δ ppm 1.36 (s, 6H), 2.64 (m, 2H), 6.37 (br. s., 2H), 6.78 (br. s., 2H), 8.16 (s, 1H), 11.61 (br. s., 2H), 13.86 (br. s., 1H).

HRMS (ESI+): calcd. for $C_{15}H_{17}N_8O$ [M+H]$^+$ 325.1520; found 325.1522.

8-amino-4,4-dimethyl-N-(4-phenyl-1,3-thiazol-2-yl)-4,5-dihydro-1H-pyrazolo[4,3-h]quinazoline-3-carboxamide (I), Cpd 60

[R1=R2=R3'=R4'=H, R3=R4=($C_1$-$C_6$)alkyl, y=0, L=CONR6aR7a, R6a=substituted heteroaryl, R7a=H]

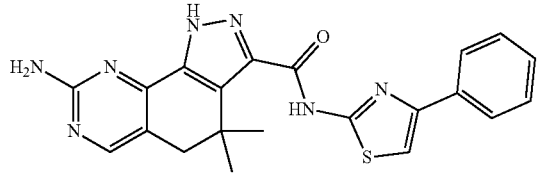 [SMILES: CC1(C)Cc2cnc(N)nc2-c2[nH]nc(C(=O)Nc3nc(-c4ccccc4)cs3)c21]

$^1$H NMR (499.7 MHz, DMSO-$d_6$) δ ppm 1.35 (s, 6H), 2.67 (s, 2H), 6.40 (br. s., 2H), 7.30-7.36 (m, 1H), 7.40-7.47 (m, 2H), 7.68 (br. s., 1H), 7.93-7.96 (m, 2H), 8.19 (s, 1H), 12.21 (br. s., 1H) 14.25 (br. s., 1H).

HRMS (ESI+): calcd. for $C_{21}H_{20}N_7OS$ [M+H]$^+$ 418.1445; found 418.1449.

8-amino-4,4-dimethyl-N-(1,3-thiazol-2-yl)-4,5-dihydro-1H-pyrazolo[4,3-h]quinazoline-3-carboxamide, (I) cpd 61

[R1=R2=R3'=R4'=H, R3=R4=($C_1$-$C_6$)alkyl, y=0, L=CONR6aR7a, R6a=unsubstituted heteroaryl, R7a=H]

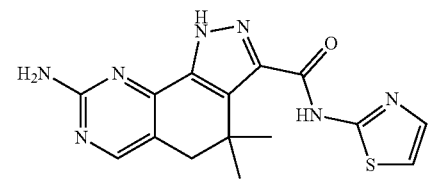 [SMILES: CC1(C)Cc2cnc(N)nc2-c2[nH]nc(C(=O)Nc3nccs3)c21]

$^1$H NMR (499.7 MHz, DMSO-$d_6$) δ ppm 1.34 (s, 6H), 2.70 (s, 2H), 6.94 (br. s., 2H) 7.29 (d, J=3.7 Hz, 1H), 7.54 (d, J=3.7 Hz, 1H), 8.22 (s, 1H), 12.22 (br. s., 1H) 14.38 (br. s., 1H).

HRMS (ESI+): calcd. for $C_{19}H_{18}N_7OS$ [M+H]$^+$ 342.1132; found 342.1125.

8-amino-N-(1,3-benzothiazol-2-yl)-4,4-dimethyl-4,5-dihydro-1H-pyrazolo[4,3-h]quinazoline-3-carboxamide (I), Cpd 62

[R1=R2=R3'=R4'=H, R3=R4=($C_1$-$C_6$)alkyl, y=0, L=CONR6aR7a, R6a=substituted heteroaryl, R7a=H]

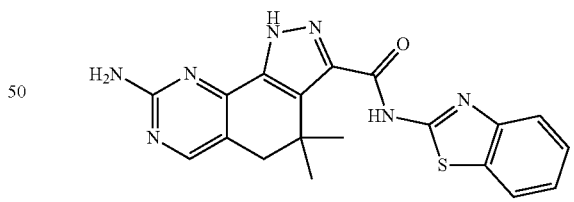

$^1$H NMR (499.7 MHz, DMSO-$d_6$) δ ppm 1.44 (s, 6H), 2.58 (s, 2H), 6.30 (s, 2H), 7.00-7.05 (m, 1H), 7.18-7.22 (m, 1H), 7.44-7.48 (m, 1H), 7.63-7.68 (m, 1H), 8.07 (s, 1H).

HRMS (ESI+): calcd. for $C_{19}H_{18}N_7OS$ [M+H]$^+$ 392.1288; found 392.1284.

8-amino-N-(6-methoxy-1,3-benzothiazol-2-yl)-4,4-dimethyl-4,5-dihydro-1H-pyrazolo[4,3-h]quinazoline-3-carboxamide (I), Cpd 63

[R1=R2=R3'=R4'=H, R3=R4=($C_1$-$C_6$)alkyl, y=0, L=CONR6aR7a, R6a=substituted heteroaryl, R7a=H]

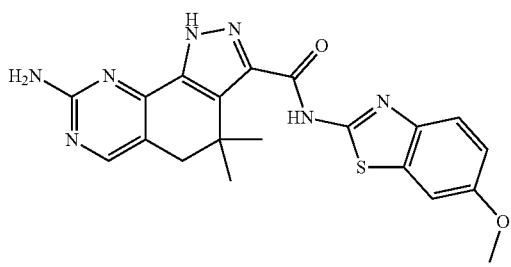 [SMILES: COc1ccc2nc(NC(=O)c3n[nH]c4c3C(C)(C)Cc3cnc(N)nc3-4)sc2c1]

¹H NMR (499.7 MHz, DMSO-d₆) δ ppm 1.36 (s, 6H), 2.68 (s, 2H), 3.82 (s, 3H), 6.41 (br. s., 2H), 7.05 (dd, J=8.8, 2.4 Hz, 1H), 7.58 (s, 1H), 7.67 (d, J=8.8 Hz, 1H). 8.20 (s, 1H), 12.21 (br. s., 1H), 14.31 (br. s., 1H).

HRMS (ESI+): calcd. for $C_{20}H_{20}N_7O_2S$ [M+H]⁺ 422.1394; found 422.1394.

8-amino-N-(6-chloro-1,3-benzothiazol-2-yl)-4,4-dimethyl-4,5-dihydro-1H-pyrazolo[4,3-h]quinazoline-3-carboxamide (I), Cpd 64

[R1=R2=R3'=R4'=H, R3=R4=($C_1$-$C_6$)alkyl, y=0, L=CONR6aR7a, R6a=substituted heteroaryl, R7a=H]

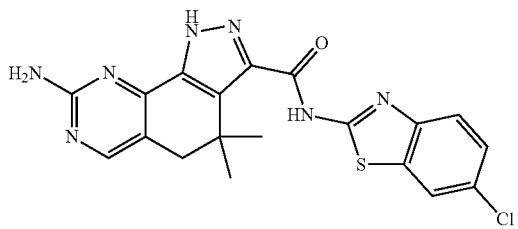 [SMILES: CC1(C)Cc2cnc(N)nc2-c2[nH]nc(C(=O)Nc3nc4ccc(Cl)cc4s3)c21]

¹H NMR (499.7 MHz, DMSO-d₆) δ ppm 1.36 (s, 6H), 2.67 (s, 2H), 6.40 (br. s., 2H), 7.47 (br. s., 1H), 7.76 (br. s., 1H), 8.14 (br. s., 1H), 8.19 (s, 1H), 12.51 (br. s., 1H), 14.38 (br. s., 1H).

HRMS (ESI+): calcd. for $C_{19}H_{17}N_7OSCl$ [M+H]⁺ 426.0899; found 426.09.

8-amino-N-(5-chloro-1,3-thiazol-2-yl)-4,4-dimethyl-4,5-dihydro-1H-pyrazolo[4,3-h]quinazoline-3-carboxamide (I), Cpd 66

[R1=R2=R3'=R4'=H, R3=R4=($C_1$-$C_6$)alkyl, y=0, L=CONR6aR7a, R6a=substituted heteroaryl, R7a=H]

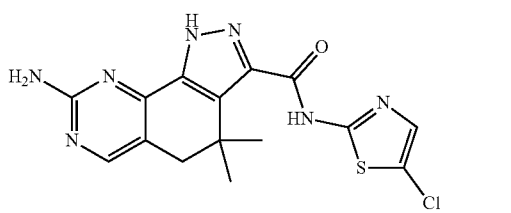 [SMILES: CC1(C)Cc2cnc(N)nc2-c2[nH]nc(C(=O)Nc3ncc(Cl)s3)c21]

¹H NMR (499.7 MHz, DMSO-d₆) δ ppm 1.33 (s, 6H), 2.66 (s, 2H), 6.40 (br. s., 2H), 7.56 (br. s., 1H), 8.19 (s, 1H), 12.54 (br. s., 1H), 14.32 (br. s., 1H).

HRMS (ESI+): calcd. for $C_{15}H_{15}N_7OSCl$ [M+H]⁺ 376.0742; found 376.0744.

Alternatively:

8-amino-N-(6-fluoro-1,3-benzothiazol-2-yl)-1,4,4-trimethyl-4,5-dihydro-1H-pyrazolo[4,3-h]quinazoline-3-carboxamide (I), Cpd 140

[R1=R3'=R4'=H, R2=R3=R4=($C_1$-$C_6$)alkyl, y=0, L=CONR6aR7a, R6a=substituted heteroaryl, R7a=H]

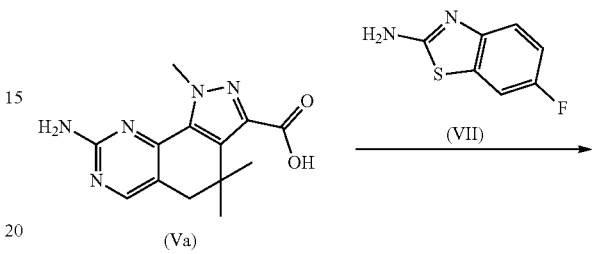

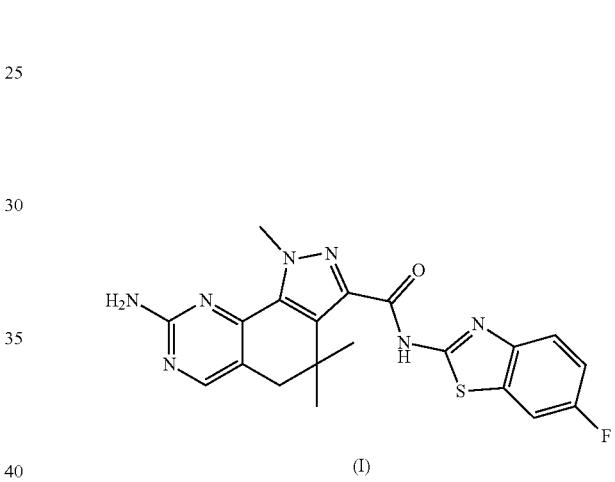

8-Amino-1,4,4-trimethyl-4,5-dihydro-1H-pyrazolo[4,3-h]quinazoline-3-carboxylic acid (Va) (50 mg, 0.183 mmol) in DCM (2 mL) was treated with 1-chloro-N,N,2-trimethyl-1-propenylamine (Ghosez's reagent, 0.292 mL, 1.8 mmol). The reaction was stirred at rt for 2 h and then treated with a solution of 6-fluoro-1,3-benzothiazol-2-amine (VII) (39 mg, 0.236 mmol), TEA (0.127 mL, 0.915 mmol) in DCM (2 mL) for 2 days, evaporated and the residue partitioned between EtOAc (10 mL) and $H_2O_2O$ (10 mL). The aqueous phase was further extracted with EtOAc (20 mL×2). The combined organic extracts were washed with brine, dried over $Na_2SO_4$, filtered and evaporated. Purification by column chromatography (DCM: 7 N $NH_3$ in MeOH=95:5) afforded the title compound (10 mg, 13%).

¹H NMR (499.7 MHz, DMSO-d₆) δ ppm 1.34 (s, 6H), 2.66 (s, 2H), 4.38 (s, 3H), 6.64 (s, 2H), 7.31 (ddd, J=8.8, 8.5, 2.7 Hz, 1H), 7.79 (dd, J=8.8, 4.7 Hz, 1H), 7.92 (dd, J=8.5, 2.7 Hz, 1H), 8.20 (s, 1H), 12.45 (br. s., 1H).

HRMS (ESI+): calcd. for $C_{20}H_{19}N_7OFS$ [M+H]⁺ 424.1351 found 424.1359.

Example 2

Sequence B or D 4,4-dimethyl-8-(methylamino)-N-{4-[2-(4-methyl-1,4'-bipiperidin-1'-yl)-2-oxoethyl]-1,3-thiazol-2-yl}-4,5-dihydro-1H-pyrazolo[4,3-h]quinazoline-3-carboxamide (I), Cpd 122

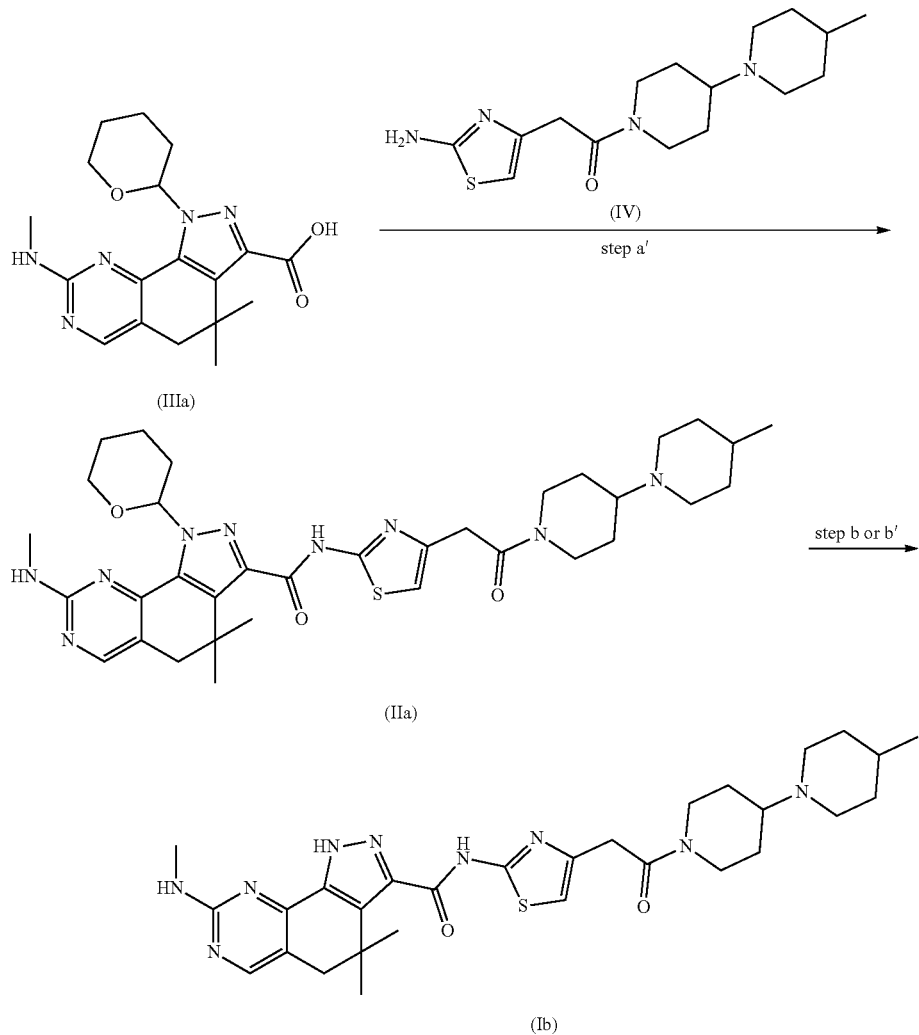

Step a'

4,4-dimethyl-8-(methylamino)-N-{4-[2-(4-methyl-1,4'-bipiperidin-1'-yl)-2-oxoethyl]-1,3-thiazol-2-yl}-1-(tetrahydro-2H-pyran-2-yl)-4,5-dihydro-1H-pyrazolo[4,3-h]quinazoline-3-carboxamide (IIa)

[R1=R3=R4=($C_1$-$C_6$)alkyl, R3'=R4'=H, PG=tetrahydropyranyl, y=1, L=CONR8, z=0, A=heteroaryl, n=1, Rc=Rd=H, R5=CONR6N7, R6 and R7=taken together form an optionally substituted heterocyclyl group, R8=H]

4,4-Dimethyl-8-(methylamino)-1-(tetrahydro-2H-pyran-2-yl)-4,5-dihydro-1H-pyrazolo[4,3-h]quinazoline-3-carboxylic acid (IIIa) (60 mg, 0.17 mmol) in dry DMF (0.7 mL) was treated with DIPEA (0.093 mL, 0.544 mmol), 2-(2-amino-1,3-thiazol-4-yl)-1-(4-methyl-1,4'-bipiperidin-1'-yl)ethanone (IV) (80 mg, 0.20 mmol) and TBTU (65 mg, 0.20 mmol). The reaction was left at rt for four days, then DMF was removed by distillation under vacuum, the residue was partitioned between DCM (20 mL) and saturated aqueous $NaHCO_3$ (10 mL); the aqueous phase was further extracted with DCM (5 mL×2). The combined organic extracts were dried over $Na_2SO_4$ and evaporated to leave 152 mg of crude product which was purified by column chromatography over silica gel (DCM: 7 N $NH_3$ in MeOH=95:5) affording 54 mg of title compound (48%).

$^1$H NMR (500 MHz, DMSO-$d_6$) δ ppm 0.85 (dd, J=6.02, 2.67 Hz, 3H) 0.398-1.15 (m, 2H) 1.27 (s, 3H) 1.34 (s, 3H) 1.47-1.80 (m, 6H) 1.88-2.11 (m, 2H) 2.39-2.47 (m, 1H) 2.59-2.69 (m, 2H) 2.71-2.83 (m, 1H) 2.87 (d, J=4.42 Hz, 3H) 2.91-3.05 (m, 1H) 3.50-3.83 (m, 4H) 3.91-4.09 (m, 2H) 4.35-4.48 (m, 1H) 6.82-6.94 (m, 1H) 6.97 (s, 1H) 7.14 (br. s., 1H) 8.25 (s, 1H) 12.28 (br. s., 1H).

HRMS (ESI+): calcd. for $C_{34}H_{48}N_9O_3S$ $[M+H]^+$ 662.3596; found 662.3597.

Operating in an analogous way, but employing suitably substituted reagents (IIIa) or (IV), the following compounds were obtained:

8-amino-N-(4-{[(1-cyclohexylpiperidin-4-yl)oxy]
methyl}-1,3-thiazol-2-yl)-4,4-dimethyl-1-(tetra-
hydro-2H-pyran-2-yl)-4,5-dihydro-1H-pyrazolo[4,3-
h]quinazoline-3-carboxamide (IIa)

[R1=R3'=R4'=H, PG=tetrahydropyranyl, R3=R4=($C_1$-$C_6$) alkyl, y=1, L=CONR8, z=0, A=heteroaryl, n=1, Rc=Rd=H, R5=OR6, R6=substituted heterocyclyl, R8=H]
$^1$H NMR (500 MHz, DMSO-$d_6$) δ ppm 0.99-1.23 (m, 4H) 1.26 (s, 3H) 1.35 (s, 3H) 1.37-1.61 (m, 4H) 1.66-1.79 (m, 4H) 1.79-2.11 (m, 4H) 2.16-2.31 (m, 2H) 2.40-2.48 (m, 1H) 2.57-2.67 (m, 2H) 2.69-2.78 (m, 2H) (br. s., 2H) 3.73-3.86 (m, 1H) 3.89-3.96 (m, 1H) 4.48 (s, 2H) 6.64 (br. s., 2H) 6.85 (dd, J=9.84, 2.52 Hz, 1H) 7.11 (s, 1H) 8.20 (s, 1H) 12.35 (br. s., 1H).
HRMS (ESI+): calcd. for $C_{32}H_{46}N_8O_3S$ [M+H]$^+$ 621.3330; found 621.3335.

8-amino-4,4-di methyl-N-[4-({[trans-4-(4-methylpi-
peridin-1-yl)cyclohexyl]oxy}methyl)-1,3-thiazol-2-
yl]-1-(tetrahydro-2H-pyran-2-yl)-4,5-dihydro-1H-
pyrazolo[4,3-h]quinazoline-3-carboxamide (IIa)

[R1=R3'=R4'=H, PG=tetrahydropyranyl, R3=R4=($C_1$-$C_6$) alkyl, y=1, L=CONR8, z=0, A=heteroaryl, n=1, Rc=Rd=H, R5=OR6, R6=substituted cycloalkyl, R8=H]
HRMS (ESI+): calcd. for $C_{33}H_{47}N_8O_3S$ [M+H]$^+$ 635.3486; found 635.3482.

8-amino-N-{4-[2-(4-cyclohexylpiperazin-1-yl)-2-
oxoethyl]-1,3-thiazol-2-yl}-4,4-dimethyl-1-(tetra-
hydro-2H-pyran-2-yl)-4,5-dihydro-1H-pyrazolo[4,3-
h]quinazoline-3-carboxamide (IIa)

[R1=R3'=R4'=H, PG=tetrahydropyranyl, R3=R4=($C_1$-$C_6$) alkyl, y=1, L=CONR8, z=0, A=heteroaryl, n=1, Rc=Rd=H, R5=CONR6N7, R6 and R7=taken together form an optionally substituted heterocyclyl group, R8=H]
$^1$H NMR (500 MHz, DMSO-$d_6$) δ ppm 1.08-1.22 (m, 5H) 1.25 (s, 3H) 1.35 (s, 3H) 1.49-1.63 (m, 3H) 1.64-1.83 (m, 5H) 2.01-2.11 (m, 1H) 2.17-2.30 (m, 2H) 2.37-2.48 (m, 4H) 2.57-2.68 (m, 2H) 3.39-3.54 (m, 4H) 3.74 (s, 2H) 3.77-3.87 (m, 1H) 3.87-3.96 (m, 1H) 6.64 (br. s., 2H) 6.85 (dd, J=9.91, 2.44 Hz, 1H) 6.96 (s, 1H) 8.20 (s, 1H) 12.29 (br. s., 1H).
HRMS (ESI+): calcd. For $C_{32}H_{44}N_9O_3S$ [M+H]$^+$ 634.3283; found 634.3289.

8-amino-N-(4-{2-[(1-cyclohexylpiperidin-4-yl)
amino]-2-oxoethyl}-1,3-thiazol-2-yl)-4,4-dimethyl-
1-(tetrahydro-2H-pyran-2-yl)-4,5-dihydro-1H-pyra-
zolo[4,3-h]quinazoline-3-carboxamide (IIa)

[R1=R3'=R4'=H, PG=tetrahydropyranyl, R3=R4=($C_1$-$C_6$) alkyl, y=1, L=CONR8, z=0, A=heteroaryl, n=1, Rc=Rd=H, R5=CONR6N7, R6=substituted heterocyclyl, R7=R8=H]
$^1$H NMR (500 MHz, DMSO-$d_6$) δ ppm 1.00-1.22 (m, 5H) 1.26 (s, 3H) 1.29-1.41 (m, 2H) 1.34 (s, 3H) 1.50-1.63 (m, 3H) 1.64-1.81 (m, 6H) 1.88-1.98 (m, 2H) 2.00-2.10 (m, 2H) 2.15-2.27 (m, 2H) 2.39-2.48 (m, 1H) 2.57-2.69 (m, 2H) 2.70-2.79 (m, 2H) 3.43-3.56 (m, 1H) 3.48 (s, 2H) 3.77-3.86 (m, 1H) 3.88-3.96 (m, 1H) 6.63 (br. s., 2H) 6.85 (dd, J=9.91, 2.44 Hz, 1H) 6.93 (s, 1H) 7.91 (d, J=7.78 Hz, 1H) 8.19 (s, 1H) 12.27 (br. s., 1H).
HRMS (ESI+): calcd. for $C_{33}H_{46}N_9O_3S$ [M+H]$^+$ 648.3439; found 648.3447.

8-amino-4,4-dimethyl-N-{4-[2-(4-methyl-1,4'-bipip-
eridin-1'-yl)-2-oxoethyl]-1,3-thiazol-2-yl}-1-(tetra-
hydro-2H-pyran-2-yl)-4,5-dihydro-1H-pyrazolo[4,3-
h]quinazoline-3-carboxamide (IIa)

[R1=R3'=R4'=H, PG=tetrahydropyranyl, R3=R4=($C_1$-$C_6$) alkyl, y=1, L=CONR8, z=0, A=heteroaryl, n=1, Rc=Rd=H, R5=CONR6N7, R6 and R7=taken together form an optionally substituted heterocyclyl group, R8=H]
$^1$H NMR (500 MHz, DMSO-$d_6$) δ ppm 0.88 (d, J=5.6 Hz, 3H) 1.26 (s, 3H) 1.34 (s, 3H) 1.43-1.89 (m, 8H) 1.87-1.98 (m, 2H) 1.98-2.13 (m, 1H) 2.40-2.47 (m, 2H) 2.52-2.57 (m, 1H) 2.60-2.67 (m, 2H) 2.81-3.23 (m, 2H) 3.76 (s, 2H) 3.79-3.87 (m, 1H) 3.88-3.94 (m, 1H) 3.99-4.12 (m, 1H) 4.39-4.53 (m, 1H) 6.64 (br. s., 2H) 6.85 (d, J=10.07 Hz, 1H) 6.98 (s, 1H) 8.20 (s, 1H) 12.30 (br. s., 1H).
HRMS (ESI+): calcd. for $C_{33}H_{46}N_9O_3S$ [M+H]$^+$ 648.3439; found 648.3460.

8-amino-4,4-dimethyl-N-(5-methyl-4,5,6,7-tetra-
hydro[1,3]thiazolo[5,4-c]pyridin-2-yl)-1-(tetrahydro-
2H-pyran-2-yl)-4,5-dihydro-1H-pyrazolo[4,3-h]qui-
nazoline-3-carboxamide (IIb)

[R1=R3'=R4'=H, PG=tetrahydropyranyl, R3=R4=($C_1$-$C_6$) alkyl, y=0, L=CONR6aR7a, R6a=substituted heteroaryl, R7a=H]
$^1$H NMR (500 MHz, DMSO-$d_6$) δ ppm 1.25 (s, 3H) 1.34 (s, 3H) 1.56 (m, 2H) 1.67-1.82 (m, 1H) 1.88-1.98 (m, 1H) 2.00-2.09 (m, 1H) 2.39 (s, 3H) 2.41-2.47 (m, 1H) 2.57-2.67 (m, 2H) 2.67-2.77 (m, 4H) 3.54 (br. s., 2H) 3.75-3.87 (m, 1H) 3.88-3.96 (m, 1H) 6.64 (br. s., 2H) 6.85 (dd, J=10.07, 2.44 Hz, 1H) 8.19 (s, 1H) 12.17 (br. s., 1H).
HRMS (ESI+): calcd. for $C_{24}H_{31}N_8O_2S$ [M+H]$^+$ 495.2285; found 495.2291.

ethyl [2-({[8-amino-4,4-dimethyl-1-(tetrahydro-2H-
pyran-2-yl)-4,5-dihydro-1H-pyrazolo[4,3-h]quinazo-
lin-3-yl]carbonyl}amino)-1,3-thiazol-4-yl](difluoro)
acetate (IIa)

[R1=R3'=R4'=H, PG=tetrahydropyranyl, R3=R4=($C_1$-$C_6$) alkyl, y=1, L=CONR8, z=0, A=heteroaryl, n=1, Rc=Rd=F, R5=COOR6, R6=($C_1$-$C_6$)alkyl, R8=H]
$^1$H NMR (500 MHz, DMSO-$d_6$) δ ppm 1.23 (t, J=7.09 Hz, 3H) 1.27 (s, 3H) 1.35 (s, 3H) 1.50-1.62 (m, 2H) 1.68-1.80 (m, 1H) 1.88-1.97 (m, 1H) 2.01-2.10 (m, 1H) 2.42-2.49 (m, 1H) 2.63 (s, 2H) 3.78-3.86 (m, 1H) 3.88-3.96 (m, 1H) 4.29 (q, J=7.12 Hz, 2H) 6.64 (br. s., 2H) 6.84 (dd, J=9.99, 2.36 Hz, 1H) 7.85 (s, 1H) 8.20 (s, 1H) 12.83 (br. s., 1H).
HRMS (ESI+): calcd. for $C_{24}H_{28}F_2N_7O_4S$ [M+H]$^+$ 548.1886; found 548.1892.

8-amino-N-(4-{[(1-cycloheptylpiperidin-4-yl)oxy]
methyl}-1,3-thiazol-2-yl)-4,4-dimethyl-1-(tetra-
hydro-2H-pyran-2-yl)-4,5-dihydro-1H-pyrazolo[4,3-
h]quinazoline-3-carboxamide (IIa)

[R1=R3'=R4'=H, PG=tetrahydropyranyl, R3=R4=($C_1$-$C_6$) alkyl, y=1, L=CONR8, z=0, A=heteroaryl, n=1, Rc=Rd=H, R5=OR6, R6=substituted heterocyclyl, R8=H]
$^1$H NMR (500 MHz, DMSO-$d_6$) δ ppm 1.26 (s, 3H) 1.34 (s, 3H) 1.37-1.52 (m, 8H) 1.52-1.64 (m, 4H) 1.64-1.78 (m, 3H) 1.79-1.89 (m, 2H) 1.89-1.97 (m, 1H) 1.99-2.10 (m, 1H) 2.16-2.26 (m, 2H) 2.42-2.48 (m, 2H) 2.60-2.70 (m, 4H)

3.78-3.95 (m, 2H) 4.47 (s, 2H) 6.63 (br. s., 2H) 6.85 (d, J=7.93 Hz, 1H) 7.10 (br. s., 1H) 8.19 (s, 1H) 12.36 (br. s., 1H).

HRMS (ESI+): calcd. for $C_{33}H_{47}N_8O_3S$ [M+H]$^+$ 635.3487; found 635.3489.

8-amino-N-[4-({[1-(4,4-difluorocyclohexyl)piperidin-4-yl]oxy}methyl)-1,3-thiazol-2-yl]-4,4-dimethyl-1-(tetrahydro-2H-pyran-2-yl)-4,5-dihydro-1H-pyrazolo[4,3-h]quinazoline-3-carboxamide (IIa)

[R1=R3'=R4'=H, PG=tetrahydropyranyl, R3=R4=($C_1$-$C_6$) alkyl, y=1, L=CONR8, z=0, A=heteroaryl, n=1, Rc=Rd=H, R5=OR6, R6=substituted heterocyclyl, R8=H]

$^1$H NMR (500 MHz, DMSO-$d_6$) δ ppm 1.26 (s, 3H) 1.35 (s, 3H) 1.40-1.61 (m, 8H) 1.64-2.12 (m, 12H) 2.16-2.27 (m, 2H) 2.38-2.47 (m, 2H) 2.61-2.65 (m, 2H) 3.35-2.42 (m, 1H) 3.77-3.95 (m, 2H) 4.48 (s, 2H) 6.64 (br. s., 2H) 6.85 (dd, J=10.07, 2.44 Hz, 1H) 7.11 (s, 1H) 8.20 (s, 1H) 12.35 (br. s., 1H).

HRMS (ESI+): calcd. for $C_{32}H_{43}F_2N_8O_3S$ [M+H]$^+$ 657.3142; found 657.3160.

8-amino-N-{4-[2-(4,4'-dimethyl-1,4'-bipiperidin-1'-yl)-2-oxoethyl]-1,3-thiazol-2-yl}-4,4-dimethyl-1-(tetrahydro-2H-pyran-2-yl)-4,5-dihydro-1H-pyrazolo[4,3-h]quinazoline-3-carboxamide (IIa)

[R1=R3'=R4'=H, PG=tetrahydropyranyl, R3=R4=($C_1$-$C_6$) alkyl, y=1, L=CONR8, z=0, A=heteroaryl, n=1, Rc=Rd=H, R5=CONR6N7, R6 and R7=taken together form an optionally substituted heterocyclyl group, R8=H]

$^1$H NMR (500 MHz, DMSO-$d_6$) δ ppm 0.87 (d, J=4.27 Hz, 6H) 0.95-1.24 (m, 3H) 1.26 (s, 3H) 1.35 (s, 3H) 1.47-1.65 (m, 4H) 1.65-1.81 (m, 3H) 1.88-2.10 (m, 4H) 2.37-2.47 (m, 1H) 2.63 (s, 2H) 2.72-2.89 (m, 2H) 3.06-3.25 (m, 1H) 3.41-3.56 (m, 1H) 3.74 (s, 2H) 3.79-3.98 (m, 2H) 6.63 (br. s., 2H) 6.85 (dd, J=10.07, 2.29 Hz, 1H) 6.95 (s, 1H) 8.20 (s, 1H).

HRMS (ESI+): calcd. for $C_{34}H_{48}N_9O_3S$ [M+H]$^+$ 662.3596; found 662.3584.

8-amino-N-[4-({[1-(4,4-dimethylcyclohexyl)piperidin-4-yl]oxy}methyl)-1,3-thiazol-2-yl]-4,4-dimethyl-1-(tetrahydro-2H-pyran-2-yl)-4,5-dihydro-1H-pyrazolo[4,3-h]quinazoline-3-carboxamide (IIa)

[R1=R3'=R4'=H, PG=tetrahydropyranyl, R3=R4=($C_1$-$C_6$) alkyl, y=1, L=CONR8, z=0, A=heteroaryl, n=1, Rc=Rd=H, R5=OR6, R6=substituted heterocyclyl, R8=H]

$^1$H NMR (500 MHz, DMSO-$d_6$) δ ppm 0.85 (s, 3H) 0.86 (s, 3H) 1.09-1.20 (m, 2H) 1.26 (s, 3H) 1.35 (s, 3H) 1.36-1.46 (m, 4H) 1.46-1.64 (m, 4H) 1.68-1.79 (m, 1H) 1.80-1.97 (m, 3H) 2.01-2.10 (m, 1H) 2.11-2.27 (m, 3H) 2.40-2.49 (m, 2H) 2.57-2.68 (m, 2H) 2.73-2.76 (m, 2H) 3.77-3.87 (m, 1H) 3.87-3.97 (m, 1H) 4.48 (s, 2H) 6.63 (br. s., 2H) 6.85 (dd, J=9.91, 2.44 Hz, 1H) 7.10 (s, 1H) 8.20 (s, 1H) 12.35 (br. s., 1H).

HRMS (ESI+): calcd. for $C_{34}H_{46}N_8O_3S$ [M+H]$^+$ 649.3643; found 649.3661.

8-amino-N-[4-({[1-(cyclohexylmethyl)piperidin-4-yl]oxy}methyl)-1,3-thiazol-2-yl]-4,4-dimethyl-1-(tetrahydro-2H-pyran-2-yl)-4,5-dihydro-1H-pyrazolo[4,3-h]quinazoline-3-carboxamide (IIa)

[R1=R3'=R4'=H, PG=tetrahydropyranyl, R3=R4=($C_1$-$C_6$) alkyl, y=1, L=CONR8, z=0, A=heteroaryl, n=1, Rc=Rd=H, R5=OR6, R6=substituted heterocyclyl, R8=H]

$^1$H NMR (500 MHz, DMSO-$d_6$) δ ppm 0.73-0.87 (m, 2H) 1.06-1.24 (m, 4H) 1.26 (s, 3H) 1.35 (s, 3H) 1.37-1.51 (m, 3H) 1.51-1.78 (m, 8H) 1.78-2.01 (m, 6H) 2.03 (d, J=7.17 Hz, 2H) 2.64 (s, 2H) 3.36-3.44 (m, 1H) 3.78-3.87 (m, 1H) 3.87-3.97 (m, 1H) 4.48 (s, 2H) 6.63 (br. s., 2H) 6.85 (dd, J=9.91, 2.44 Hz, 1H) 7.11 (s, 1H) 8.20 (s, 1H) 12.35 (br. s., 1H).

HRMS (ESI+): calcd. for $C_{33}H_{47}N_8O_3S$ [M+H]$^+$ 635.3487; found 635.3504.

8-amino-N-(4-{[(1-benzylpiperidin-4-yl)oxy]methyl}-1,3-thiazol-2-yl)-4,4-dimethyl-1-(tetrahydro-2H-pyran-2-yl)-4,5-dihydro-1H-pyrazolo[4,3-h]quinazoline-3-carboxamide (IIa)

[R1=R3'=R4'=H, PG=tetrahydropyranyl, R3=R4=($C_1$-$C_6$) alkyl, y=1, L=CONR8, z=0, A=heteroaryl, n=1, Rc=Rd=H, R5=OR6, R6=substituted heterocyclyl, R8=H]

$^1$H NMR (500 MHz, DMSO-$d_6$) δ ppm 1.26 (s, 3H) 1.35 (s, 3H) 1.39-1.63 (m, 4H) 1.63-2.14 (m, 6H) 2.57-2.60 (m, 4H) 3.39-3.47 (m, 1H) 3.44 (s, 2H) 3.77-3.87 (m, 1H) 3.87-3.97 (m, 1H) 4.48 (s, 2H) 6.63 (br. s., 2H) 6.85 (dd, J=9.91, 2.44 Hz, 1H) 7.20-7.35 (m, 5H) 8.20 (s, 1H) 12.35 (br. s., 1H).

HRMS (ESI+): calcd. for $C_{33}H_{41}N_8O_3S$ [M+H]$^+$ 629.3017; found 629.3032.

8-amino-N-{4-[2-(4,4'-dimethyl-1,4'-bipiperidin-1'-yl)-2-oxoethyl]-1,3-thiazol-2-yl}-4,4-dimethyl-1-(tetrahydro-2H-pyran-2-yl)-4,5-dihydro-1H-pyrazolo[4,3-h]quinazoline-3-carboxamide (IIa)

[R1=R3'=R4'=H, PG=tetrahydropyranyl, R3=R4=($C_1$-$C_6$) alkyl, y=1, L=CONR8, z=0, A=heteroaryl, n=1, Rc=Rd=H, R5=CONR6R7, R6 and R7=taken together form an optionally substituted heterocyclyl group, R8=H]

$^1$H NMR (500 MHz, DMSO-$d_6$) δ ppm 0.85 (s, 3H) 0.86 (s, 3H) 0.95 (br. s., 2H) 1.13-1.29 (m, 4H) 1.25 (s, 3H) 1.35 (s, 3H) 1.51-1.62 (m, 2H) 1.63-1.82 (m, 2H) 1.87-1.98 (m, 1H) 2.00-2.10 (m, 1H) 2.31-2.46 (m, 3H) 2.51-2.57 (m, 2H) 2.58-2.68 (m, 2H) 2.97 (t, J=12.66 Hz, 1H) 3.34 (m overlapped by water signal, 1H) 3.74 (s, 2H) 3.79-3.87 (m, 1H) 3.87-3.95 (m, 1H) 3.98 (d, J=12.51 Hz, 1H) 4.39 (d, J=12.66 Hz, 1H) 6.64 (s, 2H) 6.85 (d, J=9.76 Hz, 1H) 6.96 (s, 1H) 8.20 (s, 1H) 12.28 (br. s., 1H).

HRMS (ESI+): calcd. for $C_{34}H_{48}N_9O_3S$ [M+H]$^+$ 662.3596; found 662.3584.

ethyl [2-({[8-amino-4,4-dimethyl-1-(tetrahydro-2H-pyran-2-yl)-4,5-dihydro-1H-pyrazolo[4,3-h]quinazolin-3-yl]carbonyl}amino)-1,3-thiazol-4-yl]acetate (IIa)

[R1=R3'=R4'=H, PG=tetrahydropyranyl, R3=R4=($C_1$-$C_6$) alkyl, y=1, L=CONR8, z=0, A=heteroaryl, n=1, Rc=Rd=H, R5=COOR6, R6=($C_1$-$C_6$)alkyl, R8=H]

$^1$H NMR (500 MHz, DMSO-$d_6$) δ ppm 1.19 (t, J=7.09 Hz, 3H) 1.26 (s, 3H) 1.34 (s, 3H) 1.50-1.62 (m, 2H) 1.64-1.79 (m, 1H) 1.88-1.97 (m, 1H) 2.01-2.10 (m, 1H) 2.39-2.47 (m, 1H) 2.63 (s, 2H) 3.73 (s, 2H) 3.78-3.86 (m, 1H) 3.88-3.94 (m, 1H) 4.09 (q, J=7.12 Hz, 2H) 6.63 (br. s., 2H) 6.84 (dd, J=9.99, 2.36 Hz, 1H) 7.06 (s, 1H) 8.19 (s, 1H) 12.36 (br. s., 1H).

HRMS (ESI+): calcd. for $C_{24}H_{30}N_7O_4S$ [M+H]$^+$ 512.2075; found 512.2096.

8-amino-N-(4-{2-[(2,6-dimethyl-4-oxohept-5-en-2-yl)amino]-2-oxoethyl}-1,3-thiazol-2-yl)-4,4-dimethyl-1-(tetrahydro-2H-pyran-2-yl)-4,5-dihydro-1H-pyrazolo[4,3-h]quinazoline-3-carboxamide (IIa)

[R1=R3'=R4'=H, PG=tetrahydropyranyl, R3=R4=($C_1$-$C_6$) alkyl, y=1, L=CONR8, z=0, A=heteroaryl, n=1, Rc=Rd=H, R5=CONR6R7, R6=($C_1$-$C_6$)alkyl, R8=H]
$^1$H NMR (500 MHz, DMSO-$d_6$) δ ppm 1.26 (s, 3H) 1.30 (s, 6H) 1.35 (s, 3H) 1.52-1.61 (m, 2H) 1.67-1.79 (m, 1H) 1.81 (d, J=0.92 Hz, 3H) 1.88-1.98 (m, 1H) 2.03 (d, J=0.76 Hz, 3H) 2.02-2.08 (m, 1H) 2.38-2.47 (m, 1H) 2.60-2.68 (m, 2H) 2.84 (s, 2H) 3.46 (s, 2H) 3.77-3.95 (m, 2H) 6.03-6.09 (m, 1H) 6.64 (br. s., 2H) 6.85 (dd, J=9.99, 2.36 Hz, 1H) 6.94 (s, 1H) 7.71 (s, 1H) 8.20 (s, 1H) 12.26 (br. s., 1H).
HRMS (ESI+): calcd. for $C_{31}H_{41}N_8O_4S$ $[M+H]^+$ 621.2966; found 621.2983.

8-amino-N-{4-[2-(3,3-dimethyl-1,4'-bipiperidin-1'-yl)-2-oxoethyl]-1,3-thiazol-2-yl}-4,4-dimethyl-1-(tetrahydro-2H-pyran-2-yl)-4,5-dihydro-1H-pyrazolo[4,3-h]quinazoline-3-carboxamide (IIa)

[R1=R3'=R4'=H, PG=tetrahydropyranyl, R3=R4=($C_1$-$C_6$) alkyl, y=1, L=CONR8, z=0, A=heteroaryl, n=1, Rc=Rd=H, R5=CONR6R7, R6 and R7=taken together form an optionally substituted heterocyclyl group, R8=H]
HRMS (ESI+): calcd. for $C_{34}H_{48}N_9O_3S$ $[M+H]^+$ 662.3595; found 662.3600.

8-amino-4,4-dimethyl-N-{4-[2-(3-methyl-1,4'-bipiperidin-1'-yl)-2-oxoethyl]-1,3-thiazol-2-yl}-1-(tetrahydro-2H-pyran-2-yl)-4,5-dihydro-1H-pyrazolo[4,3-h]quinazoline-3-carboxamide (IIa)

[R1=R3'=R4'=H, PG=tetrahydropyranyl, R3=R4=($C_1$-$C_6$) alkyl, y=1, L=CONR8, z=0, A=heteroaryl, n=1, Rc=Rd=H, R5=CONR6R7, R6 and R7=taken together form an optionally substituted heterocyclyl group, R8=H]
$^1$H NMR (500 MHz, DMSO-$d_6$) δ ppm 0.73-0.90 (m, 3H) 1.25 (s, 3H) 1.34 (s, 3H) 1.36-1.82 (m, 10H) 1.86-2.17 (m, 2H) 2.39-2.49 (m, 1H) 2.57-2.68 (m, 2H) 2.66-2.82 (m, 2H) 2.92-3.03 (m, 1H) 3.75 (s, 2H) 3.78-3.95 (m, 2H) 3.95-4.04 (m, 1H) 4.35-4.47 (m, 1H) 6.64 (s, 2H) 6.85 (d, J=9.91 Hz, 1H) 6.96 (s, 1H) 8.20 (s, 1H) 12.28 (br. s., 1H).
HRMS (ESI+): calcd. for $C_{33}H_{46}N_9O_3S$ $[M+H]^+$ 648.3439; found 648.3459.

8-amino-N-{4-[2-(3,3-difluoro-1,4'-bipiperidin-1'-yl)-2-oxoethyl]-1,3-thiazol-2-yl}-4,4-dimethyl-1-(tetrahydro-2H-pyran-2-yl)-4,5-dihydro-1H-pyrazolo[4,3-h]quinazoline-3-carboxamide (IIa)

[R1=R3'=R4'=H, PG=tetrahydropyranyl, R3=R4=($C_1$-$C_6$) alkyl, y=1, L=CONR8, z=0, A=heteroaryl, n=1, Rc=Rd=H, R5=CONR6R7, R6 and R7=taken together form an optionally substituted heterocyclyl group, R8=H]
HRMS (ESI+): calcd. for $C_{32}H_{42}F_2N_9O_3S$ $[M+H]^+$ 670.3094; found 670.3071.

8-amino-4,4-dimethyl-N-{6-[(4-methyl-1,4'-bipiperidin-1'-yl)carbonyl]-1,3-benzothiazol-2-yl}-1-(tetrahydro-2H-pyran-2-yl)-4,5-dihydro-1H-pyrazolo[4,3-h]quinazoline-3-carboxamide (IIa)

[R1=R3'=R4'=H, PG=tetrahydropyranyl, R3=R4=($C_1$-$C_6$) alkyl, y=1, L=CONR8, z=0, A=heteroaryl, n=0, R5=CONR6R7, R6 and R7=taken together form an optionally substituted heterocyclyl group, R8=H]
$^1$H NMR (500 MHz, DMSO-$d_6$) δ ppm 0.86 (d, J=4.3 Hz, 3H), 0.99-1.16 (m, 3H), 1.16-1.26 (m, 2H), 1.29 (s, 3H) 1.38 (s, 3H) 1.38-1.49 (m, 2H) 1.50-1.63 (m, 2H) 1.62-1.82 (m, 2H) 2.01-2.21 (m, 4H) 2.63 (s, 2H) 2.75-2.88 (m, 3H) 3.56-4.01 (m, 4H) 4.08-4.59 (m, 4H) 6.65 (br. s., 2H) 6.83-6.91 (m, 1H) 7.40-7.48 (m, 1H) 7.75-7.82 (m, 1H) 8.07 (br. s., 1H) 8.21 (s, 1H) 12.43 (br. s., 1H).
HRMS (ESI+): calcd. for $C_{36}H_{46}N_9O_3S$ $[M+H]^+$ 684.3439; found 684.3440.

8-amino-N-(4-{[(1-cycloheptyl-4-methylpiperidin-4-yl)oxy]methyl}-1,3-thiazol-2-yl)-4,4-dimethyl-1-(tetrahydro-2H-pyran-2-yl)-4,5-dihydro-1H-pyrazolo[4,3-h]quinazoline-3-carboxamide (IIa)

[R1=R3'=R4'=H, PG=tetrahydropyranyl, R3=R4=($C_1$-$C_6$) alkyl, y=1, L=CONR8, z=0, A=heteroaryl, n=1, Rc=Rd=H, R5=OR6, R6=substituted heterocyclyl, R8=H]
HRMS (ESI+): calcd. for $C_{32}H_{42}F_2N_9O_3S$ $[M+H]^+$ 649.3643; found 649.3655.

4,4-dimethyl-8-(methylamino)-N-(4-methyl-1,3-thiazol-2-yl)-1-(tetrahydro-2H-pyran-2-yl)-4,5-dihydro-1H-pyrazolo[4,3-h]quinazoline-3-carboxamide (IIb)

[R1=R3=R4=($C_1$-$C_6$)alkyl, R3'=R4'=H, PG=tetrahydropyranyl, y=0, L=CONR6aR7a, R6a=substituted heteroaryl, R7a=H]
HRMS (ESI+): calcd. for $C_{22}H_{28}N_7O_2S$ $[M+H]^+$ 454.2020; found 454.2009.

8-amino-N-{4-[2-(4,4-difluoro-1,4'-bipiperidin-1'-yl)-2-oxoethyl]-1,3-thiazol-2-yl}-4,4-dimethyl-1-(tetrahydro-2H-pyran-2-yl)-4,5-dihydro-1H-pyrazolo[4,3-h]quinazoline-3-carboxamide (IIa)

[R1=R3'=R4'=H, PG=tetrahydropyranyl, R3=R4=($C_1$-$C_6$) alkyl, y=1, L=CONR8, z=0, A=heteroaryl, n=1, Rc=Rd=H, R5=CONR6R7, R6 and R7=taken together form an optionally substituted heterocyclyl group, R8=H]
HRMS (ESI+): calcd. for $C_{32}H_{42}F_2N_9O_3S$ $[M+H]^+$ 670.3094; found 670.3081.

8-amino-4,4-dimethyl-N-[4-({[1-(spiro[2.5]oct-6-yl)piperidin-4-yl]oxy}methyl)-1,3-thiazol-2-yl]-1-(tetrahydro-2H-pyran-2-yl)-4,5-dihydro-1H-pyrazolo[4,3-h]quinazoline-3-carboxamide (IIa)

[R1=R3'=R4'=H, PG=tetrahydropyranyl, R3=R4=($C_1$-$C_6$) alkyl, y=1, L=CONR8, z=0, A=heteroaryl, n=1, Rc=Rd=H, R5=OR6, R6=substituted heterocyclyl, R8=H]
HRMS (ESI+): calcd. for $C_{34}H_{46}N_9O_3S$ $[M+H]^+$ 660.3439; found 660.3441

8-amino-5,5-dimethyl-N-{4-[2-(4-methyl-1,4'-bipiperidin-1'-yl)-2-oxoethyl]-1,3-thiazol-2-yl}-1-(tetrahydro-2H-pyran-2-yl)-4,5-dihydro-1H-pyrazolo[4,3-h]quinazoline-3-carboxamide (IIa)

[R1=R3=R4=H, PG=tetrahydropyranyl, R3'=R4'=($C_1$-$C_6$) alkyl, y=1, L=CONR8, z=0, A=heteroaryl, n=1, Rc=Rd=H, R5=CONR6R7, R6 and R7=taken together form an optionally substituted heterocyclyl group, R8=H]

¹H NMR (500 MHz, DMSO-d₆) δ ppm 0.84 (d, J=6.41, 3H) 0.95-1.10 (m, 2H) 1.18 (s, 3H) 1.19-1.3 (m, 3H) 1.31 (s, 3H) 1.47-1.60 (m, 4H) 1.61-1.82 (m, 3H) 1.89-1.99 (m, 1H) 2.01-2.14 (m, 3H) 2.38-2.46 (m, 1H) 2.52-2.58 (m partially overlapped by DMSO signal, 1H) 2.69-2.80 (m, 2H) 2.84-3.06 (m, 3H) 3.75 (s, 2H) 3.78-3.87 (m, 1H) 3.88-4.06 (m, 2H) 4.33-4.44 (m, 1H) 6.67 (br. s., 2H) 6.83 (dd, J=10.14, 1.91 Hz, 1H) 6.95 (s, 1H) 8.30 (s, 1H) 11.95 (br. s., 1H).

HRMS (ESI+): calcd. for $C_{33}H_{46}N_9O_3S$ [M+H]⁺ 648.3439; found 648.3443.

8-amino-N-(4-{[(1-cycloheptylpiperidin-4-yl)oxy]methyl}-1,3-thiazol-2-yl)-5,5-dimethyl-1-(tetrahydro-2H-pyran-2-yl)-4,5-dihydro-1H-pyrazolo[4,3-h]quinazoline-3-carboxamide (IIa)

[R1=R3=R4=H, PG=tetrahydropyranyl, R3'=R4'=($C_1$-$C_6$)alkyl, y=1, L=CONR8, z=0, A=heteroaryl, n=1, Rc=Rd=H, R5=OR6, R6=substituted heterocyclyl, R8=H]

¹H NMR (500 MHz, DMSO-d₆) δ ppm 1.18 (s, 3H) 1.31 (s, 3H) 1.33-2.12 (m, 22H) 2.13-2.28 (m, 2H) 2.53-2.60 (m, 1H) 2.62-2.71 (m, 2H) 2.80-3.04 (m, 2H) 3.36-3.41 (m partially overlapped by water signal, 1H) 3.75-3.99 (m, 2H) 4.47 (s, 2H) 6.67 (br.s., 2H) 6.83 (dd, J=10.14, 2.36 Hz, 1H) 7.10 (s, 1H) 8.30 (s, 1H) 12.11 (br. s., 1H).

HRMS (ESI+): calcd. for $C_{33}H_{47}N_8O_3S$ [M+H]⁺ 635.3486; found 635.3481.

Step b 4,4-dimethyl-8-(methylamino)-N-{4-[2-(4-methyl-1,4'-bipiperidin-1'-yl)-2-oxoethyl]-1,3-thiazol-2-yl}-4,5-dihydro-1H-pyrazolo[4,3-h]quinazoline-3-carboxamide (Ib), Cpd 122

[R1=R3=R4=($C_1$-$C_6$)alkyl, R2=R3'=R4'=H, y=1, L=CONR8, z=0, A=heteroaryl, n=1, Rc=Rd=H, R5=CONR6N7, R6 and R7=taken together form an optionally substituted heterocyclyl group, R8=H]

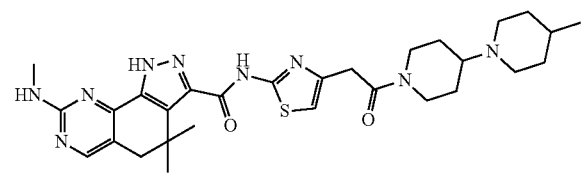 [SMILES: CNc1ncc2c(n1)-c1[nH]nc(C(=O)Nc3nc(CC(=O)N4CCC(N5CCC(C)CC5)CC4)cs3)c1C(C)(C)C2]

4,4-Dimethyl-8-(methylamino)-1-(tetrahydro-2H-pyran-2-yl)-4,5-dihydro-1H-pyrazolo[4,3-h]quinazoline-3-carboxylic acid (50 mg, 0.076 mmol) in DCM (2.1 mL) was treated with TFA (0.5 mL) at rt, stirred for 5 h, evaporated, taken up with toluene (2 mL) and evaporated twice to give 102 mg of crude product which was dissolved in DCM:MeOH 1:1 (2 mL), passed over a PL HCO₃ cartridge (MP SPE 500 mg×6 mL tube, loading: 0.9 mmol/g). The cartridge was washed with the same solvent (25 mL) and the filtrate evaporated to afford 51 mg of product which was further purified by chromatography over silica gel (DCM: 7 N NH₃ in MeOH=95:5) to furnish the title compound (22 mg, 50%).

¹H NMR (499.7 MHz, DMSO-d₆) δ ppm 0.85 (d, J=6.2 Hz, 3H), 1.00-1.16 (m, 2H), 1.17-1.38 (m, 3H), 1.33 (s, 6H), 1.50-1.62 (m, 2H), 1.65-1 78 (m, 2H), 2.00-2.20 (m, 2H), 2.66 (s, 2H), 2.70-2.84 (m, 1H), 2.87 (d, J=4.1 Hz, 3H), 2.93-3.02 (m, 1H), 3.34 (m overlapped by water signal, 1H), 3.74 (s, 2H), 3.96-4.04 (m, 1H), 4.37-4.44 (m, 1H), 6.83 (br. s., 1H), 6.94 (s, 1H), 8.21 (s, 1H), 12.06 (br. s., 1H), 14.19 (br. s., 1H).

HRMS (ESI+): calcd. for $C_{29}H_{40}N_9O_2S$ [M+H]⁺ 578.3020; found 578.3020.

Operating in an analogous way, but employing suitably intermediated (IIa), the following compounds were obtained:

8-amino-N-(4-{[(1-cyclohexylpiperidin-4-yl)oxy]methyl}-1,3-thiazol-2-yl)-4,4-dimethyl-4,5-dihydro-1H-pyrazolo[4,3-h]quinazoline-3-carboxamide (Ib), Cpd 157

[R1=R2=R3'=R4'=H, R3=R4=($C_1$-$C_6$)alkyl, y=1, L=CONR8, z=0, A=heteroaryl, n=1, Rc=Rd=H, R5=OR6, R6=substituted heterocyclyl, R8=H]

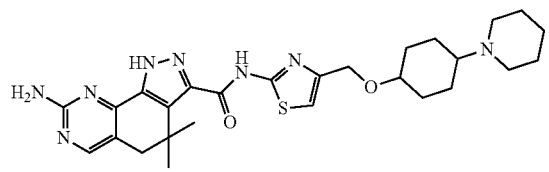 [SMILES: CC1(C)Cc2cnc(N)nc2-c2[nH]nc(C(=O)Nc3nc(COC4CCC(N5CCCCC5)CC4)cs3)c21]

¹H NMR (499.7 MHz, DMSO-d₆) δ ppm 1.00-1.08 (m, 1H), 1.12-1.23 (m, 2H), 1.33 (s, 6H), 1.38-1.48 (m, 2H) 1.53-1.60 (m, 1H), 1.67-1.76 (m, 4H), 1.84-1.90 (m, 2H), 2.18-2.33 (br. s., 3H), 2.66 (s, 2H), 2.71-2.80 (br. s., 2H), 3.33-3.42 (m partially overlapped by water signal, 1H), 4.48 (s, 2H), 6.40 (br. s., 2H), 7.09 (s, 1H), 8.19 (s, 1H), 11.92 (br. s., 1H), 14.07 (br. s., 1H).

HRMS (ESI+): calcd. for $C_{27}H_{37}N18O_2S$ [M+H]⁺ 537.2755; found 537.2756.

8-amino-4,4-di methyl-N-[4-({[trans-4-(4-methylpiperidin-1-yl)cyclohexyl]oxy}methyl)-1,3-thiazol-2-yl]-4,5-dihydro-1H-pyrazolo[4,3-h]quinazoline-3-carboxamide (Ib), Cpd 170

[R1=R2=R3'=R4'=H, R3=R4=($C_1$-$C_6$)alkyl, y=1, L=CONR8, z=0, A=heteroaryl, n=1, Rc=Rd=H, R5=OR6, R6=substituted cycloalkyl, R8=H]

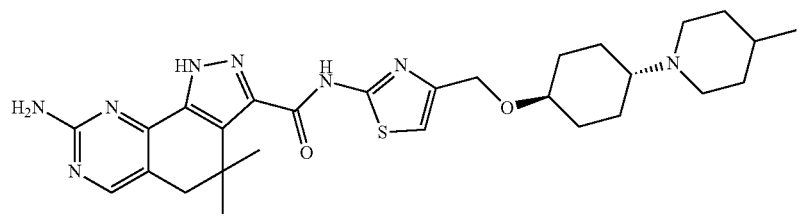 [SMILES: CC1CCN([C@H]2CC[C@H](OCc3csc(NC(=O)c4n[nH]c5c4C(C)(C)Cc4cnc(N)nc4-5)n3)CC2)CC1]

¹H NMR (499.7 MHz, DMSO-d₆) δ ppm 0.86 (d, J=6.6 Hz, 3H), 1.02-1.12 (m, 2H), 1.22-1.29 (m, 1H), 1.33 (s, 6H), 1.36-1.49 (m, 4H), 1.52-1.66 (m, 4H), 1.84-1.94 (m, 2H), 2.05-2.13 (m, 2H), 2.20 m-2.28 (m, 1H), 2.65 (s, 2H), 2.76-2.80 (m, 2H), 3.55-3.60 (m, 1H), 4.43 (s, 2H), 6.39 (br. s., 2H), 7.05 (br. s., 1H), 8.18 (s, 1H), 12.18 (br. s., 1H), 14.16 (br. s., 1H).

HRMS (ESI+): calcd. for $C_{28}H_{39}N_8O_2S$ [M+H]⁺ 551.2911; found 551.2903.

8-amino-N-{4-[2-(4-cyclohexylpiperazin-1-yl)-2-oxoethyl]-1,3-thiazol-2-yl}-4,4-dimethyl-4,5-dihydro-1H-pyrazolo[4,3-h]quinazoline-3-carboxamide (Ib), Cpd 150

[R1=R2=R3'=R4'=H, R3=R4=(C₁-C₆)alkyl, y=1, L=CONR8, z=0, A=heteroaryl, n=1, Rc=Rd=H, R5=CONR6N7, R6 and R7=taken together form an optionally substituted heterocyclyl group, R8=H]

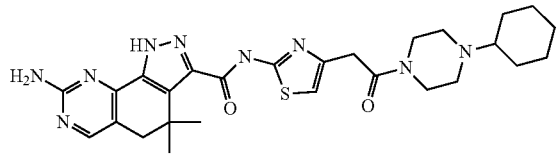 [SMILES: CC1(C)Cc2cnc(N)nc2-c2[nH]nc(C(=O)Nc3nc(CC(=O)N4CCN(C5CCCCC5)CC4)cs3)c21]

¹H NMR (499.7 MHz, DMSO-d₆) δ ppm 1.01-1.10 (m, 1H), 1.10-1.20 (m, 4H), 1.32 (s, 6H), 1.53-1.59 (m, 1H), 1.67-1.76 (m, 4H), 2.19-2.27 (m, 1H), 2.37-2.47 (m, 4H), 2.66 (s, 2H), 3.40-3.50 (m, 4H), 3.73 (s, 2H), 6.40 (br. s., 2H), 6.93 (s, 1H), 8.19 (s, 1H), 12.09 (br. s., 1H), 14.16 (br. s., 1H).

HRMS (ESI+): calcd. for $C_{27}H_{36}N_9O_2S$ [M+H]⁺ 550.2707; found 550.2704.

8-amino-N-(4-{2-[(1-cyclohexylpiperidin-4-yl)amino]-2-oxoethyl}-1,3-thiazol-2-yl)-4,4-dimethyl-4,5-dihydro-1H- pyrazolo[4,3-h]quinazoline-3-carboxamide (Ib), Cpd 145

[R1=R2=R3'=R4'=H, R3=R4=(C₁-C₆)alkyl, y=1, L=CONR8, z=0, A=heteroaryl, n=1, Rc=Rd=H, R5=CONR6N7, R6=substituted heterocyclyl, R7=R8=H]

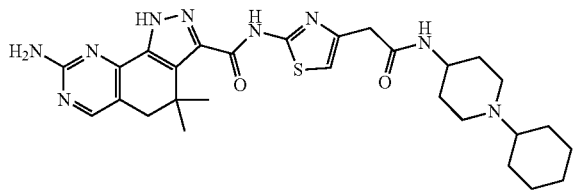 [SMILES: CC1(C)Cc2cnc(N)nc2-c2[nH]nc(C(=O)Nc3nc(CC(=O)NC4CCN(C5CCCCC5)CC4)cs3)c21]

¹H NMR (499.7 MHz, DMSO-d₆) δ ppm 1.00-1.09 (m, 1H), 1.11-1.21 (m, 2H), 1.33 (s, 6H), 1.34-1.44 (m, 2H), 1.52-1.59 (m, 1H), 1.68-1.75 (m, 8H), 2.15-2.32 (m, 3H), 2.66 (s, 2H), 2.72-2.81 (m, 2H), 3.47 (s, 2H), 3.47-3.54 (m, 1H), 6.40 (br. s., 2H), 6.92 (s, 1H), 7.93 (d, J=7.6 Hz, 1H), 8.19 (s, 1H), 12.09 (br. s., 1H), 14.20 (br. s., 1H).

HRMS (ESI+): calcd. for $C_{28}H_{38}N_9O_2S$ [M+H]⁺ 564.2864; found 564.2867.

8-amino-4,4-dimethyl-N-{4-[2-oxo-2-(4-phenylpiperazin-1-yl)ethyl]-1,3-thiazol-2-yl}-4,5-dihydro-1H-pyrazolo[4,3-h]quinazoline-3-carboxamide (Ib), Cpd 160

[R1=R2=R3'=R4'=H, R3=R4=(C₁-C₆)alkyl, y=1, L=CONR8, z=0, A=heteroaryl, n=1, Rc=Rd=H, R5=CONR6N7, R6 and R7=taken together form an optionally substituted heterocyclyl group, R8=H]

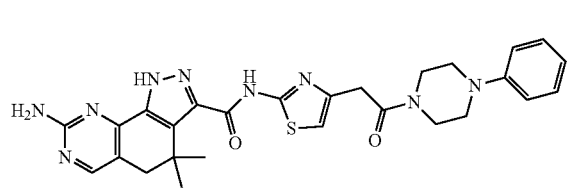 [SMILES: CC1(C)Cc2cnc(N)nc2-c2[nH]nc(C(=O)Nc3nc(CC(=O)N4CCN(c5ccccc5)CC4)cs3)c21]

¹H NMR (499.7 MHz, DMSO-d₆) δ ppm 1.32 (s, 6H), 2.64 (s, 2H), 3.05-3.17 (m, 4H), 3.59-3.65 (m, 2H), 3.68-3.73 (m, 2H), 3.79 (s, 2H), 6.38 (br. s., 2H), 6.78-6.82 (m, 1H), 6.90-6.98 (m, 3H), 7.18-7.25 (m, 2H), 8.17 (s, 1H), 12.11 (br. s., 1H), 14.17 (br. s., 1H).

HRMS (ESI+): calcd. for $C_{27}H_{30}N_9O_2S$ [M+H]⁺ 544.2238; found 544.2239.

8-amino-4,4-dimethyl-N-{4-[2-(4-methyl-1,4'-bipiperidin-1'-yl)-2-oxoethyl]-1,3-thiazol-2-yl}-4,5-dihydro-1H-pyrazolo[4,3-h]quinazoline-3-carboxamide (Ib), Cpd 58

[R1=R2=R3'=R4'=H, R3=R4=(C₁-C₆)alkyl, y=1, L=CONR8, z=0, A=heteroaryl, n=1, Rc=Rd=H, R5=CONR6R7, R6 and R7=taken together form an optionally substituted heterocyclyl group, R8=H]

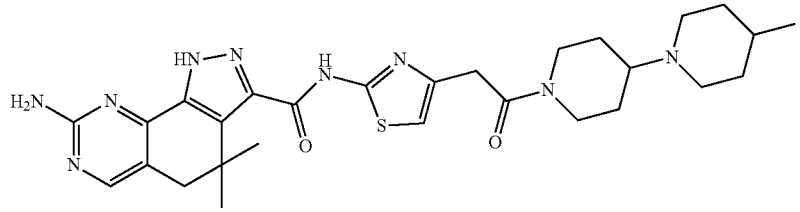 [SMILES: CC1CCN(C2CCN(C(=O)Cc3csc(NC(=O)c4n[nH]c5c4C(C)(C)Cc4cnc(N)nc4-5)n3)CC2)CC1]

¹H NMR (499.7 MHz, DMSO-d₆) δ ppm 0.84 (d, J=6.5 Hz, 3H), 1.00-1.10 (m, 2H), 1.15-1.29 (m, 3H), 1.33 (s, 6H), 1.50-1.57 (m, 2H), 1.62-1.72 (m, 2H), 1.99-2.15 (m, 2H), 2.39-2.47 (m, 1H), 2.66 (s, 2H), 2.72-2.78 (m, 2H), 2.93-3.01 (m, 1H), 3.34 (m overlapped by water signal, 1H), 3.73 (s, 2H), 3.95-4.01 (m, 1H), 4.36-4.42 (m, 1H), 6.40 (br. s., 2H), 6.93 (s, 1H), 8.19 (s, 1H), 12.07 (br. s., 1H), 14.19 (br. s., 1H).

HRMS (ESI+): calcd. for $C_{28}H_{38}N_9O_2S$ [M+H]⁺ 564.2864; found 564.2861.

8-amino-4,4-dimethyl-N-(5-methyl-4,5,6,7-tetra-hydro[1,3]thiazolo[5,4-c]pyridin-2-yl)-4,5-dihydro-1H-pyrazolo[4,3-h]quinazoline-3-carboxamide dihydrochloride (Id), Cpd 151

[R1=R2=R3'=R4'=H, R3=R4=($C_1$-$C_6$)alkyl, y=0, L=CONR6aR7a, R6a=substituted heteroaryl, R7a=H]

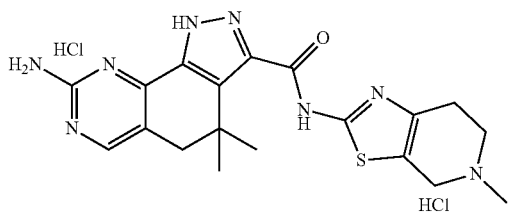 [SMILES: CN1CCc2nc(NC(=O)c3n[nH]c4c3C(C)(C)Cc3cnc(N)nc3-4)sc2C1 ; Cl ; Cl]

¹H NMR (499.7 MHz, DMSO-d₆) δ ppm 1.35 (s, 6H), 2.73 (s, 2H), 2.94 (d, J=3.7 Hz, 3H), 2.98-3.11 (m, 3H), 3.67-3.74 (m, 1H), 4.31 (dd, J=14.9, 6.8 Hz, 1H), 4.59 (d, J=14.9 Hz, 1H), 7.50 (br. s., 3H), 8.29 (s, 1H), 10.78 (br. s., 1H), 12.51 (br. s., 1H), 14.55 (br. s., 1H).

HRMS (ESI+): calcd. for $C_{27}H_{30}N_9O_2S$ [M+H]⁺ 544.2238; found 544.2239.

8-amino-N-(4-{[(1-cyclohexylpiperidin-4-yl)amino]methyl}-1,3-thiazol-2-yl)-4,4-dimethyl-4,5-dihydro-1H-pyrazolo[4,3-h]quinazoline-3-carboxamide dihydrochloride (Ib), Cpd 156

[R1=R2=R3'=R4'=H, R3=R4=($C_1$-$C_6$)alkyl, y=1, L=CONR8, z=0, A=heteroaryl, n=1, Rc=Rd=H, R5=NR6N7, R6=substituted heterocyclyl, R7=R8=H]

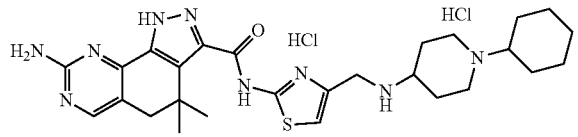 [SMILES: CC1(C)Cc2cnc(N)nc2-c2[nH]nc(C(=O)Nc3nc(CNC4CCN(C5CCCCC5)CC4)cs3)c21 ; Cl ; Cl]

¹H NMR (499.7 MHz, DMSO-d₆) δ ppm 1.04-1.22 (m, 1H), 1.22-1.34 (m, 2H) 1.35 (s, 6H), 1.39-1.49 (m, 2H), 1.59-1.67 (m, 1H), 1.80-1.90 (m, 2H), 2.07-2.24 (m, 4H), 2.26-2.34 (m, 1H), 2.33-2.42 (m, 2H), 2.73 (s, 2H), 3.00-3.10 (m, 2H), 3.10-3.19 (m, 1H), 3.45 (m overlapped by water signal, 2H), 4.22-4.31 (m, 2H), 7.44 (br. s., 2H), 7.52 (s, 1H), 8.29 (s, 1H), 9.69 (br. s., 2H), 10.49 (br. s., 1H), 12.30 (br. s., 1H).

HRMS (ESI+): calcd. for $C_{27}H_{37}N_9OS$ [M+H]⁺ 536.2915; found 536.2923.

ethyl (2-{[(8-amino-4,4-dimethyl-4,5-dihydro-1H-pyrazolo[4,3-h]quinazolin-3-yl)carbonyl]amino}-1,3-thiazol-4-yl)(difluoro)acetate (Ib), Cpd 185

[R1=R2=R3'=R4'=H, R3=R4=($C_1$-$C_6$)alkyl, y=1, L=CONR8, z=0, A=heteroaryl, n=1, Rc=Rd=F, R5=COOR6, R6=($C_1$-$C_6$)alkyl, R8=H]

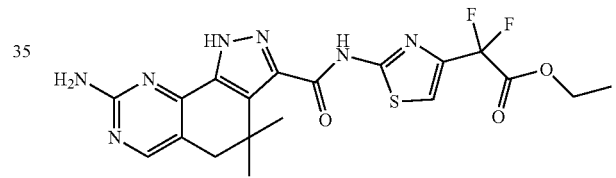

HRMS (ESI+): calcd. for $C_{19}H_{20}F_2N_7O_3S$ [M+H]⁺ 464.1311; found 464.1304.

8-amino-N-[4-({[1-(4,4-difluorocyclohexyl)piperidin-4-yl]oxy}methyl)-1,3-thiazol-2-yl]-4,4-dimethyl-4,5-dihydro-1H-pyrazolo[4,3-h]quinazoline-3-carboxamide (Ib), Cpd 189

[R1=R2=R3'=R4'=H, R3=R4=($C_1$-$C_6$)alkyl, y=1, L=CONR8, z=0, A=heteroaryl, n=1, Rc=Rd=H, R5=OR6, R6=substituted heterocyclyl, R8=H]

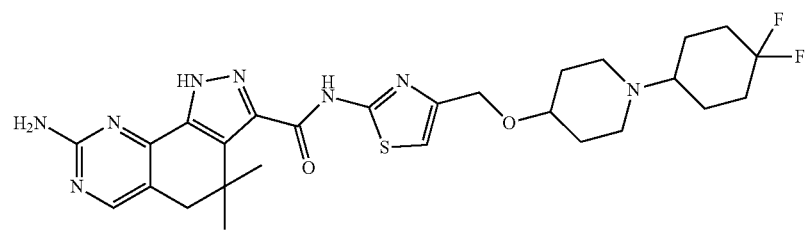 [SMILES: CC1(C)Cc2cnc(N)nc2-c2[nH]nc(C(=O)Nc3nc(COC4CCN(C5CCC(F)(F)CC5)CC4)cs3)c21]

¹H NMR (499.7 MHz, DMSO-d₆) δ ppm 1.33 (s, 6H), 1.38-1.58 (m, 4H), 1.62-1.91 (m, 6H), 1.94-2.09 (m, 2H), 2.18-2.26 (m, 2H), 2.40-2.46 (m, 1H), 2.66 (s, 2H), 2.70-2.78 (m, 2H), 4.48 (s, 2H), 6.40 (br. s., 2H), 7.09 (s, 1H), 8.19 (s, 1H), 12.12 (br. s., 1H), 14.22 (br. s., 1H).

HRMS (ESI+): calcd. for $C_{27}H_{35}F_2N_8O_2S$ [M+H]⁺ 573.2566; found 573.2559.

8-amino-N-[4-({[1-(4,4-dimethylcyclohexyl)piperidin-4-yl]oxy}methyl)-1,3-thiazol-2-yl]-4,4-dimethyl-4,5-dihydro-1H-pyrazolo[4,3-h]quinazoline-3-carboxamide (Ib), Cpd 190

[R1=R2=R3'=R4'=H, R3=R4=(C₁-C₆)alkyl, y=1, L=CONR8, z=0, A=heteroaryl, n=1, Rc=Rd=H, R5=OR6, R6=substituted heterocyclyl, R8=H]

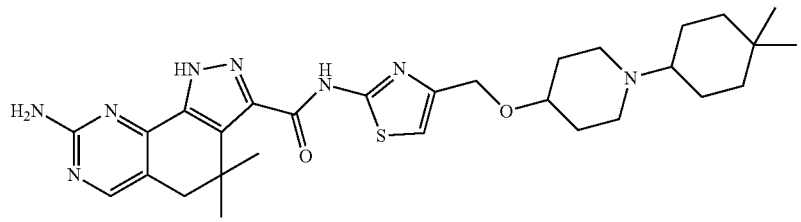 [SMILES: CC1(C)CCC(N2CCC(OCc3csc(NC(=O)c4n[nH]c5c4C(C)(C)Cc4cnc(N)nc4-5)n3)CC2)CC1]

¹H NMR (499.7 MHz, DMSO-d₆) δ ppm 0.85, 0.86 (2×s, 6H), 1.07-1.22 (m, 2H), 1.33 (s, 6H), 1.34-1.47 (m, 6H), 1.49-1.60 (m, 2H), 1.83-1.90 (m, 2H), 2.13-2.31 (m, 3H), 2.66 (s, 2H), 2.73-2.80 (m, 2H), 3.39 (m overlapped by water signal, 1H), 4.47 (s, 2H), 6.40 (br. s., 2H), 7.08 (s, 1H), 8.19 (s, 1H), 12.15 (br. s., 1H), 14.20 (br. s., 1H).

HRMS (ESI+): calcd. for $C_{29}H_{41}N_8O_2S$ [M+H]⁺ 565.3068; found 565.3068.

8-amino-N-{4-[1,1-difluoro-2-(4-methyl-1,4'-bipiperidin-1'-yl)-2-oxoethyl]-1,3-thiazol-2-yl}-4,4-dimethyl-4,5-dihydro-1H-pyrazolo[4,3-h]quinazoline-3-carboxamide (Ib), Cpd 191

[R1=R2=R3'=R4'=H, R3=R4=(C₁-C₆)alkyl, y=1, L=CONR8, z=0, A=heteroaryl, n=1, Rc=Rd=F, R5=CONR6R7, R6 and R7=taken together form an optionally substituted heterocyclyl group, R8=H]

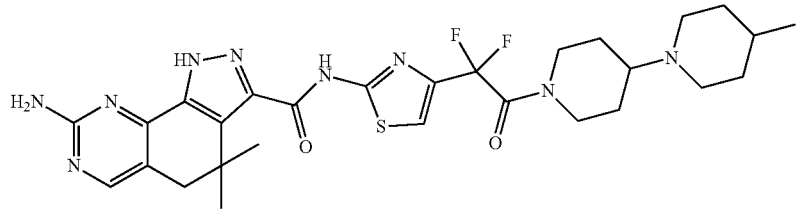 [SMILES: CC1CCN(C2CCN(C(=O)C(F)(F)c3csc(NC(=O)c4n[nH]c5c4C(C)(C)Cc4cnc(N)nc4-5)n3)CC2)CC1]

¹H NMR (499.7 MHz, DMSO-d₆) δ ppm 0.82 (d, J=6.4 Hz, 3H), 0.93-1.11 (m, 3H), 1.18-1.27 (m, 1H), 1.33 (s, 6H), 1.30-1.40 (m, 1H), 1.44-1.62 (m, 3H), 1.70-1.79 (m, 1H), 1.94-2.13 (m, 2H), 2.66 (s, 2H), 2.68-2.78 (m, 2H), 2.91-2.99 (m, 1H); 3.33 (m overlapped by water signal, 1H), 3.80-3.88 (m, 1H), 4.35-4.41 (m, 1H), 6.40 (br. s., 2H), 7.78 (br. s., 1H), 8.19 (s, 1H), 14.29 (br. s., 1H).

HRMS (ESI+): calcd. for $C_{28}H_{36}F_2N_9O_2S$ [M+H]⁺ 600.2675; found 600.2690.

8-amino-N-(4-{[(1-cycloheptylpiperidin-4-yl)oxy]methyl}-1,3-thiazol-2-yl)-4,4-dimethyl-4,5-dihydro-1H-pyrazolo[4,3-h]quinazoline-3-carboxamide (Ib), Cpd 209

[R1=R2=R3'=R4'=H, R3=R4=(C₁-C₆)alkyl, y=1, L=CONR8, z=0, A=heteroaryl, n=1, Rc=Rd=H, R5=OR6, R6=substituted heterocyclyl, R8=H]

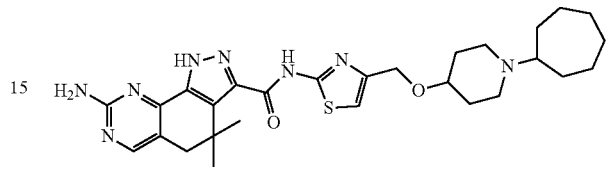

¹H NMR (499.7 MHz, DMSO-d₆) δ ppm 1.33 (s, 6H), 1.30-1.50 (m, 10H), 1.55-1.64 (m, 2H), 1.66-1.73 (m, 2H), 1.82-1.89 (m, 2H), 2.18-2.36 (m, 2H), 2.66 (s, 2H), 2.64-2.70 (m, 2H), 4.47 (s, 2H), 6.40 (br. s., 2H), 7.08 (s, 1H), 8.18 (s, 1H), 12.14 (br. s., 1H), 14.15 (br. s., 1H).

HRMS (ESI+): calcd. for $C_{28}H_{39}N_8O_2S$ [M+H]⁺ 551.2911; found 551.2907.

4,4-dimethyl-8-(methylamino)-N-(4-methyl-1,3-thiazol-2-yl)-4,5-dihydro-1H-pyrazolo[4,3-h]quinazoline-3-carboxamide (Id), Cpd 210

[R1=R3=R4=(C₁-C₆)alkyl, R2=R3'=R4'=H, y=0, L=CONR6aR7a, R6a=substituted heteroaryl, R7a=H]

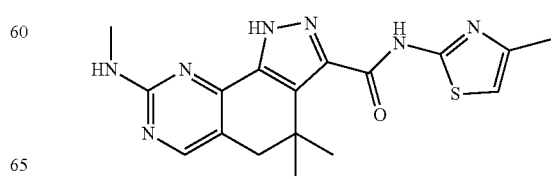

$^1$H NMR (499.7 MHz, DMSO-d$_6$) δ ppm 1.33 (s, 6H), 2.29 (d, J=0.8 Hz, 3H), 2.67 (s, 2H), 2.87 (d, J=4.1 Hz, 3H), 6.78 (br. s., 1H), 6.82 (s, 1H), 8.21 (s, 1H), 11.98 (s, 1H), 14.19 (s, 1H).

HRMS (ESI+): calcd. for C$_{17}$H$_{20}$N$_7$OS [M+H]$^+$ 370.1445; found 370.1452.

8-amino-N-[4-({[1-(cyclohexylmethyl)piperidin-4-yl]oxy}methyl)-1,3-thiazol-2-yl]-4,4-dimethyl-4,5-dihydro-1H-pyrazolo[4,3-h]quinazoline-3-carboxamide (Ib), Cpd 212

[R1=R2=R3'=R4'=H, R3=R4=(C$_1$-C$_6$)alkyl, y=1, L=CONR8, z=0, A=heteroaryl, n=1, Rc=Rd=H, R5=OR6, R6=substituted heterocyclyl, R8=H]

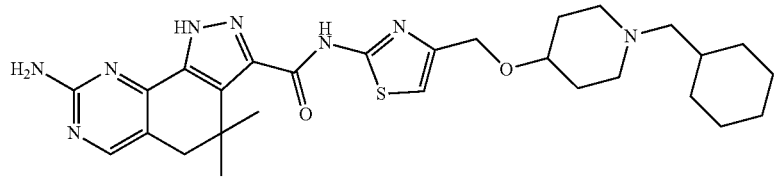 [SMILES: CC1(C)Cc2cnc(N)nc2-c2[nH]nc(C(=O)Nc3nc(COC4CCN(CC5CCCCC5)CC4)cs3)c21]

$^1$H NMR (499.7 MHz, DMSO-d$_6$) δ ppm 0.81 (br. s., 2H) 1.17 (br. s., 4H) 1.33 (s, 7H) 1.44 (d, J=3.20 Hz, 4H) 1.63 (br. s., 4H) 1.70 (d, J=12.66 Hz, 3H) 1.79-1.87 (m, 2H) 1.91-2.00 (m, 2H) 2.03 (d, J=7.02 Hz, 2H) 2.66 (s, 3H) 3.37-3.44 (m, 1H) 4.48 (s, 2H) 6.40 (br. s., 2H) 7.09 (s, 1H) 8.19 (s, 1H) 11.92-12.28 (m, 1H) 14.18 (br. s., 1H).

HRMS (ESI+): calcd. for C$_{28}$H$_{39}$N$_8$O$_2$S [M+H]$^+$ 370.1445; found 370.1452.

8-amino-N-(4-{[(1-benzylpiperidin-4-yl)oxy]methyl}-1,3-thiazol-2-yl)-4,4-dimethyl-4,5-dihydro-1H-pyrazolo[4,3-h]quinazoline-3-carboxamide (Ib), Cpd 213

[R1=R2=R3'=R4'=H, R3=R4=(C$_1$-C$_6$)alkyl, y=1, L=CONR8, z=0, A=heteroaryl, n=1, Rc=Rd=H, R5=OR6, R6=substituted heterocyclyl, R8=H]

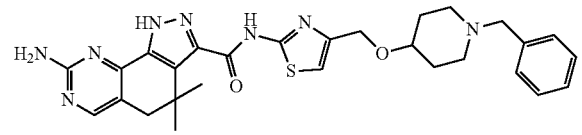 [SMILES: CC1(C)Cc2cnc(N)nc2-c2[nH]nc(C(=O)Nc3nc(COC4CCN(Cc5ccccc5)CC4)cs3)c21]

$^1$H NMR (499.7 MHz, DMSO-d$_6$) δ ppm 1.33 (s, 6H), 1.43-1.53 (m, 2H), 1.82-1.90 (m, 2H), 1.98-2.13 (m, 2H), 2.62-2.68 (m, 2H), 2.66 (s, 2H), 3.41-3.47 (m, 1H), 3.44 (s, 2H), 4.48 (s, 2H), 6.40 (br. s., 2H), 7.09 (s, 1H), 7.21-7.25 (m, 1H), 7.27-7.35 (m, 4H), 8.19 (s, 1H), 12.12 (br. s., 1H), 14.22 (br. s., 1H).

HRMS (ESI+): calcd. for C$_{28}$H$_{33}$N$_8$O$_2$S [M+H]$^+$ 545.2442; found 545.2443.

8-amino-N-{4-[2-(4,4-dimethyl-1,4'-bipiperidin-1'-yl)-2-oxoethyl]-1,3-thiazol-2-yl}-4,4-dimethyl-4,5-dihydro-1H-pyrazolo[4,3-h]quinazoline-3-carboxamide hydrochloride (Ib), Cpd 218

[R1=R2=R3'=R4'=H, R3=R4=(C$_1$-C$_6$)alkyl, y=1, L=CONR8, z=0, A=heteroaryl, n=1, Rc=Rd=H, R5=CONR6R7, R6 and R7=taken together form an optionally substituted heterocyclyl group, R8=H]

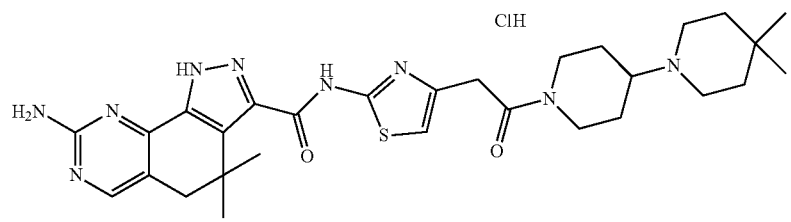 [SMILES: CC1(C)CCN(C2CCN(C(=O)Cc3csc(NC(=O)c4n[nH]c5c4C(C)(C)Cc4cnc(N)nc4-5)n3)CC2)CC1 ; Cl]

¹H NMR (499.7 MHz, DMSO-d₆) δ ppm 0.94 (br.s., 6H), 1.33 (s, 6H), 0.77-1.06 (m, 8H) 1.13-1.70 (m, 17H) 2.01-2.45 (m, 3H) 2.52-2.61 (m, 1H) 2.64-2.70 (m, 2H) 2.75-3.12 (m, 3H) 3.68-3.87 (m, 2H) 4.11 (br. s., 1H) 4.42-4.59 (m, 1H) 6.40 (br. s., 2H) 6.97 (s, 1H) 8.19 (s, 1H) 9.36 (br. s., 1H) 12.06 (br. s., 1H) 14.24 (br. s., 1H).

HRMS (ESI+): calcd. for $C_{29}H_{40}N_9O_2S$ [M+H]⁺ 578.3020; found 578.3026.

8-amino-N-{4-[2-(3,3-dimethyl-1,4'-bipiperidin-1'-yl)-2-oxoethyl]-1,3-thiazol-2-yl}-4,4-dimethyl-4,5-dihydro-1H-pyrazolo[4,3-h]quinazoline-3-carboxamide (Ib), Cpd 219

[R1=R2=R3'=R4'=H, R3=R4=($C_1$-$C_6$)alkyl, y=1, L=CONR8, z=0, A=heteroaryl, n=1, Rc=Rd=H, R5=CONR6R7, R6 and R7=taken together form an optionally substituted heterocyclyl group, R8=H]

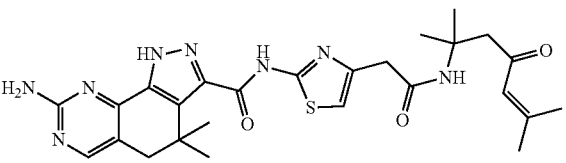

¹H NMR (499.7 MHz, DMSO-d₆) δ ppm 1.29 (s, 6H), 1.33 (s, 6H), 1.80 (s, 3H), 2.02 (s, 3H), 2.66 (s, 2H), 2.84 (s, 2H), 3.45 (s, 2H), 6.02-6.09 (m, 1H), 6.39 (br. s., 2H), 6.93 (s, 1H), 7.72 (s, 1H), 8.19 (s, 1H), 12.04 (br. s., 1H), 14.22 (s, 1H).

HRMS (ESI+): calcd. for $C_{26}H_{33}N_8O_3S$ [M+H]⁺ 537.2391; found 537.2407.

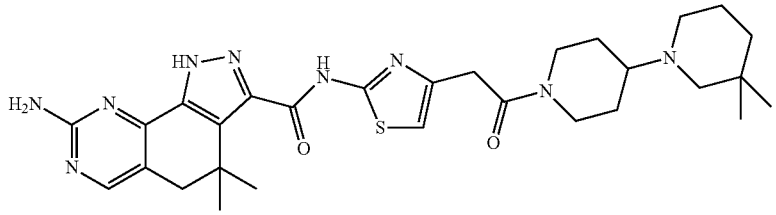 [SMILES: CC1(C)CCCN(C2CCN(C(=O)Cc3csc(NC(=O)c4n[nH]c5c4C(C)(C)Cc4cnc(N)nc4-5)n3)CC2)C1]

¹H NMR (499.7 MHz, DMSO-d₆) δ ppm 0.85 (s, 6H), 1.10-1.32 (m, 4H), 1.32 (s, 6H), 1.40-1.48 (m, 2H), 1.57-1.67 (m, 2H), 2.05 (br. s., 2H), 2.30-2.60 (m, 3H), 2.66 (s, 2H), 2.94-3.03 (m, 1H), 3.34 (m overlapped by water signal, 1H), 3.74 (s, 2H), 3.93-4.01 (m, 1H), 4.33-4.40 (m, 1H), 6.39 (br. s., 2H), 6.94 (s, 1H), 8.19 (s, 1H), 12.05 (br. s., 1H), 14.22 (br. s., 1H).

8-amino-N-{4-[2-(3,3-difluoro-1,4'-bipiperidin-1'-yl)-2-oxoethyl]-1,3-thiazol-2-yl}-4,4-dimethyl-4,5-dihydro-1H-pyrazolo[4,3-h]quinazoline-3-carboxamide (Ib), Cpd 222

[R1=R2=R3'=R4'=H, R3=R4=($C_1$-$C_6$)alkyl, y=1, L=CONR8, z=0, A=heteroaryl, n=1, Rc=Rd=H, R5=CONR6R7, R6 and R7=taken together form an optionally substituted heterocyclyl group, R8=H]

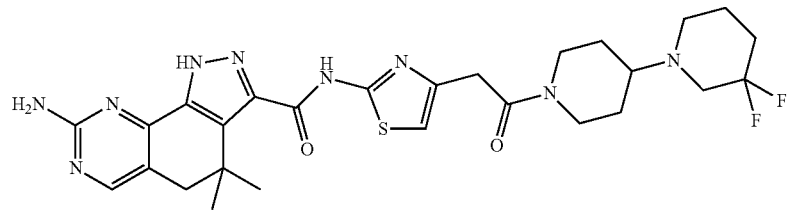 [SMILES: CC1(C)Cc2cnc(N)nc2-c2[nH]nc(C(=O)Nc3nc(CC(=O)N4CCC(N5CCCC(F)(F)C5)CC4)cs3)c21]

HRMS (ESI+): calcd. for $C_{29}H_{40}N_9O_2S$ [M+H]⁺ 578.3020; found 578.3020.

8-amino-N-(4-{2-[(2,6-dimethyl-4-oxohept-5-en-2-yl)amino]-2-oxoethyl}-1,3-thiazol-2-yl)-4,4-dimethyl-4,5-dihydro-1H-pyrazolo[4,3-h]quinazoline-3-carboxamide (Ib), Cpd 220

[R1=R2=R3'=R4'=H, R3=R4=($C_1$-$C_6$)alkyl, y=1, L=CONR8, z=0, A=heteroaryl, n=1, Rc=Rd=H, R5=CONR6R7, R6=($C_1$-$C_6$)alkyl, R7=R8=H]

¹H NMR (499.7 MHz, DMSO-d₆) δ ppm 1.21-1.33 (m, 2H), 1.33 (s, 6H), 1.55-1.63 (m, 2H), 1.63-1.73 (m, 2H), 1.78-1.89 (m, 2H), 2.43-2.73 (m, 5H), 2.66 (s, 2H), 2.94-3.02 (m, 1H), 3.34 (m overlapped by water signal, 1H), 3.74 (s, 2H), 3.96-4.04 (m, 1H), 4.37-4.45 (m, 1H), 6.40 (br. s., 2H), 6.94 (s, 1H), 8.19 (s, 1H), 12.07 (s, 1H), 14.22 (s, 1H).

HRMS (ESI+): calcd. for $C_{27}H_{34}F_2N_9O_2S$ [M+H]⁺ 586.2519; found 586.2538.

8-amino-4,4-dimethyl-N-{4-[2-(3-methyl-1,4'-bipip-eridin-1'-yl)-2-oxoethyl]-1,3-thiazol-2-yl}-4,5-di-hydro-1H-pyrazolo[4,3-h]quinazoline-3-carboxam-ide (Ib), Cpd 224

[R1=R2=R3'=R4'=H, R3=R4=($C_1$-$C_6$)alkyl, y=1, L=CONR8, z=0, A=heteroaryl, n=1, Rc=Rd=H, R5=CONR6R7, R6 and R7=taken together form an optionally substituted heterocyclyl group, R8=H]

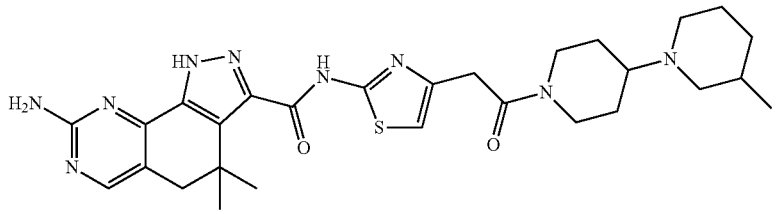 [SMILES: CC1CCCN(C2CCN(C(=O)Cc3csc(NC(=O)c4n[nH]c5c4C(C)(C)Cc4cnc(N)nc4-5)n3)CC2)C1]

$^1$H NMR (499.7 MHz, DMSO-$d_6$) δ ppm 0.79 (d, J=6.6 Hz, 3H), 1.17-1.77 (m, 9H), 1.32 (s, 6H), 1.98-2.07 (m, 2H), 2.40-2.50 (m, 2H), 2.66 (s, 2H), 2.67-2.76 (m, 2H), 2.90-3.02 (m, 1H), 3.33 (m overlapped by water signal, 1H), 3.74 (s, 2H), 3.96-4.03 (m, 1H), 4.37-4.43 (m, 1H), 6.40 (br. s., 2H), 6.94 (s, 1H), 8.19 (s, 1H), 12.06 (br. s., 1H), 14.21 (br. s., 1H).

HRMS (ESI+): calcd. for $C_{28}H_{38}N_9O_2S$ [M+H]$^+$ 564.2864; found 564.2884.

8-amino-N-(4-{[(1-cycloheptyl-4-methylpiperidin-4-yl)oxy]methyl}-1,3-thiazol-2-yl)-4,4-dimethyl-4,5-dihydro-1H-pyrazolo[4,3-h]quinazoline-3-carbox-amide (Ib), Cpd 226

[R1=R2=R3'=R4'=H, R3=R4=($C_1$-$C_6$)alkyl, y=1, L=CONR8, z=0, A=heteroaryl, n=1, Rc=Rd=H, R5=OR6, R6=substituted heterocyclyl, R8=H]

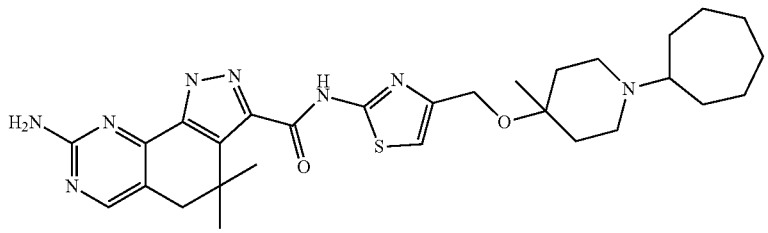 [SMILES: CC1(OCc2csc(NC(=O)c3n[nH]c4c3C(C)(C)Cc3cnc(N)nc3-4)n2)CCN(C2CCCCCC2)CC1]

$^1$H NMR (499.7 MHz, DMSO-$d_6$) δ ppm 1.17 (s, 3H), 1.33 (s, 6H), 1.30-1.82 (m, 16H), 2.36-2.60 (s, 5H), 2.66 (s, 2H), 4.38 (s, 2H), 6.40 (br. s., 2H), 7.02 (s, 1H), 8.19 (s, 1H), 12.09 (br. s., 1H), 14.20 (br. s., 1H).

HRMS (ESI+): calcd. for $C_{29}H_{41}N_8O_2S$ [M+H]$^+$ 565.3068; found 565.3053.

8-amino-N-{4-[2-(4,4'-dimethyl-1,4'-bipiperidin-1'-yl)-2-oxoethyl]-1,3-thiazol-2-yl}-4,4-dimethyl-4,5-dihydro-1H-pyrazolo[4,3-h]quinazoline-3-carbox-amide (Ib), Cpd 227

[R1=R2=R3'=R4'=H, R3=R4=($C_1$-$C_6$)alkyl, y=1, L=CONR8, z=0, A=heteroaryl, n=1, Rc=Rd=H, R5=CONR6R7, R6 and R7=taken together form an optionally substituted heterocyclyl group, R8=H]

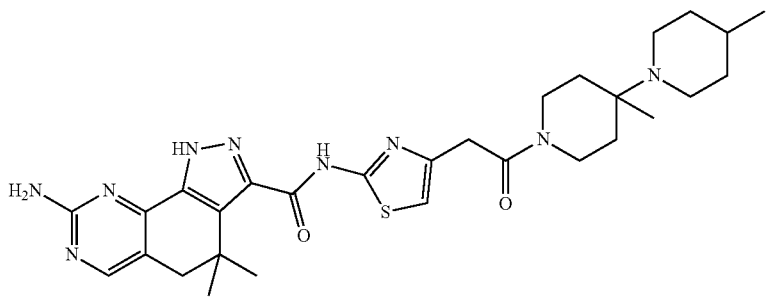 [SMILES: CC1CCN(C2(C)CCN(C(=O)Cc3csc(NC(=O)c4n[nH]c5c4C(C)(C)Cc4cnc(N)nc4-5)n3)CC2)CC1]

¹H NMR (499.7 MHz, DMSO-$d_6$) δ ppm 0.85 (s, 3H), 0.86 (d, J=6.6 Hz, 3H), 1.00-1.12 (m, 2H), 1.21-1.32 (m, 3H), 1.33 (m, 6H), 1.55-1.63 (m, 2H), 1.71-1.78 (m, 2H), 1.94-2.05 (m, 2H), 2.66 (s, 2H), 2.78-2.86 (m, 2H), 3.11-3.22 (m, 1H), 3.25-3.75 (m partially overlapped by water signal, 3H), 3.72 (s, 2H), 6.40 (br. s., 2H), 6.93 (s, 1H), 8.19 (s, 1H), 12.07 (br. s., 1H), 14.21 (br. s., 1H).

HRMS (ESI+): calcd. for $C_{29}H_{40}N_9O_2S$ [M+H]⁺ 578.3020; found 578.3026.

8-amino-4,4-dimethyl-N-{6-[(4-methyl-1,4'-bipiperidin-1'-yl)carbonyl]-1,3-benzothiazol-2-yl}-4,5-dihydro-1H-pyrazolo[4,3-h]quinazoline-3-carboxamide (Ib), Cpd 228

[R1=R2=R3'=R4'=H, R3=R4=($C_1$-$C_6$)alkyl, y=1, L=CONR8, z=0, A=heteroaryl, n=0, R5=CONR6R7, R6 and R7=taken together form an optionally substituted heterocyclyl group, R8=H]

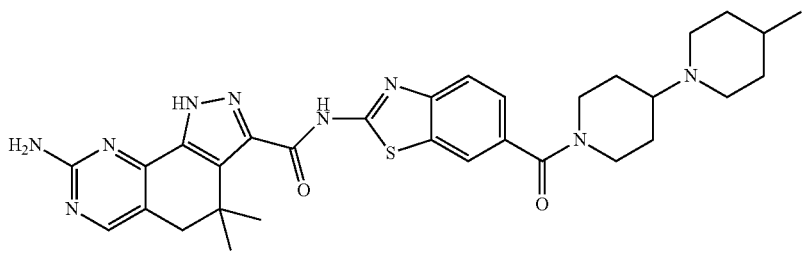 [SMILES: CC1CCN(C2CCN(C(=O)c3ccc4nc(NC(=O)c5n[nH]c6c5C(C)(C)Cc5cnc(N)nc5-6)sc4c3)CC2)CC1]

¹H NMR (500 MHz, DMSO-$d_6$) δ ppm 0.88 (d, J=7.17 Hz, 3H) 0.98-1.17 (m, 2H) 1.20-1.35 (m, 3H) 1.37 (s, 6H) 1.40-1.40 (m, 2H) 1.53-1.86 (m, 4H) 2.09-2.22 (m, 2H) 2.67 (s, 2H) 2.76-2.91 (m, 2H) 2.89-3.15 (m, 1H) 3.44-3.59 (m, 1H) 3.60-3.83 (m, 1H) 4.33-4.62 (m, 1H) 6.40 (br. s., 2H) 7.43 (d, J=6.25 Hz, 1H) 7.76 (br. s., 1H) 8.04 (br. s., 1H) 8.19 (s, 1H), 12.49 (br. s., 1H), 14.36 (br. s., 1H).

HRMS (ESI+): calcd. for $C_{31}H_{38}N_9O_2S$ [M+H]⁺ 600.2864; found 600.2858.

8-amino-N-{4-[2-(4,4-difluoro-1,4'-bipiperidin-1'-yl)-2-oxoethyl]-1,3-thiazol-2-yl}-4,4-dimethyl-4,5-dihydro-1H-pyrazolo[4,3-h]quinazoline-3-carboxamide (Ib), Cpd 229

[R1=R2=R3'=R4'=H, R3=R4=($C_1$-$C_6$)alkyl, y=1, L=CONR8, z=0, A=heteroaryl, n=1, Rc=Rd=H, R5=CONR6R7, R6 and R7=taken together form an optionally substituted heterocyclyl group, R8=H]

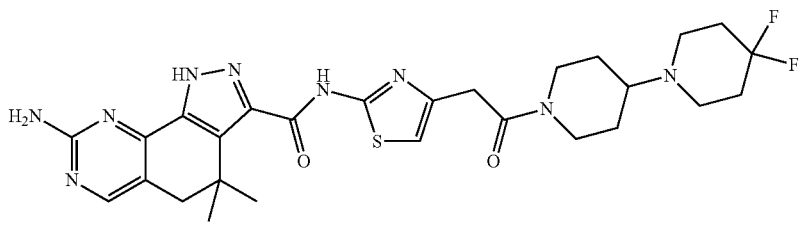 [SMILES: CC1(C)Cc2cnc(N)nc2-c2[nH]nc(C(=O)Nc3nc(CC(=O)N4CCC(N5CCC(F)(F)CC5)CC4)cs3)c21]

¹H NMR (499.7 MHz, DMSO-d₆) δ ppm 1.15-1.30 (m, 2H), 1.32 (s, 6H), 1.63-1.73 (m, 2H), 1.78-2.00 (m, 4H), 2.50-2.60 (m, 3H), 2.66 (s, 2H), 2.94-3.02 (m, 1H), 3.35 (m overlapped by water signal, 1H), 3.74 (s, 2H), 3.97-4.03 (m, 1H), 4.38-4.44 (m, 1H), 6.40 (br. s., 2H), 6.94 (s, 1H), 8.19 (s, 1H), 12.07 (br. s., 1H), 14.22 (br. s., 1H).

HRMS (ESI+): calcd. for $C_{27}H_{34}F_2N_9O_2S$ [M+H]⁺ 586.2519; found 586.2517.

8-amino-4,4-dimethyl-N-[4-({[1-(spiro[2.5]oct-6-yl)piperidin-4-yl]oxy}methyl)-1,3-thiazol-2-yl]-4,5-dihydro-1H-pyrazolo[4,3-h]quinazoline-3-carboxamide (Ib), Cpd 230

[R1=R2=R3'=R4'=H, R3=R4=(C₁-C₆)alkyl, y=1, L=CONR8, z=0, A=heteroaryl, n=1, Rc=Rd=H, R5=OR6, R6=substituted heterocyclyl, R8=H]

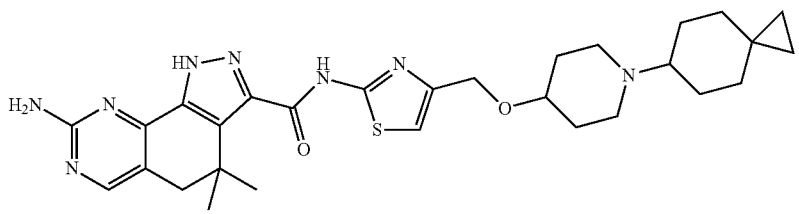 [SMILES: CC1(C)Cc2cnc(N)nc2-c2[nH]nc(C(=O)Nc3nc(COC4CCN(C5CCC6(CC5)CC6)CC4)cs3)c21]

¹H NMR (499.7 MHz, DMSO-d₆) δ ppm 0.12-0.20 (m, 2H), 0.22-0.28 (m, 2H), 0.87-0.94 (m, 2H), 1.33 (s, 6H), 1.27-1.49 (m, 4H), 1.56-1.75 (m, 4H), 1.84-1.90 (m, 2H), 2.18-2.35 (m, 3H), 2.66 (s, 2H), 2.73-2.80 (m, 2 H), 3.35 (m overlapped by water signal, 1H), 4.48 (s, 2H), 6.39 (br. s., 2H), 7.08 (s, 1H), 8.19 (s, 1H), 12.16 (br. s., 1H), 14.21 (br. s., 1H).

HRMS (ESI+): calcd. for $C_{29}H_{39}N_8O_2S$ [M+H]⁺ 563.2911; found 563.2906.

8-amino-5,5-dimethyl-N-{4-[2-(4-methyl-1,4'-bipiperidin-1'-yl)-2-oxoethyl]-1,3-thiazol-2-yl}-4,5-dihydro-1H-pyrazolo[4,3-h]quinazoline-3-carboxamide (Ib), Cpd 231

[R1=R2=R3=R4=H, R3'=R4'=(C₁-C₆)alkyl, y=1, L=CONR8, z=0, A=heteroaryl, n=1, Rc=Rd=H, R5=CONR6R7, R6 and R7=taken together form an optionally substituted heterocyclyl group, R8=H]

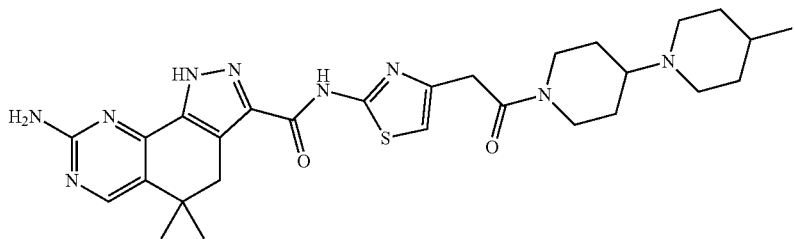 [SMILES: CC1CCN(C2CCN(C(=O)Cc3csc(NC(=O)c4n[nH]c5c4CC(C)(C)c4cnc(N)nc4-5)n3)CC2)CC1]

¹H NMR (499.7 MHz, DMSO-d₆) δ ppm 0.84 (d, J=6.6 Hz, 3H), 1.00-1.10 (m, 2H), 1.16-1.27 (m, 3H), 1.26 (s, 6H), 1.50-1.57 (m, 2H), 1.62-1.73 (m, 2H), 2.02-2.13 (m, 2H), 2.40-2.47 (m, 1H), 2.72-2.79 (m, 2H), 2.94 (s, 2H), 2.95-3.01 (m, 1H), 3.35 (m overlapped by water signal, 1H), 3.73 (s, 2H), 3.95-4.02 (m, 1H), 4.36-4.42 (m, 1H), 6.44 (br. s., 2H), 6.92 (s, 1H), 8.30 (s, 1H), 11.79 (br.s., 1H), 14.28 (br. s., 1H).

HRMS (ESI+): calcd. for $C_{28}H_{38}N_9O_2S$ [M+H]⁺ 564.2864; found 564.2869.

8-amino-N-(4-{[(1-cycloheptylpiperidin-4-yl)oxy]methyl}-1,3-thiazol-2-yl)-5,5-dimethyl-4,5-dihydro-1H-pyrazolo[4,3-h]quinazoline-3-carboxamide (Ib), Cpd 233

[R1=R2=R3'=R4'=H, R3=R4=(C₁-C₆)alkyl, y=1, L=CONR8, z=0, A=heteroaryl, n=1, Rc=Rd=H, R5=OR6, R6=substituted heterocyclyl, R8=H]

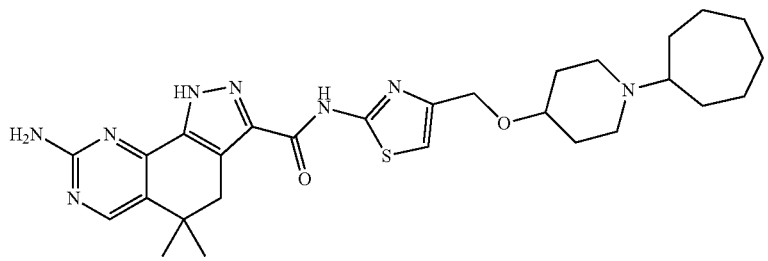 [SMILES: CC1(C)Cc2c(C(=O)Nc3nc(COC4CCN(C5CCCCCC5)CC4)cs3)n[nH]c2-c2nc(N)ncc21]

HRMS (ESI+): calcd. for $C_{27}H_{34}F_2N_9O_2S$ [M+H]⁺ 551.2911; found 551.2916.

Example 3

8-amino-4,4-dimethyl-N-{4-[(1-methylpiperidin-4-yl)carbamoyl]phenyl}-4,5-dihydro-1H-pyrazolo[4,3-h]quinazoline-3-carboxamide (Ig), Cpd 8

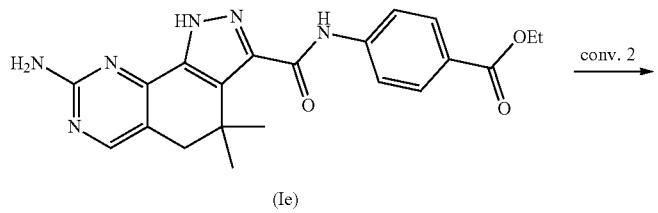

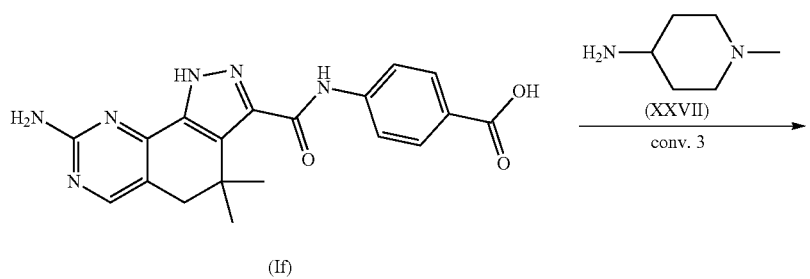

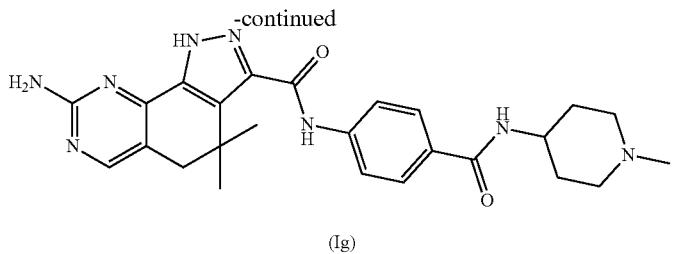

(Ig)

Conv. 2

4-{[(8-amino-4,4-dimethyl-4,5-dihydro-1H-pyrazolo[4,3-h]quinazolin-3-yl)carbonyl]amino}benzoic acid (If), Cpd 7

[R1=R2=R3'=R4'=H, R3=R4=($C_1$-$C_6$)alkyl, y=1, L=CONR8, z=n=0, A=aryl, R5=COOR6, R6=R8=H]

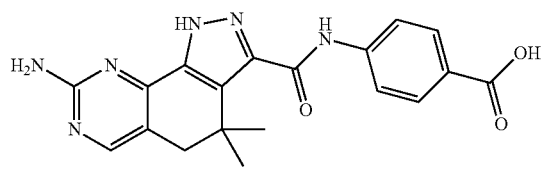 [SMILES: CC1(C)Cc2cnc(N)nc2-c2[nH]nc(C(=O)Nc3ccc(C(=O)O)cc3)c21]

Ethyl 4-{[(8-amino-4,4-dimethyl-4,5-dihydro-1H-pyrazolo[4,3-h]quinazolin-3-yl)carbonyl]amino}benzoate (1.13 g, 2.79 mmol) in EtOH (3 mL) was treated with 2 N NaOH (14 mL, 27.9 mmol) and heated at 110° C. (oil bath temperature) over 3 h. The reaction was cooled to 4° C. (ice-water bath) and AcOH (1.6 mL, 27.9 mmol) was added. The solid was filtered under suction, washed thoroughly with water, dried at 50° C. under vacuum to afford 800 mg of title compound as a white solid (76%).

$^1$H NMR (499.7 MHz, DMSO-$d_6$) δ ppm 1.34 (s, 6H), 2.66 (s, 2H), 6.39 (br. s., 2H), 7.88-8.02 (m, 4H), 8.19 (s, 1H), 10.58 (br. s., 1H), 12.75 (br. s., 1H) 14.14 (br. s., 1H).

HRMS (ESI+): calcd. for $C_{19}H_{20}N_6O_3$ [M+H]$^+$ 379.1513; found 379.1509.

Operating in an analogous way, but employing a suitably substituted compound (Ie), the following compound was obtained:

3-{[(8-amino-4,4-dimethyl-4,5-dihydro-1H-pyrazolo[4,3-h]quinazolin-3-yl)carbonyl]amino}benzoic acid (If), Cpd 18

[R1=R2=R3'=R4'=H, R3=R4=($C_1$-$C_6$)alkyl, y=1, L=CONR8, z=n=0, A=aryl, R5=COOR6, R6=R8=H]

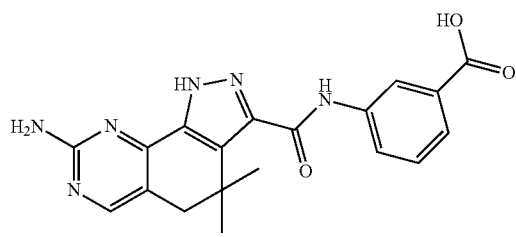 [SMILES: CC1(C)Cc2cnc(N)nc2-c2[nH]nc(C(=O)Nc3cccc(C(=O)O)c3)c21]

$^1$H NMR (400.4 MHz, DMSO-$d_6$) δ ppm 1.35 (s, 6H), 2.66 (s, 2H), 6.35 (br. s., 2H), 7.41 (t, J=7.8 Hz, 1H), 7.65 (dt, J=7.7, 1.3 Hz, 1H), 7.91 (d, J=8.3 Hz, 1H), 8.18 (s, 1H), 8.45 (br. s., 1H), 10.42 (br. s., 1H), 14.05 (br. s., 1H).

HRMS (ESI+): calcd. for $C_{19}H_{19}N_6O_3$ [M+H]$^+$ 379.1513; found 379.1496.

Alternatively:

(3-{[(8-amino-4,4-dimethyl-4,5-dihydro-1H-pyrazolo[4,3-h]quinazolin-3-yl)carbonyl]amino}phenyl)acetic acid (If), Cpd 139

[R1=R2=R3'=R4'=H, R3=R4=($C_1$-$C_6$)alkyl, y=1, L=CONR8, z=0, A=aryl, n=1, Rc=Rd=H, R5=COOR6, R6=R8=H]

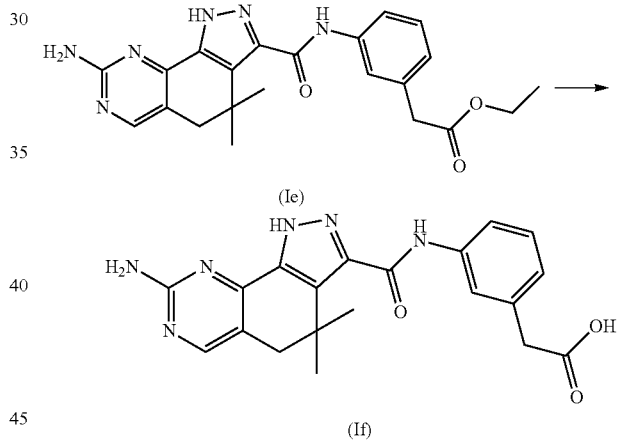

Ethyl (3-{[(8-amino-4,4-dimethyl-4,5-dihydro-1H-pyrazolo[4,3-h]quinazolin-3-yl)carbonyl]amino}phenyl)acetate (170 mg, 0.405 mmol) in EtOH (2 mL) and THF (2 mL) was treated with 2 N LiOH (2 mL, 4.05 mmol). The reaction was stirred at rt for 3 h and the volatiles were removed in vacuo. The aqueous phase was washed several times with small amounts of DCM, cooled with an ice bath and treated with AcOH (0.232 mL, 4.05 mmol). The solid was filtered with suction, washed with water, dried to afford 130 mg of title compound (82%).

$^1$H NMR (499.7 MHz, DMSO-$d_6$) δ ppm 1.33 (s, 6H), 2.64 (s, 2H), 3.45 (br. s., 2H), 6.37 (br. s., 2H), 6.96 (d, J=7.5 Hz, 1H), 7.23 (dd, J=8.2, 7.5 Hz, 1H), 7.61 (d, J=8.2 Hz, 1H), 7.71 (s, 1H), 8.17 (s, 1H), 10.28 (br. s., 1H), 14.08 (br. s., 1H).

HRMS (ESI+): calcd. for $C_{20}H_{21}N_6O_3$[M+H]$^+$ 393.1670; found 393.1668.

Operating in an analogous way, but employing suitably substituted compounds (Ie), the following compounds were obtained:

(4-{[(8-amino-4,4-dimethyl-4,5-dihydro-1H-pyrazolo[4,3-h]quinazolin-3-yl)carbonyl]amino}phenyl)acetic acid (If), Cpd 97

[R1=R2=R3'=R4'=H, R3=R4=(C$_1$-C$_6$)alkyl, y=1, L=CONR8, z=0, A=aryl, n=1, Rc=Rd=H, R5=COOR6, R6=R8=H]

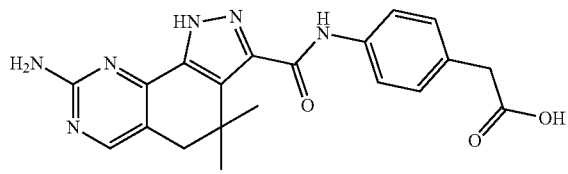 [SMILES: CC1(C)Cc2cnc(N)nc2-c2[nH]nc(C(=O)Nc3ccc(CC(=O)O)cc3)c21]

$^1$H NMR (499.7 MHz, DMSO-d$_6$) δ ppm 1.33 (s, 6H), 2.65 (s, 2H), 3.52 (s, 2H), 6.37 (br. s., 2H), 7.21 (d, J=8.4 Hz, 2H), 7.72 (d, J=8.4 Hz, 2H), 8.18 (s, 1H), 10.22 (br. s., 1H), 12.27 (br. s., 1H), 14.04 (br. s., 1H).
HRMS (ESI+): calcd. for C$_{20}$H$_{21}$N$_6$O$_3$ [M+H]$^+$ 393.1670; found 393.1668.

4-({[(8-amino-4,4-dimethyl-4,5-dihydro-1H-pyrazolo[4,3-h]quinazolin-3-yl)carbonyl]amino}methyl)benzoic acid (If), Cpd 164

[R1=R2=R3'=R4'=H, R3=R4=(C$_1$-C$_6$)alkyl, y=1, L=CONR8, z=1, Ra=Rb=H, A=aryl, n=0, R5=COOR6, R6=R8=H]

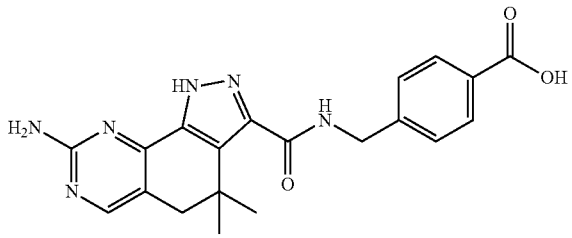 [SMILES: CC1(C)Cc2cnc(N)nc2-c2[nH]nc(C(=O)NCc3ccc(C(=O)O)cc3)c21]

$^1$H NMR (499.7 MHz, DMSO-d$_6$) δ ppm 1.30 (s, 6H), 2.62 (s, 2H), 4.49 (d, J=6.2 Hz, 2H), 6.35 (br. s., 2H), 7.42 (d, J=8.2 Hz, 2H), 7.89 (d, J=8.2 Hz, 2H), 8.16 (s, 1H), 8.88 (br. s., 1H), 13.92 (br. s., 1H).
HRMS (ESI+): calcd. for C$_{20}$H$_{21}$N$_6$O$_3$ [M+H]$^+$ 393.1670; found 393.1671.

(2-{[(8-amino-4,4-dimethyl-4,5-dihydro-1H-pyrazolo[4,3-h]quinazolin-3-yl)carbonyl]amino}-1,3-thiazol-4-yl)acetic acid (If), Cpd 42

[R1=R2=R3'=R4'=H, R3=R4=(C$_1$-C$_6$)alkyl, y=1, L=CONR8, z=0, A=heteroaryl, n=1, Rc=Rd=H, R5=COOR6, R6=R8=H]

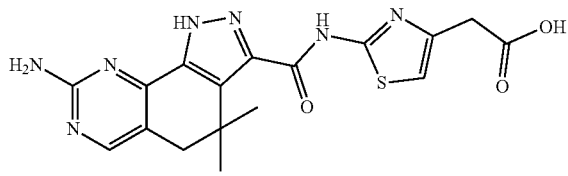 [SMILES: CC1(C)Cc2cnc(N)nc2-c2[nH]nc(C(=O)Nc3nc(CC(=O)O)cs3)c21]

$^1$H NMR (499.7 MHz, DMSO-d$_6$) δ ppm 1.33 (s, 6H), 2.66 (s, 2H), 3.63 (s, 2H), 6.40 (br. s., 2H), 7.01 (s, 1H), 8.19 (s, 1H), 12.14 (br. s., 1H), 14.18 (br. s., 1H).
HRMS (ESI+): calcd. for C$_{17}$H$_{18}$N$_7$O$_3$S [M+H]$^+$ 400.1187; found 400.1183.

(2-{[(8-amino-4,4-dimethyl-4,5-dihydro-1H-pyrazolo[4,3-h]quinazolin-3-yl)carbonyl]amino}-1,3-thiazol-5-yl)acetic acid (If), Cpd 72

[R1=R2=R3'=R4'=H, R3=R4=(C$_1$-C$_6$)alkyl, y=1, L=CONR8, z=0, A=heteroaryl, n=1, Rc=Rd=H, R5=COOR6, R6=R8=H]

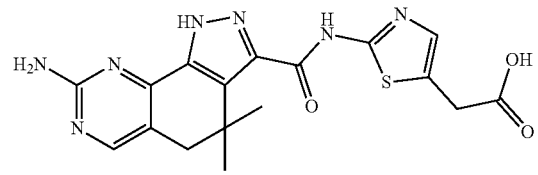 [SMILES: CC1(C)Cc2cnc(N)nc2-c2[nH]nc(C(=O)Nc3ncc(CC(=O)O)s3)c21]

$^1$H NMR (499.7 MHz, DMSO-d$_6$; evident presence of tautomers) δ ppm 1.32 and 1.33 (2×s, 6H), 2.62 and 2.66 (2×s, 2H), 3.82 (s, 2H), 6.40 (br. s., 2H), 7.31 (s, 1H), 8.12 and 8.19 (2×s, 1H), 11.96 (br. s., 1H), 13.82 and 14.23 (2×br. s., 1H).
HRMS (ESI+): calcd. for C$_{17}$H$_{18}$N$_7$O$_3$S [M+H]$^+$ 400.1187; found 400.1194.

2-{[(8-amino-4,4-dimethyl-4,5-dihydro-1H-pyrazolo[4,3-h]quinazolin-3-yl)carbonyl]amino}-1,3-thiazole-4-carboxylic acid (If), Cpd 67

[R1=R2=R3'=R4'=H, R3=R4=(C$_1$-C$_6$)alkyl, y=1, L=CONR8, z=n=0, A=heteroaryl, R5=COOR6, R6=R8=H]

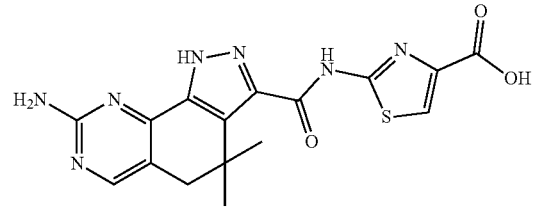 [SMILES: CC1(C)Cc2cnc(N)nc2-c2[nH]nc(C(=O)Nc3nc(C(=O)O)cs3)c21]

$^1$H NMR (499.7 MHz, DMSO-d$_6$) δ ppm 1.34 (s, 6H), 2.66 (s, 2H), 6.40 (br. s., 2H), 7.84 (br. s., 1H), 8.18 (s, 1H), 12.42 (br. s., 1H), 14.26 (br. s., 1H).
HRMS (ESI+): calcd. for C$_{16}$H$_{16}$N$_7$O$_3$S [M+H]$^+$ 386.1030; found 386.1027.

2-{[(8-amino-4,4-dimethyl-4,5-dihydro-1H-pyrazolo[4,3-h]quinazolin-3-yl)carbonyl]amino}-1,3-thiazole-5-carboxylic acid (If), Cpd 82

[R1=R2=R3'=R4'=H, R3=R4=(C$_1$-C$_6$)alkyl, y=1, L=CONR8, z=n=0, A=heteroaryl, R5=COOR6, R6=R8=H]

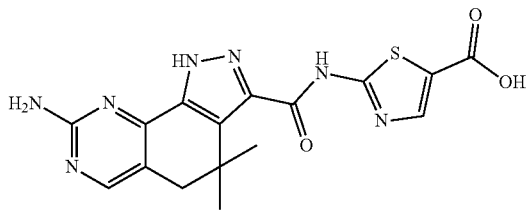 [SMILES: CC1(C)Cc2cnc(N)nc2-c2[nH]nc(C(=O)Nc3ncc(C(=O)O)s3)c21]

$^1$H NMR (499.7 MHz, DMSO-d$_6$) δ ppm 1.34 (s, 6H), 2.67 (s, 2H), 6.40 (br. s., 2H), 8.02 (br. s., 1H), 8.19 (s, 1H), 12.49 (br. s., 1H), 14.32 (br. s., 1H).

HRMS (ESI+): calcd. for C$_{16}$H$_{16}$N$_7$O$_3$S [M+H]$^+$ 386.1030; found 386.1025.

2-{[(8-amino-4,4-dimethyl-4,5-dihydro-1H-pyrazolo [4,3-h]quinazolin-3-yl)carbonyl]amino}-4-methyl-1, 3-thiazole-5-carboxylic acid (If), Cpd 176

[R1=R2=R3'=R4'=H, R3=R4=(C$_1$-C$_6$)alkyl, y=1, L=CONR8, z=n=0, A=heteroaryl, R5=COOR6, R6=R8=H]

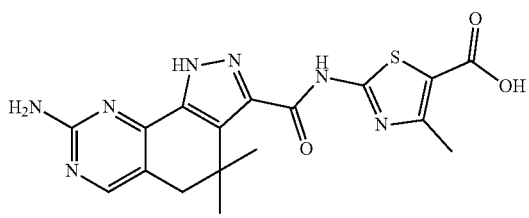 [SMILES: Cc1nc(NC(=O)c2n[nH]c3c2C(C)(C)Cc2cnc(N)nc2-3)sc1C(=O)O]

HRMS (ESI+): calcd. for C$_{17}$H$_{18}$N$_7$O$_3$S [M+H]$^+$ 400.1186; found 400.1185.

1-(2-{[(8-amino-4,4-dimethyl-4,5-dihydro-1H-pyrazolo[4,3-h]quinazolin-3-yl)carbonyl]amino}-1,3-thiazol-4-yl)cyclopropanecarboxylic acid (If), Cpd 129

[R1=R2=R3'=R4'=H, R3=R4=(C$_1$-C$_6$)alkyl, y=1, L=CONR8, z=0, A=heteroaryl, n=1, Rc and Rd=taken together form a 3-membered cycloalkyl, R5=COOR6, R6=R8=H]

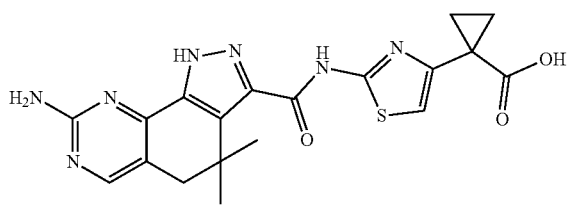 [SMILES: CC1(C)Cc2cnc(N)nc2-c2[nH]nc(C(=O)Nc3nc(C4(C(=O)O)CC4)cs3)c21]

$^1$H NMR (499.7 MHz, DMSO-d$_6$) δ ppm 1.19-1.32 (m, 2H), 1.33 (s, 6H), 1.42-1.48 (m, 2H), 2.64 (s, 2H), 6.38 (br. s., 2H), 7.13 (br. s., 1H), 8.17 (s, 1H), 12.04 (br. s., 1H), 14.16 (br. s., 1H).

HRMS (ESI+): calcd. for C$_{19}$H$_{20}$N$_7$O$_3$S [M+H]$^+$ 426.1343; found 426.1345.

(2-{[(8-amino-4,4-dimethyl-4,5-dihydro-1H-pyrazolo[4,3-h]quinazolin-3-yl)carbonyl]amino}-1,3-thiazol-4-yl)(difluoro)acetic acid (If), Cpd 186

[R1=R2=R3'=R4'=H, R3=R4=(C$_1$-C$_6$)alkyl, y=1, L=CONR8, z=0, A=heteroaryl, n=1, Rc=Rd=F, COOR6, R6=R8=H]

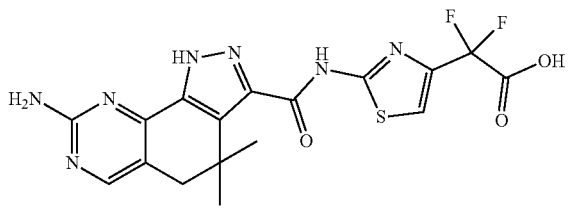 [SMILES: CC1(C)Cc2cnc(N)nc2-c2[nH]nc(C(=O)Nc3nc(C(F)(F)C(=O)O)cs3)c21]

HRMS (ESI+): calcd. for C$_{17}$H$_{16}$F$_2$N$_7$O$_3$S [M+H]$^+$ 436.0998; found 436.0996.

[2-({[8-amino-4,4-dimethyl-1-(tetrahydro-2H-pyran-2-yl)-4,5-dihydro-1H-pyrazolo[4,3-h]quinazolin-3-yl]carbonyl}amino)-1,3-thiazol-4-yl](difluoro)acetic acid (IIf)

[R1=R3'=R4'=H, PG=tetrahydropyranyl, R3=R4=(C$_1$-C$_6$) alkyl, y=1, L=CONR8, z=0, A=heteroaryl, n=1, Rc=Rd=F, R5=COOR6, R6=R8=H]

$^1$H NMR (500 MHz, DMSO-d$_6$) δ ppm 1.27 (s, 3H) 1.35 (s, 3H) 1.51-1.62 (m, 2H) 1.68-1.79 (m, 1H) 1.88-1.98 (m, 1H) 2.01-2.07 (m, 1H) 2.41-2.49 (m, 1H) 2.60-2.67 (m, 2H) 3.78-3.95 (m, 2H) 6.64 (br. s., 2H) 6.85 (d, J=10.07 Hz, 1H) 7.64 (br. s., 1H) 8.20 (s, 1H) 12.72 (s, 1H).

HRMS (ESI+): calcd. for C$_{22}$H$_{24}$F$_2$N$_7$O$_4$S [M+H]$^+$ 520.1573; found 520.1588.

[2-({[8-amino-4,4-dimethyl-1-(tetrahydro-2H-pyran-2-yl)-4,5-dihydro-1H-pyrazolo[4,3-h]quinazolin-3-yl]carbonyl}amino)-1,3-thiazol-4-yl]acetic acid (IIf)

[R1=R3'=R4'=H, PG=tetrahydropyranyl, R3=R4=(C$_1$-C$_6$) alkyl, y=1, L=CONR8, z=0, A=heteroaryl, n=1, Rc=Rd=H, R5=COOR6, R6=R8=H]

$^1$H NMR (500 MHz, DMSO-d$_6$) δ ppm 1.26 (s, 3H) 1.35 (s, 3H) 1.151-1.63 (m, 2H) 1.67-1.81 (m, 1H) 1.88-1.98 (m, 1H) 2.01-2.11 (m, 1H) 2.40-2.46 (m, 1H) 2.63 (s, 2H) 3.60 (s, 2H) 3.78-3.87 (m, 1H) 3.87-3.96 (m, 1H) 6.63 (br. s., 2H) 6.85 (dd, J=9.91, 2.44 Hz, 1H) 7.00 (s, 1H) 8.19 (s, 1H) 12.30 (br. s., 1H).

HRMS (ESI+): calcd. for C$_{22}$H$_{26}$F$_2$N$_7$O$_4$S [M+H]$^+$ 484.1762; found 484.1768.

Conv. 3

8-amino-4,4-dimethyl-N-{4-[(1-methylpiperidin-4-yl)carbamoyl]phenyl}-4,5-dihydro-1H-pyrazolo[4,3-h]quinazoline-3-carboxamide (Ig), Cpd 8

[R1=R2=R3'=R4'=H, R3=R4=(C$_1$-C$_6$)alkyl, y=1, L=CONR8, z=n=0, A=aryl, R5=CONR6R7, R6=substituted heterocyclyl, R7=R8=H]

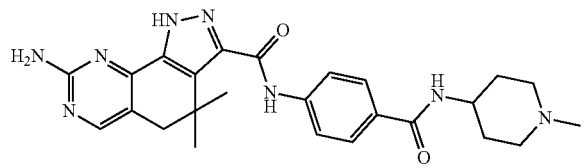 [SMILES: CN1CCC(NC(=O)c2ccc(NC(=O)c3n[nH]c4c3C(C)(C)Cc3cnc(N)nc3-4)cc2)CC1]

4-{[(8-Amino-4,4-dimethyl-4,5-dihydro-1H-pyrazolo[4,3-h]quinazolin-3-yl)carbonyl]amino}benzoic acid (22 mg, 0.058 mmol) in DMF (0.116 mL) was treated with DIPEA (0.015 mL, 0.087 mmol), 1-methylpiperidin-4-amine (XXVII) (0.011 mL, 0.0873 mmol) and TBTU (28 mg, 0.087 mmol). The reaction was stirred for 3 h at rt, the volatiles were then evaporated under vacuum, the residue partitioned between saturated aqueous NaHCO$_3$ (50 mL) and DCM (5 mL×3). The combined organic extracts were washed with brine, dried over Na$_2$SO$_4$ and evaporated to leave 29 mg of crude which was purified by column chromatography over silica gel (DCM: 7N NH$_3$ in MeOH=9:1) to give the title compound as whitish solid (8 mg, 29%).

$^1$H NMR (499.7 MHz, DMSO-d$_6$) δ ppm 1.34 (s, 6H), 1.53-1.64 (m, 2H), 1.73-1.80 (m, 2H), 1.91-2.04 (m, 2H), 2.18 (s, 3H), 2.66 (s, 2H), 2.75-2.83 (m, 2H), 3.68-3.78 (m, 1H), 6.38 (br. s., 2H), 7.80-7.90 (m, 4H), 8.14 (d, J=7.5 Hz, 1H), 8.19 (s, 1H), 10.47 (br. s., 1H), 14.10 (br. s., 1H).

HRMS (ESI+): calcd. for C$_{25}$H$_{31}$N$_8$O$_2$ [M+H]$^+$ 475.2565; found 475.2568.

Operating in an analogous way, but employing suitably substituted compounds (If) and (XXVII), the following compounds were obtained:

8-amino-N-[4-(cyclohexylcarbamoyl)phenyl]-4,4-dimethyl-4,5-dihydro-1H-pyrazolo[4,3-h]quinazoline-3-carboxamide (Ig), Cpd 16

[R1=R2=R3'=R4'=H, R3=R4=(C$_1$-C$_6$)alkyl, y=1, L=CONR8, z=n=0, A=aryl, R5=CONR6R7, R6=unsubstituted cycloalkyl, R7=R8=H]

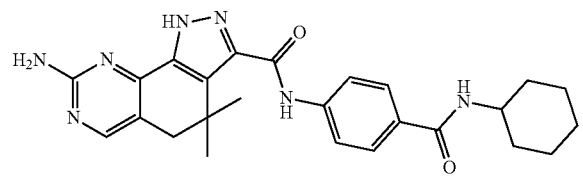 [SMILES: CC1(C)Cc2cnc(N)nc2-c2[nH]nc(C(=O)Nc3ccc(C(=O)NC4CCCCC4)cc3)c21]

$^1$H NMR (499.7 MHz, DMSO-d$_6$) δ ppm 1.08-1.20 (m, 1H), 1.21-1.33 (m, 6H), 1.35 (s, 6H), 1.58-1.64 (m, 1H), 1.68-1.86 (m, 4H), 2.66 (s, 2H), 3.79-3.80 (m, 1H), 6.38 (br. s., 2H), 7.80-7.84 (m, 2H), 7.85-7.91 (m, 2H), 8.09 (d, J=8.1 Hz, 1H), 8.19 (s, 1H), 10.44 (s, 1H), 14.12 (s, 1H).

HRMS (ESI+): calcd. for C25H30N7O2 [M+H]$^+$ 460.2456; found 460.2451.

8-amino-4,4-dimethyl-N-[4-(tetrahydro-2H-pyran-4-ylcarbamoyl)phenyl]-4,5-dihydro-1H-pyrazolo[4,3-h]quinazoline-3-carboxamide (Ig), Cpd 11

[R1=R2=R3'=R4'=H, R3=R4=(C$_1$-C$_6$)alkyl, y=1, L=CONR8, z=n=0, A=aryl, R5=CONR6R7, R6=unsubstituted heterocyclyl, R7=R8=H]

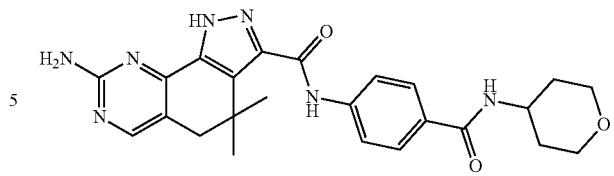

$^1$H NMR (499.7 MHz, DMSO-d$_6$) δ ppm 1.35 (s, 6H), 1.54-1.62 (m, 2H), 1.74-1.78 (m, 2H), 2.66 (s, 2H), 3.35-3.41 (m, 2H), 3.85-3.90 (m, 2H), 3.95-4.06 (m, 1H), 6.38 (br. s., 2H), 7.81-7.92 (m, 4H), 8.20 (s, 1H), 8.21 (d, J=8.1 Hz, 1H), 10.45 (s, 1H), 14.13 (s, 1H).

HRMS (ESI+): calcd. for C$_{24}$H$_{28}$N$_7$O$_3$ [M+H]$^+$ 462.2248; found 462.2242.

8-amino-4,4-dimethyl-N-(4-{[4-(pyrrolidin-1-yl)piperidin-1-yl]carbonyl}phenyl)-4,5-dihydro-1H-pyrazolo[4,3-h]quinazoline-3-carboxamide (Ig), Cpd 13

[R1=R2=R3'=R4'=H, R3=R4=(C$_1$-C$_6$)alkyl, y=1, L=CONR8, z=n=0, A=aryl, R5=CONR6R7, R6 and R7=taken together form an optionally substituted heterocyclyl group, R8=H]

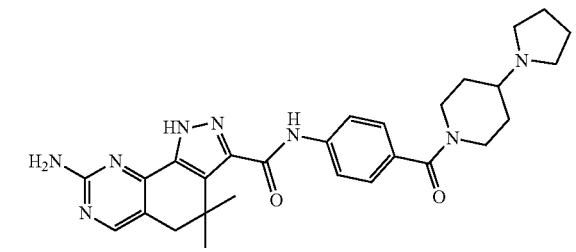

$^1$H NMR (499.7 MHz, DMSO-d$_6$) δ ppm 1.30-1.43 (m, 8H), 1.34 (s, 6H), 1.61-1.71 (m, 4H), 1.75-1.92 (br. s., 2H), 2.19-2.27 (m, 1H), 2.65 (s, 2H), 2.85-3.16 (br. s., 2H), 3.61-3.73 (br. s., 1H), 4.16-4.34 (br. s., 1H), 6.38 (br. s., 2H), 7.36 (d, J=8.5 Hz, 2H), 7.85 (d, J=8.5 Hz, 2H), 8.19 (s, 1H), 10.46 (br. s., 1H), 14.08 (br. s., 1H).

HRMS (ESI+): calcd. for C$_{26}$H$_{33}$N$_8$O$_2$ [M+H]$^+$ 515.2878; found 515.2894.

8-amino-N-(4-{[4-(dimethylamino)piperidin-1-yl]carbonyl}phenyl)-4,4-dimethyl-4,5-dihydro-1H-pyrazolo[4,3-h]quinazoline-3-carboxamide (Ig), Cpd 14

[R1=R2=R3'=R4'=H, R3=R4=(C$_1$-C$_6$)alkyl, y=1, L=CONR8, z=n=0, A=aryl, R5=CONR6R7, R6 and R7=taken together form an optionally substituted heterocyclyl group, R8=H]

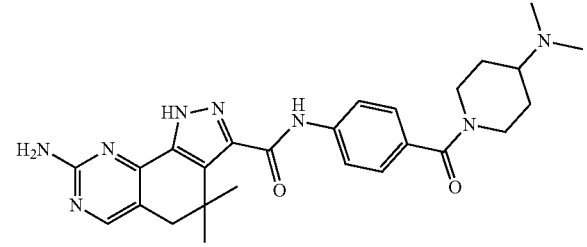

¹H NMR (499.7 MHz, DMSO-d₆) δ ppm 1.28-1.40 (m, 2H), 1.34 (s, 6H), 1.64-1.90 (br. s., 2H), 2.17 (s, 6H), 2.28-2.36 (m, 1H), 2.65 (s, 2H), 2.64-3.13 (m, 2H), 3.57-3.80 (br. s., 1H), 4.29-4.47 (br. s., 1H), 6.38 (br. s., 2H), 7.37 (d, J=8.5 Hz, 2H), 7.86 (d, J=8.5 Hz, 2H), 8.19 (s, 1H), 10.47 (br. s., 1H), 14.08 (br. s., 1H).

HRMS (ESI+): calcd. for $C_{28}H_{37}N_8O_3$ [M+H]⁺ 489.2721; found 489.2719.

8-amino-4,4-dimethyl-N-{4-[(4-methylpiperazin-1-yl)carbonyl]phenyl}-4,5-dihydro-1H-pyrazolo[4,3-h]quinazoline-3-carboxamide (Ig), Cpd 15

[R1=R2=R3'=R4'=H, R3=R4=(C₁-C₆)alkyl, y=1, L=CONR8, z=n=0, A=aryl, R5=CONR6R7, R6 and R7=taken together form an optionally substituted heterocyclyl group, R8=H]

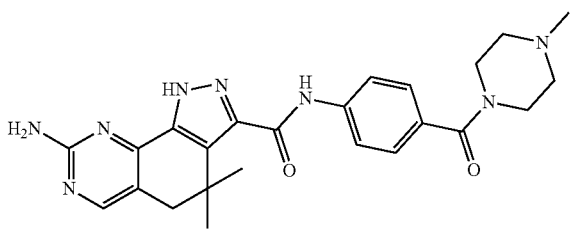

¹H NMR (400.4 MHz, DMSO-d₆) δ ppm 1.34 (s, 6H), 2.20 (s, 3H), 2.27-2.35 (br. s., 4H), 2.66 (s, 2H), 3.35-3.60 (m, 4H), 6.35 (br. s., 2H), 7.37 (d, J=8.5 Hz, 2H), 7.87 (d, J=8.5 Hz, 2H), 8.19 (s, 1H), 10.42 (br. s., 1H), 14.08 (br. s., 1H).

HRMS (ESI+): calcd. for $C_{24}H_{29}N_8O_2$ [M+H]⁺ 461.2408; found 461.2403.

8-amino-4,4-dimethyl-N-[4-(morpholin-4-ylcarbonyl)phenyl]-4,5-dihydro-1H-pyrazolo[4,3-h]quinazoline-3-carboxamide (Ig), Cpd 12

[R1=R2=R3'=R4'=H, R3=R4=(C₁-C₆)alkyl, y=1, L=CONR8, z=n=0, A=aryl, R5=CONR6R7, R6 and R7=taken together form an optionally substituted heterocyclyl group, R8=H]

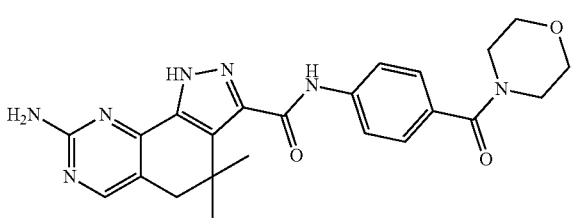 [SMILES: CC1(C)Cc2cnc(N)nc2-c2[nH]nc(C(=O)Nc3ccc(C(=O)N4CCOCC4)cc3)c21]

¹H NMR (400.4 MHz, DMSO-d₆) δ ppm 1.35 (s, 6H), 2.66 (m, 2H), 3.42-3.55 (br. s., 4H), 3.57-3.63 (br. s., 4H), 6.35 (br. s., 2H), 7.40 (d, J=8.5 Hz, 2H), 7.88 (d, J=8.5 Hz, 2H), 8.19 (s, 1H), 10.43 (s, 1H), 14.08 (br. s., 1H).

HRMS (ESI+): calcd. for $C_{23}H_{26}N_7O_3$ [M+H]⁺ 448.2092; found 448.2094.

8-amino-4,4-dimethyl-N-[4-(piperidin-1-ylcarbonyl)phenyl]-4,5-dihydro-1H-pyrazolo[4,3-h]quinazoline-3-carboxamide (Ig), Cpd 19

[R1=R2=R3'=R4'=H, R3=R4=(C₁-C₆)alkyl, y=1, L=CONR8, z=n=0, A=aryl, R5=CONR6R7, R6 and R7=taken together form an optionally substituted heterocyclyl group, R8=H]

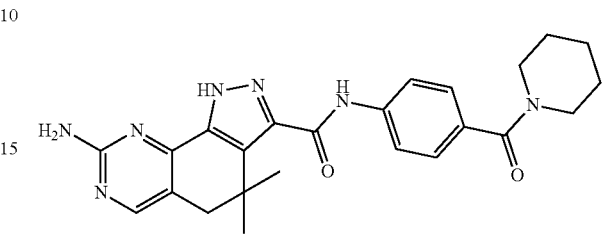

¹H NMR (400.4 MHz, DMSO-d₆) δ ppm 1.34 (s, 6H), 1.46-1.56 (br. s., 4H), 1.58-1.68 (m, 2H), 2.66 (s, 2H), 3.30-3.75 (m, 4H), 6.35 (br. s., 2H), 7.35 (d, J=8.4 Hz, 2H), 7.86 (d, J=8.2 Hz, 2H), 8.19 (s, 1H), 10.40 (br. s., 1H), 14.07 (br. s., 1H).

HRMS (ESI+): calcd. for $C_{24}H_{28}N_7O_2$ [M+H]⁺ 446.22998; found 446.2292.

8-amino-N-[4-(1,4'-bipiperidin-1'-ylcarbonyl)phenyl]-4,4-dimethyl-4,5-dihydro-1H-pyrazolo[4,3-h]quinazoline-3-carboxamide (Ig), Cpd 20

[R1=R2=R3'=R4'=H, R3=R4=(C₁-C₆)alkyl, y=1, L=CONR8, z=n=0, A=aryl, R5=CONR6R7, R6 and R7=taken together form an optionally substituted heterocyclyl group, R8=H]

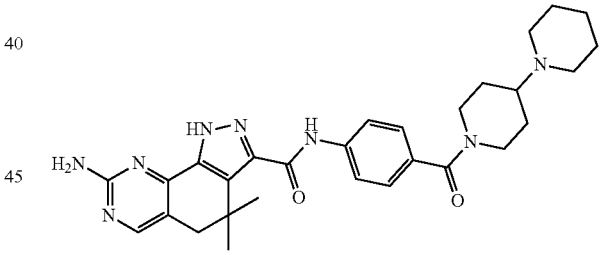

¹H NMR (400.4 MHz, DMSO-d₆) δ ppm 1.34 (s, 6H), 1.34-1.42 (m, 4H), 1.43-1.54 (m, 4H), 1.60-1.85 (br. s., 2H), 2.38-2.48 (m, 4H), 2.66 (s, 2H), 2.68-3.10 (br. s., 2H), 3.50-3.90 (br. s., 1H), 4.20-4.60 (br. s., 1H), 6.35 (br. s., 2H), 7.36 (d, J=8.7 Hz, 2H), 7.85 (d, J=8.7 Hz, 2H), 8.19 (s, 1H), 10.42 (br. s., 1H), 14.06 (br. s., 1H).

HRMS (ESI+): calcd. for $C_{29}H_{37}N_8O_2$ [M+H]⁺ 529.3034; found 529.3037.

8-amino-N-{4-[(4-hydroxypiperidin-1-yl)carbonyl]phenyl}-4,4-dimethyl-4,5-dihydro-1H-pyrazolo[4,3-h]quinazoline-3-carboxamide (Ig), Cpd 21

[R1=R2=R3'=R4'=H, R3=R4=(C₁-C₆)alkyl, y=1, L=CONR8, z=n=0, A=aryl, R5=CONR6R7, R6 and R7=taken together form an optionally substituted heterocyclyl group, R8=H]

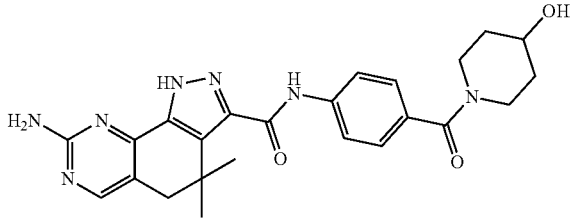 [SMILES: CC1(C)Cc2cnc(N)nc2-c2[nH]nc(C(=O)Nc3ccc(C(=O)N4CCC(O)CC4)cc3)c21]

¹H NMR (400.4 MHz, DMSO-d₆) δ ppm 1.30-1.40 (br. s, 2H), 1.35 (s, 6H), 1.68-1.78 (br. s., 2H), 2.66 (s, 2H), 3.11-3.25 (m, 2H), 3.43-3.70 (br. s., 1H), 3.69-3.78 (m, 1H), 3.80-4.10 (br. s., 1H), 4.77 (d, J=4.0 Hz, 1H), 6.34 (br. s., 2H), 7.35 (d, J=8.5 Hz, 2H), 7.86 (d, J=8.5 Hz, 2H), 8.19 (s, 1H), 10.41 (s, 1H), 14.08 (br. s., 1H).
HRMS (ESI+): calcd. for $C_{24}H_{28}N_7O_3$ [M+H]⁺ 462.2248; found 462.2244.

8-amino-N-(4-{[4-(hydroxymethyl)piperidin-1-yl]carbonyl}phenyl)-4,4-dimethyl-4,5-dihydro-1H-pyrazolo[4,3-h]quinazoline-3-carboxamide (Ig), Cpd 22

[R1=R2=R3'=R4'=H, R3=R4=($C_1$-$C_6$)alkyl, y=1, L=CONR8, z=n=0, A=aryl, R5=CONR6R7, R6 and R7=taken together form an optionally substituted heterocyclyl group, R8=H]

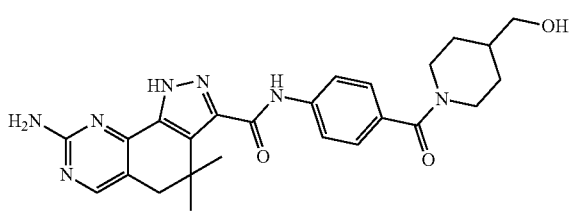 [SMILES: CC1(C)Cc2cnc(N)nc2-c2[nH]nc(C(=O)Nc3ccc(C(=O)N4CCC(CO)CC4)cc3)c21]

¹H NMR (400.4 MHz, DMSO-d₆) δ ppm 0.97-1.18 (m, 2H), 1.34 (s, 6H), 1.54-1.88 (m, 3H), 2.66 (s, 2H), 2.72-3.20 (br. s., 2H), 3.44-3.92 (br. s., 1H), 4.10-4.60 (br.s., 1H), 4.49 (t, J=5.3 Hz, 1H), 6.35 (br. s., 2H), 7.35 (d, J=8.7 Hz, 2H), 7.85 (d, J=8.7 Hz, 2H), 8.19 (s, 1H), 10.41 (br. s., 1H), 14.07 (br. s., 1H).
HRMS (ESI+): calcd. for $C_{25}H_{30}N_7O_3$[M+H]⁺ 476.2405; found 476.2396.

8-amino-N-{4-[(4,4-difluoropiperidin-1-yl)carbonyl]phenyl}-4,4-dimethyl-4,5-dihydro-1H-pyrazolo[4,3-h]quinazoline-3-carboxamide (Ig), Cpd 23

[R1=R2=R3'=R4'=H, R3=R4=($C_1$-$C_6$)alkyl, y=1, L=CONR8, z=n=0, A=aryl, R5=CONR6R7, R6 and R7=taken together form an optionally substituted heterocyclyl group, R8=H]

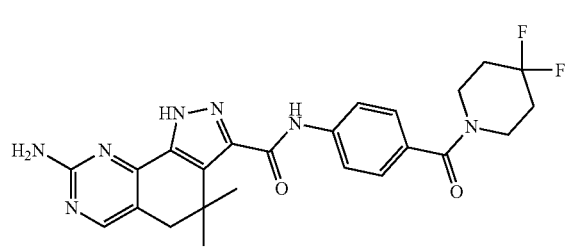 [SMILES: CC1(C)Cc2cnc(N)nc2-c2[nH]nc(C(=O)Nc3ccc(C(=O)N4CCC(F)(F)CC4)cc3)c21]

¹H NMR (400.4 MHz, DMSO-d₆) δ ppm 1.35 (s, 6H), 1.97-2.10 (m, 4H), 2.66 (s, 2H), 3.50-3.67 (br. s., 4H), 6.35 (br. s., 2H), 7.44 (d, J=8.5 Hz, 2H), 7.88 (d, J=8.5 Hz, 2H), 8.19 (s, 1H), 10.44 (s, 1H), 14.09 (br. s., 1H).
HRMS (ESI+): calcd. for $C_{24}H_{26}N_7O_2F_2$ [M+H]⁺ 482.2111; found 482.2109.

8-amino-N-{4-[(4-carbamoylpiperidin-1-yl)carbonyl]phenyl}-4,4-dimethyl-4,5-dihydro-1H-pyrazolo[4,3-h]quinazoline-3-carboxamide (Ig), Cpd 24

[R1=R2=R3'=R4'=H, R3=R4=($C_1$-$C_6$)alkyl, y=1, L=CONR8, z=n=0, A=aryl, R5=CONR6R7, R6 and R7=taken together form an optionally substituted heterocyclyl group, R8=H]

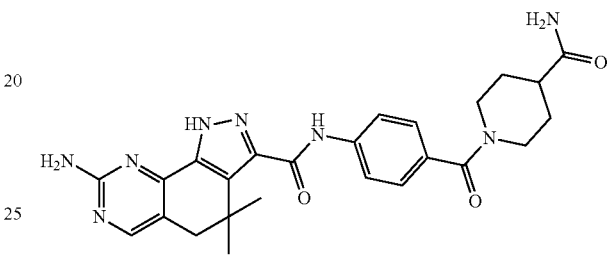

¹H NMR (400.4 MHz, DMSO-d₆) δ ppm 1.35 (s, 6H), 1.44-1.54 (m, 2H), 1.67-1.80 (br. s., 2H), 2.37 (m, 1H), 2.66 (s, 2H), 2.76-3.09 (br. s., 2H), 3.50-4.60 (br. s., 2H), 6.34 (br. s., 2H), 6.79 (s, 1H), 7.27 (s, 1H), 7.36 (d, J=8.5 Hz, 2H), 7.87 (d, J=8.5 Hz, 2H), 8.19 (s, 1H), 10.41 (s, 1H), 14.07 (br. s., 1H).
HRMS (ESI+): calcd. for $C_{25}H_{29}N_8O_3$ [M+H]⁺ 489.2357; found 489.2353.

8-amino-N-{4-[(trans-4-hydroxycyclohexyl)carbamoyl]phenyl}-4,4-dimethyl-4,5-dihydro-1H-pyrazolo[4,3-h]quinazoline-3-carboxamide (Ig), Cpd 28

[R1=R2=R3'=R4'=H, R3=R4=($C_1$-$C_6$)alkyl, y=1, L=CONR8, z=n=0, A=aryl, R5=CONR6R7, R6=substituted cycloalkyl, R7=R8=H]

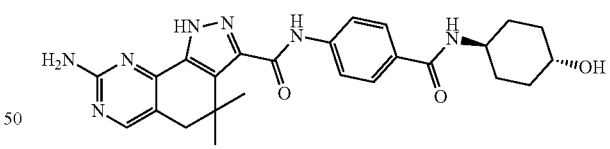

¹H NMR (400.4 MHz, DMSO-d₆) δ ppm 1.15-1.46 (m, 4H), 1.35 (s, 6H), 1.77-1.91 (m, 4H), 2.66 (s, 2H), 3.35-3.45 (m, 1H), 3.66-3.76 (m, 1H), 4.53 (d, J=4.5 Hz, 1H), 6.34 (br. s., 2H), 7.77-7.84 (m, 2H), 7.84-7.90 (m, 2H), 8.03 (d, J=7.8 Hz, 1H), 8.19 (s, 1H), 10.40 (s, 1H), 14.10 (br. s., 1H).
HRMS (ESI+): calcd. for $C_{25}H_{30}N_7O_3$ [M+H]⁺ 476.2405; found 476.2406.

8-amino-4,4-dimethyl-N-[4-(methylcarbamoyl)phenyl]-4,5-dihydro-1H-pyrazolo[4,3-h]quinazoline-3-carboxamide (Ig), Cpd 27

[R1=R2=R3'=R4'=H, R3=R4=($C_1$-$C_6$)alkyl, y=1, L=CONR8, z=n=0, A=aryl, R5=CONR6R7, R6=($C_1$-$C_6$)alkyl, R7=R8=H]

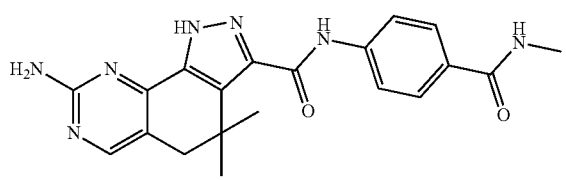 [SMILES: CNC(=O)c1ccc(NC(=O)c2n[nH]c3c2C(C)(C)Cc2cnc(N)nc2-3)cc1]

¹H NMR (400.4 MHz, DMSO-d₆) δ ppm 1.35 (s, 6H), 2.66 (s, 2H), 2.78 (d, J=4.5 Hz, 3H), 6.35 (br. s., 2H), 7.79-7.83 (m, 2H), 7.84-7.91 (m, 2H), 8.19 (s, 1H), 8.31 (q, J=4.5 Hz, 1H), 10.43 (br. s., 1H), 14.06 (br. s., 1H).

HRMS (ESI+): calcd. for $C_{20}H_{22}N_7O_2$ [M+H]⁺ 392.1830; found 392.1818.

8-amino-N-[4-(cyclobutylcarbamoyl)phenyl]-4,4-dimethyl-4,5-dihydro-1H-pyrazolo[4,3-h]quinazoline-3-carboxamide (Ig), Cpd 30

[R1=R2=R3'=R4'=H, R3=R4=($C_1$-$C_6$)alkyl, y=1, L=CONR8, z=n=0, A=aryl, R5=CONR6R7, R6=unsubstituted cycloalkyl, R7=R8=H]

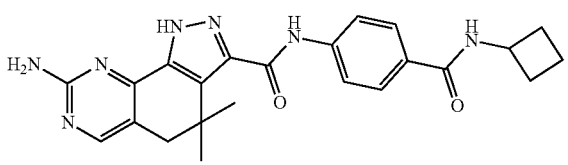 [SMILES: CC1(C)Cc2cnc(N)nc2-c2[nH]nc(C(=O)Nc3ccc(C(=O)NC4CCC4)cc3)c21]

¹H NMR (400.4 MHz, DMSO-d₆) δ ppm 1.35 (s, 6H), 1.62-1.72 (m, 2H), 2.01-2.14 (m, 2H), 2.15-2.25 (m, 2H), 2.66 (s, 2H), 4.35-4.47 (m, 1H), 6.35 (br. s., 2H), 7.80-7.90 (m, 4H), 8.19 (s, 1H), 8.48 (d, J=7.4 Hz, 1H), 10.42 (br. s., 1H), 14.08 (br. s., 1H).

HRMS (ESI+): calcd. for $C_{23}H_{26}N_7O_2$ [M+H]⁺ 432.2143; found 432.2140.

8-amino-N-[4-(cyclopropylcarbamoyl)phenyl]-4,4-dimethyl-4,5-dihydro-1H-pyrazolo[4,3-h]quinazoline-3-carboxamide (Ig), Cpd 31

[R1=R2=R3'=R4'=H, R3=R4=($C_1$-$C_6$)alkyl, y=1, L=CONR8, z=n=0, A=aryl, R5=CONR6R7, R6=unsubstituted cycloalkyl, R7=R8=H]

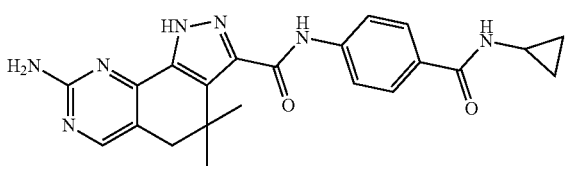 [SMILES: CC1(C)Cc2cnc(N)nc2-c2[nH]nc(C(=O)Nc3ccc(C(=O)NC4CC4)cc3)c21]

¹H NMR (400.4 MHz, DMSO-d₆) δ ppm 0.52-0.61 (m, 2H), 0.65-0.72 (m, 2H), 1.35 (s, 6H), 2.66 (s, 2H), 2.80-2.90 (m, 1H), 6.34 (br. s., 2H), 7.71-7.83 (m, 2H), 7.83-7.92 (m, 2H), 8.19 (s, 1H), 8.31 (d, J=3.9 Hz, 1H), 10.41 (s, 1H), 14.10 (br. s., 1H).

HRMS (ESI+): calcd. for $C_{22}H_{24}N_7O_2$ [M+H]⁺ 418.1986; found 418.1986.

8-amino-N-[4-(cyclopentylcarbamoyl)phenyl]-4,4-dimethyl-4,5-dihydro-1H-pyrazolo[4,3-h]quinazoline-3-carboxamide (Ig), Cpd 29

[R1=R2=R3'=R4'=H, R3=R4=($C_1$-$C_6$)alkyl, y=1, L=CONR8, z=n=0, A=aryl, R5=CONR6R7, R6=unsubstituted cycloalkyl, R7=R8=H]

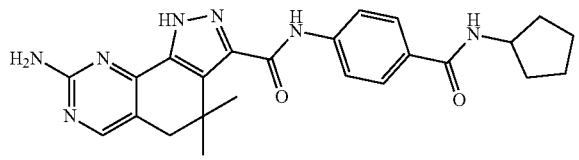 [SMILES: CC1(C)Cc2cnc(N)nc2-c2[nH]nc(C(=O)Nc3ccc(C(=O)NC4CCCC4)cc3)c21]

¹H NMR (400.4 MHz, DMSO-d₆) δ ppm 1.35 (s, 6H), 1.45-1.62 (m, 4H), 1.66-1.74 (m, 2H), 1.83-1.93 (m, 2H), 2.66 (s, 2H), 4.17-4.27 (m, 1H), 6.35 (br. s., 2H), 7.80-7.90 (m, 4H), 8.14 (d, J=7.3 Hz, 1H), 8.19 (s, 1H), 10.41 (br. s., 1H), 14.09 (br. s., 1H).

HRMS (ESI+): calcd. for $C_{24}H_{28}N_7O_2$ [M+H]⁺ 446.2299; found 446.2284.

8-amino-4,4-dimethyl-N-(4-{[4-(4-methylpiperazin-1-yl)piperidin-1-yl]carbonyl}phenyl)-4,5-dihydro-1H-pyrazolo[4,3-h]quinazoline-3-carboxamide (Ig), Cpd 41

[R1=R2=R3'=R4'=H, R3=R4=($C_1$-$C_6$)alkyl, y=1, L=CONR8, z=n=0, A=aryl, R5=CONR6R7, R6 and R7=taken together form an optionally substituted heterocyclyl group, R8=H]

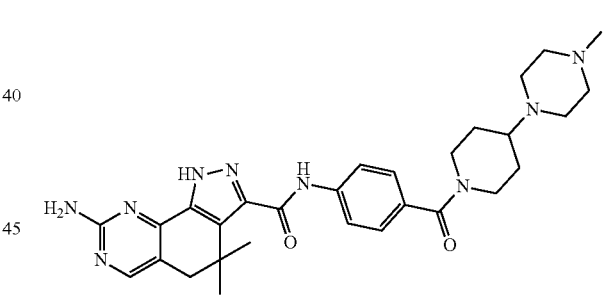

¹H NMR (499.7 MHz, DMSO-d₆) δ ppm 1.28-1.43 (m, 2H), 1.34 (s, 6H), 1.65-1.89 (m, 2H), 2.14 (s, 3H), 2.20-2.54 (m, 9H), 2.72-3.11 (m, 2H), 2.65 (s, 2H), 2.72-3.08 (m, 2H), 3.58-3.82 (m, 1H), 4.33-4.54 (m, 1H), 6.38 (br. s., 2H), 7.37 (d, J=8.5 Hz, 2H), 7.85 (d, J=8.5 Hz, 2H), 8.19 (s, 1H), 10.46 (br. s., 1H), 14.08 (br. s., 1H).

HRMS (ESI+): calcd. for $C_{29}H_{38}N_9O_2$ [M+H]⁺ 544.3143; found 544.3146.

8-amino-4,4-dimethyl-N-(4-{[4-(piperidin-1-ylmethyl)phenyl]carbamoyl}phenyl)-4,5-dihydro-1H-pyrazolo[4,3-h]quinazoline-3-carboxamide (Ig), Cpd 59

[R1=R2=R3'=R4'=H, R3=R4=($C_1$-$C_6$)alkyl, y=1, L=CONR8, z=n=0, A=aryl, R5=CONR6R7, R6=substituted aryl, R7=R8=H]

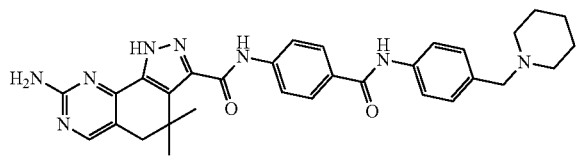 [SMILES: CC1(C)Cc2cnc(N)nc2-c2[nH]nc(C(=O)Nc3ccc(C(=O)Nc4ccc(CN5CCCCC5)cc4)cc3)c21]

¹H NMR (499.7 MHz, DMSO-d₆) δ ppm 1.33-1.43 (m, 2H), 1.36 (s, 6H), 1.45-1.53 (m, 4H), 2.26-2.37 (m, 4H), 2.67 (s, 2H), 3.39 (br. s., 2H), 6.39 (br. s., 2H), 7.25 (d, J=8.5 Hz, 2H), 7.71 (d, J=8.5 Hz, 2H), 7.96 (s, 4H), 8.20 (s, 1H), 10.12 (s, 1H), 10.54 (br. s., 1H), 14.13 (br. s., 1H).

HRMS (ESI+): calcd. for $C_{31}H_{35}N_8O_2$ [M+H]⁺ 551.2878; found 551.2898.

8-amino-4,4-dimethyl-N-{3-[(1-methylpiperidin-4-yl)carbamoyl]phenyl}-4,5-dihydro-1H-pyrazolo[4,3-h]quinazoline-3-carboxamide (Ig), Cpd 10

[R1=R2=R3'=R4'=H, R3=R4=($C_1$-$C_6$)alkyl, y=1, L=CONR8, z=n=0, A=aryl, R5=CONR6R7, R6=substituted heterocyclyl, R7=R8=H]

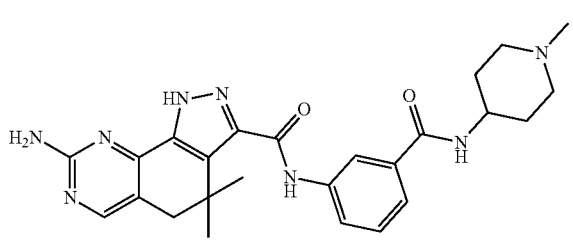 [SMILES: CN1CCC(NC(=O)c2cccc(NC(=O)c3n[nH]c4c3C(C)(C)Cc3cnc(N)nc3-4)c2)CC1]

¹H NMR (499.7 MHz, DMSO-d₆) δ ppm 1.34 (s, 6H) 1.53-1.63 (m, 2H), 1.73-1.78 (m, 2H), 1.91-1.97 (m, 2H), 2.16 (s, 3H), 2.65 (s, 2H), 2.74-2.79 (m, 2H), 3.65-3.79 (m, 1H), 6.38 (br. s., 2H), 7.40 (dd, J=8.2, 7.8 Hz, 1H), 7.52 (d, J=7.8 Hz, 1H), 7.90 (d, J=8.2 Hz, 1H), 8.19 (s, 1H), 8.21 (s, 1H), 8.23 (d, J=7.8 Hz, 1H), 10.37 (br. s., 1H) 14.07 (br. s., 1H).

HRMS (ESI+): calcd. for $C_{25}H_{31}N_8O_2$ [M+H]⁺ 475.2565; found 475.2564.

8-amino-N-[3-(cyclohexylcarbamoyl)phenyl]-4,4-dimethyl-4,5-dihydro-1H-pyrazolo[4,3-h]quinazoline-3-carboxamide (Ig), Cpd 25

[R1=R2=R3'=R4'=H, R3=R4=($C_1$-$C_6$)alkyl, y=1, L=CONR8, z=n=0, A=aryl, R5=CONR6R7, R6=unsubstituted cycloalkyl, R7=R8=H]

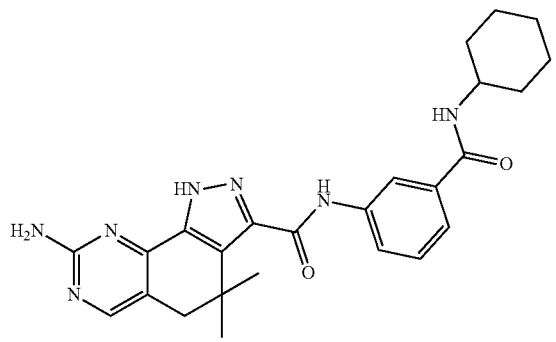 [SMILES: CC1(C)Cc2cnc(N)nc2-c2[nH]nc(C(=O)Nc3cccc(C(=O)NC4CCCCC4)c3)c21]

¹H NMR (400.4 MHz, DMSO-d₆) δ ppm 1.03-1.21 (m, 1H), 1.26-1.38 (m, 4H), 1.35 (s, 6H), 1.57-1.64 (m, 1H), 1.67-1.93 (m, 4H), 2.66 (s, 2H), 3.70-3.80 (m, 1H), 6.35 (br. s., 2H), 7.39 (dd, J=7.7, 7.2 Hz, 1H), 7.52 (d, J=7.7 Hz, 1H), 7.90 (d, J=7.2 Hz, 1H), 8.15 (d, J=8.1 Hz, 1H), 8.19 (s, 1H), 8.20 (s, 1H), 10.31 (br. s., 1H), 14.05 (br. s., 1H).

HRMS (ESI+): calcd. for $C_{25}H_{30}N_7O_2$ [M+H]⁺ 460.2456; found 460.2453.

8-amino-4,4-dimethyl-N-(3-{[4-(pyrrolidin-1-yl)piperidin-1-yl]carbonyl}phenyl)-4,5-dihydro-1H-pyrazolo[4,3-h]quinazoline-3-carboxamide (Ig), Cpd 26

[R1=R2=R3'=R4'=H, R3=R4=($C_1$-$C_6$)alkyl, y=1, L=CONR8, z=n=0, A=aryl, R5=CONR6R7, R6 and R7=taken together form an optionally substituted heterocyclyl group, R8=H]

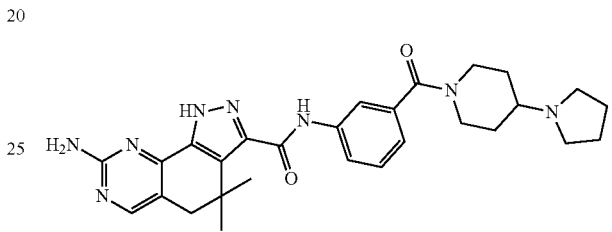

¹H NMR (400.4 MHz, DMSO-d₆) δ ppm 1.34 (s, 6H), 1.34-1.45 (m, 2H), 1.64-1.70 (m, 4H), 1.74-1.96 (m, 2H), 2.24 (m, 1H), 2.50 (m overlapped by DMSO-d₆ signal, 4H), 2.66 (s, 2H), 2.90-3.14 (m, 2H), 3.58 (br. s., 1H), 4.26 (br. s., 1H), 6.35 (s, 2H), 7.07 (dt, J=7.6, 1.2 Hz, 1H), 7.39 (dd, J=8.4, 7.6 Hz, 1H), 7.82-7.88 (m, 2H), 8.19 (s, 1H), 10.41 (br. s., 1H), 14.02 (br. s., 1H).

HRMS (ESI+): calcd. for $C_{28}H_{35}N_8O_2$ [M+H]⁺ 515.2878; found 515.2874.

tert-butyl[1-(4-{[(8-amino-4,4-dimethyl-4,5-dihydro-1H-pyrazolo[4,3-h]quinazolin-3-yl)carbonyl]amino}benzoyl) piperidin-4-yl]carbamate (Ig), Cpd 46

[R1=R2=R3'=R4'=H, R3=R4=($C_1$-$C_6$)alkyl, y=1, L=CONR8, z=n=0, A=aryl, R5=CONR6R7, R6 and R7=taken together form an optionally substituted heterocyclyl group, R8=H]

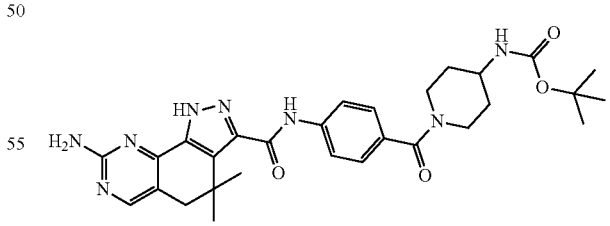

¹H NMR (499.7 MHz, DMSO-d₆) δ ppm 1.22-1.42 (m, 2H), 1.34 (s, 6H), 1.38 (s, 9H), 1.64-1.86 (m, 2H), 2.65 (s, 2H), 2.86-3.17 (m, 2H), 3.45-3.76 (m, 2H), 4.16-4.42 (m, 1H), 6.38 (br. s., 2H), 6.90 (d, J=7.6 Hz, 1H), 7.34 (d, J=8.4 Hz, 2H), 7.87 (d, J=8.4 Hz, 2H), 8.19 (s, 1H), 10.45 (br. s., 1H), 14.10 (br. s., 1H).

HRMS (ESI+): calcd. for $C_{29}H_{35}N_8O_4$ [M+H]⁺ 561.2933; found 561.2949.

8-amino-4,4-dimethyl-N-{4-[(4-oxopiperidin-1-yl)carbonyl]phenyl}-4,5-dihydro-1H-pyrazolo[4,3-h]quinazoline-3-carboxamide (Ig), Cpd 48

[R1=R2=R3'=R4'=H, R3=R4=(C$_1$-C$_6$)alkyl, y=1, L=CONR8, z=n=0, A=aryl, R5=CONR6R7, R6 and R7=taken together form an optionally substituted heterocyclyl group, R8=H]

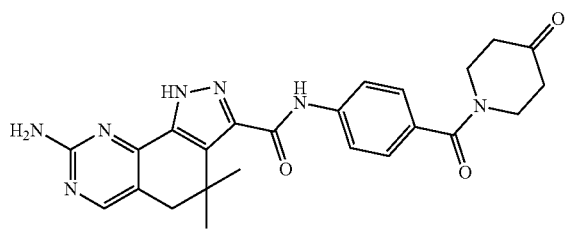 [SMILES: CC1(C)Cc2cnc(N)nc2-c2[nH]nc(C(=O)Nc3ccc(C(=O)N4CCC(=O)CC4)cc3)c21]

$^1$H NMR (499.7 MHz, DMSO-d$_6$) δ ppm 1.34 (s, 6H), 2.34-2.5 (m, 4H), 2.66 (m, 2H), 3.61-3.96 (m, 4H), 6.38 (br. s., 2H), 7.48 (d, J=8.5 Hz, 2H), 7.89 (d, J=8.5 Hz, 2H), 8.19 (s, 1H), 10.50 (br. s., 1H), 13.69 (br. s., 1H).

HRMS (ESI+): calcd. for C$_{24}$H$_{26}$N$_7$O$_3$ [M+H]$^+$ 460.2092; found 460.2104.

8-amino-N-[4-(1,4'-bipiperidin-1'-ylcarbonyl)benzyl]-4,4-dimethyl-4,5-dihydro-1H-pyrazolo[4,3-h]quinazoline-3-carboxamide (Ig), Cpd 165

[R1=R2=R3'=R4'=H, R3=R4=(C$_1$-C$_6$)alkyl, y=1, L=CONR8, z=1, Ra=Rb=H, A=aryl, n=0, R5=CONR6R7, R6 and R7=taken together form an optionally substituted heterocyclyl group, R8=H]

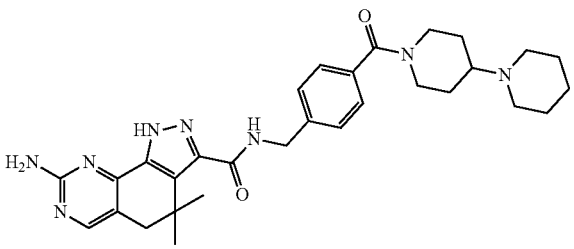 [SMILES: CC1(C)Cc2cnc(N)nc2-c2[nH]nc(C(=O)NCc3ccc(C(=O)N4CCC(N5CCCCC5)CC4)cc3)c21]

$^1$H NMR (499.7 MHz, DMSO-d$_6$) δ ppm 1.30 (s, 6H), 1.32-1.42 (m, 4H), 1.43-1.50 (m, 4H), 1.59-1.84 (br. s., 2H), 2.41-2.47 (br. s., 4H), 2.62 (s, 2H), 2.64-3.07 (br. s., 3H), 3.49-3.66 (br. s., 1H), 4.46 (d, J=6.2 Hz, 2H), 4.48 (br. s, 1H), 6.35 (br. s., 2H), 7.30-7.40 (m, 4H), 8.16 (s, 1H), 8.85 (br. s., 1H), 13.91 (br. s., 1H).

HRMS (ESI+): calcd. for C$_{30}$H$_{39}$N$_8$O$_2$ [M+H]$^+$ 543.3191; found 543.3190.

8-amino-4,4-dimethyl-N-{4-[(1-methylpiperidin-4-yl)carbamoyl]benzyl}-4,5-dihydro-1H-pyrazolo[4,3-h]quinazoline-3-carboxamide (Ig), Cpd 166

[R1=R2=R3'=R4'=H, R3=R4=(C$_1$-C$_6$)alkyl, y=1, L=CONR8, z=1, Ra=Rb=H, A=aryl, n=0, R5=CONR6R7, R6=substituted heterocyclyl, R7=R8=H]

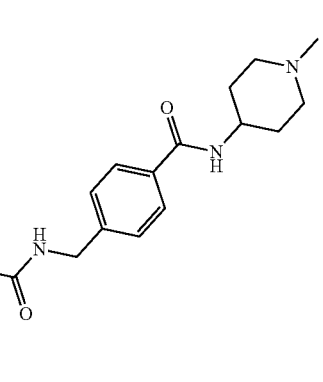

$^1$H NMR (499.7 MHz, DMSO-d$_6$) δ ppm 1.30 (s, 6H), 1.50-1.63 (m, 2H), 1.69-1.79 (m, 2H), 1.90-2.00 (m, 2H), 2.17 (s, 3H), 2.62 (s, 2H), 2.74-2.81 (m, 2H), 3.67-3.80 (m, 1H), 4.47 (d, J=6.2 Hz, 2H), 6.35 (br. s., 2H), 7.38 (d, J=8.4 Hz, 2H), 7.79 (d, J=8.4 Hz, 2H), 8.16 (s, 1H), 8.18 (d, J=7.8 Hz, 1H), 8.86 (t, J=6.2 Hz, 1H), 13.84 (br. s., 1H).

HRMS (ESI+): calcd. for C$_{26}$H$_{33}$N$_8$O$_2$ [M+H]$^+$ 489.2721; found 489.2726.

8-amino-4,4-dimethyl-N-(4-{2-[(1-methylpiperidin-4-yl)amino]-2-oxoethyl}-1,3-thiazol-2-yl)-4,5-dihydro-1H-pyrazolo[4,3-h]quinazoline-3-carboxamide (Ig), Cpd 86

[R1=R2=R3'=R4'=H, R3=R4=(C$_1$-C$_6$)alkyl, y=1, L=CONR8, z=0, A=heteroaryl, n=1, Rc=Rd=H, R5=CONR6R7, R6=substituted heterocyclyl, R7=R8=H]

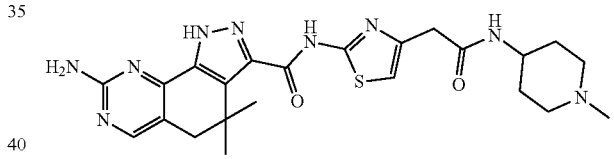

$^1$H NMR (499.7 MHz, DMSO-d$_6$) δ ppm 1.33 (s, 6H), 1.40-1.50 (m, 2H), 1.70-1.80 (m, 2H), 2.07 (br. s., 2H), 2.23 (br. s., 3H), 2.66 (s, 2H), 2.78 (br. s., 2H), 3.48 (s, 2H), 3.51-3.60 (m, 1H), 6.39 (br. s., 2H), 6.92 (s, 1H), 7.97 (d, J=7.2 Hz, 1H), 8.19 (s, 1H), 12.09 (br. s., 1H), 14.19 (br. s., 1H).

HRMS (ESI+): calcd. for C$_{23}$H$_{30}$N$_6$O$_2$S [M+H]$^+$ 496.2238; found 496.2230.

8-amino-N-{4-[2-(cyclohexylamino)-2-oxoethyl]-1,3-thiazol-2-yl}-4,4-dimethyl-4,5-dihydro-1H-pyrazolo[4,3-h]quinazoline-3-carboxamide (Ig), Cpd 35

[R1=R2=R3'=R4'=H, R3=R4=(C$_1$-C$_6$)alkyl, y=1, L=CONR8, z=0, A=heteroaryl, n=1, Rc=Rd=H, R5=CONR6R7, R6=unsubstituted cycloalkyl, R7=R8=H]

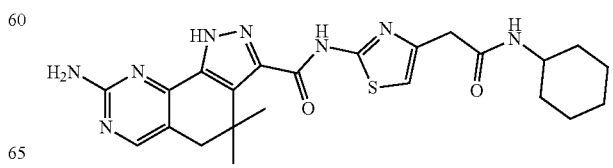

$^1$H NMR (499.7 MHz, DMSO-d$_6$) δ ppm 1.06-1.32 (m, 5H), 1.33 (s, 6H), 1.50-1.60 (m, 1H), 1.63-1.71 (m, 2H), 1.71-1.80 (m, 2H), 2.66 (s, 2H), 3.47 (s, 2H), 3.48-3.58 (m, 1H), 6.40 (br. s., 2H), 6.91 (s, 1H), 7.87 (d, J=7.9 Hz, 1H), 8.19 (s, 1H), 12.07 (br. s., 1H), 14.22 (br. s., 1H).

HRMS (ESI+): calcd. for C$_{23}$H$_{96}$N$_8$O$_2$S [M+H]$^+$ 481.2129; found 481.2111.

8-amino-N-[4-(cyclohexylcarbamoyl)-1,3-thiazol-2-yl]-4,4-dimethyl-4,5-dihydro-1H-pyrazolo[4,3-h]quinazoline-3-carboxamide (Ig), Cpd 68

[R1=R2=R3'=R4'=H, R3=R4=(C$_1$-C$_6$)alkyl, y=1, L=CONR8, z=n=0, A=heteroaryl, R5=CONR6R7, R6=unsubstituted cycloalkyl, R7=R8=H]

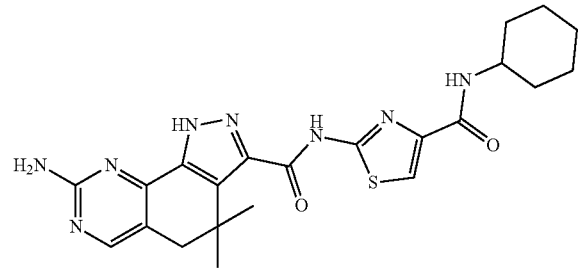 [SMILES: CC1(C)Cc2cnc(N)nc2-c2[nH]nc(C(=O)Nc3nc(C(=O)NC4CCCCC4)cs3)c21]

$^1$H NMR (499.7 MHz, DMSO-d$_6$) δ ppm 1.10-1.20 (m, 1H), 1.28-1.35 (m, 4H), 1.35 (s, 6H), 1.56-1.60 (m, 1H), 1.67-1.84 (m, 4H), 2.68 (s, 2H), 3.67-3.77 (m, 1H), 6.41 (br. s., 2H), 7.81 8s, 1H), 7.81-7.86 (m, 1H), 8.20 (s, 1H), 12.06 (br. s., 1H), 14.35 (br. s., 1H).

HRMS (ESI+): calcd. for C$_{22}$H$_{27}$N$_8$O$_2$S [M+H]$^+$ 467.1972; found 467.1988.

8-amino-4,4-dimethyl-N-{4-[(1-methylpiperidin-4-yl)carbamoyl]-1,3-thiazol-2-yl}-4,5-dihydro-1H-pyrazolo[4,3-h]quinazoline-3-carboxamide (Ig), Cpd 69

[R1=R2=R3'=R4'=H, R3=R4=(C$_1$-C$_6$)alkyl, y=1, L=CONR8, z=n=0, A=heteroaryl, R5=CONR6R7, R6=substituted heterocyclyl, R7=R8=H]

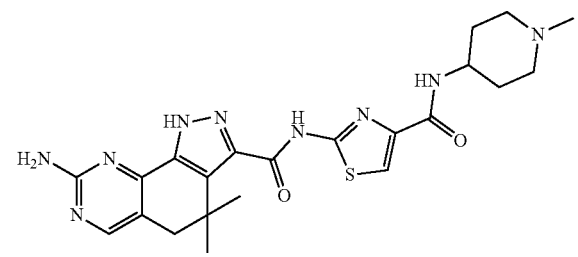 [SMILES: CN1CCC(NC(=O)c2csc(NC(=O)c3n[nH]c4c3C(C)(C)Cc3cnc(N)nc3-4)n2)CC1]

$^1$H NMR (499.7 MHz, DMSO-d$_6$) δ ppm 1.35 (s, 6H), 1.64-1.74 (m, 2H), 1.84-1.92 (m, 2H), 2.37-2.54 (m, 5H), 2.68 (s, 2H), 2.97-3.18 (br. s., 2H), 3.80-3.92 (m, 1H), 6.41 (br. s., 2H), 7.84 (s, 1H), 8.08 (br. s., 1H), 8.20 (s, 1H), 11.92 (br. s., 1H), 14.35 (br. s., 1H).

HRMS (ESI+): calcd. for C$_{22}$H$_{28}$N$_9$O$_2$S [M+H]$^+$ 482.2081; found 482.2093.

8-amino-N-[4-(1,4'-bipiperidin-1'-ylcarbonyl)-1,3-thiazol-2-yl]-4,4-dimethyl-4,5-dihydro-1H-pyrazolo[4,3-h]quinazoline-3-carboxamide (Ig), Cpd 70

[R1=R2=R3'=R4'=H, R3=R4=(C$_1$-C$_6$)alkyl, y=1, L=CONR8, z=n=0, A=heteroaryl, R5=CONR6R7, R6 and R7=taken together form an optionally substituted heterocyclyl group, R8=H]

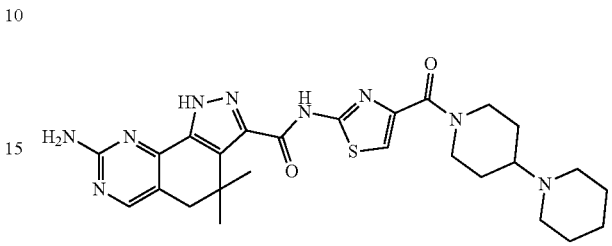

$^1$H NMR (499.7 MHz, DMSO-d$_6$) δ ppm 1.34 (s, 6H), 1.34-1.51 (m, 8H), 1.67-1.83 (br. s., 2H), 2.67 (s, 2H), 2.43-2.57 (m, 4H), 2.67 (s, 2H), 2.67-2.77 (br. s., 1H), 2.95-3.05 (br. s., 1H), 4.19-4.32 (br. s., 1H), 4.44-4.53 (br. s., 1H), 6.40 (br. s., 2H), 7.57 (s, 1H), 8.19 (s, 1H), 12.33 (br. s., 1H), 14.27 (br. s., 1H).

HRMS (ESI+): calcd. for C$_{26}$H$_{34}$N$_9$O$_2$S [M+H]$^+$ 536.2551; found 536.2561.

8-amino-4,4-dimethyl-N-(5-{2-[(1-methylpiperidin-4-yl)amino]-2-oxoethyl}-1,3-thiazol-2-yl)-4,5-dihydro-1H-pyrazolo[4,3-h]quinazoline-3-carboxamide (Ig), Cpd 74

[R1=R2=R3'=R4'=H, R3=R4=(C$_1$-C$_6$)alkyl, y=1, L=CONR8, z=0, A=heteroaryl, n=1, Rc=Rd=H, R5=CONR6R7, R6=substituted heterocyclyl, R7=R8=H]

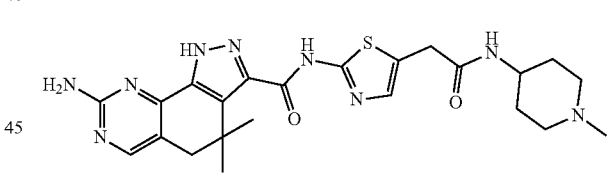

$^1$H NMR (499.7 MHz, DMSO-d$_6$) δ ppm 1.33 (s, 6H), 1.36-1.48 (m, 2H), 1.68-1.74 (m, 2H), 1.94-2.04 (m, 2H), 2.17 (s, 3H), 2.66 (s, 2H), 2.69-2.76 (m, 2H), 3.45-3.54 (m, 1H), 3.59 (s, 2H), 6.40 (br. s., 2H), 7.25 (s, 1H), 8.10 (d, J=7.3 Hz, 1H), 8.19 (s, 1H), 11.91 (br. s., 1H), 14.17 (br. s., 1H).

HRMS (ESI+): calcd. for C$_{23}$H$_{30}$N$_9$O$_2$S [M+H]$^+$ 496.2238; found 496.2232.

8-amino-4,4-dimethyl-N-{4-methyl-5-[(1-methylpiperidin-4-yl)carbamoyl]-1,3-thiazol-2-yl}-4,5-dihydro-1H-pyrazolo[4,3-h]quinazoline-3-carboxamide (Ig), Cpd 79

[R1=R2=R3'=R4'=H, R3=R4=(C$_1$-C$_6$)alkyl, y=1, L=CONR8, z=n=0, A=heteroaryl, R5=CONR6R7, R6=substituted heterocyclyl, R7=R8=H]

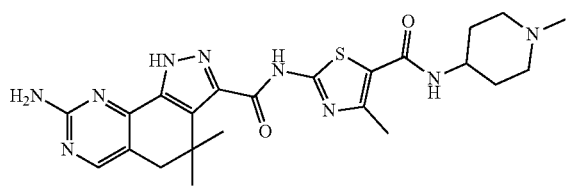 [SMILES: Cc1nc(NC(=O)c2n[nH]c3c2C(C)(C)Cc2cnc(N)nc2-3)sc1C(=O)NC1CCN(C)CC1]

¹H NMR (499.7 MHz, DMSO-d$_6$) δ ppm 1.33 (s, 6H), 1.56-1.68 (m, 2H), 1.73-1.79 (m, 2H), 2.02-2.21 (br. s., 2H), 2.25 (br. s., 3H), 2.50 (s overlapped by DMSO signal, 3H), 2.67 (s, 2H), 2.80-2.90 (m, 2H), 3.67-3.77 (m, 1H), 6.40 (br. s., 2H), 7.94 (d, J=7.3 Hz, 1H), 8.19 (s, 1H), 12.33 (br. s., 1H), 14.27 (br. s., 1H).

HRMS (ESI+): calcd. for C$_{23}$H$_{30}$N$_9$O$_2$S [M+H]$^+$ 496.2238; found 496.2238.

8-amino-N-{5-[2-(cyclohexylamino)-2-oxoethyl]-1,3-thiazol-2-yl}-4,4-dimethyl-4,5-dihydro-1H-pyrazolo[4,3-h]quinazoline-3-carboxamide (Ig), Cpd 73

[R1=R2=R3'=R4'=H, R3=R4=(C$_1$-C$_6$)alkyl, y=1, L=CONR8, z=0, A=heteroaryl, n=1, Rc=Rd=H, R5=CONR6R7, R6=unsubstituted cycloalkyl, R7=R8=H]

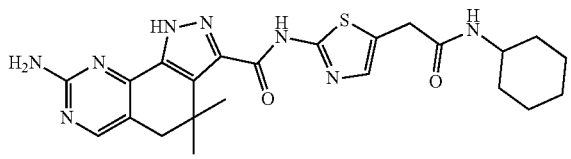 [SMILES: CC1(C)Cc2cnc(N)nc2-c2[nH]nc(C(=O)Nc3ncc(CC(=O)NC4CCCCC4)s3)c21]

¹H NMR (499.7 MHz, DMSO-d$_6$) δ ppm 1.08-1.20 (m, 2H) 1.21-1.30 (m, 3H), 1.33 (s, 6H), 1.48-1.59 (m, 1H), 1.62-1.70 (m, 2H), 1.70-1.78 (m, 2H), 2.66 (s, 2H), 3.47-3.57 (m, 1H), 3.58 (s, 2H), 6.39 (br. s., 2H), 7.24 (s, 1H), 8.03 (d, J=7.9 Hz, 1H), 8.19 (s, 1H), 11.88 (br. s., 1H), 14.22 (br. s., 1H).

HRMS (ESI+): calcd. for C$_{23}$H$_{29}$N$_8$O$_2$S [M+H]$^+$ 481.2129; found 481.2123.

8-amino-N-{5-[2-(1,4'-bipiperidin-1'-yl)-2-oxoethyl]-1,3-thiazol-2-yl}-4,4-dimethyl-4,5-dihydro-1H-pyrazolo[4,3-h]quinazoline-3-carboxamide (Ig), Cpd 75

[R1=R2=R3'=R4'=H, R3=R4=(C$_1$-C$_6$)alkyl, y=1, L=CONR8, z=0, A=heteroaryl, n=1, Rc=Rd=H, R5=CONR6R7, R6 and R7=taken together form an optionally substituted heterocyclyl group, R8=H]

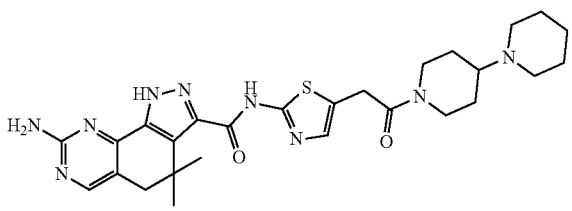 [SMILES: CC1(C)Cc2cnc(N)nc2-c2[nH]nc(C(=O)Nc3ncc(CC(=O)N4CCC(N5CCCCC5)CC4)s3)c21]

¹H NMR (499.7 MHz, DMSO-d$_6$) δ ppm 1.21-1.40 (m, 6H), 1.33 (s, 6H), 1.43-1.50 (m, 4H), 1.69-1.76 (m, 2H), 2.41-2.50 (m, 5H), 2.52-2.58 (m, 1H), 2.66 (s, 2H), 2.98-3.05 (m, 1H), 3.87-3.97 (m, 2H), 4.00-4.06 (m, 1H), 4.38-4.43 (m, 1H), 6.40 (br. s., 2H), 7.28 (s, 1H), 8.19 (s, 1H), 11.92 (br. s., 1H), 14.22 (br. s., 1H).

HRMS (ESI+): calcd. for C$_{27}$H$_{36}$N$_9$O$_2$S [M+H]$^+$ 550.2707; found 550.2698.

8-amino-N-[5-(cyclohexylcarbamoyl)-4-methyl-1,3-thiazol-2-yl]-4,4-dimethyl-4,5-dihydro-1H-pyrazolo[4,3-h]quinazoline-3-carboxamide (Ig), Cpd 77

[R1=R2=R3'=R4'=H, R3=R4=(C$_1$-C$_6$)alkyl, y=1, L=CONR8, z=n=0, A=heteroaryl, R5=CONR6R7, R6=unsubstituted cycloalkyl, R7=R8=H]

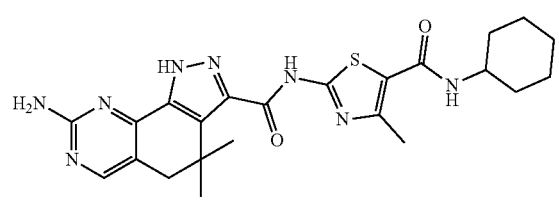 [SMILES: Cc1nc(NC(=O)c2n[nH]c3c2C(C)(C)Cc2cnc(N)nc2-3)sc1C(=O)NC1CCCCC1]

¹H NMR (499.7 MHz, DMSO-d$_6$) δ ppm 1.06-1.20 (m, 1H), 1.25-1.38 (m, 4H), 1.36 (s, 6H), 1.59-1.65 (m, 1H), 1.70-1.89 (m, 4H), 2.52 (s, 3H), 2.70 (s, 2H), 3.69-3.76 (m, 1H), 6.44 (br. s., 2H), 7.89 (d, J=7.8 Hz, 1H), 8.23 (s, 1H), 12.34 (br. s., 1H), 14.33 (br. s., 1H).

HRMS (ESI+): calcd. for C$_{23}$H$_{29}$N$_8$O$_2$S [M+H]$^+$ 481.2129; found 481.2128.

8-amino-N-[5-(1,4'-bipiperidin-1'-ylcarbonyl)-4-methyl-1,3-thiazol-2-yl]-4,4-dimethyl-4,5-dihydro-1H-pyrazolo[4,3-h]quinazoline-3-carboxamide (Ig), Cpd 78

[R1=R2=R3'=R4'=H, R3=R4=(C$_1$-C$_6$)alkyl, y=1, L=CONR8, z=n=0, A=heteroaryl, R5=CONR6R7, R6 and R7=taken together form an optionally substituted heterocyclyl group, R8=H]

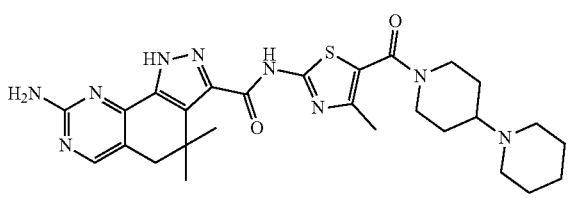 [SMILES: Cc1nc(NC(=O)c2n[nH]c3c2C(C)(C)Cc2cnc(N)nc2-3)sc1C(=O)N1CCC(N2CCCCC2)CC1]

¹H NMR (499.7 MHz, DMSO-d$_6$) δ ppm 1.32 (s, 6H), 1.34-1.43 (m, 4H), 1.45-1.52 (m, 4H), 1.75-1.82 (m, 2H), 2.27 (s, 3H), 2.40-2.55 (m overlapped by DMSO signal, 4H), 2.66 (s, 2H), 2.89-2.99 (m, 2H), 4.03-4.20 (br. s., 2H), 6.40 (br. s., 2H), 8.19 (s, 1H), 12.31 (br. s., 1H) 14.26 (br. s., 1H).

HRMS (ESI+): calcd. for C$_{27}$H$_{36}$N$_9$O$_2$S [M+H]$^+$ 550.2707; found 550.2720.

8-amino-N-[5-(cyclohexylcarbamoyl)-1,3-thiazol-2-yl]-4,4-dimethyl-4,5-dihydro-1H-pyrazolo[4,3-h]quinazoline-3-carboxamide (Ig), Cpd 83

[R1=R2=R3'=R4'=H, R3=R4=(C$_1$-C$_6$)alkyl, y=1, L=CONR8, z=n=0, A=heteroaryl, R5=CONR6R7, R6=unsubstituted cycloalkyl, R7=R8=H]

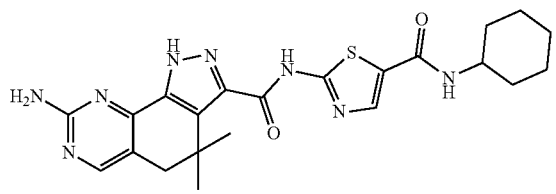 [SMILES: CC1(C)Cc2cnc(N)nc2-c2[nH]nc(C(=O)Nc3ncc(C(=O)NC4CCCCC4)s3)c21]

¹H NMR (499.7 MHz, DMSO-d₆) δ ppm 1.07-1.19 (m, 1H), 1.21-1.35 (m, 4H), 1.34 (s, 6H), 1.57-1.64 (m, 1H), 1.70-1.86 (m, 4H), 2.67 (s, 2H), 3.66-3.76 (m, 1H), 6.40 (br. s., 2H), 8.12 (s, 1H), 8.20 (s, 1H), 8.23 (d, J=7.8 Hz, 1H), 12.36 (br. s., 1H), 14.31 (br. s., 1H).

HRMS (ESI+): calcd. for $C_{22}H_{27}N_8O_2S$ [M+H]⁺ 467.1972; found 467.1978.

8-amino-N-[5-(1,4'-bipiperidin-1'-ylcarbonyl)-1,3-thiazol-2-yl]-4,4-dimethyl-4,5-dihydro-1H-pyrazolo[4,3-h]quinazoline-3-carboxamide (Ig), Cpd 84

[R1=R2=R3'=R4'=H, R3=R4=($C_1$-$C_6$)alkyl, y=1, L=CONR8, z=n=0, A=heteroaryl, R5=CONR6R7, R6 and R7=taken together form an optionally substituted heterocyclyl group, R8=H]

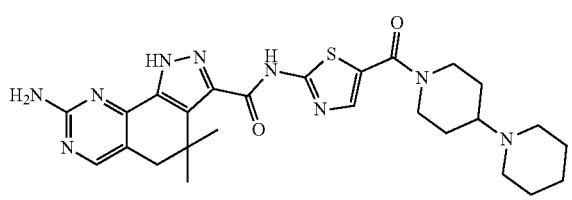 [SMILES: CC1(C)Cc2cnc(N)nc2-c2[nH]nc(C(=O)Nc3ncc(C(=O)N4CCC(N5CCCCC5)CC4)s3)c21]

¹H NMR (499.7 MHz, DMSO-d₆) δ ppm 1.34 (s, 6H), 1.35-1.58 (m, 8H), 1.79-1.87 (m, 2H), 2.39-2.65 (br. s., 5H), 2.67 (s, 2H), 2.89-3.08 (br.s., 2H), 4.33 (br. s., 2H), 6.40 (br. s., 2H), 7.83 (s, 1H), 8.20 (s, 1H), 12.44 (br. s., 1H), 14.30 (br. s., 1H).

HRMS (ESI+): calcd. for $C_{26}H_{34}N_9O_2S$ [M+H]⁺ 536.2551; found 536.2542.

8-amino-N-(4-{2-[(3R)-3-hydroxypyrrolidin-1-yl]-2-oxoethyl}-1,3-thiazol-2-yl)-4,4-dimethyl-4,5-dihydro-1H- pyrazolo[4,3-h]quinazoline-3-carboxamide (Ig), Cpd 87

[R1=R2=R3'=R4'=H, R3=R4=($C_1$-$C_6$)alkyl, y=1, L=CONR8, z=0, A=heteroaryl, n=1, Rc=Rd=H, R5=CONR6R7, R6 and R7=taken together form an optionally substituted heterocyclyl group, R8=H]

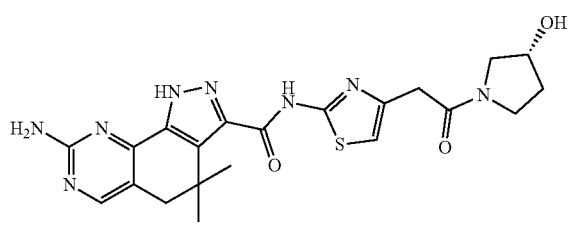 [SMILES: CC1(C)Cc2cnc(N)nc2-c2[nH]nc(C(=O)Nc3nc(CC(=O)N4CC[C@@H](O)C4)cs3)c21]

¹H NMR (499.7 MHz, DMSO-d₆; conformer mixture) δ ppm 1.33 (s, 6H), 1.68-2.00 (m, 2H), 2.66 (m, 2H), 3.23-3.71 (m, 6H), 4.22-4.27 and 4.30-4.34 (2×m, 1H) 4.92 and 5.00 (2×d, J=3.0 Hz, 1H), 6.39 (br. s., 2H), 6.95 (s, 1H), 8.19 (s, 1H), 12.06 (br. s., 1H), 14.22 (br. s., 1H).

HRMS (ESI+): calcd. for $C_{21}H_{25}N_8O_3S$ [M+H]⁺ 469.1765; found 469.1750.

8-amino-N-(4-{2-[(3S)-3-hydroxypyrrolidin-1-yl]-2-oxoethyl}-1,3-thiazol-2-yl)-4,4-dimethyl-4,5-dihydro-1H- pyrazolo[4,3-h]quinazoline-3-carboxamide (Ig), Cpd 88

[R1=R2=R3'=R4'=H, R3=R4=($C_1$-$C_6$)alkyl, y=1, L=CONR8, z=0, A=heteroaryl, n=1, Rc=Rd=H, R5=CONR6R7, R6 and R7=taken together form an optionally substituted heterocyclyl group, R8=H]

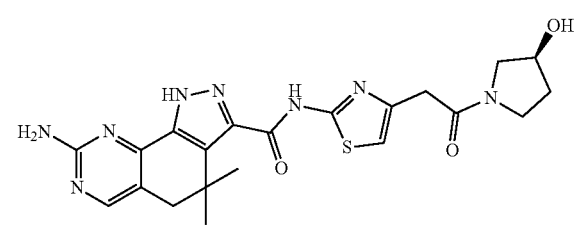 [SMILES: CC1(C)Cc2cnc(N)nc2-c2[nH]nc(C(=O)Nc3nc(CC(=O)N4CC[C@H](O)C4)cs3)c21]

¹H NMR (499.7 MHz, DMSO-d₆; conformer mixture) 8 ppm 1.33 (s, 6H), 1.68-2.00 (m, 2H), 2.66 (m, 2H), 3.23-3.71 (m, 6H), 4.22-4.27 and 4.30-4.34 (2×m, 1H) 4.92 and 5.00 (2×d, J=3.0 Hz, 1H), 6.39 (br. s., 2H), 6.95 (s, 1H), 8.19 (s, 1H), 12.06 (br. s., 1H), 14.22 (br. s., 1H).

HRMS (ESI+): calcd. for $C_{21}H_{25}N_8O_3S$ [M+H]⁺ 469.1765; found 469.1758.

8-amino-N-(4-{2-[4-(dimethylamino)piperidin-1-yl]-2-oxoethyl}-1,3-thiazol-2-yl)-4,4-dimethyl-4,5-dihydro-1H- pyrazolo[4,3-h]quinazoline-3-carboxamide (Ig), Cpd 89

[R1=R2=R3'=R4'=H, R3=R4=($C_1$-$C_6$)alkyl, y=1, L=CONR8, z=0, A=heteroaryl, n=1, Rc=Rd=H, R5=CONR6R7, R6 and R7=taken together form an optionally substituted heterocyclyl group, R8=H]

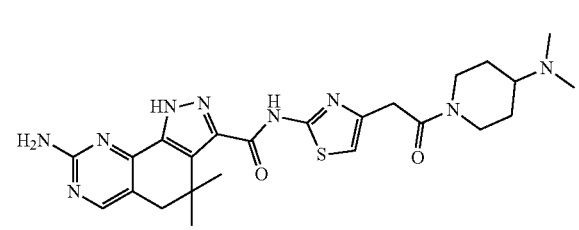 [SMILES: CN(C)C1CCN(C(=O)Cc2csc(NC(=O)c3n[nH]c4c3C(C)(C)Cc3cnc(N)nc3-4)n2)CC1]

¹H NMR (499.7 MHz, DMSO-d₆) δ ppm 1.15-1.25 (m, 2H), 1.32 (s, 6H), 1.68-1.78 (m, 2H), 2.20 (br. s., 6H), 2.37 (br.s., 1H), 2.58-2.61 (m, 1H), 2.66 (s, 2H), 2.97-3.05 (m, 1H), 3.74 (s, 2H), 3.96-4.02 (m, 1H), 4.32-4.39 (m, 1H), 6.40 (br. s., 2H), 6.94 (s, 1H), 8.19 (s, 1H), 12.07 (br.s., 1H), 14.20 (br.s., 1H).

HRMS (ESI+): calcd. for $C_{24}H_{32}N_9O_2S$ [M+H]⁺ 510.2394; found 510.2381.

8-amino-N-{4-[2-(4-carbamoylpiperidin-1-yl)-2-oxoethyl]-1,3-thiazol-2-yl}-4,4-dimethyl-4,5-dihydro-1H-pyrazolo[4,3-h]quinazoline-3-carboxamide (Ig), Cpd 90

[R1=R2=R3'=R4'=H, R3=R4=($C_1$-$C_6$)alkyl, y=1, L=CONR8,

R5=CONR6R7, R6 and R7=taken together form an optionally substituted heterocyclyl group, R8=H]

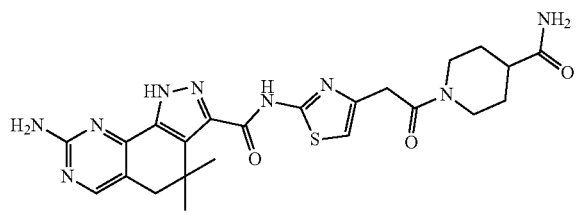 [SMILES: CC1(C)Cc2cnc(N)nc2-c2[nH]nc(C(=O)Nc3nc(CC(=O)N4CCC(C(N)=O)CC4)cs3)c21]

$^1$H NMR (499.7 MHz, DMSO-d$_6$) δ ppm 1.28-1.46 (m, 2H), 1.33 (s, 6H), 1.66-1.73 (m, 2H), 2.27-2.35 (m, 1H), 2.57-2.65 (m, 1H), 2.66 (s, 2H), 2.99-3.08 (m, 1H), 3.67-3.80 (m, 2H), 3.97-4.02 (m, 1H), 4.30-4.36 (m, 1H), 6.42 (br. s., 2H), 6.79 (br. s., 1H), 6.94 (s, 1H), 7.27 (br. s., 1H), 8.19 (s, 1H), 12.07 (br. s., 1H), 14.22 (br. s., 1H).

HRMS (ESI+): calcd. for C$_{23}$H$_{28}$N$_9$O$_3$S [M+H]$^+$ 510.2031; found 510.2021.

8-amino-N-(4-{2-[4-(hydroxymethyl)piperidin-1-yl]-2-oxoethyl}-1,3-thiazol-2-yl)-4,4-dimethyl-4,5-dihydro-1H- pyrazolo[4,3-h]quinazoline-3-carboxamide (Ig), Cpd 91

[R1=R2=R3'=R4'=H, R3=R4=(C$_1$-C$_6$)alkyl, y=1, L=CONR8, z=0, A=heteroaryl, n=1, Rc=Rd=H, R5=CONR6R7, R6 and R7=taken together form an optionally substituted heterocyclyl group, R8=H]

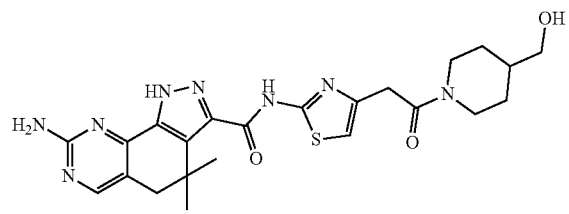 [SMILES: CC1(C)Cc2cnc(N)nc2-c2[nH]nc(C(=O)Nc3nc(CC(=O)N4CCC(CO)CC4)cs3)c21]

$^1$H NMR (499.7 MHz, DMSO-d$_6$) δ ppm 0.90-1.02 (m, 2H), 1.33 (s, 6H), 1.52-1.62 (m, 1H), 1.62-1.68 (m, 2H), 2.50-2.57 (m, 1H), 2.66 (s, 2H), 2.94-3.03 (m, 1H), 3.21-3.26 (m, 2H), 3.68-3.78 (m, 2H), 3.95-4.01 (m, 1H), 4.35-4.41 (m, 1H), 4.48 (t, J=5.3 Hz, 1H), 6.39 (br. s., 2H), 6.93 (s, 1H), 8.19 (s, 1H), 12.06 (s, 1H), 14.22 (br. s., 1H).

HRMS (ESI+): calcd. for C$_{23}$H$_{29}$N$_8$O$_3$S [M+H]$^+$ 497.2078; found 497.2082.

8-amino-N-{4-[2-(4-hydroxypiperidin-1-yl)-2-oxoethyl]-1,3-thiazol-2-yl}-4,4-dimethyl-4,5-dihydro-1H-pyrazolo[4,3-h]quinazoline-3-carboxamide (Ig), Cpd 92

[R1=R2=R3'=R4'=H, R3=R4=(C$_1$-C$_6$)alkyl, y=1, L=CONR8, z=0, A=heteroaryl, n=1, Rc=Rd=H, R5=CONR6R7, R6 and R7=taken together form an optionally substituted heterocyclyl group, R8=H]

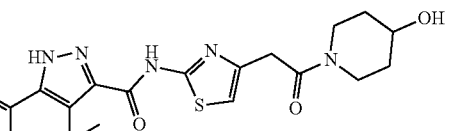

$^1$H NMR (499.7 MHz, DMSO-d$_6$) δ ppm 1.20-1.30 (m, 2H), 1.33 (s, 6H), 1.60-1.75 (m, 2H), 2.66 (s, 2H), 2.97-3.04 (m, 1H), 3.17-3.24 (m, 1H), 3.64-3.70 (m, 1H), 3.73 (s, 2H), 3.73-3.82 (m, 1H), 3.87-3.95 (m, 1H), 4.72 (d, J=4.0 Hz, 1H), 6.39 (br. s., 2H), 6.93 (s, 1H), 8.19 (s, 1H), 12.05 (s, 1H), 14.22 (br. s., 1H).

HRMS (ESI+): calcd. for C$_{22}$H$_{27}$N$_8$O$_3$S [M+H]$^+$ 483.1922; found 483.1922.

8-amino-N-(4-{2-[(3S)-3-(dimethylamino)pyrrolidin-1-yl]-2-oxoethyl}-1,3-thiazol-2-yl)-4,4-dimethyl-4,5-dihydro-1H-pyrazolo[4,3-h]quinazoline-3-carboxamide (Ig), Cpd 93

[R1=R2=R3'=R4'=H, R3=R4=(C$_1$-C$_6$)alkyl, y=1, L=CONR8, z=0, A=heteroaryl, n=1, Rc=Rd=H, R5=CONR6R7, R6 and R7=taken together form an optionally substituted heterocyclyl group, R8=H]

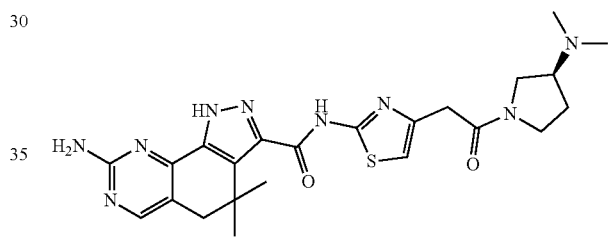

$^1$H NMR (499.7 MHz, DMSO-d$_6$; conformer mixture 1:1) δ ppm 1.33 (s, 6H), 1.58-1.80 (2×m, 1H), 1.96-2.13 (2×m, 1H), 2.17 (s, 6H), 2.66 (s, 2H), 2.96-3.02 (m, 0.5H), 3.16-3.27 (m, 1H), 3.33 (m overlapped by water signal, 1H), 3.46-3.54 (m, 1H), 3.57-3.63 (m, 0.5H), 3.64 and 3.67 (2×s, 2H), 3.71-3.77 (m, 0.5H), 3.78-3.84 (m, 0.5H), 6.39 (br. s., 2H), 6.95 and 6.96 (2×s, 1H), 8.19 (s, 1H), 12.06 (br. s., 1H), 14.21 (br. s., 1H).

HRMS (ESI+): calcd. for C$_{23}$H$_{30}$N$_6$O$_2$S [M+H]$^+$ 496.2238; found 496.2239.

8-amino-N-[4-(2-amino-2-oxoethyl)-1,3-thiazol-2-yl]-4,4-dimethyl-4,5-dihydro-1H-pyrazolo[4,3-h]quinazoline-3-carboxamide (Ig), Cpd 94

[R1=R2=R3'=R4'=H, R3=R4=(C$_1$-C$_6$)alkyl, y=1, L=CONR8, z=0, A=heteroaryl, n=1, Rc=Rd=H, R5=CONR6R7, R6=R7=R8=H]

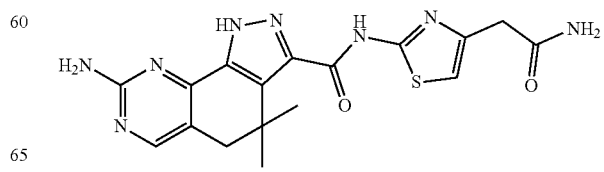

¹H NMR (499.7 MHz, DMSO-d₆) δ ppm 1.33 (s, 6H), 2.67 (s, 2H), 3.46 (s, 2H), 6.38 (br. s., 2H), 6.95 (s, 1H), 6.96 (br. s., 1H), 7.39 (br. s., 2H), 8.19 (s, 1H), 12.04 (s, 1H), 14.21 (br. s., 1H).
HRMS (ESI+): calcd. for $C_{17}H_{19}N_8O_2S$ [M+H]⁺ 399.1346; found 399.1345.

8-amino-N-[4-(2-{[3-(dimethylamino)propyl]amino}-2-oxoethyl)-1,3-thiazol-2-yl]-4,4-dimethyl-4,5-dihydro-1H-pyrazolo[4,3-h]quinazoline-3-carboxamide (Ig), Cpd 95

[R1=R2=R3'=R4'=H, R3=R4=$(C_1-C_6)$alkyl, y=1, L=CONR8, z=0, A=heteroaryl, n=1, Rc=Rd=H, R5=CONR6R7, R6=substituted $(C_1-C_6)$alkyl, R7=R8=H]

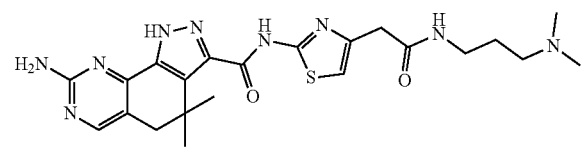 [SMILES: CN(C)CCCNC(=O)Cc1csc(NC(=O)c2n[nH]c3c2C(C)(C)Cc2cnc(N)nc2-3)n1]

¹H NMR (499.7 MHz, DMSO-d₆) δ ppm 1.32 (s, 6H), 1.52-1.61 (m, 2H), 2.19 (br. s., 6H), 2.32 (br. s., 2H), 2.66 (s, 2H), 3.03-3.15 (m, 2H), 3.49 (s, 2H), 6.40 (br. s., 2H), 6.96 (s, 1H), 7.97 (t, J=5.4 Hz, 1H), 8.19 (s, 1H), 14.22 (br. s., 1H).
HRMS (ESI+): calcd. for $C_{22}H_{30}N_9O_2S$ [M+H]⁺ 484.2238; found 484.2224.

8-amino-N-(4-{2-[(3R)-3-(dimethylamino)pyrrolidin-1-yl]-2-oxoethyl}-1,3-thiazol-2-yl)-4,4-dimethyl-4,5-dihydro-1H-pyrazolo[4,3-h]quinazoline-3-carboxamide (Ig), Cpd 116

[R1=R2=R3'=R4'=H, R3=R4=$(C_1-C_6)$alkyl, y=1, L=CONR8, z=0, A=heteroaryl, n=1, Rc=Rd=H, R5=CONR6R7, R6 and R7=taken together form an optionally substituted heterocyclyl group, R8=H]

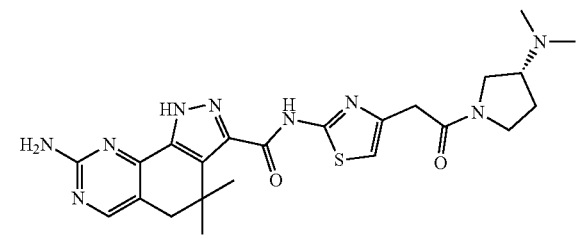 [SMILES: CN(C)[C@@H]1CCN(C(=O)Cc2csc(NC(=O)c3n[nH]c4c3C(C)(C)Cc3cnc(N)nc3-4)n2)C1]

¹H NMR (499.7 MHz, DMSO-d₆; conformer mixture 1:1) δ ppm 1.33 (s, 6H), 1.58-1.80 (2×m, 1H), 1.96-2.13 (2×m, 1H), 2.17 (s, 6H), 2.66 (s, 2H), 2.96-3.02 (m, 0.5H), 3.16-3.27 (m, 1H), 3.33 (m overlapped by water signal, 1H), 3.46-3.54 (m, 1H), 3.57-3.63 (m, 0.5H), 3.64 and 3.67 (2×s, 2H), 3.71-3.77 (m, 0.5H), 3.78-3.84 (m, 0.5H), 6.39 (br. s., 2H), 6.95 and 6.96 (2×s, 1H), 8.19 (s, 1H), 12.06 (br. s., 1H), 14.21 (br. s., 1H).
HRMS (ESI+): calcd. for $C_{23}H_{30}N_9O_2S$ [M+H]⁺ 496.22381; found 496.2232.

tert-butyl {1-[(2-{[(8-amino-4,4-dimethyl-4,5-dihydro-1H-pyrazolo[4,3-h]quinazolin-3-yl)carbonyl]amino}-1,3-thiazol-4-yl)acetyl]piperidin-4-yl}carbamate (Ig), Cpd 43

[R1=R2=R3'=R4'=H, R3=R4=$(C_1-C_6)$alkyl, y=1, L=CONR8, z=0, A=heteroaryl, n=1, Rc=Rd=H, R5=CONR6R7, R6 and R7=taken together form an optionally substituted heterocyclyl group, R8=H]

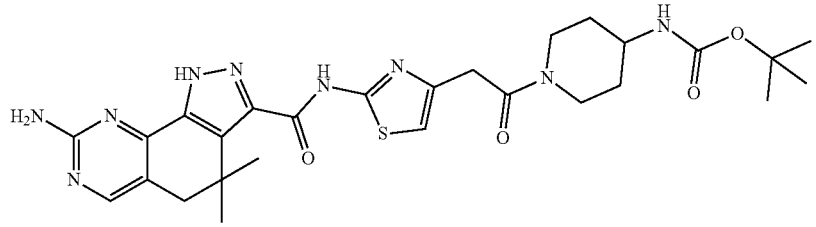 [SMILES: CC(C)(C)OC(=O)NC1CCN(C(=O)Cc2csc(NC(=O)c3n[nH]c4c3C(C)(C)Cc3cnc(N)nc3-4)n2)CC1]

¹H NMR (400.4 MHz, DMSO-d₆) δ ppm 1.10-1.29 (m, 2H), 1.34 (s, 6H), 1.38 (s, 9H), 1.66-1.76 (m, 2H), 2.65 (s, 2H), 2.70-2.76 (m, 1H), 3.05-3.14 (m, 1H), 3.41-3.51 (m, 1H), 3.72 (s, 2H), 3.90-3.98 (m, 1H), 4.18-4.25 (m, 1H), 6.35 (br. s., 2H), 6.82 (d, J=7.7 Hz, 1H), 6.89 (br. s., 1H), 8.18 (s, 1H), 12.03 (br. s., 1H), 14.14 (br. s., 1H).
HRMS (ESI+): calcd. for $C_{27}H_{36}N_9O_4S$ [M+H]⁺ 582.2606; found 582.2625.

8-amino-4,4-dimethyl-N-{4-[2-oxo-2-(4-oxopiperidin-1-yl)ethyl]-1,3-thiazol-2-yl}-4,5-dihydro-1H-pyrazolo[4,3-h]quinazoline-3-carboxamide (Ig), Cpd 45

[R1=R2=R3'=R4'=H, R3=R4=$(C_1-C_6)$alkyl, y=1, L=CONR8, z=0, A=heteroaryl, n=1, Rc=Rd=H, R5=CONR6R7, R6 and R7=taken together form an optionally substituted heterocyclyl group, R8=H]

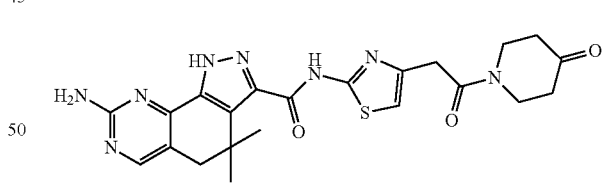

¹H NMR (400.4 MHz, DMSO-d₆) δ ppm 1.33 (s, 6H), 2.33-2.38 (m, 2H), 2.40-2.46 (m, 2H), 2.66 (s, 2H), 3.72-3.78 (m, 2H), 3.84 (s, 2H), 3.83-3.88 (m, 2H), 6.37 (br. s., 2H), 7.00 (s, 1H), 8.19 (s, 1H), 12.01 (br. s., 1H), 14.16 (br. s., 1H).
HRMS (ESI+): calcd. for $C_{22}H_{26}N_8O_3S$ [M+H]⁺ 481.1765; found 481.1761.

8-amino-4,4-dimethyl-N-(4-{2-oxo-2-[4-(pyrrolidin-1-yl)piperidin-1-yl]ethyl}-1,3-thiazol-2-yl)-4,5-dihydro-1H-pyrazolo[4,3-h]quinazoline-3-carboxamide (Ig), Cpd 37

[R1=R2=R3'=R4'=H, R3=R4=$(C_1-C_6)$alkyl, y=1, L=CONR8, z=0, A=heteroaryl, n=1, Rc=Rd=H, R5=CONR6R7, R6 and R7=taken together form an optionally substituted heterocyclyl group, R8=H]

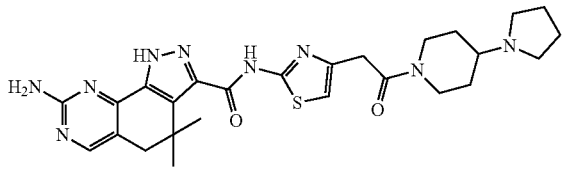 [SMILES: CC1(C)Cc2cnc(N)nc2-c2[nH]nc(C(=O)Nc3nc(CC(=O)N4CCC(N5CCCC5)CC4)cs3)c21]

$^1$H NMR (499.7 MHz, DMSO-d$_6$) δ ppm 1.26-1.38 (m, 2H), 1.36 (s, 6H), 1.65-1.79 (m, 4H), 1.81-1.94 (m, 2H), 2.44-2.66 (m, 3H), 2.69 (s, 2H), 2.72-2.81 (m, 1H), 3.09-3.16 (m, 1H), 3.78 (s, 2H), 3.91-4.00 (m, 1H), 4.20-4.80 (m, 1H), 6.43 (br. s., 2H), 6.97 (s, 1H), 8.22 (s, 1H), 12.10 (br. s., 1H), 14.26 (br. s., 1H).

HRMS (ESI+): calcd. for C$_{26}$H$_{34}$N$_9$O$_2$S [M+H]$^+$ 536.2551; found 536.2548.

8-amino-N-{4-[2-(1,4'-bipiperidin-1'-yl)-2-oxo-ethyl]-1,3-thiazol-2-yl}-4,4-dimethyl-4,5-dihydro-1H-pyrazolo[4,3-h]quinazoline-3-carboxamide (Ig), Cpd 39

[R1=R2=R3'=R4'=H, R3=R4=(C$_1$-C$_6$)alkyl, y=1, L=CONR8, z=0, A=heteroaryl, n=1, Rc=Rd=H, R5=CONR6R7, R6 and R7=taken together form an optionally substituted heterocyclyl group, R8=H]

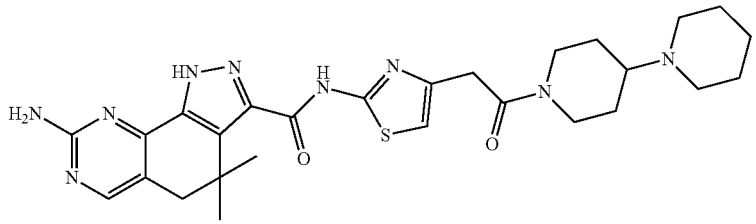 [SMILES: CC1(C)Cc2cnc(N)nc2-c2[nH]nc(C(=O)Nc3nc(CC(=O)N4CCC(N5CCCCC5)CC4)cs3)c21]

$^1$H NMR (499.7 MHz, DMSO-d$_6$) δ ppm 1.15-1.29 (m, 2H), 1.30-1.37 (m, 8H), 1.40-1.50 (m, 4H), 1.62-1.72 (m, 2H), 2.37-2.44 (m, 5H), 2.65 (s, 2H), 2.93-3.00 (m, 1H), 3.40 (m overlapped by water signal, 1H), 3.73 (s, 2H), 3.96-4.02 (m, 1H), 4.37-4.42 (m, 1H), 6.39 (br. s., 2H), 6.92 (s, 1H), 8.18 (s, 1H).

HRMS (ESI+): calcd. for C$_{27}$H$_{36}$N$_9$O$_2$S [M+H]$^+$ 550.2707; found 550.2715.

8-amino-N-{4-[2-(1,4'-bipiperidin-1'-yl)-2-oxoethyl] phenyl}-4,4-dimethyl-4,5-dihydro-1H-pyrazolo[4,3-h]quinazoline-3-carboxamide (Ig), Cpd 98

[R1=R2=R3'=R4'=H, R3=R4=(C$_1$-C$_6$)alkyl, y=1, L=CONR8, z=0, A=aryl, n=1, Rc=Rd=H, R5=CONR6R7, R6 and R7=taken together form an optionally substituted heterocyclyl group, R8=H]

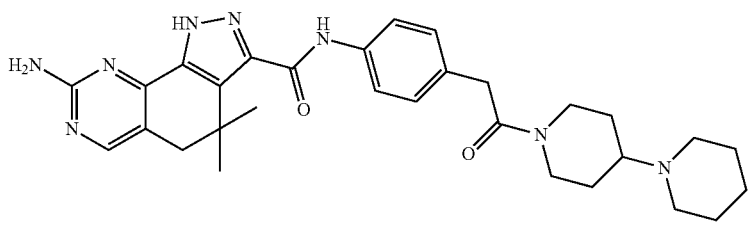 [SMILES: CC1(C)Cc2cnc(N)nc2-c2[nH]nc(C(=O)Nc3ccc(CC(=O)N4CCC(N5CCCCC5)CC4)cc3)c21]

$^1$H NMR (499.7 MHz, DMSO-d$_6$) δ ppm 1.10-1.28 (m, 2H), 1.29-1.39 (m, 8H), 1.39-1.50 (m, 4H), 1.60-1.73 (m, 2H), 2.35-2.52 (m, 5H), 2.64 (s, 2H), 2.89-2.96 (m, 1H), 3.33 (m overlapped by water signal, 1H), 3.66 (s, 2H), 3.92-3.99 (m, 1H), 4.37-4.45 (m, 1H), 6.37 (br. s., 2H), 7.17 (d, J=8.5 Hz, 2H), 7.71 (d, J=8.5 Hz, 2H), 8.18 (s, 1H), 10.21 (br. s., 1H), 14.03 (br. s., 1H).

HRMS (ESI+): calcd. for C$_{30}$H$_{39}$N$_8$O$_2$ [M+H]$^+$ 543.3191; found 543.3201.

8-amino-N-[4-(1-{[(3R)-3-(dimethylamino)pyrrolidin-1-yl]carbonyl}cyclopropyl)-1,3-thiazol-2-yl]-4,4-dimethyl-4,5-dihydro-1H-pyrazolo[4,3-h]quinazoline-3-carboxamide (Ig), Cpd 130

[R1=R2=R3'=R4'=H, R3=R4=(C$_1$-C$_6$)alkyl, y=1, L=CONR8, z=0, A=heteroaryl, n=1, Rc and Rd=taken together form a 3-membered cycloalkyl, R5=CONR6R7, R6 and R7=taken together form an optionally substituted heterocyclyl group, R8=H]

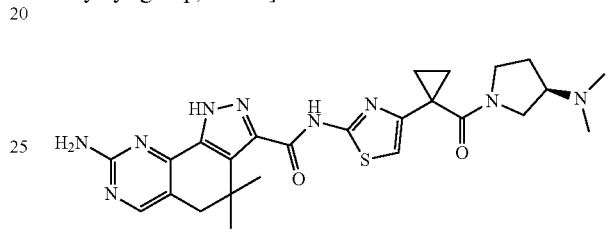

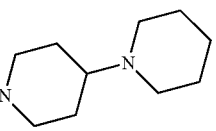

$^1$H NMR (499.7 MHz, DMSO-d$_6$; mixture of rotamers) δ ppm 1.08-1.33 (m, 4H), 1.32 (s, 6H), 1.55-1.71 (m, 1H), 1.91-2.01 (m, 1H), 2.06 (s, 3H), 2.13 (s, 3H), 2.55-2.63 (m, 1H), 2.65 (s, 2H), 2.91 (dd, J=10.5, 8.4 Hz, 0.5H), 3.05 (dd, J=11.6, 8.5 Hz, 0.5H), 3.11-3.17 (m, 0.5H), 3.25-3.32 (m partially overlapped by water signal, 1H), 3.47-3.54 (m, 1H), 3.61 (dd, J=11.6, 7.0 Hz, 0.5H), 6.39 (br. s., 2H), 6.84 and 6.88 (2×s, 1H), 8.18 (s, 1H), 12.13 (br. s., 1H), 14.20 (br. s., 1H).

HRMS (ESI+): calcd. for C$_{25}$H$_{32}$N$_9$O$_2$S [M+H]$^+$ 522.2394; found 522.2391.

8-amino-N-{4-[1-(1,4'-bipiperidin-1'-ylcarbonyl)cyclopropyl]-1,3-thiazol-2-yl}-4,4-dimethyl-4,5-dihydro-1H-pyrazolo[4,3-h]quinazoline-3-carboxamide (Ig), Cpd 131

[R1=R2=R3'=R4'=H, R3=R4=(C$_1$-C$_6$)alkyl, y=1, L=CONR8, z=0, A=heteroaryl, n=1, Rc and Rd=taken together form a 3-membered cycloalkyl, R5=CONR6R7, R6 and R7=taken together form an optionally substituted heterocyclyl group, R8=H]

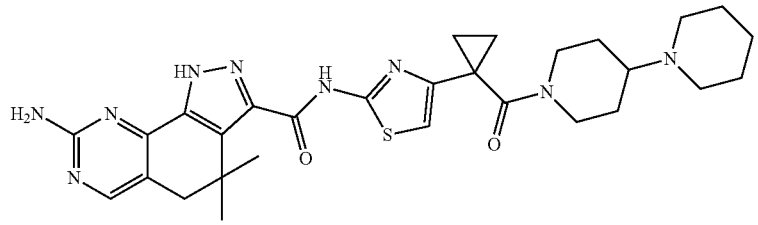 [SMILES: CC1(C)Cc2cnc(N)nc2-c2[nH]nc(C(=O)Nc3nc(C4(C(=O)N5CCC(N6CCCCC6)CC5)CC4)cs3)c21]

$^1$H NMR (499.7 MHz, DMSO-d$_6$) δ ppm 1.12-1.38 (m, 4H), 1.32 (s, 6H), 1.40-1.50 (m, 4H), 1.50-1.62 (m, 1H), 1.65-1.76 (m, 1H), 2.36-2.47 (br. s., 4H), 2.55-2.60 (m, 1H), 2.65 (s, 2H), 2.80-2.92 (br. s., 1H), 3.34 (m overlapped by water signal, 1H), 3.94-4.04 (m, 1H), 4.38-4.47 (m, 1H), 6.40 (br. s., 2H), 6.82 (s, 1H), 8.18 (s, 1H), 12.06 (br. s., 1H), 14.21 (br. s., 1H).

HRMS (ESI+): calcd. for C$_{29}$H$_{38}$N$_9$O$_2$S [M+H]$^+$ 576.2864; found 576.2838.

8-amino-N-(3-{2-[(3R)-3-(dimethylamino)pyrrolidin-1-yl]-2-oxoethyl}phenyl)-4,4-dimethyl-4,5-dihydro-1H-pyrazolo[4,3-h]quinazoline-3-carboxamide (Ig), Cpd 142

[R1=R2=R3'=R4'=H, R3=R4=(C$_1$-C$_6$)alkyl, y=1, L=CONR8, z=0, A=aryl, n=1, Rc=Rd=H, R5=CONR6R7, R6 and R7=taken together form an optionally substituted heterocyclyl group, R8=H]

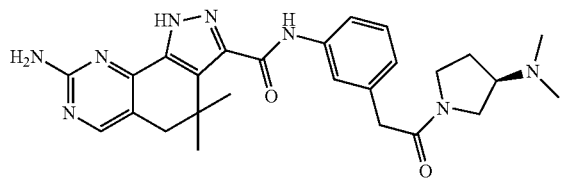 [SMILES: CN(C)[C@@H]1CCN(C(=O)Cc2cccc(NC(=O)c3n[nH]c4c3C(C)(C)Cc3cnc(N)nc3-4)c2)C1]

$^1$H NMR (499.7 MHz, DMSO-d$_6$, mixture of conformers 1:1) δ ppm 1.33 (s, 6H), 1.57-1.66 (m, 0.5H), 1.70-1.78 (m, 0.5H), 1.95-2.03 (m, 0.5H), 2.03-2.11 (m, 0.5H), 2.65 (s, 2H), 2.97 (dd, J=11.4, 8.4 Hz, 0.5H), 3.16-3.23 (m, 1H), 3.41-3.48 (m, 0.5H), 3.49-3.54 (m, 0.5H), 3.68-3.63 (m, 0.5H), 3.59 and 3.61 (2×s, 2H), 3.65-3.71 (m, 0.5H), 3.78 (dd, J=10.0, 7.2 Hz, 0.5H), 6.37 (br. s., 2H), 6.92-6.97 (m, 1H), 7.22-7.27 (m, 1H), 7.56-7.63 (m, 1H), 7.74 (m, 1H), 8.18 (s, 1H), 10.21 (br. s., 1H), 14.02 (br. s., 1H).

HRMS (ESI+): calcd. for C$_{26}$H$_{33}$N$_8$O$_2$ [M+H]$^+$ 489.2721; found 489.2721.

8-amino-N-(3-{2-[4-(dimethylamino)piperidin-1-yl]-2-oxoethyl}phenyl)-4,4-dimethyl-4,5-dihydro-1H-pyrazolo[4,3-h]quinazoline-3-carboxamide (Ig), Cpd 146

[R1=R2=R3'=R4'=H, R3=R4=(C$_1$-C$_6$)alkyl, y=1, L=CONR8, z=0, A=aryl, n=1, Rc=Rd=H, R5=CONR6R7, R6 and R7=taken together form an optionally substituted heterocyclyl group, R8=H]

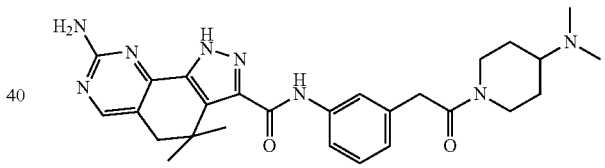

$^1$H NMR (499.7 MHz, DMSO-d$_6$) δ ppm 1.05-1.23 (m, 2H), 1.33 (s, 6H), 1.60-1.67 (m, 1H), 1.66-1.75 (m, 1H), 2.11 (s, 6H), 2.22-2.30 (m, 1H), 2.54-2.61 (m, 1H), 2.64 (s, 2H), 2.94-3.02 (m, 1H), 3.66-3.74 (m, 2H), 3.88-3.95 (m, 1H), 4.33-4.39 (m, 1H), 6.37 (br. s., 2H), 6.94 (d, J=7.6 Hz, 1H) 7.25 (dd, J=8.1, 7.6 Hz, 1H), 7.59 (d, J=8.1 Hz, 1H, 7.75 (s, 1H), 8.18 (s, 1H), 10.24 (br. s., 1H), 14.00 (br. s., 1H).

HRMS (ESI+): calcd. for C$_{27}$H$_{35}$N$_8$O$_2$ [M+H]$^+$ 503.2878; found 503.2877.

tert-butyl{1-[(3-{[(8-amino-4,4-dimethyl-4,5-dihydro-1H-pyrazolo[4,3-h]quinazolin-3-yl)carbonyl]amino}phenyl)acetyl]piperidin-4-yl}carbamate (Ig), Cpd 177

[R1=R2=R3'=R4'=H, R3=R4=(C$_1$-C$_6$)alkyl, y=1, L=CONR8, z=0, A=aryl, n=1, Rc=Rd=H, R5=CONR6R7, R6 and R7=taken together form an optionally substituted heterocyclyl group, R8=H]

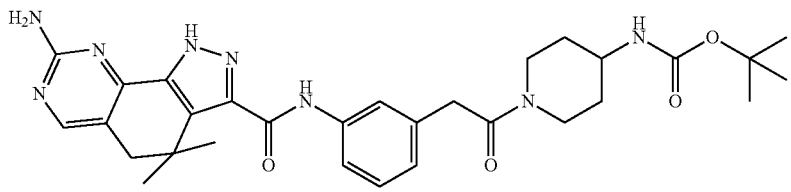 [SMILES: CC(C)(C)OC(=O)NC1CCN(C(=O)Cc2cccc(NC(=O)c3n[nH]c4c3C(C)(C)Cc3cnc(N)nc3-4)c2)CC1]

HRMS (ESI+): calcd. for $C_{30}H_{39}N_8O_0$ $[M+H]^+$ 575.3089; found 575.3084.

8-amino-N-{4-[2-(1,4'-bipiperidin-1'-yl)-1,1-difluoro-2-oxoethyl]-1,3-thiazol-2-yl}-4,4-dimethyl-4,5-dihydro-1H-pyrazolo[4,3-h]quinazoline-3-carboxamide (Ig), Cpd 183

[R1=R2=R3'=R4'=H, R3=R4=($C_1$-$C_6$)alkyl, y=1, L=CONR8, z=0, A=heteroaryl, n=1, Rc=Rd=F, R5=CONR6N7, R6 and R7=taken together form an optionally substituted heterocyclyl group, R8=H]

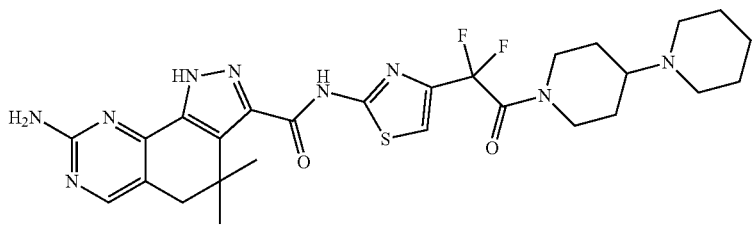 [SMILES: CC1(C)Cc2cnc(N)nc2-c2[nH]nc(C(=O)Nc3nc(C(F)(F)C(=O)N4CCC(N5CCCCC5)CC4)cs3)c21]

HRMS (ESI+): calcd. for $C_{27}H_{34}F_2N_9O_2S$ $[M+H]^+$ 586.2519; found 586.2514.

8-amino-N-{4-[1,1-difluoro-2-(4-methyl-1,4'-bipiperidin-1'-yl)-2-oxoethyl]-1,3-thiazol-2-yl}-4,4-dimethyl-1-(tetrahydro-2H-pyran-2-yl)-4,5-dihydro-1H-pyrazolo[4,3-h]quinazoline-3-carboxamide (II)

[R1=R3'=R4'=H, PG=tetrahydropyranyl, R3=R4=($C_1$-$C_6$) alkyl, y=1, L=CONR8, z=0, A=heteroaryl, n=1, Rc=Rd=F, R5=CONR6N7, R6 and R7=taken together form an optionally substituted heterocyclyl group, R8=H]

HRMS (ESI+): calcd. for $C_{33}H_{44}F_2N_9O_3S$ $[M+H]^+$ 684.3250; found 684.3102.

Example 4

8-amino-N-{4-[(4-aminopiperidin-1-yl)carbonyl]phenyl}-4,4-dimethyl-4,5-dihydro-1H-pyrazolo[4,3-h]quinazoline-3-carboxamide (I), Cpd 49

[R1=R2=R3'=R4'=H, R3=R4=($C_1$-$C_6$)alkyl, y=1, L=CONR8, z=n=0, A=aryl, R5=CONR6R7, R6 and R7=taken together form an optionally substituted heterocyclyl group, R8=H]

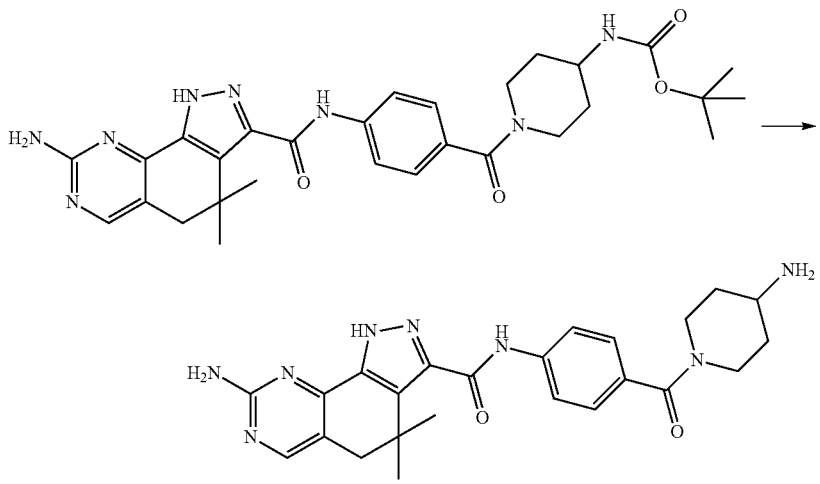

Deprotection

Tert-butyl [1-(4-{[(8-amino-4,4-dimethyl-4,5-dihydro-1H-pyrazolo[4,3-h]quinazolin-3-yl)carbonyl]amino}benzoyl)piperidin-4-yl]carbamate (350 mg, 0.625 mmol) in DCM (14 mL) was treated with HCl 4M in dioxane (4.7 mL, 18.75 mmol). The reaction was stirred at rt for 3 h. The volatiles were removed in vacuo. The solid was dissolved in water (7 mL), made alkaline to pH 10 with 33% NH$_4$OH and partitioned with n-BuOH (20 mL×2). The combined organic layers were evaporated to dryness. The crude was purified by column chromatography over silica gel (DCM: 7 N NH$_3$ in MeOH=85:15) to afford the title compound (160 mg, 56%).

$^1$H NMR (499.7 MHz, DMSO-d$_6$) δ ppm 1.17-1.37 (m, 2H), 1.34 (s, 6H), 1.70-1.90 (m, 2H), 2.66 (s, 2H), 2.82-3.18 (m, 2H), 3.57-3.80 (m, 1H), 4.20-4.40 (m, 1H), 6.38 (br. s., 2H), 7.35 (d, J=8.7 Hz, 2H), 7.87 (d, J=8.7 Hz, 2H), 8.19 (s, 1H), 10.48 (s, 1H).

HRMS (ESI+): calcd. for C$_{24}$H$_{29}$N$_8$O$_2$ [M+H]$^+$ 461.2408; found 461.2415.

Operating in an analogous way, but employing a suitably substituted compound (I), the following compound was obtained:

8-amino-N-{4-[2-(4-aminopiperidin-1-yl)-2-oxoethyl]-1,3-thiazol-2-yl}-4,4-dimethyl-4,5-dihydro-1H-pyrazolo[4,3-h]quinazoline-3-carboxamide (I), Cpd 44

[R1=R2=R3'=R4'=H, R3=R4=(C$_1$-C$_6$)alkyl, y=1, L=CONR8, z=0, A=heteroaryl, n=1, Rc=Rd=H, R5=CONR6R7, R6 and R7=taken together form an optionally substituted heterocyclyl group, R8=H]

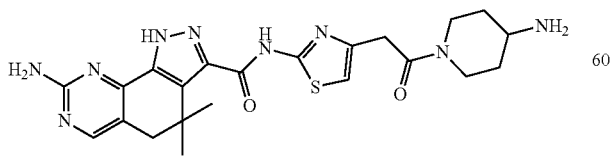

$^1$H NMR (400.4 MHz, DMSO-d$_6$) δ ppm 1.06-1.15 (m, 2H), 1.31 (s, 6H), 1.67-1.74 (m, 2H), 2.63 (s, 2H), 2.63-2.72 (m, 1H), 2.83-2.92 (m, 1H), 2.99-3.09 (m, 1H), 3.70 (s, 2H), 3.87-3.95 (m, 1H), 4.17-4.24 (m, 1H), 6.33 (br. s., 2H), 6.87 (s, 1H), 8.15 (s, 1H).

HRMS (ESI+): calcd. for C$_{22}$H$_{28}$N$_9$O$_2$S [M+H]$^+$ 482.2081; found 482.2074.

Alternatively:

8-amino-N-{3-[(4-aminopiperidin-1-yl)methyl]phenyl}-1,4,4-trimethyl-4,5-dihydro-1H-pyrazolo[4,3-h]quinazoline-3-carboxamide dihydrochloride (I), Cpd 104

[R1=R3'=R4'=H, R2=R3=R4=(C$_1$-C$_6$)alkyl, y=1, L=CONR8, z=0, A=aryl, n=1, Rc=Rd=H, R5=NR6R7, R6 and R7=taken together form an optionally substituted heterocyclyl group, R8=H]

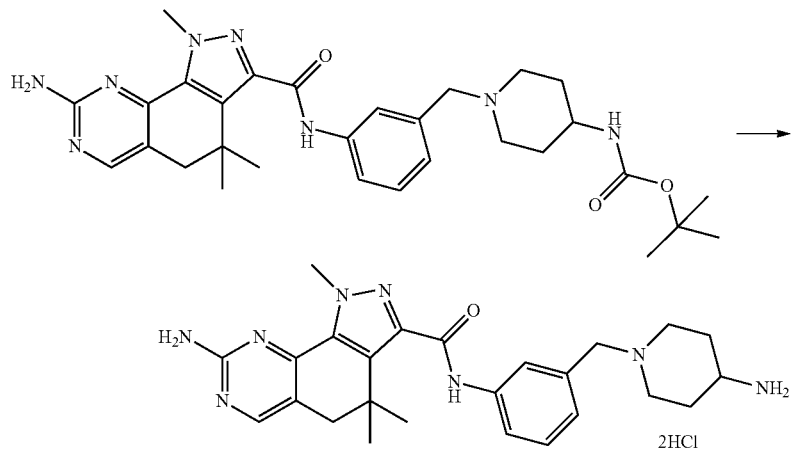

Tert-butyl [1-(3-{[(8-amino-1,4,4-trimethyl-4,5-dihydro-1H-pyrazolo[4,3-h]quinazolin-3-yl)carbonyl]amino}benzyl) piperidin-4-yl]carbamate (16 mg, 0.029 mmol) was treated with HCl 4M in dioxane (2 mL). The reaction was stirred at rt for 1 h. The volatiles were removed in vacuo to give the title compound in quantitative yield.

$^1$H NMR (499.7 MHz, DMSO-d$_6$) δ ppm 1.35 (s, 6H), 1.84-1.96 (m, 2H), 2.07-2.13 (s, 2H), 2.69 (s, 2H), 2.98-3.09 (m, 2H), 3.38 (m overlapped by water signal, 3H), 4.23-4.28 (m, 2H), 4.36 (s, 3H), 7.36 (d, J=7.6 Hz, 1H), 7.44 (t, J=8.8, 7.6 Hz, 1H), 7.51 (br. s., 3H), 7.73 (d, J=8.8 Hz, 1H), 8.07 (m, 1H), 8.26 (s, 1H), 8.28 (m, 3H), 10.50 (s, 1H), 10.53 (br. s., 1H).

HRMS (ESI+): calcd. for C$_{25}$H$_{33}$N$_8$O [M+H]$^+$ 461.2772; found 461.2770.

Operating in an analogous way, but employing suitably substituted compounds (I), the following compounds were obtained:

8-amino-N-{3-[(4-aminopiperidin-1-yl)methyl]phenyl}-4,4-dimethyl-4,5-dihydro-1H-pyrazolo[4,3-h]quinazoline-3-carboxamide dihydrochloride (I), Cpd 115

[R1=R2=R3'=R4'=H, R3=R4=(C$_1$-C$_6$)alkyl, y=1, L=CONR8, z=0, A=aryl, n=1, Rc=Rd=H, R5=NR6R7, R6 and R7=taken together form an optionally substituted heterocyclyl group, R8=H]

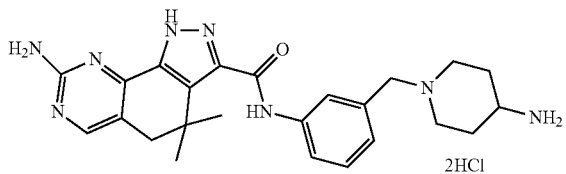 [SMILES: CC1(C)Cc2cnc(N)nc2-c2[nH]nc(C(=O)Nc3cccc(CN4CCC(N)CC4)c3)c21]

¹H NMR (499.7 MHz, DMSO-d₆) δ ppm 1.36 (s, 6H), 1.85-1.96 (m, 2H), 2.06-2.13 (m, 2H), 2.72 (s, 2H), 2.97-3.09 (m, 2H), 3.35 (m overlapped by water signal, 3H), 4.24-4.36 (m, 2H), 7.27 (br. s., 2H), 7.35 (d, J=7.8 Hz, 1H), 7.44 (dd, J=7.8 Hz, 1H), 7.73 (d, J=7.8 Hz, 1H), 8.10 (s, 1H), 8.18-8.43 (m, 4H) 10.50 (br. s., 1H).

HRMS (ESI+): calcd. for $C_{24}H_{31}N_8O$ [M+H]⁺ 447.2616; found 447.2615.

8-amino-N-{4-[(4-aminopiperidin-1-yl)methyl]phenyl}-1,4,4-trimethyl-4,5-dihydro-1H-pyrazolo[4,3-h]quinazoline-3-carboxamide dihydrochloride (I), Cpd 134

[R1=R3'=R4'=H, R2=R3=R4=(C₁-C₆)alkyl, y=1, L=CONR8, z=0, A=aryl, n=1, Rc=Rd=H, R5=NR6R7, R6 and R7=taken together form an optionally substituted heterocyclyl group, R8=H]

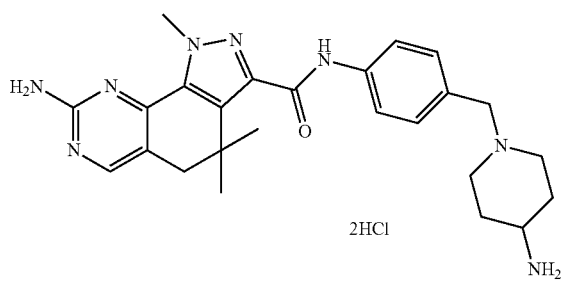 [SMILES: Cn1nc(C(=O)Nc2ccc(CN3CCC(N)CC3)cc2)c2c1-c1nc(N)ncc1CC2(C)C]

¹H NMR (499.7 MHz, DMSO-d₆) δ ppm 1.35 (s, 6H), 1.88-1.98 (m, 2H), 2.05-2.13 (m, 2H), 2.70 (s, 2H), 2.93-3.03 (m, 3H), 3.19-3.55 (m overlapped by water signal, 3H), 4.21 (d, J=4.4 Hz, 2H), 4.37 (s, 3H), 7.52-7.57 (m, 2H), 7.63 (br. s., 2H), 7.86-7.90 (m, 2H), 8.23 (br. s., 3H), 8.27 (s, 1H), 10.57 (s, 1H), 10.60-10.70 (br. s., 1H).

HRMS (ESI+): calcd. for $C_{25}H_{33}N_8O$ [M+H]⁺ 461.2772; found 461.2768.

8-amino-N-{4-[(4-aminopiperidin-1-yl)methyl]phenyl}-4,4-dimethyl-4,5-dihydro-1H-pyrazolo[4,3-h]quinazoline-3-carboxamide dihydrochloride (I), Cpd 135

[R1=R2=R3'=R4'=H, R3=R4=(C₁-C₆)alkyl, y=1, L=CONR8, z=0, A=aryl, n=1, Rc=Rd=H, R5=NR6R7, R6 and R7=taken together form an optionally substituted heterocyclyl group, R8=H]

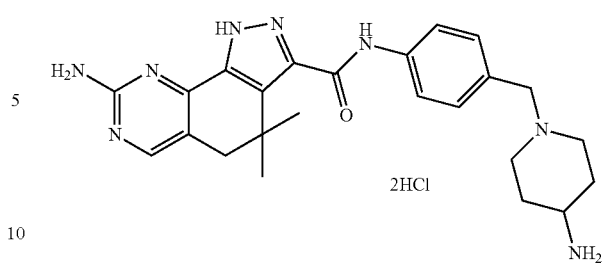

¹H NMR (499.7 MHz, DMSO-d₆) δ ppm 1.35 (s, 6H), 1.86-1.99 (m, 2H), 2.05-2.11 (m, 2H), 2.72 (s, 2H), 2.89-3.03 (m, 2H), 3.20-3.50 (m overlapped by water signal, 3H), 4.21 (d, J=4.6 Hz, 2H), 7.54 (d, J=8.4 Hz, 2H), 7.88 (d, J=8.4 Hz, 2H), 8.25 (br. s., 3H), 8.27 (s, 1H), 10.57 (s, 1H), 14.37 (br. s., 1H).

HRMS (ESI+): calcd. for $C_{24}H_{31}N_8O$ [M+H 447.2616; found 447.2613.

8-amino-N-{4-[(4-aminopiperidin-1-yl)methyl]-1,3-thiazol-2-yl}-4,4-dimethyl-4,5-dihydro-1H-pyrazolo[4,3-h]quinazoline-3-carboxamide dihydrochloride (I), Cpd 152

[R1=R2=R3'=R4'=H, R3=R4=(C₁-C₆)alkyl, y=1, L=CONR8, z=0, A=heteroaryl, n=1, Rc=Rd=H, R5=NR6R7, R6 and R7=taken together form an optionally substituted heterocyclyl group, R8=H]

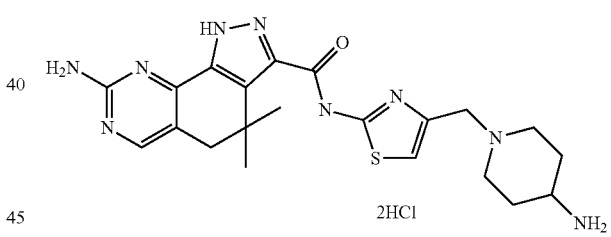

¹H NMR (499.7 MHz, DMSO-d₆) δ ppm 1.36 (s, 6H), 1.90-2.01 (m, 2H), 2.06-2.14 (m, 2H), 2.75 (s, 2H), 3.03-3.15 (m, 2H), 3.21-3.30 (m, 1H), 3.38 (m partially overlapped by water signal, 1H), 4.29 (s, 2H), 7.55 (s, 1H), 7.88 (br. s., 3H), 8.32 (s, 1H), 8.34 (br. s., 2H), 10.90 (br. s., 1H), 12.48 (br. s., 1H), 14.69 (s, 1H).

HRMS (ESI+): calcd. for $C_{21}H_{28}N_9OS$ [M+H]⁺ 454.2132; found 454.214.

8-amino-N-{3-[2-(4-aminopiperidin-1-yl)-2-oxoethyl]phenyl}-4,4-dimethyl-4,5-dihydro-1H-pyrazolo[4,3-h]quinazoline-3-carboxamide hydrochloride (I), Cpd 149

[R1=R2=R3'=R4'=H, R3=R4=(C₁-C₆)alkyl, y=1, L=CONR8, z=0, A=aryl, n=1, Rc=Rd=H, R5=CONR6R7, R6 and R7=taken together form an optionally substituted heterocyclyl group, R8=H]

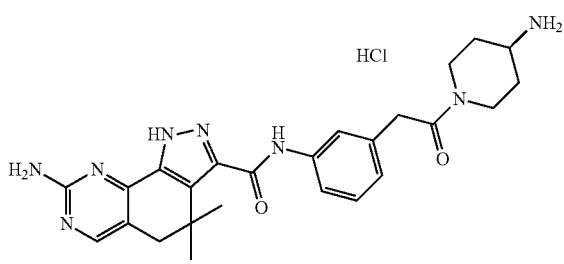 [SMILES: CC1(C)Cc2cnc(N)nc2-c2[nH]nc(C(=O)Nc3cccc(CC(=O)N4CCC(N)CC4)c3)c21 ; Cl]

¹H NMR (499.7 MHz, DMSO-d₆) δ ppm 1.35 (s, 6H), 1.26-1.38 (m, 2H), 1.85-1.93 (m, 2H), 2.64-2.73 (m, 1H), 2.73 (s, 2H), 3.02-3.11 (m, 1H), 3.19-3.28 (m, 1H), 3.68-3.78 (m, 2H), 3.98-4.06 (m, 1H), 4.36-4.42 (m, 1H), 6.96 (d, J=7.6 Hz, 1H), 7.28 (dd, J=7.5, 7.6 Hz, 1H), 7.60 (d, J=7.5 Hz, 1H), 7.74 (s, 1H), 8.00 (br. s., 3H), 8.28 (s, 1H), 10.39 (br. s., 1H), 14.37 (br. s., 1H).

HRMS (ESI+): calcd. for $C_{25}H_{31}N_8O_2$ [M+H]⁺ 475.2565; found 475.2552.

Example 5

8-amino-4,4-dimethyl-N-(4-{[4-(morpholin-4-yl)piperidin-1-yl]carbonyl}phenyl)-4,5-dihydro-1H-pyrazolo[4,3-h]quinazoline-3-carboxamide (I), Cpd 50

[R1=R2=R3'=R4'=H, R3=R4=(C₁-C₆)alkyl, y=1, L=CONR8, z=n=0, A=aryl, R5=CONR6R7, R6 and R7=taken together form an optionally substituted heterocyclyl group, R8=H]

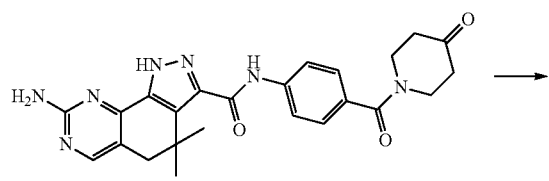

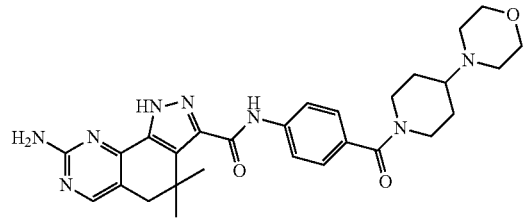

8-Amino-4,4-dimethyl-N-{4-[(4-oxopiperidin-1-yl)carbonyl]phenyl}-4,5-dihydro-1H-pyrazolo[4,3-h]quinazoline-3-carboxamide (30 mg, 0.065 mmol) in DMF (0.650 mL) was treated with morpholine (0.007 mL, 0.078 mmol), AcOH (0.004 mL, 0.075 mmol) and sodium triacetoxyborohydride (35 mg, 0.163 mmol). The reaction was stirred at rt for 2 h then further mopholine (0.003 mL) and sodium triacetoxyborohydride (20 mg) were added. The mixture was stirred overnight. The solvent was removed in vacuo, the residue was partitioned between DCM and saturated aqueous NaHCO₃; the organic layer was washed with brine, dried over Na₂SO₄ and evaporated to dryness. The crude was purified by column chromatography over silica gel (DCM: 7N NH₃ in MeOH=95:5) to give 4.6 mg of title compound (13%).

¹H NMR (499.7 MHz, DMSO-d₆) δ ppm 1.30-1.40 (m, 2H), 1.34 (s, 6H), 1.68-1.90 (m, 2H), 2.36-2.45 (m, 1H), 2.43-2.52 (m, 4H), 2.65 (s, 2H), 2.70-3.10 (m, 2H), 3.54-3.60 (m, 4H), 3.62-3.80 (m, 1H), 4.29-4.53 (m, 1H), 6.38 (br. s., 2H), 7.37 (d, J=8.5 Hz, 2H), 7.86 (d, J=8.5 Hz, 2H), 8.19 (s, 1H), 10.45 (br. s., 1H), 14.07 (br. s., 1H).

HRMS (ESI+): calcd. for $C_{28}H_{35}N_8O_3$ [M+H]⁺ 531.2827; found 531.2838.

Operating in an analogous way, but employing suitably substituted compounds (I), the following compounds were obtained:

8-amino-N-{4-[(4,4-difluoro-1,4'-bipiperidin-1'-yl)carbonyl]phenyl}-4,4-dimethyl-4,5-dihydro-1H-pyrazolo[4,3-h]quinazoline-3-carboxamide (I), Cpd 51

[R1=R2=R3'=R4'=H, R3=R4=(C₁-C₆)alkyl, y=1, L=CONR8, z=n=0, A=aryl, R5=CONR6R7, R6 and R7=taken together form an optionally substituted heterocyclyl group, R8=H]

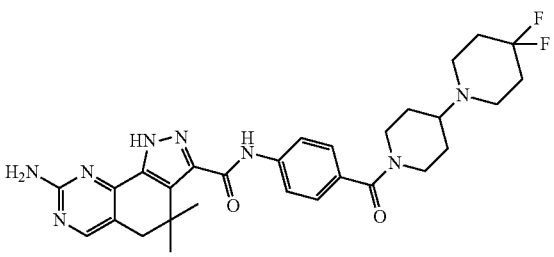 [SMILES: CC1(C)Cc2cnc(N)nc2-c2[nH]nc(C(=O)Nc3ccc(C(=O)N4CCC(N5CCC(F)(F)CC5)CC4)cc3)c21]

¹H NMR (499.7 MHz, DMSO-d₆) δ ppm 1.34 (s, 6H), 1.37-1.48 (m, 2H), 1.64-1.86 (m, 2H), 1.87-1.98 (m, 4H), 2.57-2.64 (m, 5H), 2.66 (s, 2H), 2.69-2.84 (m, 1H), 2.89-3.10 (m, 1H), 3.60-3.83 (m, 1H), 4.36-4.63 (m, 1H), 6.38 (br. s., 2H), 7.37 (d, J=8.4 Hz, 2H), 7.86 (d, J=8.4 Hz, 2H), 8.19 (s, 1H), 10.44 (br. s., 1H), 14.09 (br. s., 1H).

HRMS (ESI+): calcd. for $C_{29}H_{35}N_8O_2F_2$[M+H]⁺ 565.28468; found 565.2846.

8-amino-4,4-dimethyl-N-{4-[(4-methyl-1,4'-bipiperidin-1'-yl)carbonyl]phenyl}-4,5-dihydro-1H-pyrazolo[4,3-h]quinazoline-3-carboxamide (I), Cpd 52

[R1=R2=R3'=R4'=H, R3=R4=(C₁-C₆)alkyl, y=1, L=CONR8, z=n=0, A=aryl, R5=CONR6R7, R6 and R7=taken together form an optionally substituted heterocyclyl group, R8=H]

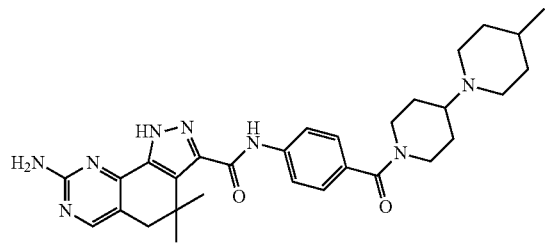 [SMILES: CC1CCN(C2CCN(C(=O)c3ccc(NC(=O)c4n[nH]c5c4C(C)(C)Cc4cnc(N)nc4-5)cc3)CC2)CC1]

¹H NMR (499.7 MHz, DMSO-d₆) δ ppm 0.86 (d, J=6.4 Hz, 3H), 1.02-1.14 (m, 2H), 1.22-1.31 (m, 1H), 1.34 (s, 6H), 1.35-1.46 (m, 2H), 1.54-1.60 (m, 2H), 1.61-1.82 (m, 2H), 2.05-2.17 (m, 2H), 2.45-2.50 (m, 1H), 2.65 (s, 2H), 2.77-

2.83 (m, 2H), 2.69-3.08 (m, 2H), 3.60-3.78 (m, 1H), 4.35-4.56 (m, 1H), 6.38 (br. s., 2H), 7.36 (d, J=8.6 Hz, 2H), 7.85 (d, J=8.6 Hz, 2H), 8.19 (s, 1H), 10.46 (br. s., 1H), 14.07 (br. s., 1H).

HRMS (ESI+): calcd. for $C_{30}H_{39}N_8O_2$ [M+H]$^+$ 543.3191; found 543.3207.

8-amino-N-(4-{2-[4-(azepan-1-yl)piperidin-1-yl]-2-oxoethyl}-1,3-thiazol-2-yl)-4,4-dimethyl-4,5-dihydro-1H- pyrazolo[4,3-h]quinazoline-3-carboxamide (I), Cpd 47

[R1=R2=R3'=R4'=H, R3=R4=($C_1$-$C_6$)alkyl, y=1, L=CONR8, z=0, A=heteroaryl, n=1, Rc=Rd=H, R5=CONR6R7, R6 and R7=taken together form an optionally substituted heterocyclyl group, R8=H]

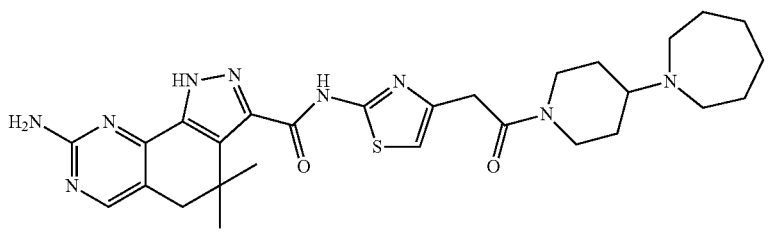 [SMILES: CC1(C)Cc2cnc(N)nc2-c2[nH]nc(C(=O)Nc3nc(CC(=O)N4CCC(N5CCCCCC5)CC4)cs3)c21]

$^1$H NMR (499.7 MHz, DMSO-d$_6$) δ ppm 1.12-1.27 (m, 2H), 1.33 (s, 6H), 1.49 (s, 8H), 1.58-1.73 (m, 2H), 2.46-2.64 (m, 5H), 2.66 (s, 2H), 2.92-3.00 (m, 1H), 3.33 (m overlapped by water signal, 1H), 3.69-3.79 (m, 2H), 3.94-4.01 (m, 1H), 4.36-4.43 (m, 1H), 6.39 (br. s., 2H), 6.94 (s, 1H), 8.19 (s, 1H), 11.98 (br. s., 1H), 14.17 (br. s., 1H).

HRMS (ESI+): calcd. for $C_{28}H_{38}N_9O_2S$ [M+H]$^+$ 564.2864; found 564.2883.

8-amino-4,4-dimethyl-N-(4-{2-[4-(methylamino)piperidin-1-yl]-2-oxoethyl}-1,3-thiazol-2-yl)-4,5-dihydro-1H-pyrazolo[4,3-h]quinazoline-3-carboxamide (I), Cpd 119

[R1=R2=R3'=R4'=H, R3=R4=($C_1$-$C_6$)alkyl, y=1, L=CONR8, z=0, A=heteroaryl, n=1, Rc=Rd=H, R5=CONR6R7, R6 and R7=taken together form an optionally substituted heterocyclyl group, R8=H]

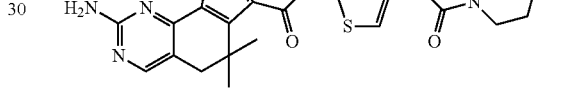

$^1$H NMR (499.7 MHz, DMSO-d$_6$) δ ppm 1.03-1.19 (m, 2H), 1.33 (s, 6H), 1.75-1.82 (m, 2H), 2.29 (s, 3H), 2.55-2.62 (m, 1H), 2.65 (s, 2H), 2.73-2.80 (m, 1H), 3.05-3.12 (m, 1H), 3.73 (s, 2H), 3.87-3.94 (m, 1H), 4.13-4.21 (m, 1H), 6.39 (br. s., 2H), 6.92 (s, 1H), 8.18 (s, 1H).

HRMS (ESI+): calcd. for $C_{23}H_{30}N_9O_2S$ [M+H]$^+$ 496.2238 found 496.2241.

Example 6

8-amino-4,4-dimethyl-N-(4-{[4-(2-oxo-1,3-oxazolidin-3-yl)piperidin-1-yl]carbonyl}phenyl)-4,5-dihydro-1H-pyrazolo[4,3-h]quinazoline-3-carboxamide (I), Cpd 56

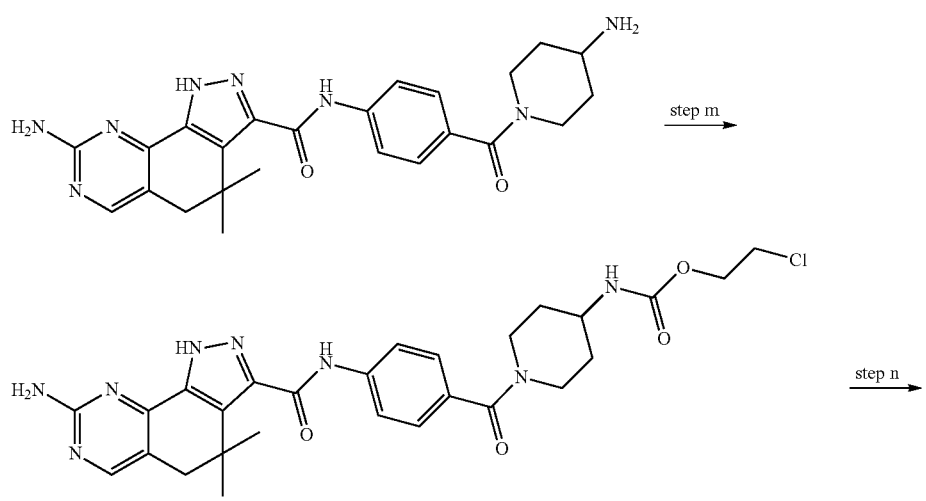

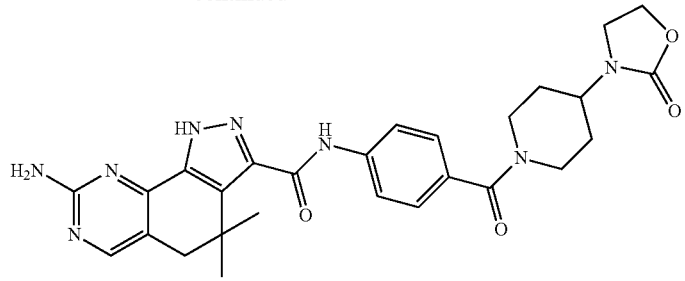

Step m

2-Chloroethyl [1-(4-{[(8-amino-4,4-dimethyl-4,5-dihydro-1H-pyrazolo[4,3-h]quinazolin-3-yl)carbonyl]amino}benzoyl)piperidin-4-yl]carbamate (I), Cpd 55

[R1=R2=R3'=R4'=H, R3=R4=($C_1$-$C_6$)alkyl, y=1, L=CONR8, z=n=0, A=aryl, R5=CONR6R7, R6 and R7=taken together form an optionally substituted heterocyclyl group, R8=H]

8-Amino-N-{4-[(4-aminopiperidin-1-yl)carbonyl]phenyl}-4,4-di methyl-4,5-dihydro-1H-pyrazolo[4,3-h]quinazoline-3-carboxamide (40 mg, 0.087 mmol) in dry THF (0.8 mL) was treated with DIPEA (0.022 mL, 0.13 mmol), cooled to −20° C. and treated dropwise with 2-chloroethyl chloroformate (0.01 mL, 0.13 mmol) in THF (0.3 mL). After 1 h, the reaction was allowed to reach rt and stirred for 2 h. The volatiles were removed in vacuo, the crude was purified by column chromatography over silica gel (DCM: 7 N $NH_3$ in MeOH=95:5) affording the title compound (10 mg, 20%).

HRMS (ESI+): calcd. for $C_{27}H_{32}ClN_8O_4$ [M+H]$^+$ 567.2230; found 567.2234.

Operating in an analogous way, but employing suitably substituted reagents, the following compounds were obtained:

8-amino-N-[4-({4-[(4-hydroxybutanoyl)amino]piperidin-1-yl}carbonyl)phenyl]-4,4-dimethyl-4,5-dihydro-1H-pyrazolo[4,3-h]quinazoline-3-carboxamide (I), Cpd 53

[R1=R2=R3'=R4'=H, R3=R4=($C_1$-$C_6$)alkyl, y=1, L=CONR8, z=n=0, A=aryl, R5=CONR6R7, R6 and R7=taken together form an optionally substituted heterocyclyl group, R8=H]

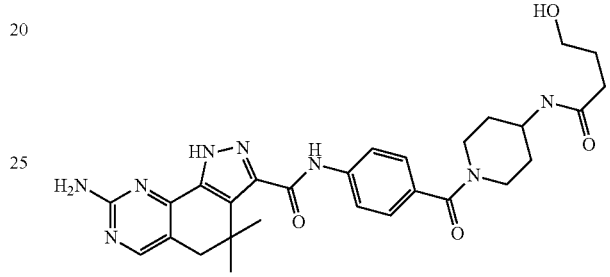

$^1$H NMR (499.7 MHz, DMSO-$d_6$) δ ppm 1.26-1.43 (m, 2H), 1.34 (s, 3H), 1.57-1.65 (m, 2H), 1.169-1.82 (m, 2H), 2.09 (t, J=7.5 Hz, 2H), 2.65 (s, 2H), 2.89-3.20 (m, 2H), 3.35-3.39 (m, 2H), 3.55-3.74 (m, 1H), 3.75-3.88 (m, 1H), 4.17-4.38 (m, 1H), 4.45 (t, J=5.2 Hz, 1H), 6.38 (br. s., 2H), 7.35 (d, J=8.5 Hz, 2H), 7.80 (d, J=7.6 Hz, 1H), 7.87 (d, J=8.5 Hz, 2H), 8.18 (s, 1H), 10.47 (br. s., 1H), 14.07 (br. s., 1H).

HRMS (ESI+): calcd. for $C_{28}H_{35}N_8O_4$ [M+H]$^+$ 547.2776; found 547.2786.

8-amino-N-[4-({4-[(4-chlorobutanoyl)amino]piperidin-1-yl}carbonyl)phenyl]-4,4-dimethyl-4,5-dihydro-1H-pyrazolo[4,3-h]quinazoline-3-carboxamide (I), Cpd 54

[R1=R2=R3'=R4'=H, R3=R4=($C_1$-$C_6$)alkyl, y=1, L=CONR8, z=n=0, A=aryl, R5=CONR6R7, R6 and R7=taken together form an optionally substituted heterocyclyl group, R8=H]

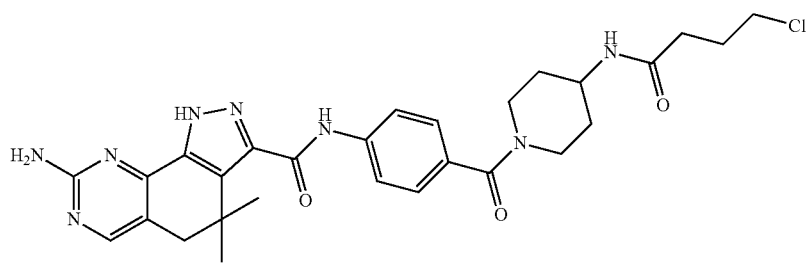 [SMILES: CC1(C)Cc2cnc(N)nc2-c2[nH]nc(C(=O)Nc3ccc(C(=O)N4CCC(NC(=O)CCCCl)CC4)cc3)c21]

¹H NMR (499.7 MHz, DMSO-d₆) δ ppm 1.34 (s, 6H), 1.69-1.84 (m, 2H), 1.88-1.98 (m, 2H), 2.19-2.24 (m, 2H), 2.66 (s, 2H), 2.91-3.30 (m, 2H), 3.62-3.67 (m, 2H), 3.76-3.89 (m, 1H), 4.10-4.40 (m, 1H), 6.38 (br. s., 2H), 7.35 (d, J=8.5 Hz, 2H), 7.87 (d, J=8.5 Hz, 2H), 7.91 (d, J=7.8 Hz, 1H), 8.19 (s, 1H), 10.46 (s, 1H), 14.11 (s, 1H).

HRMS (ESI+): calcd. for $C_{28}H_{34}ClN_8O_3$ [M+H]⁺ 565.2437; found 565.2441.

Step n

8-Amino-4,4-dimethyl-N-(4-{[4-(2-oxo-1,3-oxazolidin-3-yl)piperidin-1-yl]carbonyl}phenyl)-4,5-dihydro-1H-pyrazolo[4,3-h]quinazoline-3-carboxamide (I), Cpd 56

[R1=R2=R3'=R4'=H, R3=R4=(C₁-C₆)alkyl, y=1, L=CONR8, z=n=0, A=aryl, R5=CONR6R7, R6 and R7=taken together form an optionally substituted heterocyclyl group, R8=H]

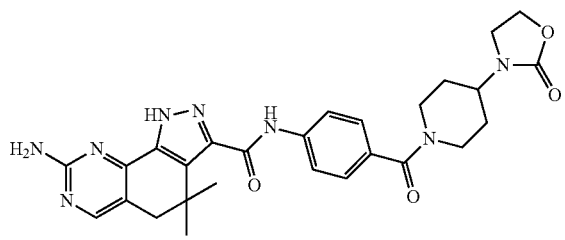 [SMILES: CC1(C)Cc2cnc(N)nc2-c2[nH]nc(C(=O)Nc3ccc(C(=O)N4CCC(N5CCOC5=O)CC4)cc3)c21]

2-Chloroethyl [1-(4-{[(8-amino-4,4-dimethyl-4,5-dihydro-1H-pyrazolo[4,3-h]quinazolin-3-yl)carbonyl]amino}benzoyl) piperidin-4-yl]carbamate (10 mg, 0.018 mmol) in dry DMF (0.350 mL), under argon and at rt, was treated with NaH (2.5 mg, 60% dispersion in mineral oil, 0.062 mmol). After 4 h the mixture was poured into water (7 mL) and partitioned with DCM several times. The combined organic layers were dried over Na₂SO₄ and evaporated to dryness. The crude was purified by column chromatography over silica gel (DCM: 8% MeOH) to afford 4 mg of title compound (43%).

¹H NMR (499.7 MHz, DMSO-d₆) δ ppm 1.34 (s, 6H), 1.56-1.77 (m, 4H), 2.65 (s, 2H), 2.89 (s, 2H), 2.72-3.22 (m, 2H), 3.49-3.55 (m, 2H), 3.60-3.92 (m, 1H), 3.73-3.83 (m, 1H), 4.22-4.29 (m, 2H), 4.36-4.67 (m, 1H), 6.38 (br. s., 2H), 7.40 (d, J=8.5 Hz, 2H), 7.87 (d, J=8.5 Hz, 2H), 8.19 (s, 1H), 10.46 (br. s., 1H), 14.09 (br. s., 1H).

HRMS (ESI+): calcd. for $C_{27}H_{31}N_8O_4$ [M+H]⁺ 531.2463; found 531.2461.

Example 7

Tert-butyl[1-(3-{[(8-amino-1,4,4-trimethyl-4,5-dihydro-1H-pyrazolo[4,3-h]quinazolin-3-yl)carbonyl]amino}benzyl)piperidin-4-yl]carbamate (Im)', Cpd 103

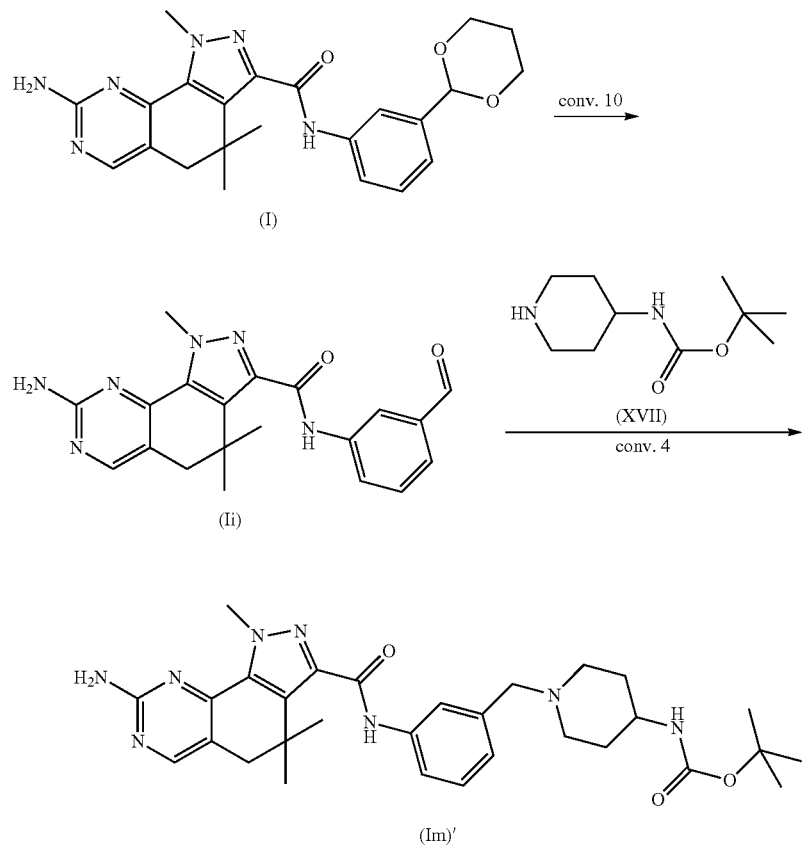

Conv. 10

8-Amino-N-(3-formylphenyl)-1,4,4-trimethyl-4,5-dihydro-1H-pyrazolo[4,3-h]quinazoline-3-carboxamide (Ii), Cpd 100

[R1=R3'=R4'=H, R2=R3=R4=(C$_1$-C$_6$)alkyl, y=1, L=CONR8, z=n=0, A=aryl, R5=COR6, R6=R8=H]

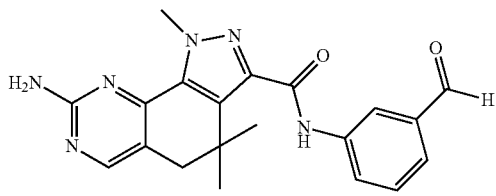 [SMILES: Cn1nc(C(=O)Nc2cccc(C=O)c2)c2c1-c1nc(N)ncc1CC2(C)C]

8-Amino-N-[3-(1,3-dioxan-2-yl)phenyl]-1,4,4-trimethyl-4,5-dihydro-1H-pyrazolo[4,3-h]quinazoline-3-carboxamide (110 mg, 0.25 mmol) in THF (5 mL) was treated with 1 N HCl (2 mL, 2 mmol) and stirred at rt for 4 h. The volatiles were removed under reduced pressure and the residue was partitioned between water (10 mL) and EtOAc (3×10 mL). The combined extracts were dried over Na$_2$SO$_4$ and evaporated to leave the title compound as white solid (85 mg, 90%).

$^1$H NMR (499.7 MHz, DMSO-d$_6$) δ ppm 1.33 (s, 6H), 2.64 (s, 2H), 4.37 (s, 3H), 6.66 (br. s., 2H), 7.55-7.61 (m, 1H), 7.63-7.67 (m, 1H), 8.02 (d, J=8.2 Hz, 1H), 8.19 (s, 1H), 8.45 (s, 1H), 10.00 (s, 1H), 10.61 (s, 1H).

HRMS (ESI+): calcd. for C$_{20}$H$_{21}$N$_6$O$_2$[M+H]$^+$ 377.1721; found 377.1720.

Operating in an analogous way, but employing suitably substituted compounds (I), the following compound was obtained:

8-amino-N-(3-formylphenyl)-4,4-dimethyl-4,5-dihydro-1H-pyrazolo[4,3-h]quinazoline-3-carboxamide (Ii), Cpd 107

[R1=R2=R3'=R4'=H, R3=R4=(C$_1$-C$_6$)alkyl, y=1, L=CONR8, z=n=0, A=aryl, R5=COR6, R6=R8=H]

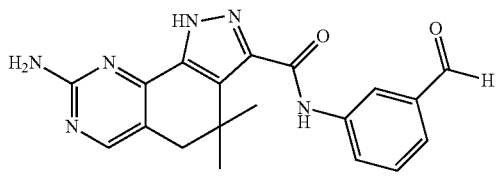 [SMILES: CC1(C)Cc2cnc(N)nc2-c2[nH]nc(C(=O)Nc3cccc(C=O)c3)c21]

$^1$H NMR (499.7 MHz, DMSO-d$_6$) δ ppm 1.35 (s, 6H), 2.67 (s, 2H), 6.41 (br. s., 2H), 7.52-7.62 (m, 1H), 7.65 (m, 1H), 8.03 (d, J=7.8 Hz, 1H), 8.20 (s, 1H), 8.47 (m, 1H), 10.00 (s, 1H), 10.58 (br. s., 1H), 14.14 (br. s., 1H).

HRMS (ESI+): calcd. for C$_{19}$H$_{19}$N$_6$O$_2$[M+H]$^+$ 363.1564; found 363.1565.

Conv. 4

Tert-butyl [1-(3-{[(8-amino-1,4,4-trimethyl-4,5-dihydro-1H-pyrazolo[4,3-h]quinazolin-3-yl)carbonyl]amino}benzyl)piperidin-4-yl]carbamate (Im)', Cpd 103

[R1=R3'=R4'=H, R2=R3=R4=(C$_1$-C$_6$)alkyl, y=1, L=CONR8, z=0, A=aryl, n=1, Rc=Rd=H, R5=NR6R7, R6 and R7=taken together form an optionally substituted heterocyclyl group, R8=H]

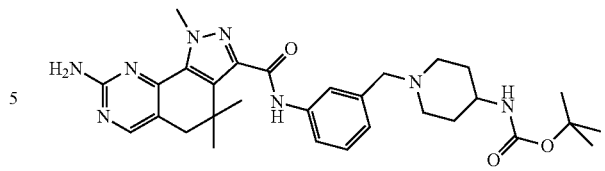

8-Amino-N-(3-formylphenyl)-1,4,4-trimethyl-4,5-dihydro-1H-pyrazolo[4,3-h]quinazoline-3-carboxamide (50 mg, 0.132 mmol) and 4-(N-Boc-amino)piperidine (XXVII) (40 mg, 0.199 mmol) in DMF (3 mL) were stirred for 2 h, then sodium triacetoxyborohydride (70 mg, 0.33 mmol) and AcOH (0.008 mL, 0.132 mmol) were added. The reaction was stirred at rt overnight. Volatiles were removed in vacuo. The residue was partitioned between DCM (20 mL) and saturated aqueous NaHCO$_3$ (5 mL). The organic layer was washed with brine, dried over Na$_2$SO$_4$, filtered and evaporated to dryness. The crude was purified by column chromatography over silica gel (DCM: 7 N NH$_3$ in MeOH=90:1) yielding the title compound (35 mg, 47%).

$^1$H NMR (499.7 MHz, DMSO-d$_6$) δ ppm 1.32 (s, 6H), 1.33-1.43 (m, 2H), 1.37 (s, 9H), 1.62-1.71 (m, 2H), 1.89-1.99 (m, 2H), 2.62 (s, 2H), 2.73-2.79 (m, 2H), 3.11-3.27 (m, 1H), 3.40 (br. s., 2H), 4.35 (s, 3H), 6.60 (br. s., 2H), 6.78 (d, J=7.9 Hz, 1H), 7.00 (d, J=7.6 Hz, 1H), 7.26 (t, J=8.1, 7.6 Hz, 1H), 7.65 (d, J=8.1 Hz, 1H), 7.73 (s, 1H), 8.18 (s, 1H), 10.24 (s, 1H).

HRMS (ESI+): calcd. for C$_{30}$H$_{41}$N$_8$O$_3$ [M+H]$^+$ 561.3296; found 561.3302.

Operating in an analogous way, but employing suitably substituted compounds (I) and reagents (XXVII), the following compounds were obtained:

8-amino-1,4,4-trimethyl-N-{3-[(4-methyl-1,4'-bipiperidin-1'-yl)methyl]phenyl}-4,5-dihydro-1H-pyrazolo[4,3-h]quinazoline-3-carboxamide (Im)', Cpd 111

[R1=R3'=R4'=H, R2=R3=R4=(C$_1$-C$_6$)alkyl, y=1, L=CONR8, z=0, A=aryl, n=1, Rc=Rd=H, R5=NR6R7, R6 and R7=taken together form an optionally substituted heterocyclyl group, R8=H]

$^1$H NMR (499.7 MHz, DMSO-d$_6$) δ ppm 0.86 (d, J=6.5 Hz, 3H), 1.01-1.12 (m, 2H), 1.22-1.34 (m, 1H), 1.32 (s, 6H), 1.39-1.48 (m, 2H), 1.53-1.61 (m, 2H), 1.62-1.69 (m, 2H), 1.85-1.93 (m, 2H), 2.05-2.13 (m, 2H), 2.16-2.26 (m, 1H), 2.62 (s, 2H), 2.76-2.88 (m, 4H), 3.40 (s, 2H), 4.35 (s, 3H), 6.60 (br. s., 2H), 6.99 (d, J=7.6 Hz, 1H), 7.25 (t, J=7.6, 8.2 Hz, 1H), 7.65 (d, J=8.2 Hz, 1H), 7.73 (s, 1H), 8.18 (s, 1H), 10.23 (s, 1H).

HRMS (ESI+): calcd. for C$_{31}$H$_{43}$N$_8$O [M+H]$^+$ 543.3555; found 543.3563.

8-amino-N-[3-(1,4'-bipiperidin-1'-ylmethyl)phenyl]-1,4,4-trimethyl-4,5-dihydro-1H-pyrazolo[4,3-h]quinazoline-3-carboxamide (Im)', Cpd 109

[R1=R3'=R4'=H, R2=R3=R4=(C$_1$-C$_6$)alkyl, y=1, L=CONR8, z=0, A=aryl, n=1, Rc=Rd=H, R5=NR6R7, R6 and R7=taken together form an optionally substituted heterocyclyl group, R8=H]

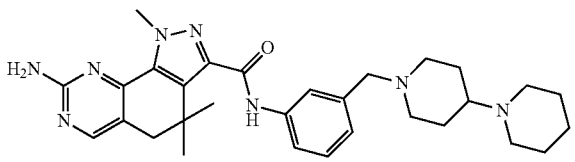 [SMILES: Cn1nc(C(=O)Nc2cccc(CN3CCC(N4CCCCC4)CC3)c2)c2c1-c1nc(N)ncc1CC2(C)C]

$^1$H NMR (499.7 MHz, DMSO-d$_6$) δ ppm 1.31 (s, 6H). 1.33-1.50 (m, 8H), 1.62-1.68 (m, 2H), 1.83-1.94 (m, 2H), 2.12-2.21 (m, 1H), 2.39-2.46 (m, 4H), 2.62 (s, 2H), 2.80-2.87 (m, 2H), 3.40 (s, 2H), 4.35 (s, 3H), 6.60 (br. s., 2H), 6.99 (d, J=7.6 Hz, 1H), 7.26 (dd, J=7.6, 8.5 Hz, 1H), 7.65 (d, J=8.5 Hz, 1H), 7.72 (m, 1H), 8.18 (s, 1H), 10.23 (s, 1H).

HRMS (ESI+): calcd. for C$_{30}$H$_{41}$N$_8$O [M+H]$^+$ 529.3398; found 529.3405.

8-amino-N-(3-{[4-(dimethylamino)piperidin-1-yl]methyl}phenyl)-1,4,4-trimethyl-4,5-dihydro-1H-pyrazolo[4,3-h]quinazoline-3-carboxamide (Im)', Cpd 101

[R1=R3'=R4'=H, R2=R3=R4=(C$_1$-C$_6$)alkyl, y=1, L=CONR8, z=0, A=aryl, n=1, Rc=Rd=H, R5=NR6R7, R6 and R7=taken together form an optionally substituted heterocyclyl group, R8=H]

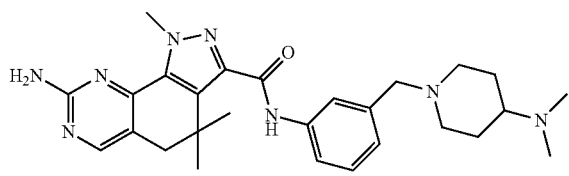 [SMILES: CN(C)C1CCN(Cc2cccc(NC(=O)c3nn(C)c4c3C(C)(C)Cc3cnc(N)nc3-4)c2)CC1]

$^1$H NMR (499.7 MHz, DMSO-d$_6$) δ ppm 1.32 (s, 6H), 1.33-1.43 (m, 2H), 1.65-1.73 (m, 2H), 1.87-1.94 (m, 2H), 1.98-2.06 (s, 1H), 2.15 (s, 6H), 2.62 (s, 2H), 2.80-2.87 (m, 2H), 3.41 (s, 2H), 4.35 (s, 3H), 6.60 (br. s., 2H), 7.00 (d, J=7.5 Hz, 1H), 7.26 (dd, J=7.9, 7.5 Hz, 1H), 7.66 (d, J=7.9 Hz, 1H), 7.73 (m, 1H), 8.18 (s, 1H), 10.23 (s, 1H).

HRMS (ESI+): calcd. for C$_{27}$H$_{37}$N$_8$O [M+H]$^+$ 489.3085; found 489.3080.

8-amino-N-{3-[(dimethylamino)methyl]phenyl}-1,4,4-trimethyl-4,5-dihydro-1H-pyrazolo[4,3-h]quinazoline-3-carboxamide (Im)', Cpd 102

[R1=R3'=R4'=H, R2=R3=R4=(C$_1$-C$_6$)alkyl, y=1, L=CONR8, z=0, A=aryl, n=1, Rc=Rd=H, R5=NR6R7, R6=R7=(C$_1$-C$_6$)alkyl, R8=H]

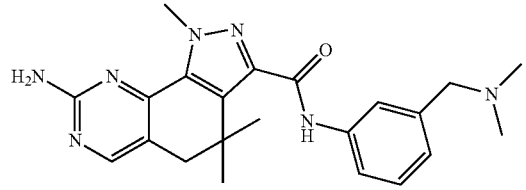 [SMILES: CN(C)Cc1cccc(NC(=O)c2nn(C)c3c2C(C)(C)Cc2cnc(N)nc2-3)c1]

$^1$H NMR (499.7 MHz, DMSO-d$_6$) δ ppm 1.32 (s, 6H), 2.16 (s, 6H), 2.62 (s, 2H), 3.37 (br. s., 2H), 4.35 (s, 3H), 6.60 (br. s., 2H), 7.00 (d, J=7.6 Hz, 1H), 7.26 (dd, J=8.2, 7.8 Hz, 1H), 7.62 (d, J=8.2 Hz, 1H), 7.80 (s, 1H), 8.18 (s, 1H), 10.23 (s, 1H).

HRMS (ESI+): calcd. for C$_{22}$H$_{28}$N$_7$O [M+H]$^+$ 406.2350; found 406.2350.

8-amino-N-[3-(1,4'-bipiperidin-1'-ylmethyl)phenyl]-4,4-dimethyl-4,5-dihydro-1H-pyrazolo[4,3-h]quinazoline-3-carboxamide (Im)', Cpd 110

[R1=R2=R3'=R4'=H, R3=R4=(C$_1$-C$_6$)alkyl, y=1, L=CONR8, z=0, A=aryl, n=1, Rc=Rd=H, R5=NR6R7, R6 and R7=taken together form an optionally substituted heterocyclyl group, R8=H]

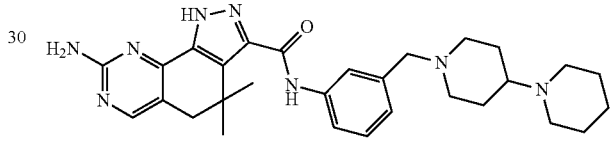

$^1$H NMR (499.7 MHz, DMSO-d$_6$) δ ppm 1.33 (s, 6H), 1.33-1.50 (m, 8H) 1.62-1.67 (m, 2H), 1.85-1.92 (m, 2H), 2.12-2.21 (m, 1H), 2.38-2.47 (m, 4H), 2.65 (s, 2H), 2.81-2.88 (m, 2H), 3.40 (s, 2H), 6.37 (br. s., 2H), 6.99 (d, J=7.6 Hz, 1H), 7.26 (dd, J=7.6, 8.2 Hz, 1H), 7.65 (d, J=8.2 Hz, 1H), 7.74 (s, 1H), 8.18 (s, 1H), 10.22 (br. s., 1H), 14.02 (br. s., 1H).

HRMS (ESI+): calcd. for C$_{29}$H$_{39}$N$_8$O [M+H]$^+$ 515.3242; found 515.3253.

8-amino-4,4-dimethyl-N-{3-[(4-methyl-1,4'-bipiperidin-1'-yl)methyl]phenyl}-4,5-dihydro-1H-pyrazolo[4,3-h]quinazoline-3-carboxamide (Im)', Cpd 112

[R1=R2=R3'=R4'=H, R3=R4=(C$_1$-C$_6$)alkyl, y=1, L=CONR8, z=0, A=aryl, n=1, Rc=Rd=H, R5=NR6R7, R6 and R7=taken together form an optionally substituted heterocyclyl group, R8=H]

$^1$H NMR (499.7 MHz, DMSO-d$_6$) δ ppm 0.85 (d, J=6.5 Hz, 3H), 1.00-1.11 (m, 2H), 1.22-1.28 (m, 1H), 1.33 (s, 6H), 1.39-1.49 (m, 2H), 1.52-1.58 (m, 2H), 1.62-1.68 (m, 2H), 1.85-1.93 (m, 2H), 2.03-2.11 (m, 2H), 2.14-2.22 (m, 1H), 2.65 (s, 2H), 2.75-2.88 (m, 4H), 3.40 (s, 2H), 6.37 (br. s., 2H), 6.99 (d, J=7.5 Hz, 1H), 7.25 (dd, J=7.5, 8.2 Hz, 1H), 7.65 (d, J=8.2 Hz, 1H), 7.74 (s, 1H), 8.18 (s, 1H), 10.22 (br. s., 1H), 14.01 (br. s., 1H).

HRMS (ESI+): calcd. for $C_{30}H_{41}N_8O_3$[M+H]$^+$ 529.3398; found 529.3395.

tert-butyl [1-(3-{[(8-amino-4,4-dimethyl-4,5-dihydro-1H-pyrazolo[4,3-h]quinazolin-3-yl)carbonyl]amino}benzyl) piperidin-4-yl]carbamate (Im)', Cpd 114

[R1=R2=R3'=R4'=H, R3=R4=(C$_1$-C$_6$)alkyl, y=1, L=CONR8, z=0, A=aryl, n=1, Rc=Rd=H, R5=NR6R7, R6 and R7=taken together form an optionally substituted heterocyclyl group, R8=H]

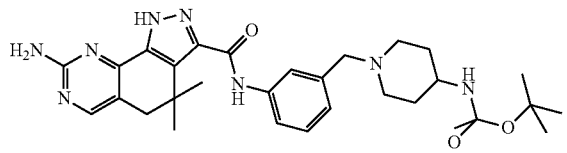 [SMILES: CC(C)(C)OC(C)(O)NC1CCN(Cc2cccc(NC(=O)c3n[nH]c4c3C(C)(C)Cc3cnc(N)nc3-4)c2)CC1]

$^1$H NMR (499.7 MHz, DMSO-d$_6$) δ ppm 1.34 (s, 6H), 1.37 (s, 9H), 1.37-1.43 (m, 2H), 1.63-1.70 (m, 2H), 1.90-1.99 (m, 2H), 2.65 (s, 2H), 2.72-2.80 (m, 1H), 3.40 (s, 2H), 3.16-3.26 (m, 1H), 3.40 (br. s., 2H), 6.37 (br. s., 2 H), 6.77 (d, J=7.8 Hz, 1H), 6.99 (d, J=7.7 Hz, 1H), 7.26 (dd, J=7.7, 8.4 Hz, 1H), 7.65 (d, J=8.4 Hz, 1H), 7.75 (br. s., 1H), 8.19 (s, 1H), 10.20 (br. s., 1H), 14.04 (br. s., 1H).

HRMS (ESI+): calcd. for $C_{30}H_{39}N_8O_3$ [M+H 547.3140; found 547.3142.

8-amino-N-(3-{[4-(dimethylamino)piperidin-1-yl]methyl}phenyl)-4,4-dimethyl-4,5-dihydro-1H-pyrazolo[4,3-h]quinazoline-3-carboxamide (Im)', Cpd 113

[R1=R2=R3'=R4'=H, R3=R4=(C$_1$-C$_6$)alkyl, y=1, L=CONR8, z=0, A=aryl, n=1, Rc=Rd=H, R5=NR6R7, R6 and R7=taken together form an optionally substituted heterocyclyl group, R8=H]

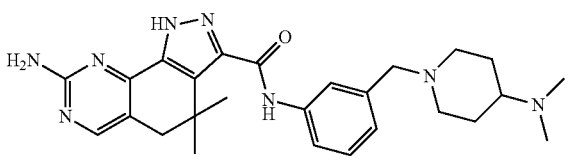 [SMILES: CN(C)C1CCN(Cc2cccc(NC(=O)c3n[nH]c4c3C(C)(C)Cc3cnc(N)nc3-4)c2)CC1]

$^1$H NMR (499.7 MHz, DMSO-d$_6$) δ ppm 1.34 (s, 6H), 1.34-1.46 (m, 2H), 1.67-1.77 (m, 2H), 1.88-1.97 (m, 2H), 2.06-2.33 (br. s., 7H), 2.65 (s, 2H), 2.81-2.89 (m, 2H), 3.42 (s, 2H), 6.37 (br. s., 2H), 7.00 (d, J=7.6 Hz, 1H), 7.26 (dd, J=7.6, 8.4 Hz, 1H), 7.65 (d, J=8.4 Hz, 1H), 7.75 (s, 1H), 8.18 (s, 1H), 10.23 (br. s., 1H), 14.02 (br. s., 1H).

HRMS (ESI+): calcd. for $C_{26}H_{35}N_8O$ [M+H]$^+$ 475.2929; found 475.2923.

Example 8

8-amino-N-(4-{2-[(3R)-3-(dimethylnitroryl)pyrrolidin-1-yl]-2-oxoethyl}-1,3-thiazol-2-yl)-4,4-dimethyl-4,5-dihydro-1H-pyrazolo[4,3-h]quinazoline-3-carboxamide (I), Cpd 154

[R1=R2=R3'=R4'=H, R3=R4=(C$_1$-C$_6$)alkyl, y=1, L=CONR8, z=0, A=heteroaryl, n=1, Rc=Rd=H, R5=CONR6R7, R6 and R7=taken together form an optionally substituted heterocyclyl group, R8=H]

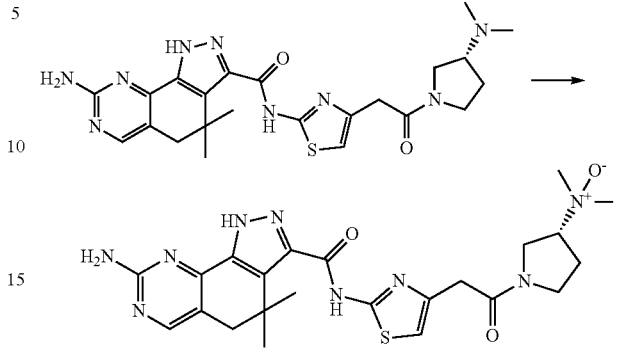

8-Amino-N-(4-{2-[(3R)-3-(dimethylamino)pyrrolidin-1-yl]-2-oxoethyl}-1,3-thiazol-2-yl)-4,4-dimethyl-4,5-dihydro-1H-pyrazolo[4,3-h]quinazoline-3-carboxamide (4.27 mg, 0.009 mmol) in DCM (0.5 mL) and MeOH (0.020 mL) was treated with mCPBA (2.7 mg, 0.009 mmol) and stirred at rt over 12 h. The volatiles were removed under reduced pressure and the residue was purified over silica gel (DCM: 7 N NH$_3$ in MeOH=from 9:1 to 8:1) to afford 4 mg of title compound (91%).

$^1$H NMR (499.7 MHz, DMSO-d$_6$) δ ppm 1.34 (s, 6H), 2.02-2.20 (m, 2H), 2.64 (s, 2H), 2.95-3.03 (s, 6H), 3.21-4.12 (m partially overlapped by water signal, 7H), 6.38 (br. s., 2H), 6.90 (br. s., 1H), 8.16 (s, 1H).

HRMS (ESI+): calcd. for $C_{23}H_{30}N_9O_3S$ [M+H]$^+$ 512.2187; found 512.2181.

Operating in an analogous way, but employing suitably substituted compounds (I), the following compound was obtained:

8-amino-1,4,4-trimethyl-N-(4-{2-[4-(1-oxidopiperidin-1-yl)piperidin-1-yl]-2-oxoethyl}-1,3-thiazol-2-yl)-4,5-dihydro-1H-pyrazolo[4,3-h]quinazoline-3-carboxamide (I), Cpd 153

[R1=R2=R3'=R4'=H, R3=R4=(C$_1$-C$_6$)alkyl, y=1, L=CONR8, z=0, A=heteroaryl, n=1, Rc=Rd=H, R5=CONR6R7, R6 and R7=taken together form an optionally substituted heterocyclyl group, R8=H]

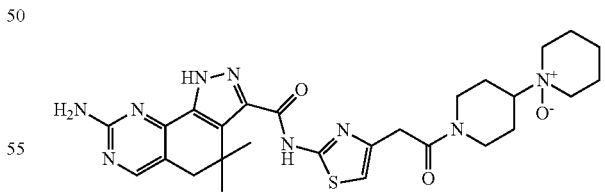

$^1$H NMR (499.7 MHz, DMSO-d$_6$) δ ppm 1.17-1.27 (m, 1H), 1.30 (s, 6H), 1.37-1.47 (m, 2H), 1.50-1.70 (m, 3H), 1.98-2.20 (m, 4H), 2.50-2.56 (m, 1H), 2.62 (s, 2H), 2.79-2.86 (m, 2H), 2.97-3.06 (m, 3H), 3.14-3.23 (m partially overlapped by water signal, 1H), 3.74 (br. s., 2H), 4.09-4.17 (m, 1H), 4.33 (s, 3H), 4.46-4.54 (m, 1H), 6.60 (br. s., 2H), 6.92 (br. s., 1H), 8.18 (s, 1H).

HRMS (ESI+): calcd. for $C_{28}H_{38}N_9O_3S$ [M+H]$^+$ 580.2813; found 580.2811.

Example 9

8-Amino-N-(4-{[(1-cyclohexylpiperidin-4-yl)amino]methyl}-1,3-thiazol-2-yl)-4,4-dimethyl-1-(tetrahydro-2H-pyran-2-yl)-4,5-dihydro-1H-pyrazolo[4,3-h]quinazoline-3-carboxamide (II)

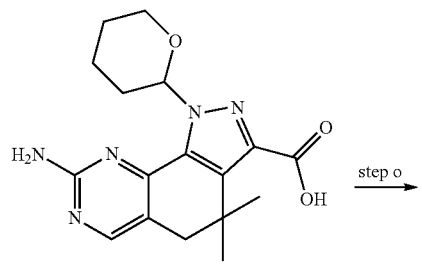

(IIIa)

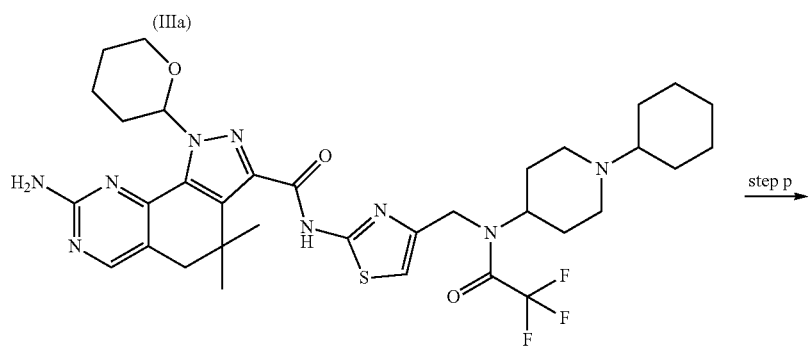

(XXIII)

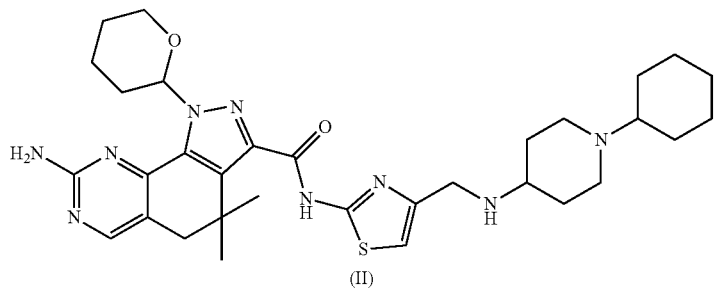

(II)

Step o

8-Amino-N-(4-{[(1-cyclohexylpiperidin-4-yl)(trifluoroacetyl)amino]methyl}-1,3-thiazol-2-yl)-4,4-dimethyl-1-(tetrahydro-2H-pyran-2-yl)-4,5-dihydro-1H-pyrazolo[4,3-h]quinazoline-3-carboxamide (XXIII)

8-Amino-4,4-dimethyl-1-(tetrahydro-2H-pyran-2-yl)-4,5-dihydro-1H-pyrazolo[4,3-h]quinazoline-3-carboxylic acid (IIIa) (50 mg, 0.145 mmol) in dry DMA (3 mL) was treated with DIPEA (0.25 mL, 1.45 mmol), N-[(2-amino-1,3-thiazol-4-yl)methyl]-N-(1-cyclohexylpiperidin-4-yl)-2,2,2-trifluoroacetamide (86 mg, 0.2 mmol) and TBTU (70 mg, 0.21 mmol). The reaction was left at rt for four days, then the mixture was diluted with EtOAc (20 mL) washed with a saturated aqueous NaHCO$_3$ (10 mL), water and brine. The combined organic extracts were dried over Na$_2$SO$_4$, filtered and evaporated. Purification by column chromatography over silica gel (DCM: 7 N NH$_3$ in MeOH=95:5) afforded the title compound (5 mg, 5%).

HRMS (ESI+): calcd. for C$_{34}$H$_{46}$F$_3$N$_9$O$_3$S [M+H]$^+$ 716.3313; found 716.3317.

Step p

8-Amino-N-(4-{[(1-cyclohexylpiperidin-4-yl)amino]methyl}-1,3-thiazol-2-yl)-4,4-dimethyl-1-(tetrahydro-2H-pyran-2-yl)-4,5-dihydro-1H-pyrazolo[4,3-h]quinazoline-3-carboxamide (II)

[R1=R3'=R4'=H, PG=tetrahydropyranyl, R3=R4=(C$_1$-C$_6$) alkyl, y=1, L=CONR8, z=0, A=heteroaryl, n=1, Rc=Rd=H, R5=NR6N7, R6=substituted heterocyclyl, R7=R8=H]

8-Amino-N-(4-{[(1-cyclohexylpiperidin-4-yl)(trifluoroacetyl)amino]methyl}-1,3-thiazol-2-yl)-4,4-dimethyl-1-(tetrahydro-2H-pyran-2-yl)-4,5-dihydro-1H-pyrazolo[4,3-h]quinazoline-3-carboxamide (4.7 mg, 0.007 mmol) in EtOH (0.2 mL) was treated with 5M NaOH (0.026 mL, 0.13 mmol) for 12 h. The reaction mixture was diluted with DCM and washed with water and brine. After anidrification over Na$_2$SO$_4$, filtration and evaporation, the title compound was isolated as a yellow solid (4 mg, 92%).

HRMS (ESI+): calcd. for $C_{32}H_{46}N_6O_2S$ [M+H]$^+$ 620.3490; found 620.3492.

Example 10

8-Amino-1-(2-methoxyethyl)-4,4-dimethyl-N-(4-methyl-1,3-thiazol-2-yl)-4,5-dihydro-1H-pyrazolo[4,3-h]quinazoline-3-carboxamide (Ic), Cpd 168

[R1=R3'=R4'=H, R2=R3=R4=(C$_1$-C$_6$)alkyl, y=0, L=CONR6aR7a, R6a=substituted heteroaryl, R7a=H]

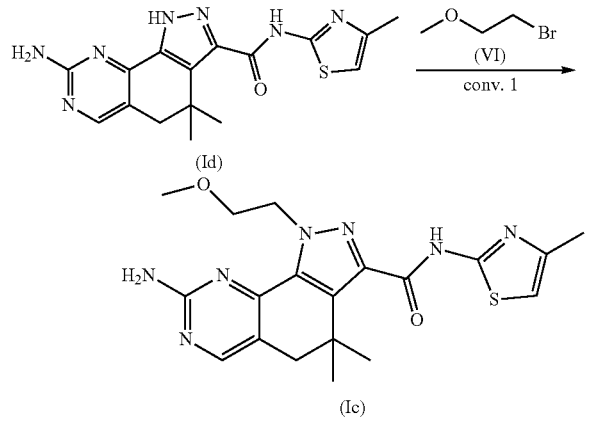

Conv. 1

NaH (60% dispersion in mineral oil, 9 mg, 0.211 mmol) was washed with 1 mL of n-hexane and left under an argon atmosphere for 20 minutes. A solution of 8-amino-4,4-dimethyl-4,5-dihydro-1H-pyrazolo[4,3-h]quinazoline-3-methyl thiazole (Id) (50 mg, 0.141 mmol) in dry DMF (1 mL) was added to NaH at 0° C. and the pale yellow solution was left at the same temperature for 1 h. 2-Bromoethyl methyl ether (VI) (0.016 mL, 0.171 mmol) was added and the solution was left at rt for 3 h. Then further 9 mg of NaH and 0.016 mL of 2-bromoethyl methyl ether were added and the solution turned light brown and was left at rt overnight. The solvent was then removed and the solid was dissolved in 15 mL of n-butanol and washed with 15 mL of water. After separation of the organic layer and solvent removal under reduced pressure, the crude was purified by column chromatography (DCM: 7 N NH$_3$ in MeOH=97:3) to give 10 mg of pure compound as whitish solid (17%).

$^1$H NMR (499.7 MHz, DMSO-d$_6$) δ ppm 1.31 (s, 6H), 2.30 (d, J=0.8 Hz, 3H), 2.63 (s, 2H), 3.24 (s, 3H), 3.86 (t, J=5.5 Hz, 2H), 5.03 (t, J=5.5 Hz, 2H), 6.61 (br. s., 2H), 6.83 (s, 1H), 8.19 (s, 1H), 12.05 (br. s., 1H).
HRMS (ESI+): calcd. for $C_{19}H_{24}N_7O_2S$ [M+H]$^+$ 414.1707; found 414.1711.

Operating in an analogous way, but employing suitably substituted compounds (I) and reagents (VI), the following compounds were obtained:

8-amino-1-ethyl-4,4-dimethyl-N-(4-methyl-1,3-thiazol-2-yl)-4,5-dihydro-1H-pyrazolo[4,3-h]quinazoline-3-carboxamide (Ic), Cpd 167

[R1=R3'=R4'=H, R2=R3=R4=(C$_1$-C$_6$)alkyl, y=0, L=CONR6aR7a, R6a=substituted heteroaryl, R7a=H]

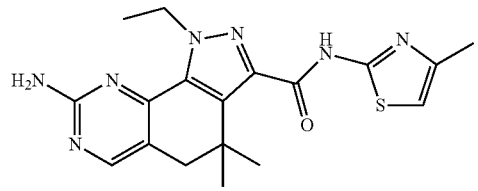 [SMILES: CCn1nc(C(=O)Nc2nc(C)cs2)c2c1-c1nc(N)ncc1CC2(C)C]

$^1$H NMR (499.7 MHz, DMSO-d$_6$) δ ppm 1.31 (s, 6H), 1.45 (t, J=7.2 Hz, 3H), 2.29 (d, J=0.8 Hz, 3H), 2.63 (s, 2H), 4.83 (q, J=7.2 Hz, 2H), 6.60 (br. s., 2H), 6.82 (d, J=0.8 Hz, 1H), 8.18 (s, 1H), 12.00 (s, 1H).
HRMS (ESI+): calcd. for $C_{18}H_{22}N_7OS$ [M+H]$^+$ 384.1601; found 384.1604.

8-amino-1-[2-(dimethylamino)ethyl]-4,4-dimethyl-N-(4-methyl-1,3-thiazol-2-yl)-4,5-dihydro-1H-pyrazolo[4,3-h]quinazoline-3-carboxamide (Ic), Cpd 169

[R1=R3'=R4'=H, R2=R3=R4=(C$_1$-C$_6$)alkyl, y=0, L=CONR6aR7a, R6a=substituted heteroaryl, R7a=H]

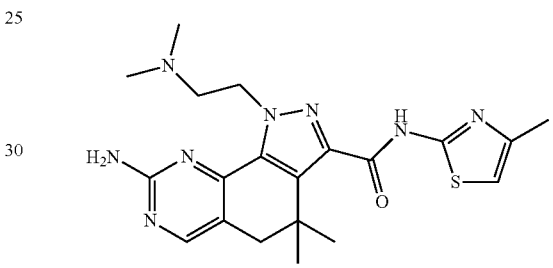

$^1$H NMR (499.7 MHz, DMSO-d$_6$) δ ppm 1.31 (s, 6H), 2.20 (br. s., 6H), 2.30 (d, J=0.8 Hz, 3H), 2.63 (s, 2H), 2.74-2.81 (br. s., 2H), 4.95 (t, J=6.6 Hz, 2H), 6.57 (br. s., 2H), 8.19 (s, 1H), 12.04 (br. s., 1H).
HRMS (ESI+): calcd. for $C_{20}H_{27}N_8OS$ [M+H]$^+$ 427.2023; found 427.2022.

8-amino-1-(cyanomethyl)-4,4-dimethyl-N-(4-methyl-1,3-thiazol-2-yl)-4,5-dihydro-1H-pyrazolo[4,3-h]quinazoline-3-carboxamide (Ic), Cpd 171

[R1=R3'=R4'=H, R2=R3=R4=(C$_1$-C$_6$)alkyl, y=0, L=CONR6aR7a, R6a=substituted heteroaryl, R7a=H]

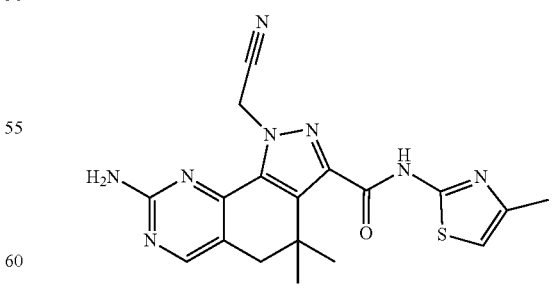

$^1$H NMR (500 MHz, DMSO-d$_6$) δ ppm 1.31 (s, 6H) 2.30 (s, 3H) 2.68 (s, 2H) 6.17 (s, 2H) 6.75 (br. s., 2H) 6.85 (s, 1H) 8.24 (s, 1H) 12.36 (br. s., 1H).
HRMS (ESI+): calcd. for $C_{18}H_{19}N_8OS$ [M+H]$^+$ 395.1397; found 395.1397.

8-amino-N,1-bis(cyanomethyl)-4,4-dimethyl-N-(4-methyl-1,3-thiazol-2-yl)-4,5-dihydro-1H-pyrazolo[4,3-h]quinazoline-3-carboxamide (Ic), Cpd 172

[R1=R3'=R4'=H, R2=R3=R4=(C$_1$-C$_6$)alkyl, y=0, L=CONR6aR7a, R6a=substituted heteroaryl, R7a=(C$_1$-C$_6$)alkyl]

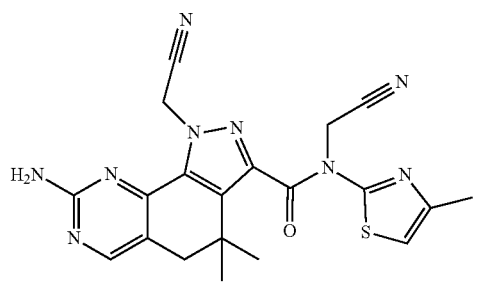 [SMILES: Cc1csc(N(CC#N)C(=O)c2nn(CC#N)c3c2C(C)(C)Cc2cnc(N)nc2-3)n1]

$^1$H NMR (500 MHz, DMSO-d$_6$) δ ppm 1.23 (s, 6H) 2.36 (d, J=1.83 Hz, 3H) 2.37 (s, 3H) 2.68 (s, 2H) 5.27 (s, 2H) 6.18 (s, 2H) 6.79 (s, 2H) 7.09 (s, 1H) 8.27 (s, 1H).

HRMS (ESI+): calcd. for C$_{20}$H$_{20}$N$_9$OS [M+H]$^+$ 434.1506; found 434.1507.

8-amino-N,1-diethyl-4,4-dimethyl-N-(4-methyl-1,3-thiazol-2-yl)-4,5-dihydro-1H-pyrazolo[4,3-h]quinazoline-3-carboxamide (Ic), Cpd 159

[R1=R3'=R4'=H, R2=R3=R4=(C$_1$-C$_6$)alkyl, y=0, L=CONR6aR7a, R6a=substituted heteroaryl, R7a=(C$_1$-C$_6$)alkyl]

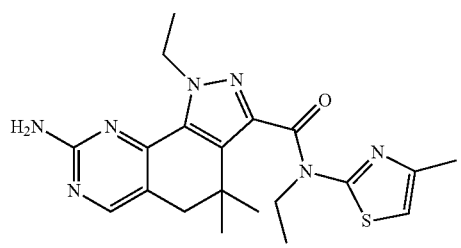 [SMILES: CCN(C(=O)c1nn(CC)c2c1C(C)(C)Cc1cnc(N)nc1-2)c1nc(C)cs1]

$^1$H NMR (499.7 MHz, DMSO-d$_6$) δ ppm 1.17 (s, 6H), 1.31 (t, J=6.9 Hz, 3H), 1.40 (t, J=7.1 Hz, 3H), 2.34 (s, 3H), 2.63 (s, 3H), 4.19 (d, J=6.9 Hz, 2H), 4.82 (d, J=7.1 Hz, 2H), 6.62 (br. s., 2H), 6.94 (m, 1H), 8.19 (s, 1H).

HRMS (ESI+): calcd. for C$_{20}$H$_{26}$N$_7$OS [M+H]$^+$ 412.1914; found 412.1913.

8-amino-4,4-dimethyl-N-{4-[(1-methylpiperidin-4-yl)carbamoyl]phenyl}-1-[3-(tetrahydro-2H-pyran-2-yloxy) propyl]-4,5-dihydro-1H-pyrazolo[4,3-h]quinazoline-3-carboxamide (Ia), Cpd 178

[R1=R3'=R4'=H, R2=R3=R4=(C$_1$-C$_6$)alkyl, y=1, L=CONR8, z=n=0, A=aryl, R5=CONR6R7, R6=substituted heterocyclyl, R7=R8=H]

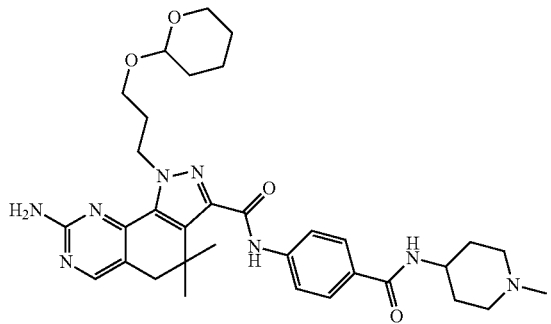 [SMILES: CN1CCC(NC(=O)c2ccc(NC(=O)c3nn(CCCOC4CCCCO4)c4c3C(C)(C)Cc3cnc(N)nc3-4)cc2)CC1]

HRMS (ESI+): calcd. for C$_{33}$H$_{46}$N$_8$O$_4$ [M+H]$^+$ 617.3558; found 617.3565.

8-amino-1-cyclopropyl-4,4-dimethyl-N-(4-methyl-1,3-thiazol-2-yl)-4,5-dihydro-1H-pyrazolo[4,3-h]quinazoline-3-carboxamide (Ic), Cpd 179

[R1=R3'=R4'=H, R2=(C$_3$-C$_5$)cycloalkyl, R3=R4=(C$_1$-C$_6$)alkyl, y=0, L=CONR6aR7a, R6a=substituted heteroaryl, R7a=H]

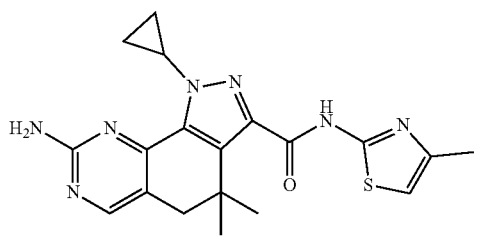 [SMILES: Cc1csc(NC(=O)c2nn(C3CC3)c3c2C(C)(C)Cc2cnc(N)nc2-3)n1]

HRMS (ESI+): calcd. for C$_{19}$H$_{22}$N$_7$OS [M+H]$^+$ 396.1601; found 396.1606.

8-amino-1-(2-{[tert-butyl(dimethyl)silyl]oxy}ethyl)-4,4-dimethyl-N-(4-methyl-1,3-thiazol-2-yl)-4,5-dihydro-1H-pyrazolo[4,3-h]quinazoline-3-carboxamide (Ic), Cpd 180

[R1=R3'=R4'=H, R2=R3=R4=(C$_1$-C$_6$)alkyl, y=0, L=CONR6aR7a, R6a=substituted heteroaryl, R7a=H]

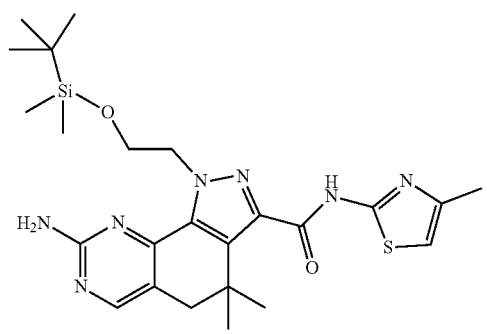 [SMILES: Cc1csc(NC(=O)c2nn(CCO[Si](C)(C)C(C)(C)C)c3c2C(C)(C)Cc2cnc(N)nc2-3)n1]

$^1$H NMR (500 MHz, DMSO-d$_6$) δ ppm 0.65 (s, 9H) 0.76 (s, 6H) 1.31 (s, 6H) 2.30 (s, 3H) 2.61 (s, 2H) 4.03 (t, J=5.11 Hz, 2H) 5.00 (t, J=5.11 Hz, 2H) 6.55 (br. s., 2H) 6.82 (s, 1H) 8.17 (s, 1H) 11.89 (s, 1H).

HRMS (ESI+): calcd. for $C_{24}H_{36}N_7O_2SSi$ $[M+H]^+$ 514.2415; found 514.2405.

8-amino-1-(2-amino-2-oxoethyl)-4,4-dimethyl-N-(4-methyl-1,3-thiazol-2-yl)-4,5-dihydro-1H-pyrazolo[4,3-h]quinazoline-3-carboxamide (Ic), Cpd 181

[R1=R3'=R4'=H, R2=R3=R4=($C_1$-$C_6$)alkyl, y=0, L=CONR6aR7a, R6a=substituted heteroaryl, R7a=H]

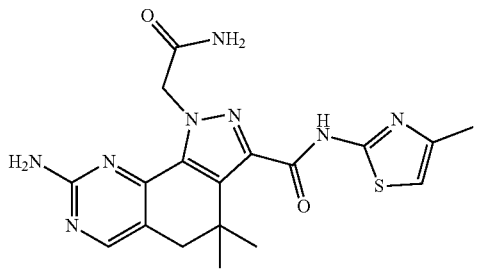 [SMILES: Cc1csc(NC(=O)c2nn(CC(N)=O)c3c2C(C)(C)Cc2cnc(N)nc2-3)n1]

$^1$H NMR (500 MHz, DMSO-$d_6$) δ ppm 1.32 (s, 6H) 2.29 (s, 3H) 2.65 (s, 2H) 5.47 (s, 2H) 6.54 (br. s., 2H) 6.83 (s, 1H) 7.29 (br. s., 1H) 7.48 (br., s. 1H) 8.19 (s, 1H) 12.03 (s, 1H).
HRMS (ESI+): calcd. for $C_{18}H_{21}N_8O_2S$ $[M+H]^+$ 413.1503; found 413.1507.

tert-butyl (2-{8-amino-4,4-dimethyl-3-[(4-methyl-1,3-thiazol-2-yl)carbamoyl]-4,5-dihydro-1H-pyrazolo[4,3-h]quinazolin-1-yl}ethyl)carbamate (Ic), Cpd 207

[R1=R3'=R4'=H, R2=R3=R4=($C_1$-$C_6$)alkyl, y=0, L=CONR6aR7a, R6a=substituted heteroaryl, R7a=H]

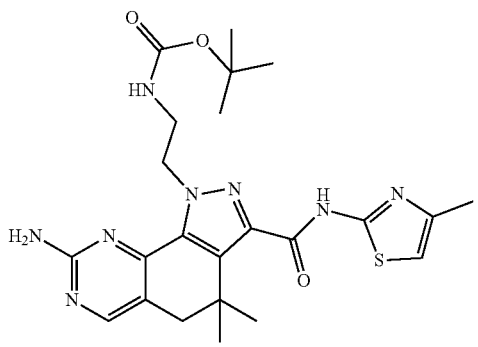 [SMILES: Cc1csc(NC(=O)c2nn(CCNC(=O)OC(C)(C)C)c3c2C(C)(C)Cc2cnc(N)nc2-3)n1]

$^1$H NMR (499.7 MHz, DMSO-$d_6$) δ ppm 1.31 (s, 6H), 1.33 (s, 9H), 2.30 (d, J=0.9 Hz, 3H), 2.63 (s, 3H), 3.48- 3.55 (m, 2H), 4.70 (t, J=6.4 Hz, 2H), 6.62 (br. s., 2H), 6.83 (s, 1H), 7.09 (t, J=5.9 Hz, 1H), 8.18 (s, 1H), 11.96 (s, 1H).
HRMS (ESI+): calcd. for $C_{23}H_{31}N_8O_3S$ $[M+H]^+$ 499.2235; found 499.2237.

8-amino-4,4-dimethyl-N-(4-methyl-1,3-thiazol-2-yl)-1-(oxetan-3-yl)-4,5-dihydro-1H-pyrazolo[4,3-h]quinazoline-3-carboxamide (Ic), Cpd 197

[R1=R3'=R4'=H, R2=heterocyclyl, R3=R4=($C_1$-$C_6$)alkyl, y=0, L=CONR6aR7a, R6a=substituted heteroaryl, R7a=H]

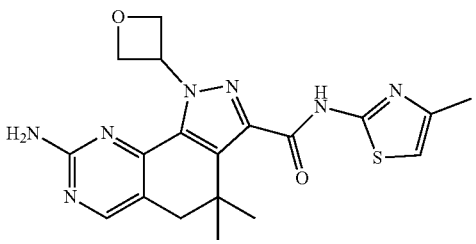 [SMILES: Cc1csc(NC(=O)c2nn(C3COC3)c3c2C(C)(C)Cc2cnc(N)nc2-3)n1]

$^1$H NMR (499.7 MHz, DMSO-$d_6$) δ ppm 1.33 (s, 6H), 2.31 (s, 3H), 2.64 (s, 2H), 5.00-5.04 (m, 2H), 5.12-5.16 (m, 2H), 6.44-6.51 (m, 1H), 6.67 (br. s., 2H), 6.84 (s, 1H), 8.18 (s, 1H), 12.34 (s, 1H).
HRMS (ESI+): calcd. for $C_{19}H_{22}N_7O_2S$ $[M+H]^+$ 412.1550; found 412.1555.

Example 11

8-Amino-1-(2-hydroxyethyl)-4,4-dimethyl-N-(4-methyl-1,3-thiazol-2-yl)-4,5-dihydro-1H-pyrazolo[4,3-h]quinazoline-3-carboxamide (I), Cpd 182

[R1=R3'=R4'=H, R2=R3=R4=($C_1$-$C_6$)alkyl, y=0, L=CONR6aR7a, R6a=substituted heteroaryl, R7a=H]

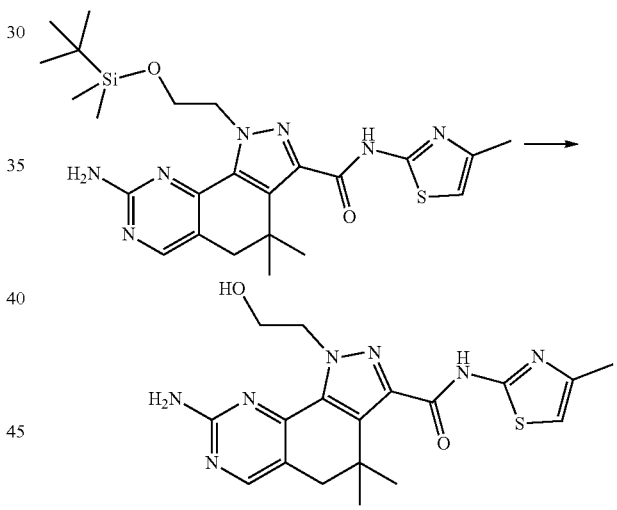

Deprotection

To a solution of 8-amino-1-(2-{[tert-butyl(dimethyl)silyl]oxy}ethyl)-4,4-dimethyl-N-(4-methyl-1,3-thiazol-2-yl)-4,5-dihydro-1H-pyrazolo[4,3-h]quinazoline-3-carboxamide (25 mg, 0.048 mmol) in THF (1 mL) at 0° C., TBAF (1M solution in THF, 0.073 mL, 0.073 mmol) was added and the reaction was let under stirring at rt overnight. After solvent removal, the mixture was diluted with water and extracted with n-butanol. The organic layer was taken to dryness under reduced pressure and the product was isolated by column chromatography (DCM:MeOH=95:5) as white solid (5.4 mg, 28%).

$^1$H NMR (500 MHz, DMSO-$d_6$) δ ppm 1.31 (s, 6H) 2.30 (s, 3H) 2.63 (s, 2H) 3.90 (q, J=5.85 Hz, 2H) 4.77-4.93 (m, 3H) 6.59 (br. s., 2H) 6.83 (s, 1H) 8.18 (s, 1H) 12.06 (br. s., 1H).
HRMS (ESI+): calcd. for $C_{18}H_{22}N_7O_2S$ $[M+H]^+$ 400.1550; found 400.1557.

Example 12

8-Amino-N-(4-{[(1-cycloheptylpiperidin-4-yl)oxy]methyl}-1,3-thiazol-2-yl)-4,4-dimethyl-4,5-dihydro-1H-pyrazolo[4,3-h]quinazoline-3-carboxamide trihydrochloride (I), Cpd 223

[R1=R2=R3'=R4'=H, R3=R4=(C$_1$-C$_6$)alkyl, y=1, L=CONR8, z=0, A=heteroaryl, n=1, Rc=Rd=H, R5=OR6, R6=substituted heterocyclyl, R8=H]

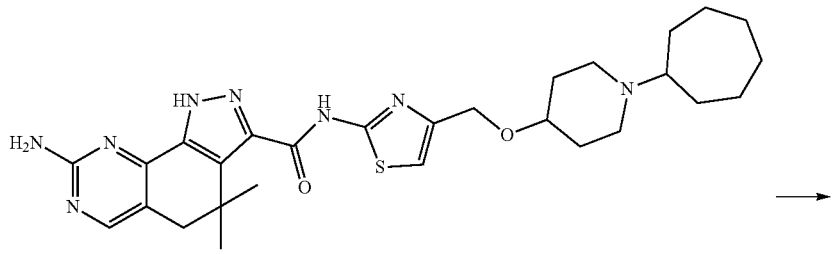

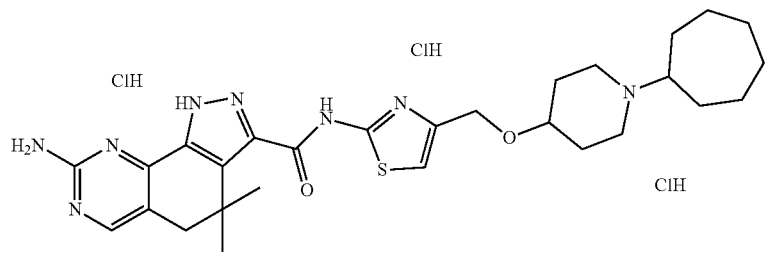

8-Amino-N-(4-{[(1-cycloheptylpiperidin-4-yl)oxy]methyl}-1,3-thiazol-2-yl)-4,4-dimethyl-4,5-dihydro-1H-pyrazolo[4,3-h]quinazoline-3-carboxamide (544 mg, 0.987 mmol) was suspended in absolute EtOH (54 mL) and treated with 2N HCl (1.48 mL, 2.963 mmol). The mixture turned to a solution and was let under stirring at room temperature for 30 min. The solvent was then removed under reduced pressure. After the addition of absolute EtOH (2 mL) and Et$_2$O (13 mL) under stirring, the white precipitate was filtered and dried under vacuo (609 mg, 93%).

$^1$H NMR (400.5 MHz, DMSO-d$_6$) δ ppm 1.36 (s, 6H), 1.33-2.21 (m, 14H), 2.74 (s, 2H), 2.95-3.19 (m, 3H), 3.23-3.34 (m, 2H), 3.59-3.68 (m partially overlapped by water signal, 1H), 3.76-3.87 (m, 1H), 4.53 (s, 2H), 7.16 and 7.21 (2×s, 1H), 7.74 (br. s., 3H), 8.29 (s, 1H), 9.86 (br.s., 1H), 9.95 (br.s., 1H), 12.34 (br. s., 1H).

HRMS (ESI+): calcd. for C$_{18}$H$_{22}$N$_7$O$_2$S [M+H]$^+$ 551.2911; found 551.2923.

Operating in an analogous way, but employing suitably substituted compounds (I), the following compounds were obtained:

8-amino-N-[4-({[1-(4,4-dimethylcyclohexyl)piperidin-4-yl]oxy}methyl)-1,3-thiazol-2-yl]-4,4-dimethyl-4,5-dihydro-1H-pyrazolo[4,3-h]quinazoline-3-carboxamide trihydrochloride (I), Cpd 221

[R1=R2=R3'=R4'=H, R3=R4=(C$_1$-C$_6$)alkyl, y=1, L=CONR8, z=0, A=heteroaryl, n=1, Rc=Rd=H, R5=OR6, R6=substituted heterocyclyl, R8=H]

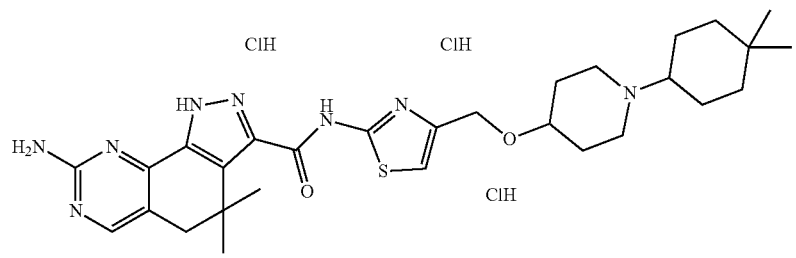 [SMILES: CC1(C)CCC(N2CCC(OCc3csc(NC(=O)c4n[nH]c5c4C(C)(C)Cc4cnc(N)nc4-5)n3)CC2)CC1 ; Cl ; Cl ; Cl]

$^1$H NMR (499.7 MHz, DMSO-d$_6$) δ ppm 0.89 (s, 6H), 1.16-1.26 (m, 2H), 1.35 (s, 6H), 1.42-1.49 (m, 2H), 1.55-1.68 (m, 2H), 1.74-1.83 (m, 1H), 1.84-1.93 (m, 2H), 2.00-2.05 (m, 2H), 2.13-2.21 (m, 1H), 2.74 (s, 2H), 2.92-3.14 (m, 3H), 3.27-3.33 (m, 2H), 3.58-3.66 (m, 1H), 4.53 (d, J=4.3 Hz, 2H), 7.17 and 7.21 (2×s, 1H), 7.67 (br. s., 3H), 8.29 (s, 1H), 9.98 (br. s., 1H), 12.36 (br. s., 1H), 14.58 (br. s., 1H).

HRMS (ESI+): calcd. for C$_{29}$H$_{41}$N$_8$O$_2$S [M+H]$^+$ 565.3068; found 565.3089.

8-amino-N-(4-{[(1-cycloheptylpiperidin-4-yl)oxy]methyl}-1,3-thiazol-2-yl)-5,5-dimethyl-4,5-dihydro-1H-pyrazolo[4,3-h]quinazoline-3-carboxamide trihydrochloride (I), Cpd 232

[R1=R2=R3'=R4'=H, R3=R4=(C$_1$-C$_6$)alkyl, y=1, L=CONR8, z=0, A=heteroaryl, n=1, Rc=Rd=H, R5=OR6, R6=substituted heterocyclyl, R8=H]

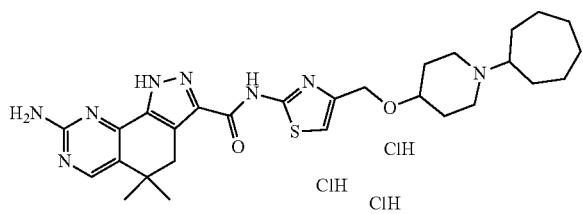 [SMILES: CC1(C)Cc2c(C(=O)Nc3nc(COC4CCN(C5CCCCCC5)CC4)cs3)n[nH]c2-c2nc(N)ncc21 ; Cl ; Cl ; Cl]

$^1$H NMR (499.7 MHz, DMSO-d$_6$) δ ppm 1.29 (s, 6H), 1.37-1.83 (m, 12H), 1.98-2.08 (m, 3H), 2.13-2.20 (m, 1H), 3.02 (s, 2H), 2.97-3.40 (m partially overlapped by water signal, 5H), 3.59-3.86 (m, 1H), 4.52 (s, 2H), 7.12 and 7.20 (2×s, 1H), 7.54 (br.s., 3H), 8.30 (s, 1H), 9.65-9.81 (br.s., 1H), 12.18 (br. s., 1H), 14.55 (br.s., 1H).

HRMS (ESI+): calcd. for C$_{27}$H$_{34}$F$_2$N$_9$O$_2$S [M+H]$^+$ 551.2911; found 551.2921.

Example 13

8-Amino-2-(2-hydroxyethyl)-4,4-dimethyl-N-(4-methyl-1,3-thiazol-2-yl)-4,5-dihydro-2H-pyrazolo[4,3-h]quinazoline-3-carboxamide (I), Cpd 196

[R1=R3'=R4'=H, R2=R3=R4=(C$_1$-C$_6$)alkyl, y=0, L=CONR6aR7a, R6a=substituted heteroaryl, R7a=H]

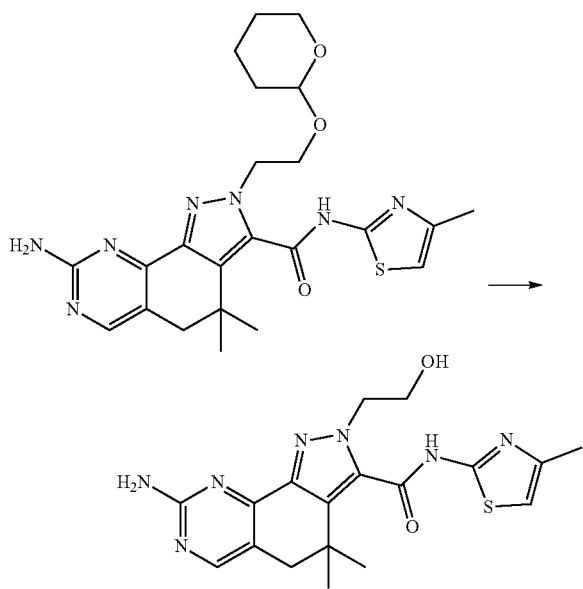

Deprotection

To a solution of 8-amino-4,4-dimethyl-N-(4-methyl-1,3-thiazol-2-yl)-2-[2-(tetrahydro-2H-pyran-2-yloxy)ethyl]-4,5-dihydro-2H-pyrazolo[4,3-h]quinazoline-3-carboxamide (24 mg, 0.05 mmol) in DCM (1.4 mL), TFA (0.36 mL) was added and the reaction was let under stirring at rt overnight. The mixture was then neutralized with a saturated solution of NaHCO$_3$ and extracted with DCM. The organic layer was dried over Na$_2$SO$_4$, filtered and taken to dryness under reduced pressure. The product was isolated by column chromatography (DCM:MeOH=95:5) as white solid (12 mg, 60%).

$^1$H NMR (499.7 MHz, DMSO-d$_6$) δ ppm 1.20 (m, 6H), 2.29 (s, 3H), 2.58 (s, 2H), 3.77 (t, J=5.6 Hz, 2H), 4.25 (br. s., 2H), 5.39 (br. s., 1H), 6.50 (s, 2H), 6.90 (br. s., 1H), 8.12 (s, 1H), 12.79 (br. s., 1H).

HRMS (ESI+): calcd. for C$_{18}$H$_{22}$N$_7$O$_2$S [M+H]$^+$ 400.1550; found 400.1555.

Operating in an analogous way, but employing suitably substituted compounds (I), the following compounds were obtained:

8-amino-1-(3-hydroxypropyl)-4,4-dimethyl-N-{4-[(1-methylpiperidin-4-yl)carbamoyl]phenyl}-4,5-dihydro-1H-pyrazolo[4,3-h]quinazoline-3-carboxamide (I), Cpd 9

[R1=R3'=R4'=H, R2=R3=R4=(C$_1$-C$_6$)alkyl, y=1, L=CONR8, z=n=0, A=aryl, R5=CONR6R7, R6=substituted heterocyclyl, R7=R8=H]

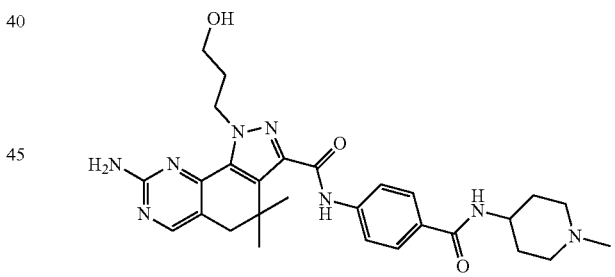

$^1$H NMR (500 MHz, DMSO-d$_6$) δ ppm 1.32 (s, 6H) 1.51-1.65 (m, 2H) 1.70-1.79 (m, 2H) 1.89-1.97 (m, 2H) 1.98-2.07 (m, 2H) 2.16 (s, 3H) 2.62 (s, 2H) 2.72-2.83 (m, 2H) 3.48-3.56 (m, 2H) 3.65-3.79 (m, 1H) 4.55 (br. s., 1H) 4.84 (t, J=7.3 Hz, 2H) 6.56 (br. s., 2H) 7.79-7.91 (m, 4H) 8.14 (d, J=7.78 Hz, 1H) 8.18 (s, 1H) 10.39 (s, 1H).

HRMS (ESI+): calcd. for C$_{28}$H$_{37}$N$_8$O$_3$ [M+H]$^+$ 533.2983; found 533.2997.

8-amino-1-(2-aminoethyl)-4,4-dimethyl-N-(4-methyl-1,3-thiazol-2-yl)-4,5-dihydro-1H-pyrazolo[4,3-h]quinazoline-3-carboxamide (I), Cpd 208

[R1=R3'=R4'=H, R2=R3=R4=(C$_1$-C$_6$)alkyl, y=0, L=CONR6aR7a, R6a=substituted heteroaryl, R7a=H]

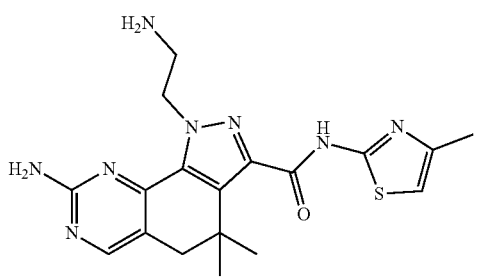 [SMILES: Cc1csc(NC(=O)c2nn(CCN)c3c2C(C)(C)Cc2cnc(N)nc2-3)n1]

$^1$H NMR (499.7 MHz, DMSO-d$_6$) δ ppm 1.31 (s, 6H), 2.29 (d, J=0.9 Hz, 3H), 2.63 (s, 2H), 2.99 (t, J=6.4 Hz, 2H), 4.77 (t, J=6.4 Hz, 2H), 6.62 (s, 2H), 6.82 (d, J=0.9 Hz, 1H), 8.18 (s, 1H).

HRMS (ESI+): calcd. for C$_{18}$H$_{23}$N$_8$OS [M+H]$^+$ 399.1710; found 399.1712.

Example 14

N-(8-Amino-1,4,4-trimethyl-4,5-dihydro-1H-pyrazolo[4,3-h]quinazolin-3-yl)-3-methoxybenzamide (Ic), Cpd 214

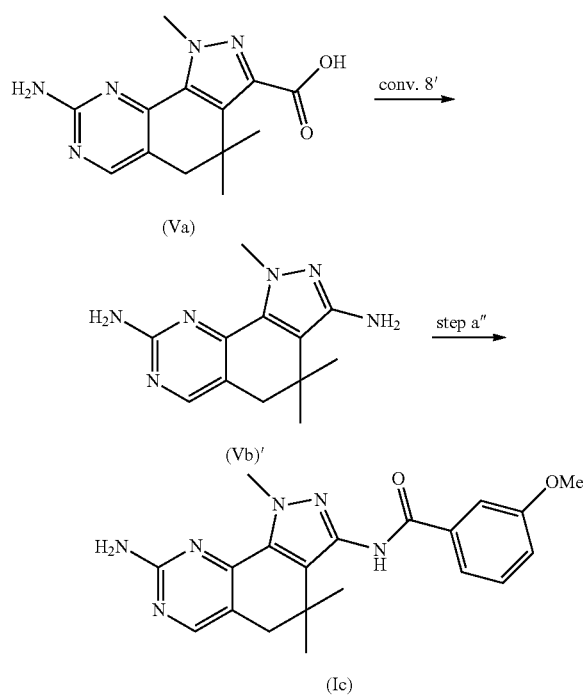

Conv. 8'

1,4,4-Trimethyl-4,5-dihydro-1H-pyrazolo[4,3-h]quinazoline-3,8-diamine (Vb)'

[R1=R3'=R4'=H, R2=R3=R4=(C$_1$-C$_6$)alkyl, W=NH$_2$]

A suspension of 8-amino-1,4,4-trimethyl-4,5-dihydro-1H-pyrazolo[4,3-h]quinazoline-3-carboxylic acid (Va) (160 mg, 0.585 mmol), TEA (0.143 mL, 1.030 mmol) and diphenylphosphoryl azide DPPA (0.160 mL, 0.743 mmol) in dry dioxane (3 mL) was stirred at rt under an argon atmosphere for 3 h. This solution was then added dropwise in 20 min to a hot solution of 2N HCl (2 mL). The mixture was left under stirring and reflux for 2 hours, then dioxane was removed under vacuum, pH was adjusted to 11 with NaOH 20% (1 mL) and the aqueous phase was extracted with DCM (10 mL×3). The combined organic extracts were dried over Na$_2$SO$_4$ and evaporated to leave 355 mg of crude product which was purified by column chromatography (DCM: 7N NH$_3$ in MeOH=95:5) affording 42 mg of title compound (30%).

$^1$H NMR (500 MHz, DMSO-d$_6$) δ ppm 1.18 (s, 6H) 4.01 (s, 3H) 2.50 2.53 (m overlapped by DMSO signal, 2H) 4.42 (s, 2H) 6.41 (s, 2H) 8.06 (s, 1H).

HRMS (ESI+): calcd. for C$_{12}$H$_{17}$N$_6$ [M+H]+ 245.1509; found 245.1515.

Operating in an analogous way, but employing a suitable substituted intermediate (Va), the following intermediate was obtained:

4,4-dimethyl-4,5-dihydro-1H-pyrazolo[4,3-h]quinazoline-3,8-diamine (Vb)'

[R1=R2=R3'=R4'=H, R3=R4=(C$_1$-C$_6$)alkyl, W=NH$_2$]

$^1$H NMR (500 MHz, DMSO-d$_6$) δ ppm 1.20 (s, 6H) 2.50 2.57 (m overlapped by DMSO signal, 2H) 4.39 (br. s., 2H) 6.22 (br. s., 2H) 8.05 (br. s., 1H) 12.09 (br. s., 1H).

HRMS (ESI+): calcd. For C$_{11}$H$_{15}$N$_6$ [M+H]+ 231.1353; found 231.1361.

Step a"

N-(8-Amino-1,4,4-trimethyl-4,5-dihydro-1H-pyrazolo[4,3-h]quinazolin-3-yl)-3-methoxybenzamide (Ic), Cpd 214

[R1=R3'=R4'=H, R2=R3=R4=(C$_1$-C$_6$)alkyl, y=0, L=NR8COR6a, R6a=substituted aryl, R8=H]

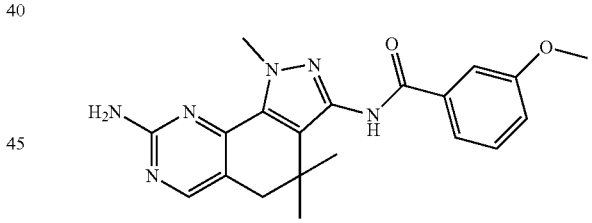

To a solution of 3-methoxylbenzoyl chloride (0.024 mL, 0.172 mmol) and TEA (0.005 mL, 0.21 mmol) in dry DCM (0.5 mL) at 0° C., a solution of 1,4,4-trimethyl-4,5-dihydro-1H-pyrazolo[4,3-h]quinazoline-3,8-diamine (42 mg, 0.172 mmol) in dry DCM (1 mL) was added. After 20 min at 0° C. the mixture was left under stirring at rt for 1 h. Then the solvent was removed under vacuum, the residue was partitioned between DCM (15 mL) and saturated aqueous NH$_4$Cl (15 mL) and the aqueous phase was further extracted with DCM (10 mL×2). The combined organic extracts were dried over Na$_2$SO$_4$ and evaporated to leave 80 mg of crude product which was purified by column chromatography over silica gel (DCM: 7 N NH$_3$/MeOH=95:5) affording the title compound (27 mg, 42%).

$^1$H NMR (499.7 MHz, DMSO-d$_6$) δ ppm 1.16 (s, 6H), 2.56 (s, 2H), 3.83 (s, 3H), 4.23 (s, 3H), 6.56 (s, 2H), 7.16 (dd, J=8.1, 2.0 Hz, 1H), 7.44 (dd, J=8.1, 7.6 Hz, 1H), 7.49 (s, 1H), 7.54 (d, J=7.6 Hz, 1H), 8.15 (s, 1H), 10.01 (s, 1H).

HRMS (ESI+): calcd. for $C_{20}H_{23}N_6O_2$ [M+H]+ 379.1877; found 379.1884.

Operating in an analogous way, but employing a suitable substituted intermediate (Vb)', the following compound was obtained:

N-(8-amino-4,4-dimethyl-4,5-dihydro-1H-pyrazolo[4,3-h]quinazolin-3-yl)-3-methoxybenzamide (Ic), Cpd 204

[R1=R2=R3'=R4'=H, R3=R4=($C_1$-$C_6$)alkyl, y=0, L=NR8COR6a, R6a=substituted aryl, R8=H]

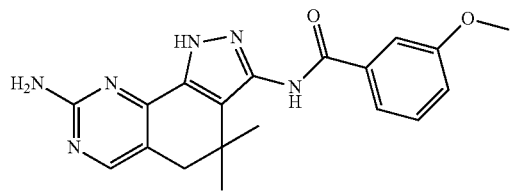 [SMILES: COc1cccc(C(=O)Nc2n[nH]c3c2C(C)(C)Cc2cnc(N)nc2-3)c1]

$^1$H NMR (499.7 MHz, DMSO-$d_6$) δ ppm 1.18 (s, 6H), 2.58 (s, 2H), 3.83 (s, 3H), 6.36 (br. s., 2H), 7.16 (d, J=8.1 Hz, 1H), 7.44 (dd, J=8.1, 7.6 Hz, 1H), 7.51 (s, 1H), 7.56 (d, J=7.6 Hz, 1H), 8.15 (s, 1H), 10.03 (s, 1H), 13.41 (s, 1H).

HRMS (ESI+): calcd. for $C_{19}H_{21}N_6O_2$ [M+H]+ 365.1721; found 365.1728.

Preparations

Preparation 1

8-Amino-4,4-dimethyl-1-(tetrahydro-2H-pyran-2-yl)-4,5-dihydro-1H-pyrazolo[4,3-h]quinazoline-3-carboxylic acid (IIIa)

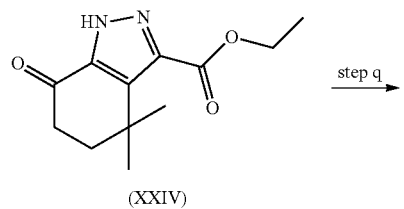

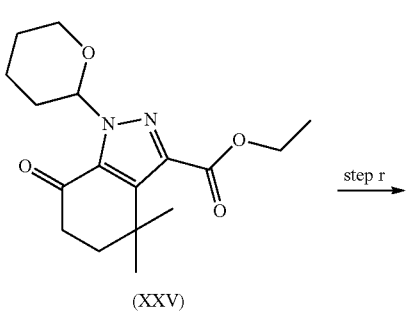

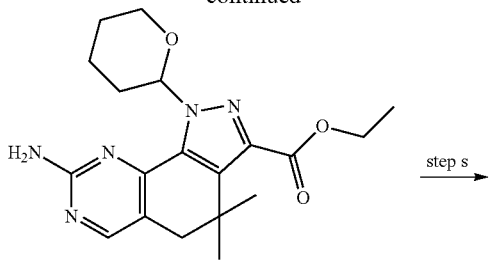

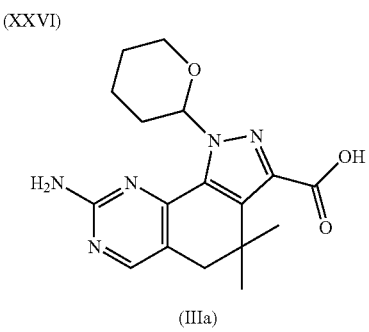

Step q

Ethyl 4,4-dimethyl-7-oxo-1-(tetrahydro-2H-pyran-2-yl)-4,5,6,7-tetrahydro-1H-indazole-3-carboxylate (XXV)

Ethyl 4,4-dimethyl-7-oxo-4,5,6,7-tetrahydro-1H-indazole-3-carboxylate (XXIV) (ref. WO2004/104007) (4.79 g, 20.29 mmol) in THF (107 mL) was treated with DHP (7.36 mL, 81.16 mmol) and PTSA.$H_2O$ (2.31 g, 12.17 mmol), stirred for 1 h at rt and then evaporated to a small volume. The residue was partitioned between EtOAc (100 mL) and saturated aqueous $NaHCO_3$ (100 mL). The organic phase was separated and the aqueous phase further extracted with EtOAc (10 mL×2). The organic extracts were combined, dried over $Na_2SO_4$, filtered and evaporated to leave 11.04 g of crude product which was purified by column chromatography (hex:EtOAc=9:1, 8:2) to afford 5.95 g of title compound (92%).

$^1$H NMR (500 MHz, DMSO-$d_6$) δ ppm 1.32 (t, J=7.17 Hz, 3H) 1.40 (d, J=5.34 Hz, 6H) 1.49-1.57 (m, 2H) 1.59-1.71 (m, 1H) 1.81-1.88 (m, 1H) 1.92 (t, J=6.63 Hz, 2H) 1.94-2.01 (m, 1H) 2.16-2.27 (m, 1H) 2.56-2.69 (m, 2H) 3.55-3.64 (m, 1H) 3.88-3.98 (m, 1H) 4.33 (q, J=7.17 Hz, 2H) 6.18 (dd, J=10.29, 2.36 Hz, 1H).

HRMS (ESI+): calcd. for $C_{17}H_{25}N_2O_4$ [M+H]$^+$ 343.1628 found 343.1627.

Operating in an analogous way, but employing suitably substituted reagents, the following intermediate compound was obtained:

ethyl 5,5-dimethyl-7-oxo-1-(tetrahydro-2H-pyran-2-yl)-4,5,6,7-tetrahydro-1H-indazole-3-carboxylate (XXV)

$^1$H NMR (500 MHz, DMSO-$d_6$) δ ppm 1.02 (s, 3H) 1.03 (s, 3H) 1.31 (t, J=7.09 Hz, 3H) 1.41-1.73 (m, 3H) 1.83-1.92 (m, 1H) 1.94-2.04 (m, 1H) 2.17-2.29 (m, 1H) 2.85 (s, 2H) 3.55-3.65 (m, 1H) 3.89-3.97 (m, 1H) 4.25-4.38 (m, 2H) 6.13 (dd, J=10.22, 2.44 Hz, 1H).

HRMS (ESI+): calcd. for $C_{17}H_{25}N_2O_4$ [M+H]$^+$ 343.1628 found 343.1632.

Step r

Ethyl 8-amino-4,4-dimethyl-1-(tetrahydro-2H-pyran-2-yl)-4,5-dihydro-1H-pyrazolo[4,3-h]quinazoline-3-carboxylate (XXVI)

Ethyl 4,4-dimethyl-7-oxo-1-(tetrahydro-2H-pyran-2-yl)-4,5,6,7-tetrahydro-1H-indazole-3-carboxylate (XXV) (5.9 g, 18.4 mmol) was dissolved in warm DMF (92 mL), treated with N,N-dimethylformamide di-tert-butyl acetal (26.5 mL, 110.4 mmol) and heated at 90° C. (oil bath temperature) for 3.5 h. The reaction was cooled to rt and DMF was removed by evaporation. The crude product was dissolved in DMF (56 mL), treated with guanidine carbonate (4.97 g, 27.6 mmol), heated at 110° C. (oil bath temperature) for 3 h, cooled to rt, evaporated and the residue partitioned between EtOAc (100 mL) and H$_2$O (100 mL). The aqueous phase was further extracted with EtOAc (20 mL×2). The combined organic extracts were washed with brine, dried over Na$_2$SO$_4$, filtered and evaporated. The crude product was purified by column chromatography (hex:EtOAc=4:6, 3:7) to give the title compound as white solid (5.53 g, 79%).

$^1$H NMR (500 MHz, DMSO-d$_6$) δ ppm 1.22 (s, 3H) 1.33 (s, 3H) 1.31 (t, J=7.00 Hz, 3H) 1.46-1.61 (m, 2H) 1.66-1.81 (m, 1H) 1.87-1.94 (m, 1H) 1.95-2.05 (m, 1H) 2.19-2.32 (m, 1H) 2.55-2.67 (m, 2H) 3.75-3.83 (m, 1H) 3.85-3.93 (m, 1H) 4.31 (q, J=7.00 Hz, 2H) 6.63 (br. s., 2H) 6.85 (dd, J=10.37, 2.14 Hz, 1H) 8.18 (s, 1H).

HRMS (ESI+): calcd. for $C_{19}H_{26}N_5O_3$ [M+H]$^+$ 372.2030; found 372.2030.

Operating in an analogous way, but employing suitably substituted reagents, the following intermediate compound was obtained:

ethyl 4,4-dimethyl-8-(methylamino)-1-(tetrahydro-2H-pyran-2-yl)-4,5-dihydro-1H-pyrazolo[4,3-h]quinazoline-3-carboxylate (XXVI)

$^1$H NMR (500 MHz, DMSO-d$_6$) δ ppm 1.23 (s, 3H) 1.33 (s, 3H) 1.32 (t, J=7.20 Hz, 3H) 1.47-1.61 (m, 2H) 1.61-1.74 (m, 1H) 1.87-1.95 (m, 1H) 1.96-2.06 (m, 1H) 2.21-2.33 (m, 1H) 2.54-2.70 (m, 2H) 2.86 (d, J=4.58 Hz, 3H) 3.56-3.77 (m, 1H) 3.86-4.02 (m, 1H) 4.31 (q, J=7.20 Hz, 2H) 6.84-6.94 (m, 1H) 7.13 (br. s., 1H) 8.23 (s, 1H).

HRMS (ESI+): calcd. for $C_{20}H_{28}N_5O_3$[M+H]$^+$ 386.2187; found 386.2188.

ethyl 8-amino-5,5-dimethyl-1-(tetrahydro-2H-pyran-2-yl)-4,5-dihydro-1H-pyrazolo[4,3-h]quinazoline-3-carboxylate (XXVI)

$^1$H NMR (500 MHz, DMSO-d$_6$) δ ppm 1.16 (s, 3H) 1.29 (s, 3H) 1.31 (t, J=7.09 Hz, 3H) 1.47-1.64 (m, 2H) 1.68-1.82 (m, 1H) 1.86-1.96 (m, 1H) 1.97-2.04 (m, 1H) 2.19-2.34 (m, 1H) 2.77-2.96 (m, 2H) 3.75-3.85 (m, 1H) 3.86-3.95 (m, 1H) 4.24-4.38 (m, 2H) 6.66 (br. s., 2H) 6.84 (dd, J=10.45, 2.21 Hz, 1H) 8.29 (s, 1H).

HRMS (ESI+): calcd. for $C_{19}H_{26}N_5O_3$[M+H]$^+$ 372.2030; found 372.2024.

Step s

8-Amino-4,4-dimethyl-1-(tetrahydro-2H-pyran-2-yl)-4,5-dihydro-1H-pyrazolo[4,3-h]quinazoline-3-carboxylic acid (IIIa)

[R1=R3'=R4'=H, PG=tetrahydropyranyl, R3=R4=(C$_1$-C$_6$) alkyl, W=COOH]

Ethyl 4,4-dimethyl-8-(methylamino)-1-(tetrahydro-2H-pyran-2-yl)-4,5-dihydro-1H-pyrazolo[4,3-h]quinazoline-3-carboxylate (4.93 g, 13.29 mmol) in EtOH (15 mL) was treated with 2N NaOH (66 mL, 133 mmol) and heated at 110° C. (oil bath temperature) over 1 h. After cooling with an ice-water bath, the mixture was treated dropwise with AcOH (7.6 mL, 133 mmol) and left at 4° C. for two days. The white solid was then filtered with suction, washed with water and dried at 50° C. under vacuum (4.13 g, 91%).

$^1$H NMR (500 MHz, DMSO-d$_6$) δ ppm 1.23 (s, 3H) 1.35 (s, 3H) 1.48-1.58 (m, 2H) 1.64-1.80 (m, 1H) 1.80-1.93 (m, 1H) 1.94-2.05 (m, 1H) 2.20-2.34 (m, 1H) 2.53-2.65 (m, 2H) 3.69-3.82 (m, 1H) 3.83-3.92 (m, 1H) 6.60 (br, s., 2H) 6.83 (dd, J=10.29, 2.21 Hz, 1H) 8.17 (s, 1H) 13.01 (br. s., 1H).

HRMS (ESI+): calcd. for $C_{17}H_{22}N_5O_3$ [M+H]$^+$ 344.1717; found 344.1714.

Operating in an analogous way, but employing suitably substituted reagents, the following intermediate compounds were obtained:

4,4-dimethyl-8-(methylamino)-1-(tetrahydro-2H-pyran-2-yl)-4,5-dihydro-1H-pyrazolo[4,3-h]quinazoline-3-carboxylic acid (IIIa)

[R1=R3=R4=(C$_1$-C$_6$)alkyl, R3'=R4'=H, PG=tetrahydropyranyl, W=COOH]

$^1$H NMR (500 MHz, DMSO-d$_6$) δ ppm 1.24 (s, 3H) 1.35 (s, 3H) 1.50-1.59 (m, 2H) 1.60-1.74 (m, 1H) 1.86-1.95 (m, 1H) 1.96-2.06 (m, 1H) 2.21-2.34 (m, 1H) 2.55-2.69 (m, 2H) 2.86 (d, J=4.58 Hz, 3H) 3.57-3.75 (m, 1H) 3.87-4.01 (m, 1H) 6.82-6.93 (m, 1H) 7.10 (br. s., 1H) 8.22 (s, 1H) 13.04 (br. s., 1H).

HRMS (ESI+): calcd. for $C_{18}H_{24}N_5O_3$ [M+H]$^+$ 358.1874; found 358.1887.

8-amino-5,5-dimethyl-1-(tetrahydro-2H-pyran-2-yl)-4,5-dihydro-1H-pyrazolo[4,3-h]quinazoline-3-carboxylic acid (IIIa)

[R1=R3=R4=H, R3'=R4'=(C$_1$-C$_6$)alkyl, PG=tetrahydropyranyl, W=COOH]

$^1$H NMR (500 MHz, DMSO-d$_6$) δ ppm 1.15 (s, 3H) 1.28 (s, 3H) 1.47-1.61 (m, 2H) 1.66-1.83 (m, 1H) 1.84-1.96 (m, 1H) 1.96-2.05 (m, 1H) 2.22-2.35 (m, 1H) 2.73-2.97 (m, 2H) 3.72-3.85 (m, 1H) 3.86-3.95 (m, 1H) 6.63 (br. s., 2H) 6.82 (dd, J=10.29, 2.21 Hz, 1H) 8.27 (s, 1H).

HRMS (ESI+): calcd. for $C_{17}H_{22}N_5O_3$ [M+H]$^+$ 344.1717; found 344.1713.

Preparation 2

Methyl 1-(2-amino-1,3-thiazol-4-yl)cyclopropanecarboxylate

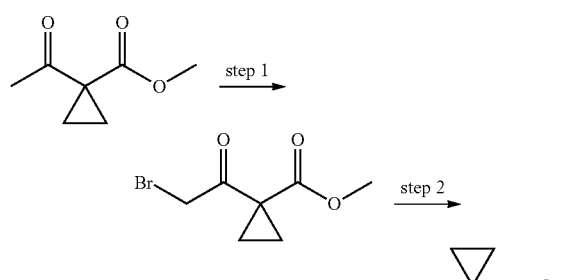

Step 1

Methyl 1-(bromoacetyl)cyclopropanecarboxylate

Methyl 1-acetylcyclopropanecarboxylate (ref. Synthetic Communications, 26, 535-530, 1996) (1.090 g, 7.68 mmol) in EtOH (3.5 mL), cooled with an ice bath, was treated with bromine (1.59 g, 10 mmol) dropwise over 15 min, under stirring. The reaction was allowed to reach rt and after 2 h was treated with water (6 mL). The solvent was evaporated and the aqueous phase was extracted with EtOAc (20 mL). The organic phase was washed with 10% sodium thiosulfate (2 mL), saturated aqueous NaHCO$_3$ and brine, dried over Na$_2$SO$_4$ and evaporated to leave 1.46 g of methyl 1-(bromoacetyl)cyclopropanecarboxylate which was employed in the following step without any further purification.

HRMS (ESI+): calcd. for C$_7$H$_{10}$BrO$_3$ [M+H]$^+$ 220.9808; found 220.9810.

Step 2

Methyl 1-(2-amino-1,3-thiazol-4-yl)cyclopropanecarboxylate

Methyl 1-(bromoacetyl)cyclopropanecarboxylate (1.46 g, 6.59 mmol) in water (3.3 mL) was treated with thiourea and heated to reflux. After 1.5 h, the reaction was cooled with an ice bath and 2N NaOH was added (3.3 mL). The solid thus precipitated was filtered with suction, washed with water and dried at 50° C. under vacuum to afford 0.428 g of title compound (33%).

$^1$H NMR (500 MHz, DMSO-d$_6$) δ ppm 1.24 (q, J=3.81 Hz, 2H) 1.32-1.40 (m, 2H) 3.59 (s, 3H) 6.52 (s, 1H) 6.90 (br. s., 2H)

HRMS (ESI+): calcd. for C$_{27}$H$_{37}$N$_{10}$O$_3$S [M+H]$^+$ 199.0536; found 199.0530.

Preparation 3

1-{1-[(2-Amino-1,3-thiazol-4-yl)acetyl]piperidin-4-yl}-3-tert-butylurea

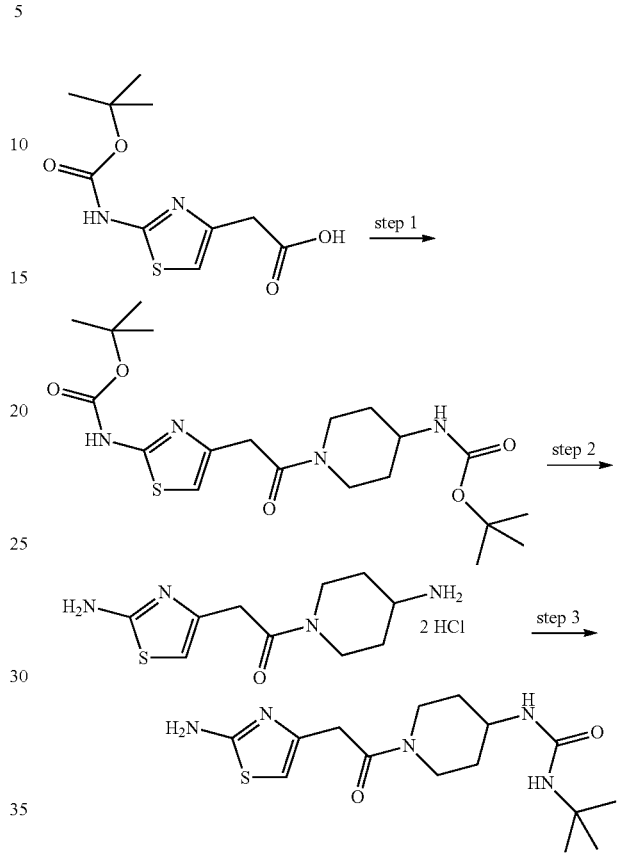

Step 1

Tert-butyl [4-(2-{4-[(tert-butoxycarbonyl)amino]piperidin-1-yl}-2-oxoethyl)-1,3-thiazol-2-yl]carbamate {2-[(Teri-butoxycarbonyl)amino]-1,3-thiazol-4-yl}acetic acid (260 mg, 1 mmol) in dry DMF (4 mL) was treated with DIPEA (0.256 mL, 1.5 mmol), 4-Boc-aminopiperidine (300 mg, 1.5 mmol) and TBTU (481 mg, 1.5 mmol). The reaction was stirred at rt for 4 h then poured into water (80 mL). The solid thus formed was filtered with suction, washed, dried at 50° C. under vacuum to afford 280 mg of title compound (63%).

$^1$H NMR (500 MHz, DMSO-d$_6$) δ ppm 1.07-1.29 (m, 2H) 1.37 (s, 9H) 1.47 (s, 9H) 1.67 (d, J=11.59 Hz, 2H) 2.66 (t, J=13.00 Hz, 1H) 3.04 (t, J=11.67 Hz, 1H) 3.56-3.71 (m, 2H) 3.88 (d, J=13.12 Hz, 1H) 4.20 (d, J=13.12 Hz, 1H) 6.79 (s, 1H) 6.83 (d, J=7.78 Hz, 1H) 11.37 (br. s., 1H).

HRMS (ESI+): calcd. for C$_{20}$H$_{33}$N$_4$O$_6$S [M+H]$^+$ 441.2166; found 441.2167.

Step 2

1-(4-Aminopiperidin-1-yl)-2-(2-amino-1,3-thiazol-4-yl)ethanone dihydrochloride Tert-butyl [4-(2-{4-[(tert-butoxycarbonyl)amino]piperidin-1-yl}-2-oxoethyl)-1,3-thiazol-2-yl]carbamate (280 mg, 0.636 mmol) in DCM (13 mL) was treated with HCl 4M in dioxane (4.8 mL). The reaction was stirred for 4 h and evaporated to dryness to afford the title compound in quantitative yield.

$^1$H NMR (500 MHz, DMSO-d$_6$) δ ppm 1.34 (qd, J=11.92, 4.19 Hz, 1H) 1.47 (qd, J=12.10, 4.12 Hz, 1H) 1.93 (t, J=12.51 Hz, 2H) 2.65-2.72 (m, 1H) 3.10 (ddd, J=14.03, 11.90, 2.29 Hz, 1H) 3.44-3.52 (m, 2H) 3.64-3.73 (m, 2H) 3.71-3.84 (m, 2H) 3.93 (d, J=14.49 Hz, 1H) 4.36 (d, J=14.49 Hz, 1H) 6.58 (s, 1H) 8.08 (br. s., 3H) 8.89 (br. s., 3H).

HRMS (ESI+): calcd. for C$_{10}$H$_{17}$N$_4$OS [M+H]$^+$ 241.1118; found 241.1122.

Step 3

1-{1-[(2-Amino-1,3-thiazol-4-yl)acetyl]piperidin-4-yl}-3-tert-butylurea 1-(4-Aminopiperidin-1-yl)-2-(2-amino-1,3-thiazol-4-yl) ethanone dihydrochloride (167 mg, 0.536 mmol) in DCM (2 mL) was treated with TEA (0.149 mL, 1.073 mmol) and tert-butyl isocyanate (0.067 mL, 0.590 mmol). After stirring overnight, the volatiles were evaporated. The residue was dissolved in DCM:MeOH 1:1 (4 mL) and passed over a PL-HCO$_3$ cartridge (MP SPE 500 mg×6 mL tube, loading: 0.9 mmol/g). The cartridge was washed with DCM (2 mL×2) and the filtrate evaporated. The oil thus obtained crystallized from DCM affording 145 mg of title compound (67%).

$^1$H NMR (500 MHz, DMSO-d$_6$) δ ppm 0.99-1.14 (m, 2H) 1.20 (s, 9H) 1.70 (dt, J=12.96, 4.12 Hz, 2H) 2.73-2.81 (m, 1H) 3.09 (ddd, J=13.65, 10.90, 2.44 Hz, 1H) 3.48 (s, 2H) 3.50-3.56 (m, 1H) 3.76-3.85 (m, 1H) 4.08 (m, J=12.81 Hz, 1H) 5.51 (s, 1H) 5.65 (d, J=7.63 Hz, 1H) 6.20 (s, 1H) 6.85 (s, 2H).

HRMS (ESI+): calcd. for C$_{15}$H$_{26}$N$_5$O$_2$S [M+H]$^+$ 340.1802; found 340.18.

Preparation 4

4-{[(1-Cyclohexylpiperidin-4-yl)oxy]methyl}-1,3-thiazol-2-amine

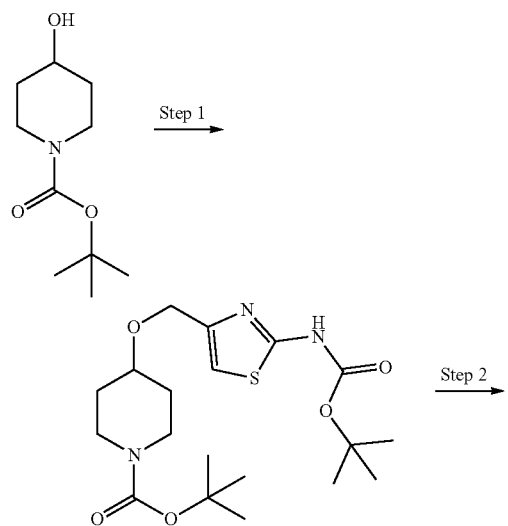

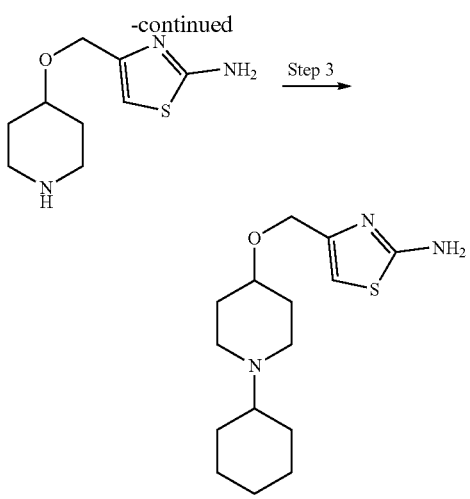

Step 1

Tert-butyl 4-({2-[(tert-butoxycarbonyl)amino]-1,3-thiazol-4-yl}methoxy)piperidine-1-carboxylate To a suspension of NaH (60% dispersion in mineral oil, 320 mg, 8 mmol) in THF (5 mL) at 0° C. under argon, 1-Boc-4-hydroxypiperidine (1.206 mg, 6 mmol) in THF (10 mL) and 15-crown-5 (0.198 mL, 1 mmol) were added. The mixture was stirred at 0° C. for 30 min, then N-Boc-4-(chloromethyl)thiazol-2-amine (496 mg, 2 mmol) was added and heated at 80° C. (oil bath temperature) for 20 min. The reaction was quenched upon addition of H$_2$O (5 mL), with cooling at 0° C. The reaction was partitioned between water (30 mL) and EtOAc (50 mL). The aqueous phase was further extracted with EtOAc (10 mL×2). The combined organic phases were washed with brine, dried over Na$_2$SO$_4$ and evaporated to dryness. The crude was purified by column chromatography over silica gel (hex:EtOAc=8:2, 6:4) to afford 80 mg of title compound (10%).

$^1$H NMR (500 MHz, DMSO-d$_6$) δ ppm 1.30-1.36 (m, 2H) 1.38 (s, 9H) 1.47 (s, 9H) 1.73-1.84 (m, 2H) 2.91-3.11 (m, 2H) 3.52-3.58 (m, 1H) 3.59-3.65 (m, 2H) 4.42 (s, 2H) 6.98 (s, 1H) 11.41 (br. s., 1H).

HRMS (ESI+): calcd. for C$_{19}$H$_{32}$N$_3$O$_5$S [M+H]$^+$ 414.2057; found 414.2061.

Operating in an analogous way, but employing suitably substituted reagents, the following compounds were obtained:

tert-butyl {4-[(1,4-dioxaspiro[4.5]dec-8-yloxy)methyl]-1,3-thiazol-2-yl}carbamate $^1$H NMR (500 MHz, DMSO-d$_6$) δ ppm 1.47 (s, 9H) 1.38-1.47 (m, 2H) 1.51-1.82 (m, 6H) 3.42-3.52 (m, 1H) 3.80-3.89 (m, 4H) 4.38 (s, 2H) 6.96 (s, 1H) 11.41 (br. s., 1H).

HRMS (ESI+): calcd. for C$_{17}$H$_{27}$N$_2$O$_5$S [M+H]$^+$ 371.1635; found 371.1627.

tert-butyl 4-({2-[(tert-butoxycarbonyl)(2,4-dimethoxybenzyl)amino]-1,3-thiazol-4-yl}methoxy)-4-methyl piperidine-1-carboxylate $^1$H NMR (500 MHz, DMSO-d$_6$) δ ppm 1.26-1.37 (m, 2H) 1.38 (s, 18H) 1.39 (s, 3H) 1.65-1.73 (m, 2H) 2.88-3.07 (m, 2H) 3.42-3.64 (m, 2H) 3.71 (s, 3H) 3.78 (s, 3H) 4.28 (s, 2H)

5.13 (s, 2H) 6.41 (dd, J=8.46, 2.36 Hz, 1H) 6.54 (d, J=2.29 Hz, 1H) 6.70 (d, J=8.39 Hz, 1H) 7.04 (s, 1H).

HRMS (ESI+): calcd. for $C_{29}H_{44}N_3O_7S$ $[M+H]^+$ 578.2895; found 578.2922.

Step 2

4-[(Piperidin-4-yloxy)methyl]-1,3-thiazol-2-amine

Tert-butyl 4-({2-[(tert-butoxycarbonyl)amino]-1,3-thiazol-4-yl}methoxy)piperidine-1-carboxylate (80 mg, 0.19 mmol) in dioxane (0.5 mL) was treated with HCl 4M in dioxane (0.5 mL). The reaction was stirred at rt overnight. The volatiles were removed in vacuo. The residue was dissolved in DCM:MeOH (5 mL, 1:1) and charged over a PL-HCO₃ MP SPE cartridge (500 mg per 6 mL tube, loading: 0.9 mmol). The cartridge was washed with DCM:MeOH (15 mL, 1:1). The filtrate was evaporated to give 30 mg of title compound (75%).

¹H NMR (500 MHz, DMSO-d₆) δ ppm 1.21-1.34 (m, 2H) 1.77-1.85 (m, 2H) 2.40-2.48 (m, 2H) 2.85-2.95 (m, 2H) 3.35-3.43 (m, 1H overlapped by water signal) 4.24 (s, 2H) 6.36 (s, 1H) 6.86 (br. s., 2H).

HRMS (ESI+): calcd. for $C_9H_{16}N_3OS$ $[M+H]^+$ 214.1009; found 214.1004.

Alternatively, the solvent was removed under vacuo and the product isolated as hydrochloride salt or, after treatment with TFA in DCM for 4 h and solvent evaporation, the title compound was isolated as trifluoroacetate salt. Operating in an analogous way, but employing suitably substituted reagents, the following compounds were obtained:

4-({[trans-4-(piperidin-1-yl)cyclohexyl]oxy}methyl)-1,3-thiazol-2-amine hydrochloride HRMS (ESI+): calcd. for $C_{15}H_{26}N_3OS$ $[M+H]^+$ 296.1791; found 296.1789.

4-{[(4-Methylpiperidin-4-yl)oxy]methyl}-1,3-thiazol-2-amine trifluoroacetate

¹H NMR (500 MHz, DMSO-d₆) δ ppm 1.22 (s, 4H) 1.49-1.67 (m, 2H) 1.88-1.96 (m, 2H) 2.93-3.17 (m, 4H) 4.17 (s, 2H) 6.42 (s, 1H) 6.92 (br. s., 2H) 8.35 (br. s., 1H).

HRMS (ESI+): calcd. for $C_{10}H_{18}N_3OS$ $[M+H]^+$ 228.1165; found 228.1170.

Step 3

4-{[(1-Cyclohexylpiperidin-4-yl)oxy]methyl}-1,3-thiazol-2-amine

4-[(Piperidin-4-yloxy)methyl]-1,3-thiazol-2-amine (40 mg, 0.188 mmol) in DMF (1.9 mL) was treated with cyclohexanone (0.023 mL, 0.226 mmol), acetic acid (0.027 mL, 0.469 mmol) and finally with sodium triacetoxyborohydride (99 mg, 0.469 mmol). The reaction was stirred at rt overnight. The volatiles were removed in vacuo and the residue partitioned between EtOAc (20 mL) and saturated aqueous NaHCO₃ (10 mL). The aqueous layer was further extracted with EtOAc (10 mL×3). The combined organic extracts were washed with brine, dried over Na₂SO₄ and evaporated. The crude was then purified by column chromatography over silica gel (DCM: 7N NH₃ in MeOH=95:5) to afford the title compound (30 mg, 54%).

¹H NMR (500 MHz, DMSO-d₆) δ ppm 0.98-1.07 (m, 1H) 1.10-1.23 (m, 4H) 1.31-1.48 (m, 2H) 1.49-1.59 (m, 1H) 1.65-1.77 (m, 4H) 1.78-1.87 (m, 2H) 2.15-2.28 (m, 3H) 2.67-2.75 (m, 2H) 3.26-3.31 (m, 1H, overlapped by water signal) 4.23 (s, 2H) 6.35 (s, 1H) 6.86 (br. s., 2H).

HRMS (ESI+): calcd. for $C_{15}H_{26}N_3OS$ $[M+H]^+$ 296.1791; found 296.1796.

Operating in an analogous way, but employing suitably substituted reagents, the following intermediates were obtained:

4-{[(1-cycloheptylpiperidin-4-yl)oxy]methyl}-1,3-thiazol-2-amine

¹H NMR (500 MHz, DMSO-d₆) δ ppm 1.23-1.54 (m, 10H) 1.53-1.64 (m, 2H) 1.65-1.74 (m, 2H) 1.76-1.86 (m, 2H) 2.12-2.24 (m, 2H) 2.41-2.48 (m, 1H) 2.60-2.66 (m, 2H) 3.23-3.33 (m, 1H) 4.22 (s, 2H) 6.35 (s, 1H) 6.85 (s, 2H).

HRMS (ESI+): calcd. for $C_{16}H_{28}N_3OS$ $[M+H]^+$ 310.1948; found 310.1960.

4-({[1-(4,4-dimethylcyclohexyl)piperidin-4-yl]oxy}methyl)-1,3-thiazol-2-amine

¹H NMR (500 MHz, DMSO-d₆) δ ppm 0.85 (s, 3H) 0.86 (s, 3H) 1.06-1.20 (m, 2H) 1.27-1.45 (m, 6H) 1.45-1.59 (m, 2H) 1.76-1.89 (m, 2H) 2.08-2.27 (m, 3H) 2.68-2.78 (m, 2H) 3.25-3.34 (m, 1H partially overlapped by water signal) 4.23 (s, 2H) 6.35 (s, 1H) 6.85 (br. s., 2H).

HRMS (ESI+): calcd. for $C_{17}H_{30}N_3OS$ $[M+H]^+$ 324.2104; found 324.2103.

4-({[1-(4,4-difluorocyclohexyl)piperidin-4-yl]oxy}methyl)-1,3-thiazol-2-amine

¹H NMR (500 MHz, DMSO-d₆) δ ppm 1.35-1.43 (m, 2H) 1.44-1.54 (m, 2H) 1.65-1.75 (m, 2H) 1.88 (s, 4H) 1.94-2.08 (m, 2H) 2.15-2.25 (m, 2H) 2.38-2.47 (m, 1H) 2.67-2.75 (m, 2H) 3.27-3.33 (m, 1H partially overlapped by water signal) 4.23 (s, 2H) 6.35 (s, 1H) 6.86 (br. s., 2H).

HRMS (ESI+): calcd. for $C_{14}H_{24}F_2N_3OS$ $[M+H]^+$ 332.1603; found 332.1612.

4-({[1-(cyclohexylmethyl)piperidin-4-yl]oxy}methyl)-1,3-thiazol-2-amine

¹H NMR (500 MHz, DMSO-d₆) δ ppm 0.69-0.88 (m, 2H) 1.05-1.25 (m, 3H) 1.36-1.48 (m, 3H) 1.56-1.73 (m, 5H) 1.76-1.85 (m, 2H) 1.88-1.98 (m, 2H) 2.01 (d, J=7.17 Hz, 2H) 2.58-2.66 (m, 2H) 3.30-3.38 (m, 1H overlapped by water signal) 4.23 (s, 2H) 6.35 (s, 1H) 6.86 (s, 2H).

HRMS (ESI+): calcd. for $C_{16}H_{28}N_3OS$ $[M+H]^+$ 310.1948; found 310.1948.

4-{[(1-benzylpiperidin-4-yl)oxy]methyl}-1,3-thiazol-2-amine

¹H NMR (500 MHz, DMSO-d₆) δ ppm 1.33-1.51 (m, 2H) 1.75-1.88 (m, 2H) 1.99-2.09 (m, 2H) 2.58-2.69 (m, 2H) 3.34-3.40 (m, 1H overlapped by water signal) 3.43 (s, 2H) 4.23 (s, 2H) 6.35 (s, 1H) 6.86 (s, 2H) 7.19-7.34 (m, 6H).

HRMS (ESI+): calcd. for $C_{16}H_{22}N_3OS$ $[M+H]^+$ 304.1478; found 304.1476.

4-{[(1-cycloheptyl-4-methylpiperidin-4-yl)oxy]methyl}-1,3-thiazol-2-amine

HRMS (ESI+): calcd. for $C_{17}H_{30}N_3OS$ $[M+H]^+$ 324.2104; found 324.2111.

4-({[1-(spiro[2.5]oct-6-yl)piperidin-4-yl]oxy}methyl)-1,3-thiazol-2-amine

HRMS (ESI+): calcd. for $C_{17}H_{28}N_3OS$ $[M+H]^+$ 322.1948; found 322.1956.

Preparation 5

Tert-butyl (4-{[(4-oxocyclohexyl)oxy]methyl}-1,3-thiazol-2-yl)carbamate

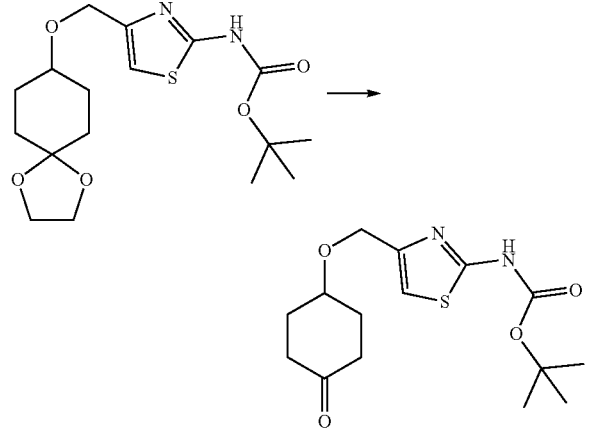

Tert-butyl {4-[(1,4-dioxaspiro[4.5]dec-8-yloxy)methyl]-1,3-thiazol-2-yl}carbamate (100 mg, 0.27 mmol) in acetone (3 mL) was treated with 0.4 mL of 1N HCl and 37° C. (oil bath temperature) for 8 h. The volatiles were removed under reduced pressure and the residue was partitioned between EtOAc (10 mL) and saturated aqueous NaHCO$_3$ (2 mL). The organic phase was dried over Na$_2$SO$_4$ and evaporated. The crude was purified by flash chromatography (hex:EtOAc=5:5, 4:6) to afford 51 mg of the title compound (58%).

$^1$H NMR (500 MHz, DMSO-d$_6$) δ ppm 1.47 (s, 9H) 1.85-2.01 (m, 4H) 2.16-2.26 (m, 2H) 2.33-2.43 (m, 2H) 3.75-3.87 (m, 1H) 4.47 (s, 2H) 7.03 (s, 1H) 11.43 (br. s., 1H).

HRMS (ESI+): calcd. for $C_{15}H_{23}N_2O_6S$ $[M+H]^+$ 327.1373; found 327.1371.

Preparation 6

2-(2-Amino-1,3-thiazol-4-yl)-1-(4-methyl-1,4'-bipiperidin-1'-yl)ethanone

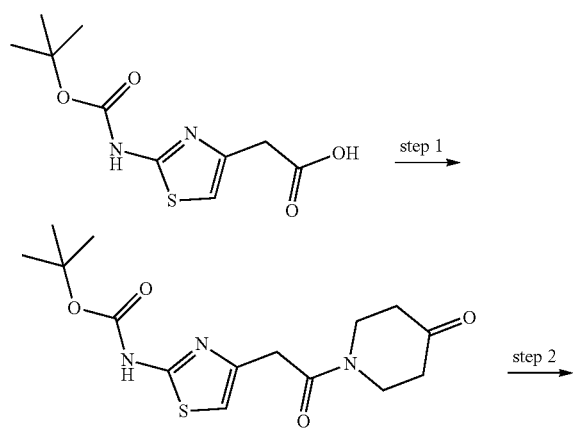

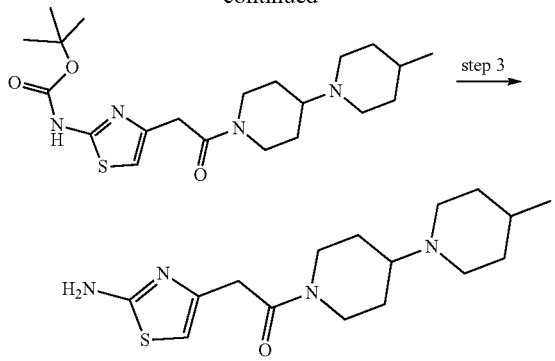

Step 1 tert-butyl {4-[2-oxo-2-(4-oxopiperidin-1-yl)ethyl]-1,3-thiazol-2-yl}carbamate

{2-[(Tert-butoxycarbonyl)amino]-1,3-thiazol-4-yl}acetic acid (400 mg, 1.5 mmol) in DMA (20 mL) was treated with DIPEA (0.530 mL, 3 mmol), 4-piperidone monohydrate hydrochloride (357 mg, 2.1 mmol) and TBTU (522 mg, 1.6 mmol). The reaction was stirred overnight, diluted with EtOAc (20 mL) and partitioned with saturated aqueous NaHCO$_3$ (5 mL), water (5 mL), brine, dried over Na$_2$SO$_4$ and evaporated. The crude was purified by flash chromatography over silica gel (DCM:MeOH=95:5) to furnish the title compound (435 mg, 85%).

$^1$H NMR (500 MHz, DMSO-d$_6$) δ ppm 1.47 (s, 9H) 2.33 (t, J=6.33 Hz, 2H) 2.40 (t, J=6.18 Hz, 2H) 3.72 (t, J=6.33 Hz, 2H) 3.75 (s, 2H) 3.80 (t, J=6.18 Hz, 2H) 6.87 (s, 1H) 11.40 (br. s., 1H).

HRMS (ESI+): calcd. for $C_{15}H_{22}N_3O_4S$ $[M+H]^+$ 340.1326; found 340.1333.

Operating in an analogous way, but employing suitably substituted reagents, the following compounds were obtained:

tert-butyl {4-[2-(1,4'-bipiperidin-1'-yl)-2-oxoethyl]-1,3-thiazol-2-yl}carbamate $^1$H NMR (500 MHz, DMSO-d$_6$) δ ppm 1.12-1.28 (m, 4H) 1.30-1.40 (m, 2H) 1.41-1.47 (m, 2H) 1.47 (s, 9H) 1.56-1.76 (m, 2H) 2.33-2.44 (m, 3H) 2.92 (t, J=11.90 Hz, 1H) 3.65 (s, 2H) 3.88-3.99 (m, 1H) 4.32-4.42 (m, 1H) 6.80 (s, 1H) 11.39 (br. s., 1H).

HRMS (ESI+): calcd. for $C_{21}H_{35}N_4O_3S$ $[M+H]^+$ 423.2425; found 423.2426.

tert-butyl (4-{2-[(1-cyclohexylpiperidin-4-yl)amino]-2-oxoethyl}-1,3-thiazol-2-yl)carbamate $^1$H NMR (500 MHz, DMSO-d$_6$) δ ppm 0.94-1.09 (m, 1H) 1.11-1.21 (m, 4H) 1.27-1.38 (m, 2H) 1.47 (s, 9H) 1.50-1.62 (m, 1H) 1.63-1.77 (m, 6H) 2.14-2.27 (m, 3H) 2.69-2.79 (m, 2H) 3.37 (s, 2H) 3.41-3.52 (m, 1H) 6.77 (s, 1H) 7.85 (d, J=7.78 Hz, 1H) 11.36 (br. s., 1H).

HRMS (ESI+): calcd. for $C_{21}H_{35}N_4O_3S$ $[M+H]^+$ 423.2425; found 423.2426.

tert-butyl {4-[2-(4-cyclohexylpiperazin-1-yl)-2-oxoethyl]-1,3-thiazol-2-yl}carbamate HRMS (ESI+): calcd. for $C_{20}H_{33}N_4O_3S$ $[M+H]^+$ 409.2268; found 409.2267.

tert-butyl {4-[2-oxo-2-(4-phenylpiperazin-1-yl) ethyl]-1,3-thiazol-2-yl}carbamate HRMS (ESI+): calcd. for $C_{20}H_{27}N_4O_3S$ $[M+H]^+$ 403.1799; found 403.1798.

tert-butyl {4-[2-(4,4'-dimethyl-1 piperidin-1'-yl)-2-oxoethyl]-1,3-thiazol-2-yl}carbamate $^1$H NMR (500 MHz, DMSO-$d_6$) δ ppm 0.84 (s, 3H) 0.87 (d, J=6.56 Hz, 3H) 0.99-1.12 (m, 2H) 1.17-1.37 (m, 3H) 1.47 (s, 9H) 1.54-1.64 (m, 2H) 1.67-1.77 (m, 2H) 1.98 (t, J=10.98 Hz, 2H) 2.75-2.86 (m, 2H) 3.13 (t, J=10.29 Hz, 1H) 3.41-3.49 (m, 1H) 3.63 (s, 2H) 3.65-3.77 (m, 1H) 6.79 (s, 1H) 11.38 (br. s., 1H).

HRMS (ESI+): calcd. for $C_{22}H_{37}N_4O_3S$ $[M+H]^+$ 437.2581; found 437.2583.

tert-butyl {4-[2-oxo-2-(2,2,6,6-tetramethyl-4-oxopiperidin-1-yl)ethyl]-1,3-thiazol-2-yl}carbamate $^1$H NMR (500 MHz, DMSO-$d_6$) δ ppm 1.46 (s, 21H) 2.64 (s, 4H) 3.73 (s, 2H) 6.84 (s, 1H) 11.33 (br. s., 1H).

HRMS (ESI+): calcd. for $C_{19}H_{30}N_3O_4S$ $[M+H]^+$ 396.1952; found 396.1955.

(2-amino-1,3-benzothiazol-6-yl)(4-methyl-1,4'-bipiperidin-1'-yl)methanone $^1$H NMR (500 MHz, DMSO-$d_6$) δ ppm 0.87 (d, J=6.56 Hz, 3H) 1.01-1.14 (m, 2H) 1.19-1.45 (m, 3H) 1.52-1.62 (m, 2H) 1.65-1.79 (m, 2H) 2.03-2.17 (m, 2H) 2.70-3.02 (m, 4H) 3.60-4.11 (m, 4H) 7.22 (dd, J=8.24, 1.53 Hz, 1H) 7.32 (d, J=8.08 Hz, 1H) 7.65 (br. s., 2H) 7.72 (d, J=1.53 Hz, 1H).

HRMS (ESI+): calcd. for $C_{16}H_{27}N_4OS$ $[M+H]^+$ 359.19; found 359.1902.

Step 2

Tert-butyl {4-[2-(4-methyl-1,4'-bipiperidin-1'-yl)-2-oxoethyl]-1,3-thiazol-2-yl}carbamate Tert-butyl {4-[2-oxo-2-(4-oxopiperidin-1-yl)ethyl]-1,3-thiazol-2-yl}carbamate (0.430 mg, 1.26 mmol) in DMF (20 mL) was treated with 4-methylpiperidine (0.838 mL, 1.5 mmol), acetic acid (0.087 mL, 1.52 mmol), sodium triacetoxyborohydride (3.1 mmol, 670 mg) and stirred over 24 h. The reaction was diluted with EtOAc, partitioned with water, dried over $Na_2SO_4$ and evaporated. The crude was purified over silica gel (DCM:MeOH=95:5) to give the title compound (270 mg, 51%).

$^1$H NMR (500 MHz, DMSO-$d_6$) δ ppm 0.86 (d, J=6.41 Hz, 3H) 0.98-1.12 (m, 2H) 1.12-1.35 (m, 3H) 1.47 (s, 9H) 1.51-1.59 (m, 2H) 1.60-1.77 (m, 2H) 1.98-2.15 (m, 2H) 2.37-2.48 (m, 2H) 2.69-2.83 (m, 2H) 2.93 (t, J=11.82 Hz, 1H) 3.65 (s, 2H) 3.87-4.01 (m, 1H) 4.30-4.42 (m, 1H) 6.80 (s, 1H) 11.39 (br. s., 1H).

HRMS (ESI+): calcd. for $C_{21}H_{35}N_4O_3S$ $[M+H]^+$ 423.2425; found 423.2427.

Operating in an analogous way, but employing suitably substituted reagents, the following compounds were obtained:

tert-butyl [4-({[trans-4-(4-methylpiperidin-1-yl)cyclohexyl]oxy}methyl)-1,3-thiazol-2-yl]carbamate HRMS (ESI+): calcd. for $C_{21}H_{36}N_3O_3S$ $[M+H]^+$ 410.2472; found 410.2473.

tert-butyl {4-[2-(3-methyl-1,4'-bipiperidin-1'-yl)-2-oxoethyl]-1,3-thiazol-2-yl}carbamate HRMS (ESI+): calcd. for $C_{21}H_{35}N_4O_3S$ $[M+H]^+$ 423.2424; found 423.2412.

tert-butyl {4-[2-(4,4-difluoro-1,4'-bipiperidin-1'-yl)-2-oxoethyl]-1,3-thiazol-2-yl}carbamate $^1$H NMR (500 MHz, DMSO-$d_6$) δ ppm 1.16-1.36 (m, 2H) 1.50 (s, 9H) 1.65-1.76 (m, 2H) 1.85-2.04 (m, 4H) 2.55-2.63 (m, 5H) 2.91-3.02 (m, 1H) 3.29-3.37 (m overlapped by water signal, 1H) 3.68 (d, J=5.49 Hz, 2H) 3.93-4.02 (m, 1H) 4.37-4.46 (m, 1H) 6.84 (s, 1H) 11.42 (br. s., 1H).

HRMS (ESI+): calcd. for $C_{20}H_{31}F_2N_4O_3S$ $[M+H]^+$ 445.2080; found 445.2089.

tert-butyl {4-[2-(3,3-dimethyl-1,4'-bipiperidin-1'-yl)-2-oxoethyl]-1,3-thiazol-2-yl}carbamate $^1$H NMR (500 MHz, DMSO-$d_6$) δ ppm 0.87 (s, 6H) 1.08-1.21 (m, 4H) 1.47 (s, 9H) 1.51-1.69 (m, 2H) 2.04 (br. s., 2H) 2.26-2.44 (m, 2H) 2.86-3.03 (m, 1H) 3.64 (d, J=9.15 Hz, 2H) 3.85-3.97 (m, 1H) 4.27-4.40 (m, 1H) 6.81 (s, 1H) 11.39 (br. s., 1H).

HRMS (ESI+): calcd. for $C_{22}H_{37}N_4O_3S$ $[M+H]^+$ 437.2581; found 437.2581.

Step 3

2-(2-Amino-1,3-thiazol-4-yl)-1-(4-methyl-1,4'-bipiperidin-1'-yl)ethanone

Tert-butyl {4-[2-(4-methyl-1,4'-bipiperidin-1-yl)-2-oxoethyl]-1,3-thiazol-2-yl}carbamate (200 mg, 0.473 mmol) in HCl 4M in dioxane (5 mL) was stirred at rt over 4 h. Volatiles were removed under reduced pressure and the residue was diluted with DCM (20 mL) and partitioned with saturated aqueous $NaHCO_3$ (5 mL) and brine. The organic layer was dried over $Na_2SO_4$ and evaporated to dryness to give the title compound as white solid (100 mg, 66%).

$^1$H NMR (500 MHz, DMSO-$d_6$) δ ppm 0.85 (s, J=6.6 Hz, 3H) 0.99-1.12 (m, 2H) 1.14-1.36 (m, 3H) 1.48-1.59 (m, 2H) 1.60-1.75 (m, 2H) 1.99-2.16 (m, 2H) 2.39-2.47 (m, 1H) 2.68-2.80 (m, 2H) 2.88-2.99 (m, 1H) 3.47 (s, 2H) 3.90-4.02 (m, 1H) 4.31-4.42 (m, 1H) 6.19 (s, 1H) 6.84 (br. s., 2H).

HRMS (ESI+): calcd. for $C_{16}H_{27}N_4OS$ $[M+H]^+$ 323.19; found 323.1899.

Alternatively, after treatment with HCl 4M in dioxane for 4 h, the solvent was removed under vacuo and the title compound isolated as hydrochloride salt.

Operating in an analogous way, but employing suitably substituted reagents, the following compounds were obtained:

2-(2-amino-1,3-thiazol-4-yl)-1-(1,4'-bipiperidin-1'-yl)ethanone hydrochloride $^1$H NMR (500 MHz, DMSO-$d_6$) δ ppm 1.31-1.56 (m, 4H) 1.60-1.90 (m, 6H) 2.03-2.21 (m, 2H) 2.53-2.63 (m, 1H)

2.79-3.00 (m, 2H) 3.06 (t, J=12.43 Hz, 1H) 3.63-3.85 (m, 3H) 3.99-4.11 (m, 1H) 4.44-4.56 (m, 1H) 6.57 (s, 1H) 8.79 (br. s., 2H).

HRMS (ESI+): calcd. for $C_{15}H_{25}N_4OS$ [M+H]$^+$ 309.1744; found 309.1742.

2-(2-amino-1,3-thiazol-4-yl)-N-(1-cyclohexylpiperidin-4-yl)acetamide $^1$H NMR (500 MHz, DMSO-d$_6$) δ ppm 0.99-1.10 (m, 1H) 1.12-1.25 (m, 4H) 1.26-1.37 (m, 2H) 1.56 (m, 1H) 1.64-1.78 (m, 6H) 2.13-2.28 (m, 3H) 2.69-2.79 (m, 2H) 3.20 (s, 2H) 3.40-3.54 (m, 1H) 6.19 (s, 1H) 6.84 (s, 2H) 7.81 (d, J=7.78 Hz, 1H).

HRMS (ESI+): calcd. for $C_{16}H_{27}N_4OS$ [M+H]$^+$ 323.19; found 323.1898.

2-(2-amino-1,3-thiazol-4-yl)-1-(4-cyclohexylpiperazin-1-yl)ethanone $^1$H NMR (500 MHz, DMSO-d$_6$) δ ppm 0.99-1.27 (m, 5H) 1.50-1.60 (m, 1H) 1.65-1.79 (m, 4H) 2.16-2.28 (m, 1H) 2.36-2.46 (m, 2H) 3.37-3.46 (m, 2H) 3.46 (s, 2H) 6.19 (s, 1H) 6.84 (s, 2H).

HRMS (ESI+): calcd. for $C_{15}H_{25}N_4OS$ [M+H]$^+$ 309.1744; found 309.1744.

2-(2-amino-1,3-thiazol-4-yl)-1-(4-phenylpiperazin-1-yl)ethanone $^1$H NMR (500 MHz, DMSO-d$_6$) δ ppm 3.04-3.11 (m, 4H) 3.54 (s, 2H) 3.56-3.62 (m, 2H) 3.62-3.68 (m, 2H) 6.24 (s, 1H) 6.80 (t, J=7.24 Hz, 1H) 6.86 (br. s., 2H) 6.94 (d, J=7.93 Hz, 2H) 7.22 (t, J=7.93 Hz, 2H).

HRMS (ESI+): calcd. for $C_{15}H_{19}N_4OS$ [M+H]$^+$ 303.1274; found 303.1275.

1-(1,4'-bipiperidin-1'-yl)-2-[2-(methylamino)-1,3-thiazol-4-yl]ethanone $^1$H NMR (500 MHz, DMSO-d$_6$) δ ppm 1.14-1.31 (m, 3H) 1.31-1.41 (m, 2H) 1.40-1.54 (m, 3H) 1.61-1.76 (m, 2H) 2.38-2.49 (m, 7H) 2.77 (d, J=4.88 Hz, 3H) 2.85-3.02 (m, 1H) 3.45-3.58 (m, 2H) 3.90-4.08 (m, 1H) 4.34-4.45 (m, 1H) 6.25 (s, 1H) 7.39 (q, J=4.58 Hz, 1H).

HRMS (ESI+): calcd. for $C_{16}H_{27}N_4OS$ [M+H]$^+$ 323.19; found 323.19.

2-[2-(methylamino)-1,3-thiazol-4-yl]-1-(4-methyl-1,4'-bipiperidin-1'-yl)ethanone HRMS (ESI+): calcd. for $C_{17}H_{29}N_4OS$ [M+H]$^+$ 337.2057; found 337.2058.

ethyl (2-amino-1,3-thiazol-4-yl)(difluoro)acetate $^1$H NMR (500 MHz, DMSO-d$_6$) δ ppm 1.23 (t, J=7.09 Hz, 3H) 4.30 (q, J=7.02 Hz, 2H) 7.08 (s, 1H) 7.35 (br. s., 2H).

HRMS (ESI+): calcd. for $C_7H_6N_2O_2F_2S$ [M+H]$^+$ 223.0348; found 223.0344. 2-(2-amino-1,3-thiazol-4-yl)-1-(4,4'-dimethyl-1,4'-bipiperidin-1'-yl)ethanone $^1$H NMR (500 MHz, DMSO-d$_6$) δ ppm 0.83 (s, 3H) 0.87 (d, J=6.56 Hz, 3H) 0.99-1.12 (m, 2H) 1.15-1.39 (m, 3H) 1.54-1.63 (m, 2H) 1.69-1.78 (m, 2H) 1.98 (t, J=10.98 Hz, 2H) 2.76-2.87 (m, 2H) 3.04-3.18 (m, 1H) 3.39-3.54 (m, 3H) 3.64-3.76 (m, 1H) 6.18 (s, 1H) 6.84 (br. s., 2H).

HRMS (ESI+): calcd. for $C_{17}H_{29}N_4OS$ [M+H]$^+$ 337.2057; found 337.2056.

2-(2-amino-1,3-thiazol-4-yl)-1-(4,4-dimethyl-1,4'-bipiperidin-1'-yl)ethanone $^1$H NMR (500 MHz, DMSO-d$_6$) δ ppm 0.86 (s, 6H) 1.14-1.31 (m, 6H) 1.68 (t, J=15.86 Hz, 2H) 2.34-2.48 (m, 5H) 2.93 (t, J=11.67 Hz, 1H) 3.25-3.37 (m overlapped by water signal, 1H) 3.47 (s, 2H) 3.96 (d, J=12.96 Hz, 1H) 4.36 (d, J=13.12 Hz, 1H) 6.19 (s, 1H) 6.85 (br. s., 2H).

HRMS (ESI+): calcd. for $C_{17}H_{29}N_4OS$ [M+H]$^+$ 337.2057; found 337.2058.

2-(2-amino-1,3-thiazol-4-yl)-1-(3,3-dimethyl-1,4'-bipiperidin-1'-yl)ethanone $^1$H NMR (500 MHz, DMSO-d$_6$) δ ppm 0.87 (s, 6H) 1.08-1.33 (m, 4H) 1.40-1.53 (m, 2H) 1.53-1.69 (m, 2H) 2.00-2.15 (m, 2H) 2.30-2.44 (m, 3H) 2.93 (t, J=11.67 Hz, 1H) 3.47 (s, 2H) 3.94 (d, J=12.96 Hz, 1H) 4.34 (d, J=13.27 Hz, 1H) 6.19 (s, 1H) 6.85 (br. s., 2H).

HRMS (ESI+): calcd. for $C_{17}H_{29}N_4OS$ [M+H]$^+$ 337.2057; found 337.2054.

2-(2-amino-1,3-thiazol-4-yl)-1-(4,4-difluoro-1,4'-bipiperidin-1'-yl)ethanone $^1$H NMR (500 MHz, DMSO-d$_6$) δ ppm 1.12-1.34 (m, 3H) 1.53-1.74 (m, 2H) 1.80-2.00 (m, 4H) 2.53-2.61 (m, 5H) 2.87-2.99 (m, 1H) 3.47 (s, 2H) 3.92-4.04 (m, 1H) 4.33-4.45 (m, 1H) 6.20 (s, 1H) 6.85 (br. s., 2H).

HRMS (ESI+): calcd. for $C_{15}H_{23}F_2N_4OS$ [M+H]$^+$ 345.1555; found 345.15551.

2-(2-amino-1,3-thiazol-4-yl)-1-(3-methyl-1,4'-bipiperidin-1'-yl)ethanone $^1$H NMR (500 MHz, DMSO-d$_6$) δ ppm 0.81 (d, J=6.56 Hz, 3H) 1.14-1.84 (m, 9H) 1.90-2.17 (m, 1H) 2.38-2.48 (m overlapped by DMSO signal, 1H) 2.64-2.84 (m, 2H) 2.88-2.98 (m, 1H) 3.47 (s, 2H) 3.98 (d, J=13.27 Hz, 1H) 4.38 (d, J=12.66 Hz, 1H) 6.20 (s, 1H) 6.85 (br. s., 2H).

HRMS (ESI+): calcd. for $C_{16}H_{27}N_4OS$ [M+H]$^+$ 323.19; found 323.1904.

2-(2-amino-1,3-thiazol-4-yl)-1-(3,3-difluoro-1,4'-bipiperidin-1'-yl)ethanone $^1$H NMR (500 MHz, DMSO-d$_6$) δ ppm 1.13-1.34 (m, 2H) 1.51-1.73 (m, 4H) 1.76-1.91 (m, 2H) 2.43-2.48 (m, 2H) 2.53-2.61 (m, 1H) 2.68 (t, J=11.59 Hz, 2H) 2.88-2.98 (m, 1H) 3.48 (s, 2H) 3.97 (d, J=14.03 Hz, 1H) 4.39 (d, J=13.27 Hz, 1H) 6.20 (s, 1H) 6.86 (br. s., 2H).

HRMS (ESI+): calcd. for $C_{15}H_{23}F_2N_4OS$ [M+H]$^+$ 345.1555; found 345.1561.

Preparation 7

Tert-butyl methyl{4-[2-(4-methyl-1,4'-bipiperidin-1'-yl)-2-oxoethyl]-1,3-thiazol-2-yl}carbamate

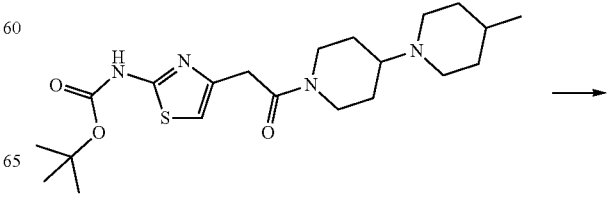

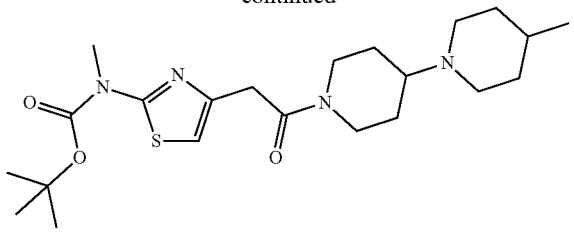

Tert-butyl {4-[2-(4-methyl-1,4'-bipiperidin-1-yl)-2-oxo-ethyl]-1,3-thiazol-2-yl}carbamate (65 mg, 0.15 mmol) in DMF (1 mL) was treated with $Cs_2CO_3$ (64 mg, 0.19 mmol), iodomethane (0.011 mL, 0.18 mmol) and stirred at rt overnight. The mixture was diluted with EtOAc (10 mL) and washed with water and brine. The organic phase was dried over $Na_2SO_4$ and evaporated to dryness to afford, after purification over silica gel (eluant EtOAc: 7N $NH_3$/MeOH=95:5), the title compound (65 mg, 99%).

$^1$H NMR (500 MHz, DMSO-$d_6$) δ ppm 0.86 (d, J=6.41 Hz, 3H) 0.95-1.40 (m, 5H) 1.52 (s, 9H) 1.49-1.74 (m, 5H) 1.97-2.20 (m, 2H) 2.65-2.87 (m, 2H) 2.87-3.05 (m, 1H) 3.42 (s, 3H) 3.60-3.77 (m, 2H) 3.93-4.08 (m, 2H) 4.32-4.46 (m, 2H) 6.89 (s, 1H).

HRMS (ESI+): calcd. for $C_{22}H_{37}N_4O_3S$ [M+H]$^+$ 437.2581; found 437.2585.

Operating in an analogous way, but employing suitably substituted reagents, the following intermediate compound was obtained:

tert-butyl {4-[2-(1,4'-bipiperidin-1'-yl)-2-oxoethyl]-1,3-thiazol-2-yl}methylcarbamate $^1$H NMR (500 MHz, DMSO-$d_6$) δ ppm 1.11-1.29 (m, 2H) 1.30-1.40 (m, 2H) 1.41-1.49 (m, 4H) 1.52 (s, 9H) 1.59-1.72 (m, 2H) 2.32-2.45 (m, 5H) 2.96 (t, J=11.67 Hz, 1H) 3.42 (s, 3H) 3.62-3.75 (m, 2H) 3.93-4.05 (m, 2H) 4.32-4.44 (m, 1H) 6.89 (s, 1H).

HRMS (ESI+): calcd. for $C_{21}H_{35}N_4O_3S$ [M+H]$^+$ 423.2425; found 423.2430.

Preparation 8

Ethyl {2-[(tert-butoxycarbonyl)amino]-1,3-thiazol-4-yl}(difluoro)acetate

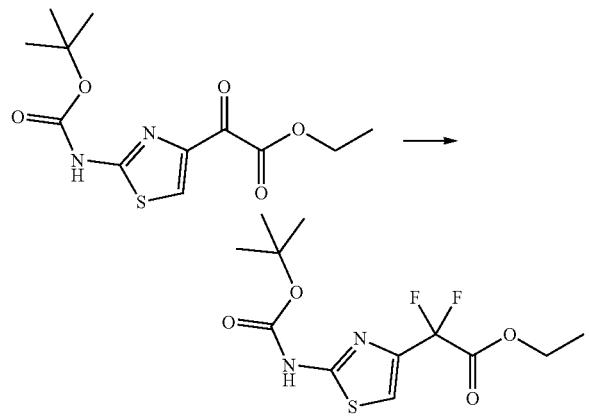

Ethyl {2-[(tert-butoxycarbonyl)amino]-1,3-thiazol-4-yl}(oxo)acetate (260 mg, 0.807 mmol) in 1,2-dichloroethane (3.3 mL) was cooled to 4° C. Diethylaminosulfur trifluoride (DAST) (0.176 mL, 1.33 mmol) was added dropwise then the reaction temperature was raised to rt and stirring continued for 20 h. Water (40 mL) was added to the reaction mixture taken at 4° C. and partitioned with EtOAc (40 mL). The aqueous phase was further extracted with EtOAc (20 mL). The combined organic extracts were washed with water (20 mL), brine, dried over $Na_2SO_4$ and evaporated to dryness to afford, after purification over silica gel (eluant hex:EtOAc=8:2), the title compound as white solid (263 mg, 82%).

$^1$H NMR (500 MHz, DMSO-$d_6$) δ ppm 1.23 (t, J=7.09 Hz, 3H) 1.47 (s, 9H) 4.31 (q, J=7.09 Hz, 2H) 7.70 (s, 1H) 11.82 (br. s., 1H).

HRMS (ESI+): calcd. for $C_{12}H_{17}N_2O_4F_2S$ [M+H]$^+$ 323.0872; found 323.0873.

Preparation 9

4-(1,4'-Bipiperidin-1'-ylmethyl)aniline

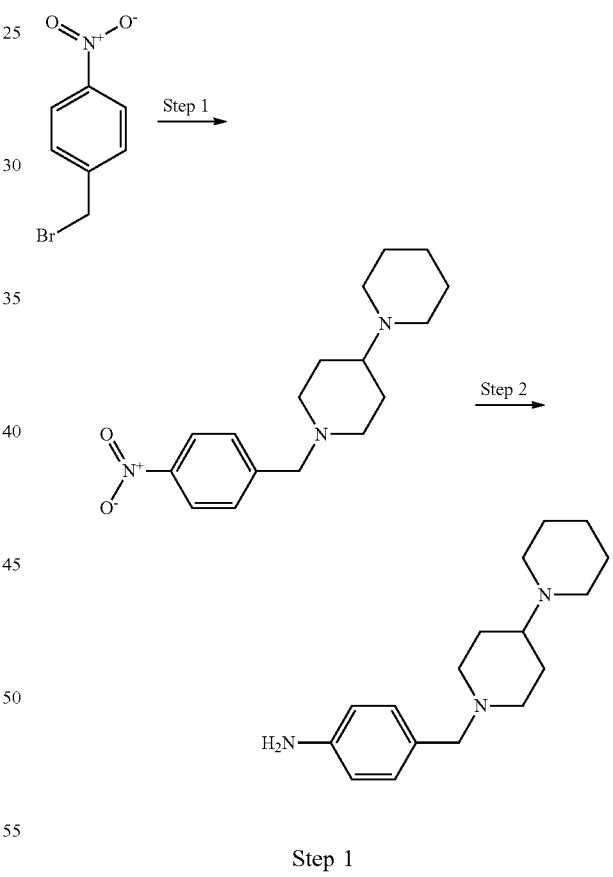

Step 1

1'-(4-Nitrobenzyl)-1,4'-bipiperidine

4-Nitrobenzyl bromide (0.3 g, 1.39 mmol) in dry acetonitrile (8 mL) was treated with 1,4'-bipiperidine (0.467 g, 2.78 mmol). The suspension was stirred at rt over 2 h. The volatiles were removed under reduced pressure, water was added (10 mL) and the mixture was extracted with EtOAc (3×10 mL). The combined organic extracts were dried over $Na_2SO_4$ and evaporated to give the title compound as yellow solid (405 mg, 96%).

¹H NMR (500 MHz, DMSO-d₆) δ ppm 1.27-1.39 (m, 2H) 1.39-1.50 (m, 6H) 1.61-1.70 (m, 2H) 1.91-1.99 (m, 2H) 2.11-2.22 (m, 1H) 2.37-2.45 (m, 4H) 2.76-2.84 (m, 2H) 3.56 (s, 2H) 7.57 (d, J=8.85 Hz, 2H) 8.16-8.20 (d, J=8.85 Hz, 2H).

HRMS (ESI+): calcd. for $C_{17}H_{26}N_3O_2$ [M+H]⁺ 304.2020; found 304.2016.

Operating in an analogous way, but employing suitably substituted reagents, the following intermediate compounds were obtained:

N,N-dimethyl-1-(4-nitrobenzyl)piperidin-4-amine

¹H NMR (500 MHz, DMSO-d₆) δ ppm 1.30-1.48 (m, 2H) 1.62-1.76 (m, 2H) 1.93-2.00 (m, 2H) 2.00-2.04 (m, 1H) 2.15 (s, 6H) 2.75-2.84 (m, 2H) 3.57 (s, 2H) 7.58 (d, J=8.69 Hz, 2H) 8.17 (d, J=8.69 Hz, 2H).

HRMS (ESI+): calcd. for $C_{14}H_{22}N_3O_2$ [M+H]⁺ 264.1707; found 264.1710.

tert-butyl [1-(4-nitrobenzyl)piperidin-4-yl]carbamate

¹H NMR (500 MHz, DMSO-d₆) δ ppm 1.37 (s, 9H) 1.37-1.45 (m, 2H) 1.59-1.71 (m, 2H) 1.94-2.04 (m, 2H) 2.67-2.77 (m, 2H) 3.13-3.27 (m, 1H) 3.56 (s, 2H) 6.79 (d, J=7.47 Hz, 1H) 7.57 (d, J=8.24 Hz, 2H) 8.19 (d, J=8.54 Hz, 2H).

HRMS (ESI+): calcd. for $C_{17}H_{26}N_3O_4$ [M+H]⁺ 336.1918; found 336.1916.

Step 2

4-(1,4'-bipiperidin-1'-ylmethyl)aniline

1'-(4-Nitrobenzyl)-1,4'-bipiperidine (405 mg, 1.33 mmol) in EtOH (5.5 mL) and water (3.3 mL) was treated with Fe powder (373 mg, 6.68 mmol) and NH₄Cl (715 mg, 13.3 mmol) and heated to 85° C. (oil bath temperature) over 2 h. EtOH was removed under vacuum and the aqueous phase was extracted with EtOAc (3×5 mL). The combined organic extracts were dried over Na₂SO₄, evaporated to dryness, purified over silica gel (DCM: 7N NH₃ in MeOH=9:1) to afford the title compound as yellow solid (136 mg, 36%) and the side-product N-(4-aminobenzyl)-4-(1,4'-bipiperidin-1'-ylmethyl)aniline.

HRMS (ESI+): calcd. for $C_{17}H_{28}N_3$ [M+H]⁺ 274.2278; found 274.2276.

N-(4-aminobenzyl)-4-(1,4'-bipiperidin-1'-ylmethyl)aniline

HRMS (ESI+): calcd. for $C_{24}H_{35}N_4$ [M+H]⁺ 379.2856; found 379.2849.

Operating in an analogous way, but employing suitably substituted reagents, the following compounds were obtained:

1-(4-aminobenzyl)-N,N-dimethylpiperidin-4-amine

¹H NMR (500 MHz, DMSO-d₆) δ ppm 1.26-1.44 (m, 2H) 1.59-1.71 (m, 2H) 1.74-1.90 (m, 2H) 1.99-2.13 (m, 1H) 2.18 (s, 6H) 2.71-2.87 (m, 2H) 3.24 (s, 2H) 4.93 (br. s., 2H) 6.48 (d, J=7.93 Hz, 2H) 6.89 (d, J=7.93 Hz, 2H).

HRMS (ESI+): calcd. for $C_{14}H_{25}N_3$ [M+H]⁺ 234.1965; found 234.1965.

tert-butyl [1-(4-aminobenzyl)piperidin-4-yl]carbamate

¹H NMR (500 MHz, DMSO-d₆) δ ppm 1.25-1.35 (m, 2H) 1.36 (s, 9H) 1.56-1.72 (m, 2H) 1.76-1.92 (m, 2H) 2.63-2.79 (m, 2H) 3.06-3.27 (m, 3H) 4.93 (br. s., 2H) 6.48 (d, J=8.39 Hz, 2H) 6.73 (d, J=7.63 Hz, 1H) 6.88 (d, J=8.39 Hz, 2H).

HRMS (ESI+): calcd. for $C_{17}H_{28}N_3O_2$ [M+H]⁺ 306.2176; found 306.2183.

Preparation 10

1-[(2-Amino-1,3-thiazol-4-yl)methyl]-N,N-dimethylpiperidin-4-amine dihydrochloride

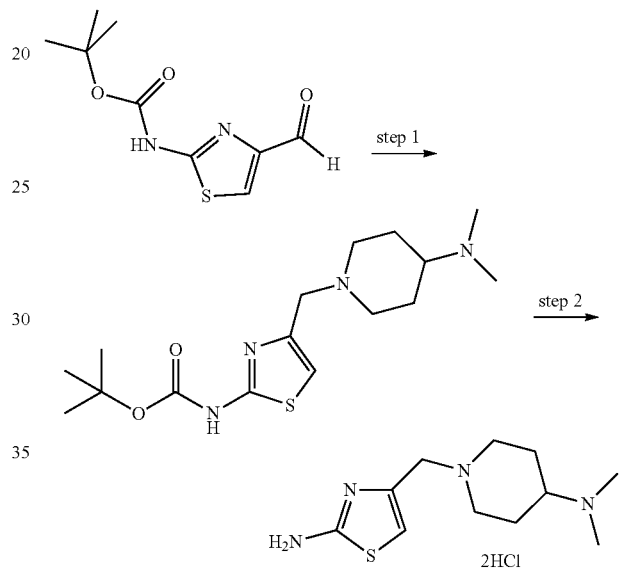

Step 1

Tert-butyl (4-{[4-(dimethylamino)piperidin-1-yl]methyl}-1,3-thiazol-2-yl)carbamate Tert-butyl (4-formyl-1,3-thiazol-2-yl)carbamate (200 mg, 0.88 mmol) in DMA (3 mL) was treated with N,N-dimethylpiperidin-4-amine (0.155 mL, 1.3 mmol) and stirred at rt over 1 h. AcOH (0.025 mL, 0.43 mmol) and sodium triacetoxyborohydride (465 mg, 2.19 mmol) were added to the reaction and stirred at rt for 20 h. The residue was partitioned between EtOAc and saturated aqueous NaHCO₃. The organic layer was dried over Na₂SO₄ and evaporated to dryness. The crude was purified by column chromatography over silica gel (DCM: 7N NH₃ in MeOH=9:1) to give the title compound as colourless oil (225 mg, 75%).

¹H NMR (500 MHz, DMSO-d₆) δ ppm 1.27-1.38 (m, 2H) 1.47 (s, 9H) 1.61-1.75 (m, 2H) 1.87-2.03 (m, 3H) 2.13 (s, 6H) 2.78-2.89 (m, 2H) 3.37 (s, 2H) 6.85 (s, 1H).

HRMS (ESI+): calcd. for $C_{16}H_{29}N_4O_2S$ [M+H]⁺ 341.2006; found 341.2008.

Operating in an analogous way, but employing suitably substituted reagents, the following intermediate compounds were obtained:

tert-butyl (4-{[(1-cyclohexylpiperidin-4-yl)amino]methyl}-1,3-thiazol-2-yl)carbamate $^1$H NMR (500 MHz, DMSO-d$_6$) δ ppm 0.92-1.23 (m, 5H) 1.47 (s, 9H) 1.50-1.59 (m, 1H) 1.63-1.80 (m, 8H) 2.09-2.17 (m, 2H) 2.17-2.25 (m, 1H) 2.28-2.36 (m, 1H) 2.69-2.78 (m, 2H) 3.63 (s, 2H) 6.82 (s, 1H) 11.29 (br. s., 1H).
HRMS (ESI+): calcd. for C$_{20}$H$_{35}$N$_4$O$_2$S [M+H]$^+$ 395.2475; found 395.2480.

tert-butyl [4-(1,4'-bipiperidin-1'-ylmethyl)-1,3-thiazol-2-yl]carbamate $^1$H NMR (500 MHz, DMSO-d$_6$) δ ppm 1.27-1.47 (m, 5H) 1.47 (s, 9H) 1.57-1.67 (m, 1H) 1.90 (t, J=10.90 Hz, 2H) 2.06-2.19 (m, 1H) 2.36-2.45 (m, 2H) 2.81-2.89 (m, 2H) 3.36 (s, 2H) 6.84 (s, 1H) 11.36 (br. s., 1H).
HRMS (ESI+): calcd. for C$_{19}$H$_{33}$N$_4$O$_2$S [M+H]$^+$ 381.2319; found 381.2318.

tert-butyl (4-{[(3R)-3-(dimethylamino)pyrrolidin-1-yl]methyl}-1,3-thiazol-2-yl)carbamate $^1$H NMR (500 MHz, DMSO-d$_6$) δ ppm 1.47 (s, 9H) 1.50-1.63 (m, 1H) 1.74-1.86 (m, 1H) 2.06 (s, 6H) 2.26 (dd, J=8.69, 6.86 Hz, 1H) 2.42 (td, J=8.69, 6.10 Hz, 1H) 2.57-2.67 (m, 2H) 2.68-2.74 (m, 1H) 3.39-3.55 (m, 2H) 6.84 (s, 1H) 7.49 (s, 1H) 11.35 (br. s., 1H).
HRMS (ESI+): calcd. for C$_{15}$H$_{27}$N$_4$O$_2$S [M+H]$^+$ 327.1849; found 327.1849.

Step 2

1-[(2-Amino-1,3-thiazol-4-yl)methyl]-N,N-dimethylpiperidin-4-amine dihydrochloride Tert-butyl (4-{[4-(dimethylamino)piperidin-1-yl]methyl}-1,3-thiazol-2-yl)carbamate (225 mg, 0.578 mmol) in HCl 4M in dioxane (10 mL, 2.5 mmol) was stirred at rt over 3 days. The volatiles were removed under reduced pressure to give the title compound in quantitative yield as a yellow solid.
$^1$H NMR (500 MHz, DMSO-d$_6$) δ ppm 1.91-2.09 (m, 2H) 2.17-2.28 (m, 2H) 2.71 (d, J=4.73 Hz, 6H) 2.93-3.08 (m, 2H) 3.46-3.62 (m, 2H partially overlapped by water signal) 4.10 (br. s., 2H) 6.84 (s, 1H) 7.40 (br. s., 2H) 10.86 (br. s., 1H).
HRMS (ESI+): calcd. for C$_{11}$H$_{21}$N$_4$S [M+H]$^+$ 241.1482; found 241.1486.

Operating in an analogous way, but employing suitably substituted reagents, the following intermediate compounds were obtained:

4-(1,4'-bipiperidin-1'-ylmethyl)-1,3-thiazol-2-amine dihydrochloride $^1$H NMR (500 MHz, DMSO-d$_6$) δ ppm 1.30-1.46 (m, 1H) 1.62-1.75 (m, 1H) 1.76-1.90 (m, 4H) 1.99-2.15 (m, 2H) 2.21-2.34 (m, 2H) 2.84-3.08 (m, 4H) 3.31-3.57 (m, 4H partially overlapped by water signal) 4.10 (br. s., 2H) 6.86 (s, 1H) 7.45 (br. s., 2H) 10.56 (br. s., 1H).
HRMS (ESI+): calcd. for C$_{14}$H$_{25}$N$_4$S [M+H]$^+$ 281.1795; found 281.1786.

4-{[(3R)-3-(dimethylamino)pyrrolidin-1-yl]methyl}-1,3-thiazol-2-amine dihydrochloride $^1$H NMR (500 MHz, DMSO-d$_6$) δ ppm 2.15-2.25 (m, 2H) 2.27-2.38 (m, 2H) 2.79 (s, 6H) 3.62-3.76 (m, 4H) 3.93-4.07 (m, 1H) 4.13 (br. s., 2H) 6.78 (s, 1H) 7.32 (br. s., 2H).
HRMS (ESI+): calcd. for C$_{10}$H$_{19}$N$_4$S [M+H]$^+$ 227.1325; found 227.1327.

N-[(2-amino-1,3-thiazol-4-yl)methyl]-N-(1-cyclohexylpiperidin-4-yl)-2,2,2-trifluoroacetamide HRMS (ESI+): calcd. for C$_{17}$H$_{26}$N$_4$OF$_3$S [M+H]$^+$ 391.1774; found 391.1775.

Preparation 11

Tert-butyl {1-[(2-amino-1,3-thiazol-4-yl)methyl]piperidin-4-yl}carbamate

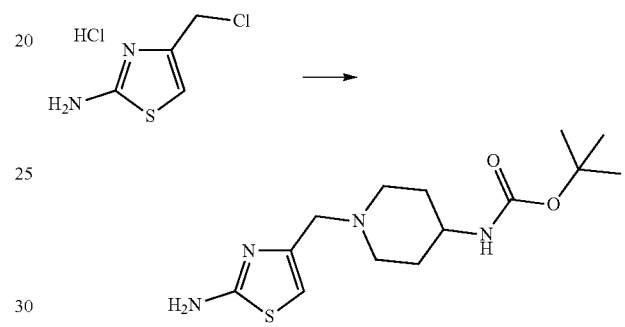

A suspension of 4-(chloromethyl)thiazol-2-amine hydrochloride (50 mg, 0.27 mmol) in THF (2 mL) was treated with 4-(N-Boc amino)-piperidine (76 mg, 0.378 mmol) and DIPEA (0.185 mL, 1.08 mmol) and stirred 16 h under reflux. The volatiles were removed under vacuum. The residue was partitioned between DCM (10 mL) and water (5 mL). The organic layer was dried over Na$_2$SO$_4$, filtered and evaporated. The crude was purified over silica gel (DCM:MeOH: 7N NH$_3$ in MeOH=9:0.5:0.5) to give 70 mg of title compound (84%).
$^1$H NMR (500 MHz, DMSO-d$_6$) δ ppm 1.28-1.36 (m, 2H) 1.36 (s, 9H) 1.58-1.71 (m, 2H) 1.86-2.02 (m, 2H) 2.72-2.86 (m, 2H) 3.08-3.27 (m, 3H) 6.25 (br. s., 1H) 6.75 (d, J=7.78 Hz, 1H) 6.81 (br. s., 2H).
HRMS (ESI+): calcd. for C$_{14}$H$_{25}$N$_4$O$_2$S [M+H]$^+$ 313.1693; found 313.17.

Preparation 12

Tert-butyl (4-{[(1-cyclohexylpiperidin-4-yl)(trifluoroacetyl)amino]methyl}-1,3-thiazol-2-yl)carbamate

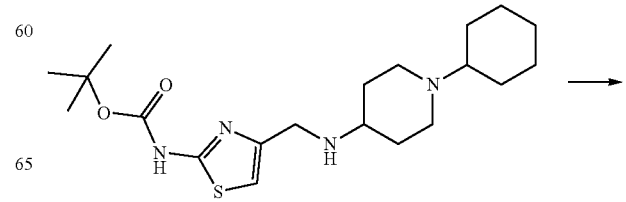

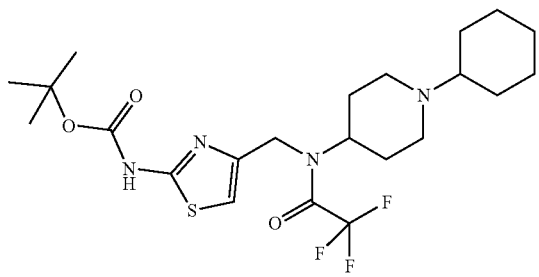

A solution of tert-butyl (4-{[(1-cyclohexylpiperidin-4-yl)amino]methyl}-1,3-thiazol-2-yl)carbamate (120 mg, 0.304 mmol) and TEA (0.085 mL, 0.609 mmol) in DCM (2 mL) was treated with TFAA (0.055 mL, 0.395 mmol) and stirred at rt over 2 h. Further TFAA (0.060 mL, 0.426 mmol) and TEA (0.127 mL, 0.01 mmol) were added at 4° C. and after stirring for further 2 h at rt, the reaction was diluted with DCM (10 mL) and washed with water. The organic phase was dried over $Na_2SO_4$, filtered and evaporated to leave 160 mg of crude as a yellow solid which was purified over silica gel (DCM:MeOH=9:0.5) to give 120 mg of title compound as a pale yellow solid (80%).

$^1$H NMR (500 MHz, DMSO-$d_6$) δ ppm 0.96-1.28 (m, 5H) 1.47 (s, 9H) 1.51-1.89 (m, 9H) 2.19 (br. s., 2H) 2.66-3.00 (m, 2H) 3.47-4.01 (m, 1H) 4.41-4.62 (m, 2H) 6.79 (s, 1H) 7.02 (s, 1H) 11.29-11.59 (m, 1H).

HRMS (ESI+): calcd. for $C_{22}H_{34}N_4O_3F_3S$ [M+H]$^+$ 491.2298; found 491.2302.

Preparation 13

4,4'-dimethyl-1,4'-bipiperidine dihydrochloride

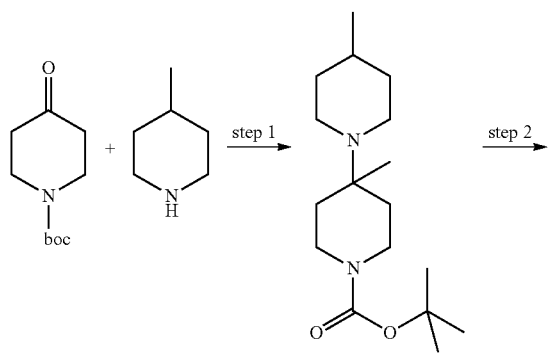

Step 1

Tert-butyl 4,4'-dimethyl-1,4'-bipiperidine-1'-carboxylate

To a solution of 4-methylpiperidine (2.1 g, 21.33 mmol) in dry toluene (18 mL), 1-Boc-4-piperidone (2.5 g, 12.55 mmol) and 1,2,3-triazole (0.65 mL, 11.22 mmol) were added. The solution was left under reflux for 20 h with a Dean-Stark trap, then it was cooled to 0° C. and a solution of $CH_3MgCl$ in THF (3.0 M, 17 mL) was added dropwise under argon atmosphere. The mixture was left at rt for 2 h, then the reaction was quenched at 0° C. with $NH_4Cl$ aq 20% (10 mL). The aqueous phase was diluted to 300 mL and the product was extracted with EtOAc (160 mL×3). The combined organic extracts were then washed with NaOH 2N (150 mL) and water (150 mL) and dried over $Na_2SO_4$ and evaporated. The crude product was purified by column chromatography over silica gel (DCM:MeOH=90:10) affording the title compound (770 mg, 21%).

$^1$H NMR (500 MHz, DMSO-$d_6$) δ ppm 0.83 (s, 3H) 0.87 (d, J=6.56 Hz, 3H) 1.01-1.12 (m, 2H) 1.20-1.28 (m, 3H) 1.38 (s, 9H) 1.54-1.64 (m, 2H) 1.69-1.77 (m, 2H) 1.97 (t, J=11.13 Hz, 2H) 2.75-2.86 (m, 2H) 3.03-3.26 (m, 2H) 3.36-3.42 (m overlapped by water signal, 2H).

HRMS (ESI+): calcd. for $C_{17}H_{33}N_2O_2$ [M+H]$^+$ 297.2537; found 297.2534.

Step 2

4,4'-dimethyl-1,4'-bipiperidine dihydrochloride

A solution of tert-butyl 4,4'-dimethyl-1,4'-bipiperidine-1'-carboxylate (738 mg, 2.49 mmol) in dry dioxane (6 mL) was treated with 4M HCl in dioxane (6 mL). The mixture was left under stirring at rt for 20 h. The solvent was then removed under vacuum and the residue was washed with $Et_2O$ and dried affording the title compound (390 mg, 58%).

$^1$H NMR (500 MHz, DMSO-$d_6$) δ ppm 0.91 (d, J=5.64 Hz, 3H) 1.38 (s, 3H) 1.54-1.72 (m, 3H) 1.75-1.84 (m, 2H) 2.02-2.08 (m, 2H) 2.11-2.18 (m, 2H) 2.84-2.95 (m, 2H) 2.99-3.06 (m, 2H) 3.37-3.49 (m partially overlapped by water signal, 4H) 8.85 (br. s., 1H) 9.01 (br. s., 1H) 9.91 (br. s., 1H).

HRMS (ESI+): calcd. for $C_{12}H_{25}N_2$ [M+H]$^+$ 197.2012; found 197.2008.

Preparation 14

Tert-butyl (2,4-dimethoxybenzyl)[4-(iodomethyl)-1,3-thiazol-2-yl]carbamate

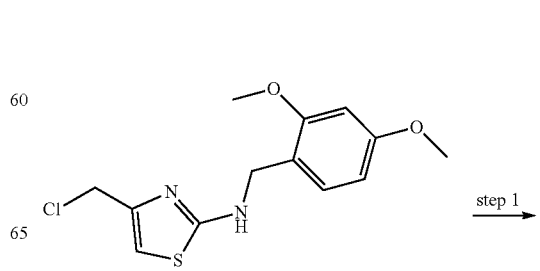

197

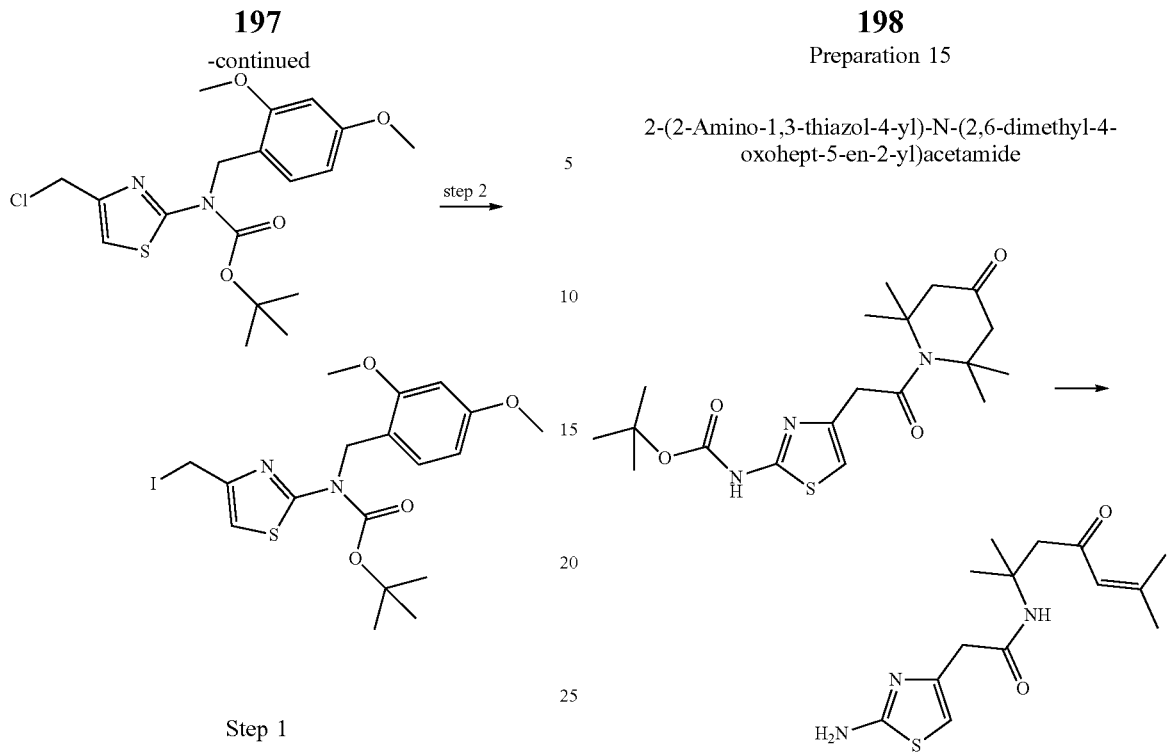

Step 1

Tert-butyl [4-(chloromethyl)-1,3-thiazol-2-yl](2,4-dimethoxybenzyl)carbamate

A solution of 4-(chloromethyl)-N-(2,4-dimethoxybenzyl)-1,3-thiazol-2-amine (ref. WO2009/015208) (670 mg, 2.2 mmol) in THF (7.6 mL) was treated with Boc₂O (576 mg, 2.64 mmol), TEA (0.523 mmol, 3.75 mmol) and finally with a catalytic amount of DMAP. The reaction was stirred at rt for 5 h, treated with water (10 mL), extracted with EtOAc (20 mL), dried over Na₂SO₄, evaporated to dryness and purified over silica gel (hex:EtOAc=8:2) to afford the title compound as a pale yellow solid (510 mg, 58%).

¹H NMR (500 MHz, DMSO-d₆) δ ppm 1.38 (s, 9H) 3.72 (s, 3H) 3.79 (s, 3H) 4.65 (s, 2H) 5.15 (s, 2H) 6.44 (dd, J=8.39, 2.29 Hz, 1H) 6.56 (d, J=2.29 Hz, 1H) 6.75 (d, J=8.39 Hz, 1H) 7.30 (s, 1H).

HRMS (ESI+): calcd. for C₁₈H₂₄ClN₂O₄S [M+H]⁺ 399.1140; found 399.1145.

Step 2

Tert-butyl (2,4-dimethoxybenzyl)[4-(iodomethyl)-1,3-thiazol-2-yl]carbamate

Tert-butyl [4-(chloromethyl)-1,3-thiazol-2-yl](2,4-dimethoxybenzyl)carbamate (500 mg, 1.26 mmol) in acetone (5 mL) was treated with NaI (1.89 g, 12.6 mmol) and stirred at rt for 13 h. The volatiles were removed under reduced pressure, water was added (25 mL) and the mixture was extracted with EtOAc (25 mL). The organic extract was dried over Na₂SO₄ and evaporated to give the title compound as yellow solid (460 mg, 74%).

HRMS (ESI+): calcd. for C₁₈H₂₄IN₂O₄S [M+H]⁺ 491.0496; found 491.0492.

198

Preparation 15

2-(2-Amino-1,3-thiazol-4-yl)-N-(2,6-dimethyl-4-oxohept-5-en-2-yl)acetamide

A solution of tert-butyl {4-[2-oxo-2-(2,2,6,6-tetramethyl-4-oxopiperidin-1-yl)ethyl]-1,3-thiazol-2-yl}carbamate (340 mg, 0.861 mmol) in DCM (24 mL) was treated with TFA (6.15 mL) and let under stirring at rt for 3.5 h. The mixture was then neutralized with a saturated solution of NaHCO₃ and extracted with DCM. The organic layer was dried over Na₂SO₄, filtered and evaporated to dryness under reduced pressure. A flash column chromatography afforded the title compound as white solid (145 mg, 57%).

¹H NMR (500 MHz, DMSO-d₆) δ ppm 1.46 (s, 6H) 1.81 (s, 3H) 2.02 (s, 3H) 2.82 (s, 2H) 3.19 (s, 2H) 6.06 (br. s., 1H) 6.20 (s, 1H) 6.84 (br. s., 2H) 7.63 (br. s., 1H).

HRMS (ESI+): calcd. for C₁₄H₂₂N₃O₂S [M+H]⁺ 296.1427; found 296.1428.

Preparation 16

8-amino-2,4,4-trimethyl-4,5-dihydro-2H-pyrazolo[4,3-h]quinazoline-3-carboxylic acid (Va)

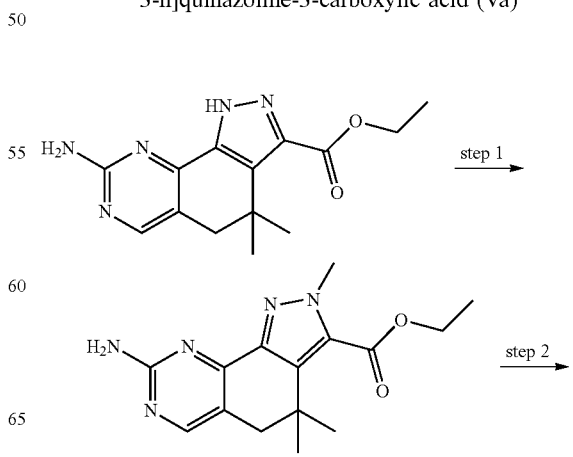

-continued

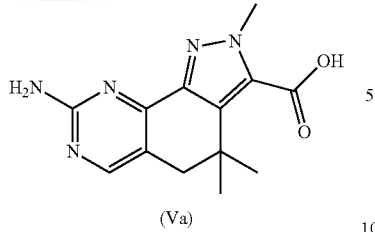

(Va)

Step 1

Ethyl 8-amino-2,4,4-trimethyl-4,5-dihydro-2H-pyrazolo[4,3-h]quinazoline-3-carboxylate A suspension of ethyl 8-amino-4,4-dimethyl-4,5-dihydro-1H-pyrazolo[4,3-h]quinazoline-3-carboxylate (428 mg, 1.490 mmol) in dry DMF (10 mL) was kept at 0° C. and a 1.0 M solution of LiOtBu in THF (1.7 mL) was added dropwise under an argon atmosphere. The mixture was left at 0° C. for 30 min then a solution of $CH_3I$ (0.2 mL, 3.213 mmol) in dry THF (8 mL) was added in 20 min and the reaction was left under stirring at rt for 15 h. Then the solvents were removed by distillation under vacuum and the residue was partitioned between DCM (30 mL) and a 10% solution of $NaH_2PO_4$ (pH4, 30 mL); the aqueous phase was further extracted with DCM (30 mL×5). The combined organic extracts were dried over $Na_2SO_4$ and evaporated to leave 766 mg of crude product which was purified by column chromatography (eluant DCM:MeOH=97:3) affording the title compound (135 mg, 30%).

$^1$H NMR (500 MHz, DMSO-$d_6$) δ ppm 1.27 (s, 6H) 1.35 (t, J=7.09 Hz, 3H) 2.60 (s, 2H) 4.02 (s, 3H) 4.38 (q, J=7.20 Hz, 2H) 6.49 (br. s., 2H) 8.12 (s, 1H).

HRMS (ESI+): calcd. for $C_{15}H_{20}N_5O_2$[M+H]+ 302.1612; found 302.1612.

Operating in an analogous way, but employing suitably substituted reagents, the following intermediate compounds were obtained:

ethyl8-amino-4,4-dimethyl-2-[2-(tetraydro-2H-pyran-2-yl oxy)ethyl]-4,5-dihydro-2H-pyrazolo[4,3-h]quinazoline-3-carboxylate $^1$H NMR (500 MHz, DMSO-$d_6$) δ ppm 1.23 (s, 3H) 1.28 (s, 3H) 1.35 (t, J=7.09 Hz, 3H) 1.35-1.43 (m, 4H) 1.44-1.55 (m, 1H) 1.55-1.69 (m, 1H) 2.60 (d, J=6.71 Hz, 2H) 3.16-3.27 (m, 2H) 3.57-3.67 (m, 1H) 3.79-3.91 (m, 1H) 4.36 (q, J=7.17 Hz, 2H) 4.44-4.47 (m, 1H) 4.50-4.69 (m, 1H) 6.53 (br.s., 2H) 8.12 (s, 1H).

HRMS (ESI+): calcd. for $C_{21}H_{30}N_5O_4$ [M+H]+ 416.2293; found 416.2297.

ethyl8-amino-4,4-dimethyl-1-[2-(tetrahydro-2H-pyran-2-yloxy)ethyl]-4,5-dihydro-1H-pyrazolo[4,3-h]quinazoline-3-carboxylate $^1$H NMR (500 MHz, DMSO-$d_6$) δ ppm 1.26 (s, 3H) 1.28-1.33 (m, 6H) 1.33-1.54 (m, 6H) 2.60 (s, 2H) 3.29-3.45 (m partially overlapped by water signal, 1H) 3.73-3.82 (m, 1H) 3.83-3.96 (m, 1H) 4.30 (q, J=7.02 Hz, 2H) 4.43-4.48 (m, 1H) 4.54 (t, J=3.13 Hz, 1H) 4.82-4.93 (m, 1H) 5.13-5.28 (m, 1H) 6.59 (br. s., 2H) 8.17 (s, 1H).

HRMS (ESI+): calcd. for $C_{21}H_{30}N_5O_4$ [M+H]+ 416.2293; found 416.2302.

ethyl8-amino-2-(2-{[tert-butyl(dimethyl)silyl]oxy}ethyl)-4,4-dimethyl-4,5-dihydro-2H-pyrazolo[4,3-h]quinazoline-3-carboxylate $^1$H NMR (500 MHz, DMSO-$d_6$) δ ppm-0.15 (s, 6H) 0.73 (s, 9H) 1.26 (s, 6H) 1.34 (t, J=7.09 Hz, 3H) 2.59 (s, 2H) 3.87 (t, J=5.19 Hz, 2H) 4.34 (q, J=7.17 Hz, 2H) 4.49 (t, J=5.19 Hz, 2H) 6.53 (br. s., 2H) 8.12 (s, 1H).

HRMS (ESI+): calcd. for $C_{22}H_{36}N_5O_3Si$ [M+H]+ 446.2582; found 446.2579.

ethyl8-amino-1-(2-{[tert-butyl(dimethyl)silyl]oxy}ethyl)-4,4-dimethyl-4,5-dihydro-1H-pyrazolo[4,3-h]quinazoline-3-carboxylate $^1$H NMR (500 MHz, DMSO-$d_6$) δ ppm-0.21 (m, 6H) 0.65 (s, 9H) 1.26-1.32 (m, 9H) 2.59 (s, 2H) 3.95 (t, J=5.03 Hz, 2H) 4.29 (q, J=7.07 Hz, 2H) 4.96 (t, J=5.03 Hz, 2H) 6.54 (br. s., 2H) 8.16 (s, 1H).

HRMS (ESI+): calcd. for $C_{22}H_{36}N_5O_3Si$ [M+H]+ 446.2582; found 446.2583.

Step b 8-amino-2,4,4-trimethyl-4,5-dihydro-2H-pyrazolo[4,3-h]quinazoline-3-carboxylic acid (Va)

[R1=R3'=R4'=H, R2=R3=R4=($C_1$-$C_6$)alkyl, W=COOH]

A suspension of ethyl 8-amino-2,4,4-trimethyl-4,5-dihydro-2H-pyrazolo[4,3-h]quinazoline-3-carboxylate (131 mg, 0.435 mmol) in EtOH (1.5 mL) was treated with 2 N NaOH (2.2 mL, 4.35 mmol) and heated at reflux for 2 h. The reaction was cooled to 0° C. and AcOH (0.25 mL, 4.35 mmol) was added dropwise. The resulting solid was filtered under suction, washed thoroughly with water, dried under vacuum to afford the title compound as white solid (101 mg, 85%).

$^1$H NMR (500 MHz, DMSO-$d_6$) δ ppm 1.28 (s, 6H) 2.59 (s, 2H) 4.01 (s, 3H) 6.47 (br. s., 2H) 8.10 (s, 1H), 13.95 (br. s., 1H).

HRMS (ESI+): calcd. for $C_{13}H_{16}N_5O_2$[M+H]+ 274.1299; found 274.1301.

Operating in an analogous way, but employing suitably substituted intermediates, the following intermediate compounds were obtained:

8-amino-4,4-dimethyl-2-[2-(tetrahydro-2H-pyran-2-yloxy)ethyl]-4,5-dihydro-2H-pyrazolo[4,3-h]quinazoline-3-carboxylic acid (Va)

[R1=R3'=R4'=H, R2=R3=R4=($C_1$-$C_6$)alkyl, W=COOH]

$^1$H NMR (500 MHz, DMSO-$d_6$) δ ppm 1.28 (s, 3H) 1.33 (s, 3H) 1.34-1.49 (m, 4H) 1.49-1.61 (m, 1H) 1.63-1.79 (m, 1H) 2.61 (d, J=4.73 Hz, 2H) 3.19-3.35 (m partially overlapped by water signal, 2H) 3.65-3.75 (m, 1H) 3.83-3.95 (m, 1H) 4.45-4.51 (m, 1H) 4.52-4.73 (m, 2H) 6.51 (br. s., 2H) 8.13 (s, 1H).

HRMS (ESI+): calcd. for $C_{19}H_{26}N_5O_4$ [M+H]+ 388.1980; found 388.1994.

8-amino-2-(2-hydroxyethyl)-4,4-dimethyl-4,5-di-hydro-2H-pyrazolo[4,3-h]quinazoline-3-carboxylic acid (Va)

[R1=R3'=R4'=H, R2=R3=R4=($C_1$-$C_6$)alkyl, W=COOH]
$^1$H NMR (500 MHz, DMSO-$d_6$) δ ppm 1.27 (s, 6H) 2.58 (s, 2H) 3.71 (t, J=5.87 Hz, 2H) 4.41 (t, J=5.80 Hz, 2H) 4.94 (br. s., 1H) 6.48 (br. s., 2H) 8.10 (s, 1H).
HRMS (ESI+): calcd. for $C_{14}H_{1}N_5O_3$ [M+H]+ 304.1404; found 304.1406.

8-amino-1-(2-hydroxyethyl)-4,4-dimethyl-4,5-di-hydro-1H-pyrazolo[4,3-h]quinazoline-3-carboxylic acid (Va)

[R1=R3'=R4'=H, R2=R3=R4=($C_1$-$C_6$)alkyl, W=COOH]
$^1$H NMR (500 MHz, DMSO-$d_6$) δ ppm 1.29 (s, 6H) 2.60 (s, 2H) 3.79 (q, J=5.80 Hz, 2H) 4.80 (q, J=6.10 Hz, 2H) 6.55 (br. s., 2H) 8.16 (s, 1H) 12.81 (br. s., 1H).
HRMS (ESI+): calcd. for $C_{14}H_{18}N_5O_3$ [M+H]+ 304.1404; found 304.1407.

The invention claimed is:
1. A compound of formula (I):

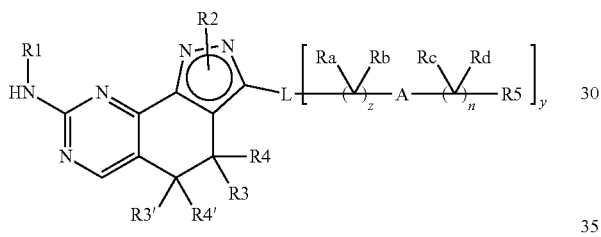

or a pharmaceutically acceptable salt thereof,
wherein:
A is ($C_3$-$C_7$)cycloalkyl, heterocyclyl, aryl, or heteroaryl, wherein the ($C_3$-$C_7$)cycloalkyl, heterocyclyl, aryl, or heteroaryl is optionally substituted with one or more independently selected substituents;
L is C(O)NR6aR7a, —C(O)NR8-, NR8C(O)R6a, or —NR8C(O)—;
R1 is hydrogen, or ($C_1$-$C_6$)alkyl;
R2 is hydrogen, ($C_1$-$C_6$)alkyl, ($C_2$-$C_6$)alkenyl, ($C_2$-$C_6$) alkynyl, ($C_3$-$C_7$)cycloalkyl, or heterocyclyl, wherein the ($C_1$-$C_6$)alkyl, ($C_2$-$C_6$)alkenyl, ($C_2$-$C_6$) alkynyl, ($C_3$-$C_7$)cycloalkyl, or heterocyclyl is optionally substituted with one or more independently selected substituents;
R3 is hydrogen or ($C_1$-$C_6$)alkyl;
R4 is hydrogen or ($C_1$-$C_6$)alkyl;
R3' is hydrogen or ($C_1$-$C_6$)alkyl;
R4' is hydrogen or ($C_1$-$C_6$)alkyl;
R5 is C(O)R6, C(O)NR6R7, C(O)OR6, NR6R7, NR7C(O)R6, NR7C(O)NR6R7, NR7C(O)OR9, or OR6;
R6 is hydrogen, ($C_1$-$C_6$)alkyl, aryl($C_1$-$C_6$)alkyl, heteroaryl($C_1$-$C_6$)alkyl, ($C_3$-$C_7$)cycloalkyl, heterocyclyl, aryl, or heteroaryl, wherein the ($C_1$-$C_6$)alkyl, aryl($C_1$-$C_6$)alkyl, heteroaryl($C_1$-$C_6$)alkyl, ($C_3$-$C_7$) cycloalkyl, heterocyclyl, aryl, or heteroaryl is optionally substituted with one or more independently selected substituents;
each R7 is independently hydrogen, ($C_1$-$C_6$)alkyl, aryl ($C_1$-$C_6$)alkyl, heteroaryl($C_1$-$C_6$)alkyl, ($C_3$-$C_7$)cycloalkyl, heterocyclyl, aryl, or heteroaryl, wherein each ($C_1$-$C_6$)alkyl, aryl($C_1$-$C_6$)alkyl, heteroaryl($C_1$-$C_6$)alkyl, ($C_3$-$C_7$)cycloalkyl, heterocyclyl, aryl, and heteroaryl is optionally and independently substituted with one or more independently selected substituents; or
R6 and R7, taken together with the nitrogen atom to which they are bonded, form a 5- or 6-membered heterocyclyl, wherein the 5- or 6-membered heterocyclyl optionally contains one additional heteroatom selected from the group consisting of nitrogen, oxygen, and sulfur, and further wherein the 5- or 6-membered heterocyclyl is optionally substituted with one or more independently selected substituents;
R6a is hydrogen, ($C_1$-$C_6$)alkyl, aryl($C_1$-$C_6$)alkyl, heteroaryl($C_1$-$C_6$)alkyl, ($C_3$-$C_7$)cycloalkyl, heterocyclyl, aryl, or heteroaryl, wherein the ($C_1$-$C_6$)alkyl, aryl($C_1$-$C_6$)alkyl, heteroaryl($C_1$-$C_6$)alkyl, ($C_3$-$C_7$) cycloalkyl, heterocyclyl, aryl, or heteroaryl is optionally substituted with one or more independently selected substituents;
R7a is hydrogen, ($C_1$-$C_6$)alkyl, aryl($C_1$-$C_6$)alkyl, heteroaryl($C_1$-$C_6$)alkyl, ($C_3$-$C_7$)cycloalkyl, heterocyclyl, aryl, or heteroaryl, wherein the ($C_1$-$C_6$)alkyl, aryl($C_1$-$C_6$)alkyl, heteroaryl($C_1$-$C_6$)alkyl, ($C_3$-$C_7$) cycloalkyl, heterocyclyl, aryl, or heteroaryl is optionally substituted with one or more independently selected substituents; or
R6a and R7a, taken together with the nitrogen atom to which they are bonded, form a 5- or 6-membered heterocyclyl, wherein the 5- or 6-membered heterocyclyl optionally contains one additional heteroatom selected from the group consisting of nitrogen, oxygen, and sulfur, and further wherein the 5- or 6-membered heterocyclyl is optionally substituted with one or more independently selected substituents;
R8 is hydrogen or ($C_1$-$C_6$)alkyl, wherein the ($C_1$-$C_6$) alkyl is optionally substituted with one or more independently selected substituents;
R9 is ($C_1$-$C_6$)alkyl, aryl($C_1$-$C_6$)alkyl, heteroaryl($C_1$-$C_6$) alkyl, ($C_3$-$C_7$)cycloalkyl, heterocyclyl, aryl, or heteroaryl, wherein the ($C_1$-$C_6$)alkyl, aryl($C_1$-$C_6$) alkyl, heteroaryl($C_1$-$C_6$) alkyl, ($C_3$-$C_7$)cycloalkyl, heterocyclyl, aryl, or heteroaryl is optionally substituted with one or more independently selected substituents;
Ra is hydrogen, fluoro, or ($C_1$-$C_6$)alkyl, wherein the ($C_1$-$C_6$) alkyl is optionally substituted with one or more independently selected substituents;
Rb is hydrogen, fluoro, or ($C_1$-$C_6$)alkyl, wherein the ($C_1$-$C_6$) alkyl is optionally substituted with one or more independently selected substituents; or
Ra and Rb, taken together with the carbon atom to which they are bonded, form a 3-membered cycloalkyl;
Rc is hydrogen, fluoro, or ($C_1$-$C_6$)alkyl, wherein the ($C_1$-$C_6$) alkyl is optionally substituted with one or more independently selected substituents;
Rd is hydrogen, fluoro, or ($C_1$-$C_6$)alkyl, wherein the ($C_1$-$C_6$) alkyl is optionally substituted with one or more independently selected substituents; or
Rc and Rd, taken together with the carbon atom to which they are bonded, form a 3-membered cycloalkyl;
y is 0 or 1;
n is 0, 1, or 2; and
z is 0, 1, or 2;

wherein the optional substituents for A, R2, R5, R6, R6a, R7, R7a, R6 and R7, R6a and R7a, R8, R9, Ra, Rb, Rc, Rd, Ra and Rb, and Rc and Rd, are independently selected from the group consisting halogen, cyano, nitro, oxo, $(C_1-C_6)$alkyl, polyfluorinated $(C_1-C_6)$alkyl, C(O)NHaryl$(C_1-C_6)$alkyl, C(O)heterocyclyl$(C_1-C_6)$alkyl, amino$(C_1-C_6)$alkyl, hydroxy$(C_1-C_6)$alkyl, $(C_3-C_7)$cycloalkyl$(C_1-C_6)$alkyl, heterocyclyl$(C_1-C_6)$alkyl, $(C_1-C_6)$alkylheterocyclyl$(C_1-C_6)$alkyl, di$(C_1-C_6)$alkylaminoheterocyclyl$(C_1-C_6)$alkyl, aryl$(C_1-C_6)$alkyl, heteroaryl$(C_1-C_6)$alkyl, $(C_2-C_6)$alkenyl, $(C_2-C_6)$alkynyl, C(NH)O$(C_1-C_6)$alkyl, C(O)H, C(O)$(C_1-C_6)$alkyl, C(O)NH$_2$, C(O)NH$(C_1-C_6)$alkyl, C(O)N$((C_1-C_6)$alkyl$)_2$, CO)NHOH, C(O)NHheterocyclyl, C(O)NHaryl, C(O)NHheteroaryl, C(O)OH, C(O)O$(C_1-C_6)$alkyl, C(O)O$(C_3-C_7)$cycloalkyl, C(O)Oaryl, C(O)$(C_3-C_7)$cycloalkyl, C(O)heterocyclyl, C(O)aryl, NH$_2$, NH$(C_1-C_6)$alkyl, N$((C_1-C_6)$alkyl$)_2$, NHC(O)H, NHC(O)$(C_1-C_6)$alkyl, NHC(O)NH$_2$, NHC(O)NH$(C_1-C_6)$alkyl, NHC(O)O$(C_1-C_6)$alkyl, NHC(O)O$(C_1-C_6)$alkyl(heterocyclyl), NHC(O)$(C_3-C_7)$cycloalkyl, NHC(O)heterocyclyl, NHC(O)aryl, NHS(O)$_2(C_1-C_6)$alkyl, NHS(O)$_2$heterocyclyl, NHS(O)$_2$aryl, NHheterocyclyl, NHaryl, N(aryl)$_2$, OH, —OCH$_2$O—, O$(C_1-C_6)$alkyl, (polyfluorinated) O$(C_1-C_6)$alkyl, (aryl) O$(C_1-C_6)$alkyl, O$(C_1-C_6)$alkylideneamino, OC(O)$(C_1-C_6)$alkyl, OC(O)heterocyclyl, OC(O)aryl, O$(C_3-C_7)$cycloalkenyl, Oheterocyclyl, Oaryl, tri$(C_1-C_6)$alkylsilyl, S$(C_1-C_6)$alkyl, Saryl, S(O)$_2(C_1-C_6)$alkyl, polyfluorinated S(O)$_2(C_1-C_6)$alkyl, S(O)$_2$NH$_2$, S(O)$_2$NH$(C_1-C_6)$alkyl, S(O)$_2$N$((C_1-C_6)$alkyl$)_2$, S(O)$_2$NHheterocyclyl, S(O)$_2$NHaryl, S(O)$_2$aryl, $(C_3-C_7)$cycloalkyl, heterocyclyl, polyfluorinated heterocyclyl, $(C_1-C_6)$alkylheterocyclyl, aryl, $(C_1-C_6)$alkylaryl, heteroaryl, and $(C_1-C_6)$alkylheteroaryl;

with provisos that:
(1) when y is 0, L is C(O)NR6aR7a or NR8C(O)R6a;
(2) when y is 1, L is —C(O)NR8- or —NR8C(O)—;
(3) R3, R4, R3', and R4' are not simultaneously hydrogen; and
(4) the following compounds of formula (I) are excluded:

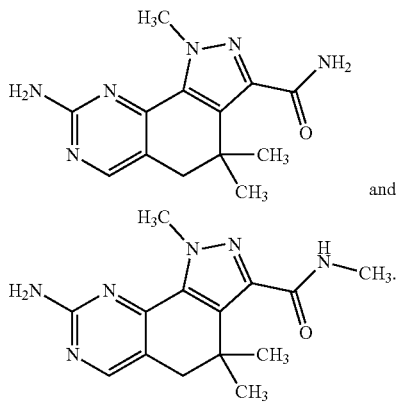

and

2. The compound according to claim 1, or a pharmaceutically acceptable salt thereof,
wherein:
A is aryl or heteroaryl, wherein the aryl or heteroaryl is optionally substituted with one or more independently selected substituents;

R2 is hydrogen, $(C_1-C_6)$alkyl, $(C_3-C_7)$cycloalkyl, or heterocyclyl, wherein the $(C_1-C_6)$alkyl, $(C_3-C_7)$cycloalkyl, or heterocyclyl is optionally substituted with one or more independently selected substituents;
R5 is C(O)NR6R7, NR6R7, NR7C(O)R6, NR7C(O)NR6R7, or OR6;
n is 0 or 1; and
z is 0 or 1.

3. The compound according to claim 2, or a pharmaceutically acceptable salt thereof,
wherein:
L is C(O)NR6aR7a, —C(O)NR8-, NR8C(O)R6a, or —NR8C(O)—;
R2 is hydrogen or $(C_1-C_6)$alkyl, wherein the $(C_1-C_6)$alkyl is optionally substituted with one or more independently selected substituents;
R5 is C(O)NR6R7, NR7C(O)R6, or OR6;
R6 is hydrogen, $(C_1-C_6)$alkyl, $(C_3-C_7)$cycloalkyl, heterocyclyl, aryl, or heteroaryl, wherein the $(C_1-C_6)$alkyl, $(C_3-C_7)$cycloalkyl, heterocyclyl, aryl, or heteroaryl is optionally substituted with one or more independently selected substituents;
R7 is hydrogen, $(C_1-C_6)$alkyl, $(C_3-C_7)$cycloalkyl, heterocyclyl, aryl, or heteroaryl, wherein the $(C_1-C_6)$alkyl, $(C_3-C_7)$cycloalkyl, heterocyclyl, aryl, or heteroaryl is optionally and independently substituted with one or more independently selected substituents; or
R6 and R7, taken together with the nitrogen atom to which they are bonded, form a 5- or 6-membered heterocyclyl, wherein the 5- or 6-membered heterocyclyl optionally contains one additional heteroatom selected from the group consisting of nitrogen, oxygen, and sulfur, and further wherein the 5- or 6-membered heterocyclyl is optionally substituted with one or more independently selected substituents;
R6a is hydrogen, $(C_3-C_7)$cycloalkyl, heterocyclyl, aryl, or heteroaryl, wherein the $(C_3-C_7)$cycloalkyl, heterocyclyl, aryl, or heteroaryl is optionally substituted with one or more independently selected substituents;
R7a is hydrogen, $(C_3-C_7)$cycloalkyl, heterocyclyl, aryl, or heteroaryl, wherein the $(C_3-C_7)$cycloalkyl, heterocyclyl, aryl, or heteroaryl is optionally substituted with one or more independently selected substituents; or
R6a and R7a, taken together with the nitrogen atom to which they are bonded, form a 5- or 6-membered heterocyclyl, wherein the 5- or 6-membered heterocyclyl optionally contains one additional heteroatom selected from the group consisting of nitrogen, oxygen, and sulfur, and further wherein the 5- or 6-membered heterocyclyl is optionally substituted with one or more independently selected substituents;
R8 is hydrogen;
Rc is hydrogen, fluoro, or $(C_1-C_3)$alkyl, wherein the $(C_1-C_3)$ alkyl is optionally substituted with one or more independently selected substituents;
Rd is hydrogen, fluoro, or $(C_1-C_3)$alkyl, wherein the $(C_1-C_3)$ alkyl is optionally substituted with one or more independently selected substituents;
n is 1; and
z is 0.

4. The compound according to claim 3, or a pharmaceutically acceptable salt thereof,
wherein:
L is C(O)NR6aR7a or —C(O)NR8-;
R1 is hydrogen or $(C_1-C_3)$alkyl;
R5 is C(O)NR6R7 or OR6;

R6 is hydrogen, $(C_1-C_6)$alkyl, $(C_3-C_7)$cycloalkyl, or heterocyclyl, wherein the $(C_1-C_6)$alkyl, $(C_3-C_7)$cycloalkyl, or heterocyclyl is optionally substituted with one or more independently selected substituents;

R7 is hydrogen, $(C_1-C_6)$alkyl, $(C_3-C_7)$cycloalkyl, or heterocyclyl, wherein the $(C_1-C_6)$alkyl, $(C_3-C_7)$cycloalkyl, or heterocyclyl is optionally and independently substituted with one or more independently selected substituents; or R6 and R7, taken together with the nitrogen atom to which they are bonded, form a 5- or 6-membered heterocyclyl, wherein the 5- or 6-membered heterocyclyl optionally contains one additional heteroatom selected from the group consisting of nitrogen, oxygen, and sulfur, and further wherein the 5- or 6-membered heterocyclyl is optionally substituted with one or more independently selected substituents;

R6a is hydrogen, heterocyclyl, aryl, or heteroaryl, wherein the heterocyclyl, aryl, or heteroaryl is optionally substituted with one or more independently selected substituents;

R7a is hydrogen, heterocyclyl, aryl, or heteroaryl, wherein the heterocyclyl, aryl, or heteroaryl is optionally substituted with one or more independently selected substituents; or R6a and R7a, taken together with the nitrogen atom to which they are bonded, form a 5- or 6-membered heterocyclyl, wherein the 5- or 6-membered heterocyclyl optionally contains one additional heteroatom selected from the group consisting of nitrogen, oxygen, and sulfur, and further wherein the 5- or 6-membered heterocyclyl is optionally substituted with one or more independently selected substituents;

R8 is hydrogen;
Rc is hydrogen; and
Rd is hydrogen.

5. The compound (cpd) according to claim 1, or a pharmaceutically acceptable salt thereof, wherein the compound, or pharmaceutically acceptable salt thereof, is selected from the group consisting of:

8-amino-N-(3-methoxyphenyl)-4,4-dimethyl-4,5-dihydro-1H-pyrazolo[4,3-h]quinazoline-3-carboxamide (cpd 1);

8-amino-N-(4-methoxyphenyl)-4,4-dimethyl-4,5-dihydro-1H-pyrazolo[4,3-h]quinazoline-3-carboxamide (cpd 2);

8-amino-4,4-dimethyl-N-[4-(trifluoromethoxy)phenyl]-4,5-dihydro-1H-pyrazolo[4,3-h]quinazoline-3-carboxamide(cpd 3);

8-amino-N-(1,3-benzodioxol-5-yl)-4,4-dimethyl-4,5-dihydro-1H-pyrazolo[4,3-h]quinazoline-3-carboxamide (cpd 4);

ethyl 4-{[(8-amino-4,4-dimethyl-4,5-dihydro-1H-pyrazolo[4,3-h]quinazolin-3-yl)carbonyl]amino}benzoate (cpd 5);

8-amino-4,4-dimethyl-N-[4-(4-methylpiperazin-1-yl)phenyl]-4,5-dihydro-1H-pyrazolo[4,3-h]quinazoline-3-carboxamide (cpd 6);

8-amino-4,4-dimethyl-N-{4-[(1-methylpiperidin-4-yl)carbamoyl]phenyl}-4,5-dihydro-1H-pyrazolo[4,3-h]quinazoline-3-carboxamide (cpd 8);

8-amino-1-(3-hydroxypropyl)-4,4-dimethyl-N-{4-[(1-methylpiperidin-4-yl)carbamoyl]phenyl}-4,5-dihydro-1H-pyrazolo [4,3-h]quinazoline-3-carboxamide (cpd 9);

8-amino-4,4-dimethyl-N-{3-[(1-methylpiperidin-4-yl)carbamoyl]phenyl}-4,5-dihydro-1H-pyrazolo[4,3-h]quinazoline-3-carboxamide (cpd 10);

8-amino-4,4-dimethyl-N-[4-(tetrahydro-2H-pyran-4-ylcarbamoyl)phenyl]-4,5-dihydro-1H-pyrazolo[4,3-h]quinazoline-3-carboxamide (cpd 11);

8-amino-4,4-dimethyl-N-(4-[4-(pyrrolidin-1-yl)piperidin-1-yl]carbonyl phenyl)-4,5-dihydro-1H-pyrazolo[4,3-h]quinazoline-3-carboxamide (cpd 13);

8-amino-N-(4-{[4-(dimethylamino)piperidin-1-yl]carbonyl}phenyl)-4,4-dimethyl-4,5-dihydro-1H-pyrazolo[4,3-h]quinazoline-3-carboxamide (cpd 14);

8-amino-N-[4-(cyclohexylcarbamoyl)phenyl]-4,4-dimethyl-4,5-dihydro-1H-pyrazolo[4,3-h]quinazoline-3-carboxamide (cpd 16);

ethyl 3-{[(8-amino-4,4-dimethyl-4,5-dihydro-1H-pyrazolo[4,3-h]quinazolin-3-yl)carbonyl]amino}benzoate (cpd 17);

3-{[(8-amino-4,4-dimethyl-4,5-dihydro-1H-pyrazolo[4,3-h]quinazolin-3-yl)carbonyl]amino}benzoic acid (cpd 18);

8-amino-N-[4-(1,4'-bipiperidin-1'-ylcarbonyl)phenyl]-4,4-dimethyl-4,5-dihydro-1H-pyrazolo[4,3-h]quinazoline-3-carboxamide (cpd 20);

8-amino-N-[3-(cyclohexylcarbamoyl)phenyl]-4,4-dimethyl-4,5-dihydro-1H-pyrazolo[4,3-h]quinazoline-3-carboxamide (cpd 25);

8-amino-4,4-dimethyl-N-(3-{[4-(pyrrolidin-1-yl)piperidin-1-yl]carbonyl phenyl)-4,5-dihydro-1H-pyrazolo[4,3-h]quinazoline-3-carboxamide (cpd 26);

8-amino-4,4-dimethyl-N-[4-(methylcarbamoyl)phenyl]-4,5-dihydro-1H-pyrazolo[4,3-h]quinazoline-3-carboxamide (cpd 27);

8-amino-N-{4-[(trans-4-hydroxycyclohexyl)carbamoyl]phenyl}-4,4-dimethyl-4,5-dihydro-1H-pyrazolo[4,3-h]quinazoline-3-carboxamide (cpd 28);

8-amino-N-[4-(cyclopentylcarbamoyl)phenyl]-4,4-dimethyl-4,5-dihydro-1H-pyrazolo[4,3-h]quinazoline-3-carboxamide (cpd 29);

8-amino-N-[4-(cyclobutylcarbamoyl)phenyl]-4,4-dimethyl-4,5-dihydro-1H-pyrazolo[4,3-h]quinazoline-3-carboxamide (cpd 30);

8-amino-N-[4-(cyclopropylcarbamoyl)phenyl]-4,4-dimethyl-4,5-dihydro-1H-pyrazolo[4,3-h]quinazoline-3-carboxamide (cpd 31);

8-amino-4,4-dimethyl-N-(4-methyl-1,3-thiazol-2-yl)-4,5-dihydro-1H-pyrazolo[4,3-h]quinazoline-3-carboxamide (cpd 32);

ethyl (2-{[(8-amino-4,4-dimethyl-4,5-dihydro-1H-pyrazolo[4,3-h]quinazolin-3-yl)carbonyl]amino}-1,3-thiazol-4-yl) acetate (cpd 33);

8-amino-N-cyclohexyl-4,4-dimethyl-4,5-dihydro-1H-pyrazolo[4,3-h]quinazoline-3-carboxamide (cpd 34);

8-amino-N-{4-[2-(cyclohexylamino)-2-oxoethyl]-1,3-thiazol-2-yl}-4,4-dimethyl-4,5-dihydro-1H-pyrazolo[4,3-h]quinazoline-3-carboxamide (cpd 35);

(8-amino-4,4-dimethyl-4,5-dihydro-1H-pyrazolo[4,3-h]quinazolin-3-yl)[4-(pyrrolidin-1-yl)piperidin-1-yl]methanone (cpd 36);

8-amino-4,4-dimethyl-N-(4-{2-oxo-2-[4-(pyrrolidin-1-yl)piperidin-1-yl]ethyl}-1,3-thiazol-2-yl)-4,5-dihydro-1H-pyrazolo [4,3-h]quinazoline-3-carboxamide (cpd 37);

(8-amino-4,4-dimethyl-4,5-dihydro-1H-pyrazolo[4,3-h]quinazolin-3-yl)(1,4'-bipiperidin-1'-yl)methanone (cpd 38);

8-amino-N-{4-[2-(1,4'-bipiperidin-1'-yl)-2-oxoethyl]-1,3-thiazol-2-yl}-4,4-dimethyl-4,5-dihydro-1H-pyrazolo[4,3-h]quinazoline-3-carboxamide (cpd 39);

8-amino-4,4-dimethyl-N-(4-{[4-(4-methylpiperazin-1-yl)piperidin-1-yl]carbonyl}phenyl)-4,5-dihydro-1H-pyrazolo[4,3-h]quinazoline-3-carboxamide (cpd 41);

(2-{[(8-amino-4,4-dimethyl-4,5-dihydro-1H-pyrazolo[4,3-h]quinazolin-3-yl)carbonyl]amino}-1,3-thiazol-4-yl)acetic acid (cpd 42);

tert-butyl {1-{[(2-([(8-amino-4,4-dimethyl-1H-pyrazolo[4,3-h]quinazolin-3-yl)carbonyl]amino}-1,3-thiazol-4-yl)acetyl]piperidin-4-yl}carbamate (cpd 43);

8-amino-N-{4-[2-(4-aminopiperidin-1-yl)-2-oxoethyl]-1,3-thiazol-2-yl}-4,4-dimethyl-4,5-dihydro-1H-pyrazolo[4,3-h]quinazoline-3-carboxamide (cpd 44);

8-amino-4,4-dimethyl-N-{4-[2-oxo-2-(4-oxopiperidin-1-yl)ethyl]-1,3-thiazol-2-yl}-4,5-dihydro-1H-pyrazolo[4,3-h]quinazoline-3-carboxamide (cpd 45);

tert-butyl [1-(4-{[(8-amino-4,4-dimethyl-4,5-dihydro-1H-pyrazolo[4,3-h]quinazolin-3-yl)carbonyl]amino}benzoyl) piperidin-4-yl]carbamate (cpd 46);

8-amino-N-(4-{2-[4-(azepan-1-yl)piperidin-1-yl]-2-oxoethyl}-1,3-thiazol-2-yl)-4,4-dimethyl-4,5-dihydro-1H-pyrazolo[4,3-h]quinazoline-3-carboxamide (cpd 47);

8-amino-N-{4-[(4-aminopiperidin-1-yl)carbonyl]phenyl}-4,4-dimethyl-4,5-dihydro-1H-pyrazolo[4,3-h]quinazoline-3-carboxamide (cpd 49);

8-amino-4,4-dimethyl-N-(4-{[4-(morpholin-4-yl)piperidin-1-yl]carbonyl}phenyl)-4,5-dihydro-1H-pyrazolo[4,3-h]quinazoline-3-carboxamide (cpd 50);

8-amino-N-{4-[(4,4-difluoro-1,4'-bipiperidin-1'-yl)carbonyl]phenyl}-4,4-dimethyl-4,5-dihydro-1H-pyrazolo[4,3-h]quinazoline-3-carboxamide (cpd 51);

8-amino-4,4-dimethyl-N-{4-[(4-methyl-1,4'-bipiperidin-1'-yl)carbonyl]phenyl}-4,5-dihydro-1H-pyrazolo[4,3-h]quinazoline-3-carboxamide (cpd 52);

8-amino-N-[4-({4-[(4-hydroxybutanoyl)amino]piperidin-1-yl}carbonyl)phenyl]-4,4-dimethyl-4,5-dihydro-1H-pyrazolo [4,3-h]quinazoline-3-carboxamide (cpd 53):

8-amino-4,4-dimethyl-N-(4-{[4-(2-oxo-1,3-oxazolidin-3-yl)piperidin-1-yl]carbonyl}phenyl)-4,5-dihydro-1H-pyrazolo[4,3-h]quinazoline-3-carboxamide (cpd 56);

8-amino-4,4-dimethyl-N-{4-[2-(4-methyl-1,4'-bipiperidin-1'-yl)-2-oxoethyl]-1,3-thiazol-2-yl}-4,5-dihydro-1H-pyrazolo [4,3-h]quinazoline-3-carboxamide (cpd 58);

8-amino-4,4-dimethyl-N-(4-{[4-(piperidin-1-ylmethyl)phenyl]carbamoyl}phenyl)-4,5-dihydro-1H-pyrazolo[4,3-h]quinazoline-3-carboxamide (cpd 59);

8-amino-4,4-dimethyl-N-(1,3-thiazol-2-yl)-4,5-dihydro-1H-pyrazolo[4,3-h]quinazoline-3-carboxamide (cpd 61);

8-amino-N-(1,3-benzothiazol-2-yl)-4,4-dimethyl-4,5-dihydro-1H-pyrazolo[4,3-h]quinazoline-3-carboxamide (cpd 62);

8-amino-N-(6-methoxy-1,3-benzothiazol-2-yl)-4,4-dimethyl-4,5-dihydro-1H-pyrazolo[4,3-h]quinazoline-3-carboxamide (cpd 63):

8-amino-N-(6-chloro-1,3-benzothiazol-2-yl)-4,4-dimethyl-4,5-dihydro-1H-pyrazolo[4,3-h]quinazoline-3-carboxamide (cpd 64);

8-amino-4,4-dimethyl-N-(5-methyl-1,3-thiazol-2-yl)-4,5-dihydro-1H-pyrazolo[4,3-h]quinazoline-3-carboxamide (cpd 65);

8-amino-N-(5-chloro-1,3-thiazol-2-yl)-4,4-dimethyl-4,5-dihydro-1H-pyrazolo[4,3-h]quinazoline-3-carboxamide (cpd 66);

2-{[(8-amino-4,4-dimethyl-4,5-dihydro-1H-pyrazolo[4,3-h]quinazolin-3-yl)carbonyl]amino}-1,3-thiazole-4-carboxylic acid (cpd 67);

8-amino-N-[4-(cyclohexylcarbamoyl)-1,3-thiazol-2-yl]-4,4-dimethyl-4,5-dihydro-1H-pyrazolo[4,3-h]quinazoline-3-carboxamide (cpd 68);

8-amino-4,4-dimethyl-N-{4-[(1-methylpiperidin-4-yl)carbamoyl]-1,3-thiazol-2-yl}-4,5-dihydro-1H-pyrazolo[4,3-h]quinazoline-3-carboxamide (cpd 69);

8-amino-N-[4-(1,4'-bipiperidin-1'-ylcarbonyl)-1,3-thiazol-2-yl]-4,4-dimethyl-4,5-dihydro-1H-pyrazolo[4,3-h]quinazoline-3-carboxamide (cpd 70);

8-amino-N-[4-(2-{4-[(tert-butylcarbamoyl)amino]piperidin-1-yl}-2-oxoethyl)-1,3-thiazol-2-yl]-4,4-dimethyl-4,5-dihydro-1H-pyrazolo[4,3-h]quinazoline-3-carboxamide (cpd 71);

(2-{[(8-amino-4,4-dimethyl-4,5-dihydro-1H-pyrazolo[4,3-h]quinazolin-3-yl)carbonyl]amino}-1,3-thiazol-5-yl)acetic acid (cpd 72);

8-amino-N-{5-[2-(cyclohexylamino)-2-oxoethyl]-1,3-thiazol-2-yl}-4,4-dimethyl-4,5-dihydro-1H-pyrazolo [4,3-h]quinazoline-3-carboxamide (cpd 73);

8-amino-4,4-dimethyl-N-(5-{2-[(1-methylpiperidin-4-yl)amino]-2-oxoethyl}-1,3-thiazol-2-yl)-4,5-dihydro-1H-pyrazolo [4,3-h]quinazoline-3-carboxamide (cpd 74);

8-amino-N-{5-[2-(1,4'-bipiperidin-1'-yl)-2-oxoethyl]-1,3-thiazol-2-yl}-4,4-dimethyl-4,5-dihydro-1H-pyrazolo [4,3-h]quinazoline-3-carboxamide (cpd 75);

8-amino-N-[5-(cyclohexylcarbamoyl)-4-methyl-1,3-thiazol-2-yl]-4,4-dimethyl-4,5-dihydro-1H-pyrazolo[4,3-h]quinazoline-3-carboxamide (cpd 77);

8-amino-N-[5-(1,4'-bipiperidin-1'-ylcarbonyl)-4-methyl-1,3-thiazol-2-yl]-4,4-dimethyl-4,5-dihydro-1H-pyrazolo[4,3-h]quinazoline-3-carboxamide (cpd 78);

8-amino-4,4-dimethyl-N-{4-methyl-5-[(1-methylpiperidin-4-yl)carbamoyl]-1,3-thiazol-2-yl}-4,5-dihydro-1H-pyrazolo[4,3-h]quinazoline-3-carboxamide (cpd 79);

8-amino-1,4,4-trimethyl-N-{4-[2-(4-methyl-1,4'-bipiperidin-1'-yl)-2-oxoethyl]-1,3-thiazol-2-yl}-4,5-dihydro-1H-pyrazolo[4,3-h]quinazoline-3-carboxamide (cpd 80);

ethyl 2-{[(8-amino-4,4-dimethyl-4,5-dihydro-1H-pyrazolo[4,3-h]quinazolin-3-yl)carbonyl]amino}-1,3-thiazole-5-carboxylate (cpd 81);

2-{[(8-amino-4,4-dimethyl-4,5-dihydro-1H-pyrazolo[4,3-h]quinazolin-3-yl)carbonyl]amino}-1,3-thiazole-5-carboxylic acid (cpd 82);

8-amino-N-[5-(1,4'-bipiperidin-1'-ylcarbonyl)-1,3-thiazol-2-yl]-4,4-dimethyl-4,5-dihydro-1H-pyrazolo[4,3-h]quinazoline-3-carboxamide (cpd 84);

1,4,4-trimethyl-8-(methylamino)-N-{4-[2-(4-methyl-1,4'-bipiperidin-1'-yl)-2-oxoethyl]-1,3-thiazol-2-yl}-4,5-dihydro-1H-pyrazolo[4,3-h]quinazoline-3-carboxamide (cpd 85);

8-amino-4,4-dimethyl-N-(4-{2-[(1-methylpiperidin-4-yl)amino]-2-oxoethyl}-1,3-thiazol-2-yl)-4,5-dihydro-1H-pyrazolo [4,3-h]quinazoline-3-carboxamide (cpd 86);

8-amino-N-(4-{2-[(3R)-3-hydroxypyrrolidin-1-yl]-2-oxoethyl}-1,3-thiazol-2-yl)-4,4-dimethyl-4,5-dihydro-1H-pyrazolo [4,3-h]quinazoline-3-carboxamide (cpd 87);

8-amino-N-(4-{2-[(3S)-3-hydroxypyrrolidin-1-yl]-2-oxoethyl}-1,3-thiazol-2-yl)-4,4-dimethyl-4,5-dihydro-1H-pyrazolo [4,3-h]quinazoline-3-carboxamide (cpd 88);

8-amino-N-(4-{2-[4-(dimethylamino)piperidin-1-yl]-2-oxoethyl}-1,3-thiazol-2-yl)-4,4-dimethyl-4,5-dihydro-1H-pyrazolo [4,3-h]quinazoline-3-carboxamide (cpd 89);

8-amino-N-{4-[2-(4-carbamoylpiperidin-1-yl)-2-oxoethyl]-1,3-thiazol-2-yl}-4,4-dimethyl-4,5-dihydro-1H-pyrazolo[4,3-h]quinazoline-3-carboxamide (cpd 90);

8-amino-N-(4-{2-[4-(hydroxymethyl)piperidin-1-yl]-2-oxoethyl}-1,3-thiazol-2-yl)-4,4-dimethyl-4,5-dihydro-1H-pyrazolo[4,3-h]quinazoline-3-carboxamide (cpd 91);

8-amino-N-{4-[2-(4-hydroxypiperidin-1-yl)-2-oxoethyl]-1,3-thiazol-2-yl}-4,4-dimethyl-4,5-dihydro-1H-pyrazolo[4,3-h]quinazoline-3-carboxamide (cpd 92);

8-amino-N-(4-{2-[(3S)-3-(dimethylamino)pyrrolidin-1-yl]-2-oxoethyl}-1,3-thiazol-2-yl)-4,4-dimethyl-4,5-dihydro-1H-pyrazolo[4,3-h]quinazoline-3-carboxamide (cpd 93);

8-amino-N-[4-(2-amino-2-oxoethyl)-1,3-thiazol-2-yl]-4,4-dimethyl-4,5-dihydro-1H-pyrazolo[4,3-h]quinazoline-3-carboxamide (cpd 94);

8-amino-N-[4-(2-{[3-(dimethylamino)propyl]amino}-2-oxoethyl)-1,3-thiazol-2-yl]-4,4-dimethyl-4,5-dihydro-1H-pyrazolo [4,3-h]quinazoline-3-carboxamide (cpd 95);

ethyl (4-{[(8-amino-4,4-dimethyl-4,5-dihydro-1H-pyrazolo[4,3-h]quinazolin-3-yl)carbonyl]amino}phenyl) acetate (cpd 96);

8-amino-N-{4-[2-(1,4'-bipiperidin-1'-yl)-2-oxoethyl]phenyl}-4,4-dimethyl-4,5-dihydro-1H-pyrazolo[4,3-h]quinazoline-3-carboxamide (cpd 98);

8-amino-N-(4-hydroxyphenyl)-4,4-dimethyl-4,5-dihydro-1H-pyrazolo[4,3-h]quinazoline-3-carboxamide (cpd 105);

8-amino-N-[3-(1,3-dioxan-2-yl)phenyl]-4,4-dimethyl-4,5-dihydro-1H-pyrazolo[4,3-h]quinazoline-3-carboxamide (cpd 106);

8-amino-N-(3-formylphenyl)-4,4-dimethyl-4,5-dihydro-1H-pyrazolo[4,3-h]quinazoline-3-carboxamide (cpd 107);

8-amino-N-{4-[2-(1,4'-bipiperidin-1'-yl)-2-oxoethyl]-1,3-thiazol-2-yl}-1,4,4-trimethyl-4,5-dihydro-1H-pyrazolo[4,3-h]quinazoline-3-carboxamide (cpd 108);

8-amino-N-[3-(1,4'-bipiperidin-1'-ylmethyl)phenyl]-1,4,4-trimethyl-4,5-dihydro-1H-pyrazolo[4,3-h]quinazoline-3-carboxamide (cpd 109);

8-amino-N-[3-(1,4'-bipiperidin-1'-ylmethyl)phenyl]-4,4-dimethyl-4,5-dihydro-1H-pyrazolo[4,3-h]quinazoline-3-carboxamide (cpd 110);

8-amino-1,4,4-trimethyl-N-{3-[(4-methyl-1,4'-bipiperidin-1'-yl)methyl]phenyl}-4,5-dihydro-1H-pyrazolo[4,3-h]quinazoline-3-carboxamide (cpd 111);

8-amino-4,4-dimethyl-N-{3-[(4-methyl-1,4'-bipiperidin-1'-yl)methyl]phenyl}-4,5-dihydro-1H-pyrazolo[4,3-h]quinazoline-3-carboxamide (cpd 112);

tert-butyl [1-(3-{[(8-amino-4,4-dimethyl-4,5-dihydro-1H-pyrazolo[4,3-h]quinazolin-3-yl)carbonyl]amino}benzyl) piperidin-4-yl]carbamate (cpd 114);

8-amino-N-(4-{2-[(3R)-3-(dimethylamino)pyrrolidin-1-yl]-2-oxoethyl}-1,3-thiazol-2-yl)-4,4-dimethyl-4,5-dihydro-1H-pyrazolo[4,3-h]quinazoline-3-carboxamide (cpd 116);

8-amino-N-(4-{[4-(dimethylamino)piperidin-1-yl]methyl}phenyl)-1,4,4-trimethyl-4,5-dihydro-1H-pyrazolo[4,3-h]quinazoline-3-carboxamide (cpd 117);

8-amino-N-(4-{[4-(dimethylamino)piperidin-1-yl]methyl}phenyl)-4,4-dimethyl-4,5-dihydro-1H-pyrazolo[4,3-h]quinazoline-3-carboxamide (cpd 118);

8-amino-4,4-dimethyl-N-(4-(2-[4-(methylamino)piperidin-1-yl]-2-oxoethyl)-1,3-thiazol-2-yl)-4,5-dihydro-1H-pyrazolo [4,3-h]quinazoline-3-carboxamide (cpd 119);

8-amino-N-{3-[2-(1,4'-bipiperidin-1'-yl)-2-oxoethyl]phenyl}-4,4-dimethyl-4,5-dihydro-1H-pyrazolo[4,3-h]quinazoline-3-carboxamide (cpd 120);

N-{4-[2-(1,4'-bipiperidin-1'-yl)-2-oxoethyl]-1,3-thiazol-2-yl}-4,4-dimethyl-8-(methylamino)-4,5-dihydro-1H-pyrazolo[4,3-h]quinazoline-3-carboxamide (cpd 121);

4,4-dimethyl-8-(methylamino)-N-{4-[2-(4-methyl-1,4'-bipiperidin-1'-yl)-2-oxoethyl]-1,3-thiazol-2-yl}-4,5-dihydro-1H-pyrazolo[4,3-h]quinazoline-3-carboxamide (cpd 122);

8-amino-N,4,4-trimethyl-N-{4-[2-(4-methyl-1,4'-bipiperidin-1'-yl)-2-oxoethyl]-1,3-thiazol-2-yl}-4,5-dihydro-1H-pyrazolo [4,3-h]quinazoline-3-carboxamide (cpd 123);

8-amino-N-{4-[2-(1,4'-bipiperidin-1'-yl)-2-oxoethyl]-1,3-thiazol-2-yl}-N,1,4,4-tetramethyl-4,5-dihydro-1H-pyrazolo[4,3-h]quinazoline-3-carboxamide (cpd 124);

8-amino-N-[4-(1,4'-bipiperidin-1'-ylmethyl)phenyl]-4,4-dimethyl-4,5-dihydro-1H-pyrazolo[4,3-h]quinazoline-3-carboxamide bistrifluoroacetate (cpd 125);

8-amino-N-[4-({[4-(1,4'-bipiperidin-1'-ylmethyl)phenyl]amino}methyl)phenyl]-4,4-dimethyl-4,5-dihydro-1H-pyrazolo[4,3-h]quinazoline-3-carboxamide bistrifluoroacetate (cpd 126);

methyl 1-(2-{[(8-amino-4,4-dimethyl-4,5-dihydro-1H-pyrazolo[4,3-h]quinazolin-3-yl)carbonyl]amino}-1,3-thiazol-4-yl) cyclopropanecarboxylate (cpd 127);

8-amino-N-[4-(1,4'-bipiperidin-1'-ylmethyl)phenyl]-1,4,4-trimethyl-4,5-dihydro-1H-pyrazolo[4,3-h]quinazoline-3-carboxamide (cpd 128);

1-(2-{[(8-amino-4,4-dimethyl-4,5-dihydro-1H-pyrazolo [4,3-h]quinazolin-3-yl)carbonyl]amino}-1,3-thiazol-4-yl) cyclopropanecarboxylic acid (cpd 129);

8-amino-N-[4-(1-{[(3R)-3-(dimethylamino)pyrrolidin-1-yl]carbonyl}cyclopropyl)-1,3-thiazol-2-yl]-4,4-dimethyl-4,5-dihydro-1H-pyrazolo[4,3-h]quinazoline-3-carboxamide (cpd 130);

8-amino-N-{4-[1-(1,4'-bipiperidin-1'-ylcarbonyl)cyclopropyl]-1,3-thiazol-2-yl}-4,4-dimethyl-4,5-dihydro-1H-pyrazolo[4,3-h]quinazoline-3-carboxamide (cpd 131);

tert-butyl [1-(4-([(8-amino-4,4-dimethyl-4,5-dihydro-1H-pyrazolo[4,3-h]quinazolin-3-yl)carbonyl]amino) benzyl)piperidin-4-yl]carbamate (cpd 133);

(3-{[(8-amino-4,4-dimethyl-4,5-dihydro-1H-pyrazolo[4,3-h]quinazolin-3-yl)carbonyl]amino}phenyl)acetic acid (139);

8-amino-N-[4-(1,4'-bipiperidin-1'-ylmethyl)-1,3-thiazol-2-yl]-1,4,4-trimethyl-4,5-dihydro-1H-pyrazolo[4,3-h] quinazoline-3-carboxamide (cpd 141);

8-amino-N-(3-{2-[(3R)-3-(dimethylamino)pyrrolidin-1-yl]-2-oxoethyl}phenyl)-4,4-dimethyl-4,5-dihydro-1H-pyrazolo[4,3-h]quinazoline-3-carboxamide (cpd 142);

8-amino-N-[4-(1,4'-bipiperidin-1'-ylmethyl)-1,3-thiazol-2-yl]-4,4-dimethyl-4,5-dihydro-1H-pyrazolo[4,3-h] quinazoline-3-carboxamide (cpd 143);

8-amino-N-(1H-imidazol-2-yl)-4,4-dimethyl-4,5-dihydro-1H-pyrazolo[4,3-h]quinazoline-3-carboxamide (cpd 144);

8-amino-N-(4-{2-[(1-cyclohexylpiperidin-4-yl)amino]-2-oxoethyl}-1,3-thiazol-2-yl)-4,4-dimethyl-4,5-dihydro-1H-pyrazolo[4,3-h]quinazoline-3-carboxamide (cpd 145);

8-amino-N-(3-{2-[4-(dimethylamino)piperidin-1-yl]-2-oxoethyl}phenyl)-4,4-dimethyl-4,5-dihydro-1H-pyrazolo[4,3-h]quinazoline-3-carboxamide (cpd 146);

8-amino-N-(4-{[(3R)-3-(dimethylamino)pyrrolidin-1-yl]methyl}-1,3-thiazol-2-yl)-1,4,4-trimethyl-4,5-dihydro-1H-pyrazolo [4,3-h]quinazoline-3-carboxamide (cpd 147);

8-amino-N-(4-{[(3R)-3-(dimethylamino)pyrrolidin-1-yl]methyl-1,3-thiazol-2-yl)-4,4-dimethyl-4,5-dihydro-1H-pyrazolo [4,3-h]quinazoline-3-carboxamide dihydrochloride (cpd 148);

8-amino-N-(3-[2-(4-aminopiperidin-1-yl)-2-oxoethyl]phenyl}-4,4-dimethyl-4,5-dihydro-1H-pyrazolo[4,3-h]quinazoline-3-carboxamide hydrochloride (cpd 149);

8-amino-N-{4-[2-(4-cyclohexylpiperazin-1-yl)-2-oxoethyl]-1,3-thiazol-2-yl}-4,4-dimethyl-4,5-dihydro-1H-pyrazolo[4,3-h]quinazoline-3-carboxamide (cpd 150);

8-amino-4,4-dimethyl-N-(5-methyl-4,5,6,7-tetrahydro[1,3]thiazolo[5,4-c]pyridin-2-yl)-4,5-dihydro-1H-pyrazolo[4,3-h]quinazoline-3-carboxamide dihydrochloride (cpd 151);

8-amino-N-{4-[(4-aminopiperidin-1-yl)methyl]-1,3-thiazol-2-yl}-4,4-dimethyl-4,5-dihydro-1H-pyrazolo[4,3-h]quinazoline-3-carboxamide dihydrochloride (cpd 152);

8-amino-1,4,4-trimethyl-N-(4-{2-[4-(1-oxidopiperidin-1-yl)piperidin-1-yl]-2-oxoethyl}-1,3-thiazol-2-yl)-4,5-dihydro-1H-pyrazolo[4,3-h]quinazoline-3-carboxamide (153);

8-amino-N-(4-{2-[(3R)-3-(dimethylnitroryl)pyrrolidin-1-yl]-2-oxoethyl}-1,3-thiazol-2-yl)-4,4-dimethyl-4,5-dihydro-1H-pyrazolo[4,3-h]quinazoline-3-carboxamide (cpd 154);

8-amino-1,4,4-trimethyl-N-(4-methyl-1,3-thiazol-2-yl)-4,5-dihydro-1H-pyrazolo[4,3-h]quinazoline-3-carboxamide (cpd 155);

8-amino-N-(4-{[(1-cyclohexylpiperidin-4-yl)amino]methyl}-1,3-thiazol-2-yl)-4,4-dimethyl-4,5-dihydro-1H-pyrazolo[4,3-h]quinazoline-3-carboxamide dihydrochloride (cpd 156);

8-amino-N-(4-{[(1-cyclohexylpiperidin-4-yl)oxy]methyl}-1,3-thiazol-2-yl)-4,4-dimethyl-4,5-dihydro-1H-pyrazolo[4,3-h]quinazoline-3-carboxamide (cpd 157);

8-amino-4,4-dimethyl-N-{4-[2-oxo-2-(4-phenylpiperazin-1-yl)ethyl]-1,3-thiazol-2-yl}-4,5-dihydro-1H-pyrazolo[4,3-h]quinazoline-3-carboxamide (cpd 160);

(8-amino-4,4-dimethyl-4,5-dihydro-1H-pyrazolo[4,3-h]quinazolin-3-yl)(4-phenylpiperazin-1-yl)methanone (cpd 161);

8-amino-N-[4-(1,4'-bipiperidin-1'-ylcarbonyl)benzyl]-4,4-dimethyl-4,5-dihydro-1H-pyrazolo[4,3-h]quinazoline-3-carboxamide (cpd 165):

8-amino-4,4-dimethyl-N-{4-[(1-methylpiperidin-4-yl)carbamoyl]benzyl}-4,5-dihydro-1H-pyrazolo[4,3-h]quinazoline-3-carboxamide (cpd 166);

8-amino-4,4-dimethyl-N-[4-({[trans-4-(4-methylpiperidin-1-yl)cyclohexyl]oxy}methyl)-1,3-thiazol-2-yl]-4,5-dihydro-1H-pyrazolo[4,3-h]quinazoline-3-carboxamide (cpd 170);

8-amino-1-(2-hydroxyethyl)-4,4-dimethyl-N-(4-methyl-1,3-thiazol-2-yl)-4,5-dihydro-1H-pyrazolo[4,3-h]quinazoline-3-carboxamide (cpd 182);

8-amino-N-(4-[2-(1,4'-bipiperidin-1'-yl)-1,1-difluoro-2-oxoethyl]-1,3-thiazol-2-yl)-4,4-dimethyl-4,5-dihydro-1H-pyrazolo[4,3-h]quinazoline-3-carboxamide (cpd 183);

8-amino-N-[4-({[1-(4,4-difluorocyclohexyl)piperidin-4-yl]oxy}methyl)-1,3-thiazol-2-yl]-4,4-dimethyl-4,5-dihydro-1H-pyrazolo[4,3-h]quinazoline-3-carboxamide (cpd 189);

8-amino-N-[4-({[1-(4,4-dimethylcyclohexyl)piperidin-4-yl]oxy}methyl)-1,3-thiazol-2-yl]-4,4-dimethyl-4,5-dihydro-1H-pyrazolo[4,3-h]quinazoline-3-carboxamide (cpd 190);

8-amino-N-{4-[1,1-difluoro-2-(4-methyl-1,4'-bipiperidin-1'-yl)-2-oxoethyl]-1,3-thiazol-2-yl}-4,4-dimethyl-4,5-dihydro-1H-pyrazolo[4,3-h]quinazoline-3-carboxamide (cpd 191);

8-amino-N-(4-{[(1-cycloheptylpiperidin-4-yl)oxy]methyl-1,3-thiazol-2-yl)-4,4-dimethyl-4,5-dihydro-1H-pyrazolo[4,3-h]quinazoline-3-carboxamide (cpd 209);

8-amino-2,4,4-trimethyl-N-(4-[2-(4-methyl-1,4'-bipiperidin-1'-yl)-2-oxoethyl]-1,3-thiazol-2-yl)-4,5-dihydro-2H-pyrazolo [4,3-h]quinazoline-3-carboxamide (cpd 211);

8-amino-N-[4-(([1-(cyclohexylmethyl)piperidin-4-yl]oxy)methyl)-1,3-thiazol-2-yl]-4,4-dimethyl-4,5-dihydro-1H-pyrazolo [4,3-h]quinazoline-3-carboxamide (cpd 212);

8-amino-N-(4-{[(1-benzylpiperidin-4-yl)oxy]methyl}-1,3-thiazol-2-yl)-4,4-dimethyl-4,5-dihydro-1H-pyrazolo [4,3-h]quinazoline-3-carboxamide (cpd 213);

8-amino-N-(4-{[(1-cycloheptylpiperidin-4-yl)oxy]methyl}-1,3-thiazol-2-yl)-1,4,4-trimethyl-4,5-dihydro-1H-pyrazolo[4,3-h]quinazoline-3-carboxamide (cpd 217);

8-amino-N-{4-[2-(4,4-dimethyl-1,4'-bipiperidin-1'-yl)-2-oxoethyl]-1,3-thiazol-2-yl}-4,4-dimethyl-4,5-dihydro-1H-pyrazolo[4,3-h]quinazoline-3-carboxamide hydrochloride (cpd 218);

8-amino-N-{4-[2-(3,3-dimethyl-1,4'-bipiperidin-1'-yl)-2-oxoethyl]-1,3-thiazol-2-yl}-4,4-dimethyl-4,5-dihydro-1H-pyrazolo [4,3-h]quinazoline-3-carboxamide (cpd 219);

8-amino-N-(4-{2-[(2,6-dimethyl-4-oxohept-5-en-2-yl)amino]-2-oxoethyl}-1,3-thiazol-2-yl)-4,4-dimethyl-4,5-dihydro-1H-pyrazolo[4,3-h]quinazoline-3-carboxamide (cpd 220);

8-amino-N-[4-({[1-(4,4-dimethylcyclohexyl)piperidin-4-yl]oxy}methyl)-1,3-thiazol-2-yl]-4,4-dimethyl-4,5-dihydro-1H-pyrazolo[4,3-h]quinazoline-3-carboxamide trihydrochloride (cpd 221);

8-amino-N-{4-[2-(3,3-difluoro-1,4'-bipiperidin-1'-yl)-2-oxoethyl]-1,3-thiazol-2-yl}-4,4-dimethyl-4,5-dihydro-1H-pyrazolo [4,3-h]quinazoline-3-carboxamide (cpd 222);

8-amino-N-(4-{[(1-cycloheptylpiperidin-4-yl)oxy]methyl}-1,3-thiazol-2-yl)-4,4-dimethyl-4,5-dihydro-1H-pyrazolo[4,3-h]quinazoline-3-carboxamide trihydrochloride (cpd 223);

8-amino-4,4-dimethyl-N-{4-[2-(3-methyl-1,4'-bipiperidin-1'-yl)-2-oxoethyl]-1,3-thiazol-2-yl}-4,5-dihydro-1H-pyrazolo [4,3-h]quinazoline-3-carboxamide (cpd 224);

8-amino-1,5,5-trimethyl-N-{4-[2-(4-methyl-1,4'-bipiperidin-1'-yl)-2-oxoethyl]-1,3-thiazol-2-yl}-4,5-dihydro-1H-pyrazolo [4,3-h]quinazoline-3-carboxamide (cpd 225);

8-amino-N-(4-{[(1-cycloheptyl-4-methylpiperidin-4-yl)oxy]methyl}-1,3-thiazol-2-yl)-4,4-dimethyl-4,5-dihydro-1H-pyrazolo[4,3-h]quinazoline-3-carboxamide (cpd 226);

8-amino-N-{4-[2-(4,4'-dimethyl-1,4'-bipiperidin-1'-yl)-2-oxoethyl]-1,3-thiazol-2-yl}-4,4-dimethyl-4,5-dihydro-1H-pyrazolo[4,3-h]quinazoline-3-carboxamide (cpd 227);

8-amino-4,4-dimethyl-N-{6-[(4-methyl-1,4'-bipiperidin-1'-yl)carbonyl]-1,3-benzothiazol-2-yl}-4,5-dihydro-1H-pyrazolo[4,3-h]quinazoline-3-carboxamide (cpd 228);

8-amino-N-{4-[2-(4,4-difluoro-1,4'-bipiperidin-1'-yl)-2-oxoethyl]-1,3-thiazol-2-yl}-4,4-dimethyl-4,5-dihydro-1H-pyrazolo [4,3-h]quinazoline-3-carboxamide (cpd 229);

8-amino-4,4-dimethyl-N-[4-({[1-(spiro[2.5]oct-6-yl)piperidin-4-yl]oxy}methyl)-1,3-thiazol-2-yl]-4,5-dihydro-1H-pyrazolo [4,3-h]quinazoline-3-carboxamide (cpd 230);

8-amino-5,5-dimethyl-N-{4-[2-(4-methyl-1,4'-bipiperidin-1'-yl)-2-oxoethyl]-1,3-thiazol-2-yl}-4,5-dihydro-1H-pyrazolo [4,3-h]quinazoline-3-carboxamide (cpd 231); and 8-amino-N-(4-{[(1-cycloheptylpiperidin-4-yl)oxy]methyl}-1,3-thiazol-2-yl)-5,5-dimethyl-4,5-dihydro-1H-pyrazolo[4,3-h]quinazoline-3-carboxamide trihydrochloride (cpd 232).

6. A pharmaceutical composition comprising at least one pharmaceutically acceptable excipient, carrier, or diluent and a therapeutically effective amount of a compound according to claim 1, or a pharmaceutically acceptable salt thereof.

7. The pharmaceutical composition according to claim 6, wherein the pharmaceutical composition further comprises one or more chemotherapeutic agents.

8. A method for inhibiting choline kinase activity in a mammal, comprising administering to the mammal in need thereof a therapeutically effective amount of a compound according to claim 1, or a pharmaceutically acceptable salt thereof.

9. The method according to claim 8, wherein the mammal is a human.

10. The method according to claim 6, wherein the mammal has a disease or disorder selected from the group consisting of a cancer, a cell proliferative disorder, an infectious disease, an immune-related disorder, and a neurodegenerative disorder.

11. The method according to claim 10, wherein the cancer is selected from the group consisting of bladder cancer, breast cancer, cervical cancer, colon cancer, esophageal cancer, gall-bladder cancer, kidney cancer, liver cancer, lung cancer, ovarian cancer, pancreatic cancer, prostate cancer, skin cancer, stomach cancer, thyroid cancer, leukemia, Burkitt's lymphoma, B-cell lymphoma, T-cell lymphoma, hairy cell lymphoma, Hodgkin's lymphoma, non-Hodgkin's lymphoma, a myelodysplastic syndrome, fibrosarcoma, rhabdomyosarcoma, astrocytoma, neuroblastoma, a glioma, and a schwannoma.

12. The method according to claim 11, wherein the lung cancer is small cell lung cancer.

13. The method according to claim 11, wherein the skin cancer is squamous cell carcinoma.

14. The method according to claim 11, wherein the leukemia is selected from the group consisting of acute lymphocytic leukemia, acute lymphoblastic leukemia, acute myelogenous leukemia, chronic myelogenous leukemia, and promyelocytic leukemia.

15. The method according to claim 10, wherein the cancer is selected from the group consisting of thyroid cancer, a carcinoma, keratoxanthoma, melanoma, osteosarcoma, seminoma, xeroderma pigmentosum, Karposi's sarcoma, a hematopoietic tumor of lymphoid lineage, a hematopoietic tumor of myeloid lineage, a tumor of mesenchymal origin, a tumor of the central nervous system, and a tumor of the peripheral nervous system.

16. The method according to claim 15, wherein the carcinoma is a teratocarcinoma.

17. The method according to claim 10, wherein the method further comprises administering to the mammal a radiation therapy in combination with at least one cytostatic or cytotoxic agent or a chemotherapy regimen in combination with at least one cytostatic or cytotoxic agent.

18. A process for preparing a compound according to claim 1, wherein the compound is of formula (Ia):

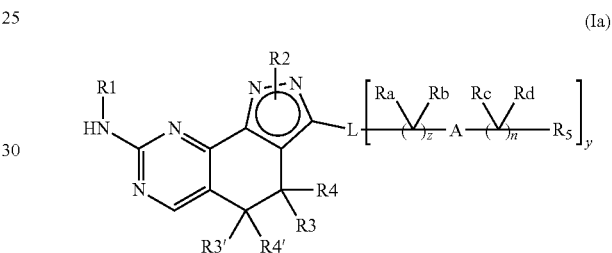

(Ia)

wherein:

A is (C₃-C₇)cycloalkyl, heterocyclyl, aryl, or heteroaryl, wherein the (C₃-C₇)cycloalkyl, heterocyclyl, aryl, or heteroaryl is optionally substituted with one or more independently selected substituents;

L is —C(O)NR8- or —NR8C(O)—;

R1 is hydrogen, or (C₁-C₆)alkyl;

R2 is (C₁-C₆)alkyl, (C₂-C₆)alkenyl, (C₂-C₆) alkynyl, (C₃-C₇)cycloalkyl, or heterocyclyl, wherein the (C₁-C₆) alkyl, (C₂-C₆)alkenyl, (C₂-C₆)alkynyl, (C₃-C₇)cycloalkyl, or heterocyclyl is optionally substituted with one or more independently selected substituents;

R3 is hydrogen or (C₁-C₆)alkyl;

R4 is hydrogen or (C₁-C₆)alkyl;

R3' is hydrogen or (C₁-C₆)alkyl;

R4' is hydrogen or (C₁-C₆)alkyl;

R5 is C(O)R6, C(O)NR6R7, C(O)OR6, NR6R7, NR7C(O)R6, NR7C(O)NR6R7, NR7C(O)OR9, or OR6;

R6 is hydrogen, (C₁-C₆)alkyl, aryl(C₁-C₆)alkyl, heteroaryl(C₁-C₆)alkyl, (C₃-C₇)cycloalkyl, heterocyclyl, aryl, or heteroaryl, wherein the (C₁-C₆)alkyl, aryl(C₁-C₆)alkyl, heteroaryl(C₁-C₆)alkyl, (C₃-C₇)cycloalkyl, heterocyclyl, aryl, or heteroaryl is optionally substituted with one or more independently selected substituents;

each R7 is independently hydrogen, (C₁-C₆)alkyl, aryl (C₁-C₆)alkyl, heteroaryl(C₁-C₆)alkyl, (C₃-C₇)cycloalkyl, heterocyclyl, aryl, or heteroaryl, wherein each (C₁-C₆)alkyl, aryl(C₁-C₆)alkyl, heteroaryl(C₁-C₆)alkyl, (C₃-C₇)cycloalkyl, heterocyclyl, aryl, and heteroaryl is optionally and independently substituted with one or more independently selected substituents; or R6 and R7, taken together with the nitrogen atom to which they are bonded, form a 5- or 6-membered heterocyclyl, wherein the 5- or 6-membered heterocyclyl optionally contains one additional heteroatom selected from the group consisting of nitrogen, oxygen, and sulfur, and further wherein the 5- or 6-membered heterocyclyl is optionally substituted with one or more independently selected substituents;

R8 is hydrogen or $(C_1-C_6)$alkyl, wherein the $(C_1-C_6)$ alkyl is optionally substituted with one or more independently selected substituents;

R9 is $(C_1-C_6)$alkyl, aryl$(C_1-C_6)$alkyl, heteroaryl$(C_1-C_6)$alkyl, $(C_3-C_7)$cycloalkyl, heterocyclyl, aryl, or heteroaryl, wherein the $(C_1-C_6)$alkyl, aryl$(C_1-C_6)$alkyl, heteroaryl$(C_1-C_6)$ alkyl, $(C_3-C_7)$cycloalkyl, heterocyclyl, aryl, or heteroaryl is optionally substituted with one or more independently selected substituents;

Ra is hydrogen, fluoro, or $(C_1-C_6)$alkyl, wherein the $(C_1-C_6)$ alkyl is optionally substituted with one or more independently selected substituents;

Rb is hydrogen, fluoro, or $(C_1-C_6)$alkyl, wherein the $(C_1-C_6)$ alkyl is optionally substituted with one or more independently selected substituents; or Ra and Rb, taken together with the carbon atom to which they are bonded, form a 3-membered cycloalkyl;

Rc is hydrogen, fluoro, or $(C_1-C_6)$alkyl, wherein the $(C_1-C_6)$ alkyl is optionally substituted with one or more independently selected substituents;

Rd is hydrogen, fluoro, or $(C_1-C_6)$alkyl, wherein the $(C_1-C_6)$ alkyl is optionally substituted with one or more independently selected substituents; or Rc and Rd, taken together with the carbon atom to which they are bonded, form a 3-membered cycloalkyl;

y is 1;

n is 0, 1, or 2; and z is 0, 1, or 2;

wherein the optional substituents for A, R2, R5, R6, R7, R6 and R7, R8, R9, Ra, Rb, Rc, Rd, Ra and Rb, and Rc and Rd, are independently selected from the group consisting halogen, cyano, nitro, oxo, $(C_1-C_6)$alkyl, polyfluorinated $(C_1-C_6)$alkyl, C(O)NHaryl$(C_1-C_6)$alkyl, C(O)heterocyclyl$(C_1-C_6)$alkyl, amino$(C_1-C_6)$alkyl, hydroxy$(C_1-C_6)$alkyl, $(C_3-C_7)$cycloalkyl$(C_1-C_6)$alkyl, heterocyclyl$(C_1-C_6)$alkyl, $(C_1-C_6)$alkylheterocyclyl$(C_1-C_6)$alkyl, di$(C_1-C_6)$alkylaminoheterocyclyl$(C_1-C_6)$alkyl, aryl$(C_1-C_6)$alkyl, heteroaryl$(C_1-C_6)$alkyl, $(C_2-C_6)$alkenyl, $(C_2-C_6)$alkynyl, C(NH)O$(C_1-C_6)$alkyl, C(O)H, C(O)$(C_1-C_6)$alkyl, C(O)NH$_2$, C(O)NH$(C_1-C_6)$alkyl, C(O)N$((C_1-C_6)$alkyl)$_2$, CO)NHOH, C(O)NHheterocyclyl, C(O)NHaryl, C(O)NHheteroaryl, C(O)OH, C(O)O$(C_1-C_6)$alkyl, C(O)O$(C_3-C_7)$cycloalkyl, C(O)Oaryl, C(O)$(C_3-C_7)$cycloalkyl, C(O)heterocyclyl, C(O)aryl, NH$_2$, NH$(C_1-C_6)$alkyl, N$((C_1-C_6)$alkyl)$_2$, NHC(O)H, NHC(O)$(C_1-C_6)$alkyl, NHC(O)NH$_2$, NHC(O)NH$(C_1-C_6)$alkyl, NHC(O)O$(C_1-C_6)$alkyl, NHC(O)O$(C_1-C_6)$alkyl(heterocyclyl), NHC(O)$(C_3-C_7)$cycloalkyl, NHC(O)heterocyclyl, NHC(O)aryl, NHS(O)$_2(C_1-C_6)$alkyl, NHS(O)$_2$heterocyclyl, NHS(O)$_2$aryl, NHheterocyclyl, NHaryl, N(aryl)$_2$, OH, —OCH$_2$O—, O$(C_1-C_W)$alkyl, (polyfluorinated) O$(C_1-C_6)$alkyl, (aryl) O$(C_1-C_6)$alkyl, O$(C_1-C_6)$alkylideneamino, OC(O)$(C_1-C_6)$alkyl, OC(O)heterocyclyl, OC(O)aryl, O$(C_3-C_7)$cycloalkenyl, Oheterocyclyl, Oaryl, tri$(C_1-C_6)$alkylsilyl, S$(C_1-C_6)$alkyl, Saryl, S(O)$_2(C_1-C_6)$alkyl, polyfluorinated S(O)$_2(C_1-C_6)$alkyl, S(O)$_2$NH$_2$, S(O)$_2$NH$(C_1-C_6)$alkyl, S(O)$_2$N$((C_1-C_6)$alkyl)$_2$, S(O)$_2$NHheterocyclyl, S(O)$_2$NHaryl, S(O)$_2$aryl, $(C_3-C_7)$cycloalkyl, heterocyclyl, polyfluorinated heterocyclyl, $(C_1-C_6)$alkylheterocyclyl, aryl, $(C_1-C_6)$alkylaryl, heteroaryl, and $(C_1-C_6)$alkylheteroaryl;

with proviso that R3, R4, R3', and R4' are not simultaneously hydrogen;

wherein the process comprises the following step:

alkylating a compound of formula (Ib):

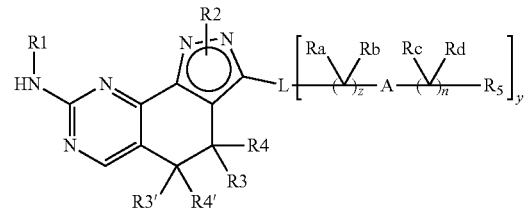

(Ib)

wherein:

A is $(C_3-C_7)$cycloalkyl, heterocyclyl, aryl, or heteroaryl, wherein the $(C_3-C_7)$cycloalkyl, heterocyclyl, aryl, or heteroaryl is optionally substituted with one or more independently selected substituents;

L is —C(O)NR8- or —NR8C(O)—;

R1 is hydrogen, or $(C_1-C_6)$alkyl;

R2 is hydrogen:

R3 is hydrogen or $(C_1-C_6)$alkyl;

R4 is hydrogen or $(C_1-C_6)$alkyl;

R3' is hydrogen or $(C_1-C_6)$alkyl;

R4' is hydrogen or $(C_1-C_6)$alkyl;

R5 is C(O)R6, C(O)NR6R7, C(O)OR6, NR6R7, NR7C(O)R6, NR7C(O)NR6R7, NR7C(O)OR9, or OR6;

R6 is hydrogen, $(C_1-C_6)$alkyl, aryl$(C_1-C_6)$alkyl, heteroaryl$(C_1-C_6)$alkyl, $(C_3-C_7)$cycloalkyl, heterocyclyl, aryl, or heteroaryl, wherein the $(C_1-C_6)$alkyl, aryl$(C_1-C_6)$alkyl, heteroaryl$(C_1-C_6)$alkyl, $(C_3-C_7)$cycloalkyl, heterocyclyl, aryl, or heteroaryl is optionally substituted with one or more independently selected substituents;

each R7 is independently hydrogen, $(C_1-C_6)$alkyl, aryl $(C_1-C_6)$alkyl, heteroaryl$(C_1-C_6)$alkyl, $(C_3-C_7)$cycloalkyl, heterocyclyl, aryl, or heteroaryl, wherein each $(C_1-C_6)$alkyl, aryl$(C_1-C_6)$alkyl, heteroaryl$(C_1-C_6)$alkyl, $(C_3-C_7)$cycloalkyl, heterocyclyl, aryl, and heteroaryl is optionally and independently substituted with one or more independently selected substituents; or R6 and R7, taken together with the nitrogen atom to which they are bonded, form a 5- or 6-membered heterocyclyl, wherein the 5- or 6-membered heterocyclyl optionally contains one additional heteroatom selected from the group consisting of nitrogen, oxygen, and sulfur, and further wherein the 5- or 6-membered heterocyclyl is optionally substituted with one or more independently selected substituents;

R8 is hydrogen or $(C_1-C_6)$alkyl, wherein the $(C_1-C_6)$ alkyl is optionally substituted with one or more independently selected substituents;

R9 is $(C_1-C_6)$alkyl, aryl$(C_1-C_6)$alkyl, heteroaryl$(C_1-C_6)$alkyl, $(C_3-C_7)$cycloalkyl, heterocyclyl, aryl, or heteroaryl, wherein the $(C_1-C_6)$alkyl, aryl$(C_1-C_6)$alkyl, heteroaryl$(C_1-C_6)$ alkyl, $(C_3-C_7)$cycloalkyl, heterocyclyl, aryl, or heteroaryl is optionally substituted with one or more independently selected substituents;

Ra is hydrogen, fluoro, or (C₁-C₆)alkyl, wherein the (C₁-C₆) alkyl is optionally substituted with one or more independently selected substituents;

Rb is hydrogen, fluoro, or (C₁-C₆)alkyl, wherein the (C₁-C₆) alkyl is optionally substituted with one or more independently selected substituents; or Ra and Rb, taken together with the carbon atom to which they are bonded, form a 3-membered cycloalkyl;

Rc is hydrogen, fluoro, or (C₁-C₆)alkyl, wherein the (C₁-C₆) alkyl is optionally substituted with one or more independently selected substituents;

Rd is hydrogen, fluoro, or (C₁-C₆)alkyl, wherein the (C₁-C₆) alkyl is optionally substituted with one or more independently selected substituents; or Rc and Rd, taken together with the carbon atom to which they are bonded, form a 3-membered cycloalkyl;

y is 1;

n is 0, 1, or 2; and z is 0, 1, or 2;

wherein the optional substituents for A, R5, R6, R7, R6 and R7, R8, R9, Ra, Rb, Rc, Rd, Ra and Rb, and Rc and Rd, are independently selected from the group consisting halogen, cyano, nitro, oxo, (C₁-C₆)alkyl, polyfluorinated (C₁-C₆)alkyl, C(O)NHaryl(C₁-C₆)alkyl, C(O)heterocyclyl(C₁-C₆)alkyl, amino(C₁-C₆)alkyl, hydroxy (C₁-C₆)alkyl, (C₃-C₇)cycloalkyl(C₁-C₆)alkyl, heterocyclyl(C₁-C₆)alkyl, (C₁-C₆)alkylheterocyclyl (C₁-C₆)alkyl, di(C₁-C₆)alkylaminoheterocyclyl(C₁-C₆) alkyl, aryl(C₁-C₆)alkyl, heteroaryl(C₁-C₆)alkyl, (C₂-C₆)alkenyl, (C₂-C₆)alkynyl, C(NH)O(C₁-C₆)alkyl, C(O)H, C(O)(C₁-C₆)alkyl, C(O)NH₂, C(O)NH(C₁-C₆) alkyl, C(O)N((C₁-C₆)alkyl)₂, CO)NHOH, C(O)NlHheterocyclyl, C(O)NHaryl, C(O)NHheteroaryl, C(O)OH, C(O)O(C₁-C₆)alkyl, C(O)O(C₃-C₇)cycloalkyl, C(O)Oaryl, C(O)(C₃-C₇)cycloalkyl, C(O)heterocyclyl, C(O)aryl, NH₂, NH(C₁-C₆)alkyl, N((C₁-C₆)alkyl)₂, NHC(O)H, NHC(O)(C₁-C₆)alkyl, NHC(O)NH₂, NHC(O)NH(C₁-C₆)alkyl, NHC(O)O(C₁-C₆)alkyl, NHC(O)O(C₁-C₆)alkyl(heterocyclyl), NHC(O)(C₃-C₇)cycloalkyl, NHC(O)heterocyclyl, NHC(O)aryl, NHS(O)₂(C₁-C₆)alkyl, NHS(O)₂heterocyclyl, NHS(O)₂aryl, NHheterocyclyl, NHaryl, N(aryl)₂, OH, —OCH₂O—, O(C₁-C₆)alkyl, (polyfluorinated) O(C₁-C₆)alkyl, (aryl) O(C₁-C₆)alkyl, O(C₁-C₆)alkylideneamino, OC(O)(C₁-C₆)alkyl, OC(O)heterocyclyl, OC(O)aryl, O(C₃-C₇)cycloalkenyl, Oheterocyclyl, Oaryl, tri(C₁-C₆)alkylsilyl, S(C₁-C₆)alkyl, polyfluorinated S(O)₂(C₁-C₆)alkyl, S(O)₂ NH₂, S(O)₂NH(C₁-C₆)alkyl, S(O)₂N((C₁-C₆)alkyl)₂, S(O)₂NHheterocyclyl, S(O)₂NHaryl, S(O)₂aryl, (C₃-C₇)cycloalkyl, heterocyclyl, polyfluorinated heterocyclyl, (C₁-C₆)alkylheterocyclyl, aryl, (C₁-C₆)alkylaryl, heteroaryl, and (C₁-C₆)alkylheteroaryl;

with proviso that R3, R4, R3', and R4' are not simultaneously hydrogen;

with a compound of formula (VI):

R2-J (VI)

wherein:

R2 is (C₁-C₆)alkyl, (C₂-C₆)alkenyl, (C₂-C₆) alkynyl, (C₃-C₇)cycloalkyl, or heterocyclyl, wherein the (C₁-C₆) alkyl, (C₂-C₆)alkenyl, (C₂-C₆)alkynyl, (C₃-C₇)cycloalkyl, or heterocyclyl is optionally substituted with one or more substituents independently selected from the group consisting of halogen, cyano, nitro, oxo, (C₁-C₆) alkyl, polyfluorinated (C₁-C₆)alkyl, C(O)NHaryl(C₁-C₆)alkyl, C(O)heterocyclyl(C₁-C₆)alkyl, amino(C₁-C₆)alkyl, hydroxy(C₁-C₆)alkyl, (C₃-C₇)cycloalkyl(C₁-C₆)alkyl, heterocyclyl(C₁-C₆)alkyl, (C₁-C₆) alkylheterocyclyl(C₁-C₆)alkyl, di(C₁-C₆) alkylaminoheterocyclyl(C₁-C₆)alkyl, aryl(C₁-C₆)alkyl, heteroaryl(C₁-C₆)alkyl, (C₂-C₆)alkenyl, (C₂-C₆)alkynyl, C(NH)O(C₁-C₆)alkyl, C(O)H, C(O)(C₁-C₆)alkyl, C(O)NH₂, C(O)NH(C₁-C₆)alkyl, C(O)N((C₁-C₆) alkyl)₂, CO)NHOH, C(O)NHheterocyclyl, C(O)NHaryl, C(O)NHheteroaryl, C(O)OH, C(O)O(C₁-C₆)alkyl, C(O)O(C₃-C₇)cycloalkyl, C(O)Oaryl, C(O)(C₃-C₇)cycloalkyl, C(O)heterocyclyl, C(O)aryl, NH₂, NH(C₁-C₆)alkyl, N((C₁-C₆)alkyl)₂, NHC(O)H, NHC(O)(C₁-C₆)alkyl, NHC(O)NH₂, NHC(O)NH(C₁-C₆)alkyl, NHC(O)O(C₁-C₆)alkyl, NHC(O)O(C₁-C₆)alkyl (heterocyclyl), NHC(O)(C₃-C₇)cycloalkyl, NHC(O)heterocyclyl, NHC(O)aryl, NHS(O)₂(C₁-C₆)alkyl, NHS(O)₂heterocyclyl, NHS(O)₂aryl, NHheterocyclyl, NHaryl, N(aryl)₂, OH, —OCH₂O—, O(C₁-C₆)alkyl, (polyfluorinated) O(C₁-C₆)alkyl, (aryl) O(C₁-C₆)alkyl, O(C₁-C₆)alkylideneamino, OC(O)(C₁-C₆)alkyl, OC(O)heterocyclyl, OC(O)aryl, O(C₃-C₇)cycloalkenyl, Oheterocyclyl, Oaryl, tri(C₁-C₆)alkylsilyl, S(C₁-C₆)alkyl, Saryl, S(O)₂(C₁-C₆)alkyl, polyfluorinated S(O)₂(C₁-C₆)alkyl, S(O)₂NH₂, S(O)₂NH(C₁-C₆)alkyl, S(O)₂N((C₁-C₆)alkyl)₂, S(O)₂NHheterocyclyl, S(O)₂NHaryl, S(O)₂aryl, (C₃-C₇)cycloalkyl, heterocyclyl, polyfluorinated heterocyclyl, (C₁-C₆)alkylheterocyclyl, aryl, (C₁-C₆)alkylaryl, heteroaryl, and (C₁-C₆)alkylheteroaryl; and J is Br, I, OH, OS(O)₂CH₃, or OS(O)₂-Ph-CH₃;

to yield the compound of formula (Ia) above.

19. A process for preparing a compound according to claim 1, wherein the compound is of formula (Ia):

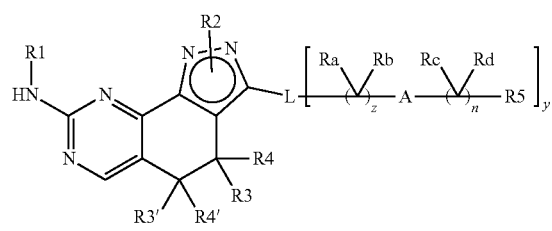

(Ia)

wherein:

A is (C₃-C₇)cycloalkyl, heterocyclyl, aryl, or heteroaryl, wherein the (C₃-C₇)cycloalkyl, heterocyclyl, aryl, or heteroaryl is optionally substituted with one or more independently selected substituents;

L is —C(O)NR8- or —NR8C(O)—;

R1 is hydrogen, or (C₁-C₆)alkyl;

R2 is (C₁-C₆)alkyl, (C₂-C₆)alkenyl, (C₂-C₆) alkynyl, (C₃-C₇)cycloalkyl, or heterocyclyl, wherein the (C₁-C₆) alkyl, (C₂-C₆)alkenyl, (C₂-C₆) alkynyl, (C₃-C₇)cycloalkyl, or heterocyclyl is optionally substituted with one or more independently selected substituents;

R3 is hydrogen or (C₁-C₆)alkyl;

R4 is hydrogen or (C₁-C₆)alkyl;

R3' is hydrogen or (C₁-C₆)alkyl;

R4' is hydrogen or (C₁-C₆)alkyl;

R5 is C(O)R6, C(O)NR6R7, C(O)OR6, NR6R7, NR7C(O)R6, NR7C(O)NR6R7, NR7C(O)OR9, or OR6;

R6 is hydrogen, (C₁-C₆)alkyl, aryl(C₁-C₆)alkyl, heteroaryl(C₁-C₆)alkyl, (C₃-C₇)cycloalkyl, heterocyclyl, aryl, or heteroaryl, wherein the $(C_1-C_6)$alkyl, aryl$(C_1-C_6)$alkyl, heteroaryl$(C_1-C_6)$alkyl, $(C_3-C_7)$cycloalkyl, heterocyclyl, aryl, or heteroaryl is optionally substituted with one or more independently selected substituents;

each R7 is independently hydrogen, $(C_1-C_6)$alkyl, aryl $(C_1-C_6)$alkyl, heteroaryl$(C_1-C_6)$alkyl, $(C_3-C_7)$cycloalkyl, heterocyclyl, aryl, or heteroaryl, wherein each $(C_1-C_6)$alkyl, aryl$(C_1-C_6)$alkyl, heteroaryl$(C_1-C_6)$alkyl, $(C_3-C_7)$cycloalkyl, heterocyclyl, aryl, and heteroaryl is optionally and independently substituted with one or more independently selected substituents; or R6 and R7, taken together with the nitrogen atom to which they are bonded, form a 5- or 6-membered heterocyclyl, wherein the 5- or 6-membered heterocyclyl optionally contains one additional heteroatom selected from the group consisting of nitrogen, oxygen, and sulfur, and further wherein the 5- or 6-membered heterocyclyl is optionally substituted with one or more independently selected substituents;

R8 is hydrogen or $(C_1-C_6)$alkyl, wherein the $(C_1-C_6)$ alkyl is optionally substituted with one or more independently selected substituents;

R9 is $(C_1-C_6)$alkyl, aryl$(C_1-C_6)$alkyl, heteroaryl$(C_1-C_6)$ alkyl, $(C_3-C_7)$cycloalkyl, heterocyclyl, aryl, or heteroaryl, wherein the $(C_1-C_6)$alkyl, aryl$(C_1-C_6)$alkyl, heteroaryl$(C_1-C_6)$ alkyl, $(C_3-C_7)$cycloalkyl, heterocyclyl, aryl, or heteroaryl is optionally substituted with one or more independently selected substituents;

Ra is hydrogen, fluoro, or $(C_1-C_6)$alkyl, wherein the $(C_1-C_6)$ alkyl is optionally substituted with one or more independently selected substituents;

Rb is hydrogen, fluoro, or $(C_1-C_6)$alkyl, wherein the $(C_1-C_6)$ alkyl is optionally substituted with one or more independently selected substituents; or Ra and Rb, taken together with the carbon atom to which they are bonded, form a 3-membered cycloalkyl;

Rc is hydrogen, fluoro, or $(C_1-C_6)$alkyl, wherein the $(C_1-C_6)$ alkyl is optionally substituted with one or more independently selected substituents;

Rd is hydrogen, fluoro, or $(C_1-C_6)$alkyl, wherein the $(C_1-C_6)$ alkyl is optionally substituted with one or more independently selected substituents; or Rc and Rd, taken together with the carbon atom to which they are bonded, form a 3-membered cycloalkyl;

y is 1;

n is 0, 1, or 2; and z is 0, 1, or 2;

wherein the optional substituents for A, R2, R5, R6, R7, R6 and R7, R8, R9, Ra, Rb, Rc, Rd, Ra and Rb, and Rc and Rd, are independently selected from the group consisting halogen, cyano, nitro, oxo, $(C_1-C_6)$alkyl, polyfluorinated $(C_1-C_6)$alkyl, C(O)NHaryl$(C_1-C_6)$alkyl, C(O)heterocyclyl$(C_1-C_6)$alkyl, amino$(C_1-C_6)$alkyl, hydroxy$(C_1-C_6)$alkyl, $(C_3C)$cycloalkyl$(C_1-C_6)$alkyl, heterocyclyl$(C_1-C_6)$alkyl, $(C_1-C_6)$alkylheterocyclyl$(C_1-C_6)$alkyl, di$(C_1-C_6)$alkylaminoheterocyclyl$(C_1-C_6)$alkyl, aryl$(C_1-C_6)$alkyl, heteroaryl$(C_1-C_6)$alkyl, $(C_2-C_6)$alkenyl, $(C_2-C_6)$alkynyl, C(NH)O$(C_1-C_6)$alkyl, C(O)H, C(O)$C_1-C_6)$alkyl, C(O)NH$_2$, C(O)NH$(C_1-C_6)$alkyl, C(O)N$((C_1-C_6)$alkyl$)_2$, CO)NHOH, C(O)NHheterocyclyl, C(O)NHaryl, C(O)NHeteroaryl, C(O)OH, C(O)O$(C_1-C_6)$alkyl, C(O)O$(C_3-C_7)$cycloalkyl, C(O)Oaryl, C(O)$(C_3-C_7)$cycloalkyl, C(O)heterocyclyl, C(O)aryl, NH$_2$, NH$(C_1-C_6)$alkyl, N$((C_1-C_6)$alkyl$)_2$, NHC(O)H, NHC(O)$(C_1-C_6)$alkyl, NHC(O)NH$_2$, NHC(O)NH$(C_1-C_6)$alkyl, NHC(O)O$(C_1-C_6)$alkyl, NHC(O)O$(C_1-C_6)$alkyl (heterocyclyl), NHC(O)$(C_3-C_7)$cycloalkyl, NHC(O)heterocyclyl, NHC(O)aryl, NHS(O)$_2(C_1-C_6)$alkyl, NHS(O)$_2$heterocyclyl, NHS(O)$_2$aryl, NHheterocyclyl, NHaryl, N(aryl)$_2$, OH, —OCH$_2$O—, O$(C_1-C_6)$alkyl, (polyfluorinated) O$(C_1-C_6)$alkyl, (aryl) O$(C_1-C_6)$alkyl, O$(C_1-C_6)$alkylideneamino, OC(O)$(C_1-C_6)$alkyl, OC(O)heterocyclyl, OC(O)aryl, O$(C_3-C_7)$cycloalkenyl, Oheterocyclyl, Oaryl, tri$(C_1-C_6)$alkylsilyl, S$(C_1-C_6)$alkyl, Saryl, S(O)$_2(C_1-C_6)$alkyl, polyfluorinated S(O)$_2(C_1-C_6)$alkyl, S(O)$_2$NH$_2$, S(O)$_2$NH$(C_1-C_6)$alkyl, S(O)$_2$N$((C_1-C_6)$alkyl$)_2$, S(O)$_2$NHheterocyclyl, S(O)$_2$NHaryl, S(O)$_2$aryl, $(C_3-C_7)$cycloalkyl, heterocyclyl, polyfluorinated heterocyclyl, $(C_1-C_6)$alkylheterocyclyl, aryl, $(C_1-C_6)$alkylaryl, heteroaryl, and $(C_1-C_6)$alkylheteroaryl;

with proviso that R3, R4, R3', and R4' are not simultaneously hydrogen;

wherein the process comprises the following step of SEQUENCE A:

reacting a compound of formula (V):

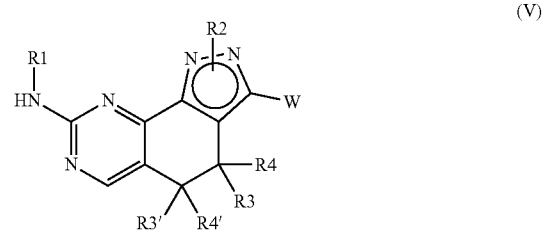

wherein:

W is C(O)OH or NHR8;

R1 is hydrogen, or $(C_1-C_6)$alkyl;

R2 is $(C_1-C_6)$alkyl, $(C_2-C_6)$alkenyl, $(C_2-C_6)$ alkynyl, $(C_3-C_7)$cycloalkyl, or heterocyclyl, wherein the $(C_1-C_6)$ alkyl, $(C_2-C_6)$alkenyl, $(C_2-C_6)$ alkynyl, $(C_3-C_7)$cycloalkyl, or heterocyclyl is optionally substituted with one or more independently selected substituents;

R3 is hydrogen or $(C_1-C_6)$alkyl;

R4 is hydrogen or $(C_1-C_6)$alkyl;

R3' is hydrogen or $(C_1-C_6)$alkyl;

R4' is hydrogen or $(C_1-C_6)$alkyl; and

R8 is hydrogen or $(C_1-C_6)$alkyl, wherein the $(C_1-C_6)$ alkyl is optionally substituted with one or more independently selected substituents;

wherein the optional substituents for R2 and R8 are independently selected from the group consisting halogen, cyano, nitro, oxo, $(C_1-C_6)$alkyl, polyfluorinated $(C_1-C_6)$alkyl, C(O)NHaryl$(C_1-C_6)$alkyl, C(O)heterocyclyl$(C_1-C_6)$alkyl, amino$(C_1-C_6)$alkyl, hydroxy$(C_1-C_6)$ alkyl, $(C_3-C_7)$cycloalkyl$(C_1-C_6)$alkyl, heterocyclyl$(C_1-C_6)$alkyl, $(C_1-C_6)$alkylheterocyclyl$(C_1-C_6)$alkyl, di$(C_1-C_6)$alkylaminoheterocyclyl$(C_1-C_6)$alkyl, aryl$(C_1-C_6)$alkyl, heteroaryl$(C_1-C_6)$alkyl, $(C_2-C_6)$alkenyl, $(C_2-C_6)$alkynyl, C(NH)O$(C_1-C_6)$alkyl, C(O)H, C(O)$(C_1-C_6)$alkyl, C(O)NH$_2$, C(O)NH$(C_1-C_6)$alkyl, C(O)N$((C_1-C_6)$alkyl$)_2$, CO)NHOH, C(O)NHheterocyclyl, C(O)NHaryl, C(O)NHeteroaryl, C(O)OH, C(O)O$(C_1-C_6)$alkyl, C(O)O$(C_3-C_7)$cycloalkyl, C(O)Oaryl, C(O)$(C_3-C_7)$cycloalkyl, C(O)heterocyclyl, C(O)aryl, NH$_2$, NH$(C_1-C_6)$alkyl, N$((C_1-C_6)$alkyl$)_2$, NHC(O)H, NHC(O)$(C_1-C_6)$alkyl, NHC(O)NH$_2$, NHC(O)NH$(C_1-C_6)$alkyl, NHC(O)O$(C_1-C_6)$alkyl, NHC(O)O$(C_1-C_6)$alkyl (heterocyclyl), NHC(O)(C$_3$-C$_7$)cycloalkyl, NHC(O) heterocyclyl, NHC(O)aryl, NHS(O)$_2$(C$_1$-C$_6$)alkyl, NHS(O)$_2$heterocyclyl, NHS(O)$_2$aryl, NHheterocyclyl, NHaryl, N(aryl)$_2$, OH, —OCH$_2$O—, O(C$_1$-C$_6$)alkyl, (polyfluorinated) O(C$_1$-C$_6$)alkyl, (aryl) O(C$_1$-C$_6$)alkyl, O(C$_1$-C$_6$)alkylideneamino, OC(O)(C$_1$-C$_6$)alkyl, OC(O)heterocyclyl, OC(O)aryl, O(C$_3$-C$_7$)cycloalkenyl, Oheterocyclyl, Oaryl, tri(C$_1$-C$_6$)alkylsilyl, S(C$_1$-C$_6$)alkyl, Saryl, S(O)$_2$(C$_1$-C$_6$)alkyl, polyfluorinated S(O)$_2$(C$_1$-C$_6$)alkyl, S(O)$_2$NH$_2$, S(O)$_2$NH(C$_1$-C$_6$)alkyl, S(O)$_2$N((C$_1$-C$_6$)alkyl)$_2$, S(O)$_2$NHheterocyclyl, S(O)$_2$NHaryl, S(O)$_2$aryl, (C$_3$-C$_7$)cycloalkyl, heterocyclyl, polyfluorinated heterocyclyl, (C$_1$-C$_6$)alkylheterocyclyl, aryl, (C$_1$-C$_6$)alkylaryl, heteroaryl, and (C$_1$-C$_6$)alkylheteroaryl;

with proviso that R3, R4, R3', and R4' are not simultaneously hydrogen;

with a compound of formula (IV):

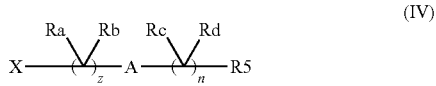

(IV)

wherein:

A is (C$_3$-C$_7$)cycloalkyl, heterocyclyl, aryl, or heteroaryl, wherein the (C$_3$-C$_7$)cycloalkyl, heterocyclyl, aryl, or heteroaryl is optionally substituted with one or more independently selected substituents;

X is C(O)OH or NHR8;

R5 is C(O)R6, C(O)NR6R7, C(O)OR6, NR6R7, NR7C(O)R6, NR7C(O)NR6R7, NR7C(O)OR9, or OR6;

R6 is hydrogen, (C$_1$-C$_6$)alkyl, aryl(C$_1$-C$_6$)alkyl, heteroaryl(C$_1$-C$_6$)alkyl, (C$_3$-C$_7$)cycloalkyl, heterocyclyl, aryl, or heteroaryl, wherein the (C$_1$-C$_6$)alkyl, aryl(C$_1$-C$_6$)alkyl, heteroaryl(C$_1$-C$_6$)alkyl, (C$_3$-C$_7$)cycloalkyl, heterocyclyl, aryl, or heteroaryl is optionally substituted with one or more independently selected substituents;

each R7 is independently hydrogen, (C$_1$-C$_6$)alkyl, aryl(C$_1$-C$_6$)alkyl, heteroaryl(C$_1$-C$_6$)alkyl, (C$_3$-C$_7$)cycloalkyl, heterocyclyl, aryl, or heteroaryl, wherein each (C$_1$-C$_6$)alkyl, aryl(C$_1$-C$_6$)alkyl, heteroaryl(C$_1$-C$_6$)alkyl, (C$_3$-C$_7$)cycloalkyl, heterocyclyl, aryl, and heteroaryl is optionally and independently substituted with one or more independently selected substituents; or R6 and R7, taken together with the nitrogen atom to which they are bonded, form a 5- or 6-membered heterocyclyl, wherein the 5- or 6-membered heterocyclyl optionally contains one additional heteroatom selected from the group consisting of nitrogen, oxygen, and sulfur, and further wherein the 5- or 6-membered heterocyclyl is optionally substituted with one or more independently selected substituents;

R8 is hydrogen or (C$_1$-C$_6$)alkyl, wherein the (C$_1$-C$_6$) alkyl is optionally substituted with one or more independently selected substituents;

Ra is hydrogen, fluoro, or (C$_1$-C$_6$)alkyl, wherein the (C$_1$-C$_6$) alkyl is optionally substituted with one or more independently selected substituents;

Rb is hydrogen, fluoro, or (C$_1$-C$_6$)alkyl, wherein the (C$_1$-C$_6$) alkyl is optionally substituted with one or more independently selected substituents; or Ra and Rb, taken together with the carbon atom to which they are bonded, form a 3-membered cycloalkyl;

Rc is hydrogen, fluoro, or (C$_1$-C$_6$)alkyl, wherein the (C$_1$-C$_6$) alkyl is optionally substituted with one or more independently selected substituents;

Rd is hydrogen, fluoro, or (C$_1$-C$_6$)alkyl, wherein the (C$_1$-C$_6$) alkyl is optionally substituted with one or more independently selected substituents; or Rc and Rd, taken together with the carbon atom to which they are bonded, form a 3-membered cycloalkyl;

n is 0, 1, or 2; and z is 0, 1, or 2;

wherein the optional substituents for A, R5, R6, R7, R6 and R7, R8, Ra, Rb, Rc, Rd, Ra and Rb, and Rc and Rd, are independently selected from the group consisting halogen, cyano, nitro, oxo, (C$_1$-C$_6$)alkyl, polyfluorinated (C$_1$-C$_6$)alkyl, C(O)NHaryl(C$_1$-C$_6$)alkyl, C(O)heterocyclyl(C$_1$-C$_6$)alkyl, amino(C$_1$-C$_6$)alkyl, hydroxy (C$_1$-C$_6$)alkyl, (C$_3$-C$_7$)cycloalkyl(C$_1$-C$_6$)alkyl, heterocyclyl(C$_1$-C$_6$)alkyl, (C$_1$-C$_6$)alkylheterocyclyl (C$_1$-C$_6$)alkyl, di(C$_1$-C$_6$)alkylaminoheterocyclyl(C$_1$-C$_6$) alkyl, aryl(C$_1$-C$_6$)alkyl, heteroaryl(C$_1$-C$_6$)alkyl, (C$_2$-C$_6$)alkenyl, (C$_2$-C$_6$)alkynyl, C(NH)O(C$_1$-C$_6$)alkyl, C(O)H, C(O)(C$_1$-C$_6$)alkyl, C(O)NH$_2$, C(O)NH(C$_1$-C$_6$) alkyl, C(O)N((C$_1$-C$_6$)alkyl)$_2$, CO)NHOH, C(O) NlHheterocyclyl, C(O)NHaryl, C(O)NHheteroaryl, C(O)OH, C(O)O(C$_1$-C$_6$)alkyl, C(O)O(C$_3$-C$_7$)cycloalkyl, C(O)Oaryl, C(O)(C$_3$-C$_7$)cycloalkyl, C(O)heterocyclyl, C(O)aryl, NH$_2$, NH(C$_1$-C$_6$)alkyl, N((C$_1$-C$_6$)alkyl)$_2$, NHC(O)H, NHC(O)(C$_1$-C$_6$)alkyl, NHC(O)NH$_2$, NHC(O)NH(C$_1$-C$_6$)alkyl, NHC(O)O(C$_1$-C$_6$)alkyl, NHC(O)O(C$_1$-C$_6$)alkyl(heterocyclyl), NHC(O)(C$_3$-C$_7$) cycloalkyl, NHC(O)heterocyclyl, NHC(O)aryl, NHS (O)$_2$(C$_1$-C$_6$)alkyl, NHS(O)$_2$heterocyclyl, NHS(O)$_2$ aryl, NHheterocyclyl, NHaryl, N(aryl)$_2$, OH, —OCH$_2$O—, O(C$_1$-C$_6$)alkyl, (polyfluorinated) O(C$_1$-C$_6$)alkyl, (aryl) O(C$_1$-C$_6$)alkyl, O(C$_1$-C$_6$)alkylideneamino, OC(O)(C$_1$-C$_6$)alkyl, OC(O)heterocyclyl, OC(O)aryl, O(C$_3$-C$_7$)cycloalkenyl, Oheterocyclyl, Oaryl, tri(C$_1$-C$_6$)alkylsilyl, S(C$_1$-C$_6$)alkyl, Saryl, S(O)$_2$ (C$_1$-C$_6$)alkyl, polyfluorinated S(O)$_2$(C$_1$-C$_6$)alkyl, S(O)$_2$ NH$_2$, S(O)$_2$NH(C$_1$-C$_6$)alkyl, S(O)$_2$N((C$_1$-C$_6$)alkyl)$_2$, S(O)$_2$NHheterocyclyl, S(O)$_2$NHaryl, S(O)$_2$aryl, (C$_3$-C$_7$)cycloalkyl, heterocyclyl, polyfluorinated heterocyclyl, (C$_1$-C$_6$)alkylheterocyclyl, aryl, (C$_1$-C$_6$)alkylaryl, heteroaryl, and (C$_1$-C$_6$)alkylheteroaryl;

with provisos that:

(1) when W is C(O)OH, X is NHR8; and (2) when W is NHR8, X is C(O)OH, to yield the compound of formula (Ia) above.

20. A process for preparing a compound according to claim 1, wherein the compound is of formula (Ib):

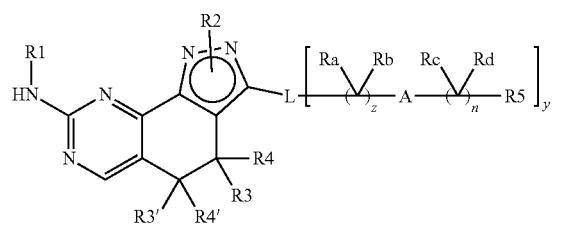

(Ib)

wherein:

A is (C$_3$-C$_7$)cycloalkyl, heterocyclyl, aryl, or heteroaryl, wherein the (C$_3$-C$_7$)cycloalkyl, heterocyclyl, aryl, or heteroaryl is optionally substituted with one or more independently selected substituents;

L is —C(O)NR8- or —NR8C(O)—;

R1 is hydrogen, or $(C_1-C_6)$alkyl;

R2 is hydrogen;

R3 is hydrogen or $(C_1-C_6)$alkyl;

R4 is hydrogen or $(C_1-C_6)$alkyl;

R3' is hydrogen or $(C_1-C_6)$alkyl;

R4' is hydrogen or $(C_1-C_6)$alkyl;

R5 is C(O)R6, C(O)NR6R7, C(O)OR6, NR6R7, NR7C(O)R6, NR7C(O)NR6R7, NR7C(O)OR9, or OR6;

R6 is hydrogen, $(C_1-C_6)$alkyl, aryl$(C_1-C_6)$alkyl, heteroaryl$(C_1-C_6)$alkyl, $(C_3-C_7)$cycloalkyl, heterocyclyl, aryl, or heteroaryl, wherein the $(C_1-C_6)$alkyl, aryl$(C_1-C_6)$alkyl, heteroaryl$(C_1-C_6)$alkyl, $(C_3-C_7)$cycloalkyl, heterocyclyl, aryl, or heteroaryl is optionally substituted with one or more independently selected substituents;

each R7 is independently hydrogen, $(C_1-C_6)$alkyl, aryl$(C_1-C_6)$alkyl, heteroaryl$(C_1-C_6)$alkyl, $(C_3-C_7)$cycloalkyl, heterocyclyl, aryl, or heteroaryl, wherein each $(C_1-C_6)$alkyl, aryl$(C_1-C_6)$alkyl, heteroaryl$(C_1-C_6)$alkyl, $(C_3-C_7)$cycloalkyl, heterocyclyl, aryl, and heteroaryl is optionally and independently substituted with one or more independently selected substituents; or R6 and R7, taken together with the nitrogen atom to which they are bonded, form a 5- or 6-membered heterocyclyl, wherein the 5- or 6-membered heterocyclyl optionally contains one additional heteroatom selected from the group consisting of nitrogen, oxygen, and sulfur, and further wherein the 5- or 6-membered heterocyclyl is optionally substituted with one or more independently selected substituents;

R8 is hydrogen or $(C_1-C_6)$alkyl, wherein the $(C_1-C_6)$ alkyl is optionally substituted with one or more independently selected substituents;

R9 is $(C_1-C_6)$alkyl, aryl$(C_1-C_6)$alkyl, heteroaryl$(C_1-C_6)$alkyl, $(C_3-C_7)$cycloalkyl, heterocyclyl, aryl, or heteroaryl, wherein the $(C_1-C_6)$alkyl, aryl$(C_1-C_6)$alkyl, heteroaryl$(C_1-C_6)$ alkyl, $(C_3-C_7)$cycloalkyl, heterocyclyl, aryl, or heteroaryl is optionally substituted with one or more independently selected substituents;

Ra is hydrogen, fluoro, or $(C_1-C_6)$alkyl, wherein the $(C_1-C_6)$ alkyl is optionally substituted with one or more independently selected substituents;

Rb is hydrogen, fluoro, or $(C_1-C_6)$alkyl, wherein the $(C_1-C_6)$ alkyl is optionally substituted with one or more independently selected substituents; or Ra and Rb, taken together with the carbon atom to which they are bonded, form a 3-membered cycloalkyl;

Rc is hydrogen, fluoro, or $(C_1-C_6)$alkyl, wherein the $(C_1-C_6)$ alkyl is optionally substituted with one or more independently selected substituents;

Rd is hydrogen, fluoro, or $(C_1-C_6)$alkyl, wherein the $(C_1-C_6)$ alkyl is optionally substituted with one or more independently selected substituents; or Rc and Rd, taken together with the carbon atom to which they are bonded, form a 3-membered cycloalkyl;

y is 1;

n is 0, 1, or 2; and z is 0, 1, or 2;

wherein the optional substituents for A, R5, R6, R7, R6 and R7, R8, R9, Ra, Rb, Rc, Rd, Ra and Rb, and Rc and Rd, are independently selected from the group consisting halogen, cyano, nitro, oxo, $(C_1-C_6)$alkyl, polyfluorinated $(C_1-C_6)$alkyl, C(O)NHaryl$(C_1-C_6)$alkyl, C(O)heterocyclyl$(C_1-C_6)$alkyl, amino$(C_1-C_6)$alkyl, hydroxy $(C_1-C_6)$alkyl, $(C_3-C_7)$cycloalkyl$(C_1-C_6)$alkyl, heterocyclyl$(C_1-C_6)$alkyl, $(C_1-C_6)$alkylheterocyclyl$(C_1-C_6)$alkyl, di$(C_1-C_6)$alkylaminoheterocyclyl$(C_1-C_6)$alkyl, aryl$(C_1-C_6)$alkyl, heteroaryl$(C_1-C_6)$alkyl, $(C_2-C_6)$alkenyl, $(C_2-C_6)$alkynyl, C(NH)O$(C_1-C_6)$alkyl, C(O)H, C(O)$(C_1-C_6)$alkyl, C(O)NH$_2$, C(O)NH$(C_1-C_6)$alkyl, C(O)N$((C_1-C_6)$alkyl)$_2$, CO)NHOH, C(O)NHheterocyclyl, C(O)NHaryl, C(O)NHheteroaryl, C(O)OH, C(O)O$(C_1-C_6)$alkyl, C(O)O$(C_3-C_7)$cycloalkyl, C(O)Oaryl, C(O)$(C_3-C_7)$cycloalkyl, C(O)heterocyclyl, C(O)aryl, NH$_2$, NH$(C_1-C_6)$alkyl, N$((C_1-C_6)$alkyl)$_2$, NHC(O)H, NHC(O)$(C_1-C_6)$alkyl, NHC(O)NH$_2$, NHC(O)NH$(C_1-C_6)$alkyl, NHC(O)O$(C_1-C_6)$alkyl, NHC(O)O$(C_1-C_6)$alkyl(heterocyclyl), NHC(O)$(C_3-C_7)$cycloalkyl, NHC(O)heterocyclyl, NHC(O)aryl, NHS(O)$_2$$(C_1-C_6)$alkyl, NHS(O)$_2$heterocyclyl, NHS(O)$_2$aryl, NHheterocyclyl, NHaryl, N(aryl)$_2$, OH, —OCH$_2$O—, O$(C_1-C_6)$alkyl, (polyfluorinated) O$(C_1-C_6)$alkyl, (aryl) O$(C_1-C_6)$alkyl, O$(C_1-C_6)$alkylideneamino, OC(O)$(C_1-C_6)$alkyl, OC(O)heterocyclyl, OC(O)aryl, O$(C_3-C_7)$cycloalkenyl, Oheterocyclyl, Oaryl, tri$(C_1-C_6)$alkylsilyl, S$(C_1-C_6)$alkyl, Saryl, S(O)$_2$$(C_1-C_6)$alkyl, polyfluorinated S(O)$_2$$(C_1-C_6)$alkyl, S(O)$_2$NH$_2$, S(O)$_2$NH$(C_1-C_6)$alkyl, S(O)$_2$N$((C_1-C_6)$alkyl)$_2$, S(O)$_2$NHheterocyclyl, S(O)$_2$NHaryl, S(O)$_2$aryl, $(C_3-C_7)$cycloalkyl, heterocyclyl, polyfluorinated heterocyclyl, $(C_1-C_6)$alkylheterocyclyl, aryl, $(C_1-C_6)$alkylaryl, heteroaryl, and $(C_1-C_6)$alkylheteroaryl;

with proviso that R3, R4, R3', and R4' are not simultaneously hydrogen;

wherein the process comprises the following steps of SEQUENCE B:

a) reacting a compound of formula (III):

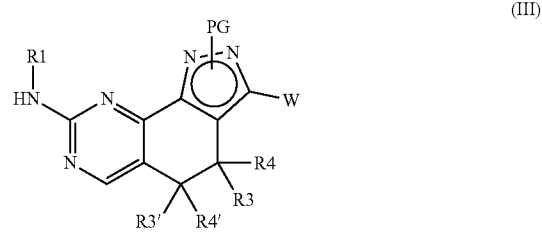

wherein:

PG is CH$_2$OCH$_2$CH$_2$Si(CH$_3$)$_3$, COOR10, C(Ph)$_3$, or tetrahydropyranyl;

W is C(O)OH or NHR8;

R1 is hydrogen, or $(C_1-C_6)$alkyl;

R3 is hydrogen or $(C_1-C_6)$alkyl;

R4 is hydrogen or $(C_1-C_6)$alkyl;

R3' is hydrogen or $(C_1-C_6)$alkyl;

R4' is hydrogen or $(C_1-C_6)$alkyl;

R8 is hydrogen or $(C_1-C_6)$alkyl, wherein the $(C_1-C_6)$ alkyl is optionally substituted with one or more independently selected substituents; and R10 is $(C_1-C_6)$alkyl or aryl$(C_1-C_6)$alkyl;

wherein the optional substituents for R2, and R8 are independently selected from the group consisting halogen, cyano, nitro, oxo, $(C_1-C_6)$alkyl, polyfluorinated $(C_1-C_6)$alkyl, C(O)NHaryl$(C_1-C_6)$alkyl, C(O)heterocyclyl$(C_1-C_6)$alkyl, amino$(C_1-C_6)$alkyl, hydroxy$(C_1-C_6)$alkyl, $(C_3-C_7)$cycloalkyl$(C_1-C_6)$alkyl, heterocyclyl$(C_1-C_6)$alkyl, $(C_1-C_6)$alkylheterocyclyl$(C_1-C_6)$alkyl, di$(C_1-C_6)$alkylaminoheterocyclyl$(C_1-C_6)$alkyl, aryl$(C_1-C_6)$ alkyl, heteroaryl($C_1$-$C_6$)alkyl, ($C_2$-$C_6$)alkenyl, ($C_2$-$C_6$)alkynyl, C(NH)O($C_1$-$C_6$)alkyl, C(O)H, C(O)($C_1$-$C_6$)alkyl, C(O)NH$_2$, C(O)NH($C_1$-$C_6$)alkyl, C(O)N(($C_1$-$C_6$)alkyl)$_2$, CO)NHOH, C(O)NHheterocyclyl, C(O)NHaryl, C(O)NHheteroaryl, C(O)OH, C(O)O($C_1$-$C_6$)alkyl, C(O)O($C_3$-$C_7$)cycloalkyl, C(O)Oaryl, C(O)($C_3$-$C_7$)cycloalkyl, C(O)heterocyclyl, C(O)aryl, NH$_2$, NH($C_1$-$C_6$)alkyl, N(($C_1$-$C_6$)alkyl)$_2$, NHC(O)H, NHC(O)($C_1$-$C_6$)alkyl, NHC(O)NH$_2$, NHC(O)NH($C_1$-$C_6$)alkyl, NHC(O)O($C_1$-$C_6$)alkyl, NHC(O)O($C_1$-$C_6$)alkyl(heterocyclyl), NHC(O)($C_3$-$C_7$)cycloalkyl, NHC(O)heterocyclyl, NHC(O)aryl, NHS(O)$_2$($C_1$-$C_6$)alkyl, NHS(O)$_2$heterocyclyl, NHS(O)$_2$aryl, NHheterocyclyl, NHaryl, N(aryl)$_2$, OH, —OCH$_2$O—, O($C_1$-$C_6$)alkyl, (polyfluorinated) O($C_1$-$C_6$)alkyl, (aryl) O($C_1$-$C_6$)alkyl, O($C_1$-$C_6$)alkylideneamino, OC(O)($C_1$-$C_6$)alkyl, OC(O)heterocyclyl, OC(O)aryl, O($C_3$-$C_7$)cycloalkenyl, Oheterocyclyl, Oaryl, tri($C_1$-$C_6$)alkylsilyl, S($C_1$-$C_6$)alkyl, Saryl, S(O)$_2$($C_1$-$C_6$)alkyl, polyfluorinated S(O)$_2$($C_1$-$C_6$)alkyl, S(O)$_2$NH$_2$, S(O)$_2$NH($C_1$-$C_6$)alkyl, S(O)$_2$N(($C_1$-$C_6$)alkyl)$_2$, S(O)$_2$NHheterocyclyl, S(O)$_2$NHaryl, S(O)$_2$aryl, ($C_3$-$C_7$)cycloalkyl, heterocyclyl, polyfluorinated heterocyclyl, ($C_1$-$C_6$)alkylheterocyclyl, aryl, ($C_1$-$C_6$)alkylaryl, heteroaryl, and ($C_1$-$C_6$) alkylheteroaryl;

with proviso that R3, R4, R3', and R4' are not simultaneously hydrogen;

with a compound of formula (IV):

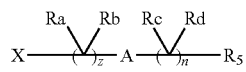

(IV)

wherein:

A is ($C_3$-$C_7$)cycloalkyl, heterocyclyl, aryl, or heteroaryl, wherein the ($C_3$-$C_7$)cycloalkyl, heterocyclyl, aryl, or heteroaryl is optionally substituted with one or more independently selected substituents;

X is C(O)OH or NHR8;

R5 is C(O)R6, C(O)NR6R7, C(O)OR6, NR6R7, NR7C(O)R6, NR7C(O)NR6R7, NR7C(O)OR9, or OR6;

R6 is hydrogen, ($C_1$-$C_6$)alkyl, aryl($C_1$-$C_6$)alkyl, heteroaryl($C_1$-$C_6$)alkyl, ($C_3$-$C_7$)cycloalkyl, heterocyclyl, aryl, or heteroaryl, wherein the ($C_1$-$C_6$)alkyl, aryl($C_1$-$C_6$)alkyl, heteroaryl($C_1$-$C_6$)alkyl, ($C_3$-$C_7$)cycloalkyl, heterocyclyl, aryl, or heteroaryl is optionally substituted with one or more independently selected substituents;

each R7 is independently hydrogen, ($C_1$-$C_6$)alkyl, aryl($C_1$-$C_6$)alkyl, heteroaryl($C_1$-$C_6$)alkyl, ($C_3$-$C_7$)cycloalkyl, heterocyclyl, aryl, or heteroaryl, wherein each ($C_1$-$C_6$)alkyl, aryl($C_1$-$C_6$)alkyl, heteroaryl($C_1$-$C_6$)alkyl, ($C_3$-$C_7$)cycloalkyl, heterocyclyl, aryl, and heteroaryl is optionally and independently substituted with one or more independently selected substituents; or R6 and R7, taken together with the nitrogen atom to which they are bonded, form a 5- or 6-membered heterocyclyl, wherein the 5- or 6-membered heterocyclyl optionally contains one additional heteroatom selected from the group consisting of nitrogen, oxygen, and sulfur, and further wherein the 5- or 6-membered heterocyclyl is optionally substituted with one or more independently selected substituents;

R8 is hydrogen or ($C_1$-$C_6$)alkyl, wherein the ($C_1$-$C_6$) alkyl is optionally substituted with one or more independently selected substituents;

Ra is hydrogen, fluoro, or ($C_1$-$C_6$)alkyl, wherein the ($C_1$-$C_6$) alkyl is optionally substituted with one or more independently selected substituents;

Rb is hydrogen, fluoro, or ($C_1$-$C_6$)alkyl, wherein the ($C_1$-$C_6$) alkyl is optionally substituted with one or more independently selected substituents; or Ra and Rb, taken together with the carbon atom to which they are bonded, form a 3-membered cycloalkyl;

Rc is hydrogen, fluoro, or ($C_1$-$C_6$)alkyl, wherein the ($C_1$-$C_6$) alkyl is optionally substituted with one or more independently selected substituents;

Rd is hydrogen, fluoro, or ($C_1$-$C_6$)alkyl, wherein the ($C_1$-$C_6$) alkyl is optionally substituted with one or more independently selected substituents; or Rc and Rd, taken together with the carbon atom to which they are bonded, form a 3-membered cycloalkyl;

n is 0, 1, or 2; and z is 0, 1, or 2;

wherein the optional substituents for A, R5, R6, R7, R6 and R7, R8, Ra, Rb, Rc, Rd, Ra and Rb, and Rc and Rd, are independently selected from the group consisting halogen, cyano, nitro, oxo, ($C_1$-$C_6$)alkyl, polyfluorinated ($C_1$-$C_6$)alkyl, C(O)NHaryl($C_1$-$C_6$)alkyl, C(O)heterocyclyl($C_1$-$C_6$)alkyl, amino($C_1$-$C_6$)alkyl, hydroxy ($C_1$-$C_6$)alkyl, ($C_3$-$C_7$)cycloalkyl($C_1$-$C_6$)alkyl, heterocyclyl($C_1$-$C_6$)alkyl, ($C_1$-$C_6$)alkylheterocyclyl ($C_1$-$C_6$)alkyl, di($C_1$-$C_6$)alkylaminoheterocyclyl($C_1$-$C_6$) alkyl, aryl($C_1$-$C_6$)alkyl, heteroaryl($C_1$-$C_6$)alkyl, ($C_2$-$C_6$)alkenyl, ($C_2$-$C_6$)alkynyl, C(NH)O($C_1$-$C_6$)alkyl, C(O)H, C(O)($C_1$-$C_6$)alkyl, C(O)NH$_2$, C(O)NH($C_1$-$C_6$) alkyl, C(O)N(($C_1$-$C_6$)alkyl)$_2$, CO)NHOH, C(O)NHheterocyclyl, C(O)NHaryl, C(O)NHheteroaryl, C(O)OH, C(O)O($C_1$-$C_6$)alkyl, C(O)O($C_3$-$C_7$)cycloalkyl, C(O)Oaryl, C(O)($C_1$-$C_7$)cycloalkyl, C(O)heterocyclyl, C(O)aryl, NH$_2$, NH($C_1$-$C_6$)alkyl, N(($C_1$-$C_6$)alkyl)$_2$, NHC(O)H, NHC(O)($C_1$-$C_6$)alkyl, NHC(O)NH$_2$, NHC(O)NH($C_1$-$C_6$)alkyl, NHC(O)O($C_1$-$C_6$)alkyl, NHC(O)O($C_1$-$C_6$)alkyl(heterocyclyl), NHC(O)($C_3$-$C_7$)cycloalkyl, NHC(O)heterocyclyl, NHC(O)aryl, NHS(O)$_2$($C_1$-$C_6$)alkyl, NHS(O)$_2$heterocyclyl, NHS(O)$_2$aryl, NHheterocyclyl, NHaryl, N(aryl)$_2$, OH, —OCH$_2$O—, O($C_1$-$C_6$)alkyl, (polyfluorinated) O($C_1$-$C_6$)alkyl, (aryl) O($C_1$-$C_6$)alkyl, O($C_1$-$C_6$)alkylideneamino, OC(O)($C_1$-$C_6$)alkyl, OC(O)heterocyclyl, OC(O)aryl, O($C_3$-$C_7$)cycloalkenyl, Oheterocyclyl, Oaryl, tri($C_1$-$C_6$)alkylsilyl, S($C_1$-$C_6$)alkyl, Saryl, S(O)$_2$($C_1$-$C_6$)alkyl, polyfluorinated S(O)$_2$($C_1$-$C_6$)alkyl, S(O)$_2$NH$_2$, S(O)$_2$NH($C_1$-$C_6$) alkyl, S(O)$_2$N(($C_1$-$C_6$)alkyl)$_2$, S(O)$_2$NHheterocyclyl, S(O)$_2$NHaryl, S(O)$_2$aryl, ($C_3$-$C_7$)cycloalkyl, heterocyclyl, polyfluorinated heterocyclyl, ($C_1$-$C_6$)alkylheterocyclyl, aryl, ($C_1$-$C_6$)alkylaryl, heteroaryl, and ($C_1$-$C_6$) alkylheteroaryl;

with provisos that:
(1) when W is C(O)OH, X is NHR8; and
(2) when W is NHR8, X is C(O)OH;
to yield a compound of formula (IIa):

(IIa)

[Structure: R1-HN attached to a bicyclic system with PG-N=N, R3, R3', R4, R4' substituents, and L-[(CRaRb)$_z$-A-(CRcRd)$_n$]$_y$-R5 chain]

wherein:
PG is CH$_2$OCH$_2$CH$_2$Si(CH$_3$)$_3$, COOR10, C(Ph)$_3$, or tetrahydropyranyl;
A is (C$_3$-C$_7$)cycloalkyl, heterocyclyl, aryl, or heteroaryl, wherein the (C$_3$-C$_7$)cycloalkyl, heterocyclyl, aryl, or heteroaryl is optionally substituted with one or more independently selected substituents;
L is —C(O)NR8- or —NR8C(O)—;
R1 is hydrogen, or (C$_1$-C$_6$)alkyl;
R2 is hydrogen;
R3 is hydrogen or (C$_1$-C$_6$)alkyl;
R4 is hydrogen or (C$_1$-C$_6$)alkyl;
R3' is hydrogen or (C$_1$-C$_6$)alkyl;
R4' is hydrogen or (C$_1$-C$_6$)alkyl;
R5 is C(O)R6, C(O)NR6R7, C(O)OR6, NR6R7, NR7C(O)R6, NR7C(O)NR6R7, NR7C(O)OR9, or OR6;
R6 is hydrogen, (C$_1$-C$_6$)alkyl, aryl(C$_1$-C$_6$)alkyl, heteroaryl(C$_1$-C$_6$)alkyl, (C$_3$-C$_7$)cycloalkyl, heterocyclyl, aryl, or heteroaryl, wherein the (C$_1$-C$_6$)alkyl, aryl(C$_1$-C$_6$)alkyl, heteroaryl(C$_1$-C$_6$)alkyl, (C$_3$-C$_7$)cycloalkyl, heterocyclyl, aryl, or heteroaryl is optionally substituted with one or more independently selected substituents;
each R7 is independently hydrogen, (C$_1$-C$_6$)alkyl, aryl(C$_1$-C$_6$)alkyl, heteroaryl(C$_1$-C$_6$)alkyl, (C$_3$-C$_7$)cycloalkyl, heterocyclyl, aryl, or heteroaryl, wherein each (C$_1$-C$_6$)alkyl, aryl(C$_1$-C$_6$)alkyl, heteroaryl(C$_1$-C$_6$)alkyl, (C$_3$-C$_7$)cycloalkyl, heterocyclyl, aryl, and heteroaryl is optionally and independently substituted with one or more independently selected substituents; or
R6 and R7, taken together with the nitrogen atom to which they are bonded, form a 5- or 6-membered heterocyclyl, wherein the 5- or 6-membered heterocyclyl optionally contains one additional heteroatom selected from the group consisting of nitrogen, oxygen, and sulfur, and further wherein the 5- or 6-membered heterocyclyl is optionally substituted with one or more independently selected substituents;
R8 is hydrogen or (C$_1$-C$_6$)alkyl, wherein the (C$_1$-C$_6$) alkyl is optionally substituted with one or more independently selected substituents;
R9 is (C$_1$-C$_6$)alkyl, aryl(C$_1$-C$_6$)alkyl, heteroaryl(C$_1$-C$_6$) alkyl, (C$_3$-C$_7$)cycloalkyl, heterocyclyl, aryl, or heteroaryl, wherein the (C$_1$-C$_6$)alkyl, aryl(C$_1$-C$_6$)alkyl, heteroaryl(C$_1$-C$_6$) alkyl, (C$_3$-C$_7$)cycloalkyl, heterocyclyl, aryl, or heteroaryl is optionally substituted with one or more independently selected substituents;
R10 is (C$_1$-C$_6$)alkyl or aryl(C$_1$-C$_6$)alkyl;
Ra is hydrogen, fluoro, or (C$_1$-C$_6$)alkyl, wherein the (C$_1$-C$_6$) alkyl is optionally substituted with one or more independently selected substituents;
Rb is hydrogen, fluoro, or (C$_1$-C$_6$)alkyl, wherein the (C$_1$-C$_6$) alkyl is optionally substituted with one or more independently selected substituents; or
Ra and Rb, taken together with the carbon atom to which they are bonded, form a 3-membered cycloalkyl;
Rc is hydrogen, fluoro, or (C$_1$-C$_6$)alkyl, wherein the (C$_1$-C$_6$) alkyl is optionally substituted with one or more independently selected substituents;
Rd is hydrogen, fluoro, or (C$_1$-C$_6$)alkyl, wherein the (C$_1$-C$_6$) alkyl is optionally substituted with one or more independently selected substituents; or
Rc and Rd, taken together with the carbon atom to which they are bonded, form a 3-membered cycloalkyl;
y is 1;
n is 0, 1, or 2; and
z is 0, 1, or 2;
wherein the optional substituents for A, R5, R6, R7, R6 and R7, R8, R9, Ra, Rb, Rc, Rd, Ra and Rb, and Rc and Rd, are independently selected from the group consisting halogen, cyano, nitro, oxo, (C$_1$-C$_6$)alkyl, polyfluorinated (C$_1$-C$_6$)alkyl, C(O)NHaryl(C$_1$-C$_6$)alkyl, C(O)heterocyclyl(C$_1$-C$_6$)alkyl, amino(C$_1$-C$_6$)alkyl, hydroxy (C$_1$-C$_6$)alkyl, (C$_3$-C$_7$)cycloalkyl(C$_1$-C$_6$)alkyl, heterocyclyl(C$_1$-C$_6$)alkyl, (C$_1$-C$_6$)alkylheterocyclyl (C$_1$-C$_6$)alkyl, di(C$_1$-C$_6$)alkylaminoheterocyclyl(C$_1$-C$_6$) alkyl, aryl(C$_1$-C$_6$)alkyl, heteroaryl(C$_1$-C$_6$)alkyl, (C$_2$-C$_6$)alkenyl, (C$_2$-C$_6$)alkynyl, C(NH)O(C$_1$-C$_6$)alkyl, C(O)H, C(O)(C$_1$-C$_6$)alkyl, C(O)NH$_2$, C(O)NH(C$_1$-C$_6$) alkyl, C(O)N((C$_1$-C$_6$)alkyl)$_2$, CO)NHOH, C(O)NHheterocyclyl, C(O)NHaryl, C(O)NHheteroaryl, C(O)OH, C(O)O(C$_1$-C$_6$)alkyl, C(O)O(C$_3$-C$_7$)cycloalkyl, C(O) Oaryl, C(O)(C$_3$-C$_7$)cycloalkyl, C(O)heterocyclyl, C(O)aryl, NH$_2$, NH(C$_1$-C$_6$)alkyl, N((C$_1$-C$_6$)alkyl)$_2$, NHC(O)H, NHC(O)(C$_1$-C$_6$)alkyl, NHC(O)NH$_2$, NHC(O)NH(C$_1$-C$_6$)alkyl, NHC(O)O(C$_1$-C$_6$)alkyl, NHC(O) O(C$_1$-C$_6$)alkyl(heterocyclyl), NHC(O)(C$_3$-C$_7$)cycloalkyl, NHC(O)heterocyclyl, NHC(O)aryl, NHS(O)$_2$(C$_1$-C$_6$)alkyl, NHS(O)$_2$heterocyclyl, NHS(O)$_2$aryl, NHheterocyclyl, NHaryl, N(aryl)$_2$, OH, —OCH$_2$O—, O(C$_1$-C$_6$)alkyl, (polyfluorinated) O(C$_1$-C$_6$)alkyl, (aryl) O(C$_1$-C$_6$)alkyl, O(C$_1$-C$_6$)alkylideneamino, OC(O)(C$_1$-C$_6$)alkyl, OC(O)heterocyclyl, OC(O)aryl, O(C$_3$-C$_7$)cycloalkenyl, Oheterocyclyl, Oaryl, tri(C$_1$-C$_6$)alkylsilyl, S(C$_1$-C$_6$)alkyl, Saryl, S(O)$_2$(C$_1$-C$_6$)alkyl, polyfluorinated S(O)$_2$(C$_1$-C$_6$)alkyl, S(O)$_2$NH$_2$, S(O)$_2$NH(C$_1$-C$_6$) alkyl, S(O)$_2$N((C$_1$-C$_6$)alkyl)$_2$, S(O)$_2$NHheterocyclyl, S(O)$_2$NHaryl, S(O)$_2$aryl, (C$_3$-C$_7$)cycloalkyl, heterocyclyl, polyfluorinated heterocyclyl, (C$_1$-C$_6$)alkylheterocyclyl, aryl, (C$_1$-C$_6$)alkylaryl, heteroaryl, and (C$_1$-C$_6$) alkylheteroaryl;
with proviso that R3, R4, R3', and R4' are not simultaneously hydrogen; and
b) deprotecting the compound of formula (IIa) above, to yield the compound of formula (Ib) above.

21. A process for preparing a compound according to claim 1, wherein the compound is of formula (Ic):

(Ic)

[Structure: R1-HN attached to bicyclic system with R2, R3, R3', R4, R4' substituents, and L-[(CRaRb)$_z$-A-(CRcRd)$_n$]$_y$-R5 chain]

wherein:

L is C(O)NR6aR7a or NR8C(O)R6a;

R1 is hydrogen, or $(C_1-C_6)$alkyl;

R2 is hydrogen, $(C_1-C_6)$alkyl, $(C_2-C_6)$alkenyl, $(C_2-C_6)$alkynyl, $(C_3-C_7)$cycloalkyl, or heterocyclyl, wherein the $(C_1-C_6)$alkyl, $(C_2-C_6)$alkenyl, $(C_2-C_6)$ alkynyl, $(C_3-C_7)$cycloalkyl, or heterocyclyl is optionally substituted with one or more independently selected substituents;

R3 is hydrogen or $(C_1-C_6)$alkyl;

R4 is hydrogen or $(C_1-C_6)$alkyl;

R3' is hydrogen or $(C_1-C_6)$alkyl;

R4' is hydrogen or $(C_1-C_6)$alkyl;

R6a is hydrogen, $(C_1-C_6)$alkyl, aryl$(C_1-C_6)$alkyl, heteroaryl$(C_1-C_6)$alkyl, $(C_3-C_7)$cycloalkyl, heterocyclyl, aryl, or heteroaryl, wherein the $(C_1-C_6)$alkyl, aryl$(C_1-C_6)$alkyl, heteroaryl$(C_1-C_6)$alkyl, $(C_3-C_7)$cycloalkyl, heterocyclyl, aryl, or heteroaryl is optionally substituted with one or more independently selected substituents;

R7a is hydrogen, $(C_1-C_6)$alkyl, aryl$(C_1-C_6)$alkyl, heteroaryl$(C_1-C_6)$alkyl, $(C_3-C_7)$cycloalkyl, heterocyclyl, aryl, or heteroaryl, wherein the $(C_1-C_6)$alkyl, aryl$(C_1-C_6)$alkyl, heteroaryl$(C_1-C_6)$alkyl, $(C_3-C_7)$cycloalkyl, heterocyclyl, aryl, or heteroaryl is optionally substituted with one or more independently selected substituents; or R6a and R7a, taken together with the nitrogen atom to which they are bonded, form a 5- or 6-membered heterocyclyl, wherein the 5- or 6-membered heterocyclyl optionally contains one additional heteroatom selected from the group consisting of nitrogen, oxygen, and sulfur, and further wherein the 5- or 6-membered heterocyclyl is optionally substituted with one or more independently selected substituents;

R8 is hydrogen or $(C_1-C_6)$alkyl, wherein the $(C_1-C_6)$ alkyl is optionally substituted with one or more independently selected substituents;

y is 0;

wherein the optional substituents for R6a, R7a, R6a and R7a, R8, are independently selected from the group consisting halogen, cyano, nitro, oxo, $(C_1-C_6)$alkyl, polyfluorinated $(C_1-C_6)$alkyl, C(O)NHaryl$(C_2-C_6)$alkyl, C(O)heterocyclyl$(C_1-C_6)$alkyl, amino$(C_2-C_6)$alkyl, hydroxy$(C_2-C_6)$alkyl, $(C_3-C_7)$cycloalkyl$(C_1-C_6)$ alkyl, heterocyclyl$(C_2-C_6)$alkyl, $(C_1-C_6)$ alkylheterocyclyl$(C_2-C_6)$alkyl, di$(C_1-C_6)$ alkylaminoheterocyclyl$(C_2-C_6)$alkyl, aryl$(C_2-C_6)$alkyl, heteroaryl$(C_2-C_6)$alkyl, $(C_2-C_6)$alkenyl, $(C_2-C_6)$alkynyl, C(NH)O$(C_2-C_6)$alkyl, C(O)H, C(O)$(C_1-C_6)$alkyl, C(O)NH$_2$, C(O)NH$(C_2-C_6)$alkyl, C(O)N$((C_2-C_6)$ alkyl$)_2$, CO)NHOH, C(O)NHheterocyclyl, C(O) NHaryl, C(O)NHheteroaryl, C(O)OH, C(O)O$(C_1-C_6)$ alkyl, C(O)O$(C_1-C_7)$cycloalkyl, C(O)Oaryl, C(O)$(C_3-C_7)$cycloalkyl, C(O)heterocyclyl, C(O)aryl, NH$_2$, NH$(C_1-C_6)$alkyl, N$((C_2-C_6)$alkyl$)_2$, NHC(O)H, NHC (O)$(C_2-C_6)$alkyl, NHC(O)NH$_2$, NHC(O)NH$(C_1-C_6)$alkyl, NHC(O)O$(C_1-C_6)$alkyl, NHC(O)O$(C_1-C_6)$alkyl (heterocyclyl), NHC(O)$(C_3-C_7)$cycloalkyl, NHC(O) heterocyclyl, NHC(O)aryl, NHS(O)$_2(C_1-C_6)$alkyl, NHS(O)$_2$heterocyclyl, NHS(O)$_2$aryl, NHheterocyclyl, NHaryl, N(aryl)$_2$, OH, —OCH$_2$O—, O$(C_2-C_6)$alkyl, (polyfluorinated) O$(C_2-C_6)$alkyl, (aryl) O$(C_2-C_6)$alkyl, O$(C_2-C_6)$alkylideneamino, OC(O)$(C_2-C_6)$alkyl, OC(O)heterocyclyl, OC(O)aryl, O$(C_3-C_7)$cycloalkenyl, Oheterocyclyl, Oaryl, tri$(C_1-C_6)$alkylsilyl, S$(C_1-C_6)$alkyl, Saryl, S(O)$_2(C_1-C_6)$alkyl, polyfluorinated S(O)$_2(C_2-C_6)$alkyl, S(O)$_2$NH$_2$, S(O)$_2$NH$(C_2-C_6)$alkyl, S(O)$_2$N$((C_2-C_6)$alkyl$)_2$, S(O)$_2$NHheterocyclyl, S(O)$_2$ NHaryl, S(O)$_2$aryl, $(C_3-C_7)$cycloalkyl, heterocyclyl, polyfluorinated heterocyclyl, $(C_1-C_6)$alkylheterocyclyl, aryl, $(C_1-C_6)$alkylaryl, heteroaryl, and $(C_1-C_6)$ alkylheteroaryl;

with provisos that:

(1) R3, R4, R3', and R4' are not simultaneously hydrogen; and (2) the following compounds of formula (Ic) are excluded:

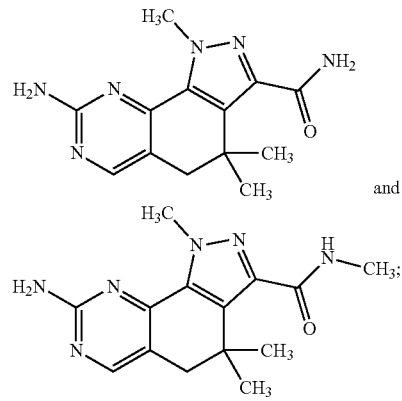

and wherein the process comprises the following step of SEQUENCE C:

reacting a compound of formula (V):

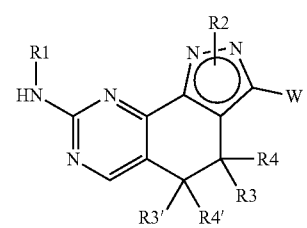

(V)

wherein:

W is C(O)OH or NHR8;

R1 is hydrogen, or $(C_1-C_6)$alkyl;

R2 is hydrogen, $(C_1-C_6)$alkyl, $(C_2-C_6)$alkenyl, $(C_2-C_6)$ alkynyl, $(C_3-C_7)$cycloalkyl, or heterocyclyl, wherein the $(C_1-C_6)$alkyl, $(C_2-C_6)$alkenyl, $(C_2-C_6)$ alkynyl, $(C_3-C_7)$cycloalkyl, or heterocyclyl is optionally substituted with one or more independently selected substituents;

R3 is hydrogen or $(C_1-C_6)$alkyl;

R4 is hydrogen or $(C_1-C_6)$alkyl;

R3' is hydrogen or $(C_1-C_6)$alkyl;

R4' is hydrogen or $(C_1-C_6)$alkyl; and

R8 is hydrogen or $(C_1-C_6)$alkyl, wherein the $(C_1-C_6)$ alkyl is optionally substituted with one or more independently selected substituents;

wherein the optional substituents for R2, and R8 are independently selected from the group consisting halogen, cyano, nitro, oxo, $(C_1-C_6)$alkyl, polyfluorinated $(C_1-C_6)$alkyl, C(O)NHaryl$(C_1-C_6)$alkyl, C(O)heterocyclyl$(C_1-C_6)$alkyl, amino$(C_1-C_6)$alkyl, hydroxy$(C_1-C_6)$ alkyl, $(C_3-C_7)$cycloalkyl$(C_1-C_6)$alkyl, heterocyclyl$(C_1-C_6)$alkyl, $(C_1-C_6)$alkylheterocyclyl$(C_1-C_6)$alkyl, di$(C_1-C_6)$alkylaminoheterocyclyl$(C_1-C_6)$alkyl, aryl$(C_1-C_6)$alkyl, heteroaryl$(C_1-C_6)$alkyl, $(C_2-C_6)$alkenyl, $(C_2-C_6)$ alkynyl, C(NH)O(C$_1$-C$_6$)alkyl, C(O)H, C(O)(C$_1$-C$_6$)alkyl, C(O)NH$_2$, C(O)NH(C$_1$-C$_6$)alkyl, C(O)N((C$_1$-C$_6$)alkyl)$_2$, CO)NHOH, C(O)NHheterocyclyl, C(O)NHaryl, C(O)NHheteroaryl, C(O)OH, C(O)O(C$_1$-C$_6$)alkyl, C(O)O(C$_3$-C$_7$)cycloalkyl, C(O)Oaryl, C(O)(C$_3$-C$_7$)cycloalkyl, C(O)heterocyclyl, C(O)aryl, NH$_2$, NH(C$_1$-C$_6$)alkyl, N((C$_1$-C$_6$)alkyl)$_2$, NHC(O)H, NHC(O)(C$_1$-C$_6$)alkyl, NHC(O)NH$_2$, NHC(O)NH(C$_1$-C$_6$)alkyl, NHC(O)O(C$_1$-C$_6$)alkyl, NHC(O)O(C$_1$-C$_6$)alkyl (heterocyclyl), NHC(O)(C$_3$-C$_7$)cycloalkyl, NHC(O)heterocyclyl, NHC(O)aryl, NHS(O)$_2$(C$_1$-C$_6$)alkyl, NHS(O)$_2$heterocyclyl, NHS(O)$_2$aryl, NHheterocyclyl, NHaryl, N(aryl)$_2$, OH, —OCH$_2$O—, O(C$_1$-C$_6$)alkyl, (polyfluorinated) O(C$_1$-C$_6$)alkyl, (aryl) O(C$_1$-C$_6$)alkyl, O(C$_1$-C$_6$)alkylideneamino, OC(O)(C$_1$-C$_6$)alkyl, OC(O)heterocyclyl, OC(O)aryl, O(C$_3$-C$_7$)cycloalkenyl, Oheterocyclyl, Oaryl, tri(C$_1$-C$_6$)alkylsilyl, S(C$_1$-C$_6$)alkyl, Saryl, S(O)$_2$(C$_1$-C$_6$)alkyl, polyfluorinated S(O)$_2$(C$_1$-C$_6$)alkyl, S(O)$_2$NH$_2$, S(O)$_2$NH(C$_1$-C$_6$)alkyl, S(O)$_2$N((C$_1$-C$_6$)alkyl)$_2$, S(O)$_2$NHheterocyclyl, S(O)$_2$NHaryl, S(O)$_2$aryl, (C$_3$-C$_7$)cycloalkyl, heterocyclyl, polyfluorinated heterocyclyl, (C$_1$-C$_6$)alkylheterocyclyl, aryl, (C$_1$-C$_6$)alkylaryl, heteroaryl, and (C$_1$-C$_6$)alkylheteroaryl;
with proviso that R3, R4, R3', and R4' are not simultaneously hydrogen;
with a compound of formula (VII) or formula (VIII):

HNR6aR7a (VII) or

R6aC(O)OH (VIII)

wherein:
R6a is hydrogen, (C$_1$-C$_6$)alkyl, aryl(C$_1$-C$_6$)alkyl, heteroaryl(C$_1$-C$_6$)alkyl, (C$_3$-C$_7$)cycloalkyl, heterocyclyl, aryl, or heteroaryl, wherein the (C$_1$-C$_6$)alkyl, aryl(C$_1$-C$_6$)alkyl, heteroaryl(C$_1$-C$_6$)alkyl, (C$_3$-C$_7$)cycloalkyl, heterocyclyl, aryl, or heteroaryl is optionally substituted with one or more independently selected substituents; and
R7a is hydrogen, (C$_1$-C$_6$)alkyl, aryl(C$_1$-C$_6$)alkyl, heteroaryl(C$_1$-C$_6$)alkyl, (C$_3$-C$_7$)cycloalkyl, heterocyclyl, aryl, or heteroaryl, wherein the (C$_1$-C$_6$)alkyl, aryl(C$_1$-C$_6$)alkyl, heteroaryl(C$_1$-C$_6$)alkyl, (C$_3$-C$_7$)cycloalkyl, heterocyclyl, aryl, or heteroaryl is optionally substituted with one or more independently selected substituents; or
R6a and R7a, taken together with the nitrogen atom to which they are bonded, form a 5- or 6-membered heterocyclyl, wherein the 5- or 6-membered heterocyclyl optionally contains one additional heteroatom selected from the group consisting of nitrogen, oxygen, and sulfur, and further wherein the 5- or 6-membered heterocyclyl is optionally substituted with one or more independently selected substituents;
wherein the optional substituents for R6a, R7a, and R6a and R7a, are independently selected from the group consisting halogen, cyano, nitro, oxo, (C$_1$-C$_6$)alkyl, polyfluorinated (C$_1$-C$_6$)alkyl, C(O)NHaryl(C$_1$-C$_6$)alkyl, C(O)heterocyclyl(C$_1$-C$_6$)alkyl, amino(C$_1$-C$_6$)alkyl, hydroxy(C$_1$-C$_6$)alkyl, (C$_3$-C$_7$)cycloalkyl(C$_1$-C$_6$)alkyl, heterocyclyl(C$_1$-C$_6$)alkyl, (C$_1$-C$_6$)alkylheterocyclyl(C$_1$-C$_6$)alkyl, di(C$_1$-C$_6$)alkylaminoheterocyclyl(C$_1$-C$_6$)alkyl, aryl(C$_1$-C$_6$)alkyl, heteroaryl(C$_1$-C$_6$)alkyl, (C$_2$-C$_6$)alkenyl, (C$_2$-C$_6$)alkynyl, C(NH)O(C$_1$-C$_6$)alkyl, C(O)H, C(O)(C$_1$-C$_6$)alkyl, C(O)NH$_2$, C(O)NH(C$_1$-C$_6$)alkyl, C(O)N((C$_1$-C$_6$)alkyl)$_2$, CO)NHOH, C(O)NHheterocyclyl, C(O)NHaryl, C(O)NHheteroaryl, C(O)OH, C(O)O(C$_1$-C$_6$)alkyl, C(O)O(C$_3$-C$_7$)cycloalkyl, C(O)Oaryl, C(O)(C$_3$-C$_7$)cycloalkyl, C(O)heterocyclyl, C(O)aryl, NH$_2$, NH(C$_1$-C$_6$)alkyl, N((C$_1$-C$_6$)alkyl)$_2$, NHC(O)H, NHC(O)(C$_1$-C$_6$)alkyl, NHC(O)NH$_2$, NHC(O)NH(C$_1$-C$_6$)alkyl, NHC(O)O(C$_1$-C$_6$)alkyl, NHC(O)O(C$_1$-C$_6$)alkyl (heterocyclyl), NHC(O)(C$_3$-C$_7$)cycloalkyl, NHC(O)heterocyclyl, NHC(O)aryl, NHS(O)$_2$(C$_1$-C$_6$)alkyl, NHS(O)$_2$heterocyclyl, NHS(O)$_2$aryl, NHheterocyclyl, NHaryl, N(aryl)$_2$, OH, —OCH$_2$O—, O(C$_1$-C$_6$)alkyl, (polyfluorinated) O(C$_1$-C$_6$)alkyl, (aryl) O(C$_1$-C$_6$)alkyl, O(C$_1$-C$_6$)alkylideneamino, OC(O)(C$_1$-C$_6$)alkyl, OC(O)heterocyclyl, OC(O)aryl, O(C$_3$-C$_7$)cycloalkenyl, Oheterocyclyl, Oaryl, tri(C$_1$-C$_6$)alkylsilyl, S(C$_1$-C$_6$)alkyl, Saryl, S(O)$_2$(C$_1$-C$_6$)alkyl, polyfluorinated S(O)$_2$(C$_1$-C$_6$)alkyl, S(O)$_2$NH$_2$, S(O)$_2$NH(C$_1$-C$_6$)alkyl, S(O)$_2$N((C$_1$-C$_6$)alkyl)$_2$, S(O)$_2$NHheterocyclyl, S(O)$_2$NHaryl, S(O)$_2$aryl, (C$_3$-C$_7$)cycloalkyl, heterocyclyl, polyfluorinated heterocyclyl, (C$_1$-C$_6$)alkylheterocyclyl, aryl, (C$_1$-C$_6$)alkylaryl, heteroaryl, and (C$_1$-C$_6$)alkylheteroaryl;
with provisos that:
(1) when W is C(O)OH, the compound of formula (V) is reacted with a compound of formula (VII); and
(2) when W is NHR8, the compound of formula (V) is reacted with a compound of formula (VIII);
to yield the compound of formula (Ic) above.

22. A process for preparing a compound according to claim 1, wherein the compound is of formula (Id):

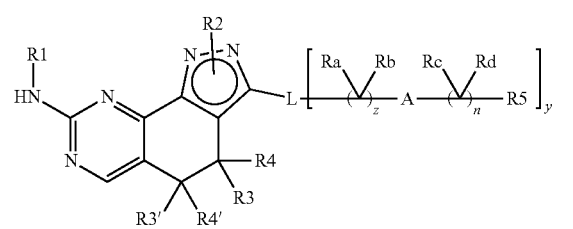

(Id)

wherein:
L is C(O)NR6aR7a or NR8C(O)R6a;
R1 is hydrogen, or (C$_1$-C$_6$)alkyl;
R2 is hydrogen;
R3 is hydrogen or (C$_1$-C$_6$)alkyl;
R4 is hydrogen or (C$_1$-C$_6$)alkyl;
R3' is hydrogen or (C$_1$-C$_6$)alkyl;
R4' is hydrogen or (C$_1$-C$_6$)alkyl;
R6a is hydrogen, (C$_1$-C$_6$)alkyl, aryl(C$_1$-C$_6$)alkyl, heteroaryl(C$_1$-C$_6$)alkyl, (C$_3$-C$_7$)cycloalkyl, heterocyclyl, aryl, or heteroaryl, wherein the (C$_1$-C$_6$)alkyl, aryl(C$_1$-C$_6$)alkyl, heteroaryl(C$_1$-C$_6$)alkyl, (C$_3$-C$_7$)cycloalkyl, heterocyclyl, aryl, or heteroaryl is optionally substituted with one or more independently selected substituents;
R7a is hydrogen, (C$_1$-C$_6$)alkyl, aryl(C$_1$-C$_6$)alkyl, heteroaryl(C$_1$-C$_6$)alkyl, (C$_3$-C$_7$)cycloalkyl, heterocyclyl, aryl, or heteroaryl, wherein the (C$_1$-C$_6$)alkyl, aryl(C$_1$-C$_6$)alkyl, heteroaryl(C$_1$-C$_6$)alkyl, (C$_3$-C$_7$)cycloalkyl, heterocyclyl, aryl, or heteroaryl is optionally substituted with one or more independently selected substituents; or
R6a and R7a, taken together with the nitrogen atom to which they are bonded, form a 5- or 6-membered heterocyclyl, wherein the 5- or 6-membered heterocyclyl optionally contains one additional heteroatom selected from the group consisting of nitrogen, oxygen, and sulfur, and further wherein the 5- or 6-membered heterocyclyl is optionally substituted with one or more independently selected substituents;

R8 is hydrogen or $(C_1-C_6)$alkyl, wherein the $(C_1-C_6)$ alkyl is optionally substituted with one or more independently selected substituents;

y is 0;

wherein the optional substituents for R6a, R7a, R6a and R7a, R8, are independently selected from the group consisting halogen, cyano, nitro, oxo, $(C_1-C_6)$alkyl, polyfluorinated $(C_1-C_6)$alkyl, C(O)NHaryl$(C_1-C_6)$alkyl, C(O)heterocyclyl$(C_1-C_6)$alkyl, amino$(C_1-C_6)$alkyl, hydroxy$(C_1-C_6)$alkyl, $(C_3-C_7)$cycloalkyl$(C_1-C_6)$alkyl, heterocyclyl$(C_1-C_6)$alkyl, $(C_1-C_6)$alkylheterocyclyl$(C_1-C_6)$alkyl, di$(C_1-C_6)$alkylaminoheterocyclyl$(C_1-C_6)$alkyl, aryl$(C_1-C_6)$alkyl, heteroaryl$(C_1-C_6)$alkyl, $(C_2-C_6)$alkenyl, $(C_2-C_6)$alkynyl, C(NH)O$(C_1-C_6)$alkyl, C(O)H, C(O)$(C_1-C_6)$alkyl, C(O)NH$_2$, C(O)NH$(C_1-C_6)$alkyl, C(O)N$((C_1-C_6)$alkyl$)_2$, CO)NHOH, C(O)NHheterocyclyl, C(O)NHaryl, C(O)NHheteroaryl, C(O)OH, C(O)O$(C_1-C_6)$alkyl, C(O)O$(C_3-C_7)$cycloalkyl, C(O)Oaryl, C(O)$(C_3-C_7)$cycloalkyl, C(O)heterocyclyl, C(O)aryl, NH$_2$, NH$(C_1-C_6)$alkyl, N$((C_1-C_6)$alkyl$)_2$, NHC(O)H, NHC(O)$(C_1-C_6)$alkyl, NHC(O)NH$_2$, NHC(O)NH$(C_1-C_6)$alkyl, NHC(O)O$(C_1-C_6)$alkyl, NHC(O)O$(C_1-C_6)$alkyl(heterocyclyl), NHC(O)$(C_3-C_7)$cycloalkyl, NHC(O)heterocyclyl, NHC(O)aryl, NHS(O)$_2(C_1-C_6)$alkyl, NHS(O)$_2$heterocyclyl, NHS(O)$_2$aryl, NHheterocyclyl, NHaryl, N(aryl)$_2$, OH, —OCH$_2$O—, O$(C_1-C_6)$alkyl, (polyfluorinated) O$(C_1-C_6)$alkyl, (aryl) O$(C_1-C_6)$alkyl, O$(C_1-C_6)$alkylideneamino, OC(O)$(C_1-C_6)$alkyl, OC(O)heterocyclyl, OC(O)aryl, O$(C_3-C_7)$cycloalkenyl, Oheterocyclyl, Oaryl, tri$(C_1-C_6)$alkylsilyl, S$(C_1-C_6)$alkyl, Saryl, S(O)$_2(C_1-C_6)$alkyl, polyfluorinated S(O)$_2(C_1-C_6)$alkyl, S(O)$_2$NH$_2$, S(O)$_2$NH$(C_1-C_6)$alkyl, S(O)$_2$N$((C_1-C_6)$alkyl$)_2$, S(O)$_2$NHheterocyclyl, S(O)$_2$NHaryl, S(O)$_2$aryl, $(C_3-C_7)$cycloalkyl, heterocyclyl, polyfluorinated heterocyclyl, $(C_1-C_6)$alkylheterocyclyl, aryl, $(C_1-C_6)$alkylaryl, heteroaryl, and $(C_1-C_6)$alkylheteroaryl;

with proviso that R3, R4, R3', and R4' are not simultaneously hydrogen;

wherein the process comprises the following steps of SEQUENCE D:

a) reacting a compound of formula (III):

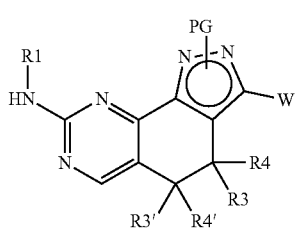

(III)

wherein:

PG is CH$_2$OCH$_2$CH$_2$Si(CH$_3$)$_3$, COOR10, C(Ph)$_3$, or tetrahydropyranyl;

W is C(O)OH or NHR8;

R1 is hydrogen, or $(C_1-C_6)$alkyl;

R3 is hydrogen or $(C_1-C_6)$alkyl;

R4 is hydrogen or $(C_1-C_6)$alkyl;

R3' is hydrogen or $(C_1-C_6)$alkyl;

R4' is hydrogen or $(C_1-C_6)$alkyl;

R8 is hydrogen or $(C_1-C_6)$alkyl, wherein the $(C_1-C_6)$ alkyl is optionally substituted with one or more independently selected substituents; and R10 is $(C_1-C_6)$alkyl or aryl$(C_1-C_6)$alkyl;

wherein the optional substituents for R2, and R8 are independently selected from the group consisting halogen, cyano, nitro, oxo, $(C_1-C_6)$alkyl, polyfluorinated $(C_1-C_6)$alkyl, C(O)NHaryl$(C_1-C_6)$alkyl, C(O)heterocyclyl$(C_1-C_6)$alkyl, amino$(C_1-C_6)$alkyl, hydroxy$(C_1-C_6)$alkyl, $(C_3-C_7)$cycloalkyl$(C_1-C_6)$alkyl, heterocyclyl$(C_1-C_6)$alkyl, $(C_1-C_6)$alkylheterocyclyl$(C_1-C_6)$alkyl, di$(C_1-C_6)$alkylaminoheterocyclyl$(C_1-C_6)$alkyl, aryl$(C_1-C_6)$alkyl, heteroaryl$(C_1-C_6)$alkyl, $(C_2-C_6)$alkenyl, $(C_2-C_6)$alkynyl, C(NH)O$(C_1-C_6)$alkyl, C(O)H, C(O)$(C_1-C_6)$alkyl, C(O)NH$_2$, C(O)NH$(C_1-C_6)$alkyl, C(O)N$((C_1-C_6)$alkyl$)_2$, CO)NHOH, C(O)NHheterocyclyl, C(O)NHaryl, C(O)NHheteroaryl, C(O)OH, C(O)O$(C_1-C_6)$alkyl, C(O)O$(C_3-C_7)$cycloalkyl, C(O)Oaryl, C(O)$(C_3-C_7)$cycloalkyl, C(O)heterocyclyl, C(O)aryl, NH$_2$, NH$(C_1-C_6)$alkyl, N$((C_1-C_6)$alkyl$)_2$, NHC(O)H, NHC(O)$(C_1-C_6)$alkyl, NHC(O)NH$_2$, NHC(O)NH$(C_1-C_6)$alkyl, NHC(O)O$(C_1-C_6)$alkyl, NHC(O)O$(C_1-C_6)$alkyl(heterocyclyl), NHC(O)$(C_3-C_7)$cycloalkyl, NHC(O)heterocyclyl, NHC(O)aryl, NHS(O)$_2(C_1-C_6)$alkyl, NHS(O)$_2$heterocyclyl, NHS(O)$_2$aryl, NHheterocyclyl, NHaryl, N(aryl)$_2$, OH, —OCH$_2$O—, O$(C_1-C_6)$alkyl, (polyfluorinated) O$(C_1-C_6)$alkyl, (aryl) O$(C_1-C_6)$alkyl, O$(C_1-C_6)$alkylideneamino, OC(O)$(C_1-C_6)$alkyl, OC(O)heterocyclyl, OC(O)aryl, O$(C_3-C_7)$cycloalkenyl, Oheterocyclyl, Oaryl, tri$(C_1-C_6)$alkylsilyl, S$(C_1-C_6)$alkyl, Saryl, S(O)$_2(C_1-C_6)$alkyl, polyfluorinated S(O)$_2(C_1-C_6)$alkyl, S(O)$_2$NH$_2$, S(O)$_2$NH$(C_1-C_6)$alkyl, S(O)$_2$N$((C_1-C_6)$alkyl$)_2$, S(O)$_2$NHheterocyclyl, S(O)$_2$NHaryl, S(O)$_2$aryl, $(C_3-C_7)$cycloalkyl, heterocyclyl, polyfluorinated heterocyclyl, $(C_1-C_6)$alkylheterocyclyl, aryl, $(C_1-C_6)$alkylaryl, heteroaryl, and $(C_1-C_6)$alkylheteroaryl;

with proviso that R3, R4, R3', and R4' are not simultaneously hydrogen;

with a compound of formula (VII) or formula (VIII):

HNR6aR7a (VII) or

R6aC(O)OH (VIII)

wherein:

R6a is hydrogen, $(C_1-C_6)$alkyl, aryl$(C_1-C_6)$alkyl, heteroaryl$(C_1-C_6)$alkyl, $(C_3-C_7)$cycloalkyl, heterocyclyl, aryl, or heteroaryl, wherein the $(C_1-C_6)$alkyl, aryl$(C_1-C_6)$alkyl, heteroaryl$(C_1-C_6)$alkyl, $(C_3-C_7)$cycloalkyl, heterocyclyl, aryl, or heteroaryl is optionally substituted with one or more independently selected substituents; and R7a is hydrogen, $(C_1-C_6)$alkyl, aryl$(C_1-C_6)$alkyl, heteroaryl$(C_1-C_6)$alkyl, $(C_3-C_7)$cycloalkyl, heterocyclyl, aryl, or heteroaryl, wherein the $(C_1-C_6)$alkyl, aryl$(C_1-C_6)$alkyl, heteroaryl$(C_1-C_6)$alkyl, $(C_3-C_7)$cycloalkyl, heterocyclyl, aryl, or heteroaryl is optionally substituted with one or more independently selected substituents; or R6a and R7a, taken together with the nitrogen atom to which they are bonded, form a 5- or 6-membered heterocyclyl, wherein the 5- or 6-membered heterocyclyl optionally contains one additional heteroatom selected from the group consisting of nitrogen, oxygen, and sulfur, and further wherein the 5- or 6-membered heterocyclyl is optionally substituted with one or more independently selected substituents;

wherein the optional substituents for R6a, R7a, and R6a and R7a, are independently selected from the group consisting halogen, cyano, nitro, oxo, $(C_1-C_6)$alkyl, polyfluorinated $(C_1-C_6)$alkyl, $C(O)NHaryl(C_1-C_6)$alkyl, $C(O)$heterocyclyl$(C_1-C_6)$alkyl, amino$(C_1-C_6)$alkyl, hydroxy$(C_1-C_6)$alkyl, $(C_3-C_7)$cycloalkyl$(C_1-C_6)$alkyl, heterocyclyl$(C_1-C_6)$alkyl, $(C_1-C_6)$alkylheterocyclyl$(C_1-C_6)$alkyl, di$(C_1-C_6)$alkylaminoheterocyclyl$(C_1-C_6)$alkyl, aryl$(C_1-C_6)$alkyl, heteroaryl$(C_1-C_6)$alkyl, $(C_2-C_6)$alkenyl, $(C_2-C_6)$alkynyl, $C(NH)O(C_1-C_6)$alkyl, $C(O)H$, $C(O)(C_1-C_6)$alkyl, $C(O)NH_2$, $C(O)NH(C_1-C_6)$alkyl, $C(O)N((C_1-C_6)$alkyl$)_2$, $CO)NHOH$, $C(O)NH$heterocyclyl, $C(O)NHaryl$, $C(O)NH$heteroaryl, $C(O)OH$, $C(O)O(C_1-C_6)$alkyl, $C(O)O(C_3-C_7)$cycloalkyl, $C(O)Oaryl$, $C(O)(C_3-C_7)$cycloalkyl, $C(O)$heterocyclyl, $C(O)$aryl, $NH_2$, $NH(C_1-C_6)$alkyl, $N((C_1-C_6)$alkyl$)_2$, $NHC(O)H$, $NHC(O)(C_1-C_6)$alkyl, $NHC(O)NH_2$, $NHC(O)NH(C_1-C_6)$alkyl, $NHC(O)O(C_1-C_6)$alkyl, $NHC(O)O(C_1-C_6)$alkyl(heterocyclyl), $NHC(O)(C_3-C_7)$cycloalkyl, $NHC(O)$heterocyclyl, $NHC(O)$aryl, $NHS(O)_2(C_1-C_6)$alkyl, $NHS(O)_2$heterocyclyl, $NHS(O)_2$aryl, $NH$heterocyclyl, $NHaryl$, $N(aryl)_2$, $OH$, $-OCH_2O-$, $O(C_1-C_6)$alkyl, (polyfluorinated) $O(C_1-C_6)$alkyl, (aryl) $O(C_1-C_6)$alkyl, $O(C_1-C_6)$alkylideneamino, $OC(O)(C_1-C_6)$alkyl, $OC(O)$heterocyclyl, $OC(O)$aryl, $O(C_3-C_7)$cycloalkenyl, $O$heterocyclyl, $O$aryl, tri$(C_1-C_6)$alkylsilyl, $S(C_1-C_6)$alkyl, $S$aryl, $S(O)_2(C_1-C_6)$alkyl, polyfluorinated $S(O)_2(C_1-C_6)$alkyl, $S(O)_2NH_2$, $S(O)_2NH(C_1-C_6)$alkyl, $S(O)_2N((C_1-C_6)$alkyl$)_2$, $S(O)_2NH$heterocyclyl, $S(O)_2NHaryl$, $S(O)_2aryl$, $(C_3-C_7)$cycloalkyl, heterocyclyl, polyfluorinated heterocyclyl, $(C_1-C_6)$alkylheterocyclyl, aryl, $(C_1-C_6)$alkylaryl, heteroaryl, and $(C_1-C_6)$alkylheteroaryl;

with provisos that:
(1) when W is C(O)OH, the compound of formula (III) is reacted with a compound of formula (VII); and
(2) when W is NHR8, the compound of formula (III) is reacted with a compound of formula (VIII);
to yield a compound of formula (Ib):

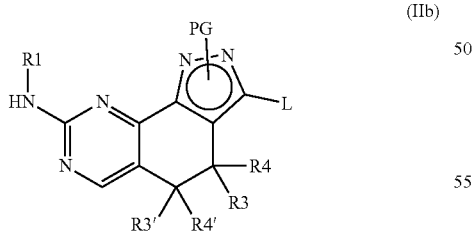

(IIb)

wherein:
PG is $CH_2OCH_2CH_2Si(CH_3)_3$, COOR10, $C(Ph)_3$, or tetrahydropyranyl;
L is $C(O)NR6aR7a$ or $NR8C(O)R6a$;
R1 is hydrogen, or $(C_1-C_6)$alkyl;
R3 is hydrogen or $(C_1-C_6)$alkyl;
R4 is hydrogen or $(C_1-C_6)$alkyl;
R3' is hydrogen or $(C_1-C_6)$alkyl;
R4' is hydrogen or $(C_1-C_6)$alkyl;

R6a is hydrogen, $(C_1-C_6)$alkyl, aryl$(C_1-C_6)$alkyl, heteroaryl$(C_1-C_6)$alkyl, $(C_3-C_7)$cycloalkyl, heterocyclyl, aryl, or heteroaryl, wherein the $(C_1-C_6)$alkyl, aryl$(C_1-C_6)$alkyl, heteroaryl$(C_1-C_6)$alkyl, $(C_3-C_7)$cycloalkyl, heterocyclyl, aryl, or heteroaryl is optionally substituted with one or more independently selected substituents;

R7a is hydrogen, $(C_1-C_6)$alkyl, aryl$(C_1-C_6)$alkyl, heteroaryl$(C_1-C_6)$alkyl, $(C_3-C_7)$cycloalkyl, heterocyclyl, aryl, or heteroaryl, wherein the $(C_1-C_6)$alkyl, aryl$(C_1-C_6)$alkyl, heteroaryl$(C_1-C_6)$alkyl, $(C_3-C_7)$cycloalkyl, heterocyclyl, aryl, or heteroaryl is optionally substituted with one or more independently selected substituents; or R6a and R7a, taken together with the nitrogen atom to which they are bonded, form a 5- or 6-membered heterocyclyl, wherein the 5- or 6-membered heterocyclyl optionally contains one additional heteroatom selected from the group consisting of nitrogen, oxygen, and sulfur, and further wherein the 5- or 6-membered heterocyclyl is optionally substituted with one or more independently selected substituents;

R8 is hydrogen or $(C_1-C_6)$alkyl, wherein the $(C_1-C_6)$ alkyl is optionally substituted with one or more independently selected substituents;

R10 is $(C_1-C_6)$alkyl or aryl$(C_1-C_6)$alkyl;

wherein the optional substituents for R6a, R7a, R6a and R7a, and R8 are independently selected from the group consisting halogen, cyano, nitro, oxo, $(C_1-C_6)$alkyl, polyfluorinated $(C_1-C_6)$alkyl, $C(O)NHaryl(C_1-C_6)$alkyl, $C(O)$heterocyclyl$(C_1-C_6)$alkyl, amino$(C_1-C_6)$alkyl, hydroxy$(C_1-C_6)$alkyl, $(C_3-C_7)$cycloalkyl$(C_1-C_6)$alkyl, heterocyclyl$(C_1-C_6)$alkyl, $(C_1-C_6)$alkylheterocyclyl$(C_1-C_6)$alkyl, di$(C_1-C_6)$alkylaminoheterocyclyl$(C_1-C_6)$alkyl, aryl$(C_1-C_6)$alkyl, heteroaryl$(C_1-C_6)$alkyl, $(C_2-C_6)$alkenyl, $(C_2-C_6)$alkynyl, $C(NH)O(C_1-C_6)$alkyl, $C(O)H$, $C(O)(C_1-C_6)$alkyl, $C(O)NH_2$, $C(O)NH(C_1-C_6)$alkyl, $C(O)N((C_1-C_6)$alkyl$)_2$, $CO)NHOH$, $C(O)NH$heterocyclyl, $C(O)NHaryl$, $C(O)NH$heteroaryl, $C(O)OH$, $C(O)O(C_1-C_6)$alkyl, $C(O)O(C_3-C_7)$cycloalkyl, $C(O)Oaryl$, $C(O)(C_3-C_7)$cycloalkyl, $C(O)$heterocyclyl, $C(O)$aryl, $NH_2$, $NH(C_1-C_6)$alkyl, $N((C_1-C_6)$alkyl$)_2$, $NHC(O)H$, $NHC(O)(C_1-C_6)$alkyl, $NHC(O)NH_2$, $NHC(O)NH(C_1-C_6)$alkyl, $NHC(O)O(C_1-C_6)$alkyl, $NHC(O)O(C_1-C_6)$alkyl (heterocyclyl), $NHC(O)(C_3-C_7)$cycloalkyl, $NHC(O)$heterocyclyl, $NHC(O)$aryl, $NHS(O)_2(C_1-C_6)$alkyl, $NHS(O)_2$heterocyclyl, $NHS(O)_2$aryl, $NH$heterocyclyl, $NHaryl$, $N(aryl)_2$, $OH$, $-OCH_2O-$, $O(C_1-C_6)$alkyl, (polyfluorinated) $O(C_1-C_6)$alkyl, (aryl) $O(C_1-C_6)$alkyl, $O(C_1-C_6)$alkylideneamino, $OC(O)(C_1-C_6)$alkyl, $OC(O)$heterocyclyl, $OC(O)$aryl, $O(C_3-C_7)$cycloalkenyl, $O$heterocyclyl, $O$aryl, tri$(C_1-C_6)$alkylsilyl, $S(C_1-C_6)$alkyl, $S$aryl, $S(O)_2(C_1-C_6)$alkyl, polyfluorinated $S(O)_2(C_1-C_6)$alkyl, $S(O)_2NH_2$, $S(O)_2NH(C_1-C_6)$alkyl, $S(O)_2N((C_1-C_6)$alkyl$)_2$, $S(O)_2NH$heterocyclyl, $S(O)_2NHaryl$, $S(O)_2aryl$, $(C_3-C_7)$cycloalkyl, heterocyclyl, polyfluorinated heterocyclyl, $(C_1-C_6)$alkylheterocyclyl, aryl, $(C_1-C_6)$alkylaryl, heteroaryl, and $(C_1-C_6)$alkylheteroaryl;

with proviso that R3, R4, R3', and R4' are not simultaneously hydrogen; and b) deprotecting the compound of formula (IIb) above, to yield the compound of formula (Id) above.

23. A process for preparing a compound according to claim 1, wherein the compound is of formula (Ic):

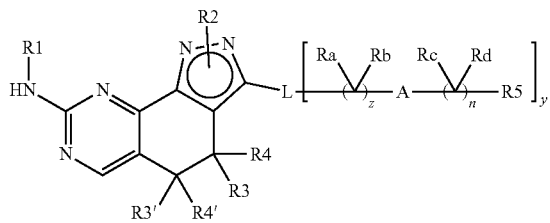

(Ic)

wherein:
L is C(O)NR6aR7a or NR8C(O)R6a;
R1 is hydrogen, or $(C_1-C_6)$alkyl;
R2 is hydrogen, $(C_1-C_6)$alkyl, $(C_2-C_6)$alkenyl, $(C_2-C_6)$alkynyl, $(C_3-C_7)$cycloalkyl, or heterocyclyl, wherein the $(C_1-C_6)$alkyl, $(C_2-C_6)$alkenyl, $(C_2-C_6)$ alkynyl, $(C_3-C_7)$cycloalkyl, or heterocyclyl is optionally substituted with one or more independently selected substituents;
R3 is hydrogen or $(C_1-C_6)$alkyl;
R4 is hydrogen or $(C_1-C_6)$alkyl;
R3' is hydrogen or $(C_1-C_6)$alkyl;
R4' is hydrogen or $(C_1-C_6)$alkyl;
R6a is hydrogen, $(C_1-C_6)$alkyl, aryl$(C_1-C_6)$alkyl, heteroaryl$(C_1-C_6)$alkyl, $(C_3-C_7)$cycloalkyl, heterocyclyl, aryl, or heteroaryl, wherein the $(C_1-C_6)$alkyl, aryl$(C_1-C_6)$alkyl, heteroaryl$(C_1-C_6)$alkyl, $(C_3-C_7)$cycloalkyl, heterocyclyl, aryl, or heteroaryl is optionally substituted with one or more independently selected substituents;
R7a is hydrogen, $(C_1-C_6)$alkyl, aryl$(C_1-C_6)$alkyl, heteroaryl$(C_1-C_6)$alkyl, $(C_3-C_7)$cycloalkyl, heterocyclyl, aryl, or heteroaryl, wherein the $(C_1-C_6)$alkyl, aryl$(C_1-C_6)$alkyl, heteroaryl$(C_1-C_6)$alkyl, $(C_3-C_7)$cycloalkyl, heterocyclyl, aryl, or heteroaryl is optionally substituted with one or more independently selected substituents; or
R6a and R7a, taken together with the nitrogen atom to which they are bonded, form a 5- or 6-membered heterocyclyl, wherein the 5- or 6-membered heterocyclyl optionally contains one additional heteroatom selected from the group consisting of nitrogen, oxygen, and sulfur, and further wherein the 5- or 6-membered heterocyclyl is optionally substituted with one or more independently selected substituents;
R8 is hydrogen or $(C_1-C_6)$alkyl, wherein the $(C_1-C_6)$ alkyl is optionally substituted with one or more independently selected substituents;
y is 0;
wherein the optional substituents for R6a, R7a, R6a and R7a, R8, are independently selected from the group consisting halogen, cyano, nitro, oxo, $(C_1-C_6)$alkyl, polyfluorinated $(C_1-C_6)$alkyl, C(O)NHaryl$(C_1-C_6)$alkyl, C(O)heterocyclyl$(C_1-C_6)$alkyl, amino$(C_1-C_6)$alkyl, hydroxy$(C_1-C_6)$alkyl, $(C_3-C_7)$cycloalkyl$(C_1-C_6)$alkyl, heterocyclyl$(C_1-C_6)$alkyl, $(C_1-C_6)$alkylheterocyclyl$(C_1-C_6)$alkyl, di$(C_1-C_6)$alkylaminoheterocyclyl$(C_1-C_6)$alkyl, aryl$(C_1-C_6)$alkyl, heteroaryl$(C_1-C_6)$alkyl, $(C_2-C_6)$alkenyl, $(C_2-C_6)$alkynyl, C(NH)O$(C_1-C_6)$alkyl, C(O)H, C(O)$(C_1-C_6)$alkyl, $C(O)NH_2$, C(O)NH$(C_1-C_6)$alkyl, C(O)N$((C_1-C_6)$alkyl$)_2$, CO)NHOH, C(O)NHheterocyclyl, C(O)NHaryl, C(O)NHheteroaryl, C(O)OH, C(O)O$(C_1-C_6)$alkyl, C(O)O$(C_3-C_7)$cycloalkyl, C(O)Oaryl, C(O)$(C_3-C_7)$cycloalkyl, C(O)heterocyclyl, C(O)aryl, $NH_2$, NH$(C_1-C_6)$alkyl, N$((C_1-C_6)$alkyl$)_2$, NHC(O)H, NHC(O)$(C_1-C_6)$alkyl, $NHC(O)NH_2$, NHC(O)NH$(C_1-C_6)$alkyl, NHC(O)O$(C_1-C_6)$alkyl, NHC(O)O$(C_1-C_6)$alkyl (heterocyclyl), NHC(O)$(C_3-C_7)$cycloalkyl, NHC(O)heterocyclyl, NHC(O)aryl, $NHS(O)_2(C_1-C_6)$alkyl, $NHS(O)_2$heterocyclyl, $NHS(O)_2$aryl, NHheterocyclyl, NHaryl, N(aryl)$_2$, OH, —$OCH_2O$—, O$(C_1-C_6)$alkyl, (polyfluorinated) O$(C_1-C_6)$alkyl, (aryl) O$(C_1-C_6)$alkyl, O$(C_1-C_6)$alkylideneamino, OC(O)$(C_1-C_6)$alkyl, OC(O)heterocyclyl, OC(O)aryl, O$(C_3-C_7)$cycloalkenyl, Oheterocyclyl, Oaryl, tri$(C_1-C_6)$alkylsilyl, S$(C_1-C_6)$alkyl, Saryl, $S(O)_2(C_1-C_6)$alkyl, polyfluorinated $S(O)_2(C_1-C_6)$alkyl, $S(O)_2NH_2$, $S(O)_2NH(C_1-C_6)$alkyl, $S(O)_2N((C_1-C_6)$alkyl$)_2$, $S(O)_2$NHheterocyclyl, $S(O)_2$NHaryl, $S(O)_2$aryl, $(C_3-C_7)$cycloalkyl, heterocyclyl, polyfluorinated heterocyclyl, $(C_1-C_6)$alkylheterocyclyl, aryl, $(C_1-C_6)$alkylaryl, heteroaryl, and $(C_1-C_6)$ alkylheteroaryl;
with provisos that:
(1) R3, R4, R3', and R4' are not simultaneously hydrogen; and
(2) the following compounds of formula (Ic) are excluded:

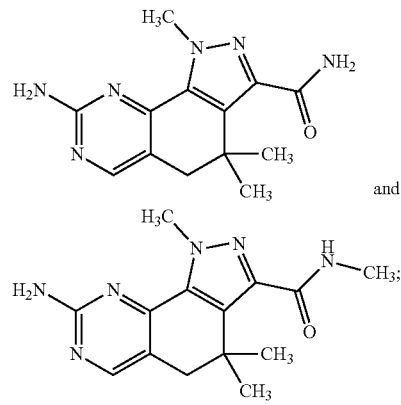

and wherein the process comprises the following step:
alkylating a compound is of formula (Id):

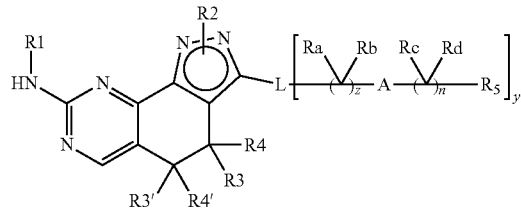

(Id)

wherein:
L is C(O)NR6aR7a or NR8C(O)R6a;
R1 is hydrogen, or $(C_1-C_6)$alkyl;
R2 is hydrogen;
R3 is hydrogen or $(C_1-C_6)$alkyl;
R4 is hydrogen or $(C_1-C_6)$alkyl;
R3' is hydrogen or $(C_1-C_6)$alkyl;
R4' is hydrogen or $(C_1-C_6)$alkyl;
R6a is hydrogen, $(C_1-C_6)$alkyl, aryl$(C_1-C_6)$alkyl, heteroaryl$(C_1-C_6)$alkyl, $(C_3-C_7)$cycloalkyl, heterocyclyl, aryl, or heteroaryl, wherein the $(C_1-C_6)$alkyl, aryl$(C_1-$ $C_6$)alkyl, heteroaryl($C_1$-$C_6$)alkyl, ($C_3$-$C_7$)cycloalkyl, heterocyclyl, aryl, or heteroaryl is optionally substituted with one or more independently selected substituents;

R7a is hydrogen, ($C_1$-$C_6$)alkyl, aryl($C_1$-$C_6$)alkyl, heteroaryl($C_1$-$C_6$)alkyl, ($C_3$-$C_7$)cycloalkyl, heterocyclyl, aryl, or heteroaryl, wherein the ($C_1$-$C_6$)alkyl, aryl($C_1$-$C_6$)alkyl, heteroaryl($C_1$-$C_6$)alkyl, ($C_3$-$C_7$)cycloalkyl, heterocyclyl, aryl, or heteroaryl is optionally substituted with one or more independently selected substituents; or R6a and R7a, taken together with the nitrogen atom to which they are bonded, form a 5- or 6-membered heterocyclyl, wherein the 5- or 6-membered heterocyclyl optionally contains one additional heteroatom selected from the group consisting of nitrogen, oxygen, and sulfur, and further wherein the 5- or 6-membered heterocyclyl is optionally substituted with one or more independently selected substituents;

R8 is hydrogen or ($C_1$-$C_6$)alkyl, wherein the ($C_1$-$C_6$) alkyl is optionally substituted with one or more independently selected substituents;

y is 0;

wherein the optional substituents for R6a, R7a, R6a and R7a, R8, are independently selected from the group consisting halogen, cyano, nitro, oxo, ($C_1$-$C_6$)alkyl, polyfluorinated ($C_1$-$C_6$)alkyl, C(O)NHaryl($C_1$-$C_6$)alkyl, C(O)heterocyclyl($C_1$-$C_6$)alkyl, amino($C_1$-$C_6$)alkyl, hydroxy($C_1$-$C_6$)alkyl, ($C_3$-$C_7$)cycloalkyl($C_1$-$C_6$)alkyl, heterocyclyl($C_1$-$C_6$)alkyl, ($C_1$-$C_6$)alkylheterocyclyl($C_1$-$C_6$)alkyl, di($C_1$-$C_6$)alkylaminoheterocyclyl($C_1$-$C_6$)alkyl, aryl($C_1$-$C_6$)alkyl, heteroaryl($C_1$-$C_6$)alkyl, ($C_2$-$C_6$)alkenyl, ($C_2$-$C_6$)alkynyl, C(NH)O($C_1$-$C_6$)alkyl, C(O)H, C(O)($C_1$-$C_6$)alkyl, C(O)NH$_2$, C(O)NH($C_1$-$C_6$)alkyl, C(O)N(($C_1$-$C_6$)alkyl)$_2$, CO)NHOH, C(O)NHheterocyclyl, C(O)NHaryl, C(O)NHheteroaryl, C(O)OH, C(O)O($C_1$-$C_6$)alkyl, C(O)O($C_3$-$C_7$)cycloalkyl, C(O)Oaryl, C(O)($C_3$-$C_7$)cycloalkyl, C(O)heterocyclyl, C(O)aryl, NH$_2$, NH($C_1$-$C_6$)alkyl, N(($C_1$-$C_6$)alkyl)$_2$, NHC(O)H, NHC(O)($C_1$-$C_6$)alkyl, NHC(O)NH$_2$, NHC(O)NH($C_1$-$C_6$)alkyl, NHC(O)O($C_1$-$C_6$)alkyl, NHC(O)O($C_1$-$C_6$)alkyl(heterocyclyl), NHC(O)($C_3$-$C_7$)cycloalkyl, NHC(O)heterocyclyl, NHC(O)aryl, NHS(O)$_2$($C_1$-$C_6$)alkyl, NHS(O)$_2$heterocyclyl, NHS(O)$_2$aryl, NHheterocyclyl, NHaryl, N(aryl)$_2$, OH, —OCH$_2$O—, O($C_1$-$C_6$)alkyl, (polyfluorinated) O($C_1$-$C_6$)alkyl, (aryl) O($C_1$-$C_6$)alkyl, O($C_1$-$C_6$)alkylideneamino, OC(O)($C_1$-$C_6$)alkyl, OC(O)heterocyclyl, OC(O)aryl, O($C_3$-$C_7$)cycloalkenyl, Oheterocyclyl, Oaryl, tri($C_1$-$C_6$)alkylsilyl, S($C_1$-$C_6$)alkyl, Saryl, S(O)$_2$($C_1$-$C_6$)alkyl, polyfluorinated S(O)$_2$($C_1$-$C_6$)alkyl, S(O)$_2$NH$_2$, S(O)$_2$NH($C_1$-$C_6$)alkyl, S(O)$_2$N(($C_1$-$C_6$)alkyl)$_2$, S(O)$_2$NHheterocyclyl, S(O)$_2$NHaryl, S(O)$_2$aryl, ($C_3$-$C_7$)cycloalkyl, heterocyclyl, polyfluorinated heterocyclyl, ($C_1$-$C_6$)alkylheterocyclyl, aryl, ($C_1$-$C_6$)alkylaryl, heteroaryl, and ($C_1$-$C_6$) alkylheteroaryl;

with proviso that R3, R4, R3', and R4' are not simultaneously hydrogen;

with a compound of formula (VI):

R2-J    (VI)

wherein:

R2 is ($C_1$-$C_6$)alkyl, ($C_2$-$C_6$)alkenyl, ($C_2$-$C_6$) alkynyl, ($C_3$-$C_7$)cycloalkyl, or heterocyclyl, wherein the ($C_1$-$C_6$) alkyl, ($C_2$-$C_6$)alkenyl, ($C_2$-$C_6$) alkynyl, ($C_3$-$C_7$)cycloalkyl, or heterocyclyl is optionally substituted with one or more independently selected substituents independently selected from the group consisting halogen, cyano, nitro, oxo, ($C_1$-$C_6$)alkyl, polyfluorinated ($C_1$-$C_6$)alkyl, C(O)NHaryl($C_1$-$C_6$)alkyl, C(O)heterocyclyl ($C_1$-$C_6$)alkyl, amino($C_1$-$C_6$)alkyl, hydroxy($C_1$-$C_6$)alkyl, ($C_3$-$C_7$)cycloalkyl($C_1$-$C_6$)alkyl, heterocyclyl($C_1$-$C_6$)alkyl, ($C_1$-$C_6$)alkylheterocyclyl($C_1$-$C_6$)alkyl, di($C_1$-$C_6$)alkylaminoheterocyclyl($C_1$-$C_6$)alkyl, aryl($C_1$-$C_6$) alkyl, heteroaryl($C_1$-$C_6$)alkyl, ($C_2$-$C_6$)alkenyl, ($C_2$-$C_6$) alkynyl, C(NH)O($C_1$-$C_6$)alkyl, C(O)H, C(O)($C_1$-$C_6$) alkyl, C(O)NH$_2$, C(O)NH($C_1$-$C_6$)alkyl, C(O)N(($C_1$-$C_6$)alkyl)$_2$, CO)NHOH, C(O)NHheterocyclyl, C(O)NHaryl, C(O)NHheteroaryl, C(O)OH, C(O)O($C_1$-$C_6$) alkyl, C(O)O($C_3$-$C_7$)cycloalkyl, C(O)Oaryl, C(O)($C_3$-$C_7$)cycloalkyl, C(O)heterocyclyl, C(O)aryl, NH$_2$, NH($C_1$-$C_6$)alkyl, N(($C_1$-$C_6$)alkyl)$_2$, NHC(O)H, NHC(O)($C_1$-$C_6$)alkyl, NHC(O)NH$_2$, NHC(O)NH($C_1$-$C_6$)alkyl, NHC(O)O($C_1$-$C_6$)alkyl, NHC(O)O($C_1$-$C_6$)alkyl (heterocyclyl), NHC(O)($C_3$-$C_7$)cycloalkyl, NHC(O)heterocyclyl, NHC(O)aryl, NHS(O)$_2$($C_1$-$C_6$)alkyl, NHS(O)$_2$heterocyclyl, NHS(O)$_2$aryl, NHheterocyclyl, NHaryl, N(aryl)$_2$, OH, —OCH$_2$O—, O($C_1$-$C_6$)alkyl, (polyfluorinated) O($C_1$-$C_6$)alkyl, (aryl) O($C_1$-$C_6$)alkyl, O($C_1$-$C_6$)alkylideneamino, OC(O)($C_1$-$C_6$)alkyl, OC(O)heterocyclyl, OC(O)aryl, O($C_3$-$C_7$)cycloalkenyl, Oheterocyclyl, Oaryl, tri($C_1$-$C_6$)alkylsilyl, S($C_1$-$C_6$)alkyl, Saryl, S(O)$_2$($C_1$-$C_6$)alkyl, polyfluorinated S(O)$_2$($C_1$-$C_6$)alkyl, S(O)$_2$NH$_2$, S(O)$_2$NH($C_1$-$C_6$)alkyl, S(O)$_2$N(($C_1$-$C_6$)alkyl)$_2$, S(O)$_2$NHheterocyclyl, S(O)$_2$NHaryl, S(O)$_2$aryl, ($C_3$-$C_7$)cycloalkyl, heterocyclyl, polyfluorinated heterocyclyl, ($C_1$-$C_6$)alkylheterocyclyl, aryl, ($C_1$-$C_6$)alkylaryl, heteroaryl, and ($C_1$-$C_6$) alkylheteroaryl; and J is Br, I, OH, OS(O)$_2$CH$_3$, or OS(O)$_2$-Ph-CH$_3$;

to yield the compound of formula (Ic) above.

* * * * *